United States Patent
Church et al.

(10) Patent No.: US 12,012,670 B2
(45) Date of Patent: Jun. 18, 2024

(54) HIGH-THROUGHPUT IMMUNE SEQUENCING

(71) Applicant: President and Fellows of Harvard College, Cambridge, MA (US)

(72) Inventors: George M. Church, Brookline, MA (US); Francois Vigneault, Medford, MA (US); Uri Laserson, Boston, MA (US); Ido Bachelet, Brookline, MA (US)

(73) Assignee: President and Fellows of Harvard College, Cambridge, MA (US)

( * ) Notice: Subject to any disclaimer, the term of this patent is extended or adjusted under 35 U.S.C. 154(b) by 1332 days.

(21) Appl. No.: 16/513,945

(22) Filed: Jul. 17, 2019

(65) Prior Publication Data

US 2020/0095704 A1    Mar. 26, 2020

Related U.S. Application Data

(63) Continuation of application No. 13/878,400, filed as application No. PCT/US2011/055801 on Oct. 11, 2011, now Pat. No. 10,392,726.

(Continued)

(51) Int. Cl.
*C12N 15/10* (2006.01)
*C07K 16/00* (2006.01)
(Continued)

(52) U.S. Cl.
CPC .............. *C40B 10/00* (2013.01); *C07K 16/00* (2013.01); *C12N 15/10* (2013.01); *C12Q 1/6806* (2013.01);
(Continued)

(58) Field of Classification Search
CPC ...... C07K 16/00; C12N 15/10; C12Q 1/6806; C12Q 1/6869; C12Q 1/6881;
(Continued)

(56) References Cited

U.S. PATENT DOCUMENTS 6,432,360 B1   8/2002   Church
6,485,944 B1   11/2002  Church et al.
(Continued)

FOREIGN PATENT DOCUMENTS

WO   2005/082098 A2   9/2005
WO   2006/073504 A2   7/2006
(Continued)

OTHER PUBLICATIONS

Liao H X., et al., "High-throughput isolation of immunoglobulin genes from single human B cells and expression as monoclonal antibodies" Journal of Virological Methods. Elsevier BV. N L. vol. 158. No. 1-2. Jun. 1, 2009 (Jun. 1, 2009). pp. 171-179.
(Continued)

*Primary Examiner* — Jeremy C Flinders
(74) *Attorney, Agent, or Firm* — Banner & Witcoff, Ltd.

(57) ABSTRACT

This disclosure provides methods for monitoring an immune response. Methods comprise linking a polynucleotide sequence encoding a heavy chain variable region and a polynucleotide sequence encoding a light chain variable region from a single lymphocyte from a biological sample obtained before an immune response and linking a polynucleotide sequence encoding a heavy chain variable region and a polynucleotide sequence encoding a light chain variable region from a single lymphocyte from a biological sample obtained during or after an immune response. Methods further comprise performing high-throughput sequencing of the linked (paired) sequences from before the immune (Continued)

response and from during or after the immune response, and comparing the resulting sequence reads.

14 Claims, 104 Drawing Sheets

Specification includes a Sequence Listing.

Related U.S. Application Data

(60) Provisional application No. 61/391,337, filed on Oct. 8, 2010.

(51) Int. Cl.

| | |
|---|---|
| *C07K 16/06* | (2006.01) |
| *C12Q 1/6806* | (2018.01) |
| *C12Q 1/6881* | (2018.01) |
| *C12Q 1/6883* | (2018.01) |
| *C40B 10/00* | (2006.01) |
| *C40B 30/04* | (2006.01) |
| *C40B 40/08* | (2006.01) |
| *G16B 20/00* | (2019.01) |
| *G16B 30/00* | (2019.01) |
| *C12Q 1/6874* | (2018.01) |

(52) U.S. Cl.
CPC ............ *C12Q 1/6881* (2013.01); *C40B 30/04* (2013.01); *C40B 40/08* (2013.01); *G16B 20/00* (2019.02); *G16B 30/00* (2019.02); *C07K 16/065* (2013.01); *C12Q 1/6874* (2013.01); *C12Q 1/6883* (2013.01); *C12Q 2535/00* (2013.01); *C12Q 2535/122* (2013.01); *C12Q 2600/112* (2013.01); *C12Q 2600/158* (2013.01)

(58) Field of Classification Search
CPC .............. C12Q 1/6883; C12Q 2535/00; C12Q 2535/122; C12Q 2600/112; C12Q 2600/158; C40B 10/00; C40B 30/04; C40B 40/08; G16B 20/00; G16B 30/00
See application file for complete search history.

(56) References Cited

U.S. PATENT DOCUMENTS

| | | | |
|---|---|---|---|
| 6,511,803 B1 | 1/2003 | Church et al. | |
| 7,425,431 B2 | 9/2008 | Church et al. | |
| 2007/0141048 A1 | 6/2007 | Oleksiewicz et al. | |
| 2007/0161001 A1 | 7/2007 | Leshkowitz | |
| 2008/0269068 A1 | 10/2008 | Church et al. | |
| 2009/0018024 A1 | 1/2009 | Church et al. | |
| 2010/0040606 A1 | 2/2010 | Lantto et al. | |
| 2010/0151471 A1 | 6/2010 | Faham et al. | |
| 2011/0312505 A1* | 12/2011 | Reddy .................... | G16B 40/30 435/7.92 |

FOREIGN PATENT DOCUMENTS

| | | |
|---|---|---|
| WO | 2007/065433 A2 | 6/2007 |
| WO | 2008/104184 A2 | 9/2008 |
| WO | 2008/106980 A2 | 9/2008 |
| WO | 2010/053587 A2 | 5/2010 |
| WO | 2012/048340 A2 | 4/2012 |

OTHER PUBLICATIONS

Reddy Sai T., et al. "Monoclonal antibodies isolated without screening by analyzing the variable-gene repertoire of plasma cells". Nature Biotechnology. Nature Publishing Group. New York. NY. US. vol 1 • 28. No. 9. Sep. 1, 2010 (Sep. 1, 2010). pp. 965-969.
Boyd, Scott D., et al., Supplementary Materials for "Measurement and Clinical Monitoring of Human Lymphocyte Clonality by Massively Parallel V-D-J Pyrosequencing."
Chapal, N., et al.,"In-Cell Assembly of scFv from Human Thyroid-Infiltrating B Cells," BioTechniques, Sep. 1997, pp. 518-524, vol. 23, No. 3.
Meijer, Per-Johan et al.,"Isolation of Human Antibody Repertoires with Preservation of the Natural Heavy and Light Chain Pairing," J. Mol. Biol., Feb. 14, 2006, pp. 764-772, vol. 358, Elsevier Ltd.
Office Action issued for corresponding Canadian Patent Application No. 2,814,047, dated Apr. 7, 2015.
Meijer, Per-Johan et al., "Human Antibody Repertoires," Therapeutic Antibodies, 2009, pp. 261-277, vol. 525, Human Press.
Office Action issued for corresponding European Patent Application No. 11831760.1, dated May 2, 2016.
Therapeutic Antibodies (2009) 525 261-277.
Campbell, Peter J., et al.,"Subclonal phylogenetic structures in cancer revealed by ultra-deep sequencing," PNAS (2008) 105(35)13081-13086.
Boyd, Scott D. et al., "Measurement and clinical monitoring of human lymphocyte clonality by massively parallel VDJ pyrosequencing," Sci Transl. Med (2009) 1 (12) 12 ra23 (published on Dec. 23, 2009).
Dufner et al. (Trends in Biotechnology, 2006, vol. 24 No. 11).
Parameswaran et al. (Nucleic Acids Research, 2007, 35:e130).
Dhiman, Neelam et al.,"Next-generation sequencing: a transformative tool for vaccinology," Expert Rev Vaccines. Aug. 2009 ; 8(8): 963-967. doi:10.1586/erv.09.67.

* cited by examiner

Fig. 15A time series k-means (k=100); euclidean dist; Run 4, 5, 7; all clones; values are frequencies
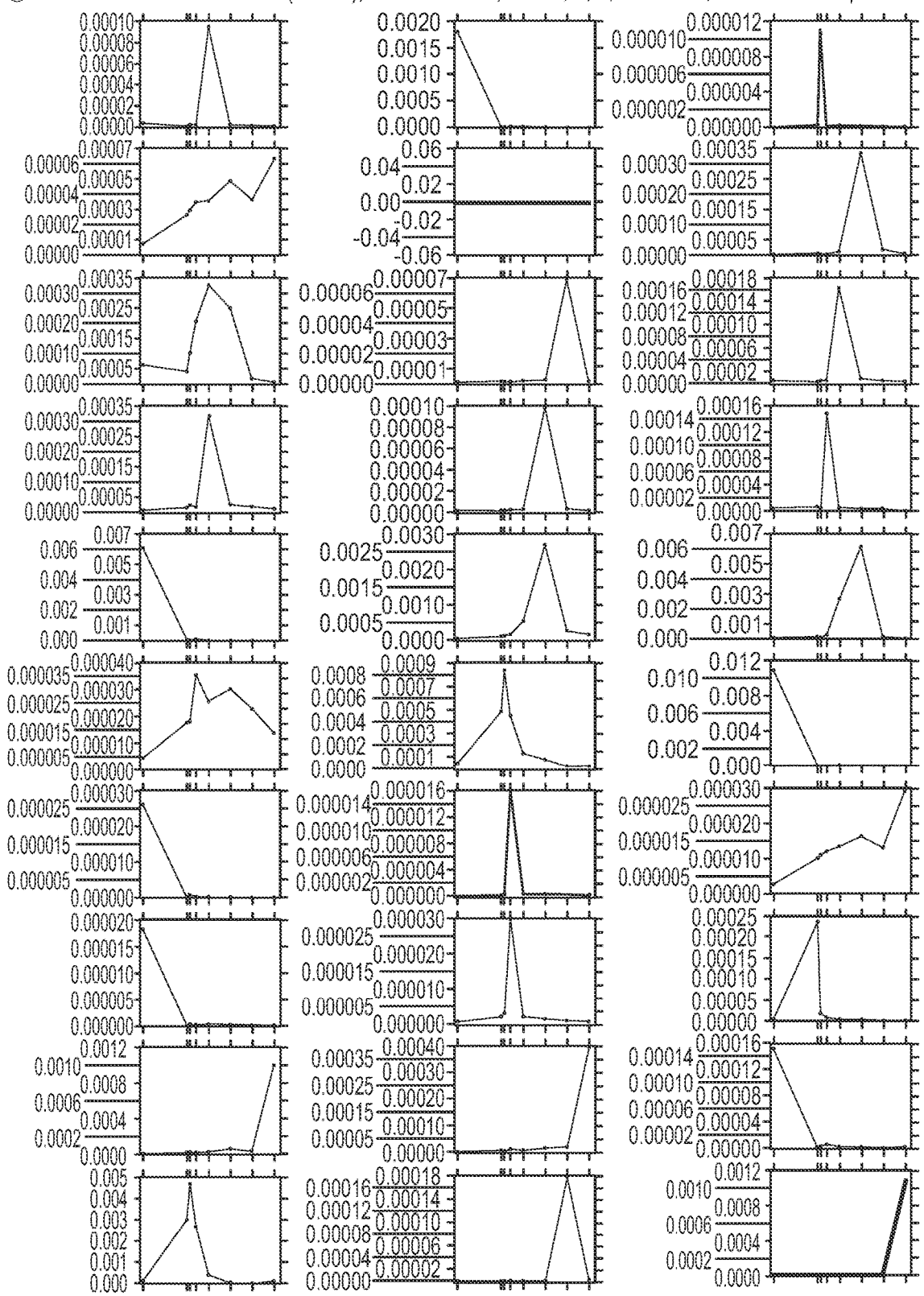

FIG. 15B time series k-means (k=100); euclidean dist; Run 4, 5, 7; all clones; values are frequencies
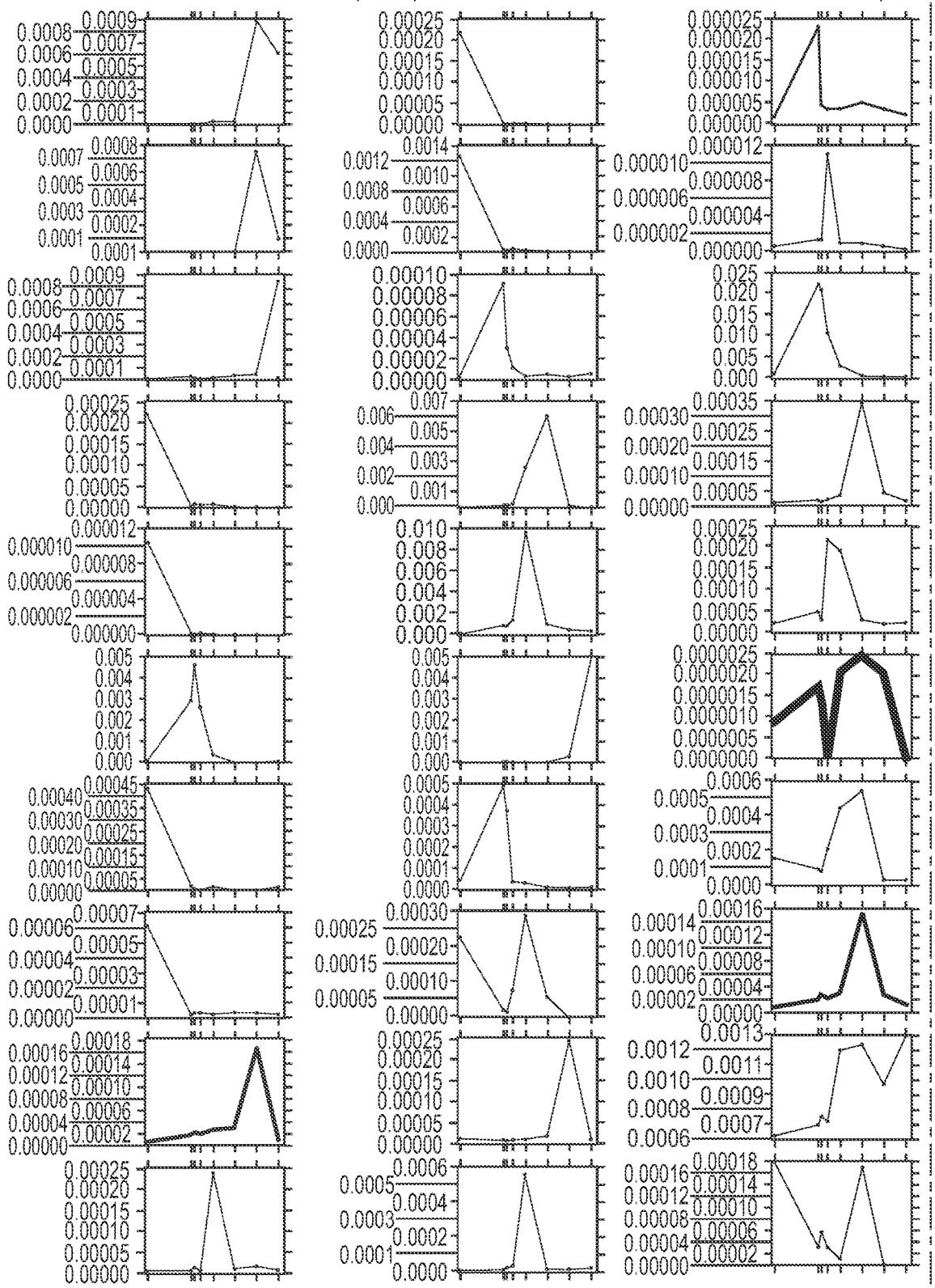

time series k-means (k=100); euclidean dist;
Run 4, 5, 7; clones seen>=2 times; values are frequencies time series k-means (k=100); euclidean dist;
Run 4, 5, 7; clones seen>=2 times; values are frequencies

```
  9 : CGCGTTGCTCTTTTAAGAGGTGTGTCCAGTGTCAGGTGCAGCTGGTGGAGTCTGGGGGAGGCGTGG :  72
      ||||||||||||||||||||||||||||||||||||||||||||||||||||||||||||||||
 28 : CTCGTTGCTCTTTTAAGAGGTGTGTCCAGTGTCAGGTGCAGCTGGTGGAGTCTGGGGGAGGCGTGG :  91

73 : TCCAGCCTGGGAGGTCCCTGAGACTCTCCTGTGCAGCCTCTGATTCACCTTCAGTAGCTATGG    : 136
      ||||||||||||||||||||||||||||||||||||||||||||||||||||| ||||||||
 92 : TCCAGCCTGGGAGGTCCCTGAGACTCTCCTGTGCAGCCTCTGATTCACCTTCAGTAGGTATGG    : 155

137 : CATGCACTGGGTCCGCCAGGCTCCAGGCAAGGGGCTGGAGTGGGTGGCAGTTATATCATATATGAT : 200
      ||||||||||||||||||||||||||||||||||||||||||||||||||| ||||||||||||
156 : CATGCACTGGGTCCGCCAGGCTCCAGGCAAGGGGCTGGAGTGGGTGGCAGTGATATCATATATGAT : 219

201 : GGAAGTAATAAATACTATGCAGACTCCGTGAAGGGCCGATTCACCATCTCCAGAGACAATTCCA   : 264
      |||||||||||| |||||||||||||||||||||||||||||||||||||||||||||||||
220 : GGAAGTAATAAATGGTATGCAGACTCCGTGAAGGGCCGATTCACCATCTCCAGAGACAATTCCA   : 283

265 : AGAACACGCTGTATCTGCAAATGAACAGCCTGAGAGCTGAGGACACGGCTGTGTATTACTGTGC   : 328
      ||||||||||||||||||||||||||||||||||||||||||||||||||||||||||||||
284 : AGAACACTCTGTTTCTGCAAATGCACAGCCTGAGAGCTGCGGACACGGGTGTATATTACTGTGC   : 347

329 : GAGAGA---ACTT-ACTATGGTTCGGGGAGTTCCTG--ACTACTGGGCCAGGGAACCCTGGTC    : 386
      ||||||   |||| |                 |     ||||||||||||||||||||||||
348 : GAAAGATCAACTTTACTTTGGTTCGCAGAGTCCCGGGCACTACTGGGCCAGGGAACCCTGGTC    : 411

387 : ACCGTCTCCCTCA : 398 (SEQ ID NO:133)
      |||||||||||||
412 : ACCGTCTCCCTCA : 423 (SEQ ID NO:134)
```

Fig. 21

```
  6 : TGGCGTGCGTTGCTCTTTTAAGAGGTGTCCAGTGTCAGGTGTGCAGCTGTGGTGAGTCTGGGGGAGGCG :  69
      ||||| |||||||||||||||||||||||||||||||||||||||||||||||||||||||||||||
 25 : TTCCTCGTTGCTCTTTTAAGAGGTGTCCAGTGTCAGGTGTGCAGCTGTGGTGAGTCTGGGGGAGGCG :  88

70 : TGGTCCAGCCTGGGAGGTCCCTGAGACTCTCCTGTGCAGCCTCTGGATTCACCTTCAGTAGCTA : 133
      ||||||||||||||||||||||||||||||||||||||||||||||||||||||||||||||||
 89 : TGGTCCAGCCTGGGAGGTCCCTGAGACTCTCCTGTGCAGCCTCTGGATTCACCTTCAGTAGTA : 152

134 : TGGCATGCACTGGGTCCGCCAGGCTCCAGGCAAGGGGCTGGAGTGGGTGGCAGTTATATCATAT : 197
      |||||||||||||||||||||||||||||||||||||||||||||||||||| |||||||||
153 : TGGCATGCACTGGGTCCGCCAGGCTCCAGGCAAGGGGCTGGAGTGGGTGGCAGTGATATCATAT : 216

198 : GATGGAAGTAATAAATACTATGCAGACTCCGTGAAGGGCCGATTCACCATCTCCAGAGACAATT : 261
      ||||||||||||||| ||||||||||||||||||||||||||||||||||||||||||||||
217 : GATGGAAGTAATAAATGGTATGCAGACTCCGTGAAGGGCCGATTCACCATCTCCAGAGACAATT : 280

262 : CCAAGAACACGCTGTATCTGCAAATGAACAGCCTGAGAGCTGAGGACACGGCTGTGTATTACTG : 325
      |||||||| |||||||| ||||||||| ||||||||||||||||||||| |||||||||||||
281 : CCAAGAACACTCTGTTTCTGCAAATGCACAGCCTGAGAGCTGCGGACACGGGTGTATATTACTG : 344

326 : TGCGAAAGATCTGGCCTACTATGGTTCGGGGAGTTATTACGACTACTGGGGCCAGGGAACCCTG : 389
      |||||||||||| ||| ||| || |||| ||||||||| ||||||||||||||||||||||
345 : TGCGAAAGATCAACTTTACTTTGGTTCGCAGAGTCCCGGGCACTACTGGGGTCCAGGGAACCCTG : 408

390 : GTCACCGTCTCCTCA : 404  (SEQ ID NO:135)
      |||||||||||||||
409 : GTCACCGTCTCCTCA : 423  (SEQ ID NO:136)
```

Fig. 22

```
  1 : CysAlaArgGlnThrPheAspTyrTrp    :   9  (SEQ ID NO:137)
      |||||||||||||||||||||||||||
      CysAlaArgGlnThrPheAspTyrTrp
238 : TGTGCGAGACAAACTTTTGACTACTGG    : 264  (SEQ ID NO:138)
```

Fig. 23

```
 74 : TCTCTGAAGATCTCCTGTAAGGGTTCTGGATACAGCTTTACCAGCTACTGGATCGGCTGGGTGC : 137
      SerLeuLysIleSerCysLysGlySerGlyTyrSerPheThrSerTyrTrpIleGlyTrpValA
      ||||||||||||||||||||||||||||||| ||||||||||  : |||||||||||||||||
      SerLeuLysIleSerCysLysGlySerGlyTyrSerPheThrAsnTyrTrpIleGlyTrpValA
  1 : TCTCTGAAGATCTCCTGTAAGGGTTCTGGATACAGCTTTACCAACTACTGGATCGGCTGGGTGC :  64

138 : GCCAGATGCCCGGGAAAGGCCTGGAGTGGATGGGGATCATCTATCCTGGTGACTCTGATACCAG : 200
      rgGlnMetProGlyLysGlyLeuGluTrpMetGlyIleIleTyrProGlyAspSerAspThrAr
      |||||||||||||||||||||||||||||||||||| ||  |||||||||||||||||||||
      rgGlnMetProGlyLysGlyLeuGluTrpMetGlyIleIleTyrProGlyAspSerAspThrAr
 65 : GCCAGATGCCCGGGAAAGGCCTGGAGTGGATGGGGATCATCTATCCTGGTGACTCTGATACCAG : 127

201 : ATACAGCCCGTCCTTCCAAGGCCAGTCACCATCTCAGCCGACAAGTCCATCAGCACCGCCTAC : 263
      gTyrSerProSerPheGlnGlyGlnValThrIleSerAlaAspLysSerIleSerThrAlaTyr
      |||||||||||||||||||||||||||||||||||||||||||||||||||||||||||||
      gTyrSerProSerPheGlnGlyGlnValThrIleSerAlaAspLysSerIleSerThrAlaTyr
128 : ATACAGCCCGTCCTTCCAAGGCCAGTCACCATCTCAGCCGACAAGTCCATCAGCACCGCCTAC : 190

264 : CTGCAGTGGAGCAGCCTGAAGGCCTCTGAAGACACCGCCATGTATTACTGTGCGAGACAGACTTTTG : 329
      LeuGlnTrpSerSerLeuLysAlaSerAspThrAlaMetTyrTyrCysAlaArgGlnThrPheA
      |||||||||||||||||||||||| |||||||||||||||||||||||||||||||+||||||
      LeuGlnTrpSerSerLeuLysAlaSerAspThrAlaMetTyrTyrCysAlaArgGlnThrPheA
191 : CTGCAGTGGAGCAGCCTGAAGGCCTCGGACACCGCCATGTATTACTGTGCGAGAACTTTTG : 256

330 : ACTACTGGGGCCAGGGAACCCTGGTC : 355 (SEQ ID NO:139)
      spTyrTrpGlyGlnGlyThrLeuVal
      ||||||||||||||||||||||||||
      spTyrTrpGlyGlnGlyThrLeuVal
257 : ACTACTGGGGCCAGGGAACCCTGGTC : 282 (SEQ ID NO:140)
```

Fig. 24

| | DR1 | % | OR1 | % | OR2 | % | SR1 | % | TR1 | % | OR3 | % | SR2 | % | Total |
|---|---|---|---|---|---|---|---|---|---|---|---|---|---|---|---|
| Total reads | 1,183,769 | 100 | 455,187 | 100 | 1,147,232 | 100 | 622,356 | 100 | 1,473,502 | 100 | 1,268,232 | 100 | 1,004,209 | 100 | 7,154,487 |
| Size-filtered reads | 793,976 | 67 | 396,339 | 87 | 994,138 | 87 | 491,747 | 79 | 1,087,398 | 74 | 1,021,570 | 81 | 709,138 | 71 | 5,494,306 |
| Num with barcode | 783,514 | 66 | 388,467 | 85 | 978,201 | 85 | 470,122 | 76 | 1,038,683 | 70 | 947,307 | 75 | 676,660 | 67 | 5,282,954 |
| Num with BC and isotype | 549,751 | 46 | 264,802 | 58 | 675,828 | 59 | 271,529 | 44 | 517,539 | 35 | 618,670 | 49 | 434,549 | 43 | 3,332,668 |
| Num with BC, isotype, and VJ aln | 411,370 | 35 | 214,338 | 4 | 546,118 | 48 | 218,622 | 35 | 423,888 | 29 | 486,541 | 38 | 350,936 | 35 | 2,651,813 |
| Num with BC, VJ aln | 578,114 | 49 | 310,792 | 68 | 785,941 | 69 | 354,136 | 57 | 743,527 | 50 | 727,521 | 57 | 527,222 | 53 | 4,027,253 |
| barcode|01 | n/a | | 76,904 | 19 | 193,546 | 19 | 203,132 | 41 | 492 | 0 | 424,293 | 42 | 288,285 | 41 | 1,186,652 |
| barcode|02 | n/a | | 62,404 | 16 | 153,280 | 15 | 37,082 | 8 | 177,188 | 16 | 73,609 | 7 | 53,070 | 7 | 556,633 |
| barcode|03 | n/a | | 47,901 | 12 | 117,265 | 12 | 55,773 | 11 | 154,035 | 14 | 91,313 | 9 | 80,222 | 11 | 546,509 |
| barcode|04 | n/a | | 46,742 | 12 | 115,577 | 12 | 35,350 | 7 | 108,827 | 10 | 73,035 | 7 | 51,734 | 7 | 431,265 |
| barcode|05 | n/a | | 31,452 | 8 | 79,290 | 8 | 48,500 | 10 | 192,850 | 18 | 89,292 | 9 | 72,972 | 10 | 514,356 |
| barcode|06 | n/a | | 41,098 | 10 | 109,170 | 11 | 33,395 | 7 | 164,853 | 15 | 74,007 | 7 | 47,885 | 7 | 470,408 |
| barcode|08 | n/a | | 36,920 | 9 | 89,610 | 9 | 37,904 | 8 | 163,523 | 15 | 80,067 | 8 | 54,807 | 8 | 462,831 |
| barcode|09 | n/a | | 45,046 | 11 | 120,463 | 12 | 18,986 | 4 | 76,915 | 7 | 41,691 | 4 | 27,685 | 4 | 330,786 |
| no barcode | n/a | | 7,872 | 2 | 15,937 | 2 | 21,625 | 4 | 48,715 | 4 | 74,263 | 7 | 32,478 | 5 | 200,890 |
| IGHA | 239,447 | 31 | 99,500 | 26 | 252,049 | 26 | 113,414 | 24 | 129,354 | 12 | 293,256 | 31 | 197,176 | 29 | 1,324,196 |
| IGHD | 1,950 | 0 | 12,498 | 3 | 31,868 | 3 | 8,634 | 2 | 28,929 | 3 | 20,042 | 2 | 13,434 | 2 | 117,355 |
| IGHE | 20 | 0 | 18 | 0 | 55 | 0 | 23 | 0 | 71 | 0 | 58 | 0 | 36 | 0 | 281 |
| IGHG | 127,371 | 16 | 59,533 | 15 | 160,522 | 16 | 62,561 | 13 | 124,327 | 12 | 151,614 | 16 | 94,596 | 1 | 780,524 |
| IGHM | 180,963 | 23 | 93,253 | 24 | 231,334 | 24 | 86,897 | 18 | 234,858 | 23 | 153,700 | 16 | 129,307 | 19 | 1,110,312 |
| no isotype | 233,763 | 30 | 123,665 | 32% | 302,373 | 31 | 198,593 | 42 | 521,144 | 50 | 328,637 | 35 | 242,111 | 36 | 1,950,286 |

Fig. 26

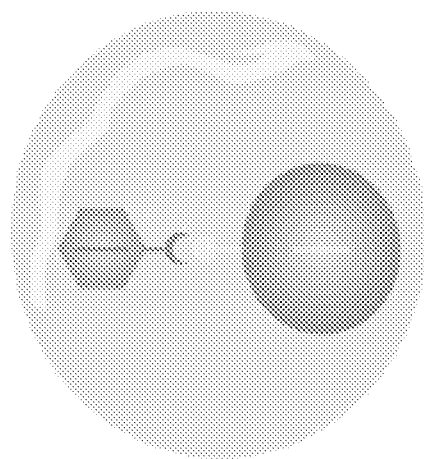
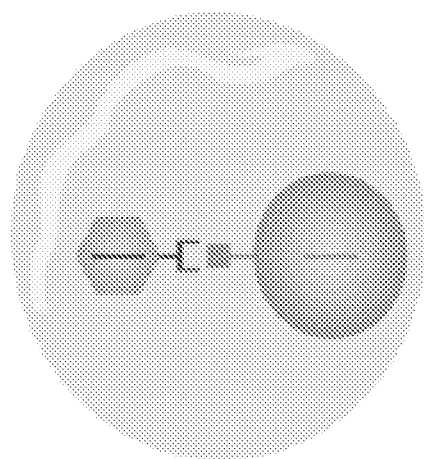
Fig. 38

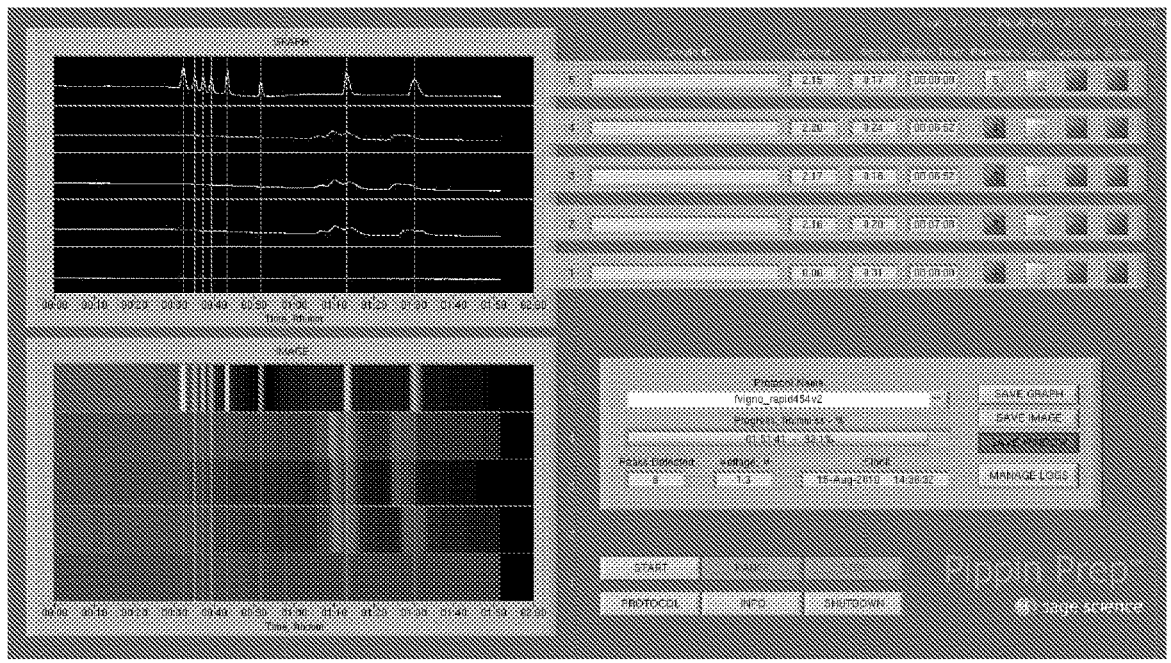
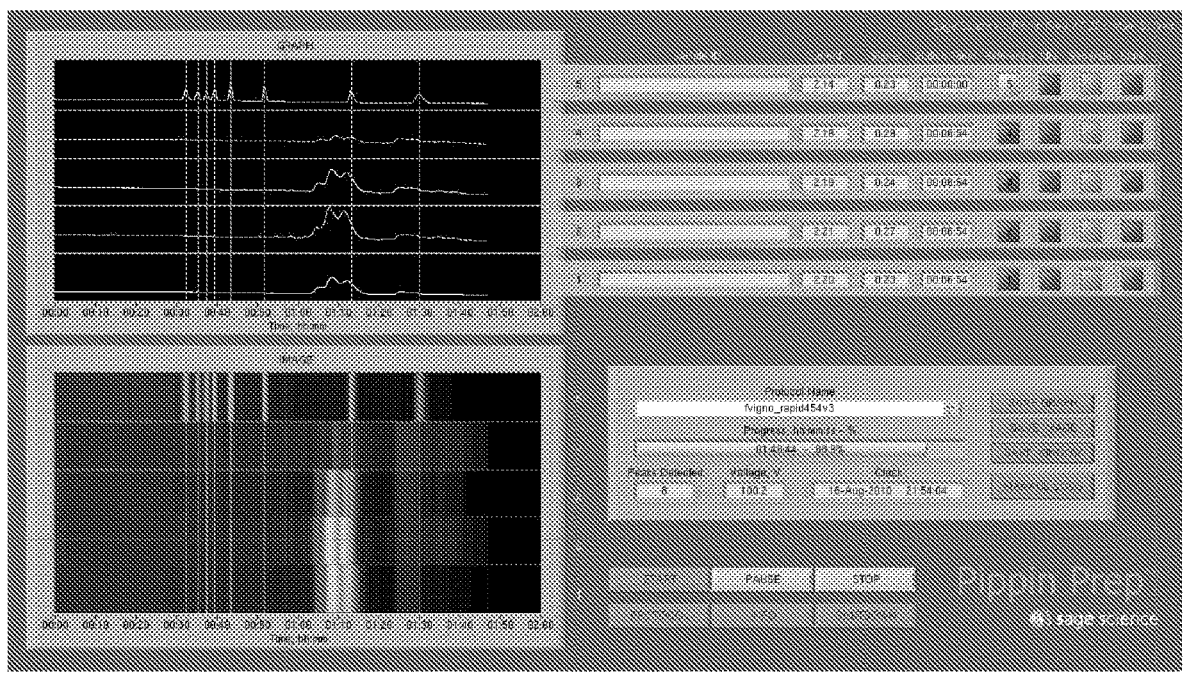
Fig. 54

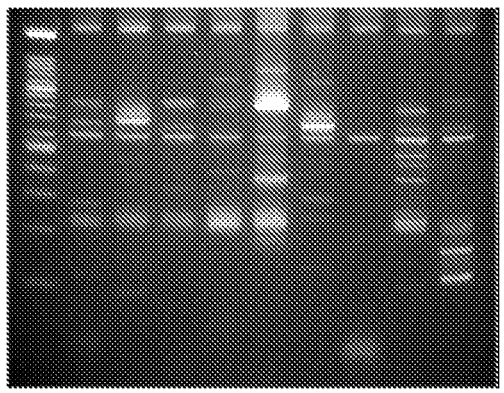
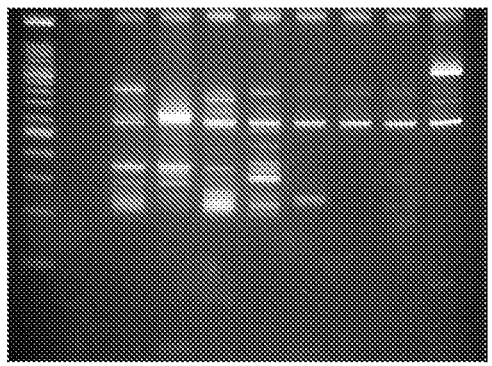
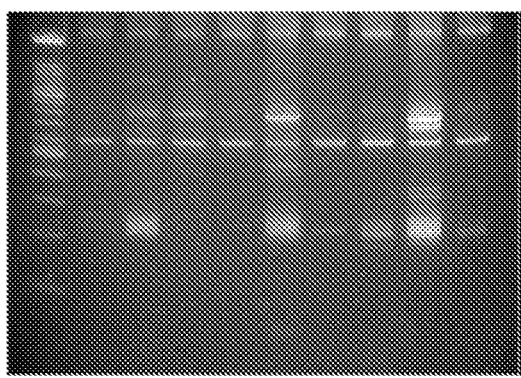
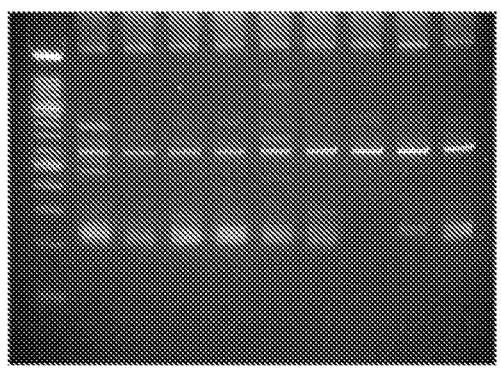
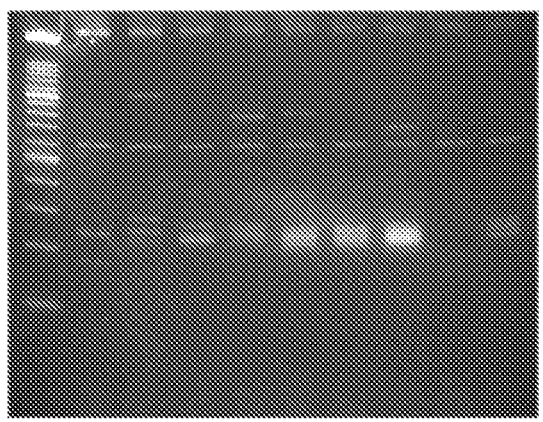
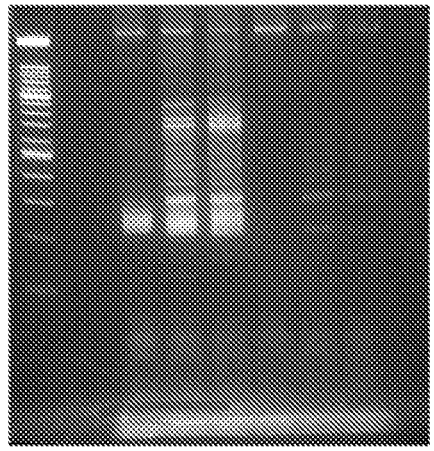
Fig. 59

Fig. 66A
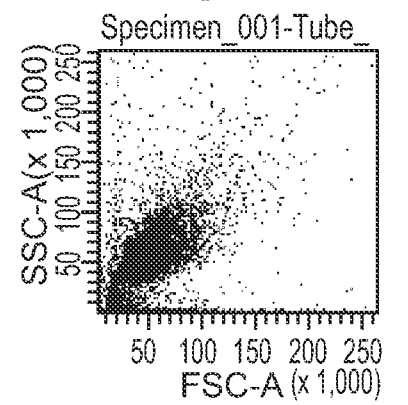
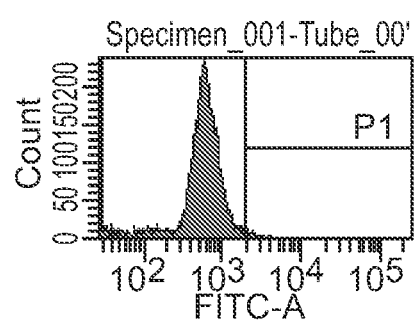
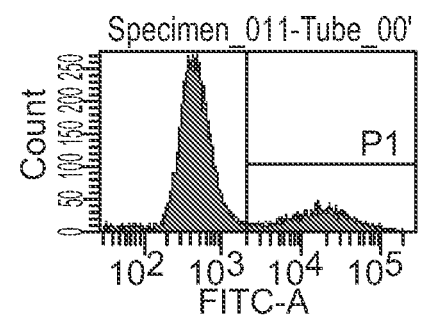
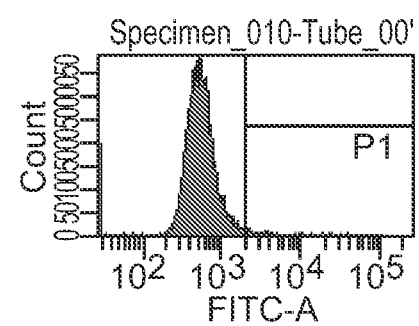
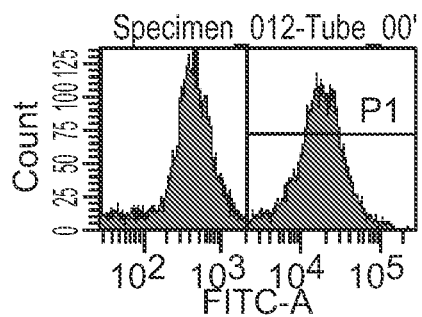
Fig. 66B
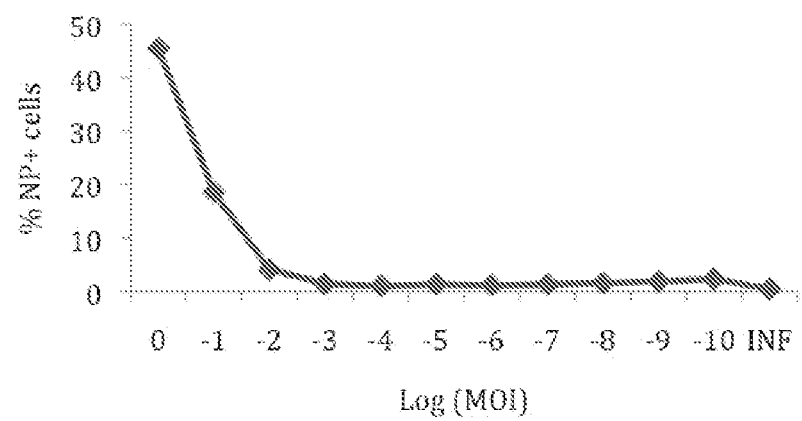

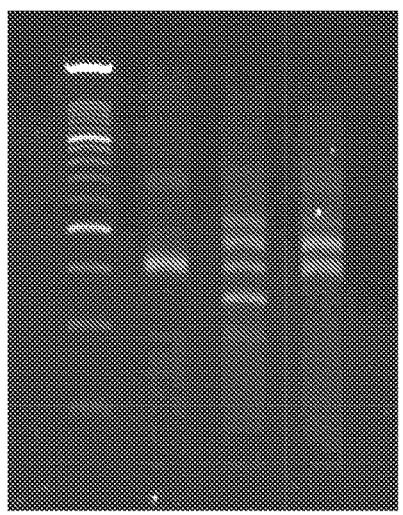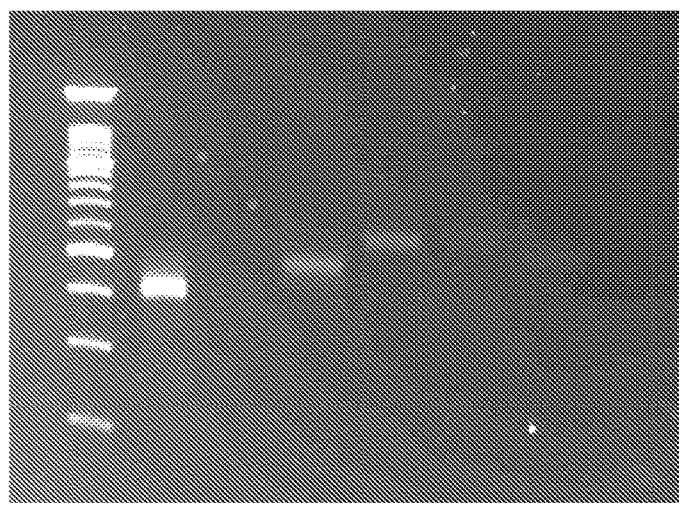
Fig. 73

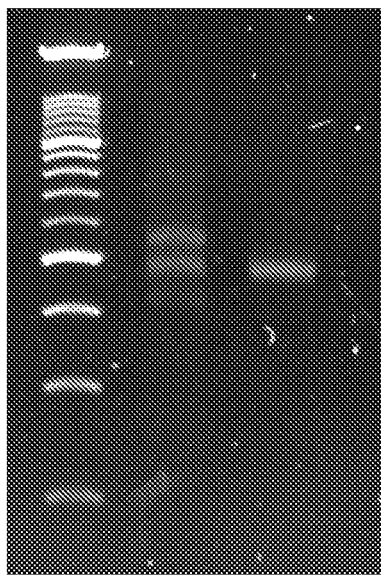
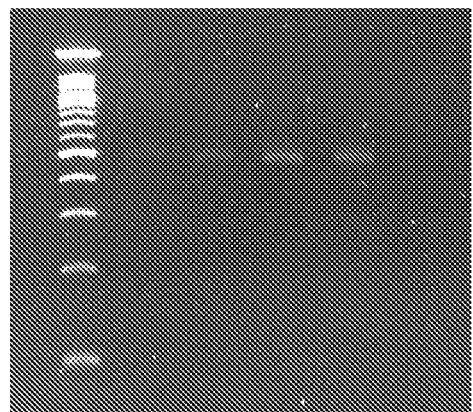
Fig. 76

HIGH-THROUGHPUT IMMUNE SEQUENCING

RELATED APPLICATION DATA

This application is a continuation application which claims priority to U.S. patent application Ser. No. 13/878,400, filed on Jul. 17, 2013; which is a National Stage Application under 35 U.S.C. 371 of PCT application PCT/US11/55801, filed Oct. 11, 2011; which claims the benefit of U.S. Provisional Application No. 61/391,337, filed on Oct. 8, 2010 each of which are hereby incorporated by reference in their entireties.

STATEMENT OF GOVERNMENT INTERESTS

This invention was made with government support under HG003170 awarded by the National Institutes of Health. The Government has certain rights in the invention.

FIELD

The present invention relates to methods and compositions for diagnostics and therapeutics.

Computer Program Listing Appendix

A computer program listing is provided as an appendix to the application. The appendix includes a text file with a file name of "Computer Program Listing Appendix.txt", created on Nov. 6, 2023, with a size of 144,582 bytes. The content of this appendix is expressly incorporated herein by reference in its entirety for all purposes.

BACKGROUND

The function of the adaptive immune system is largely mediated by lymphocytes (B and T cells) that express a diverse repertoire of immune receptors against virtually any foreign substance (Abbas et al., Cellular and Molecular Immunology, Edn. 6th. (Saunders Elsevier, Philadelphia; 2007); Murphy et al., Janeway's Immunobiology, Edn. 7th. (Garland Science, New York; 2008); Paul, Fundamental Immunology, Edn. 6th. (Wolters Kluwer/Lippincott Williams & Wilkins, Philadelphia; 2008)). In order to generate the repertoire of antibodies necessary for antigen recognition, each lymphocyte independently constructs a unique receptor through the process of VDJ recombination. Id. Each cell randomly selects a single V, D, and J gene segment through genetic recombination, introducing additional non-germline-encoded nucleotides at the junctions (FIG. 1). This process creates antibody diversity, the majority of which is encoded in the heavy chain complementarity determining region 3 (CDR3) (Rock et al. (1994) J. Exp. Med. 179:323; Xu and Davis (2000) Immunity 13:37). The complexity and dynamics of a single human immune repertoire have yet to be deeply probed, and the ability to track the repertoire dynamically has not been demonstrated in any organism.

SUMMARY

Characterizing the diversity and dynamics of the immune repertoire or "VDJ-ome" has significant implications in understanding the immune system, particularly in the context of personalized diagnostics and therapeutic discovery. Accordingly, the present invention is directed in part to methods and compositions that enable personalized clinical diagnostics and therapeutics utilizing the unique nucleic acid sequence information contained in an individual immune system. Toward this goal, high-throughput, high-resolution methods and compositions for profiling the antibody repertoire of a single individual are provided. For example, embodiments of the present invention include the use of high-throughput sequencing technology to dynamically track the nature and extent of antibodies produced by an individual as a result of an immune reaction, to clone full antibodies of paired light and heavy chains from millions of single cells in parallel, and to select for high-affinity antibodies against multiple antigens in a single reaction.

In certain exemplary embodiments, methods for determining an immune state of an individual are provided. The methods include the steps of obtaining nucleic acid sequences encoding lymphocyte receptors from the biological sample, and performing high-throughput sequencing of the amplified nucleic acid sequences to determine a plurality of sequences representing the immune state of the biological sample. In certain aspects, the biological sample is selected from the group consisting of blood, saliva, synovial fluid, cultured cells, a tissue section and a biopsy. In certain aspects, the biological sample is obtained from an individual. In other aspects, an immune state of the individual is determined. In still other aspects, the methods further include the step of amplifying the nucleic acid sequences encoding lymphocyte receptors prior to the step of high-throughput sequencing, optionally using primers specific to heavy chain or light chain nucleic acid sequences. In yet other aspects, the methods include the step of obtaining lymphocytes (e.g., T cells, B cells or a combination thereof) from the biological sample prior to the step of purifying. According to one aspect, an individual's T cell receptor usage is correlated with the individual's MHC type to diagnose certain diseases or conditions. In certain aspects, the nucleic acid sequences encode one or more of V regions (heavy chain or light chain), D regions (heavy chain or light chain), J regions (heavy chain or light chain) and combinations thereof. In other aspects, the nucleic acid sequences are DNA (e.g., genomic DNA) or RNA (e.g., mRNA). In still other aspects, the methods include the step of comparing the immune state of the individual to a control sample to diagnose a disease or a disorder such as, e.g., an infection, an autoimmune disorder, a cellular proliferative disorder and any combination thereof. In other aspects, the plurality of sequences includes at least one common nucleic acid sequence.

In certain exemplary embodiments, methods for monitoring the effect of an agent on an immune state of a biological sample are provided. The methods include the steps of isolating lymphocytes from the first biological sample, purifying a first set of nucleic acid sequences encoding lymphocyte receptors, performing high-throughput sequencing of the purified first set of nucleic acid sequences to provide a first reference library, contacting a second biological sample with an agent, isolating lymphocytes from the second biological sample, purifying a second set of nucleic acid sequences encoding lymphocyte receptors, performing high-throughput sequencing of the purified second set of nucleic acid sequences to provide a second reference library, and comparing the sequences of the first reference library and the second reference library to monitor the affect of an agent on an immune state of the biological sample. In certain aspects, the agent is selected from the group consisting of an antigen, a vaccine, a drug, a small molecule, a biologic and any combination thereof. In other aspects, the biological sample is selected from the group consisting of blood, saliva, synovial fluid, cultured cells, a tissue section and a biopsy. In other aspects, the biological sample is obtained from an individual. In still other aspects, an immune state of the individual is determined. In yet other aspects, the individual is afflicted with a disease or disorder selected from the group consisting of an infection, an autoimmune disorder, a cellular proliferative disorder and any combination thereof. In certain aspects, efficacy of the agent for treating a disease or a disorder is determined. In other aspects, a prognosis for treating a disease or a disorder is determined. In other aspects, the sequencing steps are performed simultaneously or at separate times. In certain aspects, multiple samples are obtained over a time course and, optionally, the steps of isolating, purifying and performing high-throughput sequencing are performed for each of the multiple samples obtained over the time course.

In certain exemplary embodiments, methods for monitoring an immune response of a biological sample are provided. The methods include the steps of obtaining a first biological sample at a first point in time, isolating lymphocytes from the first biological sample, purifying a first set of nucleic acid sequences encoding lymphocyte receptors, performing high-throughput sequencing of the purified first set of nucleic acid sequences to provide a first reference library, obtaining a second biological sample at a second point in time, isolating lymphocytes from the second biological sample, purifying a second set of nucleic acid sequences encoding lymphocyte receptors, performing high-throughput sequencing of the purified second set of nucleic acid sequences to provide a second reference library, and comparing the sequences of the first reference library and the second reference library to track an immune response in a biological sample. In certain aspects, the immune response is against an agent selected from the group consisting of an antigen, a vaccine, a drug, a small molecule, a biologic and any combination thereof. In other aspects, wherein the sequencing steps are performed simultaneously or at separate times. In yet other aspects, multiple samples are obtained over a time course and, optionally, the steps of isolating, purifying and performing high-throughput sequencing are performed for each of the multiple samples obtained over the time course. In still other aspects, a disease or disorder diagnosis is determined. In other aspects, the biological sample is selected from the group consisting of blood, saliva, synovial fluid, cultured cells, a tissue section and a biopsy. In still other aspects, the biological sample is obtained from an individual. In other aspects, the immune state of the individual is determined.

Further features and advantages of certain embodiments of the present invention will become more fully apparent in the following description of the embodiments and drawings thereof, and from the claims.

BRIEF DESCRIPTION OF THE DRAWINGS

The patent or application file contains at least one drawing executed in color. Copies of this patent or patent application publication with color drawing(s) will be provided by the Office upon request and payment of the necessary fee. The foregoing and other features and advantages of the present invention will be more fully understood from the following detailed description of illustrative embodiments taken in conjunction with the accompanying drawings in which:

(FIG. 2A) The number of unique clones (top) and corresponding reads (bottom) shared between two sequencing replicate runs (SR1 and SR2) and an independent technical replicate run (TR1). A small number of shared unique clones accounted for the majority of reads. (FIG. 2B) Day 1 scatter plot of SR1 versus TR1 of clone frequencies demonstrated strong correlation and reproducibility of the sampling approach described herein. (FIG. 2C) For multiple sample sizes, bootstrap distributions were sampled by computing the Pearson correlation between 50 pairs of independently drawn samples. This showed that $10^5$ reads were sufficient to achieve high correlations among independent samples. (FIG. 2D) Clone frequency abundance distributions from diversity replicate 1 (DR1) and all time points from SR1+SR2+TR1. Clone frequencies spanned multiple orders of magnitude and were power-law distributed with approximately inverse square scaling. (FIG. 2E) Unique sequences were observed and estimates of the expressed human heavy chain diversity in 1 mL blood samples were made using the Chao1 and ACE non-parametric estimators. Numbers were computed using clone counts (post-clustering, error-corrected) as well as unique CDR3 junction sequences (unprocessed, non-clustered) (top). Estimates of the total expressed human heavy chain diversity in blood using multiple non-parametric estimators and the Arstila method (Arstila et al. (1999) *Science* 286:958) (bottom).

(FIG. 3A) Distribution of all functional V and J segments observed in replicate runs across all time points shows highly non-uniform usage of gene segments. Circle sizes are proportional to read counts. (FIG. 3B) The CDR3 junction length distribution of all reads in SR1+SR2+TR1 (light) and all Ig heavy chain junctions in IMGT/LIGM (dark) showed large variability in CDR3 loop size. The sawtooth pattern reflected in-frame junctions. (FIG. 3C) Representative examples of CDR3 pseudo-spectratypes for various V-J combinations at multiple time points. The 16 amino acid peak was annotated in all spectratypes. Annotated numbers showed expansions of clones identified in FIG. 4B, which confirmed the utility of the spectratype method for identifying candidates of interest.

(FIG. 4A) The time series of all clones in SR1+SR2+TR1 revealed significant fluctuations of the repertoire through time. A handful of clones showed significantly higher expression, while the extent of the fluctuations is shown on a logarithmic scale (inset). The appearance of many gradually rising clones from day −14 to day 0 was due to the lack of sampling resolution among these time points. (FIG. 4B) Self-organizing map (SOM) clustering of clone time series, where each cluster was located at a constant map position, and colors represent clone expression levels. Groups of clusters with similar dynamic behavior were selected and the corresponding clones are plotted as time series. Time series were colored based on the most common isotype observed at the time of peak expression. Annotations referred to specific clones of interest corresponding to specific spectratype peaks in FIG. 3C. (FIG. 4C) Dynamics of the global isotype distribution indicated potential class switching. Thick lines represented the mean of 6 replicate runs (shown as thin lines) with one standard deviation. (FIG. 4D) Specific isotype distributions for selected annoted clones; stacked bar charts represented the isotype distribution at a given time point, while the black line represents the clone frequency time series. Numbers referred to maximum clone frequency, with the corresponding number of reads. Isotype color scheme is consistent among panels B, C, and D.

FIG. 6A FACS of coated beads. FIG. 6B depicts the fluorescent intensity of antibody candidates. FIG. 6C depicts where correct interaction between the antigen and antibody would result in a shift of the peaks during FACS analysis.

FIG. 7A depicts frequency change in QCM analysis. FIG. 7B depicts the binding affinity (with kD calculation) of the newly discovered antibody. FIG. 7C depicts the potential of the methods and compositions described herein for efficiently identifying antibody candidates.

(FIG. 12A) Chao 1, linear and logarithmic axis. (FIG. 12B) ACE, linear and logarithmic axis. (FIG. 12C) Number of unique sequences discovered, linear and logarithmic axis. (FIG. 12D) Estimator value versus number of reads. Lack of positive correlation indicates that estimator values are independent of the sample sizes, and thus are sampled sufficiently.

FIG. 13A depicts the first part of the clones. FIG. 13B depicts the rest part of the clones.

(FIG. 15A) Clustering of all clones into 100 clusters using the Euclidean distance metric. (FIG. 15B) Similar clustering of all clones observed in at least two time points. Curves represent cluster means; their thickness is proportional to cluster size.

(FIG. 19B) number of clusters obtained as a function of distance at which the linkage tree was cut. Both plots show rapid descents to 4.5 edits, followed by shoulders. This indicated 4.5 edits as the proper distance to clip the linkage tree to define clones.

(FIG. 20B) correlation between the standard deviation of the log(fold change) and the duration of the transition.

FIG. 21 depicts a first example alignment for hepatitis. Query: FXQ8H8O01DXEUI rank=0514859 x=1493.0 y=2520.0 length=408; Target: 155621|anti-hepatitis B virus (HBV) surface antigen (HBsAg) (human); Model: affine: local:dna2dna; Raw score: 1740; Query range: 8→398; Target range: 27→423; aln_summary: FXQ8H8O01DXEUI 408 8 398+155621 423 27 423+1740 390 372 95.38.

FIG. 22 depicts a second example alignment for hepatitis. Query: FX4D8HT02FMIIW rank=0345098 x=2189.0 y=2486.0 length=408; Target: 155621|anti-hepatitis B virus (HBV) surface antigen (HBsAg) (human); Model: affine: local:dna2dna; Raw score: 1743; Query range: 5→404; Target range: 24→423; aln_summary: FX4D8HT02FMIIW 408 5 404+155621 423 24 423+1743 399 371 92.

FIG. 23 depicts a junction-only alignment. Query: FXQ8H8O01CY52L [translate(1)]; Target: AR161172|anti-digoxin; Model: protein2dna:local; Raw score: 58; Query range: 0→9; Target range: 237→264; aln_summary: FXQ8H8O01CY52L 9 0 9. AR161172 282 237 264+58 9 9 100.00.

FIG. 24 depicts a full-read alignment. Query: FXQ8H8O01CY52L; Target: AR161172|anti-digoxin; Model: coding2coding; Raw score: 512; Query range: 73→355; Target range: 0→282; aln_summary: FXQ8H8O01CY52L 390 73 355+AR161172 282 0 282+ 512 94 93 98.94.

FIG. 26 shows a table depicting read sequencing distribution and analysis.

FIG. 38 schematically depicts a comparison of libraries against libraries for combinatorial selection of replicating antigen-antibody pairs (Bowley et al. (2009) *Proc. Natl. Acad. Sci. USA* 106(5):1380).

FIG. 54 depicts samples run on a pippin preparation.

FIG. 59 depicts gels showing individual primer testing.

FIGS. 66A-66B depict neutralization assays. FIG. 66A depicts FACS results. FIG. 66B depicts a graph of neutralization results.

FIG. 73 depicts gels pre-pippin extraction (left panel) and post-pippin extraction (right panel).

FIG. 76 depicts pippin test gels.

DETAILED DESCRIPTION

Figure 1:
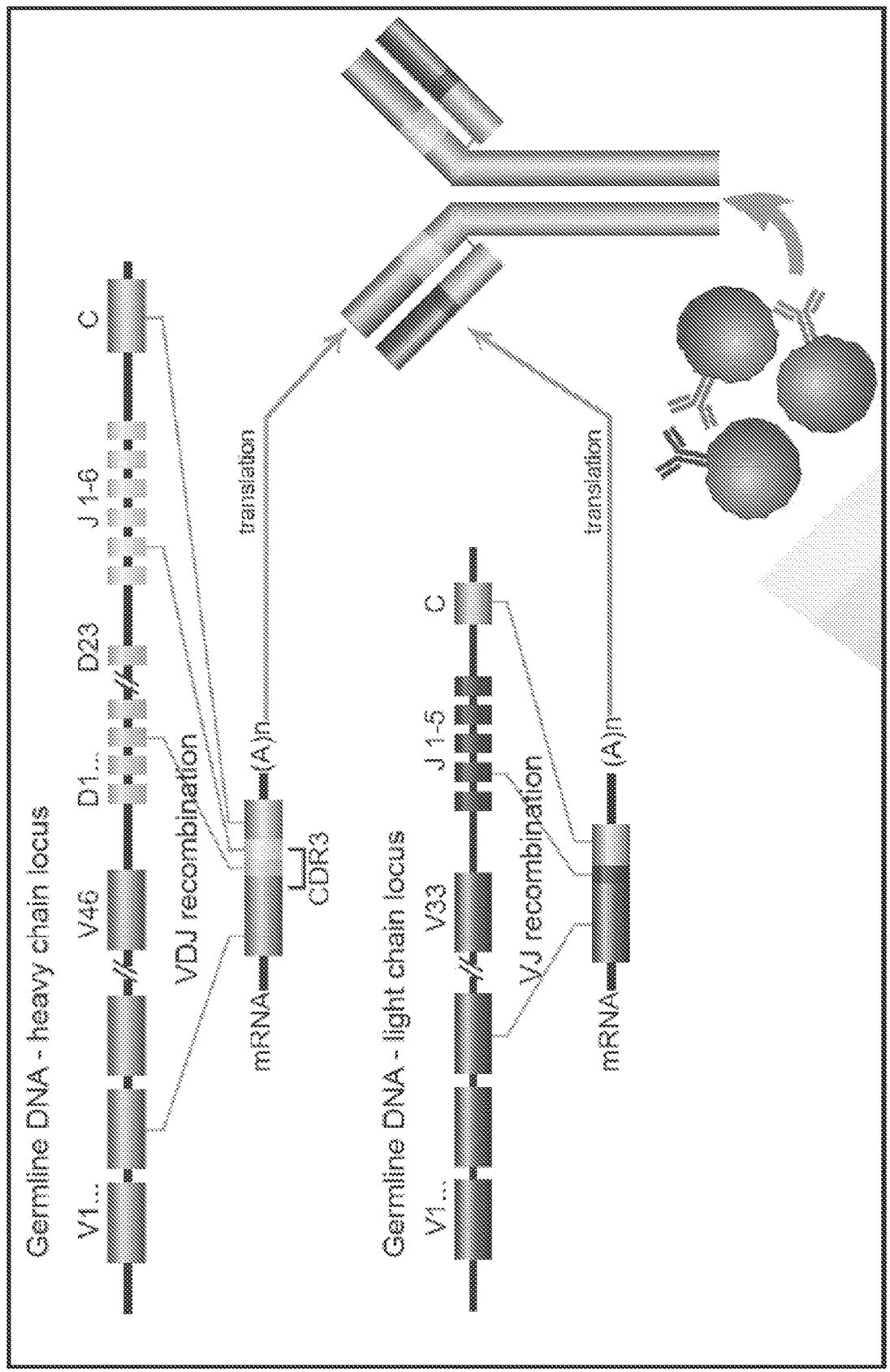
FIG. 1 depicts an overview of VDJ recombination and experimental design. An antibody contains a heavy chain and a light chain, where a unique V, D, and J segment are ligated together from a set of germline-encoded genes.

In certain exemplary embodiments, a set of technologies and analytical tools to efficiently survey the information recorded in the immune system, therefore enabling personalized clinical diagnostics and/or therapeutics, are provided. Certain aspects of the invention utilize next-generation sequencing in order to screen large amounts of antibody coding sequences from millions of single cells in a single reaction, in contrast to one cell per well assays typically performed in the art. Certain aspects of the invention are directed to sequencing and identifying portions of antibody coding sequences. Other aspects of the invention are directed to methods for expressing complex antibody libraries e.g., for use with functional screens and/or evolution analyses against a library of antigens or proteins. In certain aspects, the methods and compositions described herein can be used for biomarker identification for development of diagnostic or screening assays against infectious diseases, cellular proliferative disorders such as cancer, allergies and/or autoimmune disorders. In other aspects, the methods and compositions described herein can be used for the discovery and development of therapeutics, using, e.g., monoclonal, multi-pooled monoclonal, polyclonal, fragment, full and/or partial antibody sequence(s).

Certain additional exemplary embodiments utilize the characterization of the diversity and dynamics of the immune repertoire according to the methods described herein to identify vaccine targets and neutralizing antibodies. Such characterization on an individual level is useful in methods of diagnosis and/or prognosis of autoimmunity and/or allergic diseases. The characterization methods described herein are further useful to create databases of antigen/antibody affinities which are useful for predicting antibody specificity from sequence and for diagnosis of diseases or conditions characterized by certain antigen/ antibody affinities. The characterization methods described herein are still further useful in methods of determining transplant rejection and histo-incompatibility based on analysis of the components of the immune repertoire of an individual at a single point in time or at various points in time. Antibodies characterized according to the methods described herein are useful in methods to extract and identify certain immune effectors and antigens from a sample or subject.

In certain exemplary embodiments, methods for determining the genetic state of a plurality of individual immune cells (e.g., lymphocytes) at a given point in time (e.g., a "snapshot" of a collection of individual immune cells) are provided. In certain aspects, the identity of heavy and/or light chains (i.e., an immune receptor nucleic acid sequence) for each of a plurality of receptors will be ascertained at one or more given points in time. A collection of immune cell identities is also referred to herein as an "immune repertoire" or a "VDJ-ome."

Embodiments of the characterization methods described herein enable the identification, creation and/or use of rapid response antibodies in diagnostic, therapeutic or research methods. Such rapid response antibodies are expressed quickly, typically within hours, as a result of an immune challenge. According to aspects of the present invention, the rapid response antibodies can be characterized in their breadth of affinity against targets or antigens and their ability to stimulate other required host immune functions, Rapid response antibodies identified by the methods described herein can be used as an initial therapeutic agent to rapidly assist the immune system in responding to a disease or other condition while the immune system develops additional antibodies.

Embodiments of the present invention further include the use of human IGHV3-23-derived sequences or human IGHV1-69-derived sequences identified using high-throughput sequencing in functionally-used antibodies. For purposes of the present invention, derived sequences include the sequence itself, as well as any fragments or mutants thereof.

Major factors in the failure of monoclonal antibody development have been the lack of transition from animal model to human as well as limited capacity of screening sufficient amount of antibody candidates in order to allow efficient discovery of therapeutics. The methods and compositions described herein solve these issues by allowing screening of the immune repertoire or immune response directly from one or more humans, therefore producing antibody candidates that are fully human (i.e., not humanized antibodies), thus avoiding the risks of immunogenicity. In certain aspects, the methods and compositions described herein are not limited in their throughput, allowing screening of an unlimited amount of antibody coding sequences simultaneously, which would not be possible using classical immunological methods.

Figure 5:
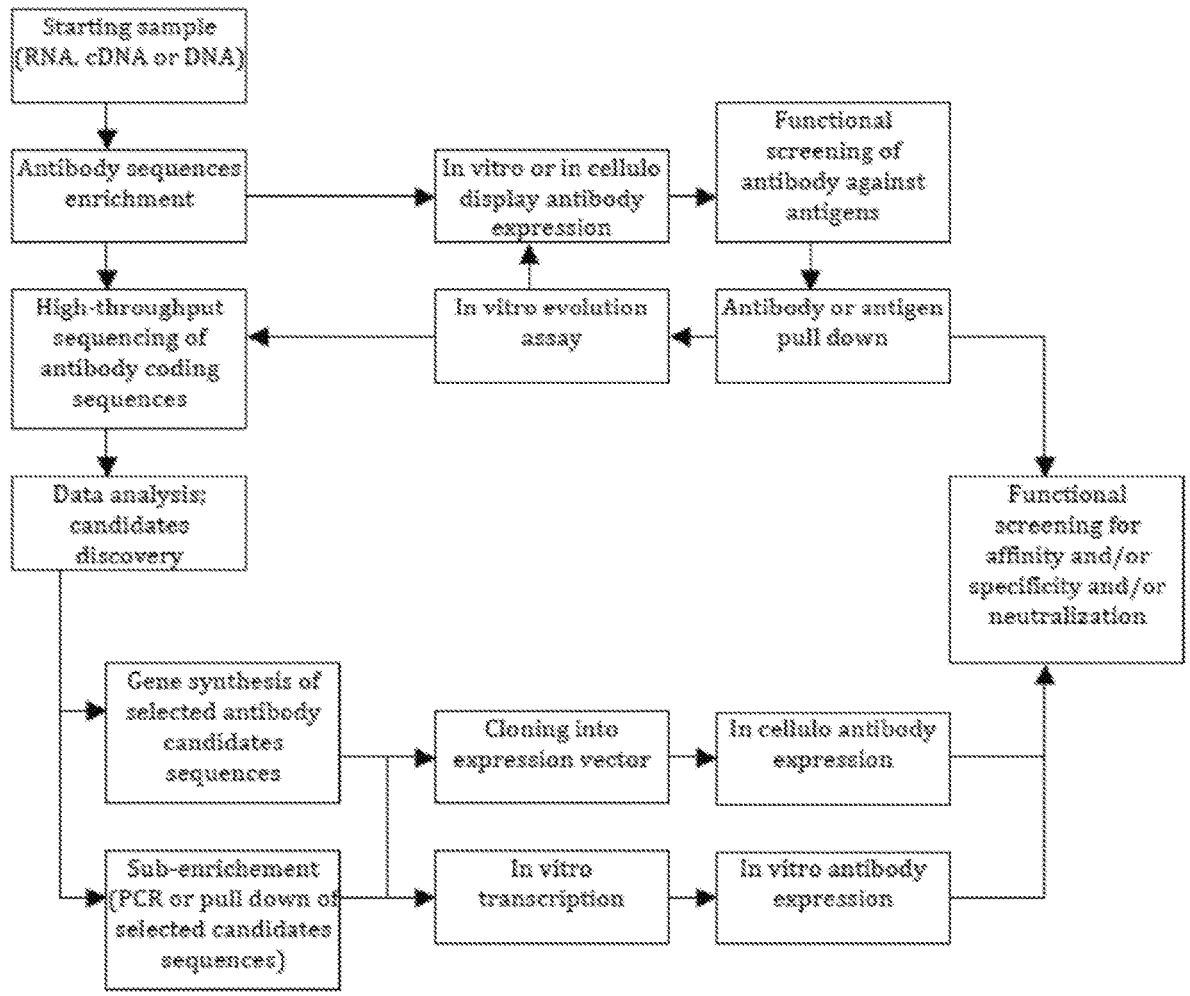
FIG. 5 schematically depicts high throughput immune sequencing and analysis of immune and antibody repertoire.
Figure 25:
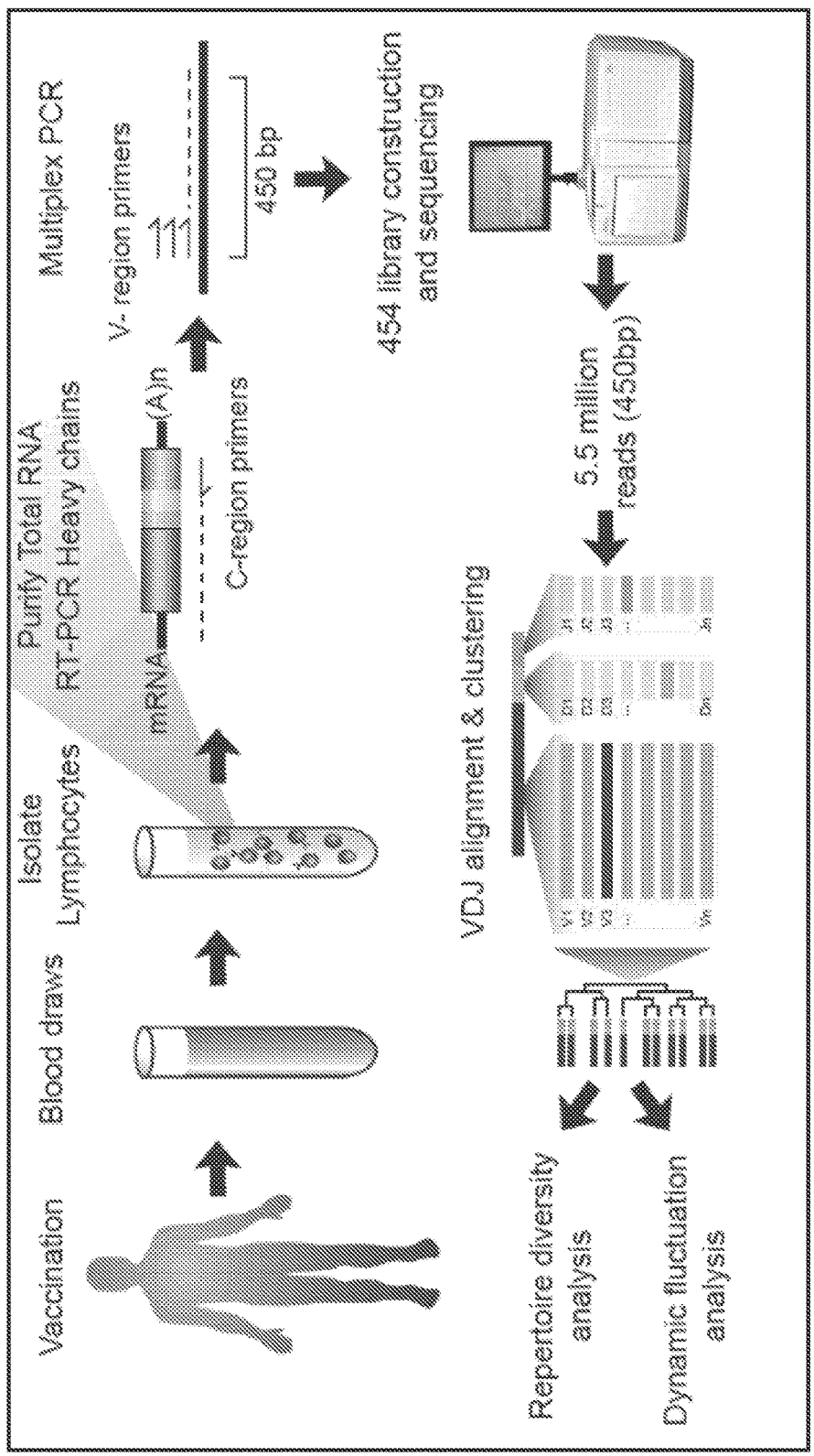
FIG. 25 depicts an overview of an experimental design according to certain aspects of the invention. Lymphocyte total RNA was extracted from blood samples collected at multiple time points following the vaccination of a human individual. A multiplex set of gene-specific primers were used to amplify the immunoglobulin heavy chain from B cell RNA, and processed into 454-compatible sequencing libraries. The sequences were aligned and clustered for repertoire analysis.

Since the methods and compositions described herein enable a large amount of sequences to be screened per sample, efficient investigation of the immune reaction in an individual can be performed. For example, the presence of one or more natural immune reaction(s) or specific antibody sequences made by the patient can be used as a diagnostic screen on a subject, e.g., a patient having a current or previous infection. The methods and compositions described herein allow for the instantaneous determination of antibody sequences in an individual at any point in time (e.g., because the RNA and/or DNA coding for the antibody protein is sequenced), instead of having to conduct complex and non-multiplexable protein sequence determination. An overview of certain methods described herein is shown in FIG. 5. An application of the methods according to certain aspects of the invention is depicted in FIG. 25.

According to certain aspects, methods of characterizing components of an immune response in an individual using high-throughput sequencing methods described herein enable selection of specific antibody sequences, including IgA isotype antibodies, useful in diagnosing a disease or condition, or therapeutically treating a disease or condition. The methods described herein enable methods of comparing immune reaction components in an individual at different points in time (time-series information) which is further useful in assigning function to identified antibodies. Such methods include the identification of antibodies useful in diagnostic or therapeutic methods, and include the identification of human-derived single domain antibodies (nanobodies) which are useful as affinity reagents, for example, as diagnostic or therapeutic biomarkers. The methods describe herein also allow the identification of human-derived sequences using high-throughput sequencing which can then be formatted into different affinity molecules, such as diabodies, nanobodies, doubles scFv and other components defined below as being an antibody.

According to alternate aspects, once the methods described herein are used to identify the components in an individual resulting from an immune response (referred to herein as an immune repertoire), the components can be cloned and expressed to create antibody libraries using either cell-free expression systems or cloning into expression vectors for in-cell expression. The antibodies can then be tested or screened for their ability to bind to antigens, their affinity and/or neutralization ability. In addition, once the methods described herein are used to identify the components in an individual resulting from an immune response, the components can be cloned followed by gene synthesis of selected antibodies based on functional information and then expressed to create antibody libraries using either cell-free expression systems or cloning into expression vectors for in-cell expression. The antibodies can then be tested or screened for their ability to bind to antigens, their affinity and/or neutralization ability. According to certain aspects, the antibodies resulting from the immune response that are identified by the methods described herein can be synthesized using parallel synthesis assembly from oligonucleotides or gene fragment derived standard oligonucleotide synthesis chemistry, from on chip printing synthesis, or any other method known to those skilled in the art.

According to an additional aspect, the antibodies identified by the high-throughput methods described herein are cloned directly into surface-display technologies including yeast, phage, bacterial, mammalian, ribosomal, mRNA display and the like and then screened for functional specificity or affinity or neutralization ability. An additional aspect of this embodiment includes the antibodies being cloned directly into surface-display technologies and then evolved by directed evolution approaches known to those skilled in the art and optionally, characterizing the directed evolution approaches at various points in time, at any step or at any cycle using high-throughput sequencing to identify the state of enrichment, level of diversity, etc. Such directed evolution methods can be performed with a single antigen, multiple antigens, or a large library of antigens in a single reaction.

As used herein, the terms "subject," "individual" and "host" are intended to include living organisms such as mammals. Examples of subjects and hosts include, but are not limited to, horses, cows, camels, sheep, pigs, goats, dogs, cats, rabbits, guinea pigs, rats, mice (e.g., humanized mice), gerbils, non-human primates (e.g., macaques), humans and the like, non-mammals, including, e.g., non-mammalian vertebrates, such as birds (e.g., chickens or ducks) fish (e.g., sharks) or frogs (e.g., *Xenopus*), and non-mammalian invertebrates, as well as transgenic species thereof.

In certain aspects, a subject refers to a single organism (e.g., human). In certain aspects, or a group of individuals composing a small cohort having either a common immune factor to study and/or disease, and/or a cohort of individuals without the disease (e.g., negative/normal control) are provided. A subject from whom samples are obtained can either be inflicted with a disease and/or disorder (e.g., one or more allergies, infections, cancers or autoimmune disorders or the like) or be injected with an agent (e.g., one or more of a vaccine, an antigen of interest, a drug, a small molecule, a biologic or the like) to stimulate an immune challenge, and be compared against a negative control subject which is not affected by the disease and/or not contacted with the agent.

In certain aspects, one or more biological samples are isolated from one or more subjects. As used herein, a "biological sample" may be a single cell or many cells. A biological sample may comprise a single cell type or a combination of two or more cell types. A biological sample further includes a collection of cells that perform a similar function such as those found, for example, in a tissue. As used herein, a tissue includes, but is not limited to, epithelial tissue (e.g., skin, the lining of glands, bowel, skin and organs such as the liver, lung, kidney), endothelium (e.g., the lining of blood and lymphatic vessels), mesothelium (e.g., the lining of pleural, peritoneal and pericardial spaces), mesenchyme (e.g., cells filling the spaces between the organs, including fat, muscle, bone, cartilage and tendon cells), blood cells (e.g., red and white blood cells), neurons, germ cells (e.g., spermatozoa, oocytes), amniotic fluid cells, placenta, stem cells and the like. A tissue sample includes microscopic samples as well as macroscopic samples. In certain aspects, a biological sample is peripheral blood. In other aspects, a biological sample is a fluid such as saliva, synovial fluid, or the like. In still other aspects, a biological sample is from one or more cell cultures, tissue sections and/or biopsies.

In certain exemplary embodiments, an immune cell (e.g., a lymphocyte) fraction is isolated from a biological sample using any technique known to one of ordinary skill in the art. In certain aspects, a lymphocyte fraction is isolated using ficoll centrifugation. In other aspects, a lymphocyte fraction is immobilized on a substrate or a support (e.g., a substrate that binds one or more of B cells and/or T cells). The support can be simple square grids, checkerboard (e.g., offset) grids, hexagonal arrays and the like. Suitable supports include, but are not limited to, slides, beads, chips, particles, strands, gels, sheets, tubing, spheres, containers, capillaries, pads, slices, films, culture dishes, plates (e.g., 96-well, 48-well, 24-well, 12-well, eight-well, six-well, four-well, single-well and the like), cell surfaces (e.g., *S. aureus* cells) and the like. In various embodiments, a solid support may be biological, non-biological, organic, inorganic, or any combination thereof.

In certain exemplary embodiments, beads and bead-based arrays are provided. As used herein, the term "bead" refers to a discrete particle that may be spherical (e.g., microspheres) or have an irregular shape. Beads may be as small as approximately 0.1 µm in diameter or as large approximately several millimeters in diameter. Beads may comprise a variety of materials including, but not limited to, paramagnetic materials, ceramic, plastic, glass, polystyrene, methylstyrene, acrylic polymers, titanium, latex, sepharose, cellulose, nylon and the like.

In accordance with certain examples, a support (e.g., a bead) may have functional groups attached to its surface which can be used to bind one or more reagents described herein to the bead. One or more reagents can be attached to a support (e.g., a bead) by hybridization, covalent attachment, magnetic attachment, affinity attachment and the like. For example, a support (e.g., a bead) can be coated with a secondary antibody for use with a primary antibody. In another example, a support (e.g., a bead) may be coated with glycidyl ether (epoxy) reactive groups and/or p-toluenesulphonyl (tosyl) reactive groups for use with a primary antibody. Beads coated with a variety of substrates are commercially available (Dynabeads, Invitrogen). Supports (e.g., beads) may also be functionalized using, for example, solid-phase chemistries known in the art (see, e.g., U.S. Pat. No. 5,919,523).

As used herein, the term "attach" refers to both covalent interactions and noncovalent interactions. A covalent interaction is a chemical linkage between two atoms or radicals formed by the sharing of a pair of electrons (i.e., a single bond), two pairs of electrons (i.e., a double bond) or three pairs of electrons (i.e., a triple bond). Covalent interactions are also known in the art as electron pair interactions or electron pair bonds. Noncovalent interactions include, but are not limited to, van der Waals interactions, hydrogen bonds, weak chemical bonds (i.e., via short-range noncovalent forces), hydrophobic interactions, ionic bonds and the like. A review of noncovalent interactions can be found in Alberts et al., in *Molecular Biology of the Cell,* 3d edition, Garland Publishing, 1994.

In certain exemplary embodiments, nucleic acid sequences (e.g., DNA and/or RNA) are extracted from immune cells (e.g., lymphocytes, e.g., B cells and/or T cells). In certain aspects, nucleic acid sequences (e.g., DNA and/or RNA) are extracted from one or more enriched fractions immune cells (e.g., lymphocytes, e.g., B cells and/or T cells). In other aspects, nucleic acid sequences (e.g., DNA and/or RNA) are extracted from samples that have not been enriched for immune cells. In certain aspects, specific subsets of cell populations are preliminarily enriched, e.g., using FACS or paramagnetic beads, therefore allowing enrichment of a memory B cell versus plasma cell fraction, which can be useful to increase the quality of the data for downstream use, e.g., for use in prognosing, diagnosing and the like. In certain aspects, at least 25, 50, 100, 200, 300, 400, 500, 600, 700, 800, 900, 1,000, 2,000, 3,000, 4,000, 5,000, 6,000, 7,000, 8,000, 9,000, 10,000, 15,000, 20,000, 25,000, 30,000, 35,000, 40,000, 45,000, 50,000, 55,000, 60,000, 65,000, 70,000, 75,000, 80,000, 85,000, 90,000, 95,000, 100,000, 150,000, 200,000, 250,000, 300,000, 450, 000, 500,000, 550,000, 600,000, 650,000, 700,000, 750,000, 800,000, 850,000, 900,000, 950,000, 1,000,000, 1,500,000, 2,000,000, 2,500,000, 3,000,000, 3,500,000, 4,000,000, 4,500,000, 5,000,000, 5,500,000, 6,000,000, 6,500,000, 7,000,000, 7,500,000, 8,000,000, 8,500,000, 9,000,000, 9,500,000, 10,000,000, 20,000,000, 30,000,000, 40,000, 000, 50,000,000, 60,000,000, 70,000,000, 80,000,000, 90,000,000, 100,000,000, 200,000,000, 300,000,000, 400, 000,000, 500,000,000, 600,000,000, 700,000,000, 800,000, 000, 900,000,000, 1,000,000,000, 2,000,000,000, 3,000, 000,000, 4,000,000,000, 5,000,000,000, 6,000,000,000, 7,000,000,000, 8,000,000,000, 9,000,000,000, 10,000,000, 000, 15,000,000,000, 20,000,000,000, 30,000,000,000, 40,000,000,000, 50,000,000,000, 60,000,000,000, 70,000,000,000, 80,000,000,000, 90,000,000,000, 100,000,000,000, 200,000,000,000, 300,000,000,000, 400,000,000,000, 500,000,000,000, 600,000,000,000, 700,000,000,000, 800,000,000,000, 900,000,000,000, 1,000,000,000,000, 2,000,000,000,000, 3,000,000,000,000, 4,000,000,000,000, 5,000,000,000,000, 6,000,000,000,000, 7,000,000,000,000, 8,000,000,000,000, 9,000,000,000,000, 10,000,000,000,000 or more different nucleic acid sequences (e.g., DNA (e.g., genomic) and/or RNA (e.g., mRNA)) or any values in between and/or range(s) defined by the above numbers or ranges in between or overlapping are extracted from immune cells.

In certain exemplary embodiments, non-specific primers, degenerate primers, or specific primers (e.g., primers that hybridize to J and/or C-regions for the heavy and/or light chains of B or T cells) are used to amplify nucleic acid sequences (e.g., DNA and/or RNA). In certain aspects, cDNA (if using mRNA) or DNA (if using genomic DNA) is amplified by PCR using primer sets that hybridize to the antibody coding gene of the heavy and light chains of B cells and/or T cells. In certain aspects, the one set of primers hybridizes to V regions and another set of primers hybridizes to the C regions. In other aspects, certain primer sets hybridize to other locations on the V region or upstream in the leaders region (which is favorable for RNA sample, allowing amplification of properly spliced RNA converted cDNA and not of DNA), while other primer sets hybridize downstream of the C-region, and/or to the J region.

In certain aspects, a segment spanning the CDR3 region is amplified using primers that hybridize to either side of the CDR3 region. The further apart the primers are on the VDJ segments, the more antibody sequence will be recovered and sequenced, thus adding additional immune state information (e.g., information regarding CDR1, CDR2 and CDR3 regions and/or hypermutation(s) across the antibody coding segments). Because there are many V, D, J and C regions, degenerate primers can be designed that hybridize to many segments, or a single primer sequence can be used for each of these segments in order to amplify representatively the repertoire of the subject (e.g., via multiplex PCR). In other aspects, amplification of a very specific unique set of VDJ combination is performed using one set of primers. In certain aspects, pull down-assays can be used to enrich immune cell nucleic acid sequences (e.g., RNA and/or DNA). In certain aspects, a pull-down assay using either RNA or DNA probe complementary to some part of the VDJ segments of interests is performed. In certain aspects, labels are used to enrich immune cell nucleic acid sequences (e.g., RNA and/or DNA) (e.g., fluorophores for FACS sorting, biotin with streptavidin, covalently coated beads, and the like). Targeted enrichment strategies can also be used such as the use of molecular inversion probes, or by the use of array hybridization.

As used herein, the term "hybridization" refers to the process in which two single-stranded polynucleotides bind non-covalently to form a stable double-stranded polynucleotide. The term "hybridization" may also refer to triple-stranded hybridization. The resulting (usually) double-stranded polynucleotide is a "hybrid" or "duplex." "Hybridization conditions" will typically include salt concentrations of less than about 1 M, more usually less than about 500 mM and even more usually less than about 200 mM. Hybridization temperatures can be as low as 5° C., but are typically greater than 22° C., more typically greater than about 30° C., and often in excess of about 37° C. Hybridizations are usually performed under stringent conditions, i.e., conditions under which a probe will hybridize to its target subsequence. Stringent conditions are sequence-dependent and are different in different circumstances. Longer fragments may require higher hybridization temperatures for specific hybridization. As other factors may affect the stringency of hybridization, including base composition and length of the complementary strands, presence of organic solvents and extent of base mismatching, the combination of parameters is more important than the absolute measure of any one alone. Generally, stringent conditions are selected to be about 5° C. lower than the $T_m$ for the specific sequence at s defined ionic strength and pH. Exemplary stringent conditions include salt concentration of at least 0.01 M to no more than 1 M Na ion concentration (or other salts) at a pH 7.0 to 8.3 and a temperature of at least 25° C. For example, conditions of SXSSPE (750 mM NaCl, 50 mM Na phosphate, 5 mM EDTA, pH 7.4) and a temperature of 25-30° C. are suitable for allele-specific probe hybridizations. For stringent conditions, see for example, Sambrook, Fritsche and Maniatis, *Molecular Cloning A Laboratory Manual,* 2nd Ed. Cold Spring Harbor Press (1989) and Anderson *Nucleic Acid Hybridization,* $1^{st}$ Ed., BIOS Scientific Publishers Limited (1999). "Hybridizing specifically to" or "specifically hybridizing to" or like expressions refer to the binding, duplexing, or hybridizing of a molecule substantially to or only to a particular nucleotide sequence or sequences under stringent conditions when that sequence is present in a complex mixture (e.g., total cellular) DNA or RNA.

In certain exemplary embodiments, methods for amplifying nucleic acid sequences are provided. Exemplary methods for amplifying nucleic acids include the polymerase chain reaction (PCR) (see, e.g., Mullis et al. (1986) *Cold Spring Harb. Symp. Quant. Biol.* 51 Pt 1:263 and Cleary et al. (2004) *Nature Methods* 1:241; and U.S. Pat. Nos. 4,683,195 and 4,683,202), anchor PCR, RACE PCR, ligation chain reaction (LCR) (see, e.g., Landegran et al. (1988) *Science* 241:1077-1080; and Nakazawa et al. (1994) *Proc. Natl. Acad. Sci. U.S.A.* 91:360-364), self sustained sequence replication (Guatelli et al. (1990) *Proc. Natl. Acad. Sci. U.S.A.* 87:1874), transcriptional amplification system (Kwoh et al. (1989) *Proc. Natl. Acad. Sci. U.S.A.* 86:1173), Q-Beta Replicase (Lizardi et al. (1988) *BioTechnology* 6:1197), recursive PCR (Jaffe et al. (2000) *J. Biol. Chem.* 275:2619; and Williams et al. (2002) *J. Biol. Chem.* 277:7790), the amplification methods described in U.S. Pat. Nos. 6,391,544, 6,365,375, 6,294,323, 6,261,797, 6,124,090 and 5,612,199, isothermal amplification (e.g., rolling circle amplification (RCA), hyperbranched rolling circle amplification (HRCA), strand displacement amplification (SDA), helicase-dependent amplification (HDA), PWGA) or any other nucleic acid amplification method using techniques well known to those of skill in the art.

"Polymerase chain reaction," or "PCR," refers to a reaction for the in vitro amplification of specific DNA sequences by the simultaneous primer extension of complementary strands of DNA. In other words, PCR is a reaction for making multiple copies or replicates of a target nucleic acid flanked by primer binding sites, such reaction comprising one or more repetitions of the following steps: (i) denaturing the target nucleic acid, (ii) annealing primers to the primer binding sites, and (iii) extending the primers by a nucleic acid polymerase in the presence of nucleoside triphosphates. Usually, the reaction is cycled through different temperatures optimized for each step in a thermal cycler instrument. Particular temperatures, durations at each step, and rates of change between steps depend on many factors well-known to those of ordinary skill in the art, e.g., exemplified by the references: McPherson et al., editors, *PCR: A Practical Approach and PCR2: A Practical Approach* (IRL Press, Oxford, 1991 and 1995, respectively). For example, in a conventional PCR using Taq DNA polymerase, a double stranded target nucleic acid may be denatured at a temperature greater than 90° C., primers annealed at a temperature in the range 50-75° C., and primers extended at a temperature in the range 72-78° C.

The term "PCR" encompasses derivative forms of the reaction, including but not limited to, RT-PCR, real-time PCR, nested PCR, quantitative PCR, multiplexed PCR, assembly PCR and the like. Reaction volumes range from a few hundred nanoliters, e.g., 200 nL, to a few hundred microliters, e.g., 200 microliters. "Reverse transcription PCR," or "RT-PCR," means a PCR that is preceded by a reverse transcription reaction that converts a target RNA to a complementary single stranded DNA, which is then amplified, e.g., Tecott et al., U.S. Pat. No. 5,168,038. "Real-time PCR" means a PCR for which the amount of reaction product, i.e., amplicon, is monitored as the reaction proceeds. There are many forms of real-time PCR that differ mainly in the detection chemistries used for monitoring the reaction product, e.g., Gelfand et al., U.S. Pat. No. 5,210,015 ("Taqman"); Wittwer et al., U.S. Pat. Nos. 6,174,670 and 6,569,627 (intercalating dyes); Tyagi et al., U.S. Pat. No. 5,925,517 (molecular beacons). Detection chemistries for real-time PCR are reviewed in Mackay et al., *Nucleic Acids Research*, 30:1292-1305 (2002). "Nested PCR" means a two-stage PCR wherein the amplicon of a first PCR becomes the sample for a second PCR using a new set of primers, at least one of which binds to an interior location of the first amplicon. As used herein, "initial primers" in reference to a nested amplification reaction mean the primers used to generate a first amplicon, and "secondary primers" mean the one or more primers used to generate a second, or nested, amplicon. "Multiplexed PCR" means a PCR wherein multiple target sequences (or a single target sequence and one or more reference sequences) are simultaneously carried out in the same reaction mixture, e.g. Bernard et al. (1999) *Anal. Biochem.*, 273:221-228 (two-color real-time PCR). Usually, distinct sets of primers are employed for each sequence being amplified. "Quantitative PCR" means a PCR designed to measure the abundance of one or more specific target sequences in a sample or specimen. Techniques for quantitative PCR are well-known to those of ordinary skill in the art, as exemplified in the following references: Freeman et al., *Biotechniques*, 26:112-126 (1999); Becker-Andre et al., *Nucleic Acids Research*, 17:9437-9447 (1989); Zimmerman et al., *Biotechniques*, 21:268-279 (1996); Diviacco et al., *Gene*, 122:3013-3020 (1992); Becker-Andre et al., *Nucleic Acids Research*, 17:9437-9446 (1989); and the like.

In certain exemplary embodiments, methods of determining the sequence identities of nucleic acid sequences are provided. Determination of the sequence of a nucleic acid sequence of interest (e.g., immune cell nucleic acid sequences) can be performed using variety of sequencing methods known in the art including, but not limited to, sequencing by hybridization (SBH), sequencing by ligation (SBL), quantitative incremental fluorescent nucleotide addition sequencing (QIFNAS), stepwise ligation and cleavage, fluorescence resonance energy transfer (FRET), molecular beacons, TaqMan reporter probe digestion, pyrosequencing, fluorescent in situ sequencing (FISSEQ), FISSEQ beads (U.S. Pat. No. 7,425,431), wobble sequencing (PCT/US05/27695), multiplex sequencing (U.S. Ser. No. 12/027,039, filed Feb. 6, 2008; Porreca et al (2007) *Nat. Methods* 4:931), polymerized colony (POLONY) sequencing (U.S. Pat. Nos. 6,432,360, 6,485,944 and 6,511,803, and PCT/US05/06425); nanogrid rolling circle sequencing (ROLONY) (U.S. Ser. No. 12/120,541, filed May 14, 2008), allele-specific oligo ligation assays (e.g., oligo ligation assay (OLA), single template molecule OLA using a ligated linear probe and a rolling circle amplification (RCA) readout, ligated padlock probes, and/or single template molecule OLA using a ligated circular padlock probe and a rolling circle amplification (RCA) readout) and the like. High-throughput sequencing methods, e.g., on cyclic array sequencing using platforms such as Roche 454, Illumina Solexa, ABI-SOLiD, ION Torrents, Complete Genomics, Pacific Bioscience, Helicos, Polonator platforms (Worldwide Web Site: Polonator.org), and the like, can also be utilized. High-throughput sequencing methods are described in U.S. Ser. No. 61/162,913, filed Mar. 24, 2009. A variety of light-based sequencing technologies are known in the art (Landegren et al. (1998) *Genome Res.* 8:769-76; Kwok (2000) *Pharmocogenomics* 1:95-100; and Shi (2001) *Clin. Chem.* 47:164-172).

In certain exemplary embodiments, enriched VDJ segments are transformed so that they can be compatible with next-generation high-throughput sequencing technologies. In certain aspects, compatible sequencing adapters are ligated or added using PCR and primers with overhang on the VDJ segments. In other aspects, the adapter is bar-coded so that many samples can be pooled together and sequenced on a single instrument run. According to one aspect, samples belonging to the same research study are processed as much as possible in the same manner at the same time to achieve high degree of correlation and maximize quality of the data obtained. Ideally, read length should be sufficient to enable the identification of each V, D, and J, segment originated from each unique molecule. Use of bar-coding can also be used to achieve remapping of short segments to their original starting molecule (PMID: 20081835).

In certain exemplary embodiments, sequencing data are aligned against known or expected V, D and J segments using personal database, NCBI databases, IMGT databases or the like to aid in the identification of V, D and J segments. In this manner, V and J segments can be identified, allowing the extraction of the central junctional region of the V with D and D with J segments, composing the CDR3 region. All the sequencing reads (e.g., millions), can be binned according to their V and J usage, and clustered for their unique CDR3 using various clustering algorithms described herein. This will allow grouping of highly similar VDJ segments into VDJ clones, which likely encode for the same or a highly similar antibody. Each read (or unique VDJ segments sequenced) and/or each VDJ clone (or highly similar VDJ segments from a same cluster group) can then be analyzed for biological relevancy (e.g., for a disease, disorder and/or immune response).

Figure 4A:
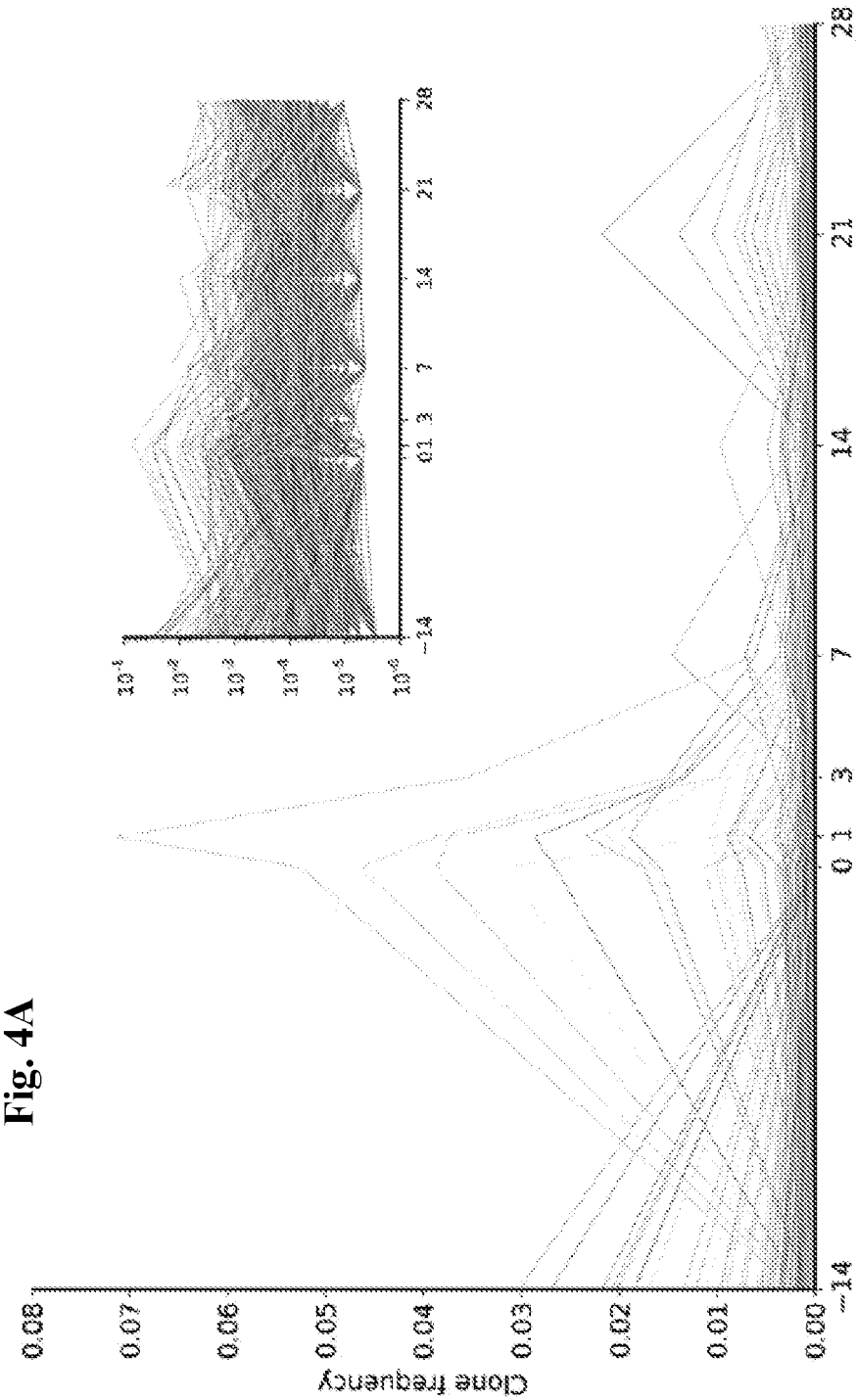
FIGS. 4A-4D depict dynamic repertoire analysis.
Figure 4B:
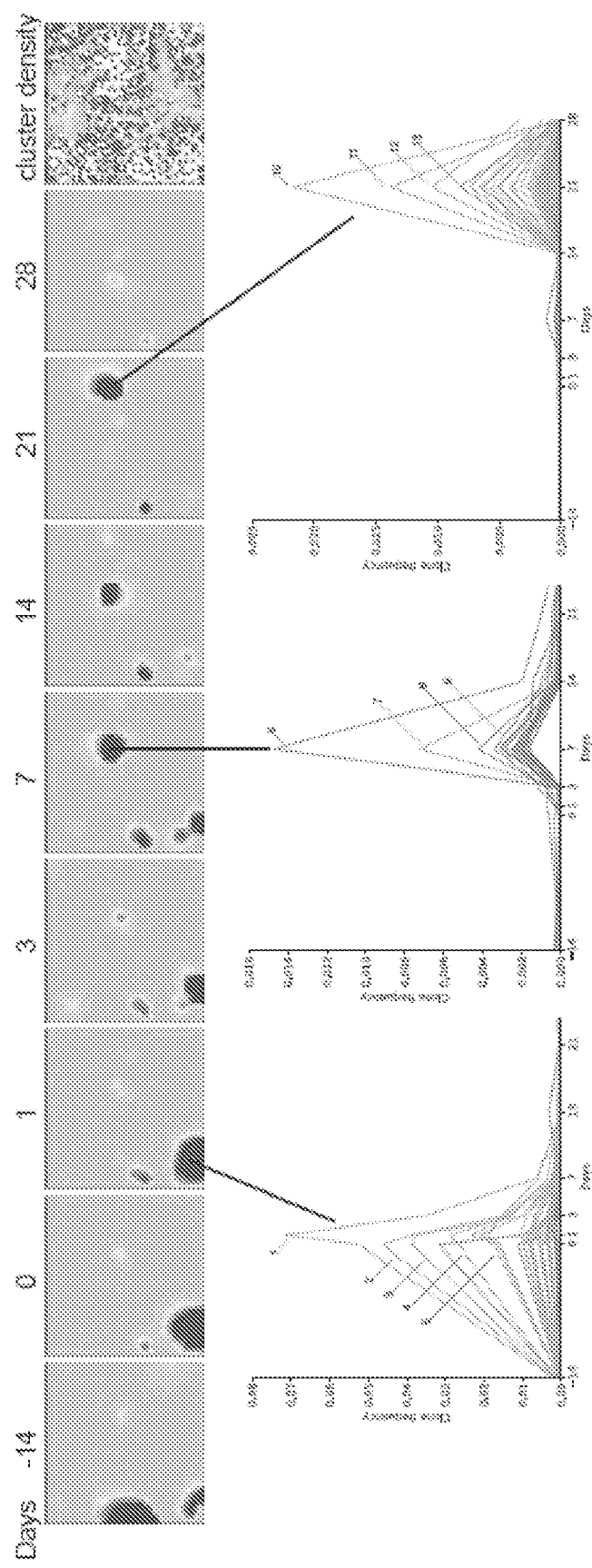

Clone frequency can be plotted to examine reproducibility among experiments and/or to identify unique or relevant VDJ clones of different expression across different samples or cohorts. In the case of time course study, clone frequency can be plotted in a time course plot to identify the dynamic of expression of the antibody expressed in the subject (FIG. 4A). This allows for zoning on potential antibody sequences that are part of the immune response against the immune challenge that represents potential therapeutic or relevant biomarkers against the immune challenge (FIG. 4B). In the case of static analysis research for a disease (for example various samples from a cohort having a disease against a cohort not having the disease), comparative clustering of which sequence has been made and at which frequency in one cohort against another can reveal therapeutics or biomarker candidates. Further study of the divergence of an antibody sequence (such as somatic hyper-mutation accumulation) of VDJ reads or clones can also be used to reveal potential candidates of interest as well as other biological information that can be derived from the data such as isotype distribution of the antibodies (such as IgA, IgD, IgE, IgG and IgM), which can be used to focus on a specific type of antibody or pseudo-spectratyping, for example.

In certain exemplary embodiments, methods of determining and/or analyzing an immune state of an individual include the step obtaining immune cells from a biological sample are provided. As used herein, the term "immune cell" is intended to include, but is not limited to, a cell that is of hematopoietic origin and that plays a role in the immune response. Immune cells include, but are not limited to, lymphocytes, such as B cells and T cells; natural killer cells; and myeloid cells, such as monocytes, macrophages, eosinophils, mast cells, basophils, and granulocytes.

The term "antigen presenting cell" includes professional antigen presenting cells (e.g., B lymphocytes, monocytes, dendritic cells, and Langerhans cells) as well as other antigen presenting cells (e.g., keratinocytes, endothelial cells, astrocytes, fibroblasts, and oligodendrocytes).

As used herein, the term "immune response" includes, but is not limited to, T cell-mediated and/or B cell-mediated immune responses that are influenced by modulation of T cell costimulation. Exemplary immune responses include B cell responses (e.g., antibody production) T cell responses (e.g., cytokine production, and cellular cytotoxicity) and activation of cytokine responsive cells, e.g., macrophages. As used herein, the term "down-modulation" with reference to the immune response includes a diminution in any one or more immune responses, while the term "up-modulation" with reference to the immune response includes an increase in any one or more immune responses. It will be understood that up-modulation of one type of immune response may lead to a corresponding down-modulation in another type of immune response. For example, up-modulation of the production of certain cytokines (e.g., IL-10) can lead to down-modulation of cellular immune responses.

As used herein, the term "antibody" refers to immunoglobulin molecules and immunologically active portions of immunoglobulin molecules, i.e., molecules that contain an antigen binding site which specifically binds (immunoreacts with) an antigen. The term "antibody" is understood in its full general term to include components in the immune chain including an antibody, immunoglobulin, B cell receptor, antibody heavy chain, antibody light chain, T cell receptor (TCR), TCR alpha chain, TCR beta chain, TCR gamma chain, TCR delta chain or any variations or modification of antibody chains and further including scFV, Fab, Fab2, Fab3, Bis-scFv, minibody, triabody, diabody, tetrabody, nanobody and any and all various isotype variants of antibodies including IgG, IgA, IgD, IgM and IgE. Examples of immunologically active portions of immunoglobulin molecules include F(ab) and F(ab')2 fragments which can be generated by treating the antibody with an enzyme such as pepsin. In certain exemplary embodiments, polyclonal and monoclonal antibodies are provided that bind one or more immune cell antigens. The terms "monoclonal antibody" and "monoclonal antibody composition," as used herein, refer to a population of antibody molecules that contains only one species of an antigen binding site capable of immunoreacting with a particular epitope of an immune cell antigen. A monoclonal antibody composition thus typically displays a single binding affinity for a particular immune cell antigen with which it immunoreacts.

In certain exemplary embodiments, screening assays for identifying immune system modulators, i.e., candidate or test compounds or agents (e.g., antibodies, peptides, cyclic peptides, peptidomimetics, small molecules, small organic molecules, or other drugs) are provided. The test compounds described herein can be obtained using any of the numerous approaches in combinatorial library methods known in the art, including: biological libraries; spatially addressable parallel solid phase or solution phase libraries; synthetic library methods requiring deconvolution; the "one-bead one-compound" library method; and synthetic library methods using affinity chromatography selection. The biological library approach is limited to peptide libraries, while the other four approaches are applicable to peptide, non-peptide oligomer or small molecule libraries of compounds (Lam, K. S. (1997) *Anticancer Drug Des.* 12:145).

In certain exemplary embodiments, one or more agents or pharmaceutically acceptable salts thereof described herein are provided in a pharmaceutically acceptable carrier. As used herein, the language "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Pharmaceutically acceptable carriers and their formulations are known to those skilled in the art and described, for example, in Remington's Pharmaceutical Sciences, (19th edition), ed. A. Gennaro, 1995, Mack Publishing Company, Easton, PA.

In certain exemplary embodiments, pharmaceutical formulations of one or more agents described herein or pharmaceutically acceptable salts thereof, are administered by intravenous injection, intraperitoneal injection, oral administration or by other parenteral routes (e.g. intradermal, subcutaneous, oral (e.g., inhalation), transdermal (topical), transmucosal, and rectal administration), or by intrathecal and intraventricular injections into the CNS, in an admixture with a pharmaceutically acceptable carrier adapted for the route of administration.

Solutions or suspensions used for parenteral, intradermal, subcutaneous or central nervous system application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

Methods well known in the art for making formulations are found, for example, in Remington's Pharmaceutical Sciences (19th edition), ed. A. Gennaro, 1995, Mack Publishing Company, Easton, PA. Compositions intended for oral use may be prepared in solid or liquid forms according to any method known to the art for the manufacture of pharmaceutical compositions. The compositions may optionally contain sweetening, flavoring, coloring, perfuming, and/or preserving agents in order to provide a more palatable preparation. Solid dosage forms for oral administration include capsules, tablets, pills, powders, and granules. In such solid forms, the active compound is admixed with at least one inert pharmaceutically acceptable carrier or excipient. These may include, for example, inert diluents, such as calcium carbonate, sodium carbonate, lactose, sucrose, starch, calcium phosphate, sodium phosphate, or kaolin. Binding agents, buffering agents, and/or lubricating agents (e.g., magnesium stearate) may also be used. Tablets and pills can additionally be prepared with enteric coatings.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, CREMOPHOR EL™ (BASF, Parsippany, NJ) or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In certain exemplary embodiments, isotonic agents, for example, sugars, polyalcohols such as mannitol, sorbitol, and/or sodium chloride, will be included in the composition. Prolonged absorption of the injectable compositions can be brought about by including in the composition an agent which delays absorption, for example, aluminum monostearate and gelatin.

Sterile, injectable solutions can be prepared by incorporating agents described herein or pharmaceutically acceptable salts thereof in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, exemplary methods of preparation are vacuum drying and freeze-drying which yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: A binder such as microcrystalline cellulose, gum tragacanth or gelatin; an excipient such as starch or lactose, a disintegrating agent such as alginic, acid, Primogel, or corn starch; a lubricant such as magnesium stearate or Sterotes; a glidant: such as colloidal silicon dioxide; a sweetening agent such as sucrose or saccharin; or a flavoring agent such as peppermint, methyl salicylate, or orange flavoring.

In one embodiment, one or more agents described herein or pharmaceutically acceptable salts thereof are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These may be prepared according to methods known to those skilled in the art, for example, as described in U.S. Pat. No. 4,522,811.

Nasal compositions generally include nasal sprays and inhalants. Nasal sprays and inhalants can contain one or more active components and excipients such as preservatives, viscosity modifiers, emulsifiers, buffering agents and the like. Nasal sprays may be applied to the nasal cavity for local and/or systemic use. Nasal sprays may be dispensed by a non-pressurized dispenser suitable for delivery of a metered dose of the active component. Nasal inhalants are intended for delivery to the lungs by oral inhalation for local and/or systemic use. Nasal inhalants may be dispensed by a closed container system for delivery of a metered dose of one or more active components.

In one embodiment, nasal inhalants are used with an aerosol. This is accomplished by preparing an aqueous aerosol, liposomal preparation or solid particles containing the compound. A non-aqueous (e.g., fluorocarbon propellant) suspension could be used. Sonic nebulizers may be used to minimize exposing the agent to shear, which can result in degradation of the compound.

Ordinarily, an aqueous aerosol is made by formulating an aqueous solution or suspension of the agent together with conventional pharmaceutically acceptable carriers and stabilizers. The carriers and stabilizers vary with the requirements of the particular compound, but typically include nonionic surfactants (Tweens, Pluronics, or polyethylene glycol), innocuous proteins like serum albumin, sorbitan esters, oleic acid, lecithin, amino acids such as glycine, buffers, salts, sugars or sugar alcohols. Aerosols generally are prepared from isotonic solutions.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

One or more agents described herein or pharmaceutically acceptable salts thereof can also be prepared in the form of suppositories (e.g., with conventional suppository bases such as cocoa butter and other glycerides) or retention enemas for rectal delivery.

In one embodiment, one or more agents described herein or pharmaceutically acceptable salts thereof are prepared with carriers that will protect them against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral, parenteral or CNS direct delivery compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals.

Toxicity and therapeutic efficacy of one or more agents described herein or pharmaceutically acceptable salts thereof can be determined by standard pharmaceutical procedures in cell cultures, experimental animals or in an individual, e.g., in a human. The dose ratio between toxic and therapeutic effects is the therapeutic index and it can be expressed as the ratio LD50/ED50. Compounds which exhibit large therapeutic indices are preferred. While compounds that exhibit toxic side effects may be used, care should be taken to design a delivery system that targets such compounds to the site of affected tissue in order to minimize potential damage to uninfected cells and, thereby, reduce side effects.

Data obtained from monitoring the immune state of an individual can be used in formulating a range of dosage for use in the individual (e.g., personalized medicine). The dosage typically will lie within a range of circulating concentrations that include the ED50 with little or no toxicity. The dosage may vary within this range depending upon the dosage form employed and the route of administration utilized. For any compound used in the method of the invention, the therapeutically effective dose can be estimated initially from cell culture assays. A dose may be formulated in animal models to achieve a circulating plasma concentration range that includes the IC50 (i.e., the concentration of the test compound which achieves a half-maximal inhibition of symptoms) as determined in cell culture. Such information can be used to more accurately determine useful doses in humans. Levels in plasma may be measured, for example, by high performance liquid chromatography.

Monitoring the influence of a pharmaceutical composition on the immune response of an individual can be applied not only in basic drug screening, but also in clinical trials. For example, the effectiveness of a pharmaceutical composition determined by a screening assay as described herein to alter the immune response of a subject can be monitored in clinical trials.

In certain exemplary embodiments, a method for monitoring the effectiveness of treatment of a subject with an agent described herein including the steps of (i) obtaining a pre-administration sample from a subject prior to administration of the agent; (ii) detecting the level of expression of one or more immune system nucleic acid sequences in the preadministration sample; (iii) obtaining one or more post-administration samples from the subject; (iv) detecting the level of one or more immune system nucleic acid sequences in the post-administration samples; (v) comparing the level of expression of one or more immune system nucleic acid sequences in the pre-administration sample with the level of expression of one or more immune system nucleic acid sequences in the post administration sample or samples; and (vi) altering the administration of the agent to the subject accordingly, is provided. According to such an embodiment, altered expression levels of one or more immune system nucleic acid sequences may be used as an indicator of the effectiveness of an agent, even in the absence of an observable phenotypic response.

In certain exemplary embodiments, a method for diagnosing, prognosing, monitoring, treating, ameliorating and/or preventing in a subject a disease, disorder, symptom and/or condition is provided. Subjects at risk for a disease and/or disorder described herein can be identified by, for example, by any or a combination of diagnostic or prognostic assays as described herein. Administration of a prophylactic agent can occur prior to the manifestation of symptoms characteristic of a disease or disorder, such that the disease or disorder is prevented or, alternatively, delayed in its progression. Depending on the type disease or disorder, one or more agents or pharmaceutically acceptable salts thereof can be used for treating the subject. The appropriate agent can be determined based on screening assays described herein.

In certain exemplary embodiments, methods of prognosing, diagnosing and/or monitoring one or more disorders or diseases associated with an infectious agent are provided. Infectious agents include, but are not limited to, viruses, bacteria, fungi, parasites, infectious proteins and the like.

Viruses include, but are not limited to, DNA or RNA animal viruses. As used herein, RNA viruses include, but are not limited to, virus families such as Picornaviridae (e.g., polioviruses), Reoviridae (e.g., rotaviruses), Togaviridae (e.g., encephalitis viruses, yellow fever virus, rubella virus), Orthomyxoviridae (e.g., influenza viruses), Paramyxoviridae (e.g., respiratory syncytial virus, measles virus, mumps virus, parainfluenza virus), Rhabdoviridae (e.g., rabies virus), Coronaviridae, Bunyaviridae, Flaviviridae, Filoviridae, Arenaviridae, Bunyaviridae and Retroviridae (e.g., human T cell lymphotropic viruses (HTLV), human immunodeficiency viruses (HIV)). As used herein, DNA viruses include, but are not limited to, virus families such as Papovaviridae (e.g., papilloma viruses), Adenoviridae (e.g., adenovirus), Herpesviridae (e.g., herpes simplex viruses), and Poxviridae (e.g., variola viruses).

Bacteria include, but are not limited to, gram positive bacteria, gram negative bacteria, acid-fast bacteria and the like.

As used herein, gram positive bacteria include, but are not limited to, *Actinomedurae, Actinomyces israelii, Bacillus anthracis, Bacillus cereus, Clostridium botulinum, Clostridium difficile, Clostridium perfringens, Clostridium*

*tetani, Corynebacterium, Enterococcus faecalis, Listeria monocytogenes, Nocardia, Propionibacterium acnes, Staphylococcus aureus, Staphylococcus epiderm, Streptococcus mutans, Streptococcus pneumoniae* and the like.

As used herein, gram negative bacteria include, but are not limited to, *Afipia felis, Bacteroides, Bartonella bacilliformis, Bortadella pertussis, Borrelia burgdorferi, Borrelia recurrentis, Brucella, Calymmatobacterium granulomatis, Campylobacter, Escherichia coli, Francisella tularensis, Gardnerella vaginalis, Haemophilius aegyptius, Haemophilius ducreyi, Haemophilius influenziae, Helicobacter pylori, Legionella pneumophila, Leptospira interrogans, Neisseria meningitidia, Porphyromonas gingivalis, Providencia sturti, Pseudomonas aeruginosa, Salmonella enteridis, Salmonella typhi, Serratia marcescens, Shigella boydii, Streptobacillus moniliformis, Streptococcus pyogenes, Treponema pallidum, Vibrio cholerae, Yersinia enterocolitica, Yersinia pestis* and the like.

As used herein, acid-fast bacteria include, but are not limited to, *Myobacterium avium, Myobacterium leprae, Myobacterium* tuberculosis and the like.

As used herein, other bacteria not falling into the other three categories include, but are not limited to, *Bartonella henseiae, Chlamydia psittaci, Chlamydia trachomatis, Coxiella burnetii, Mycoplasma pneumoniae, Rickettsia akari, Rickettsia prowazekii, Rickettsia rickettsii, Rickettsia tsutsugamushi, Rickettsia typhi, Ureaplasma urealyticum, Diplococcus pneumoniae, Ehrlichia chafensis, Enterococcus faecium, Meningococci* and the like.

As used herein, fungi include, but are not limited to, *Aspergilli, Candidae, Candida albicans, Coccidioides immitis, Cryptococci*, and combinations thereof.

As used herein, parasitic microbes include, but are not limited to, *Balantidium coli, Cryptosporidium parvum, Cyclospora cayatanensis, Encephalitozoa, Entamoeba histolytica, Enterocytozoon bieneusi, Giardia lamblia, Leishmaniae, Plasmodii, Toxoplasma gondii, Trypanosomae*, trapezoidal amoeba and the like.

As used herein, parasites include worms (e.g., helminthes), particularly parasitic worms including, but not limited to, Nematoda (roundworms, e.g., whipworms, hookworms, pinworms, ascarids, filarids and the like), Cestoda (e.g., tapeworms)

As used herein, infectious proteins include prions. Disorders caused by prions include, but are not limited to, human disorders such as Creutzfeldt-Jakob disease (CJD) (including, e.g., iatrogenic Creutzfeldt-Jakob disease (iCJD), variant Creutzfeldt-Jakob disease (vCJD), familial Creutzfeldt-Jakob disease (fCJD), and sporadic Creutzfeldt-Jakob disease (sCJD)), Gerstmann-Sträussler-Scheinker syndrome (GSS), fatal familial insomnia (fFI), sporadic fatal insomnia (sFI), kuru, and the like, as well as disorders in animals such as scrapie (sheep and goats), bovine spongiform encephalopathy (BSE) (cattle), transmissible mink encephalopathy (TME) (mink), chronic wasting disease (CWD) (elk, mule deer), feline spongiform encephalopathy (cats), exotic ungulate encephalopathy (EUE) (nyala, oryx, greater kudu), spongiform encephalopathy of the ostrich and the like.

In certain exemplary embodiments, methods of prognosing, diagnosing and/or monitoring one or more cellular proliferative disorders are provided. Cellular proliferative disorders are intended to include disorders associated with rapid proliferation. As used herein, the term "cellular proliferative disorder" includes disorders characterized by undesirable or inappropriate proliferation of one or more subset(s) of cells in a multicellular organism. The term "cancer" refers to various types of malignant neoplasms, most of which can invade surrounding tissues, and may metastasize to different sites (see, for example, PDR Medical Dictionary 1st edition (1995), incorporated herein by reference in its entirety for all purposes). The terms "neoplasm" and "tumor" refer to an abnormal tissue that grows by cellular proliferation more rapidly than normal. Id. Such abnormal tissue shows partial or complete lack of structural organization and functional coordination with the normal tissue which may be either benign (i.e., benign tumor) or malignant (i.e., malignant tumor).

The language "treatment of cellular proliferative disorders" is intended to include the prevention of the induction, onset, establishment or growth of neoplasms in a subject or a reduction in the growth of pre-existing neoplasms in a subject. The language also can describe inhibition of the invasion of neoplastic cells into neighboring tissues or the metastasis of a neoplasm from one site to another. Examples of the types of neoplasms intended to be encompassed by the present invention include but are not limited to those neoplasms associated with cancers of the breast, skin, bone, prostate, ovaries, uterus, cervix, liver, lung, brain, larynx, gallbladder, pancreas, rectum, parathyroid, thyroid, adrenal gland, immune system, neural tissue, head and neck, colon, stomach, bronchi, and/or kidneys.

Cellular proliferative disorders can further include disorders associated with hyperproliferation of vascular smooth muscle cells such as proliferative cardiovascular disorders, e.g., atherosclerosis and restenosis. Cellular proliferation disorders can also include disorders such as proliferative skin disorders, e.g., X-linked ichthyosis, psoriasis, atopic dermatitis, allergic contact dermatitis, epidermolytic hyperkeratosis, and seborrheic dermatitis. Cellular proliferative disorders can further include disorders such as autosomal dominant polycystic kidney disease (ADPKD), mastocystosis, and cellular proliferation disorders caused by infectious agents such as viruses.

In certain exemplary embodiments, methods of prognosing, diagnosing and/or monitoring one or more autoimmune disorders are provided. As used herein, the term "autoimmune disorder" is a disease or disorder caused by a subject producing an inappropriate immune response against its own tissues. As used herein, an autoimmune disorder includes, but is not limited to, disorders such as Addison's disease, alopecia areata, ankylosing spondylitis, antiphospholipid syndrome, autoimmune hemolytic anemia, autoimmune hepatitis, autoimmune inner ear disease (AIED), autoimmune lymphoproliferative syndrome (ALPS), autoimmune thrombocytopenic purpura (ATP), Balo disease, Bechet disease, bullous pemphigoid, cardiomyopathy, celiac sprue-dermatitis herpetiformis, chronic fatigue immune dysfunction syndrome (CFIDS), chronic inflammatory demyelinating polyneuropathy, cicatricial pemphigoid, cold agglutinin disease, CREST syndrome, Crohn's disease, Degos disease, dermatomyositis, dermatomyositis-juvenile, discoid lupus, essential mixed cryoglobulinemia, fibromyalgia-fibromyositis, Graves' disease, Guillain-Barré, Hashimoto thyroiditis, idiopathic pulmonary fibrosis, idiopathic thrombocytopenia purpura (ITP), IgA nephropathy, insulin-dependent diabetes, juvenile arthritis, lichen planus, lupus, Ménière disease, mixed connective tissue disease, multiple sclerosis, myasthemia gravis, pemphigus vulgaris, pernicious anemia, polyarteritis nodosa, polychondritis, polyglandular syndromes, polymyalgia rheumatica, polymyositis and dermatomyositis, primary agammaglobulinemia, primary biliary cirrhosis, psoriasis, Raynaud phenomenon, Reiter syndrome, rheumatic fever, rheumatoid arthritis, sarcoidosis, scleroderma, Sjögren syndrome, stiff-person syndrome, Takayasu arthritis, temporal arteritis/giant cell arteritis, ulcerative colitis, vasculitis, vitiligo, Wegener granulomatosis and the like (See the American Autoimmune Related Diseases Association, Inc. website: aarda.org).

In certain exemplary embodiments, the nature and characteristics of symptoms, conditions, diseases and/or disorders are reduced by the methods of the present invention compared to the nature and characteristics of symptoms, conditions, diseases and/or disorders observed in a patient or a sample (e.g., a test sample or a sample taken from a subject prior to, during or after treatment). In certain aspects, the nature and characteristics of symptoms, conditions and diseases and/or disorder phenotypes are reduced by about 5%, 10%, 15%, 20%, 25%, 30%, 35%, 40%, 45%, 50%, 55%, 60%, 65%, 70%, 75%, 80%, 85%, 90%, 91%, 92%, 93%, 94%, 95%, 96%, 97%, 98%, 99%, 99.9% or more, or any range(s) in between.

In certain exemplary embodiments, a method for modulating, ameliorating, preventing and/or treating diseases, symptoms and/or disorders as described herein includes the step of administering a therapeutically effective amount of an agent to a subject. As defined herein, a therapeutically effective amount of agent (i.e., an effective dosage) ranges from about 0.0001 to 30 mg/kg body weight, from about 0.001 to 25 mg/kg body weight, from about 0.01 to 20 mg/kg body weight, from about 0.1 to 15 mg/kg body weight, or from about 1 to 10 mg/kg, 2 to 9 mg/kg, 3 to 8 mg/kg, 4 to 7 mg/kg, or 5 to 6 mg/kg body weight. The skilled artisan will appreciate that certain factors may influence the dosage required to effectively treat a subject, including but not limited to the severity of the disease or disorder, previous treatments, the general health and/or age of the subject, and other diseases present. Moreover, treatment of a subject with a therapeutically effective amount of one or agents or pharmaceutically acceptable salts thereof can include a single treatment or, in certain exemplary embodiments, can include a series of treatments. It will also be appreciated that the effective dosage of agent used for treatment may increase or decrease over the course of a particular treatment. Changes in dosage may result from the results of diagnostic assays as described herein. The pharmaceutical compositions can be included in a container, pack, or dispenser together with instructions for administration.

Embodiments of the present invention are still further directed to methods of pairing heavy and light chains by matching their relative clone frequencies or by matching their similar time series. Further embodiments include pairing heavy and light chains at the single cell level simultaneously in many cells in parallel in a single reaction medium. Such methods include high-throughput sequencing of components resulting from an immune reaction using methods for insulating cells including in-cell biochemistry on formaldehyde cross-linked/permeabilized cells, emulsion encapsulated cells, agarose-bead encapsulated cells, liposome transfection of single cells, small oligonucleotide-transfection of single cells including locked nucleic acids or fluorescent probes, and the like. Such methods reduce cross contamination and incorrect pairings. Methods of pairing heavy and light chains described herein utilize enzymatic methods including SOE-PCR which may result in incorporation of scFv liner sequences, direct ligation which may result in incorporation of scFv linker sequence and may also include bimolecular or trimolecular ligations, USER cloning, bead capture such as by either amplification onto beads or hybridization onto beads or capture by pre-annealed oligonucleotides with immune chain-specific complementary sequences.

Embodiments of the present invention are even still further directed to methods of obtaining full immune chain molecules by hybridization using CDR3 information. Such an embodiment includes the use of short-read sequencing technologies to select CDR3 sequences and using these CDR3 sequences to hybridize to a full immune chain molecule using complementary oligonucleotides.

Embodiments of the present invention still further include methods for reducing cross-contamination or incorrect pairing of heavy and light chains by bead-attached exonucleases and methods for monitoring cross-contamination or incorrect pairing of heavy and light chains by real-time PCR. The same or similar methods for pairing of heavy and light chains described herein can also be extended to the screening of antibody libraries against antigen libraries. According to one aspect, large and complex libraries of affinity reagents such as antibodies, nanobodies and the like are screened against large and complex libraries of antigen targets in a single reaction, followed by coupling DNA coding for the antibody sequence to the DNA coding for the antigen sequence.

Embodiments of the invention include the use of computer software to automate design and/or analysis of nucleic acid sequences. Such software may be used in conjunction with individuals performing polynucleotide synthesis by hand or in a semi-automated fashion or combined with an automated synthesis system. In at least some embodiments, the gene/oligonucleotide design/analysis software is implemented in a program written in the JAVA programming language. The program may be compiled into an executable that may then be run from a command prompt in the WINDOWS XP operating system. Exemplary software code is set forth as Appendix D. Unless specifically set forth in the claims, the invention is not limited to implementations using the same algorithms, organizational structure or other specific features of the exemplary software code. The invention is similarly not limited to implementation using a specific programming language, operating system environment or hardware platform.

It is to be understood that the embodiments of the present invention which have been described are merely illustrative of some of the applications of the principles of the present invention. Numerous modifications may be made by those skilled in the art based upon the teachings presented herein without departing from the true spirit and scope of the invention. The contents of all references, patents and published patent applications cited throughout this application are hereby incorporated by reference in their entirety for all purposes.

The following examples are set forth as being representative of the present invention. These examples are not to be construed as limiting the scope of the invention as these and other equivalent embodiments will be apparent in view of the present disclosure, tables, figures, appendices and accompanying claims.

Example I

Tracking Human Immune Response Dynamics Through VDJ Sequencing

Peripheral blood samples were drawn from a subject at −14 days prior to vaccination, approximately one hour after vaccination (day 0), and 1, 3, 7, 14, 21, and 28 days post-vaccination. For each sample, total RNA was extracted from peripheral blood leukocytes, from which cDNA and bar-coded 454 sequencing libraries were generated using primers specific for the entire V H region (FIG. 1B). B cell mRNA was analyzed to avoid cross-priming the germline DNA, to avoid non-functional receptor rearrangements, to benefit from possible clonal expansion of antigen-specific cells, and to take advantage of higher mRNA copy-numbers in antibody-expressing cells. The Roche 454 sequencing platform was used, as it provided read-lengths long enough to cover the entire $V_H$ region.

Figure 8:
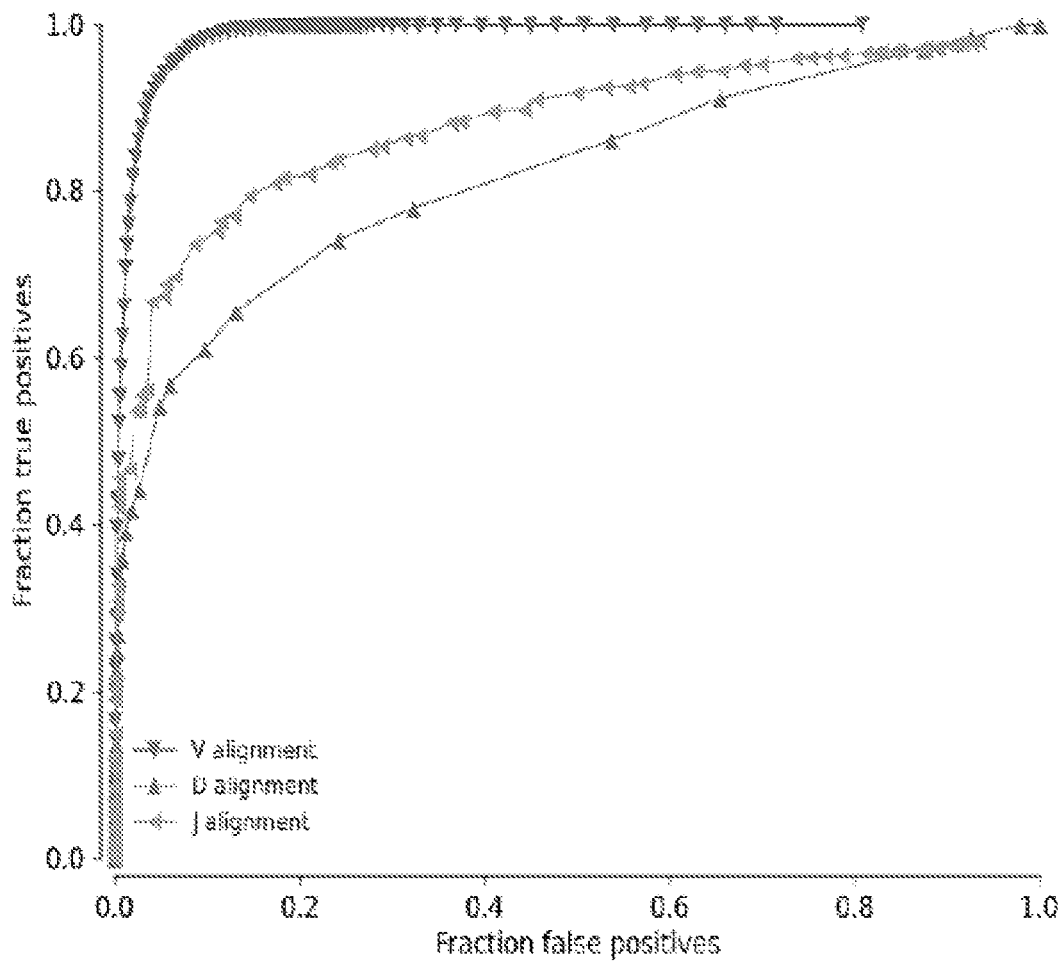
FIG. 8 depicts a graph showing ROC curves for the VDJ alignment algorithm described herein using IMGT/V-QUEST results as a reference. As expected, V region alignments were the most reliable, followed by J, followed by D.

Through the course of 7 runs of 454 GS FLX sequencing, approximately 5.5 million size-filtered reads were obtained that were subsequently aligned to the reference IMGT database (Worldwide Web Site: imgt.cines.fr/) (Lefranc et al. (2009) Nucleic Acids Res. 37:D1006). To do so, the V, then J, and finally D regions were identified, as their decreasing length allowed for the most reliable identification. The novel algorithm described herein selected the few best matches by comparing word frequencies and scores them using dynamic programming alignment (Durbin, R., Eddy, S. R., Krogh, A. & Mitchison, G. Biological Sequence Analysis: Probabilistic Models of Proteins and Nucleic Acids. (Cambridge Univ. Press, Cambridge; 1998)). To define clones, the algorithm then partitioned the reads according to their V-J usage and clusters their CDR3 junctions using agglomerative hierarchical clustering with edit distance as the metric (Gan, G., Ma, C. & Wu, J. Data Clustering: Theory, Algorithms, and Applications. (SIAM American Statistical Association, Philadelphia, PA, Alexandria, VA; 2007)). While V and J region matches were generally unambiguous, D region identifications were not focused on as the algorithms often produced ambiguous alignments due to the short length of the D regions along with the highly mutated nature of the CDR3 (FIG. 8). A total of 4,027,253 reads successfully passed this process (including bar-code identification), from which the immunoglobulin isotype was identified by searching for the corresponding primer sequences at the constant region end of the read (FIG. 26).

Figure 2A:
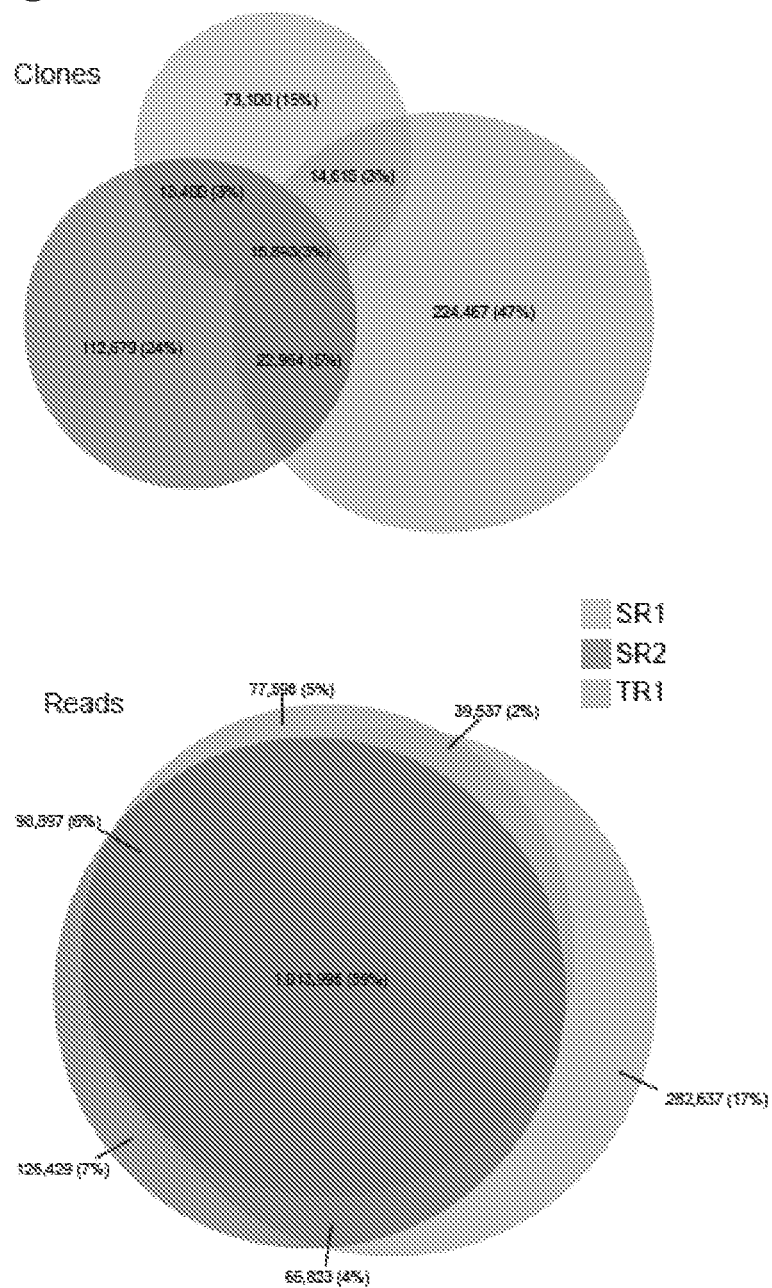
FIGS. 2A-2E depict technical reproducibility and immune diversity of certain methods described herein.
Figure 2B:
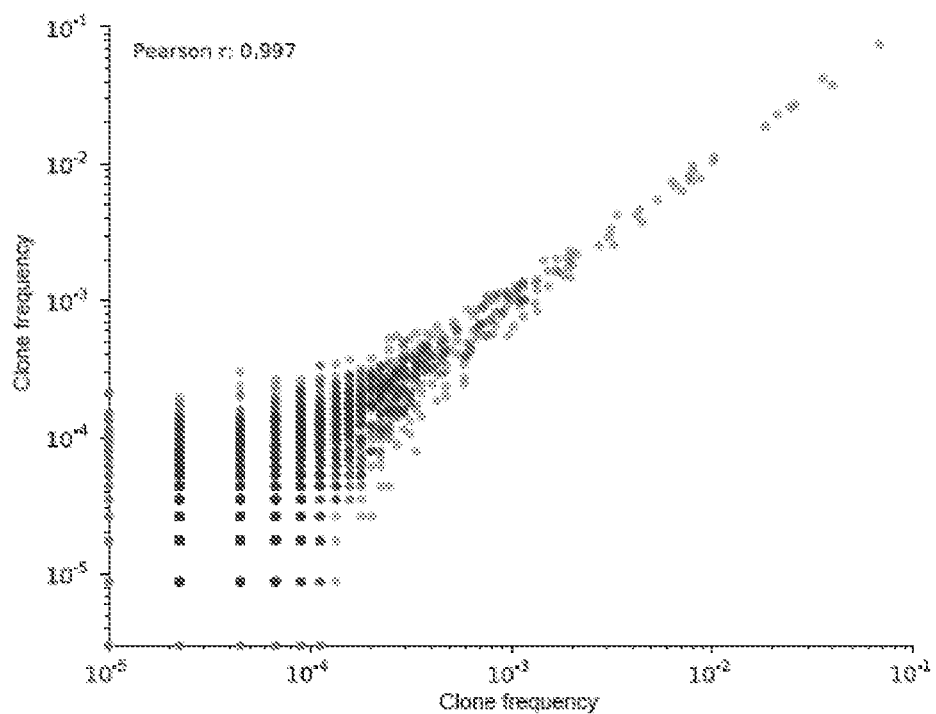
Figure 2C:
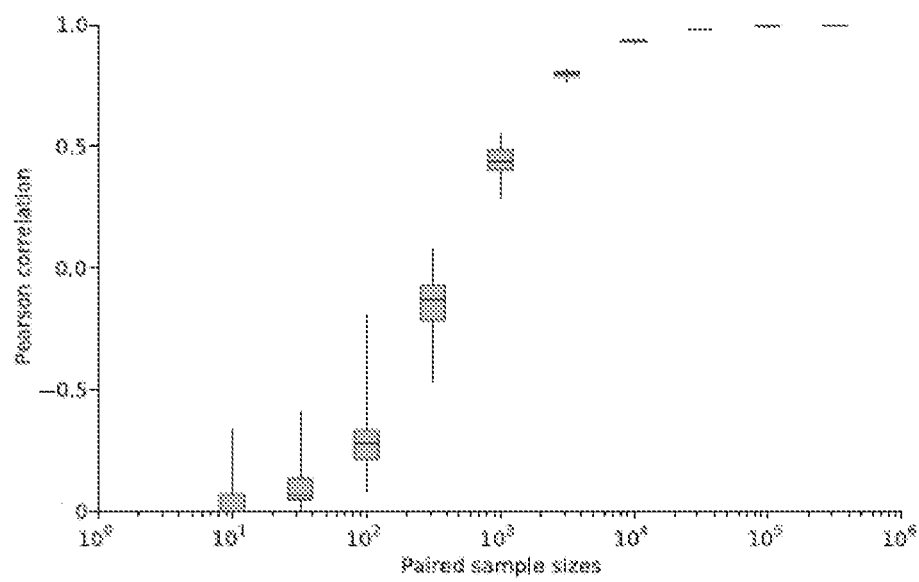
Figure 9:
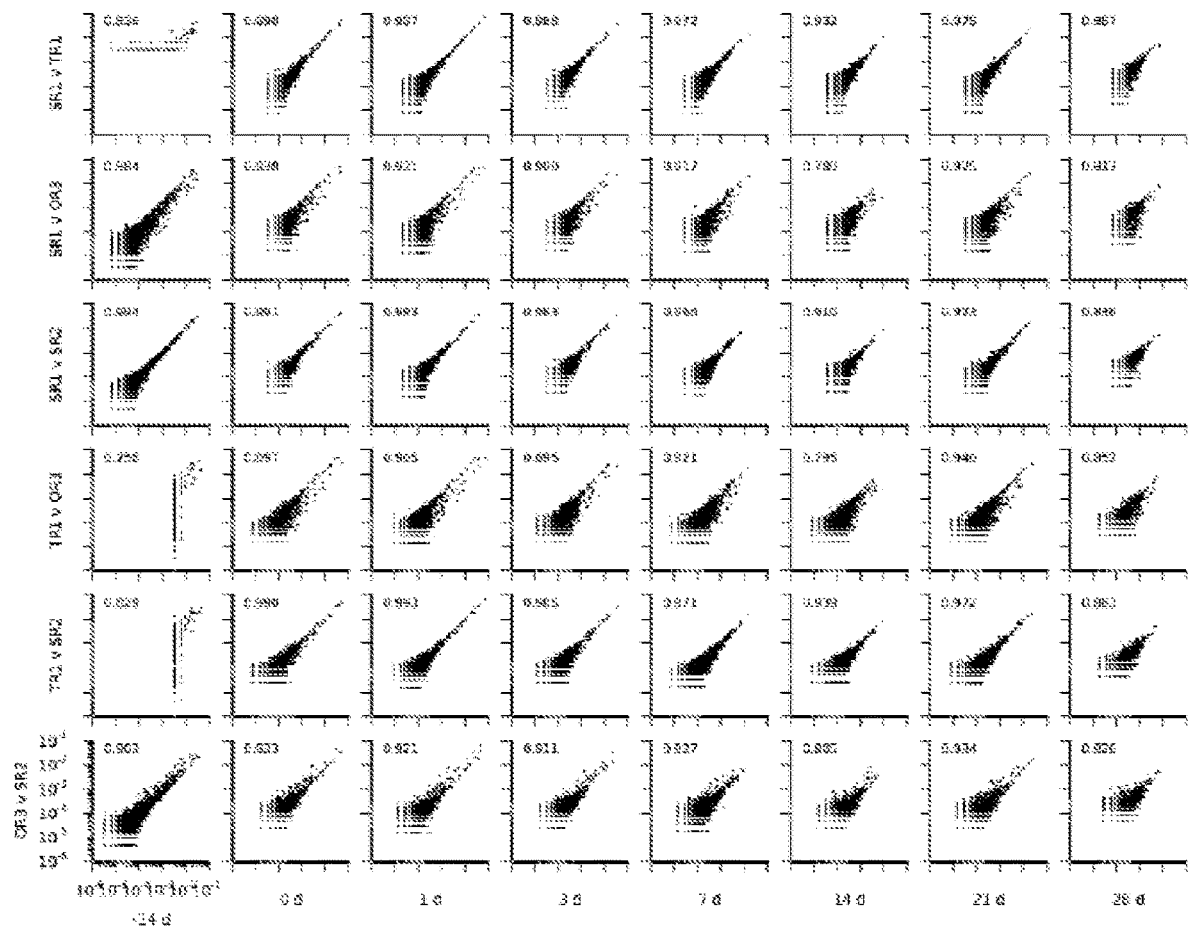
FIG. 9 depicts scatter plots showing correlation of expression levels among replicates SR1, SR2, TR1, and OR3. Points in red are zero-valued. Barcode 1 (−14 d) was significantly lost in the preparation of replicate TR1. Note that OR3 consistently showed worse correlation. As it was produced with a freshly mixed primer set, without intending to be bound by scientific theory, this indicated that the protocol described herein was highly sensitive to the primer concentrations.
Figure 10:
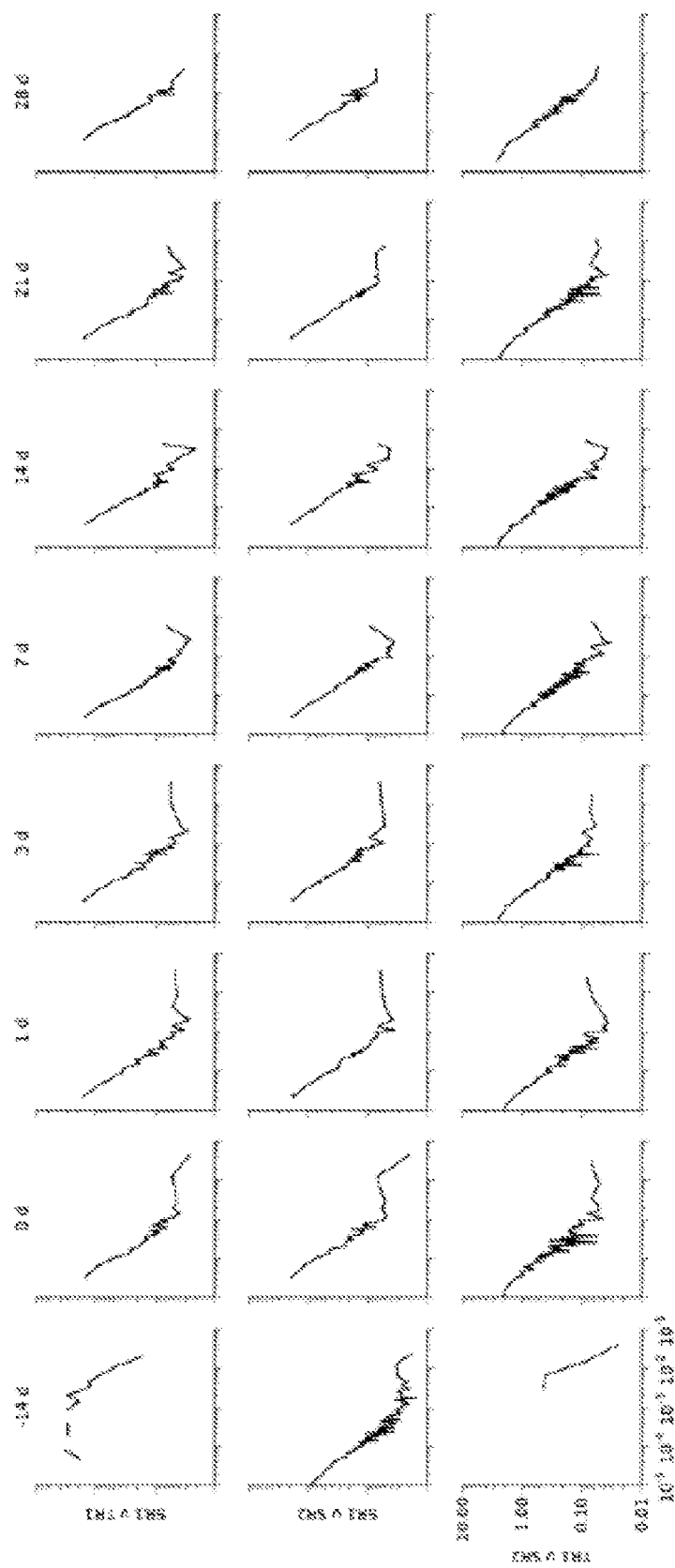
FIG. 10 graphically depicts coefficients of variation (CV) computed for various replicate comparisons. Higher clone frequencies showed smaller CV, consistent with the higher reproducibility of high-expression clones. CV values of 0.5 were attained at frequencies of $10^{-4}$ to $10^{-3}$, indicating limits to the ability to accurately quantitate clone frequency before the onset of Poisson noise.

Since the potential human repertoire diversity is estimated to be quite significant (up to $10^{14}$ by some estimates) (Davis et al. (1988) Nature 334:395), the technical feasibility and reproducibility of the methods described herein established as follows. A library of all time points was sequenced twice (sequencing replicates SR1 and SR2), and a completely independent third library prepared from the same RNA samples was sequenced once (technical replicate TR1). Among these three sequencing runs, 477,118 unique clones were identified where only 3% were shared between the three runs and 14% were observed in at least two runs (FIG. 2A). However, those shared clones accounted for 59% and 71% of all reads respectively, indicating that the highly expressed clones are actually sampled significantly between replicate runs. This was further validated by a strong correlation between technical replicate samples, confirming technical reproducibility of the approach described herein (FIGS. 2B and 9). Furthermore, resampling of the data showed that $10^5$ reads were sufficient to obtain high correlations between replicates (FIG. 2C). By computing coefficients of variation (CV), it was determined that reliable quantification of clone frequencies as low as $10^{-4}$ could be obtained, though this number was dependent on a given sample's sequencing depth (FIG. 10).

Figure 2D:
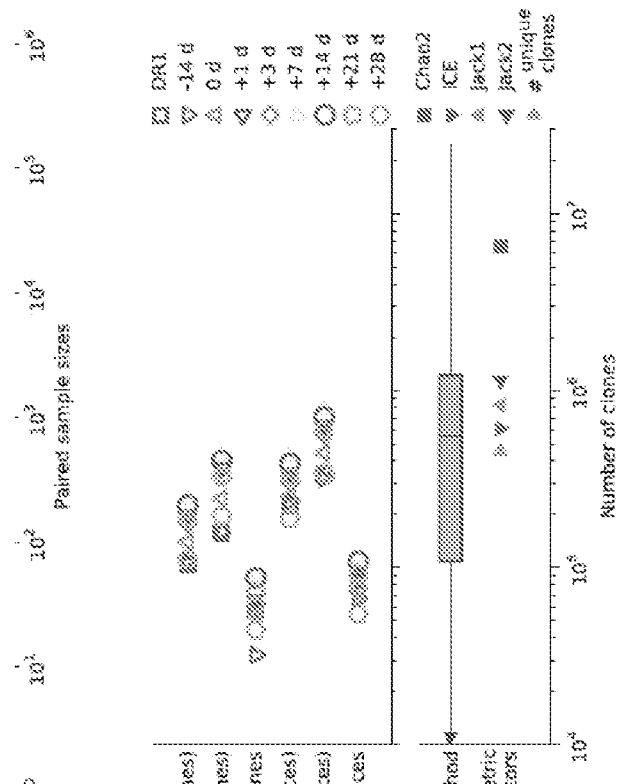
Figure 2E:
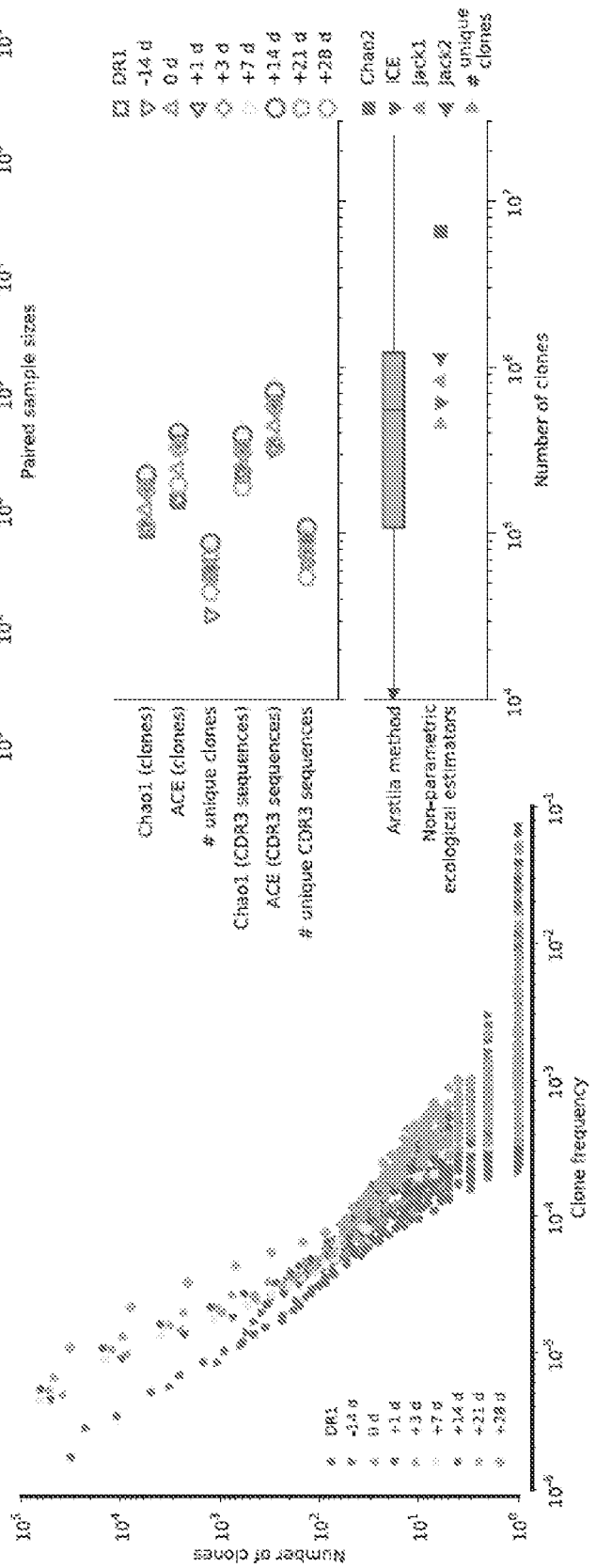
Figure 11:
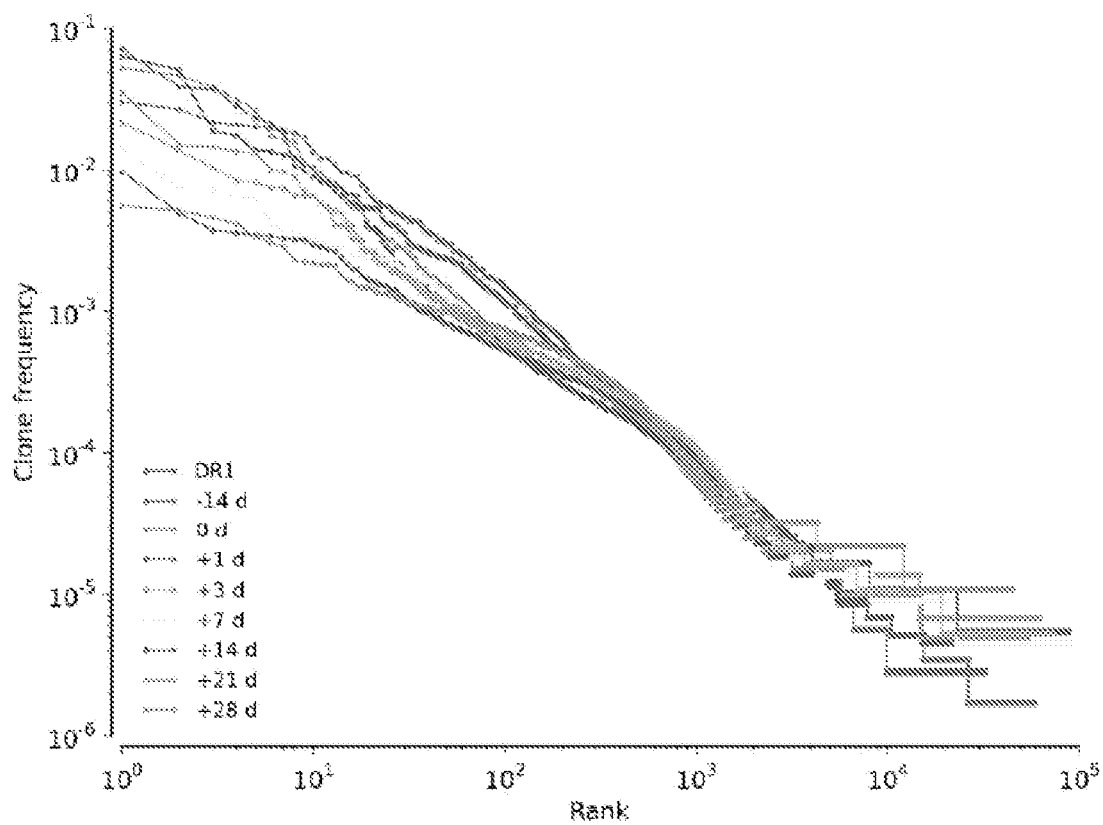
FIG. 11 graphically depicts clone frequency rank accumulation for replicate DR1 and the various time points of SR1+SR2+TR1.
Figure 12A:
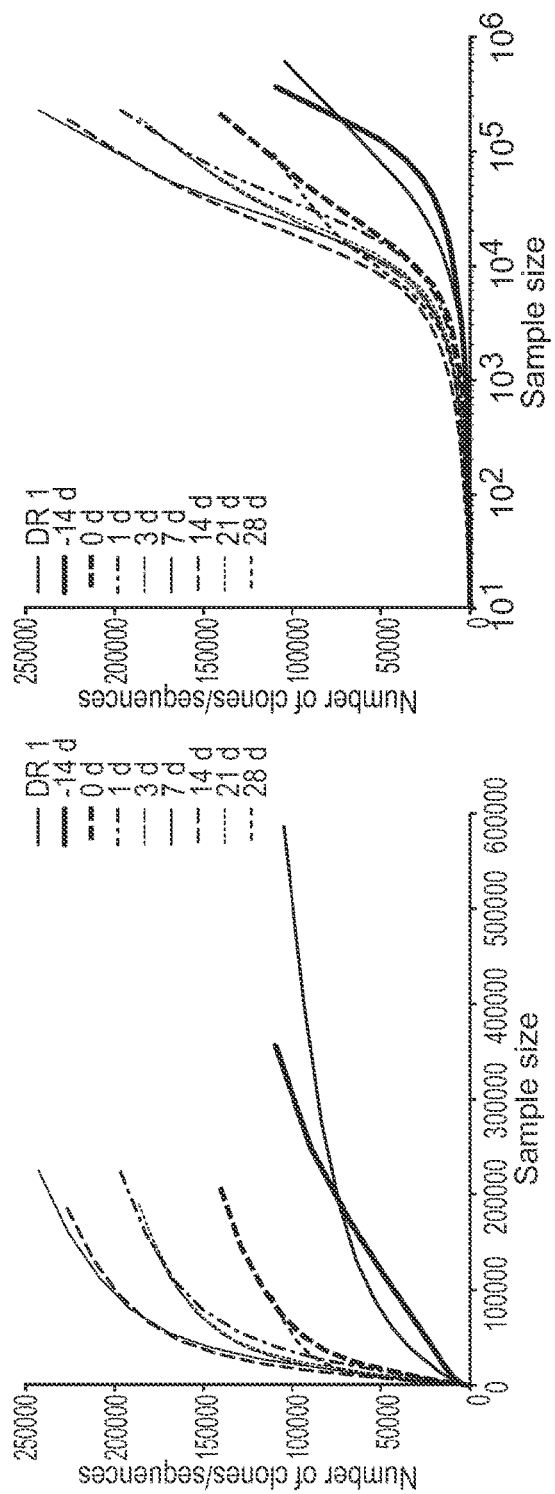
FIGS. 12A-12D depict rarefaction curves using sampling without replacement. The final values (computed on the full data sets) are summarized herein.
Figure 12B:
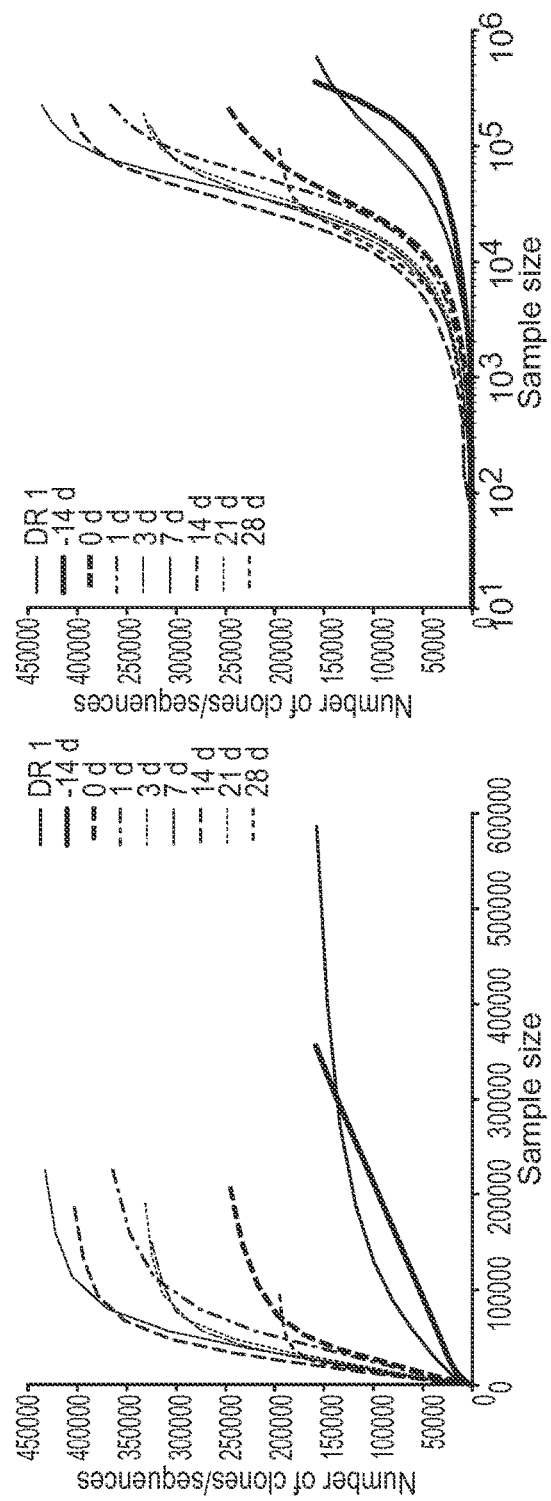
Figures 12C, 12D:
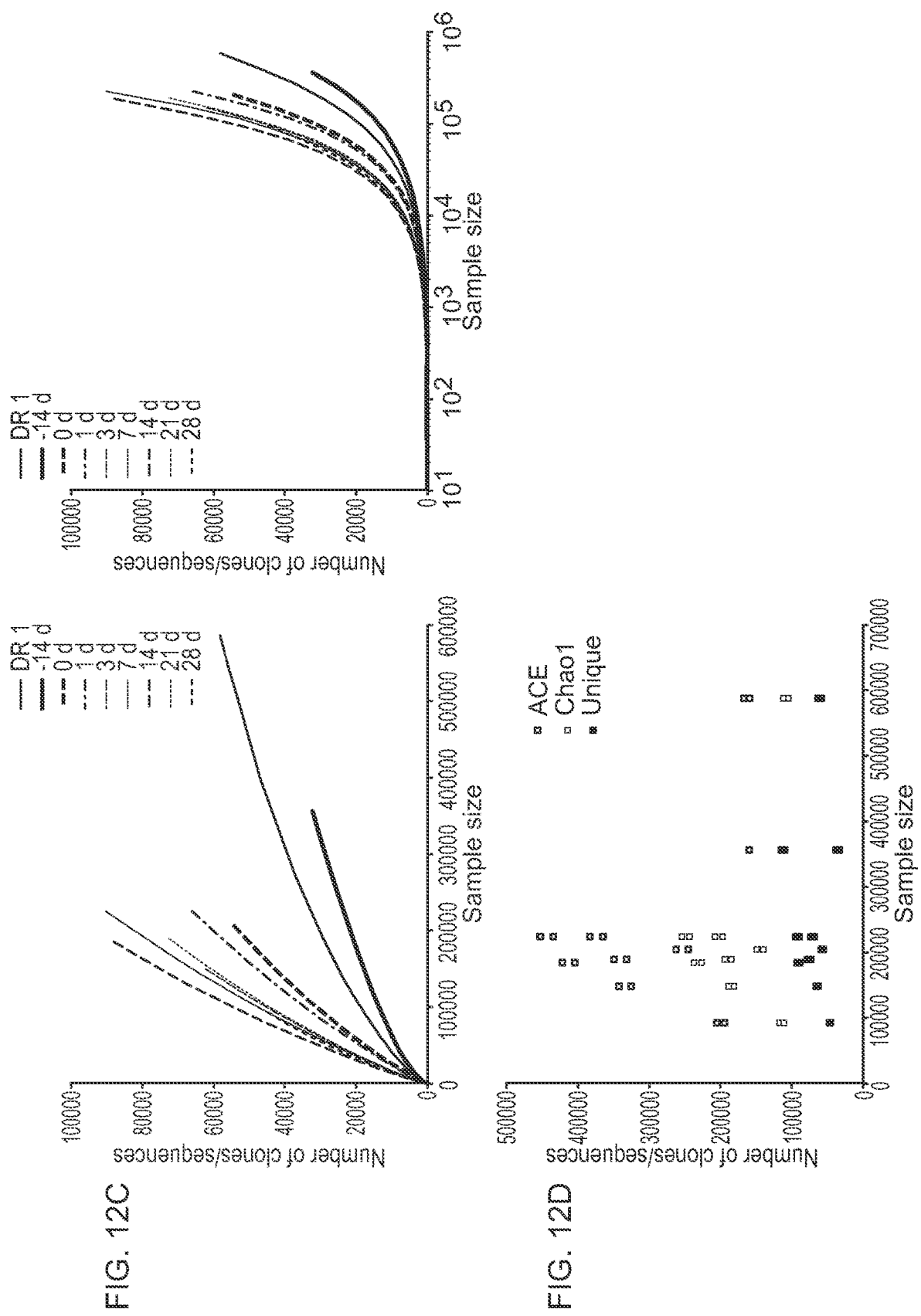

Methods developed to assess ecological population structures exist. (Magurran, A. E. Measuring Biological Diversity. (Blackwell Pub., Malden, Ma.; 2004)). Rank-abundance and clone-size distribution plots showed that the clonal structure follows a power law distribution with an exponent of 1.97 across >2 decades (FIGS. 2D and 11). Without intending to be bound by scientific theory, this could reflect the evolutionary selection pressures experienced by the cells during the processes of differentiation and affinity maturation (Caldarelli et al. (2002) Phys. Rev. Lett. 89:258702; Bianconi and Barabasi (2001) Europhysics Letters 54:436). To estimate the total $V_H$ repertoire diversity in a typical 1 mL blood sample, the Chao1 and ACE non-parametric species richness estimators were used (Magurran, Supra). A full sequencing run was also committed to a single time point (run DR1; day −14) to obtain a more reliable estimate. Inflection points and convexity were observed in almost all re-sampled estimator curves, indicating that the samples were sufficient to make reliable estimates (FIGS. 12A-12D). It was determined that a 1 mL blood sample contained approximately 100,000-500,000 unique heavy chain clones, depending on the blood sample and estimator used (FIG. 2E). Finally, as only considering immunoglobulin heavy chains were considered, and without intending to be bound by scientific theory, it is expected the actual diversity will be at least an order of magnitude greater when paired with light chains. These data demonstrate that adequate sampling of the human repertoire diversity can be achieved in a single 1 mL blood draw, indicating the potential utility of such an approach as a personalized clinical diagnostic tool to identify current or previous pathogen exposure (Lerner et al. (1991) Proc. Natl. Acad. Sci. USA 88:9705). A large database of specificity-annotated antibody sequences will be generated.

Figure 3A:
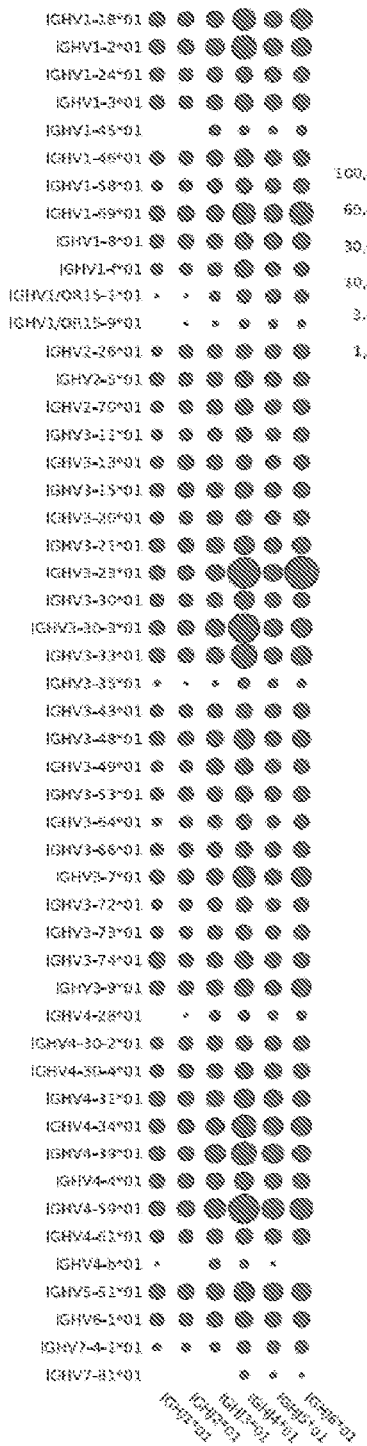
FIGS. 3A-3C depict static repertoire analysis.
Figure 3B:
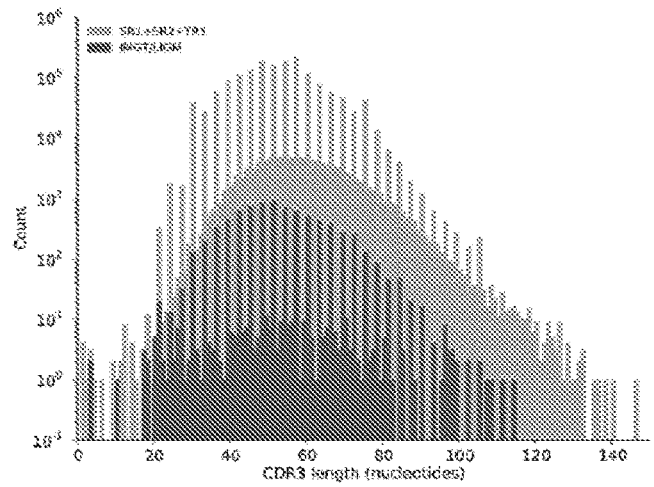
Figure 3C:
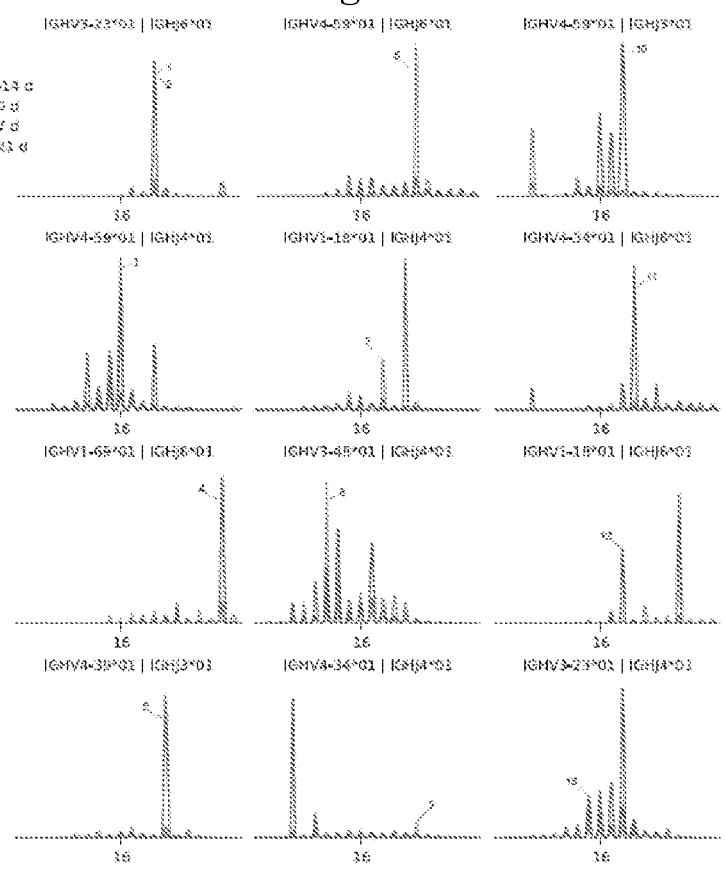
Figure 13A:
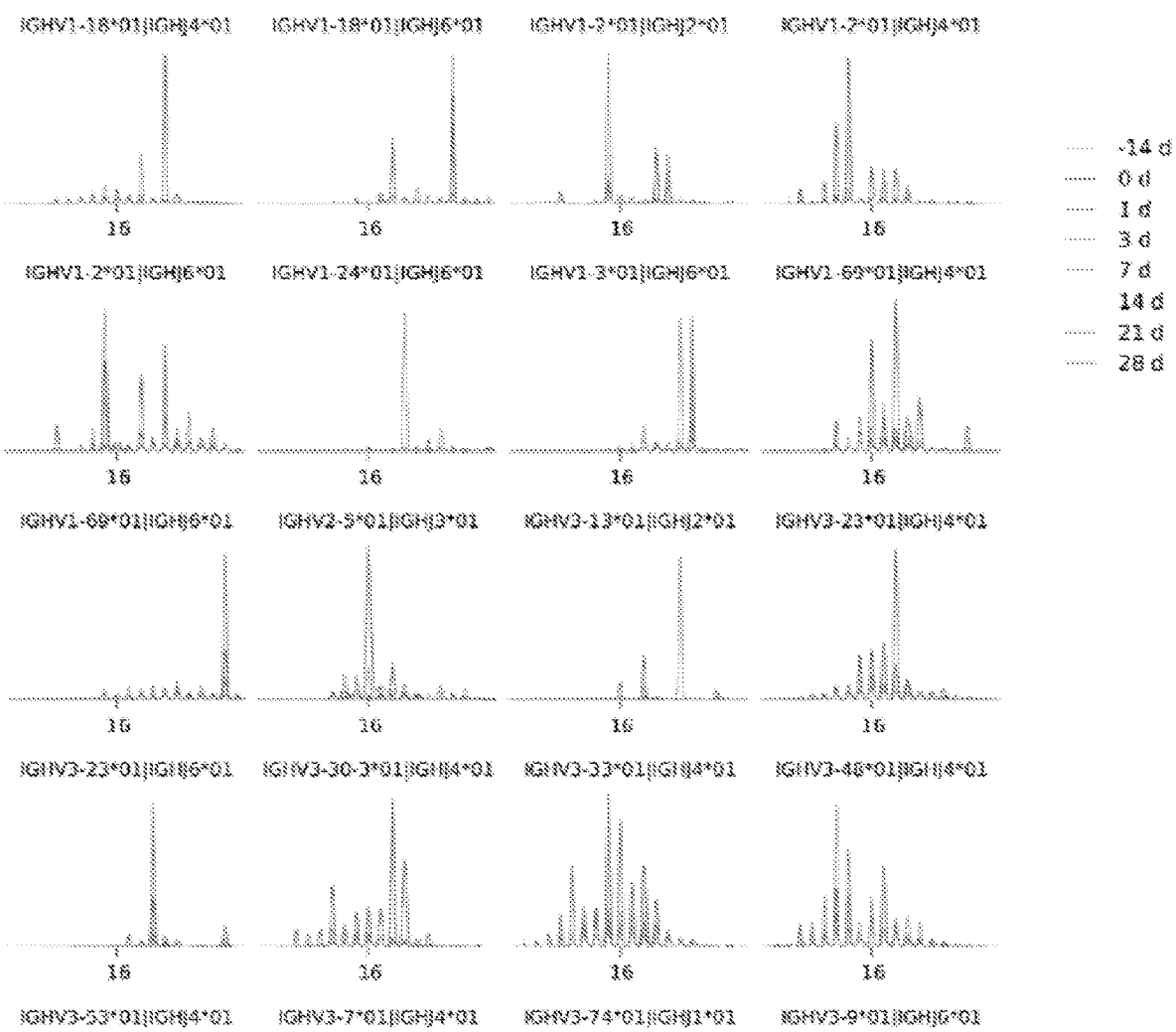
FIGS. 13A-13B depict CDR3 pseudo-spectratypes for various V-J combinations at multiple time points for all the clones selected from FIG. 4B.
Figure 13B:
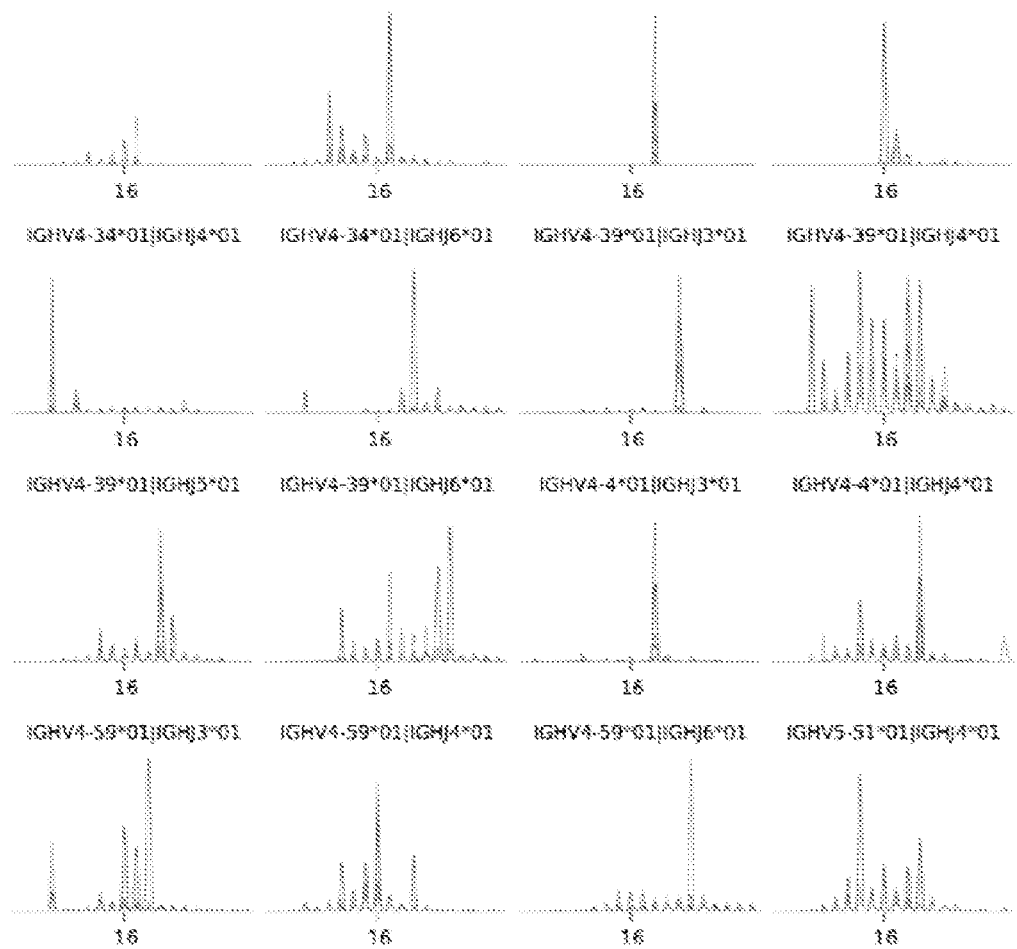

Next the characteristics of the static immune repertoire were assessed. Overall, V and J usage was highly non-uniform (FIG. 3A). The most frequently observed V segments were IGHV3-23 (11.4% of all reads), IGHV4-59 (8.5%), IGHV3-30-3 (7.3%) while the most frequent J segments were IGHJ4 (35.1%) and IGHJ6 (18.9%), consistent with previous studies (Boyd, Supra; Brezinschek et al. (1995) J. Immunol. 155:190; Glanville et al. (2009) Proc. Natl. Acad. Sci. USA (106:20216). The distribution of CDR3 junction lengths was then analyzed (FIG. 3B). The two-sided, 95th percentile of the observed CDR3 lengths was 33 nucleotides (nt) to 75 nt, with median length of 54 nt (with longest observed junction at 146 nt), which shows similarity to the T cell receptor CDR3 size distribution (Freeman et al., Supra) and IMGT/LIGM data (Lefranc, Supra). In an attempt to compare with traditional low-resolution methods for analyzing immune repertoires, pseudo-spectratype plots were also generated in which receptor-length diversity is used as a surrogate for overall diversity (FIG. 3C and FIGS. 13A-13B) (Pannetier et al. (1993) Proc. Natl. Acad. Sci. USA 90:4319). Finally, the immunoglobulin isotype distribution was analyzed, and it was observed that IgM antibodies were the most abundant (37% of all reads), followed by IgA (36%), IgG (23%), IgD (4%), and IgE (0.01%). Though expressed mRNA levels in circulating B cells were measured, these numbers were still consistent with the subject's age and expected plasma protein titers (Lefranc, M.-P. & Lefranc, G. E. The Immunoglobulin Factsbook. (Academic Press, San Diego; 2001)). Altogether, these results show the first in-depth profile of the expressed immunoglobulin heavy chain repertoire in an individual human.

Figure 14:
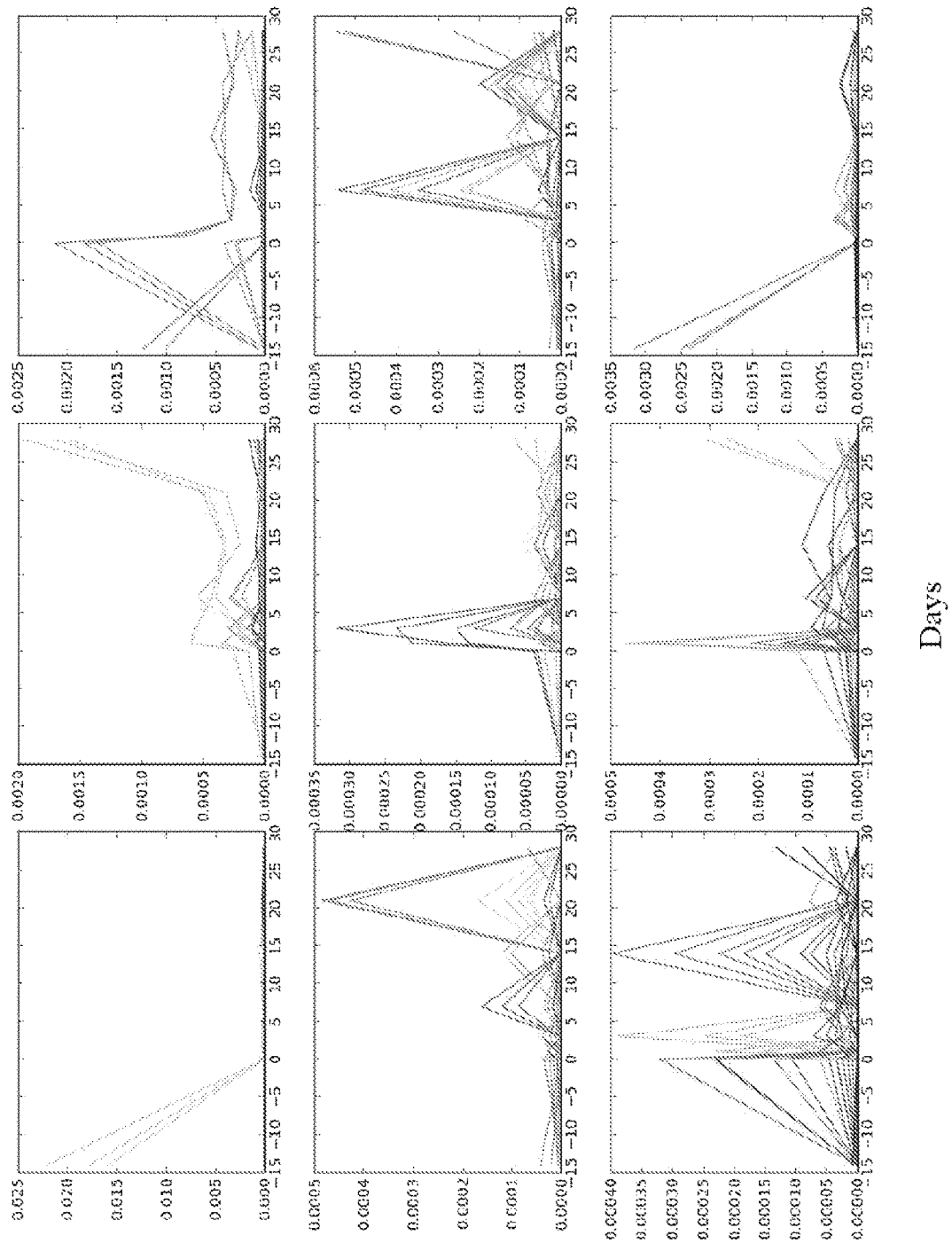
FIG. 14 depicts replicate plots of time series of randomly selected clones. Each panel contains 10 randomly selected clones, plotted using data from SRL SR2, and TR1, separately. Unique clones are plotted in the same color. Clones qualitatively tracked one another from separate replicates, showing high reproducibility of time series between replicates.
Figure 15A:
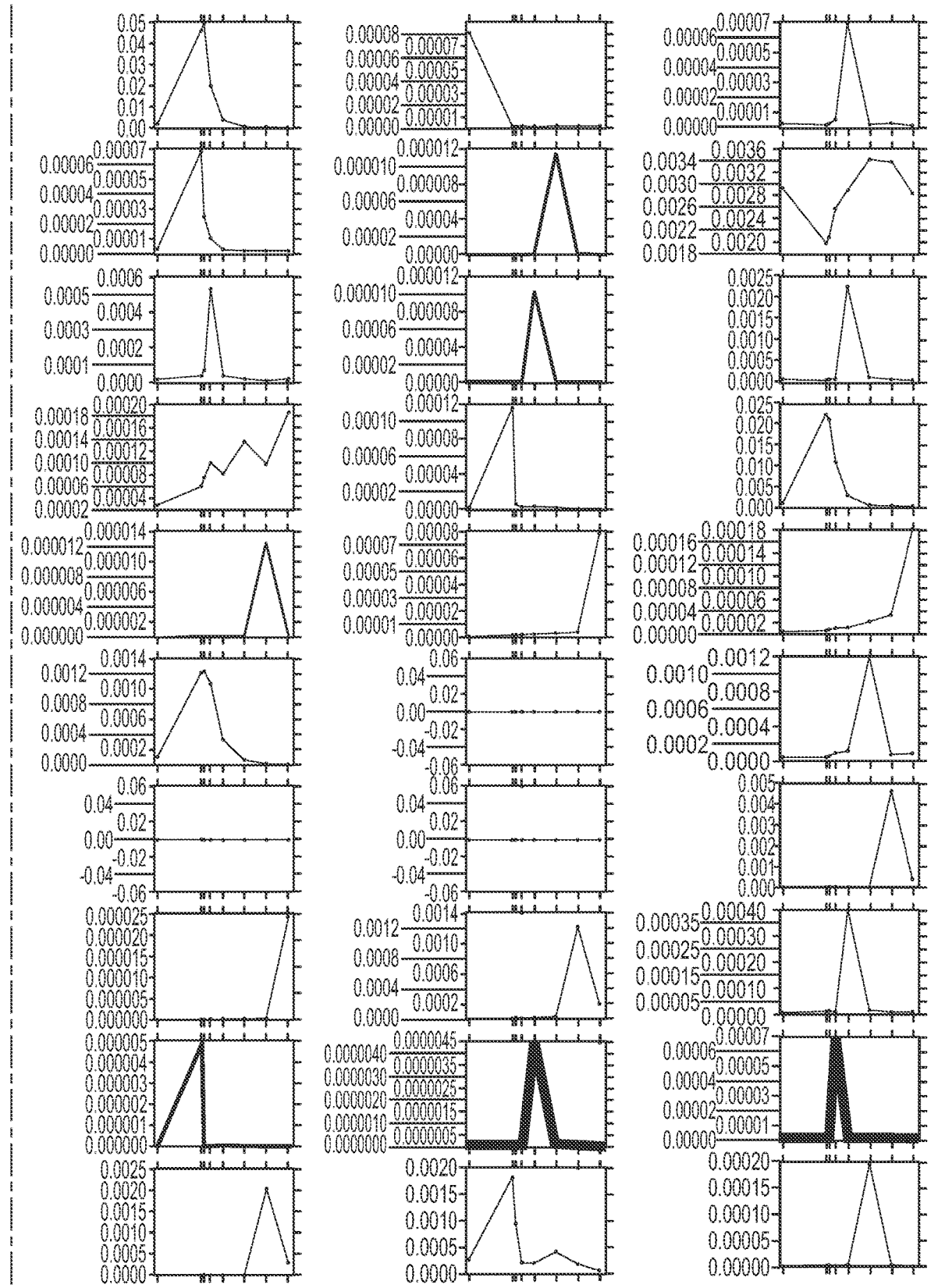
FIGS. 15A-15B depict k-means clustering of clone time series.
Figure 15A:
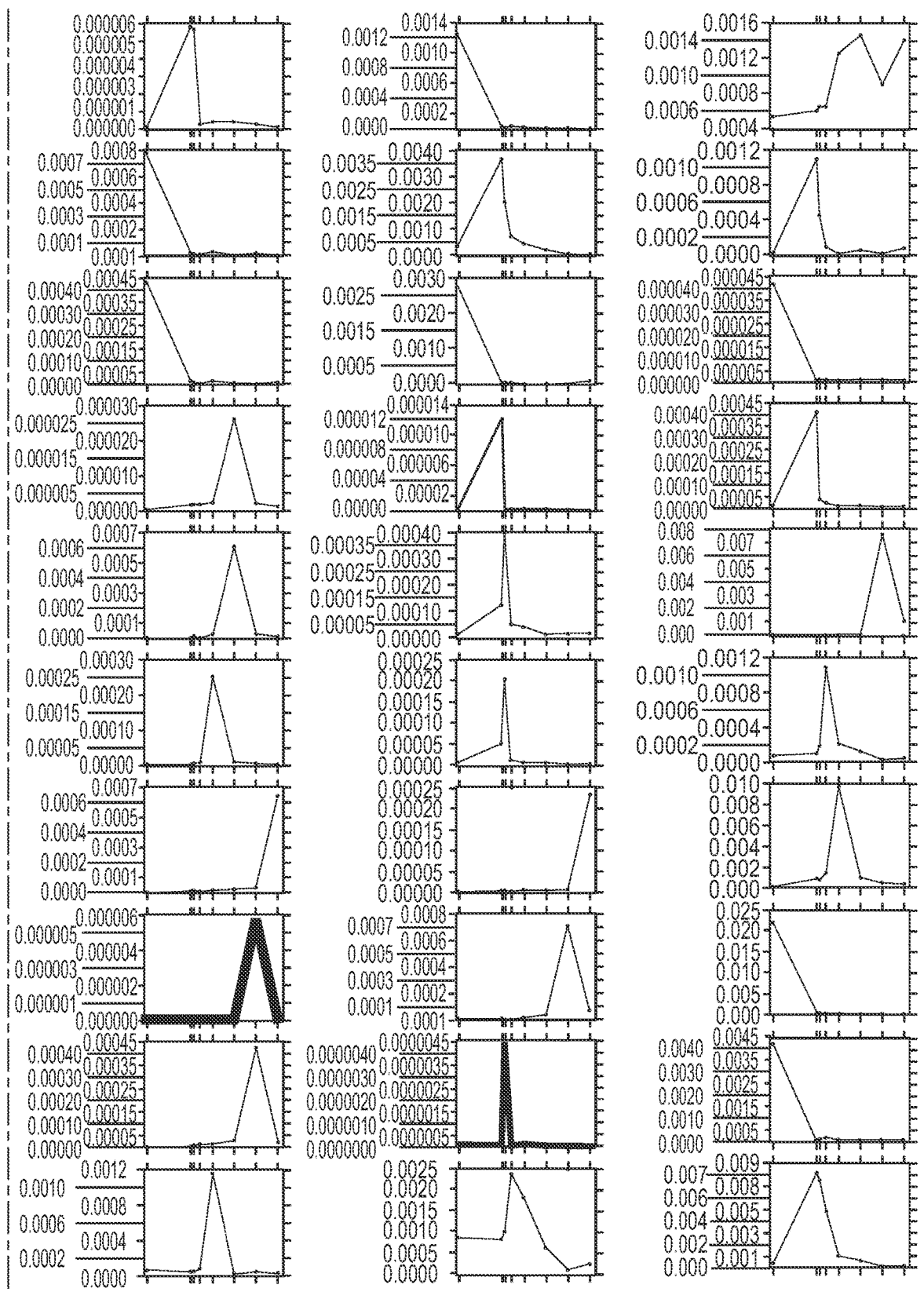
Figure 15A:
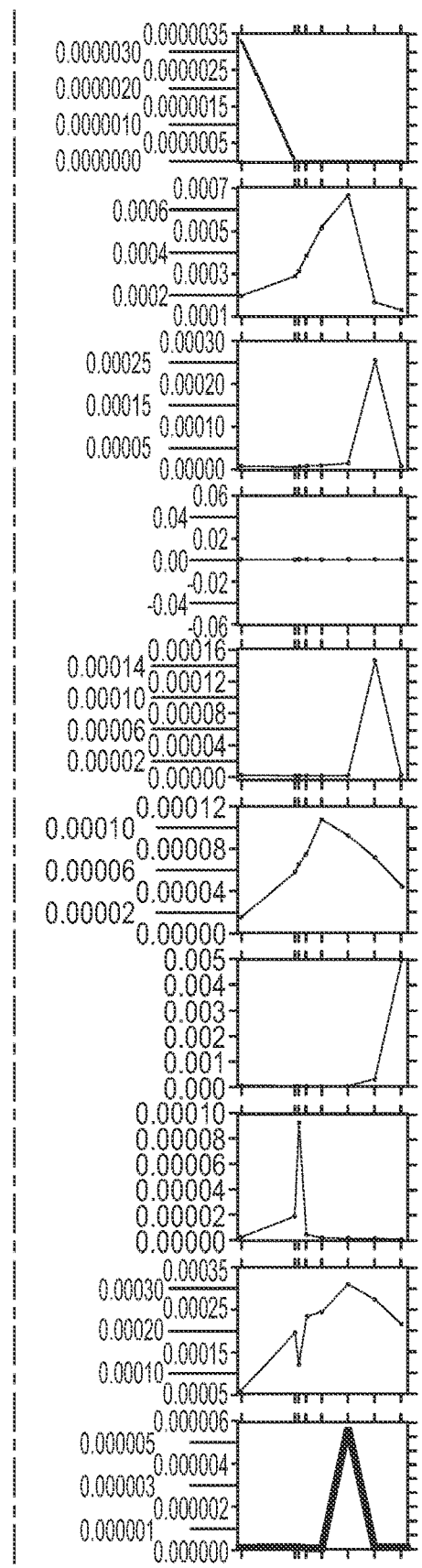
Figure 15B:
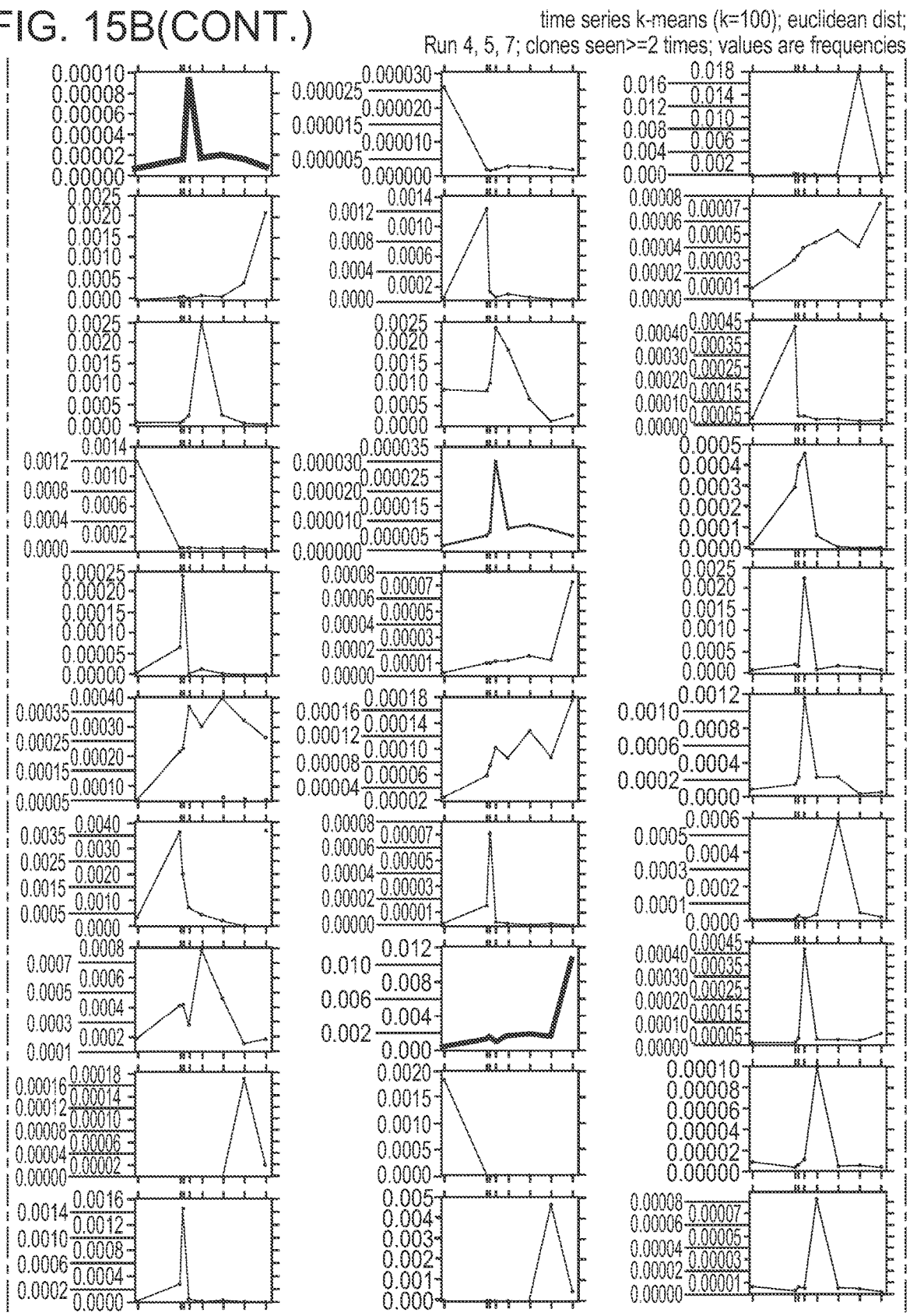
Figure 15B:
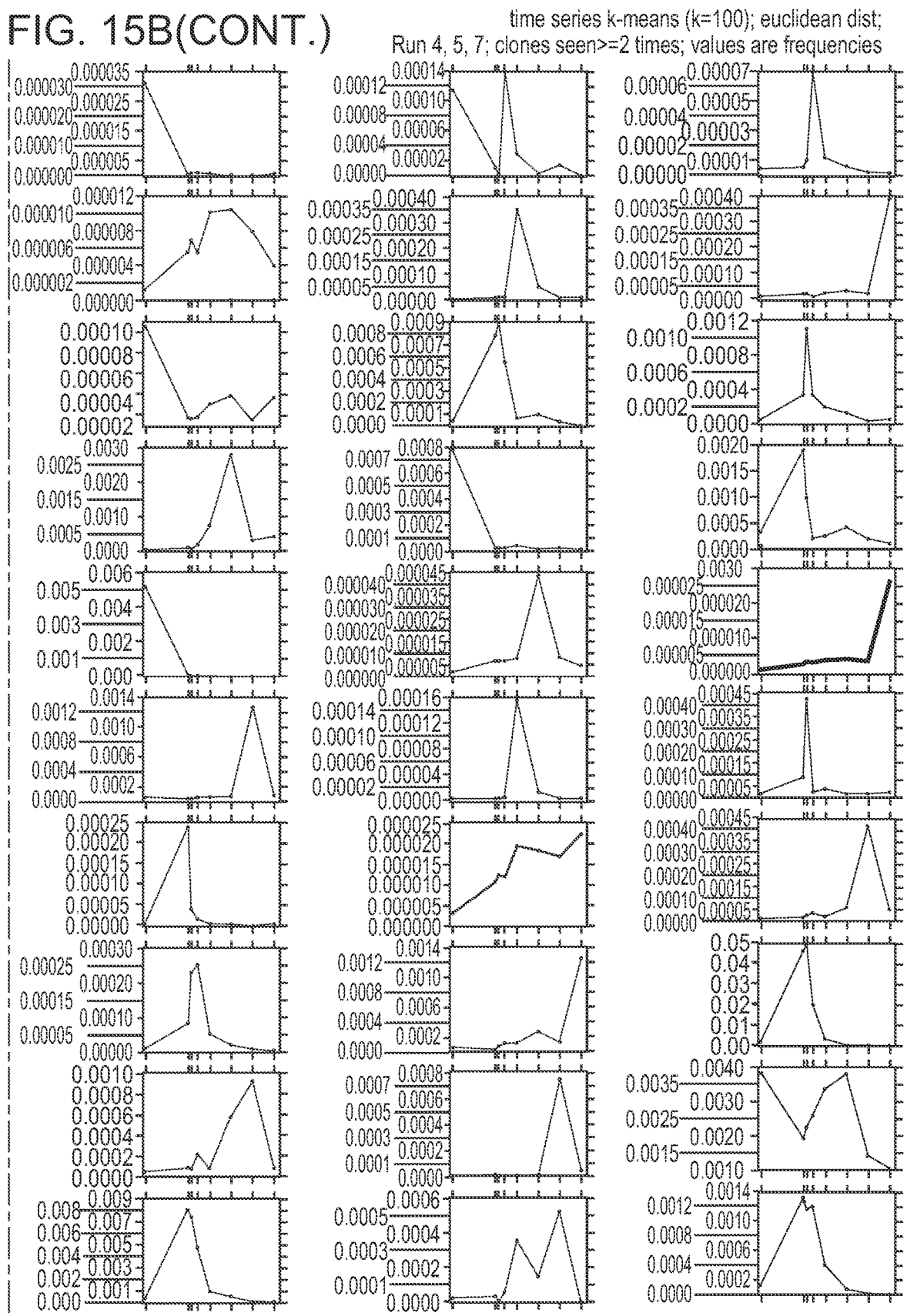
Figure 15B:
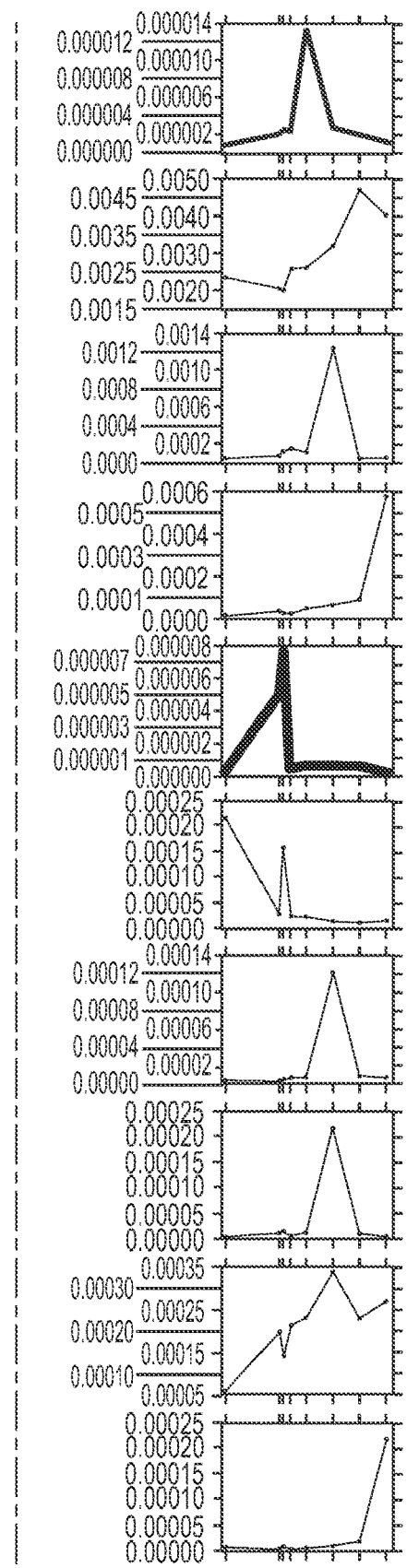

While the above analyses were focused on establishing reproducibility and profiling the static VDJ-ome, it was of great interest to survey the dynamic fluctuations of the immune repertoire. In the hope of capturing at least one immunological event, responses were induced to multiple immune challenges by vaccinating the subject against three pathogens for which his medical history suggests he should have immune memory: influenza (3 strains), hepatitis A, and hepatitis B. The clone frequencies were tracked through time to produce almost 500,000 time series over the eight time points, revealing the high complexity of the repertoire dynamics (FIG. 4A). By randomly selecting clones across technical replicate runs, strong correlations were qualitatively observed at varying levels of expression, which further confirmed the reproducibility of the approach described herein (FIG. 14). Initial clustering of the time series using a k-means algorithm showed that the most populated clusters were of ephemeral clones of various expression levels observed in each individual time point. However, after removing such single time point clones, the resulting clusters exhibited a vast array of dynamic behaviors (FIGS. 15A-15B).

Traditionally, attempts to characterize responses to immune challenges are performed by sorting for cells with certain surface markers, allowing the generation of antigen-specific antibodies by analyzing the heavy and light chains of single cells (Paul, Supra; Wrammert et al. (2008) *Nature* 453:667). In contrast to this approach, an attempt to identify antigen-specific lymphocytes without prior knowledge of specific antigens or cell-activation states and without using functional assays was performed. In an attempt to identify clones specific to the immune challenges, a self-organizing map (SOM) clustering method was used (Kohonen, T. Self-Organizing Maps, Edn. 2nd. (Springer, Berlin; New York; 1997); Eichler et al. (2003) *Bioinformatics* 19:2321). This revealed groups of clones at days 7 and 21 that exhibited the typically expected activation patterns of antibody-secreting cells (ASC) and memory B cells (FIG. 4B) (Abbas et al., Supra; Murphy et al., Supra; Wrammert et al., Supra). These clones also corresponded to the major peaks observed in the computed pseudo-spectratypes (identified by the numbers associated with each peak in FIG. 3C). Surprisingly, the most dynamic and highly expressed clones (by orders of magnitude) were observed at day 0 (approximately 1 hr after vaccination) and day 1, with a significant drop at day 3 (FIG. 4A). While the possibility that the subject was inadvertently experiencing an immune response unrelated to the vaccines cannot be excluded, it is believed that a vaccination-induced memory response was observed. While memory responses are known for rapidly generating high antibody titers, they are expected to peak 3-5 days post-exposure (Abbas et al., Supra; Murphy et al., Supra; Paul, Supra). While the highest exposure-induced serum titers may occur at days 3-5, the highest mRNA expression levels of the corresponding cells were observed at day 1, suggesting that functional studies relying on cDNA repertoire cloning of samples collected on days 3-5 would likely miss candidates of interest. However, it is important to note that \ mRNAs of circulating B cells were sampled, which precede the accumulation of actual antibody proteins. In contrast with the responses of days 7 and 21, the rapid onset and greater magnitude of the day 1 memory response indicates that these clones may have been overlooked in functional studies of therapeutic monoclonal antibody discovery (Wrammert et al., Supra; Lanzavecchia et al. (2006) *Immunol. Rev.* 211:303; Jin et al. (2009) *Nat. Med.* 15:1088).

Next, global fluctuations in the isotype distribution over the course of the experiment were observed. Interestingly, a small rise of IgG was observed at day 7, while at day 21, a concurrent rise in IgA and drop in IgM was observed, indicating potential class switching in vaccine-induced clones (FIG. 4C) (Cerutti (2008) Nat. Rev. Immunol. 8:421).

Figure 4D:
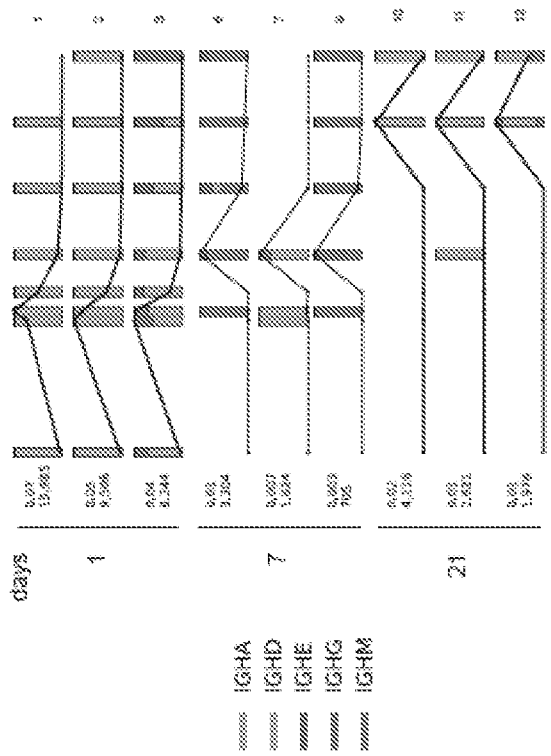
Figure 4C:
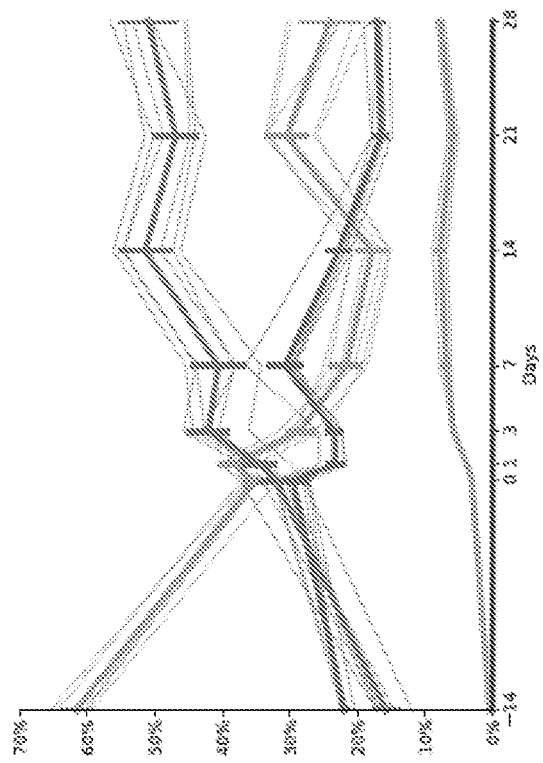
Figure 16A:
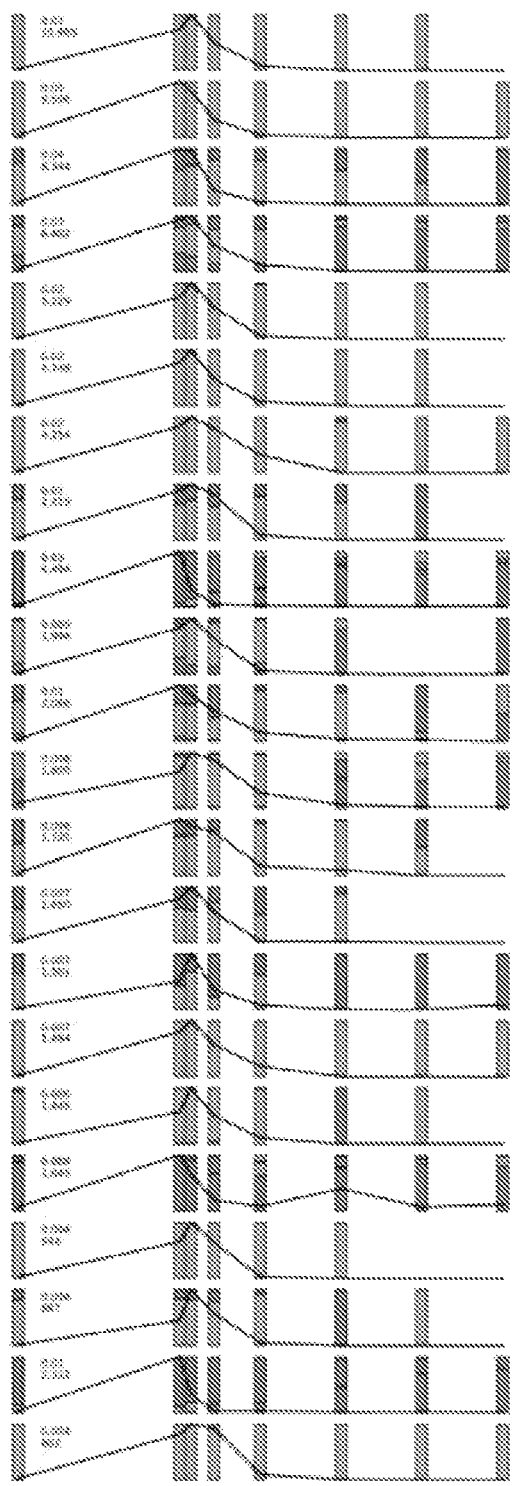
FIGS. 16A-16C depict isotype distributions of the most highly expressed clones at days 1 (FIG. 16A), 7 (FIG. 16B), and 21 (FIG. 16C). Stacked bar charts represent the isotype distribution at a given time point, while the black line represents the clone frequency time series. Numbers refer to maximum clone frequency, with the corresponding number of reads. IgA; green, IgG; red, IgM; blue.
Figure 16B:
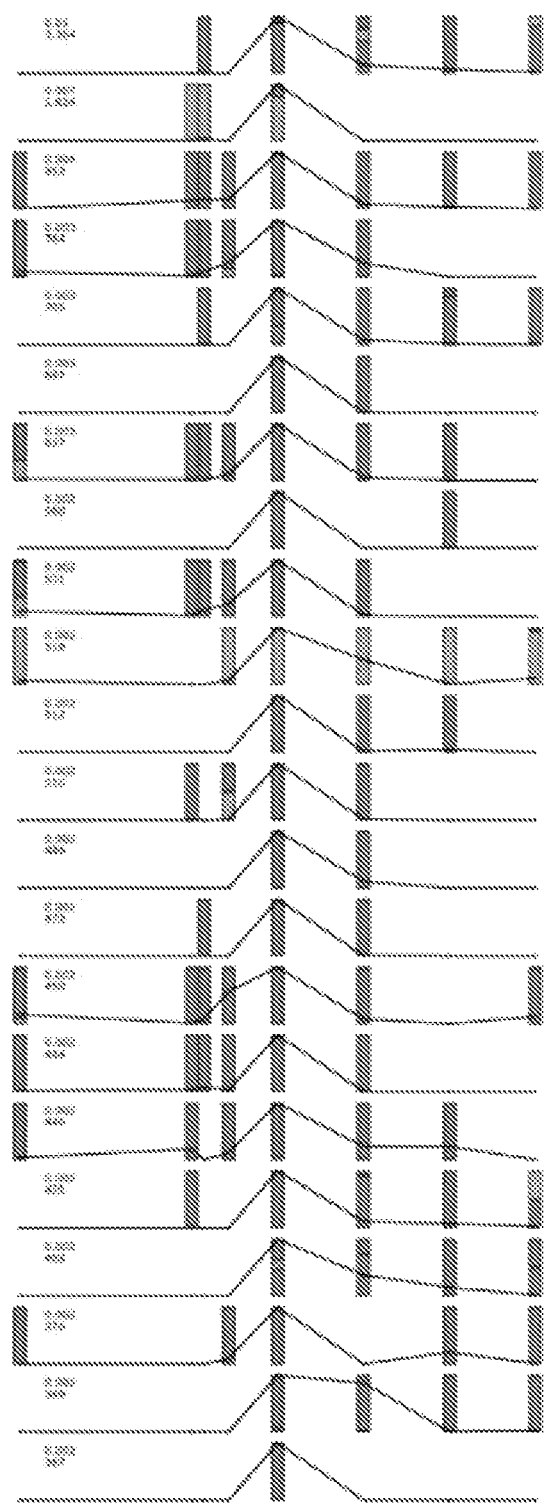
Figure 16C:
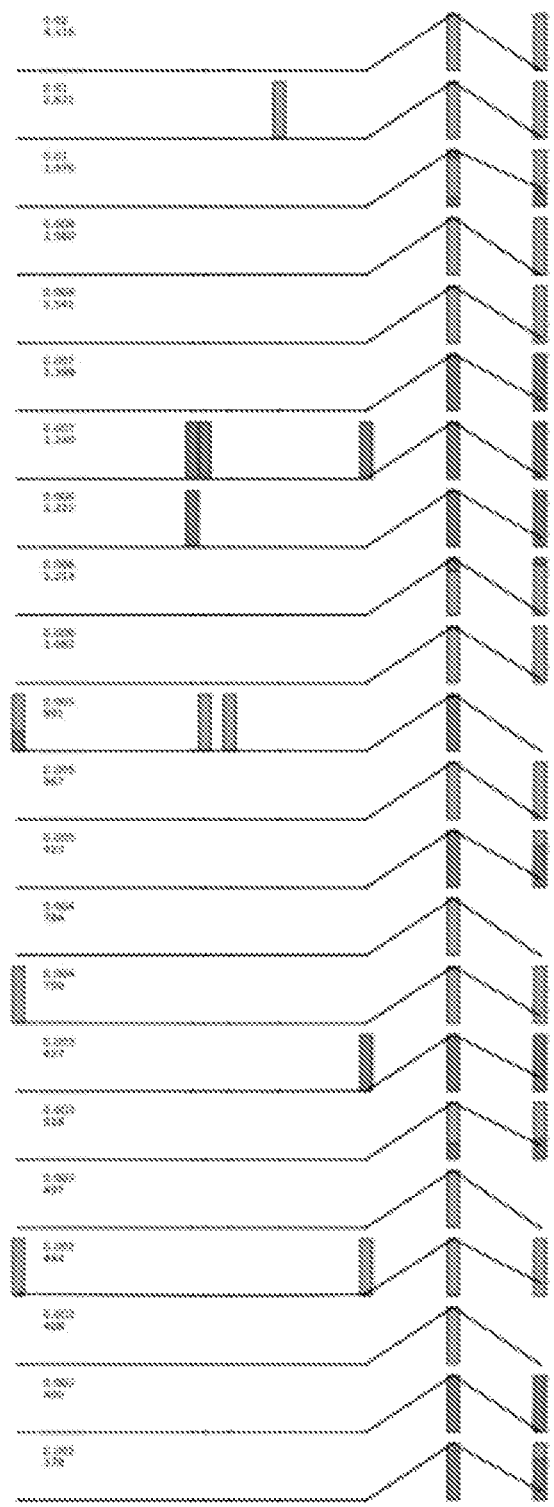

To obtain a more detailed view of isotype dynamics, the isotype distributions of the SOM-selected clones were analyzed (FIG. 4D and FIG. 16). The day 7 clones were primarily composed of the IgM and IgG isotype, while the day 21 clones were mostly composed of IgM and IgA. Most interestingly, the day 1 clones were dominated by IgA, reflecting an important role for this isotype in antiviral defense (Cerutti, Supra; Qiao et al. (2006) *Nat. Immunol.* 7:302). Such an IgA memory response is characteristic of re-exposure to influenza antigens (Cox et al. (2006) *Vaccine* 24:6577; Wright et al. (1983) *Infect. Immun.* 40:1092). While IgA antibodies are largely responsible for defense in mucosal secretions (Cerutti, Supra; Stavnezer (1996) *Adv. Immunol.* 61:79), it is reported that influenza vaccination (both nasal and intramuscular) elicits a rapid, strong, and short-lived systemic response of influenza-specific IgA ASC in peripheral blood (Cox et al., Supra). Nevertheless, the magnitude of the response observed in the hours following vaccination indicates a novel effector role for plasma IgA in antiviral memory, and highlights IgA as a potential non-traditional immunotherapy in viral diseases.

Figure 6A:
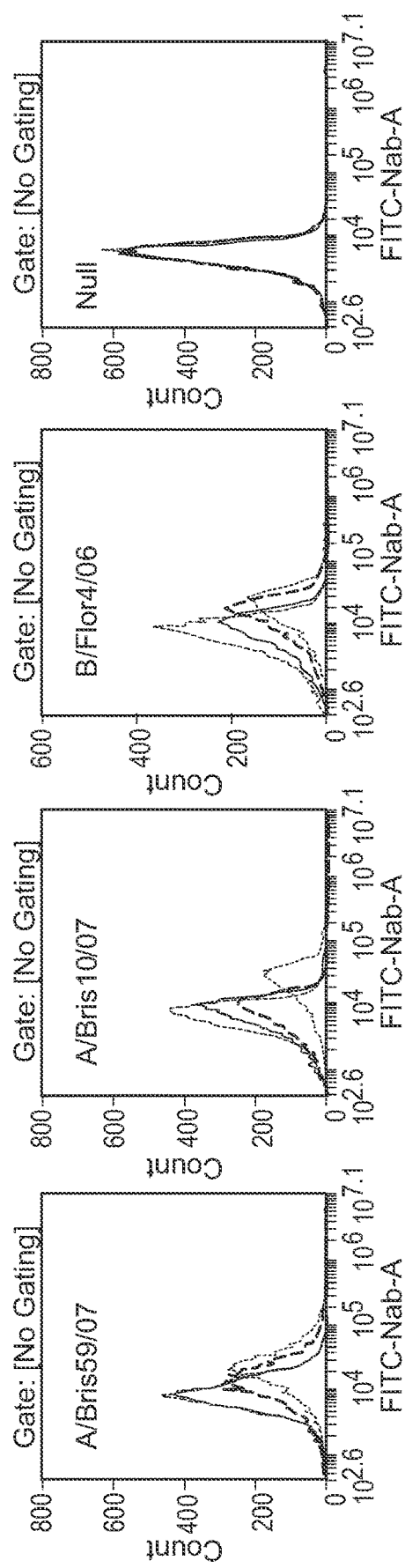
FIGS. 6A-6C graphically depict FACS sorting analysis of selected sequences of FIGS. 4A-4D.
Figure 6B:
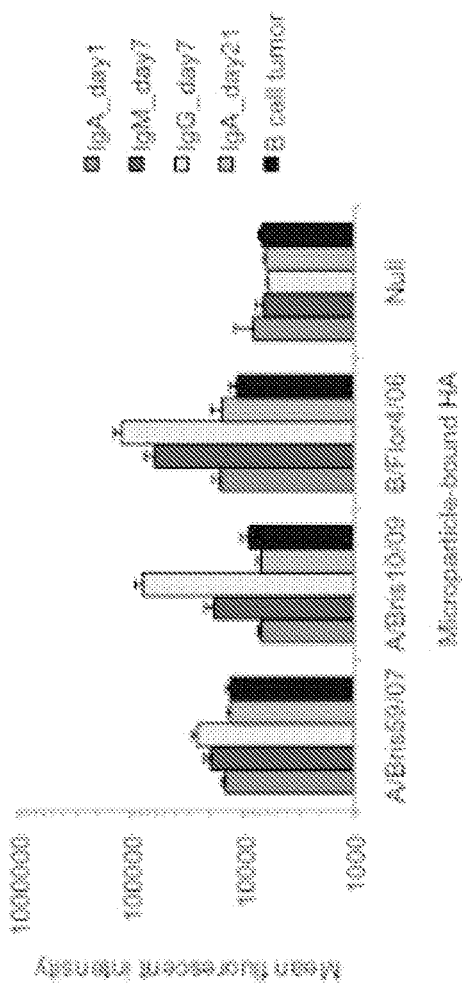
Figure 6C:
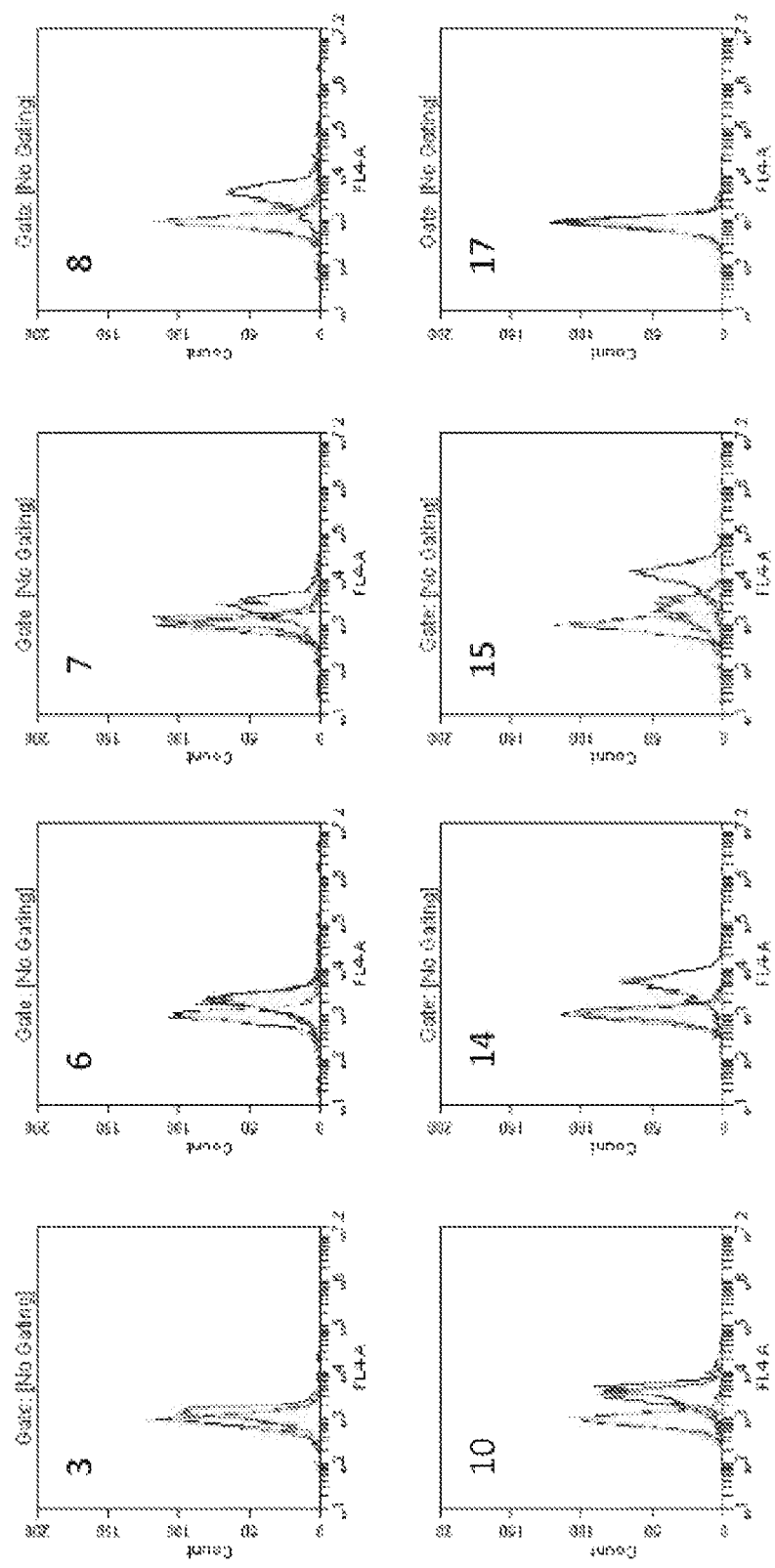
Figure 7A:
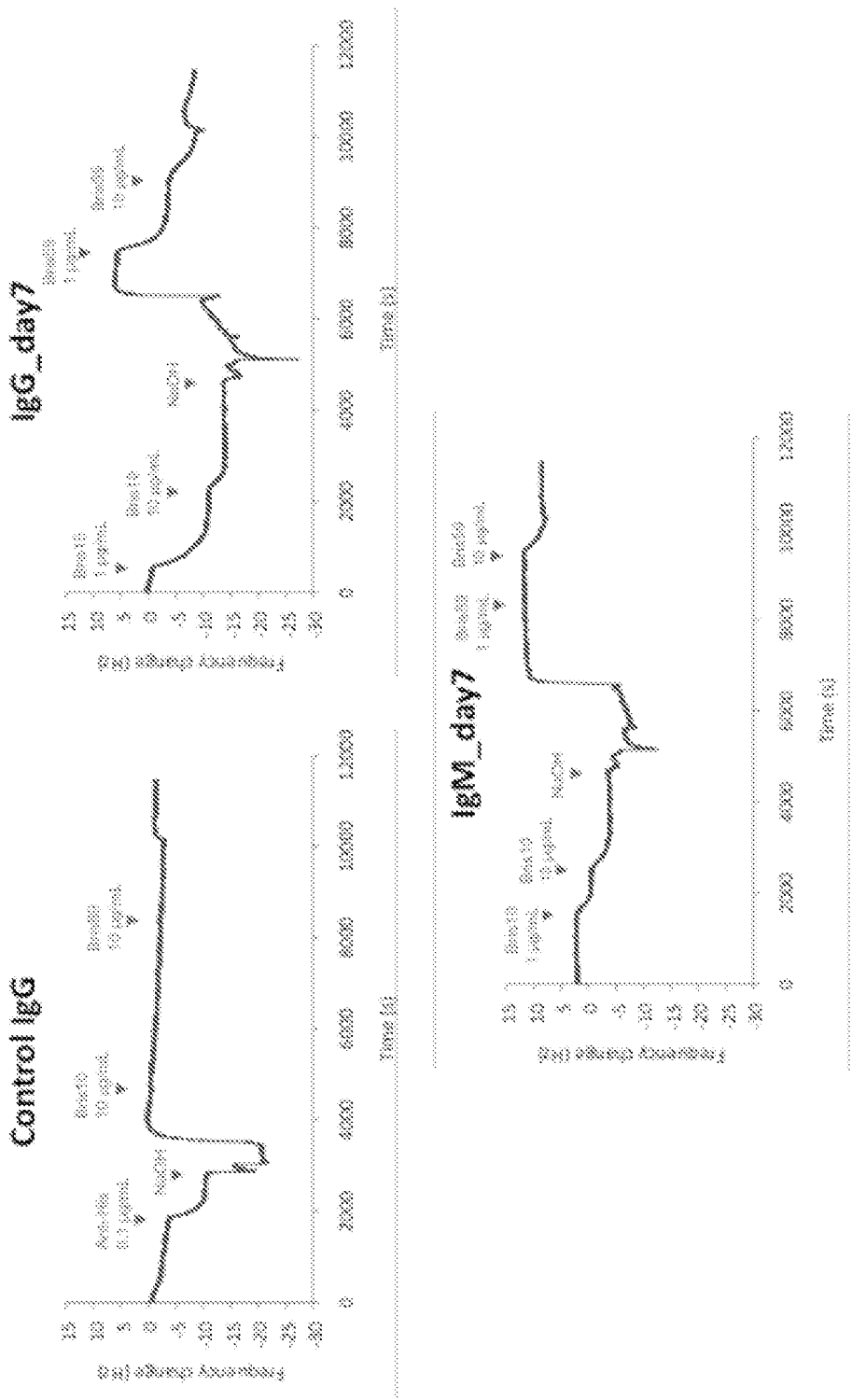
FIGS. 7A-7C graphically depict quartz crystal microbalance (QCM) analysis.
Figure 7B:
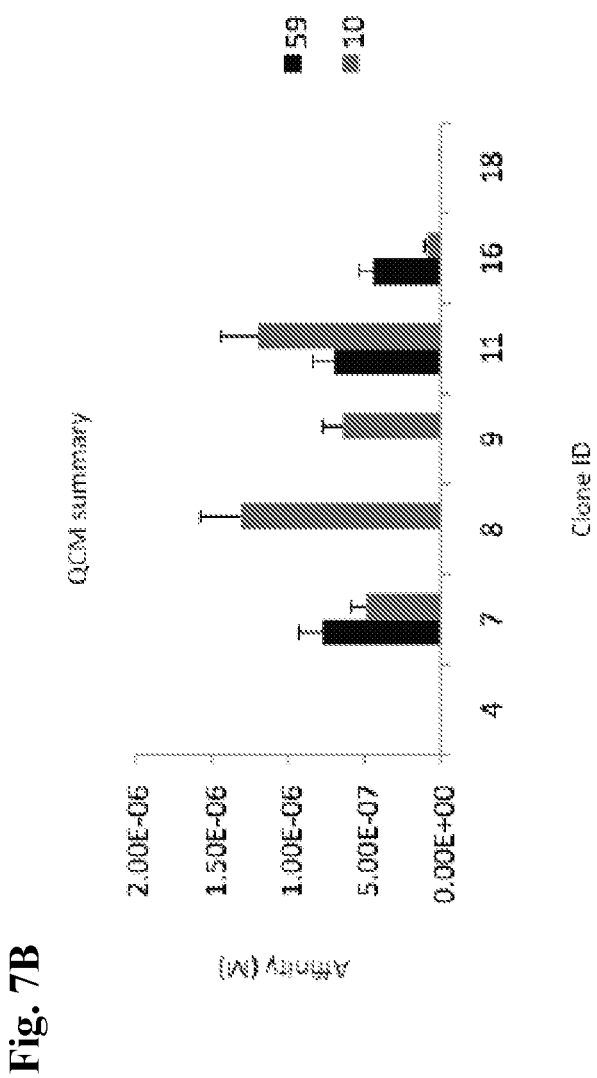
Figure 7C:
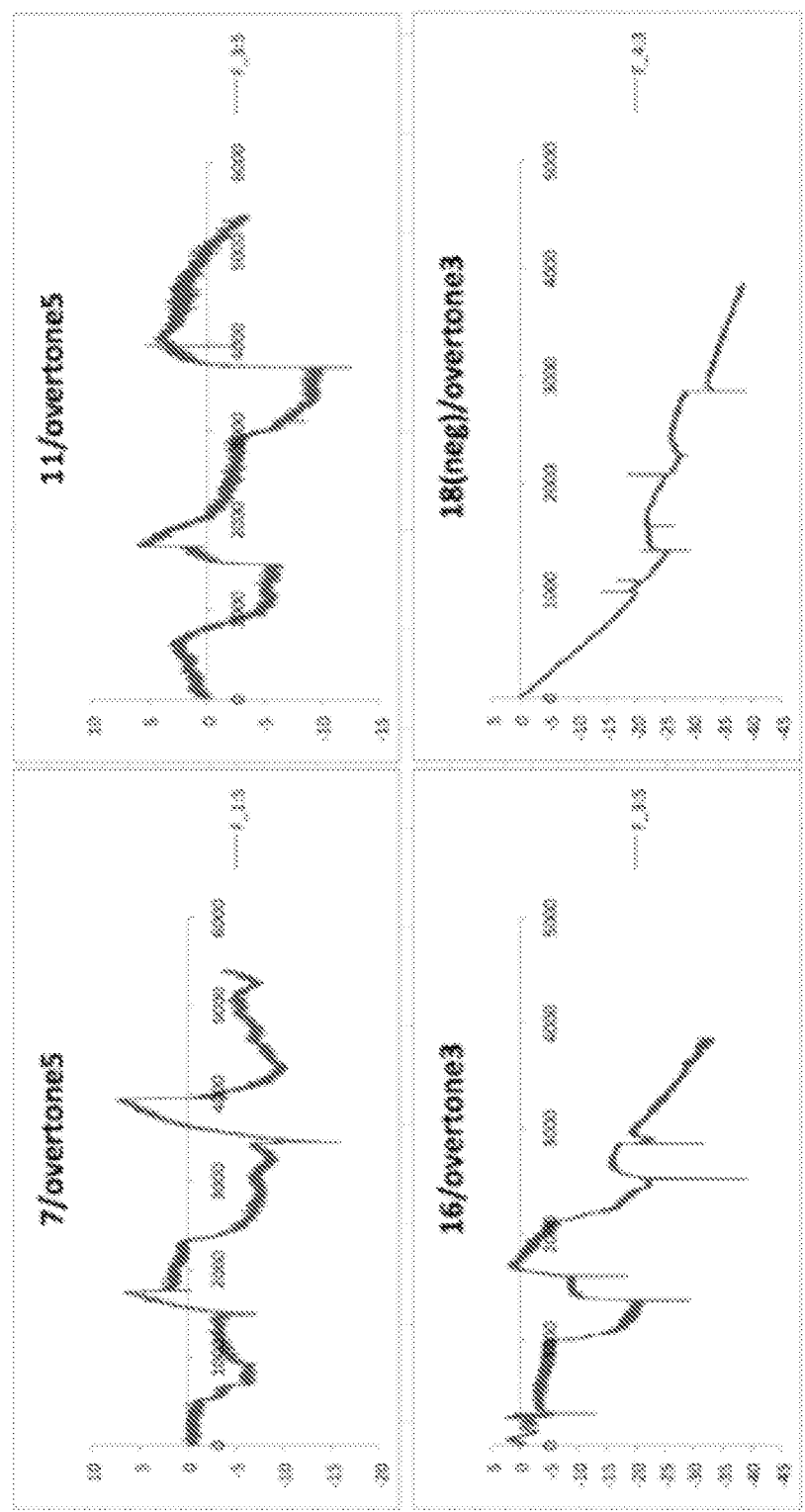

FIG. 6 depicts FACS sorting analysis of the some of the selected sequences of FIG. 4, where the hemagglutinin antigen (Brisbane 10 or Brisbane 59) was coated on beads and the antibody candidates were fluorescently labeled such that correct interaction between the antigen and antibody would result in a shift of the peaks during FACS analysis. Further quartz crystal microbalance (QCM) analysis in FIG. 7 further demonstrates the binding affinity (with kD calculation) of the newly discovered antibody, demonstrating the potential of the methods and compositions described herein for efficiently identifying antibody candidates.

Figure 17A:
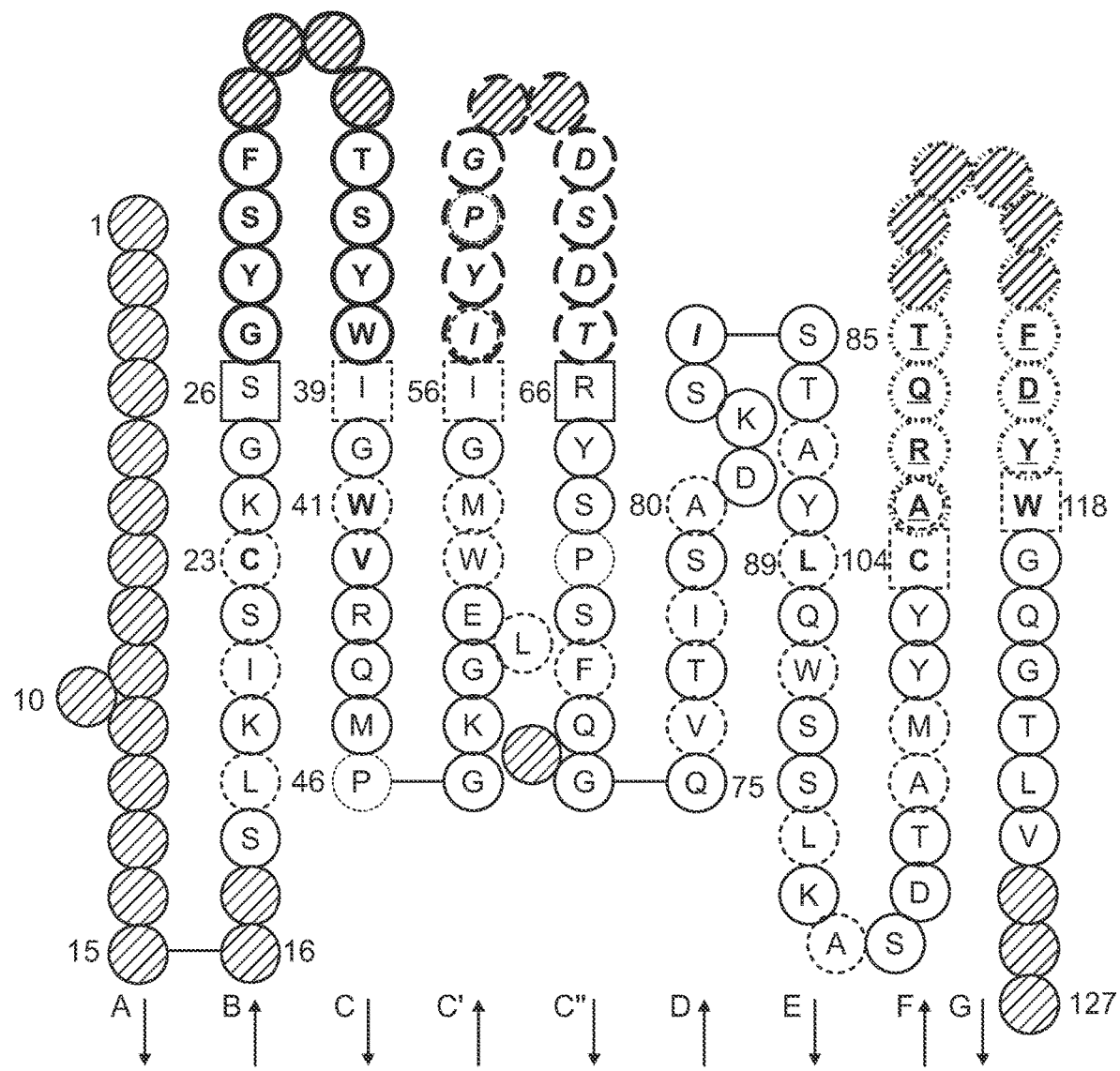
FIGS. 17A-17B depict Collier de Perles (Ruiz and Lefranc (2002) *Immunogenetics* 53:857) representation of the anti-digoxin LMGT/LIGM entry (FIG. 17A) (AR161172; top) and of the corresponding sequencing read found in a subject (FIG. 17B) (FXQ8H8O01CY52L; bottom).
Figure 17B:
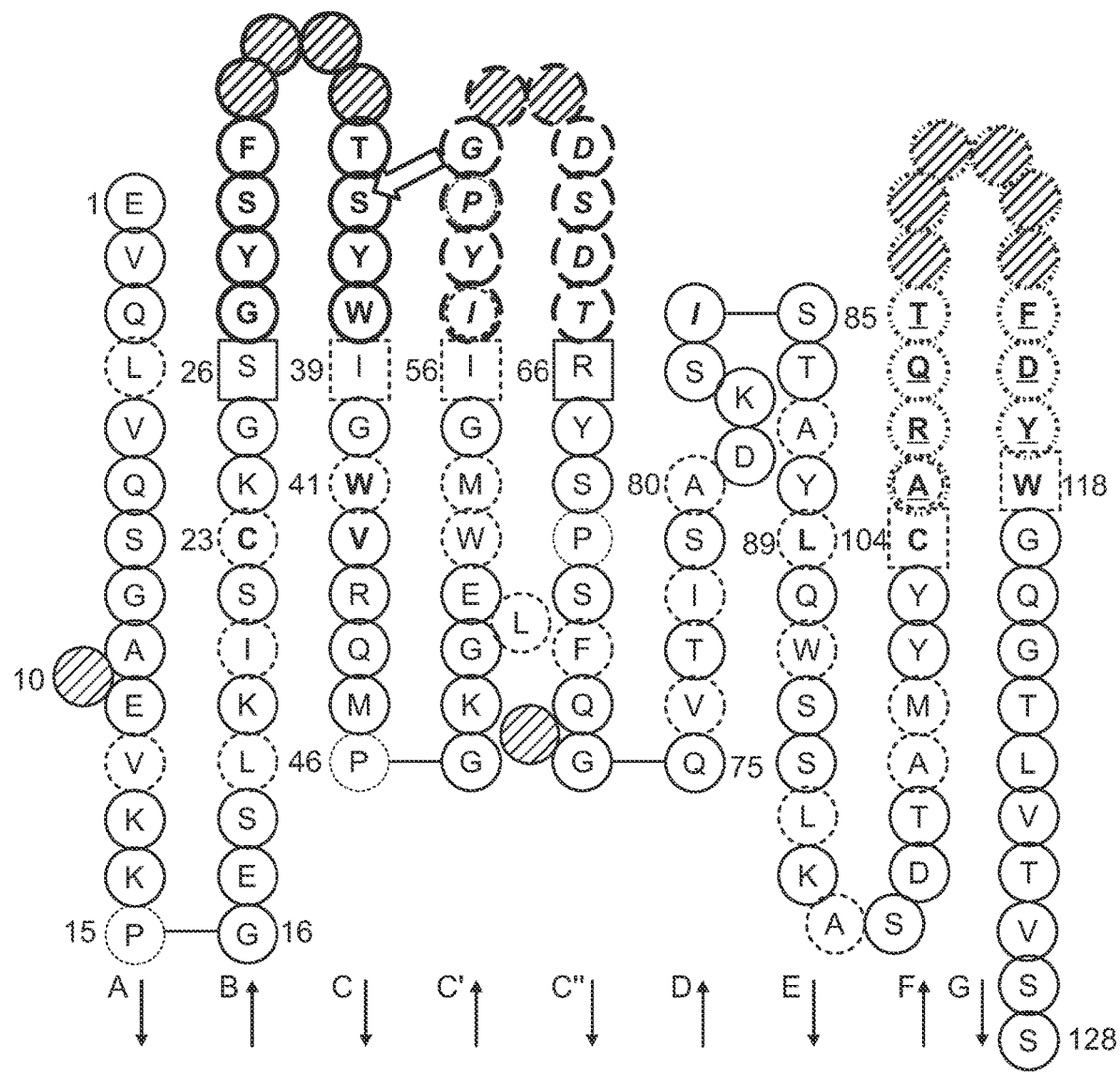

In accordance with aspect of the invention being a personalized diagnostic tool, the reads were aligned to the subset of antibody sequences in the IMGT/LIGM database for which there are known antigen specificities (Lefranc et al., Supra). The CDRs were attempted to be perfectly matched. As the specificity-annotated IMGT/LIGM data set was quite small (fewer than 9,000 sequences), it was not expected that close-to-perfect matches would be found. Surprisingly, however, a single clone of sequences successfully matched an anti-digoxin antibody with a single amino-acid mutation at the periphery of CDR1 (FIG. 17). As the subject experienced two cardiac episodes in 1989 and 1994, it could not be ruled out that he was administered digoxin and developed sensitivity to it. As for the SOM-selected candidates of days 1, 7, and 21, multiple matches were found with various levels of sequence identity, some of which matched influenza-specific or hepatitis-specific antibodies.

The high-throughput sequencing analysis of the human B cell antibody heavy-chain repertoire in response to a vaccine in a time course experiment is described herein. It has been demonstrated herein that, without prior knowledge of antigens or cell activation states, one milliliter blood samples were sufficient to reproducibly track the immune system's dynamics, despite the large diversity and rapid fluctuations of its repertoire. Because of this impressive diversity and the influence of exposure history, the response made during human vaccination is an important component of personalized medicine and required characterization at the individual level. Thus, in the context of personalized medicine, the approach described herein has been successfully demonstrated for clinical diagnostics and therapeutic discovery.

REFERENCES

Freeman et al. (2009) *Genome Res.* 19:1817
Weinstein wt al. (2009) *Science* 324:807
Boyd et al. (2009) *Sci. Transl. Med.* 1:12ra23
Allison (2008) *Nat. Biotechnol.* 26:509
Wrammert et al. (2008) *Nature* 453:667
Draenert et al. (2006) *J. Exp. Med.* 203:529
Pereyra et al. (2008) *J. Infect. Dis.* 197:563
Weinstein et al. (2009) *Science* 324:807
Freeman et al. (2009) *Genome Res.* 19:1817
Glanville et al. (2009) *Proc. Natl. Acad. Sci. USA* 106:20216
Kenneth et al. (2008) Janeway's Immunobiology. Garland Science, New York, 7th ed.
Lefranc and Lefranc (2001) The Immunoglobulin Factsbook. Academic Press, San Diego
Moore and Clayton (2003) *Nature* 426:725
Lerner et al. (1001) *Proc. Natl. Acad. Sci. USA* 88:9705
Brezinschek et al. (1998) *J. Immunol.* 160:4762
Brezinschek et al. (1995) *J. Immunol.* 155:190
Pannetier et al. (1995) *Immunol. Today* 16:176
Pannetier et al. (1993) *Proc. Natl. Acad. Sci. USA* (1993) 90:4319
Marasco and Sui (2007) *Nat. Biotechnol.* 25:1421

Example II

Repertoire Cloning of Paired Antibody Heavy and Light Chains

To rigorously confirm that certain clones are involved in immune responses or to discover new antibodies against antigens of interest, it is desirable to successfully capture both the heavy and light chains of individual antibodies. Because of the lack of methods for capturing paired VH and VL chains in high-throughput, protocols known in the art involve sorting single cells into individual wells and performing PCR for the heavy and light chains serially (e.g., Meijer et al. (2006) *J. Mol. Biol.* 358:764). However, even with automated liquid handling robots, typical throughputs are practically limited to $10^6$ (at great expense). Another popular solution is to capture heavy and light chain repertoires separately, and associate them randomly with each other in expression vectors (Wright et al. (2009) *Proc. Natl. Acad. Sci. USA* 106:19078). However, heavy and light chain pairing is likely far from randomly distributed. Accordingly, these methods do not provide accurate portrayals of the underlying repertoires.

This example describes a general method for capturing paired heavy and light chains in millions of single cells in a single-reaction format. Multiple methods are provided that allow the simultaneous manipulation of millions of cells in parallel, while keeping them isolated from each other to maintain the natural chain pairing.

Methods for Single-Cell Coupling of Chains

Multiple methods are provided for coupling the heavy and light chains from single cells. The overall methods are split into two parts: the chain-linking biochemistry and the cell insulation method. Solutions for each part are primarily chosen independently, and multiple combinations are explored.

Figure 27:
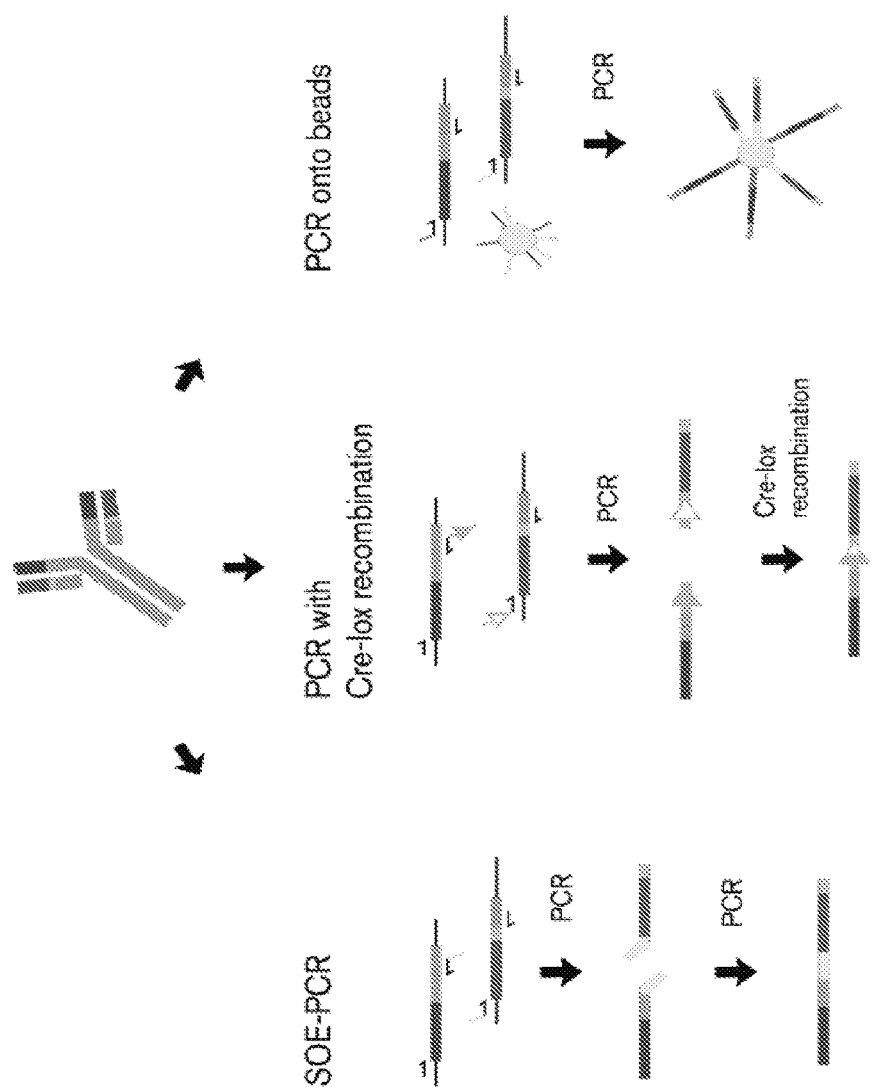
FIG. 27 schematically depicts exemplary chain coupling methods.

Certain of the biochemical methods are PCR based. A choice between amplifying the target chains from the genomic DNA or performing RT-PCR is made based on the nature of the expressed mRNAs. The former requires no reverse transcription step but has the risk of amplifying non-functional receptors, while the latter can benefit from higher copy numbers and should only capture functional, expressed receptors. The physical cross-linking optionally occurs through multiple mechanisms. The first is standard splicing-by-overlap-extension PCR (SOE-PCR) (or fusion PCR or crossover PCR), whereby two of the PCR primers have complementary sequences so that the two amplicons function as primers and they fuse to each other (Heckman and Pease (2007) *Nat. Protocol.* 2:924). One advantage to this method is that the overlap sequence can be designed so that the fused construct is immediately in a usable scFv format. The next mechanism is similar to the SOE-PCR in that tags are incorporated into the PCR primers. In this case, the tags contain loxP sites, so that fusion will occur upon Cre-mediated recombination (Albert et al. (1995) *Plant J.* 7:649; Chapal et al. (1997) *Biotechniques* 23:518). Finally, in the case of emulsion methods, another biochemical option is to amplify both the heavy and light chains onto beads (Diehl et al. (2006) *Nat. Methods* 3:551; Shendure et al. (2005) *Science* 309:1728). One advantage is that the beads can be processed immediately for sequencing on bead-based next-generation sequencing systems. However, this also can be a disadvantage, as it can limit the range of options after chain coupling. An alternative bead-based method is to amplify both chains onto beads, and then couple the chains on the beads. This increases the specificity of the entire process, albeit at increased complexity of the protocol. Each of these methods are summarized in FIG. 27.

The cell insulation methods fall into two main categories: in-cell methods and emulsion methods. For in-cell methods (Embleton et al. (1992) *Nucleic Acids Res.* 20:3831), the cells are fixed in formalin and permeabilized to allow the diffusion of biochemical reagents into the cell. The cell membrane functions as the barrier that prevents cross-contamination of heavy and light chains between cells. The advantages of this general approach are the relative simplicity of fixing the cells and also the ability to serially apply reagent sets to all cells in parallel. However, without intending to be bound by scientific theory, the permeabilization may potentially increase the chance that Ig chains will leak out of cells and lead to cross-contamination.

Figure 28:
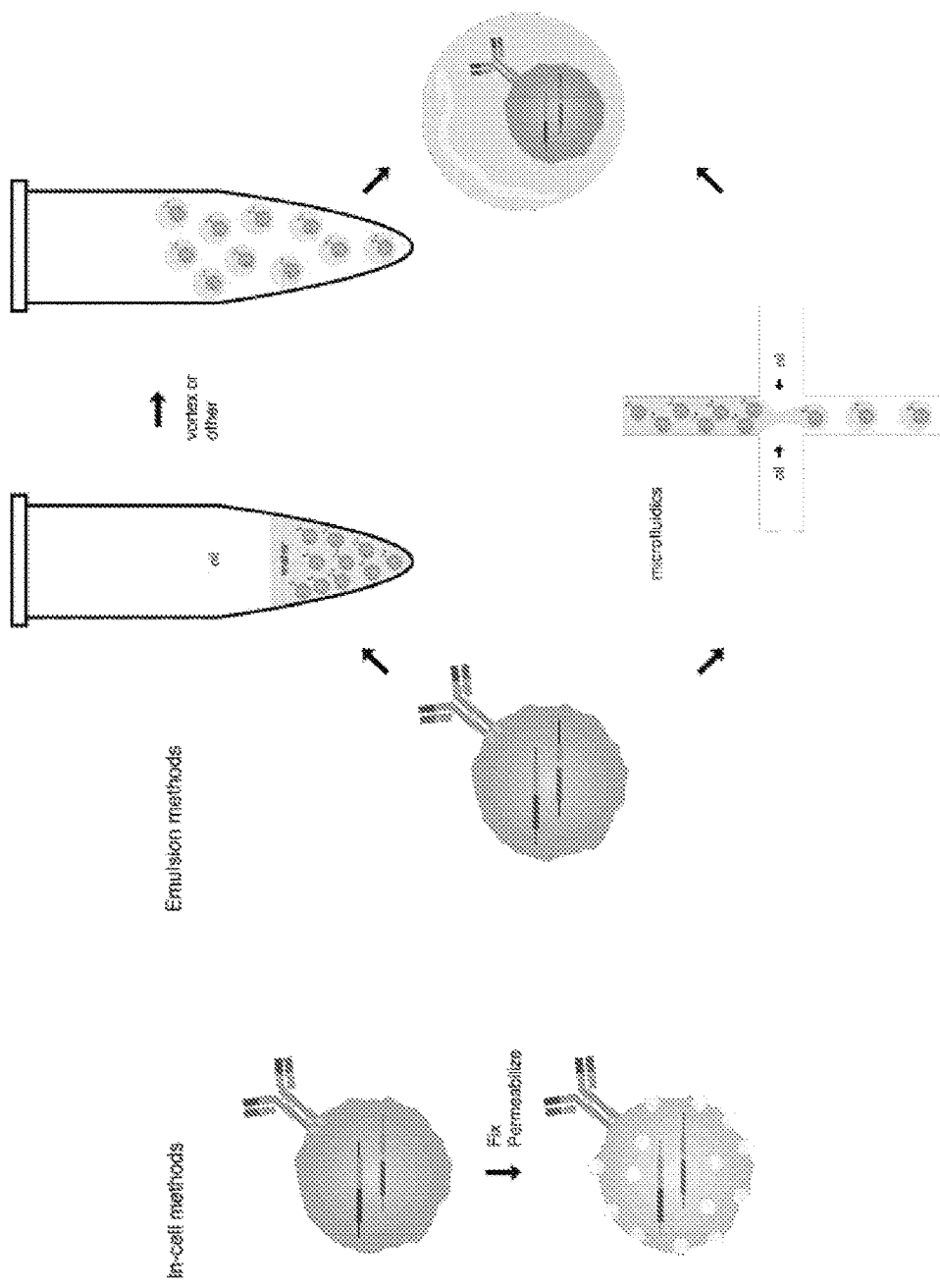
FIG. 28 schematically depicts exemplary cell insulation methods.

For the emulsion-based methods, single cells are placed into individual compartments of a water-in-oil emulsion (Clausell-Tormos et al. (2008) *Chem. Biol.* 15:427; Leamon et al. (2006) *Nat. Methods* 3:541). An advantage of such an approach is that the oil-based separation of compartments can potentially provide nearly absolute insulation from chain cross-contamination. But while the oil-separated compartments can stop any exchange of material between compartments, a common problem of thermal cycling emulsions is that compartments fuse together, leading to non-clonality. Furthermore, it is considerably more difficult to manipulate emulsions. Emulsions are generally formed using physical methods (e.g., vortexing) that depend on Poisson statistics to achieve clonality (Nakano et al. (2005) *J. Biosci. Bioeng.* 99:293; Williams et al. (2006) *Nat. Methods* 3:545). However, this tends to lead to a small fraction of non-clonal compartments, and also leads to a large number of unoccupied compartments. To combat these problems, emulsions are generated using microfluidic technology (Clausell-Tormos et al., supra). A disadvantage to using emulsion methods is that once an emulsion is formed, it is difficult to exchange additional material with the compartments in a controlled fashion. However, a technology for fusing emulsion droplets in a controlled fashion (Tewhey et al. (2009) *Nat. Biotechnol.* 27:1025; Meyers and Gelfand (1991) *Biochemistry* 30:7661) is used to address this disadvantage. Finally, emulsion PCR is optionally performed using conditions that are far from standardized protocols. The cell insulation methods are summarized in FIG. 28.

Figure 29:
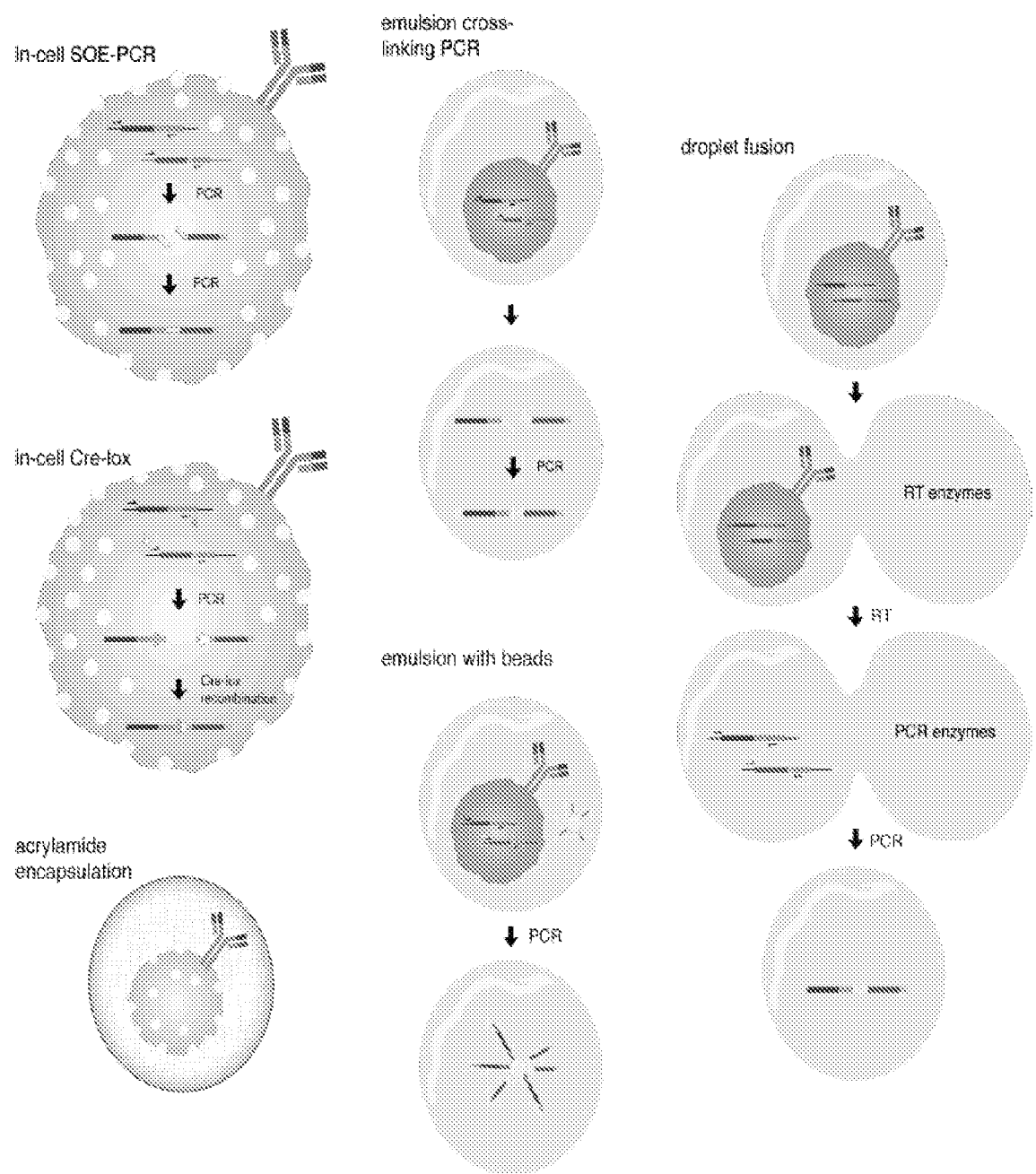
FIG. 29 schematically depicts exemplary methods for coupling heavy and light chains.

With these general considerations, at least six strategies have been identified to achieve robust coupling of heavy and light chains. These strategies are depicted in FIG. 29 and include, but are not limited to: 1) emulsion PCR from gDNA; 2) in-cell RT and SOE-PCR or Cre-Lox coupling; 3) Tth-mediated emulsion RT-PCR; 4) acrylamide-encapsulated in-cell RT-PCR; 5) emulsion PCR onto beads; and 6) emulsion RT-PCR with droplet fusion.

Emulsion PCR from gDNA

This is the simplest emulsion-based approach. The cells are placed in the emulsion along with reagents for a traditional PCR reaction. SOE-PCR is then performed using the gDNA as a template.

In-Cell RT and SOE-PCR or Cre-Lox Coupling

This involves fixing cells in formalin and permeabilizing them using one of several methods (e.g., proteinase K) (Chapal et al., supra; Embleton et al., supra). Because all cells are in solution, a traditional RT-PCR reaction is performed by applying the relevant enzymes serially.

Tth-Mediated Emulsion RT-PCR

It is desirable to capture the Ig chains from the mRNA sequence, as this avoids any non-functional receptor rearrangements and also benefits from the potentially higher copy-numbers of expressed cells. However, emulsion PCR only allows the addition of biochemical reagents one time. Therefore, Tth polymerase, which is capable of performing both RT and PCR (Myers and Gelfand, supra), is used. The performance of the polymerase is characterized and it is used in the context of emulsions.

Acrylamide-Encapsulated In-Cell RT-PCR

This technique is similar to the in-cell RT-PCR, but involves the additional step of encapsulating individual cells in polyacrylamide gels (Yokoyama et al. (1990) *Jinrui Idengaku Zasshi* 35:131), which adds an additional layer of protection from cross-contamination.

Emulsion PCR onto Beads

As an alternative to SOE-PCR for cross-linking the heavy and light chains, the two chains are captured by conventional PCR onto beads (Diehl et al., supra). Each emulsion compartment aims to have a single cell and a single bead. The beads are coated with two different primers: one for the heavy chain and one for the light chain. After breaking the emulsion, the beads are optionally manipulated in a variety of ways. One method, which can increase the specificity of the technique, is to cross-link the two chains on the beads using a modified Cre-Lox system.

Emulsion RT-PCR with Droplet Fusion

As an alternative to using Tth polymerase, emulsion droplets are fused in a controlled manner. In this way, "bags" of enzymes can be serially fused with the emulsion compartments to perform separate biochemical steps, such as RT followed by PCR. This approach allows the use of robust and well characterized enzymes to separately perform RT and PCR.

Design of Primers and Vectors for Multiple Chain-Coupling

Primers are designed for the various RT and PCR protocols described herein. Primers include, but are not limited to: RT primers; multiplex PCR primers for the V and J segments for cDNA (the V primers are specific for cDNA as they will span the L1-L2 exon boundary for the leader sequence); multiplex PCR primers for the V and J segments for gDNA (these are used during emulsion PCR); PCR primers that are immobilized on beads; PCR primers that contain complementary tags for overlap PCR (it is important that the overlap is suitable as a linker sequence for an scFv chain and will place the heavy and light chain in-frame); PCR primers that contain LoxP sites for cross linking heavy and light chains (Chapal et al., supra); and primers that incorporate common sequences into primers for easily adapting sequences to next-generation sequencing and for easily cloning sequences into various expression vectors (i.e., for various protein display technologies). Furthermore, vectors are designed that are suitable for a variety of display technologies, using standard vectors through the use of Gateway cloning protocols.

Optimization of PCR Conditions for Cross-Linking PCR

PCR reaction conditions are optimized in several stages. First gDNA or mRNA prepared from clonal populations of cells is used to ensure that the heavy and light chains are cross-linked in an idealized environment. After robust PCR conditions are achieved, Ig chains (from whole cells) are cross-linked in solutions using either SOE-PCR or Cre-Lox recombination. Microfluidic technology is used to place single cells into emulsion compartments 100 µm in diameter (approximately 0.5 nL) (Clausell-Tormos et al., supra). In certain embodiments, the compartment size is reduced to ensure that the emulsion does not break during thermal cycling. A cell concentration equivalent to 20 µm emulsion compartments, which would correspond to about $1.5 \times 10^6$ cells in a typical 50 µL reaction, can be used.

Optimization of Cell Insulation Protocol

Heavy and light chains are cross-linked in single cells. Using a single monoclonal cell line, multiple methods for insulating single cells and performing PCR are performed. After cell fixation using formalin, permeabilization of the cell is performed (detergents such as Nonidet P40 (Embleton et al., supra) may be too aggressive for such use). Proteinase K digestions can be used to permeabilize cells by chewing away membrane proteins and pores (Bagasra (2007) *Nat. Protocol.* 2:2782). Overlapping tags are used to cross-link the two amplicons during PCR. An alternative method involves incorporating LoxP sites into the two internal primers and to cross-linking the two chains via Cre recombination (Chapal et al., supra).

Characterization of Cross-Contamination in Chain Cross-Linking

Following successful cross-linking of heavy and light chains in single cells, the level of cross-contamination is measured. The Embleton et al. study found that when mixing two known hybridoma cell lines at 1:1 and 9:1 ratios, they observed no mispaired amplicons (Embleton et al., supra). However, these ratios are far too lenient compared with real effective ratios from complex mixtures. Accordingly, the level of mispairing using two cell lines in ratios up to $10^6$:1 are characterized. Furthermore, the method used in Embleton et al. relied on capturing clones from the "rare" cell line using traditional screening methods. These methods are not practical when attempted on more stringent cell ratios, as the rare cell type may never be observed. To address this, PCR-based methods are provided that are far more sensitive than the method used in Embleton et al.

PCR-Based Cross-Contamination Assay

A TaqMan assay is used in order to quantify the level of cross-contamination. Without intending to be bound by scientific theory, after performing the single-cell cross-linking PCR, four species are expected in the combined mixture: A-a, A-b, B-a, B-b (where A and B are the two clones and A versus a is heavy versus light chain). As the scFv linker sequence connecting the heavy and light chains is the same for all species, one TaqMan probe with fluorophore X is used to hybridize to this common portion.

Separately, four constructs of the same length that are amplified by only one of the four primer combinations, which all contain a common unique sequence that hybridizes to a second TaqMan probe with fluorophore Y are used. The synthetic constructs are set to known concentrations. A real time PCR reaction is used in which the experimental mixture of four constructs is split into four separate tubes. Each tube is then amplified with one of the four primer combinations along with the corresponding synthetic template at a known concentration. Each tube is also amplified in the presence of both TaqMan probes. Fluorescence is measured at both wavelengths at each cycle. Ultimately, the fluorescence measurements of Y are used as a standard to compare the relative concentrations of the various species in the starting mixture.

Quantification of Cross-Contamination

Following PCR-based mispairing, the levels of cross-contamination at different ratios of the two cell lines are measured. For in-cell PCR methods, one source of cross-contamination is mRNA/cDNA that has leaked into the supernatant solution. In order to combat this problem, different permeabilization parameters, e.g., such as modifying proteinase K digestion, times are assayed.

For emulsion-based methods, one source of cross-contamination is the existence of non-clonal compartments. This can occur during the formation of the emulsion when multiple cells are placed into a single compartment, as well as during thermal cycling of the emulsion, where different emulsion compartments can fuse together. In order to avoid non-clonality at the emulsion formation step, microfluidic platforms are provided to determine emulsion formation methods that are easier to control. A variety of different emulsion oils and/or surfactants and/or reduced size emulsion compartments are provided to avoid droplet fusion during thermal cycling.

The level of cross-contamination is obtained using mixtures of two known cell lines (A and B) at A:B ratios ranging from 1:1 through $10^6$:1. As the concentration of A increases relative to B, the likelihood that a B chain will mispair with an A chain will increase, leading to a higher relative amount of mispaired B chains. Given a complex mixture of lymphocytes obtained from blood, the lowest frequency level for which heavy-light chain pairing is accurately ascertained is determined.

Creation of scFv Libraries from Complex Samples

Complex blood-derived samples of lymphocytes are used to generate new 454 sequencing libraries. Certain of the vaccination samples collected are sequenced to confirm reproducibility.

Analysis of Properties of Chain Pairing Including Total Diversity Estimates

The newly generated full scFv data is run through an informatics pipeline to determine VDJ usage and split the data into unique clones. This data provides the most accurate estimates to date of expressed antibody diversities. Furthermore, many studies assume that heavy and light chain pairing is independent and random. However, without intending to be bound by scientific theory, it is believed that generating actual paired heavy and light chains will show that the distribution is far from random, and provides novel methods to characterize it.

Characterizing Multiple Solutions to Influenza H1N1 Infection

A new protocol to collect blood samples from volunteers who will be immunized to the H1N1 influenza strain ("swine flu") is provided. The protocol selects volunteers who have not been exposed to swine flu and also volunteers that contracted the disease and fought it successfully. The immune responses of people who have been exposed to the virus can thus be compared with the immune of to those who have not been exposed to it (though they likely contracted some other strain of influenza at some time in their history).

Furthermore, each sample obtained from a subject that successfully fought H1N1 infection contains a unique immunological solution to combating the virus. Commercially available protein preparations of glycosylated H1N1 hemagglutinin and neuraminidase are obtained, and the expressed scFv libraries from each individual is cloned using an in vitro display system (e.g., phage display). Anti-flu antibodies are functionally enriched using standard panning techniques, and the resulting enriched scFv pools are sequenced using a next-generation sequencing technology. This allows the direct observation of how different individuals fight H1N1, and also confirms the results obtained by sequencing the repertoire without panning against antigen.

In addition, samples are saved in order to express the putative responding antibodies and characterize their interaction against larger antigen libraries.

Example III

High-Throughput Characterization and Selection of Antibody Repertoires Against Pathogen Libraries A similar approach to that described above is used to characterize antigen-antibody interactions in high-throughput. Current technologies require selecting for new antibodies against a single antigen at a time (Carter (2006) *Nat. Rev. Immunol.* 6:343). A typical experiment involves purifying and immobilizing some antigen of interest, and exposing it to some type of protein display technology encoding a library of candidate antibody sequences (typically in scFv format). After multiple rounds of panning, washing and amplifying, a small number of clones is sequenced and carried through for further analysis. Alternatively, an animal is immunized with the antigen of interest to generate a polyclonal response. Antigen-specific lymphocytes are then harvested (to obtain the polyclonal response) and screened to obtain high-affinity monoclonal antibodies. Id. Methods are provided that allow the selection of new antibodies against multiple antigens in parallel.

Two chains of nucleic acids are coupled together. Antibodies can be encoded in a protein display format (e.g., phage (Clackson et al. (1991) *Nature* 352:624; McCafferty et al. (1990) *Nature* 348:552), yeast (Boder and Wittrup (1997) *Nat. Biotechnol.* 15:553; Boder et al. (2000) *Proc. Natl. Acad. Sci. USA* 97:10701; Chao et al. (2006) *Nat. Protoc.* 1:755), or ribosome display (Zahnd et al. (2007) *Nat. Methods* 4:269)) and antigens are packaged with their coding information (e.g., peptide libraries in display format, or whole virus particles). The two libraries are allowed to interact and interacting complexes are selected (Bowley et al. (2009) *Proc. Natl. Acad. Sci. USA* 106:1380). The coding chains of the interacting antigen and antibody are then physically coupled using methods similar to those described herein. This will allow the characterization of antigen-specific antibodies for multiple antigens in parallel. Ultimately, this type of approach will be scaled up to assay very large antigen libraries against very large antigen libraries (e.g., entire human proteome, all known viral proteins and the like).

One unique aspect of the methods described herein is that protocols for capturing full antibodies will have already formatted the captured repertoires in an scFv format, allowing for easy expression using one of the protein display technologies. Compared with many previous studies that generate random antibody libraries, each antibody in the libraries described herein are generated by a functioning, natural immune system. In this way, millions of years of evolution can be used to provide efficient antibody libraries that will allow one of skill in the art the ability to quickly discover new functional antibodies.

Methods for Multiplex Affinity Selections

One approach for capturing antigen-antibody (Ag-Ab) interactions involves placing single Ag-Ab complexes into individual emulsion compartments. In order to properly display antibodies and antigens, several choices are suitable including, but not limited to: phage, yeast, or ribosome display, whole viral particles (in the case of viral antigens). Ribosome display offers the largest potential libraries and is fully in vitro. Phage display is the oldest method and provides large library sizes. Yeast display offers the smallest library sizes, but is particularly appropriate for antigen libraries as it can carry larger payloads and has glycosylation machinery (Hoogenboom (2005) *Nat. Biotechnol.* 23:1105). Use of whole virus particles provides access to the most realistic antigens, but has a potentially large genome and additional safety concerns for lab work. It is important to note that because naturally expressed repertoires are cloned, the maximum library size of all of these technologies is expected to be sufficient to capture the diversity of sequences in any practical blood samples or antigen sets. Phage-Ab against yeast-Ag is a promising general approach for library-against-library selections (Bowley et al., supra). Yeast is well suited to larger protein fragments, the two systems can replicate independently. Additionally, ribosome-Ab against ribosome-Ag is also utilized as this system is entirely in vitro. This will enable coupling methods that do not depend on emulsions. Finally, these methods are also used against whole viral particles.

For the phage-based systems, an emulsion-based method is used to capture interacting antibodies and antigens. After several or more rounds of affinity selection, phage-Ab-yeast-Ag duplexes are double-purified using magnetic sorting or FACS to eliminate non-interacting particles. Id. These duplexes are then placed into individual emulsion compartments where a cross-linking PCR reaction will physically associate the Ag and Ab coding sequence. These cross-linked species are then prepared for next-generation sequencing and interactions are detected by analyzing the sequencing data. When the Ag used is whole virus particles, the genome sequence can be relatively large. However, as a relatively small number of unique viruses is assayed, the method is sufficient to find a unique barcode to identify the specific strain of virus.

For the fully in vitro ribosome display system, in addition to attempting the emulsion based protocol, non-emulsion methods are used. A proximity ligation assay (Soderberg et al. (2006) Nat. Methods 3:995) is used to capture unique tags on both Ag and Ab libraries. These tags will supply enough information to obtain the full corresponding sequences.

Assaying a Positive Control for Ab-Ag Interaction

A single Ag-Ab pair that is known to interact with high affinity and specificity is cross-linked. An scFv fragment is created in a phage display format from a sequence known to bind to influenza neuraminidase, along with the corresponding antigen fragment in a yeast display format. Preparations of the two species are allowed to interact in solution, and methods described herein are used to cross-link the two coding chains.

In a first method, only the flu antibody and flu antigen are allowed to interact in solution, and PCR is used to cross-link the two coding strands. The primers are assayed for cross-linking via overlap PCR and/or Cre/lox recombination. Likewise, the same positive control Ab and Ag pair are placed into a commercial ribosome display system the pair is allowed to interact. Reverse transcription and cross-linking PCR are performed using the methods described herein to assay for successful fusion of the Ab and Ag coding strands.

Quantification of Double-Purification Enrichment for Interacting Ab-Ag Pairs

In addition to the positive control Ab-Ag pair, a second, orthogonal Ab-Ag pair, along with a phage-Ab that is not specific for any antigen used and a yeast-Ag that is not specific for any of the antibodies are chosen. After allowing the mixture to interact, cognate Ab-Ag complexes are purified by flow cytometry of yeast cells using fluorescent anti-phage antibody, as described in (Bowley et al., supra). From the sorted cells, cross-linking and PCR are performed and the amount of contaminating DNA from the phage and yeast that are expected to not show binding affinity is measured. In order to reduce the amount of background, double-purification is performed followed by amplification of the phage and yeast libraries separately. Id. For the ribosome display system, two different affinity tags are encoded into the Ag library and the Ab library (e.g., His and flag tags). His-tag purification is then performed followed by flag-tag purification to obtain interacting particles.

Quantification of Insulation of Ab-Ag Complexes in Emulsions

Figure 30:
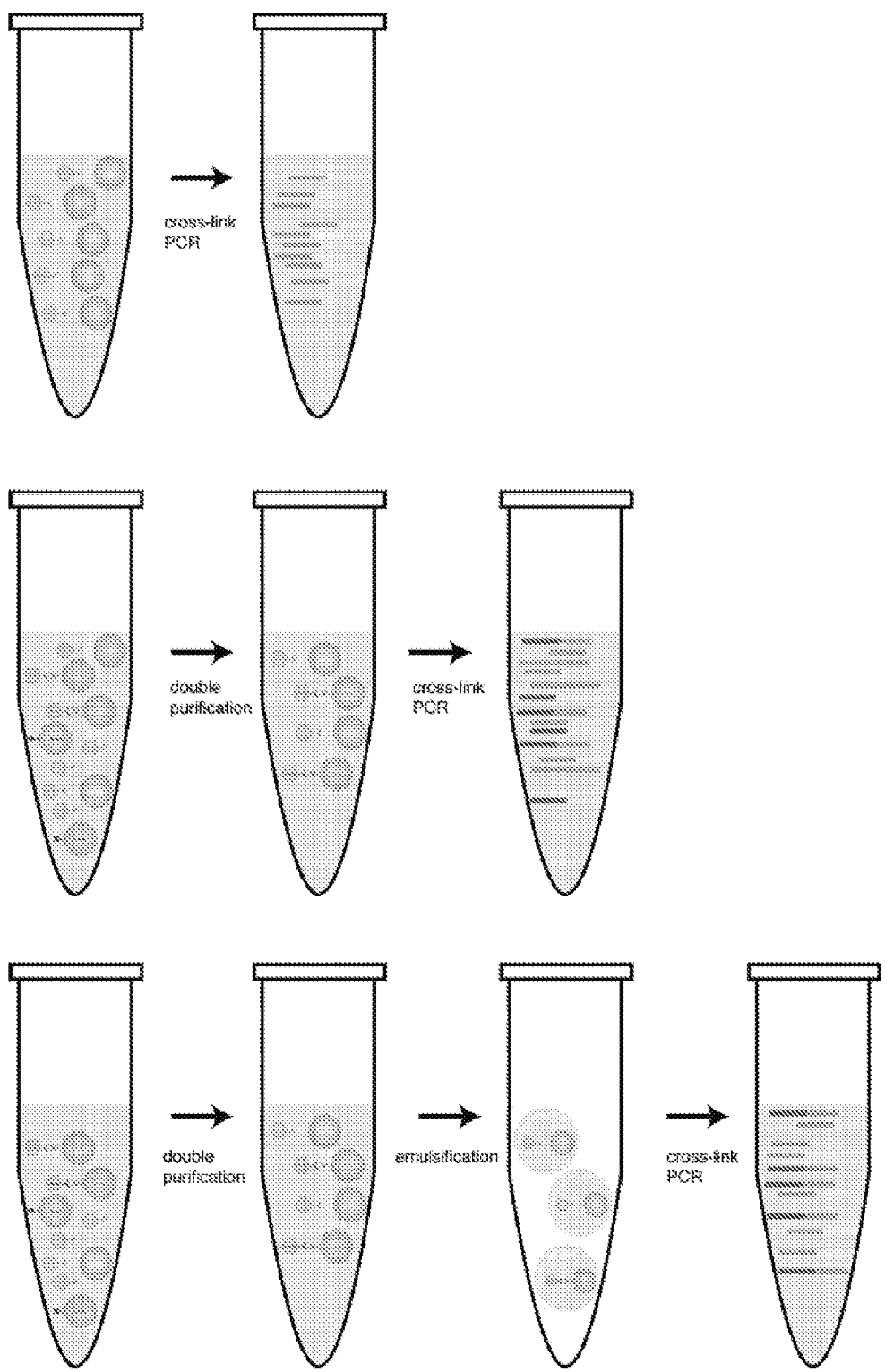
FIG. 30 schematically depicts exemplary methods for multiplex affinity selections.
Figure 31:
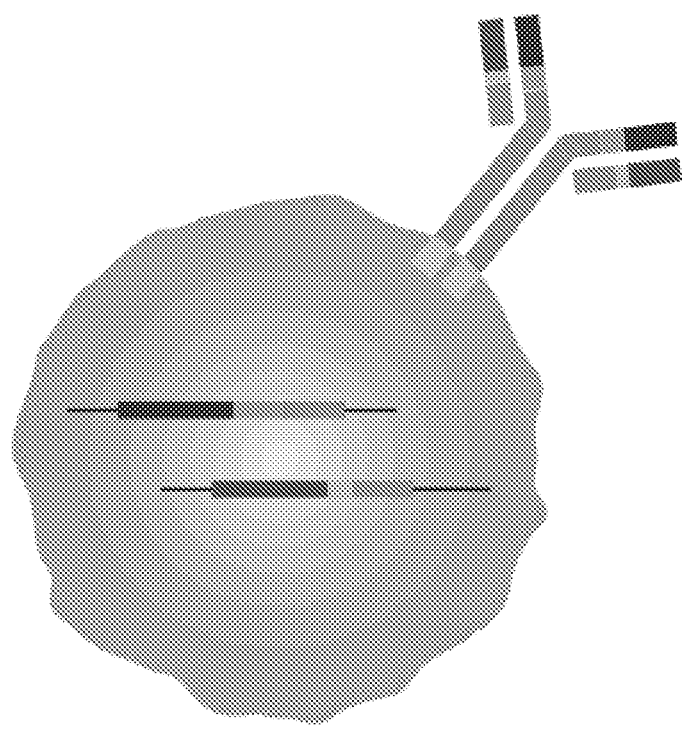
FIG. 31 depicts an immune cell presenting an antibody containing a heavy chain and a light chain.
Figure 32:
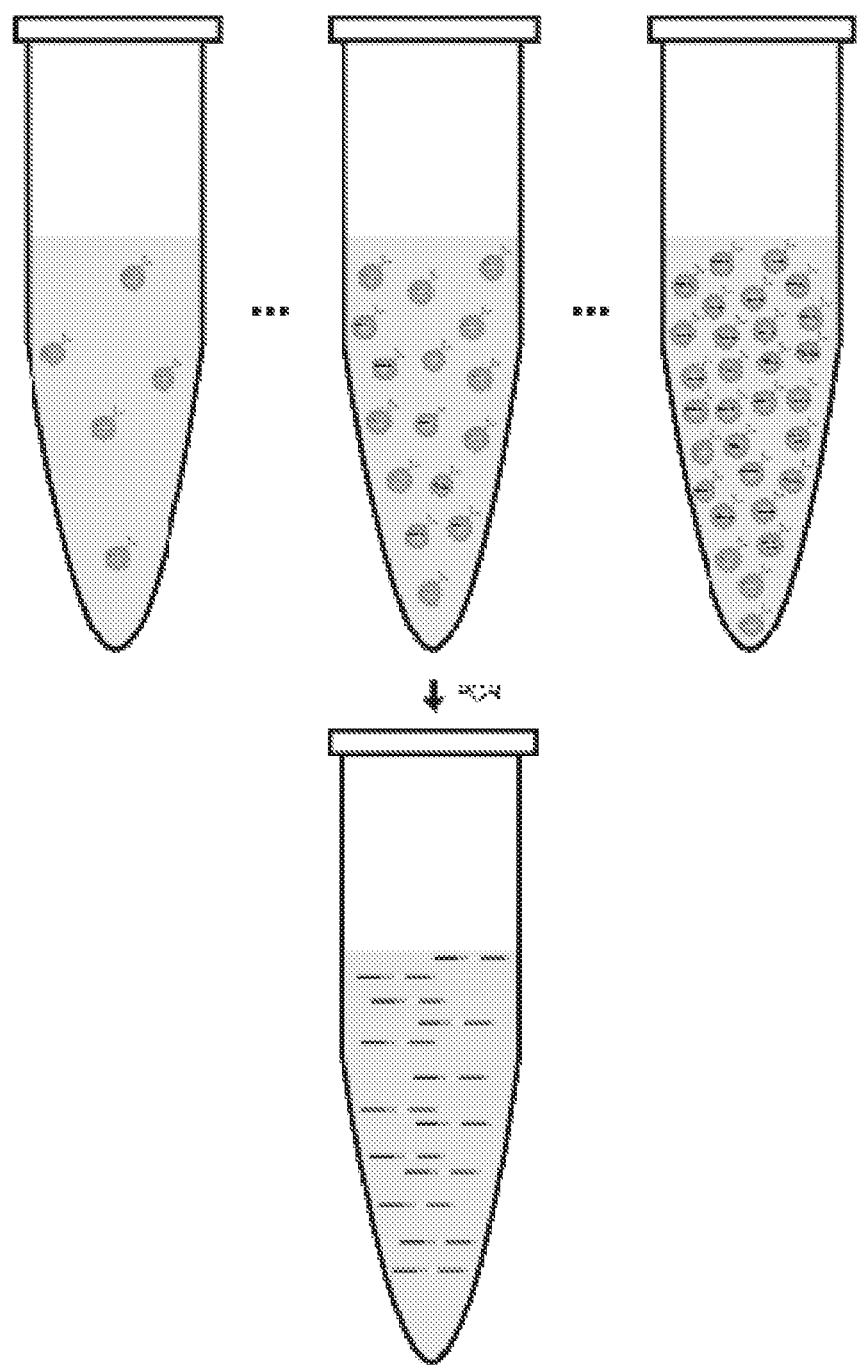
FIG. 32 schematically depicts a method of optimizing cross-linking PCR.
Figure 33:
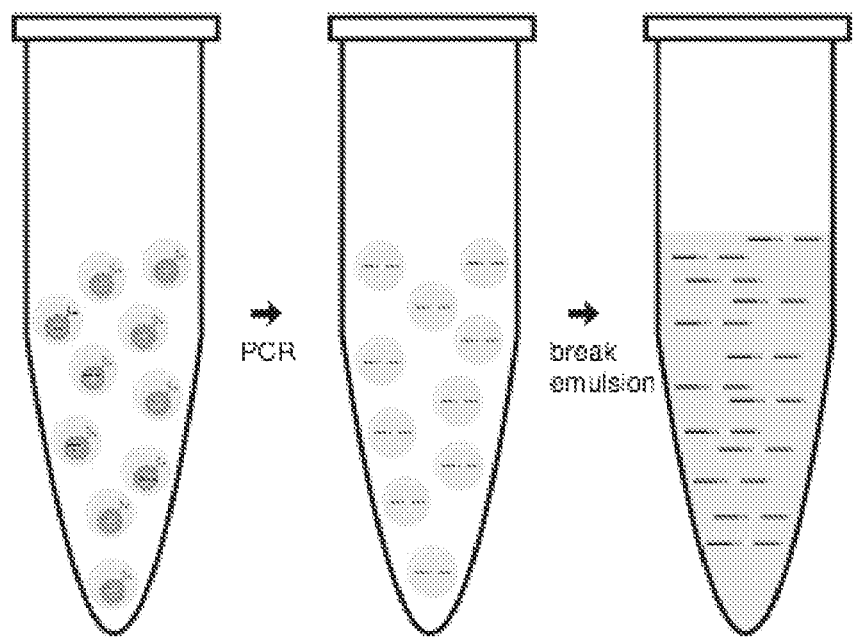
FIG. 33 schematically depicts a method of optimizing cell insulation.
Figure 34:
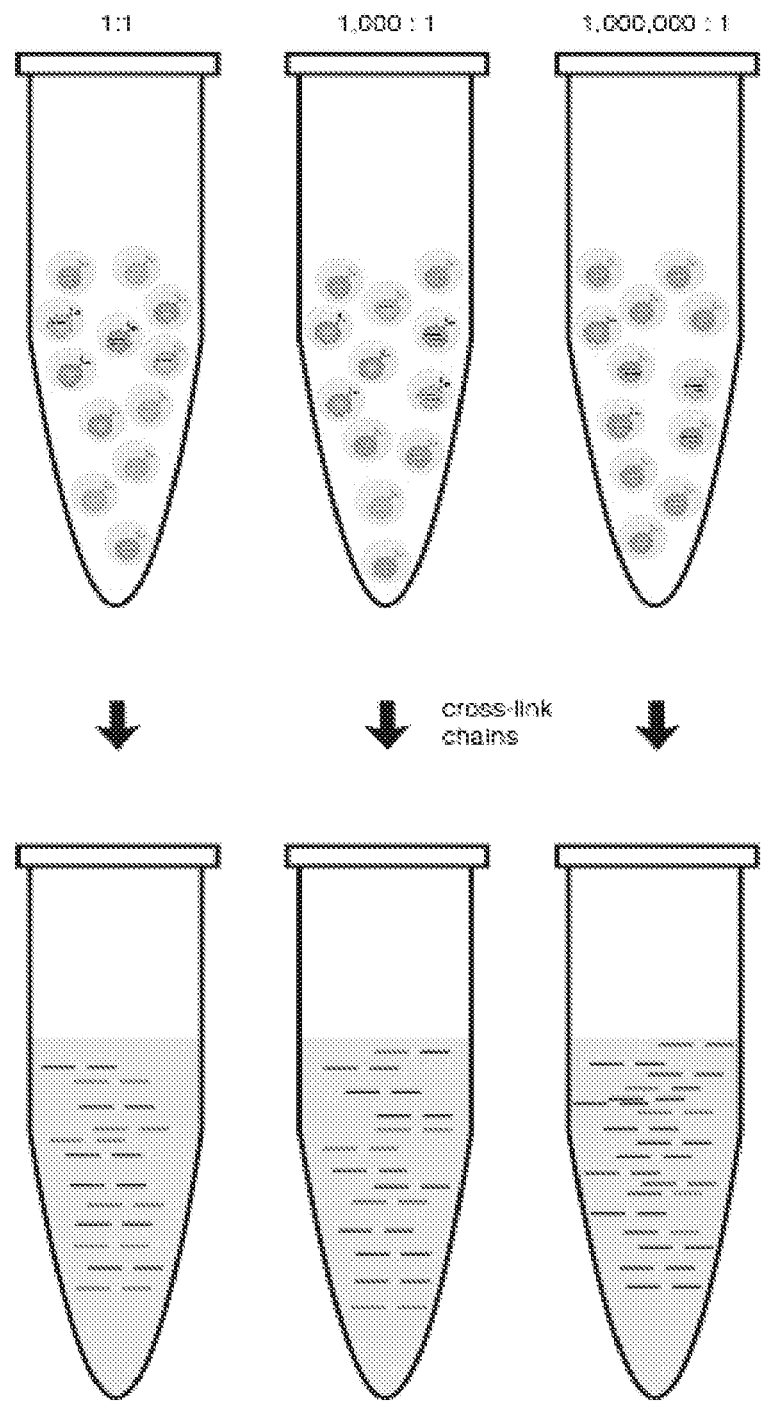
FIG. 34 schematically depicts a method of characterizing cross-contamination.
Figure 35:
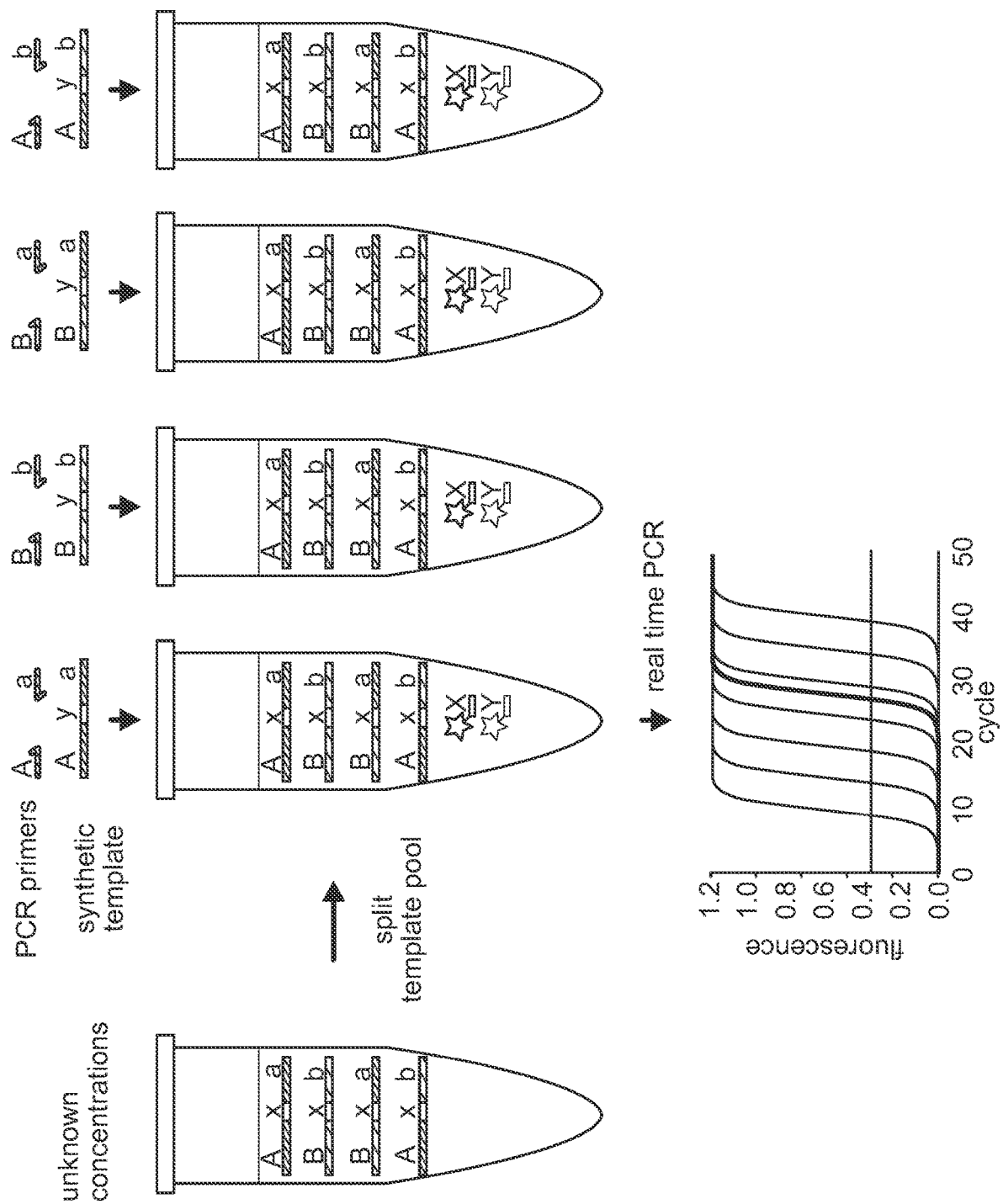
FIG. 35 schematically depicts a method of characterizing cross-contamination using a TaqMan assay.
Figure 36:
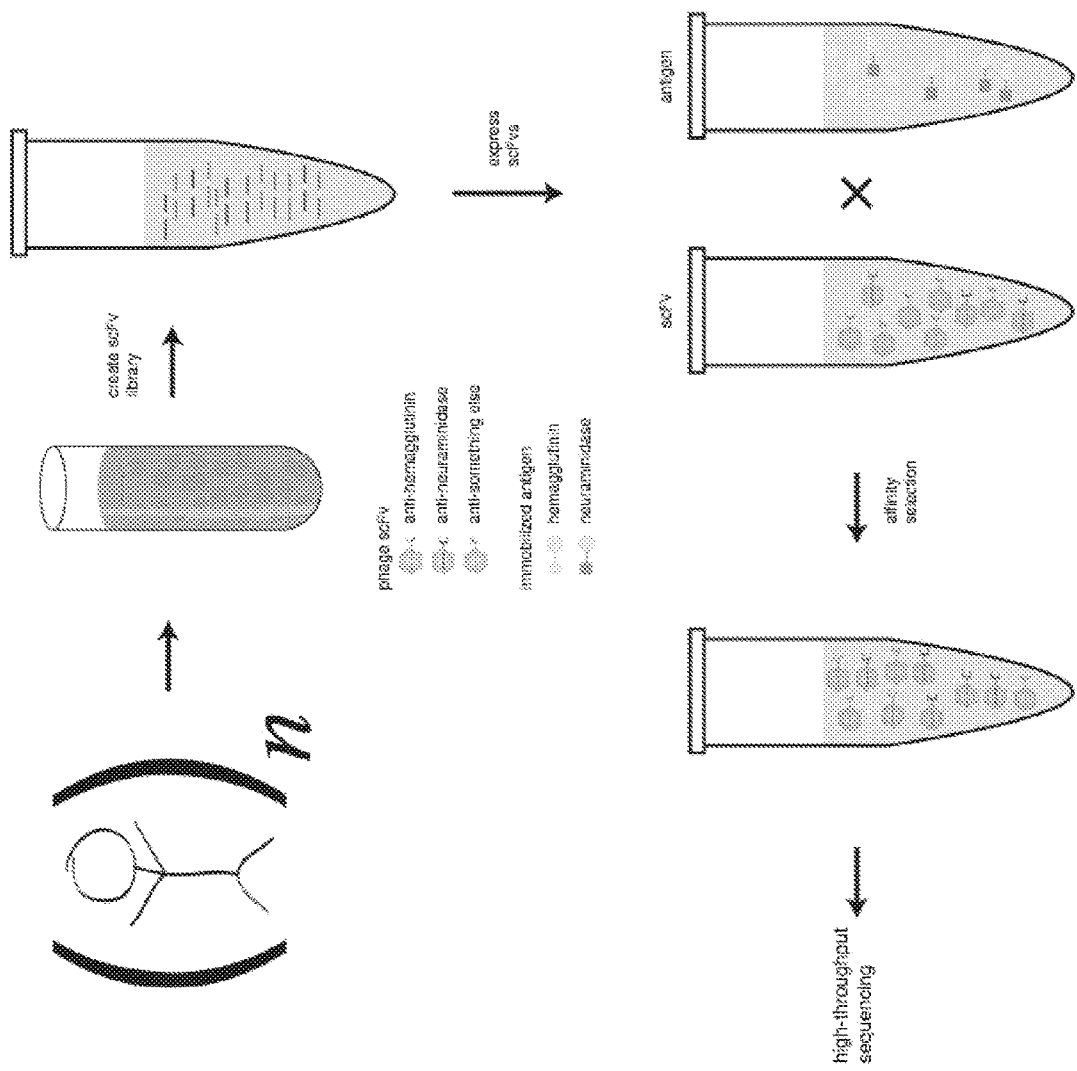
FIG. 36 schematically depicts generation of an antibody-antigen lookup table for influenza virus.
Figure 37:
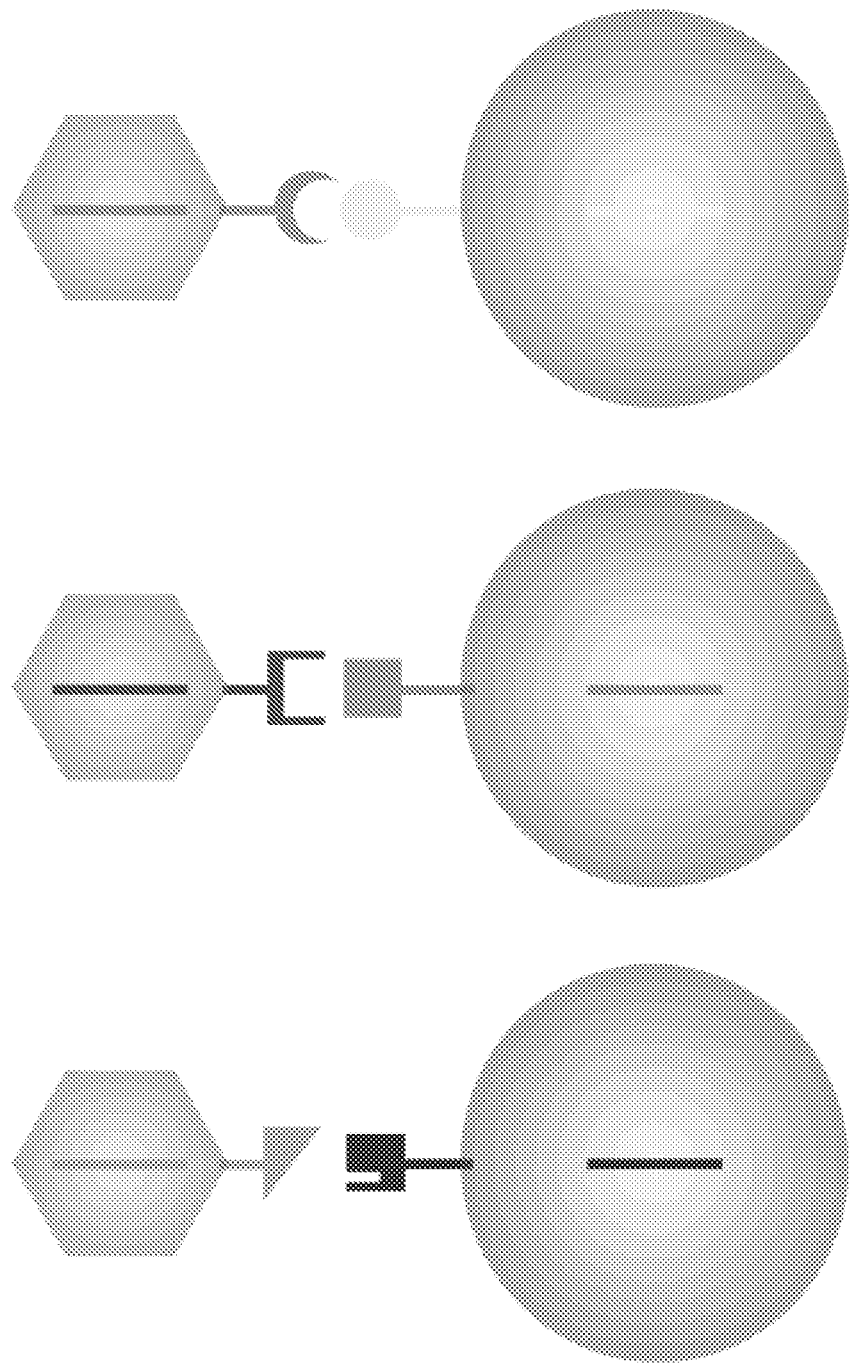
FIG. 37 schematically depicts antibodies coupled to antigens.
Figure 39:
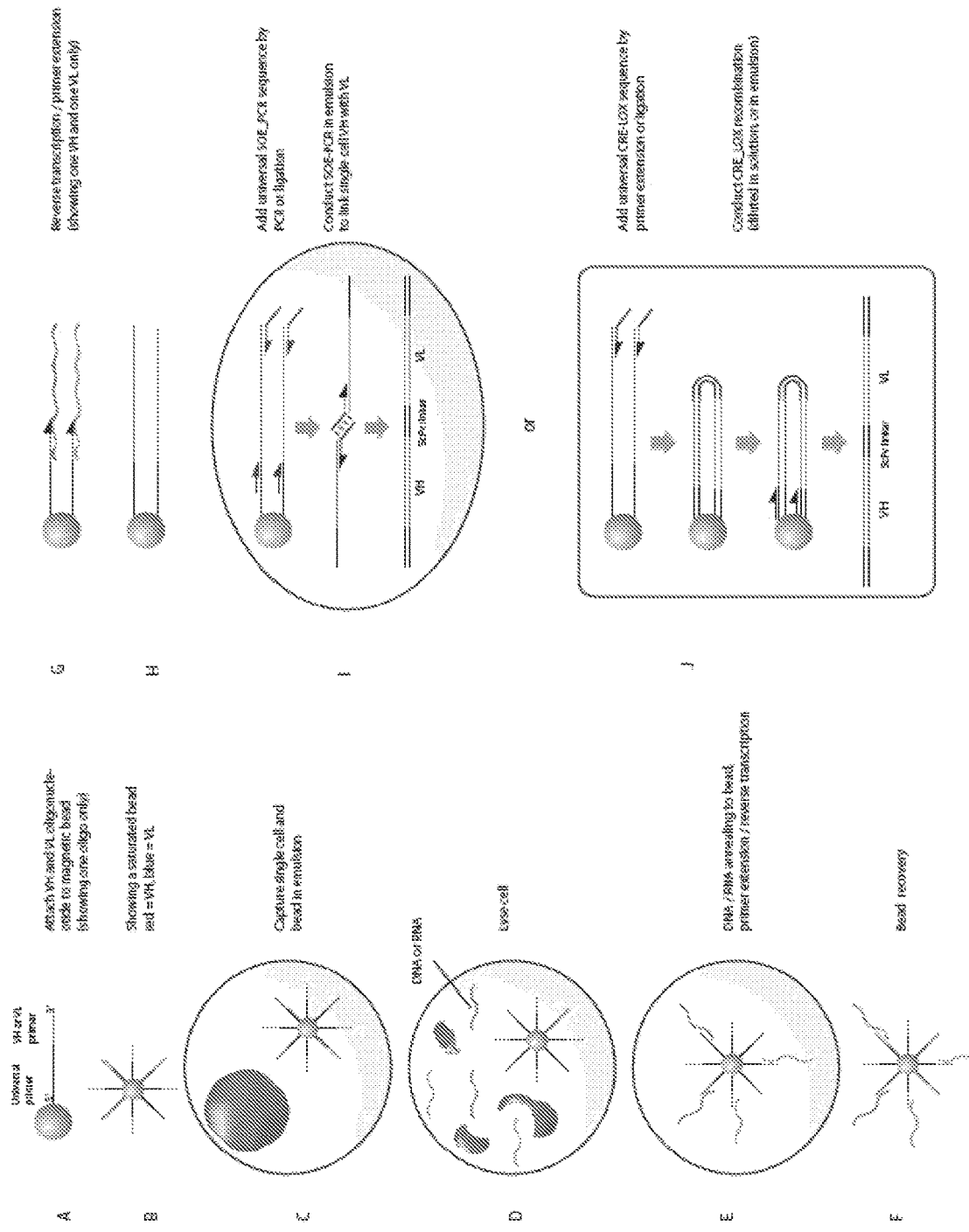
FIG. 39 schematically depicts exemplary bead emulsion capture methods in steps A-J.
Figure 40:
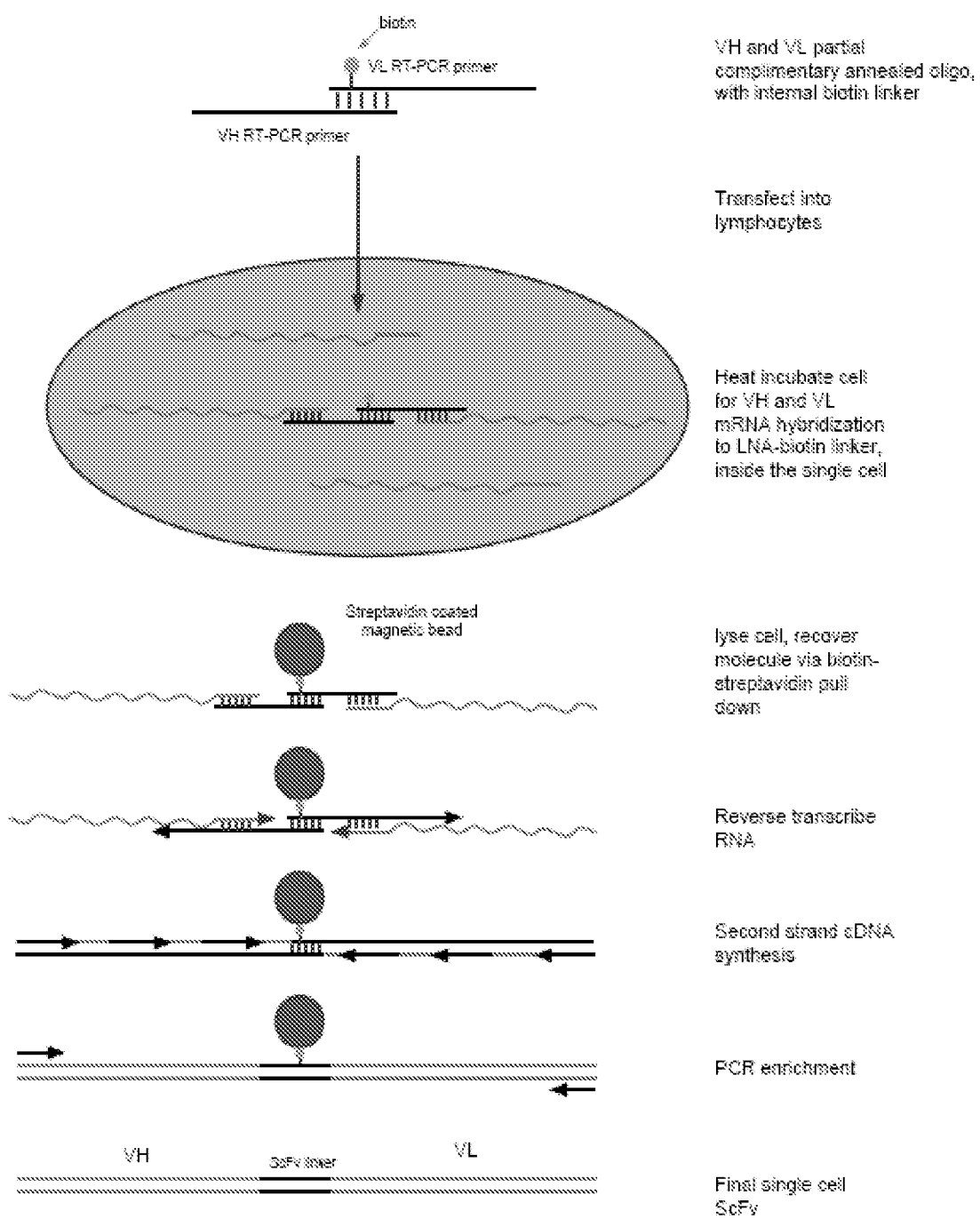
FIG. 40 schematically depicts small oligonucleotide transfection of single cells.
Figure 41:
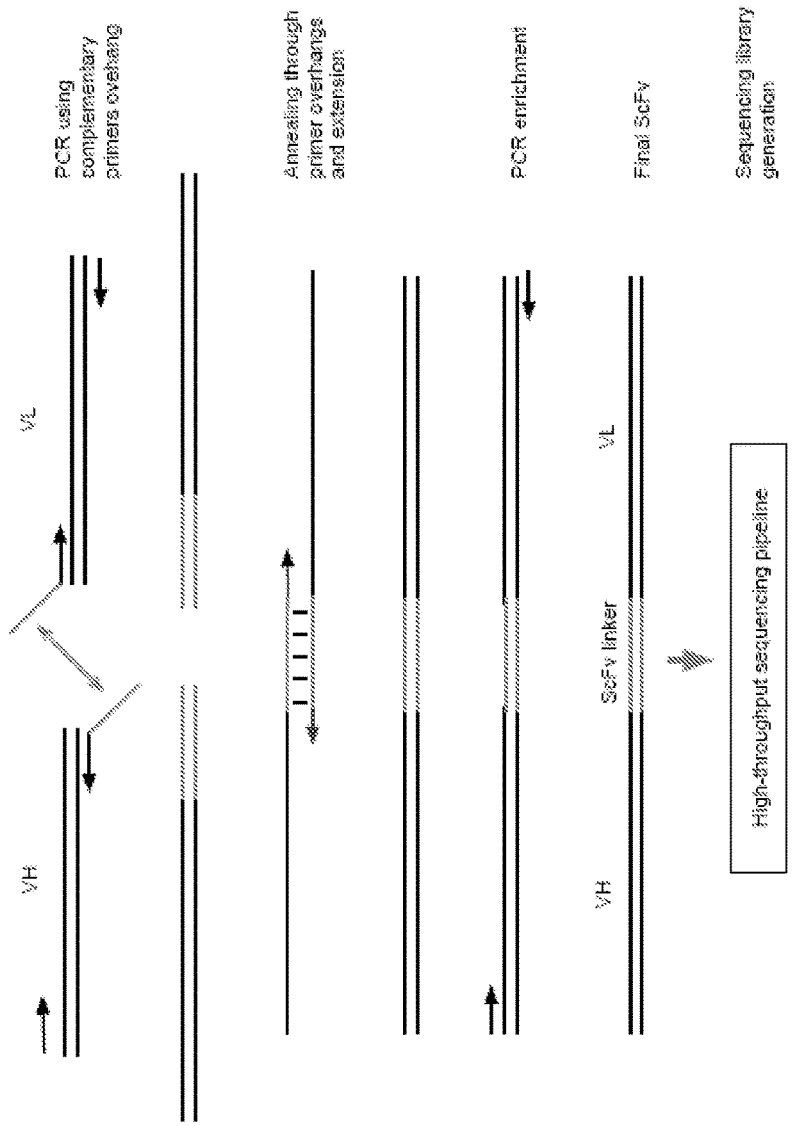
FIG. 41 schematically depicts SOE-PCR.
Figure 42:
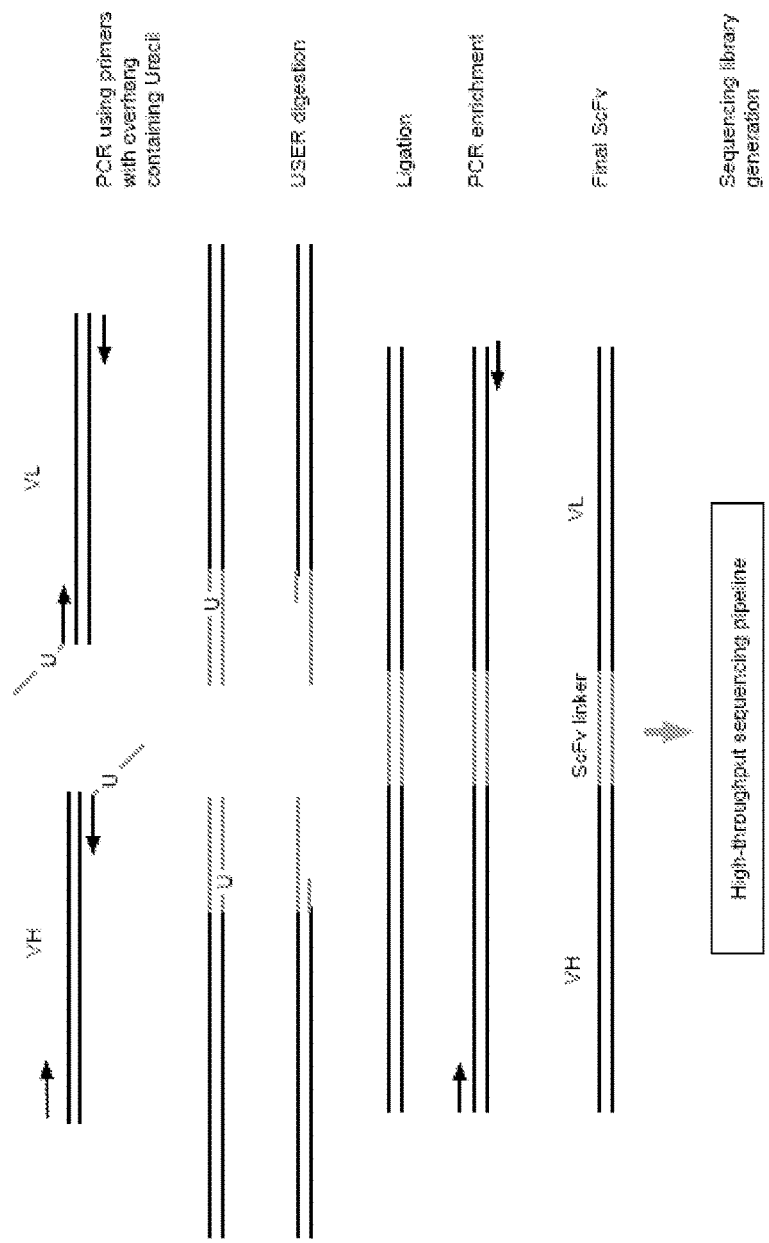
FIG. 42 schematically depicts SOE-PCR USER ligation.
Figure 43:
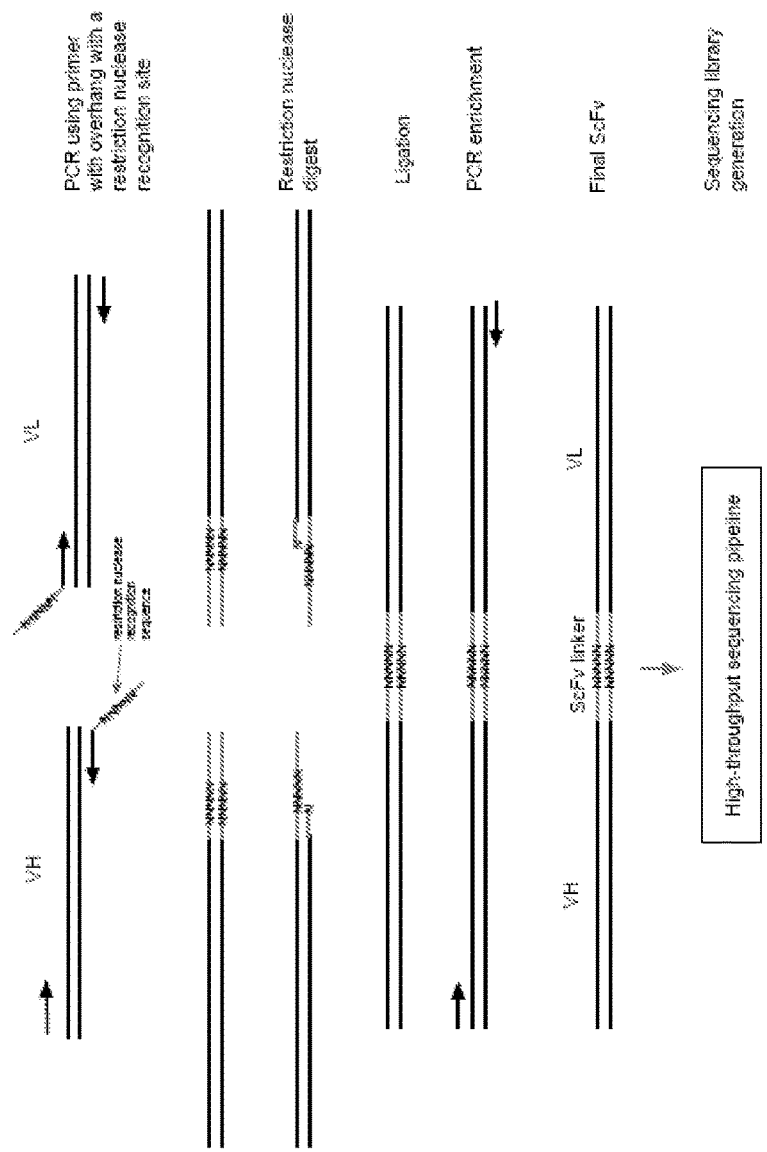
FIG. 43 schematically depicts SOE-PCR restriction ligation.
Figure 44:
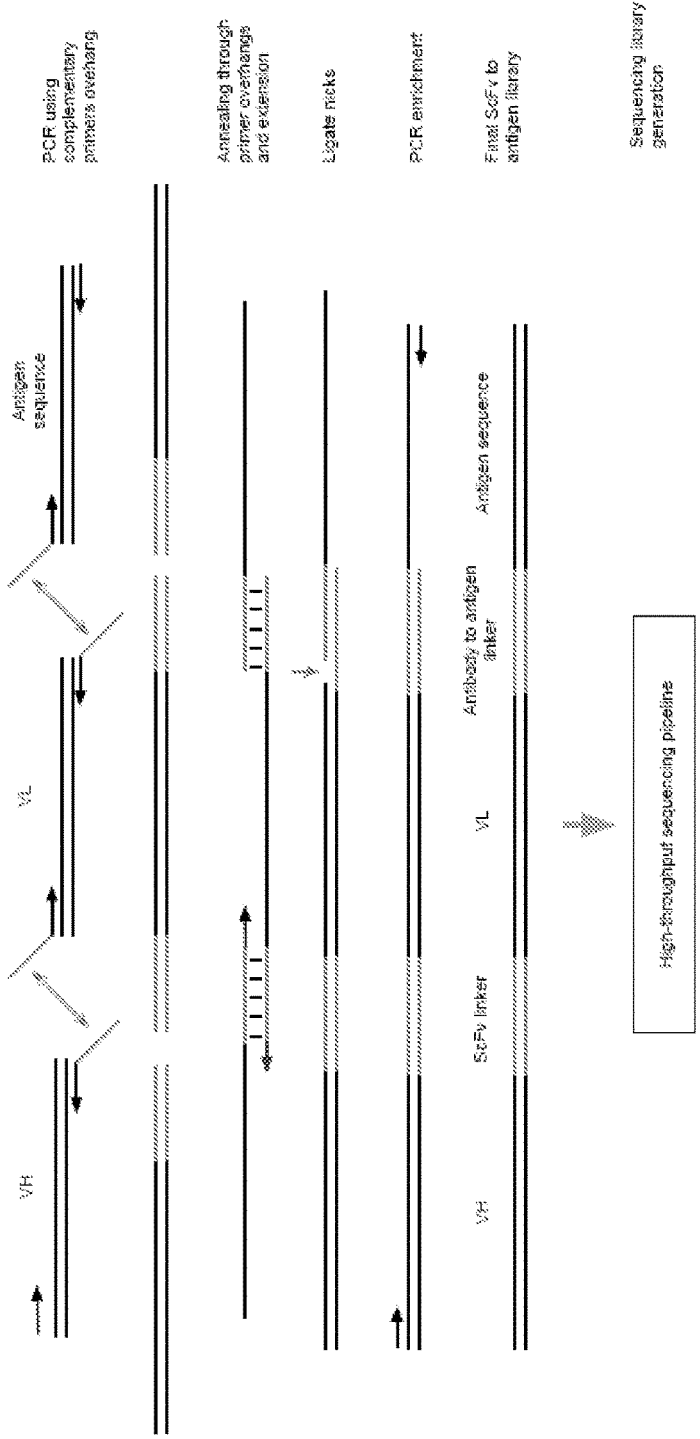
FIG. 44 schematically depicts 3×SOE-PCR.
Figure 45:
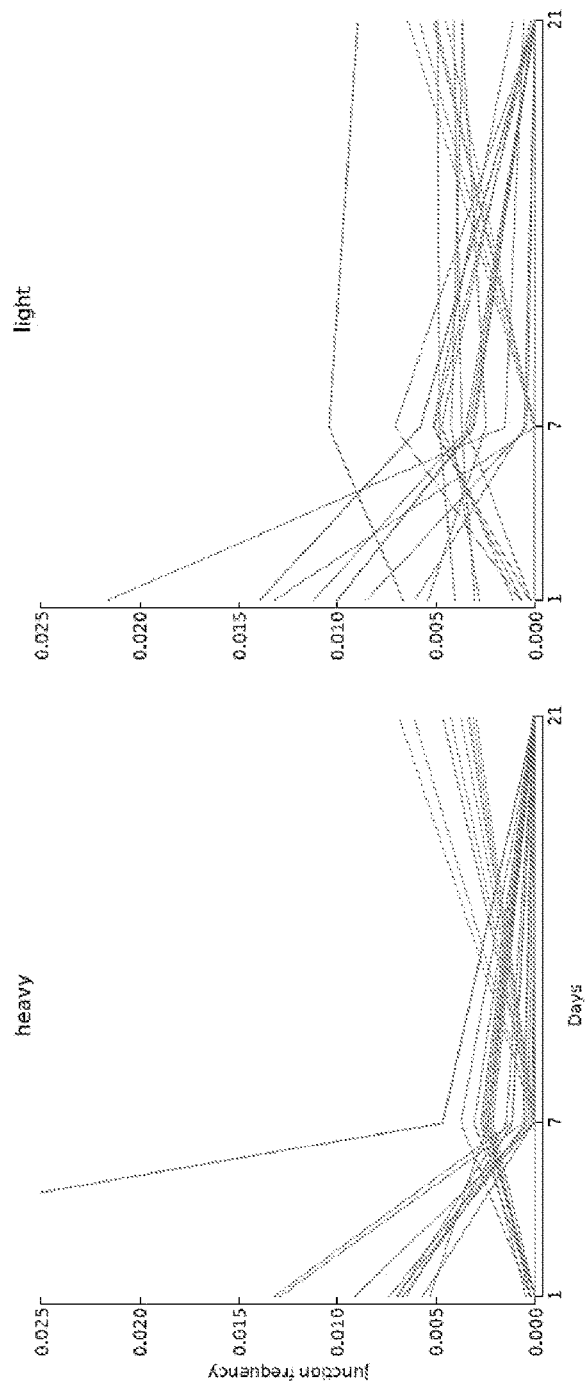
FIG. 45 graphically depicts heavy and light chain distributions.

After performing selection for interacting particles, the Ab-Ag complexes are placed into emulsions using methods described herein. In parallel, more extreme ratios of the two orthogonal positive control pairs are progressively assayed to determine the amount of cross contamination during the coding strand fusion. A summary is set forth at FIG. 30.

Initial Controls for Ribosome Display Proximity Ligation

One advantage of the ribosome display methods described herein is that the entire system is in vitro and the coding sequences are exposed to solution. Using only one of the positive control Ab-Ag pairs, rolling circle-based proximity ligation system (Soderberg et al., supra) is assayed. The two libraries contain unique sequence(s) that function as barcode (s). Additional probes are added to the reaction which form closed circles when the two strands of the Ab and Ag mRNAs are in close proximity to each other.

The same assay is then performed with two positive controls following double purification for interacting complexes. This will elucidate whether the proximity ligation assay is specific only for Ab-Ag pairs that are actually interacting, or whether the circles can be closed promiscuously.

Building Ab-Ag Lookup Table Using Viral Display Libraries

After successfully linking the coding chains of interacting Ab-Ag pairs of a small number of controls, the method is applied to complex libraries. Phage display and ribosome display libraries of naturally expressed scFvs that were cloned as described herein are made. For the vaccination samples, a small library of viral proteins that correspond to the same strains to which the subjects were exposed is generated. These libraries are then used to characterize which antibodies bind to which proteins. Results obtained are correlated with the antibody clones that were identified to react to the administered vaccines in the patients.

In addition to generating viral protein libraries artificially, a similar method is used with full viral particles. Viruses are a convenient system for this strategy, as they function as their own protein display particles. Furthermore, since only a small number of viral strains is needed, it is enough to identify which strain has been captured by cross-linking with one or more unique genomic barcode sequences.

Example IV

Materials and Methods

Biological Samples and Immunization

Peripheral blood samples were drawn into 9 mL K3-EDTA tubes from a single individual 14 days prior and 0, 1, 3, 7, 14, 21, and 28 days following vaccination. Vaccines administered were as follows: Hepatitis A+B (Twinrix) and seasonal influenza vaccine, including strains A/Brisbane/59/2007 (H1N1-like), A/Brisbane/10/2007 (H3N2-like), and B/Florida/4/2006.

RNA Extraction

Blood samples where immediately processed through a filtering unit to isolate the leukocyte fraction (Leuko-LOCK™, Ambion, Austin, TX), then stored at −80° C. until all samples were obtained. Total RNA was later extracted according to the manufacturer's protocol. RNA integrity and concentration was assessed using a NanoDrop spectrophotometer (Thermo Scientific, Wilmington, DE) and a 2100 Bionanalyzer (Agilent, Foster City, CA).

cDNA Synthesis and PCR

For each sample, 2×1 μg of total RNA was reverse transcribed in 2 independent 20 μL reactions using Super-Script™ III reverse transcriptase (Invitrogen, Carlsbad, CA) at 55° C. for 60 min in the presence of 5 pmole of C-region gene-specific primer mix (IGHC-RT) (Table 1), followed by enzyme inactivation and RNase H digestion (Epicentre Biotechnologies, Madison, WI) according to Invitrogen protocols. Each 20 μl, cDNA reaction was then split in 4×50 μL PCR reactions each, for a total of 8 independent PCR reactions per originating sample. PCR was performed in the presence of 200 nM dNTPs (Enzymatics, Beverly, MA), 25 pmole of V-region gene-specific primer mix (IGHV-PCR), 25 pmole of C-region gene-specific primer mix (IGHC-PCR), and 1 U of Phusion™ Hot Start High-Fidelity DNA Polymerase (New England Biolabs, Ipswich, MA) and thermal cycled as follows: 98° C. for 1 min, 16 cycles of 98° C. for 10 sec, 62° C. for 20 sec, 72° C. for 20 sec, followed by 72° C. for 5 min and then cooled down to 4° C. Following PCR, all reactions originating from the same sample where pooled into one 400 μL mixture to which 160 U of Exonuclease I (Epicentre Biotechnologies, Madison, WI) was added and incubated at 37° C. for 45 min. Samples were then purified using the QIAquick PCR Purification Kit (Qiagen, Valencia, CA) and eluted in 36 μL of EB buffer according to the manufacturer's protocol.

TABLE 1

| Reverse transcription oligonucleotides C-region gene specific primers mix (IGHC-RT) | |
|---|---|
| VDJ-20080707-IGHG | AGGGYGCCAGGGGGAAGA (SEQ ID NO: 133) |
| VDJ-20080707-IGHM | GGAGACGAGGGGGAAAAGG (SEQ ID NO: 134) |
| VDJ-20080707-IGHA | CAGCGGGAAGACCTTGGG (SEQ ID NO: 135) |
| VDJ-20080707-IGHD | CACATCCGGAGCCTTGGT (SEQ ID NO: 136) |
| VDJ-20080707-IGHE | TCAAGGGGAAGACGGATGG (SEQ ID NO: 137) |
| PCR oligonucleotides C-region gene specific primers (IGHC-PCR) | |
| VDJ-20080924-IGHG-1 | CCGATGGGCCCTTGGTGG (SEQ ID NO: 138) |
| VDJ-20080924-IGHG-2 | CGGATGGGCCCTTGGTGG (SEQ ID NO: 139) |
| VDJ-20080924-IGHM | GGGTTGGGGCGGATGCAC (SEQ ID NO: 140) |
| VDJ-20080924-IGHA | CCTTGGGGCTGGTCGGGG (SEQ ID NO: 141) |
| VDJ-20080924-IGHD | CATCCGGAGCCTTGGTGG (SEQ ID NO: 142) |
| VDJ-20080924-IGHE | CGGATGGGCTCTGTGTGG (SEQ ID NO: 143) |
| V-region gene specific primers (IGHV-PCR) | |
| VDJ-20080924-IGHV1-1 | GAGCAGCGACAGGTGCCC (SEQ ID NO: 144) |
| VDJ-20080924-IGHV1-2 | CAGCAGCCACAGGTGCCC (SEQ ID NO: 145) |
| VDJ-20080924-IGHV1-3 | GCAGCAGCTACAGGTGTCC (SEQ ID NO: 146) |
| VDJ-20080924-IGHV1-4 | CTGTAGCACCAGGTGCCC (SEQ ID NO: 147) |
| VDJ-20080924-IGHV1-5 | GCTGTAGCTCCAGGTGCTC (SEQ ID NO: 148) |
| VDJ-20080924-IGHV1-6 | CAGCACCAACAGGTGCCC (SEQ ID NO: 149) |
| VDJ-20080924-IGHV1-7 | CAGCAGCCACAGNTGCCT (SEQ ID NO: 150) |

TABLE 1-continued

| | |
|---|---|
| VDJ-20080924-IGHV1-8 | CAGCAGCTACAAGTGCCC (SEQ ID NO: 151) |
| VDJ-20080924-IGHV1-9 | CAGCAGCCACAGGAGCCC (SEQ ID NO: 152) |
| VDJ-20080924-IGHV1-10 | CAGCAGCCACAGGTGTCC (SEQ ID NO: 153) |
| VDJ-20080924-IGHV1-11 | CAGCAGCTACAGGCACCC (SEQ ID NO: 154) |
| VDJ-20080924-IGHV1-12 | CCTGTTTTTGGTGCCC (SEQ ID NO: 155) |
| VDJ-20080924-IGHV1-13 | TGGCAGCACCAGGCGCCC (SEQ ID NO: 156) |
| VDJ-20080924-IGHV1-14 | TCATAGCTGCAGGTGCCC (SEQ ID NO: 157) |
| VDJ-20080924-IGHV2-1 | CTGTCCCGTCCTGGGTCT (SEQ ID NO: 158) |
| VDJ-20080924-IGHV2-2 | ACCATCCCTTCATGGGTCT (SEQ ID NO: 159) |
| VDJ-20080924-IGHV2-3 | CCACCCCTTCCTGGGTCT (SEQ ID NO: 160) |
| VDJ-20080924-IGHV3-1 | TTCTGTGCTATATTAAAGCTGTCC (SEQ ID NO: 161) |
| VDJ-20080924-IGHV3-2 | TTGTTGCTATTTTAAAAGGTGTCC (SEQ ID NO: 162) |
| VDJ-20080924-IGHV3-3 | CGTTGCTCTTTTAAGAGGTGTCC (SEQ ID NO: 163) |
| VDJ-20080924-IGHV3-4 | TTGTTGCTATTTTTAAAGGTGTCC (SEQ ID NO: 164) |
| VDJ-20080924-IGHV3-5 | TTGTTGCTATATTAGAAGGTGTCC (SEQ ID NO: 165) |
| VDJ-20080924-IGHV3-6 | GCTATTTTAAAAGGTGTCC (SEQ ID NO: 166) |
| VDJ-20080924-IGHV3-7 | TTGTTGCTATTTTAGAAGGTGTCC (SEQ ID NO: 167) |
| VDJ-20080924-IGHV3-8 | TTGTGGCTATTTTAAAAGGTGTCC (SEQ ID NO: 168) |
| VDJ-20080924-IGHV3-9 | TTGTTGTTATTTTACAAGGTGTCC (SEQ ID NO: 169) |
| VDJ-20080924-IGHV3-10 | TTCCTGCTATTTTAAAAGGTGTCC (SEQ ID NO: 170) |
| VDJ-20080924-IGHV3-11 | TTGCTGCTATTTTAAAAGGTGTCC (SEQ ID NO: 171) |
| VDJ-20080924-IGHV3-12 | TTTTGGCTATTTTAAAAGGTGTCC (SEQ ID NO: 172) |
| VDJ-20080924-IGHV3-13 | TTGTGGCTAAAATAAAAGGTGTCC (SEQ ID NO: 173) |
| VDJ-20080924-IGHV3-14 | TTGTTGCTATAATAAAAGGTGTCC (SEQ ID NO: 174) |
| VDJ-20080924-IGHV3-15 | TTGCTGGTATTTTAAAAGGTGTCC (SEQ ID NO: 175) |
| VDJ-20080924-IGHV3-16 | TTGTTGGTATTTTAAAAGGTGTCC (SEQ ID NO: 176) |
| VDJ-20080924-IGHV4-1 | CAGCTCCCAGATGGGTCC (SEQ ID NO: 177) |
| VDJ-20080924-IGHV4-2 | CGGCTCCCAGATGGGTCC (SEQ ID NO: 178) |
| VDJ-20080924-IGHV4-3 | GCTCCCAGATGTGGGTCC (SEQ ID NO: 179) |
| VDJ-20080924-IGHV5-1 | GGCTGTTCTCCAAGGAGTCT (SEQ ID NO: 180) |
| VDJ-20080924-IGHV5-2 | CCTCCACAGTGAGTGAGTCT (SEQ ID NO: 181) |
| VDJ-20080924-IGHV5-3 | CCTAGCTATTCTCCAAGGAGTCT (SEQ ID NO: 182) |
| VDJ-20080924-IGHV6-1 | GCCTCCCATGGGGTGTCC (SEQ ID NO: 183) |
| VDJ-20080924-IGHV6-2 | GGGCCTCCATGGGTGTCC (SEQ ID NO: 184) |
| VDJ-20080924-IGHV7-1 | CAGCAGCAACAGGTGCCC (SEQ ID NO: 185) |
| VDJ-20080924-IGHV7-2 | GCAGCAGCAACAGGTACCT (SEQ ID NO: 186) |

454 library construction oligonucleotides
Adapter A oligonucleotides

| | |
|---|---|
| 454 adapter A1_MID1 | C*C*A*T*CTCATCCCTGCGTGTCTCCGACTCAGACGAGT*G*C*G*T (SEQ ID NO: 187) |
| 454 adapter A2_MID2 | C*C*A*T*CTCATCCCTGCGTGTCTCCGACTCAGACGCTC*G*A*C*A (SEQ ID NO: 188) |
| 454 adapter A3_MID3 | C*C*A*T*CTCATCCCTGCGTGTCTCCGACTCAGAGACGC*A*C*T*C (SEQ ID NO: 189) |

TABLE 1-continued

```
454 adapter A4_MID4    C*C*A*T*CTCATCCCTGCGTGTCTCCGACTCAGAGCACT*G*T*A*G (SEQ ID NO: 190)

454 adapter A5_MID5    C*C*A*T*CTCATCCCTGCGTGTCTCCGACTCAGATCAGA*C*A*C*G (SEQ ID NO: 191)

454 adapter A6_MID6    C*C*A*T*CTCATCCCTGCGTGTCTCCGACTCAGATATCG*C*G*A*G (SEQ ID NO: 192)

454 adapter A8_MID8    C*C*A*T*CTCATCCCTGCGTGTCTCCGACTCAGCTCGCG*T*G*T*C (SEQ ID NO: 193)

454 adapter A9_MID9    C*C*A*T*CTCATCCCTGCGTGTCTCCGACTCAGTAGTAT*C*A*G*C (SEQ ID NO: 194)

454 adapter A10_MID10  C*C*A*T*CTCATCCCTGCGTGTCTCCGACTCAGTCTCTA*T*G*C*G (SEQ ID NO: 195)

454 adapter            A*C*G*C*ACTCGTCTGAGTCG*G*A*G*A (SEQ ID NO: 196)
Aprime1_MID1

454 adapter            T*G*T*C*GAGCGTCTGAGTCG*G*A*G*A (SEQ ID NO: 197)
Aprime2_MID2

454 adapter            G*A*G*T*GCGTCTCTGAGTCG* G*A*G*A (SEQ ID NO: 198)
Aprime3_MID3

454 adapter            C*T*A*C*AGTGCTCTGAGTCG*G*A*G*A (SEQ ID NO: 199)
Aprime4_MID4

454 adapter            C*G*T*G*TCTGATCTGAGTCG*G*A*G*A (SEQ ID NO: 200)
Aprime5_MID5

454 adapter            C*T*C*G*CGATATCTGAGTCG*G*A*G*A (SEQ ID NO: 201)
Aprime6_MID6

454 adapter            G*A*C*A*CGCGAGCTGAGTCG*G*A*G*A (SEQ ID NO: 202)
Aprime8_MID8

454 adapter            G*C*T*G*ATACTACTGAGTCG*G*A*G*A (SEQ ID NO: 203)
Aprime9_MID9

454 adapter            C*G*C*A*TAGAGACTGAGTCG*G*A*G*A (SEQ ID NO: 204)
Aprime10_MID10

Adapter B oligonucleotides 454 adapter B          /5BioTEG/C*C*T*A*TCCCCTGTGTGCCTTGGCAGTC*T*C*A*G (SEQ ID NO: 205)

454 adapter B prime    C*T*G*A*GACT*G*C*C*A (SEQ ID NO: 206)
```

454 GS FLX Library Construction and Sequencing

Immunoglobulin $V_H$ PCR samples where processed following the 454 GS FLX Titanium General Library Preparation protocol. Briefly, samples where blunt ended and 5' phosphorylated using End-It™ DNA End-Repair Kit (Epicentre Biotechnologies, Madison, WI) in 50 µL reactions according to manufacturer's instructions, followed by QIAquick PCR Purification (Qiagen, Valencia, CA) in the presence of 5 µL of 3M NaOAc, pH 5.5. Roche 454 compatible DNA adapters containing a unique molecular identifier bar-code (MID) for each sample were ligated in a 100 µL reaction volume in the presence of 30 pmoles of both adapter A (including MID 1 to 8) and adapter B (identical for all samples) and 1200 U of Rapid T4 DNA Ligase (Enzymatics, Beverly, MA) at 22° C. for 30 min. In order to remove unligated adapters, samples where purified using a 1:1 ratio of AMPure XP beads (Agencourt Bioscience Corporation, Beverly MA) and eluted in 50 µL of 10 mM Tris-HCL. The ends of the ligated fragments of the library-adapters were filled-in in 100 µL reactions using 32 U of Bst DNA Polymerase (NEB, Ipswich, MA) in the presence of 625 µM dNTPs and 1× ThermoPol Reaction Buffer. Reactions where purified using the MinElute PCR Purification Kit (Qiagen, Valencia, CA), and eluted in 15 µL of EB buffer. Samples were separated on 6% Novex® TBE Gels (Invitrogen, Carlsbad, CA) at 200 volts for 26 min, from which the proper band (approximately 450 bp) was extracted at 50° C. for 1 hr and resuspended in 20 µL of 10 mM Tris-HCL as detailed previously (Vigneault et al. (2008) *Nat. Methods* 5:777). All steps related to the single-stranded template DNA (sstDNA) library isolation were found to be unnecessary for subsequent emulsion PCR and 454 sequencing. Library concentrations were determined using a 2100 Bionanalyzer (Agilent, Foster City, CA), then diluted to equivalent concentrations. All 8 blood samples, each representing a unique time point and characterized by a unique MID bar-code, were then pooled at an equimolar concentration. Emulsion PCR, bead enrichment and 454 GS FLX sequencing were performed at the 454 Life Sciences facility according to the manufacturer's standard protocol. This entire process (including cDNA synthesis and PCR) was repeated independently multiple times, or specifically on one sample only in order to generate complete technical replicates for the various analyses of the study.

Informatics Pipeline

Raw sequencing data was analyzed with the 454 amplicon pipeline to produce quality-trimmed reads. The reads were size filtered for the appropriate amplicon size (350-500 bp) and converted to coding strands by comparing k-mer compositions of the query reads against the IMGT/GENE-DB (Giudicelli et al. 2005 *Nucleic Acids Res.* 33:D256) database and its reverse complement. The reads were then aligned to the IMGT/GENE-DB reference database to determine the V, D, and J usage, and extract the CDR3 junction region. Briefly, k-mer compositions of query sequences were compared with reference segments to find the top matches, and the best match was chosen using traditional dynamic programming alignment. Reads were then partitioned by V-J usage, and their CDR3 junctions were clustered using single-linkage or complete-linkage agglomerative hierarchical clustering with the Levenshtein edit distance as metric. Clones were defined by cutting the linkage tree at 4.5 edits. By partitioning reads into the separate time points (by identifying their MID bar-code), a time series was defined for each clone. The time series were clustered using k-means clustering with k=100 and the Euclidean distance metric. To eliminate trivial clones that appeared at single time points, clones showing positive counts in at least two time points were filtered. Time series were also clustered using self-organizing maps (SOM) as implemented in the GEDI software package. The analysis software described herein is available for download as a python module (Worldwide Web Site: arep.med.harvard.edu/vdj).

Primer Design

All oligonucleotides were ordered from Integrated DNA Technologies (IDT, Coralville, IA). For the design of the upstream variable-region oligonucleotides (IGHV-PCR), the L-PART1 and L-PART2 sequences were extracted from all IMGT/GENE-DB 3 reference segments annotated as "functional" or "ORF." These two segments are spliced together in vivo to form the leader sequence. The primer sequence was positioned to cross the exon-exon boundary to ensure amplification from cDNA rather than gDNA. The primers were arranged to have 6 nucleotides 3' of the exon boundary, and ranged from 18-24 nucleotides in length to target their predicted melting temperatures to 60° C. All duplicate sequences where eliminated. For the design of the downstream constant-region oligonucleotides (IGHC-RT and IGHC-PCR), the first 100 nucleotides of the CH1 exon were extracted from the IMGT/GENE-DB[3]. Oligonucleotides were then selected as close as possible to the 5' end of the C-region (close to the variable region of the receptor), starting with 3 nt from the end. These were hand-picked both for IGHC-RT and IGHC-PCR to take advantage of sequence conservation between different variants, and to ensure that isotypes would be distinguishable. All oligonucleotide sequences are shown in Table 1.

Control Library

In order to assess PCR bias and amplification efficiency, total RNA from multiple individuals was extracted, pooled together, and reverse transcribed as described in the Methods Summary. Independent PCR reactions were conducted for each C-region gene-specific primer (IGHC-PCR) for 25 cycles, from which the proper band of interested was gel extracted as described previously (Vigneault et al., Supra). To monitor the amplification efficiency of the constant region primers, the individual PCR amplicons were quantified using the 2100 Bionanalyzer (Agilent, Foster City, CA), followed by real-time PCR performed in triplicate using the KAPA SYBR® FAST qPCR Kit (Kapa Biosystems, Woburn, MA) on a Bio-Rad CFX96 real time PCR instrument (Bio-Rad, Hercules, CA). Both linear regression PCR (LinRegPCR) (Ramakers et al. (2003) *Neurosci. Lett.* 339: 62) and standard dilution curve analysis were used to determine and compare amplification efficiencies (Table 2).

TABLE 2

| Individual primer/ reaction | LinRegPCR mean efficiency on uniform template concentration (triplicate of 1/125) | LinRegPCR mean efficiency on STD curves series (1/5 dilution series) | STD curve mean efficiency (1/10 dilution series) | Average efficiency |
| --- | --- | --- | --- | --- |
| VDJ-20080924-IGHG-1 | 1.774 | 1.650 | 1.803 | 1.742 |
| VDJ-20080924-IGHG-2 | 1.784 | 1.740 | 1.824 | 1.783 |
| VDJ-20080924-IGHM | 1.729 | 1.757 | 1.766 | 1.751 |
| VDJ-20080924-IGHA | 1.777 | 1.731 | 1.782 | 1.763 |
| VDJ-20080924-IGHD | 1.779 | 1.726 | 1.755 | 1.753 |
| VDJ-20080924-IGHE | 1.607 | 1.541 | 1.831 | 1.660 |

Positive Strand Identification of 454 Sequencing Reads

Figure 18:
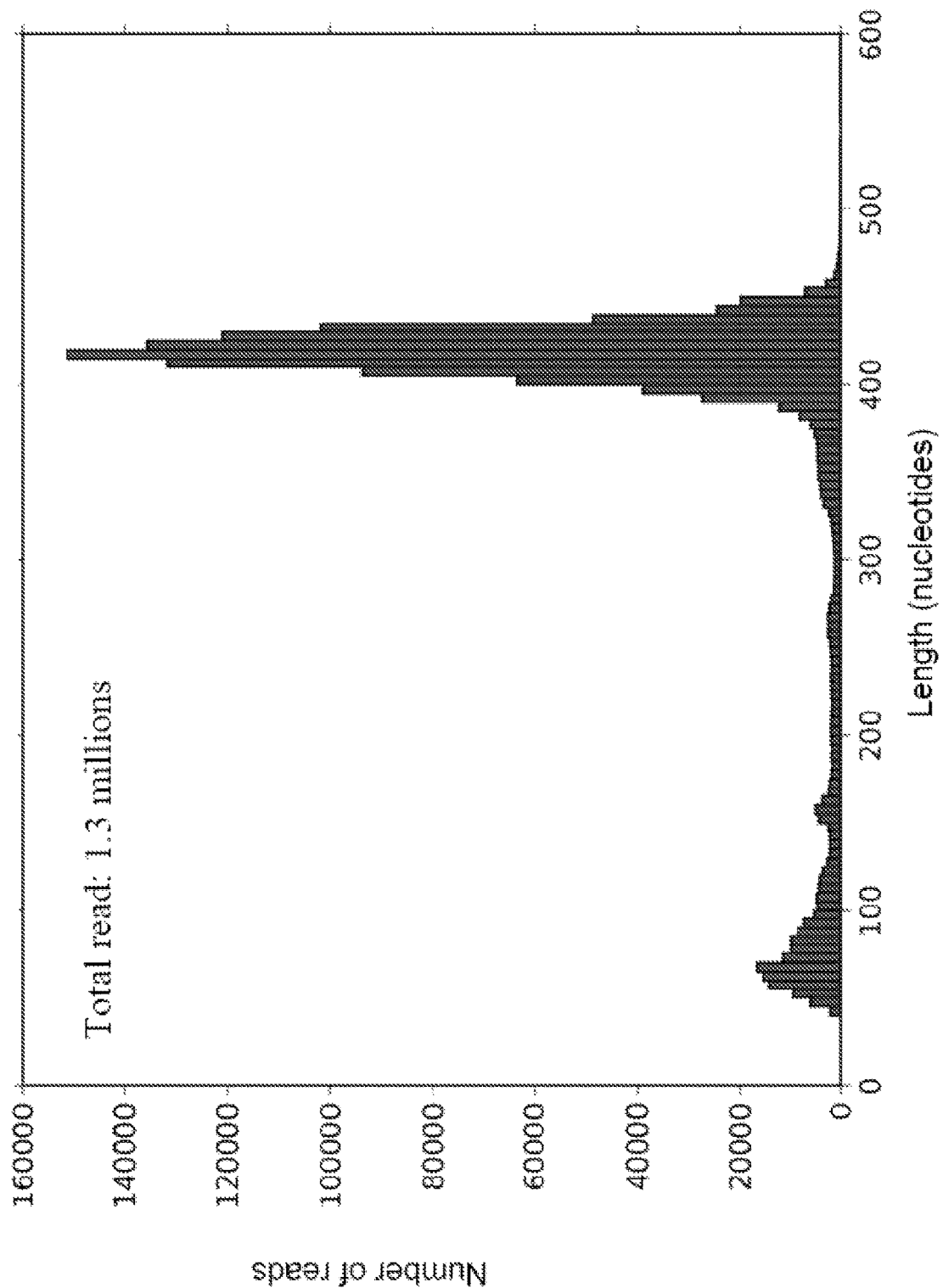
FIG. 18 graphically depicts the raw high quality read length distribution of a single run of 454 GS FLX sequencing. The most significant peak occurred at the expected size of 420 bp.

Following size-filtering of reads for the expected $V_H$ size (FIG. 18), coding strands were identified, as it was important for the subsequent alignment pipeline. To do so k-mers were pre-computed using the Positive Strand comb (Table 3) for the entire reference segment database, and separately for its reverse complement. The same k-mers for the query read were then computed, and the coding strand determined by computing the number of shared k-mers of the positive versus negative version of the database.

TABLE 3

| Comb | Pattern |
| --- | --- |
| Positive Strand | 111111111111 |
| Alignment A | 111011001011010111 |
| Alignment B | 1111000100010011010111 |
| Alignment C | 111111111111 |
| Alignment D | 110100001100010101111 |
| Alignment E | 1110111010001111 |
| Mini-Alignment A | 111011 |
| Mini-Alignment B | 110111 |

VDJ Alignment Overview

VDJ alignment allows identification of which V, D, and J segments are used in a given sequencing read. For each segment, a heuristic method was employed by computing k-mer counts using multiple seed combs (Table 3). The candidate segments were ranked by the amount of overlap in their k-mer distributions. A full dynamic programming alignment was then performed on the highest scoring candidates to determine the best match.

VDJ Alignment Process

To maximize the number of distinguishing nucleotides, the alignment was performed in order of decreasing segment length (V then J then D). In order to minimize the amount of off-target sequence (especially for the k-mer counts), the previously aligned V or J region was pruned off before attempting alignment of the next segment. In order to align the V and J segments, 11-mer or 12-mer seeds were computed using the combs listed in Table 3. The k-mer counts were also pre-computed on all reference segments. The top 5 reference V segments and the top 2 reference J segments were chosen for dynamic programming alignment and scoring. Since it was known that the V and J segments must reside at the ends of the reads, a method that is similar to the Needleman-Wunsch algorithm (Needleman and Wunsch (1970) *J. Mol. Biol.* 48:443) was used. In contrast to the canonical algorithm, zero initial conditions were used to allow the start of the alignment to occur anywhere without penalty. The alignment was then reconstructed and scored by starting at the maximum value of the score matrix along the last row or last column, and backtracing. Finally, the identified V or J segments were removed before proceeding to the J or D alignment, respectively.

D Region Alignment

The D alignments were performed similarly. However, the two Mini-Alignment 5-mer seeds listed in Table 3 were used to pick the top 10 reference D segments to carry through to dynamic programming alignment. In this case, the canonical Smith-Waterman local alignment algorithm (Smith and Waterman (1981) *J. Mol. Biol.* 147:195) was performed, as no prior information as to where the D segment should reside was available.

CDR3 Extraction

The V and J segments were pruned according to the IMGT annotations for the CDR3 junction region: from the second conserved cysteine residue in the V region through the conserved tryptophan or phenylalanine in the J region. This segment was stored as the junction region of the corresponding variable region.

VDJ Alignment Performance

Since there was currently no large database of human heavy chain immunoglobulin sequences to validate the performance of the algorithm, the aligner was calibrated using the V-QUEST algorithm provided as part of the IMGT database. 66,497 reads from three different sequencing runs were aligned using the V-QUEST alignment software. For each read, the dynamic programming alignment scores for the V, D, and J regions were computed separately for every possible reference segment, in addition to the correct segment produced with the V-QUEST aligner. ROC curves showed that V region alignment was the most reliable, followed by J, followed by D, as expected (FIG. 8). The D region showed the most ambiguous alignment, which was expected due to its short length and high mutated nature. Therefore, the D region alignments were ignored in downstream analyses, and the V and J alignments were focused upon, along with the corresponding CDR3 junction region. The ROC curves were used to choose scoring thresholds to keep the number of falsely matched alignments to approximately 10% or lower.

Sequence Clustering

Sequence clustering was performed in order to group the sequences (reads) into unique clones. This process was primarily used to associate sequences that originated from the same cell/clone, while allowing minor variations attributable to sequencing errors. Single- or complete-linkage agglomerative hierarchical clustering was used with Levenshtein edit distance as the metric. To make the clustering process more tractable, the reads were partitioned based on V-J identity. Within each partition, sequence clustering was performed using only the CDR3 junction sequence. Furthermore, all identical junctions were collapsed prior to clustering to improve performance. Because cluster distances only depended on the unique cluster members, this did not affect the final clustering results (though this is not true for average-linkage clustering methods). As described herein, cluster sizes varied over several orders of magnitude. Below are multiple alignments (using CLUSTALW) of several smaller clusters as illustrations. Most of the differences between sequences were indels near homopolymers, which are the most common mutation type for 454 sequencing.

```
Example Cluster 1:
                                             (SEQ ID NO: 1)
1 TGTGCGAGAGAGGGCTACGGTGACTACCGTTACTACTACGGTATGGAC
GTCTGG 54

(SEQ ID NO: 2)
2 TGTGCGAGAGAGGGCTACGGTGACTACCGTTACTACTACGGTATGGAC
GTCTGG 54

(SEQ ID NO: 3)
5 TGTGCGAGAGAGGGCTACGGTGACTACCGTTACTACTACGGTATGGAC
GTCTGG 54

(SEQ ID NO: 4)
6 TGTGCGAGAGAGGGCTACGGTGACTACCGTTACTACTACGGTATGGAC
GTCTGG 54

(SEQ ID NO: 5)
3 TGTGCGAGAGAGGACTACGGTGACTAC-GT--
CTACTACGGTATGGACGTCTGG 51

(SEQ ID NO: 6)
4 TGTGCGAGAGGGTACTACGGTGACTACGG---
CCACTACGGTATGGACGTCTGG 51

Example Cluster 2:
                                             (SEQ ID NO: 7)
1 TGTGCGGCAGTTCCCCCCCCT-NAGGGAACGACATTTT-GGGGTGC
TTTT-GAGATCTGG 57

(SEQ ID NO: 8)
3 TGTGCGGCAGTTCCCCCCCCT-NAGGGAACGACATTTT-
GGGGTGCTTTTTGAGATCTGG 58

(SEQ ID NO: 9)
9 TGTGCGGCAGTTCCCCCCCCT-
CAGGGAACGACATTTTTGGGGTGCTTTTTGAGATCTGG 59

(SEQ ID NO: 10)
22 TGTGCGGCAGTTCCCCCCCCT-CAGGGAACGACATTTT-
GGGGTGCTTTTTGAGATCTGG 58

(SEQ ID NO: 11)
5 TGTGCGGCAGTTCCCCCCCCCTCAGGGAACGACATTTT-GGGGTGC
TTTT-GAGATCTGG 58

(SEQ ID NO: 12)
24 TGTGCGGCAGTTCCCCCCCTC---AGGAACGACATTT---GGGTGC
TTTT-GAGATCTGG 53

(SEQ ID NO: 13)
6 TGTGCGGCAGTTCCCCCCCTC--AGGGAACGACATTTT-GGGGTGC
TTTT-GAGATCTGG 56

(SEQ ID NO: 14)
10 TGTGCGGCAGTTCCCCCCCTC--AGGGAACGACATTTT-GGGGTGC
TTTT-GAGATCTGG 56

(SEQ ID NO: 15)
11 TGTGCGGCAGTTCCCCCCCTC--AGGGAACGACATTTT-GGGGTGC
TTTT-GAGATCTGG 56

(SEQ ID NO: 16)
13 TGTGCGGCAGTTCCCCCCCTC--AGGGAACGACATTTT-GGGGTGC
TTTT-GAGATCTGG 56
```

```
                                                   (SEQ ID NO: 17)
19 TGTGCGGCAGTTCCCCCCCTC--AGGGAACGACATTTT-GGGGTGC
TTTT-GAGATCTGG 56

(SEQ ID NO: 18)
21 TGTGCGGCAGTTCCCCCCCTC--AGGGAACGACATTTT-GGGGTGC
TTTT-GAGATCTGG 56

(SEQ ID NO: 19)
4 TGTGCGGCAGTTCCCCCCCCT-CAGGGAACGACATTTT-GGGGTGC
TTTT-GAGATCTGG 57

(SEQ ID NO: 20)
17 TGTGCGGCAGTTCCCCCCCCT-CAGGGAACGACATTTT-GGGGTGC
TTTT-GAGATCTGG 57

(SEQ ID NO: 21)
8 TGTGCGGCAGTTCCCCCCCCT-CAGGGAACGACATTTT-GGGGTGC
TTTT-GAGATCTGG 57

(SEQ ID NO: 22)
18 TGTGCGGCAGTTCCCCC--CT-CAGGGAACGACATTTT-GGGGTGC
TTTT-GAGATCTGG 55

(SEQ ID NO: 23)
23 TGTGCGGCAGTTCCCCCCCCT-CAGGGAACGACATTTT-GGGGTGC
TTTT-GAGATCTGG 57

(SEQ ID NO: 24)
12 TGTGCGGCAGTTCCCCCCCCT-
CAGGGAACGACATTTTTGGGGTGCTTTTTGAGATCTGG 59

(SEQ ID NO: 25)
14 TGTGCGGCAGTTCCCCCCCCT-CAGGGAACGACATTTT-
GGGGTGCTTTTTGAGATCTGG 58

(SEQ ID NO: 26)
16 TGTGCGGCAGTTCCCCCCCCT-CAGGGAACGACATTTT-GGGGTGC
TTTT-GAGATCTGG 57

(SEQ ID NO: 27)
0 TGTGCGGCAGTTCCCCCCCCT-CAGGGAACGACATTTT-GGGGTGC
TTTT-GAGATCTGG 57

(SEQ ID NO: 28)
7 TGTGCGGCAGTTCCCCCCCCT-CAGGGAACGACATTTT-
GGGGTGCTTTTTGAGATCTGG 58

(SEQ ID NO: 29)
2 TGTGCGGCAGTTCCCCCCCCT-CAGGGAACGACATTTT-
GGGGTGCTTTTTGAGATCTGG 58

(SEQ ID NO: 7)
20 TGTGCGGCAGTTCCCCCCTCA---GGGAACGACATTT--GGGGTGC
TTT--GAGATCTGG 53

(SEQ ID NO: 30)
15 TGTGCGGCAGTTCCCCCCCCTCCAGGGAACGACATTT--GGGGTGC
TTTT-GAGATCTGG 57
```

Example Cluster 3:

```
                                                   (SEQ ID NO: 31)
4 TGTGCGACGG-TGGGA-GTTCCCC-ACCGGTTTT-GATATCTGG 40

(SEQ ID NO: 32)
79 TGTGCGACGG-TGGGACGTTCCCCTACCGGTTTT-GATATCTGG 42

(SEQ ID NO: 33)
1 TGTGCGACGG-TGGGA-GTTCCC--ACCGGTTTT-GATATCTGG 39

(SEQ ID NO: 34)
16 TGTGCGACGG-TGGGA-GTTCCC--AC-GGTTTT-GATATCTGG 38

(SEQ ID NO: 35)
3 TGTGCGACGG-TGGGA-GTTCCC--ACCGGTTTT-GATATCTGG 39

(SEQ ID NO: 36)
6 TGTGCGACGG-TGGGA-GTTCCC--ACCGGTTTT-GATATCTGG 39

(SEQ ID NO: 37)
8 TGTGCGACGG-TGGGA-GTTCCC--ACCGGTTTT-GATATCTGG 39

(SEQ ID NO: 38)
11 TGTGCGACGG-TGGGA-GTTCCC--ACCGGTTTT-GATATCTGG 39

(SEQ ID NO: 39)
20 TGTGCGACGG-TGGGA-GTTCCC--ACCGGTTTT-GATATCTGG 39

(SEQ ID NO: 40)
27 TGTGCGACGG-TGGGA-GTTCCC--ACCGGTTTT-GATATCTGG 39

(SEQ ID NO: 41)
32 TGTGCGACGG-TGGGA-GTTCCC--ACCGGTTTT-GATATCTGG 39

(SEQ ID NO: 42)
38 TGTGCGACGG-TGGGA-GTTCCC--ACCGGTTTT-GATATCTGG 39

(SEQ ID NO: 43)
43 TGTGCGACGG-TGGGA-GTTCCC--ACCGGTTTT-GATATCTGG 39

(SEQ ID NO: 44)
49 TGTGCGACGG-TGGGA-GTTCCC--ACCGGTTTT-GATATCTGG 39

(SEQ ID NO: 45)
55 TGTGCGACGG-TGGGA-GTTCCC--ACCGGTTTT-GATATCTGG 39

(SEQ ID NO: 46)
59 TGTGCGACGG-TGGGA-GTTCCC--ACCGGTTTT-GATATCTGG 39

(SEQ ID NO: 47)
64 TGTGCGACGG-TGGGA-GTTCCC--ACCGGTTTT-GATATCTGG 39

(SEQ ID NO: 48)
69 TGTGCGACGG-TGGGA-GTTCCC--ACCGGTTTT-GATATCTGG 39

(SEQ ID NO: 49)
74 TGTGCGACGG-TGGGA-GTTCCC--ACCGGTTTT-GATATCTGG 39

(SEQ ID NO: 50)
12 TGTGCGACGG-TGGGA-GTTCTC--ACCGGTTTTTGATATCTGG 40

(SEQ ID NO: 51)
67 TGTGCGACGG-TGGGA-GTTC-C--ACCGGTTTT-GATATCTGG 38

(SEQ ID NO: 52)
70 TGTGCGACGG-TGGGA-ATTC-C--ACCGGTTTT-GATATCTGG 38

(SEQ ID NO: 53)
10 TGTGCGACGG-TGGGA-GTTCCC--ACCGGTTTTTGATATCTGG 40

(SEQ ID NO: 54)
24 TGTGCGACGG-TGGGA-GTTCCC--ACCGGTTTTTGATATCTGG 40

(SEQ ID NO: 55)
34 TGTGCGACGG-TGGGA-GTTCCC--ACCGGTTTTTGATATCTGG 40

(SEQ ID NO: 56)
44 TGTGCGACGG-TGGGA-GTTCCC--ACCGGTTTTTGATATCTGG 40

(SEQ ID NO: 57)
47 TGTGCGACGG-TGGGA-GTTCCC--ACCGGTTTTTGATATCTGG 40
```

-continued

```
                                            (SEQ ID NO: 58)
85 TGTGCGACGG-TGGGA-GTTCCC--ACCGGTTTTTGATATCTGG 40

(SEQ ID NO: 59)
87 TGTGCGACGG-TGGGA-GTTCCC--ACCGGTTTTTGATATCTGG 40

(SEQ ID NO: 60)
13 TGTGCGACGG-TGGGA-GTTCCC--ACCGGTTTT-GATATCTGG 39

(SEQ ID NO: 61)
15 TGTGCGACGG-TGGGA-GTTCCC--ACCGGTTTT-GATATCTGG 39

(SEQ ID NO: 62)
22 TGTGCGACGG-TGGGA-GTTCCC--ACCGGTTTT-GATATCTGG 39

(SEQ ID NO: 63)
28 TGTGCGACGG-TGGGA-GTTCCC--ACCGGTTTT-GATATCTGG 39

(SEQ ID NO: 64)
33 TGTGCGACGG-TGGGA-GTTCCC--ACCGGTTTT-GATATCTGG 39

(SEQ ID NO: 65)
39 TGTGCGACGG-TGGGA-GTTCCC--ACCGGTTTT-GATATCTGG 39

(SEQ ID NO: 66)
45 TGTGCGACGG-TGGGA-GTTCCC--ACCGGTTTT-GATATCTGG 39

(SEQ ID NO: 67)
50 TGTGCGACGG-TGGGA-GTTCCC--ACCGGTTTT-GATATCTGG 39

(SEQ ID NO: 68)
56 TGTGCGACGG-TGGGA-GTTCCC--ACCGGTTTT-GATATCTGG 39

(SEQ ID NO: 69)
61 TGTGCGACGG-TGGGA-GTTCCC--ACCGGTTTT-GATATCTGG 39

(SEQ ID NO: 70)
65 TGTGCGACGG-TGGGA-GTTCCC--ACCGGTTTT-GATATCTGG 39

(SEQ ID NO: 71)
71 TGTGCGACGG-TGGGA-GTTCCC--ACCGGTTTT-GATATCTGG 39

(SEQ ID NO: 72)
78 TGTGCGACGG-TGGGA-GTTCCC--ACCGGTTTT-GATATCTGG 39

(SEQ ID NO: 73)
83 TGTGCGACGG-TGGGA-GTTCCC--ACCGGTTTT-GATATCTGG 39

(SEQ ID NO: 74)
89 TGTGCGACGG-TGGGA-GTTCCC--ACCGGTTTT-GATATCTGG 39

(SEQ ID NO: 75)
92 TGTGCGACGG-TGGGA-GTTCCC--ACCGGTTTT-GATATCTGG 39

(SEQ ID NO: 76)
95 TGTGCGACGG-TGGGA-GTTCCC--ACCGGTTTT-GATATCTGG 39

(SEQ ID NO: 77)
98 TGTGCGACGG-TGGGA-GTTCCC--ACCGGTTTT-GATATCTGG 39

(SEQ ID NO: 78)
101 TGTGCGACGG-TGGGA-GTTCCC--ACCGGTTTT-
GATATCTGG 39

(SEQ ID NO: 79)
23 TGTGCGACGG-TGG-A-GTTCCC--ACCGGTTTT-GATATCTGG 38

(SEQ ID NO: 80)
51 TGTGCGACGG-TGG-A-GTTCCC--ACCGGTTTT-GATATCTGG 38

(SEQ ID NO: 81)
80 TGTGCGACGG-TGG-A-GTTCCC--ACCGGTTTT-GATATCTGG 38

(SEQ ID NO: 82)
17 TGTGCGACGG-TGGGA-GTTCCC--ACCGGTTTT-GATATCTGG 39

(SEQ ID NO: 83)
25 TGTGCGACGG-TGGGA-GTTCCC--ACCGGTTTT-GATATCTGG 39

(SEQ ID NO: 84)
30 TGTGCGACGG-TGGGA-GTTCCC--ACCGGTTTT-GATATCTGG 39

(SEQ ID NO: 85)
35 TGTGCGACGG-TGGGA-GTTCCC--ACCGGTTTT-GATATCTGG 39

(SEQ ID NO: 86)
40 TGTGCGACGG-TGGGA-GTTCCC--ACCGGTTTT-GATATCTGG 39

(SEQ ID NO: 87)
46 TGTGCGACGG-TGGGA-GTTCCC--ACCGGTTTT-GATATCTGG 39

(SEQ ID NO: 88)
52 TGTGCGACGG-TGGGA-GTTCCC--ACCGGTTTT-GATATCTGG 39

(SEQ ID NO: 89)
57 TGTGCGACGG-TGGGA-GTTCCC--ACCGGTTTT-GATATCTGG 39

(SEQ ID NO: 90)
62 TGTGCGACGG-TGGGA-GTTCCC--ACCGGTTTT-GATATCTGG 39

(SEQ ID NO: 91)
66 TGTGCGACGG-TGGGA-GTTCCC--ACCGGTTTT-GATATCTGG 39

(SEQ ID NO: 92)
72 TGTGCGACGG-TGGGA-GTTCCC--ACCGGTTTT-GATATCTGG 39

(SEQ ID NO: 93)
81 TGTGCGACGG-TGGGA-GTTCCC--ACCGGTTTT-GATATCTGG 39

(SEQ ID NO: 94)
84 TGTGCGACGG-TGGGA-GTTCCC--ACCGGTTTT-GATATCTGG 39

(SEQ ID NO: 95)
90 TGTGCGACGG-TGGGA-GTTCCC--ACCGGTTTT-GATATCTGG 39

(SEQ ID NO: 96)
93 TGTGCGACGG-TGGGA-GTTCCC--ACCGGTTTT-GATATCTGG 39

(SEQ ID NO: 97)
96 TGTGCGACGG-TGGGA-GTTCCC--ACCGGTTTT-GATATCTGG 39

(SEQ ID NO: 98)
99 TGTGCGACGG-TGGGA-GTTCCC--ACCGGTTTT-GATATCTGG 39

(SEQ ID NO: 99)
100 TGTGCGACGG-TGGGA-GTTCCC--ACCGGTTTT-
GATATCTGG 39

(SEQ ID NO: 100)
97 TGTGCGACGG-TGGGA-GTTCCC--ACCGGTTTT-GATATCTGG 39

(SEQ ID NO: 101)
94 TGTGCGACGG-TGGGA-GTTCCC--ACCGGTTTT-GATATCTGG 39

(SEQ ID NO: 102)
91 TGTGCGACGG-TGGGA-GTTCCC--ACCGGTTTT-GATATCTGG 39

(SEQ ID NO: 103)
86 TGTGCGACGG-TGGGA-GTTCCC--ACCGGTTTT-GATATCTGG 39

(SEQ ID NO: 104)
82 TGTGCGACGG-TGGGA-GTTCCC--ACCGGTTTT-GATATCTGG 39

(SEQ ID NO: 105)
77 TGTGCGACGG-TGGGA-GTTCCC--ACCGGTTTT-GATATCTGG 39

(SEQ ID NO: 106)
75 TGTGCGACGG-TGGGA-GTTCCC--ACCGGTTTT-GATATCTGG 39

(SEQ ID NO: 107)
73 TGTGCGACGG-TGGGA-GTTCCC--ACCGGTTTT-GATATCTGG 39

(SEQ ID NO: 108)
68 TGTGCGACGG-TGGGA-GTTCCC--ACCGGTTTT-GATATCTGG 39

(SEQ ID NO: 109)
63 TGTGCGACGG-TGGGA-GTTCCC--ACCGGTTTT-GATATCTGG 39
```

-continued

```
                                                 (SEQ ID NO: 110)
58 TGTGCGACGG-TGGGA-GTTCCC--ACCGGTTTT-GATATCTGG 39

(SEQ ID NO: 111)
53 TGTGCGACGG-TGGGA-GTTCCC--ACCGGTTTT-GATATCTGG 39

(SEQ ID NO: 112)
48 TGTGCGACGG-TGGGA-GTTCCC--ACCGGTTTT-GATATCTGG 39

(SEQ ID NO: 113)
41 TGTGCGACGG-TGGGA-GTTCCC--ACCGGTTTT-GATATCTGG 39

(SEQ ID NO: 114)
37 TGTGCGACGG-TGGGA-GTTCCC--ACCGGTTTT-GATATCTGG 39

(SEQ ID NO: 115)
31 TGTGCGACGG-TGGGA-GTTCCC--ACCGGTTTT-GATATCTGG 39

(SEQ ID NO: 116)
26 TGTGCGACGG-TGGGA-GTTCCC--ACCGGTTTT-GATATCTGG 39

(SEQ ID NO: 117)
19 TGTGCGACGG-TGGGA-GTTCCC--ACCGGTTTT-GATATCTGG 39

(SEQ ID NO: 118)
 9 TGTGCGACGG-TGGGA-GTTCCC--ACCGGTTTT-GATATCTGG 39

(SEQ ID NO: 119)
 7 TGTGCGACGG-TGGGA-GTTCCC--ACCGGTTTT-GATATCTGG 39

(SEQ ID NO: 120)
 5 TGTGCGACGG-TGGGA-GTTCCC--ACCGGTTTT-GATATCTGG 39

(SEQ ID NO: 121)
 2 TGTGCGACGG-TGGGA-GTTCCC--ACCGGTTTT-GATATCTGG 39

(SEQ ID NO: 122)
14 TGTGCGACGG-TGGGA-GTTCCC-TACCGGTTTT-GATATCTGG 40

(SEQ ID NO: 123)
21 TGTGCGACGG-TGGGA-GTTCCC-TACCGGTTTT-GATATCTGG 40

(SEQ ID NO: 124)
42 TGTGCGACGG-TGGGA-GTTCCC-TACCGGTTTT-GATATCTGG 40

(SEQ ID NO: 125)
102 TGTGCGACGG-TGGGA-GTTCCC-TACCGGTTTT-
GATATCTGG 40

(SEQ ID NO: 126)
18 TGTGCGACGG-TGGGA-GTTCCC--ACCGGTTT--GATATCTGG 38

(SEQ ID NO: 127)
54 TGTGCGACGG-TGGGA-GTTCCCCTACCGGTTTT-GATATCTGG 41

(SEQ ID NO: 128)
60 TGTGCGACGG-TGGGA-GTTCCCCTACCGGTTTT-GATATCTGG 41

(SEQ ID NO: 129)
76 TGTGCGACGGGTGGGACGTTCCCCTACCGGTTTT-GATATCTGG 43

(SEQ ID NO: 130)
88 TGTGCGACGG-TGGGA-CTTCCC--ACCGCTTTT-GATTTCTGG 39

(SEQ ID NO: 131)
29 TGTGCGACGG-TGGGA-GTTCCC--ACCGGTTTTGATTATCGTG 40

(SEQ ID NO: 132)
36 TGTGCGACGG-TGGGACGTTCCCCTACCGGTTTTGAT-ATCGTG 42

********** *** * *** * ** * *** ** *
```

Figure 19A:
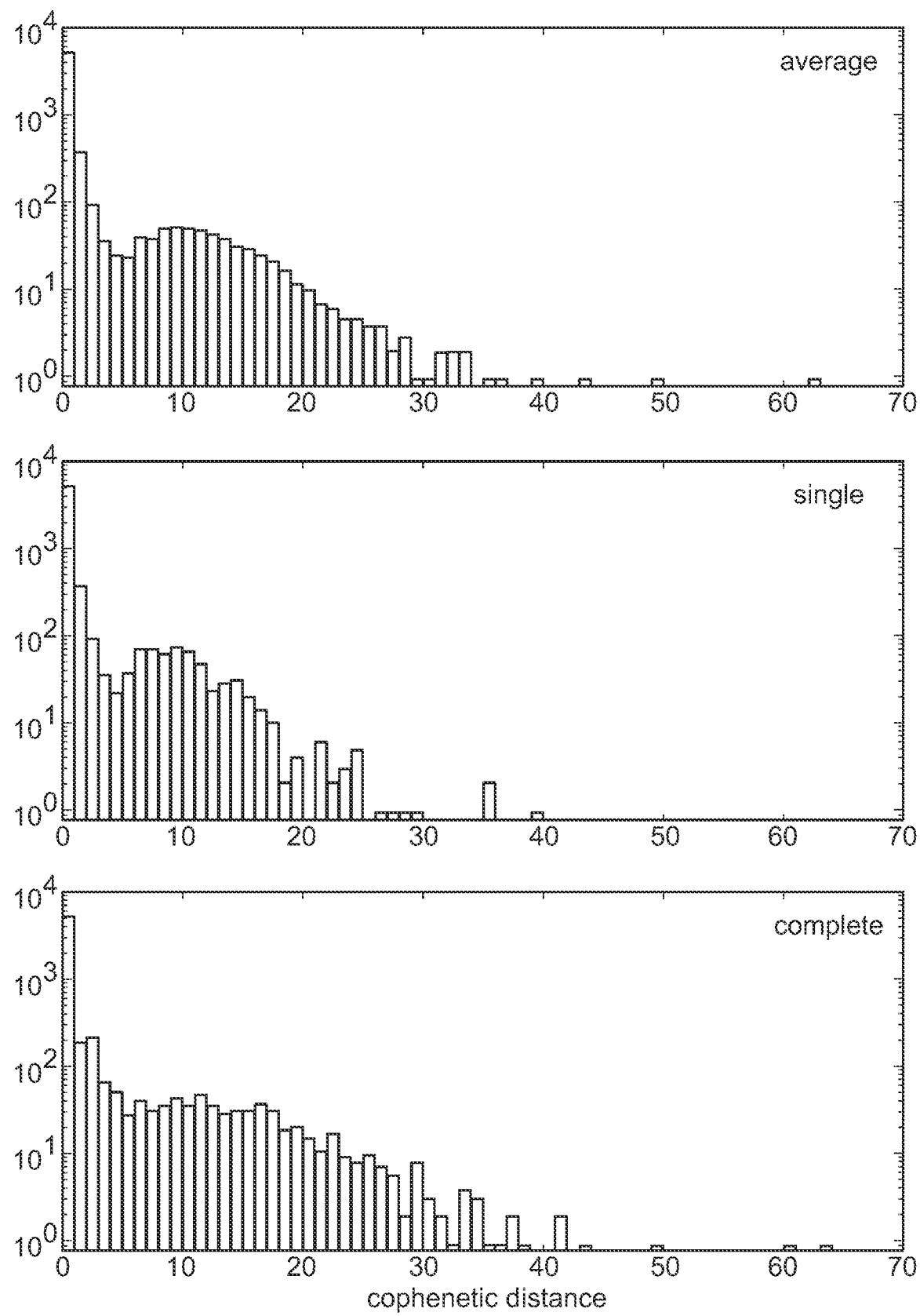
FIGS. 19A-19B depict (FIG. 19A) distribution of cophenetic distances for single and complete linkage hierarchical clustering on sequences from a V-J combination with a small number of reads.
Figure 19B:
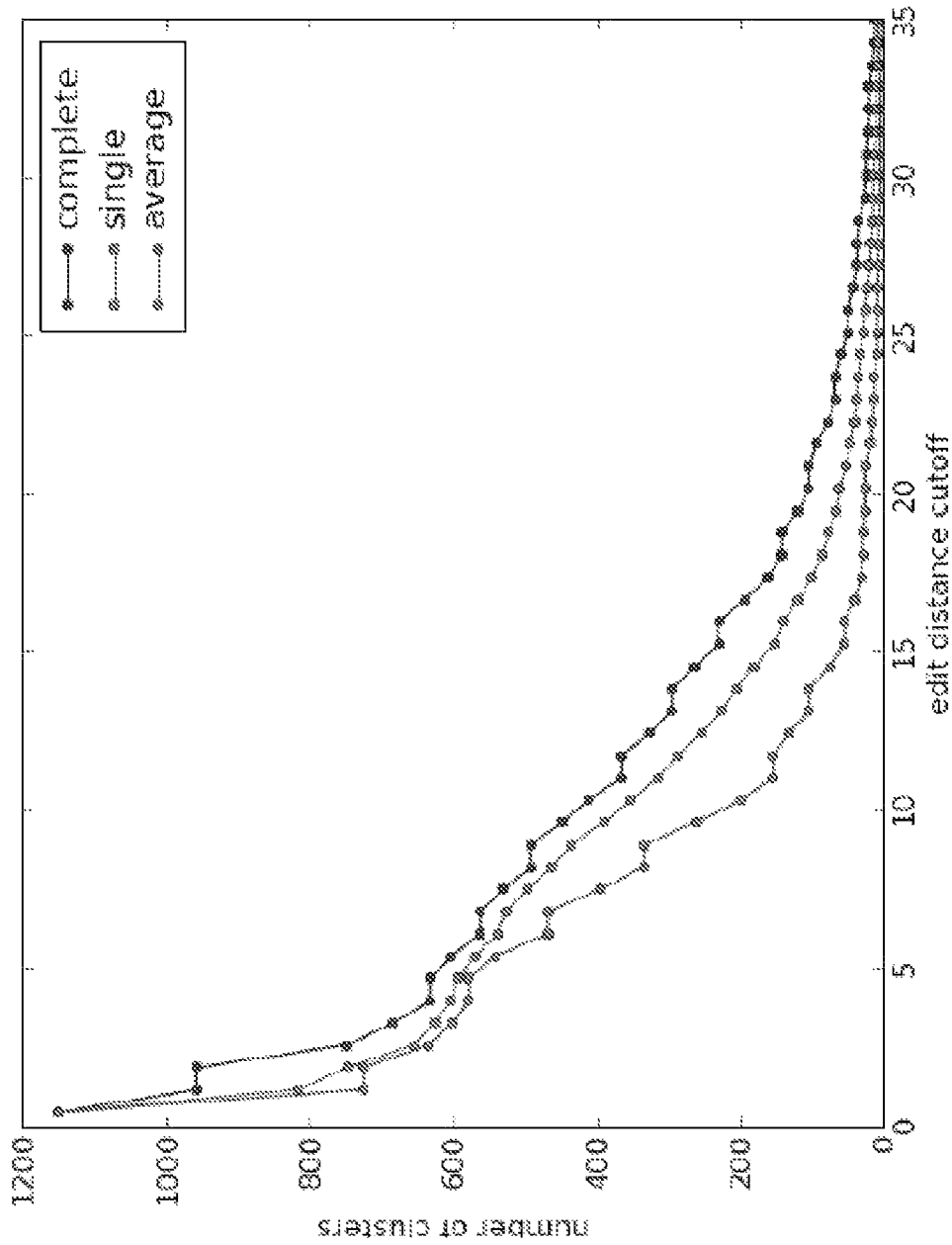

The distribution of cophenetic distances observed in the linkage tree was then examined in order to determine the optimal distance to clip the tree. It was expected that a large number of linkage events occurring at low cophenetic distance that represent sequencing errors would be observed. Indeed, a rapid drop in the distribution was observed until a distance of 4-5 edits, after which the distribution showed a shoulder and a slower descent (FIG. 19A). This was consistent with the observed relationship between distance cutoff and number of clusters obtained (FIG. 19B), as there was also a rapid drop at short distance followed by a shoulder and marked slowing.

Time Series Clustering: k-Means

While the sequence clustering described above was performed on combined data for all eight time points, each unique clone identifier was further partitioned into the 8 time points by identifying the 454 MID bar-codes. Each clone thus defined a time series where the number of reads was a proxy for expression level. As an initial analysis, k-means clustering was performed on all time series using combined data from runs SRL SR2, and TR1. The k-means algorithm was performed on clone frequencies (read counts in a given time point normalized by the number of reads) using the Euclidean distance metric with 100 clusters (chosen arbitrarily). The largest clusters contained clones that appeared for a single time point and disappeared. This was observed at a variety of expression levels and at all time points (FIG. 15A). When these clusters were filtered out and k-means clustering performed again, a large variety of dynamic behavior was observed. However, some of the largest clusters were still clones that rapidly rose and fell in frequency (FIG. 15B).

Time Series Clustering: Self-Organizing Maps (SOM)

Due to the arbitrary selection in clone number for k-means clustering and the large diversity of dynamic behavior, the time series was clustered using a SOM method as implemented in the GEDI software package (Eichler et al. (2003) *Bioinformatics* 19:2321). Each tile within a mosaic represented a mini-cluster of clones that have highly similar expression patterns across all the analyzed time points. By defining a topology on the tiles, similar clusters are grouped together, allowing simple determination of the proper number of cluster groups. The same clones are forced to the same mosaic position for all SOM maps, allowing direct comparison of the clones based on the overall mosaic pattern. The color of tiles indicated the centroid value of gene expression level for each mini-cluster. SOM clustering was performed on a rectangular, 50×49 grid using random initialization. An Euclidean distance was defined on the time series, and two training iteration phases were performed (20 and 80). Following clustering, clusters of interest were manually identified for further analysis.

Reproducibility, Sampling Requirements, and Limits of Quantitation

Multiple analyses were performed to determine whether the VDJ-ome was sampled deep enough and to what level the dynamics could be reliably quantified (i.e., the limit of quantitation (Currie (1968) *Analytical Chemistry* 40:586)). The replicate time series of randomly chosen clones was plotted (from runs SR1, SR2, and TR1) to get a qualitative view of the replication (FIG. 15). Scatter plots of replicate runs showed high levels of correlation (FIG. 9, Pearson correlations shown). To determine the sampling characteristics of the samples, pairs of subsamples of the data were drawn of different sizes and correlation coefficients were computed (FIG. 2C). The correlation coefficients approached unity at a sampling level of $10^5$. To determine limits of quantitation, scatter plots were generated for each time point of a given replicate against another. The data were binned on one axis and the mean and standard deviation were computed on the other axis. Using these values, the coefficient of variation (CV) was computed as a function of expression level (FIG. 10). It was expected that higher expression levels would have lower relative variances and so should have resulted in smaller CVs. The noise in the middle of the curves was an artifact of the weighted sampling scheme used, and noise was also observed at high expression levels due to poor sampling. A lower limit CV of approximately 0.5 occurred at clone frequencies of $<10^{-4}\text{-}10^{-3}$, depending on the samples. Sampling of lower frequency clones rapidly approached the Poisson noise regime (CV of 1). Different numbers of reads in different time points/replicates caused the onset of Poisson noise at different frequencies.

Diversity Estimates

Multiple methods were utilized to estimate antibody diversity. To estimate typical diversities of small 1 mL blood samples, the Chao1 and ACE abundance-based estimators were used (Magurran, A.E. Measuring Biological Diversity. (Blackwell Pub., Malden, MA; 2004)). Briefly, Chao1 and ACE were derived as non-parametric abundance-based estimators for diversity. Following Magurran, if $S_{obs}$ was the number of species observed in the sample, $F_1$ was the number of species observed once (singletons), and $F_2$ was the number of species observed twice (doubletons), then the Chao1 estimator was defined as $$S_{Chao1} = S_{obs} + \frac{F_1^2}{2F_2}.$$

If $S_{rare}$ was the number of rare species (species with less than or equal to 10 observations), $S_{abund}$ was the number of abundant species (species with greater than 10 observations), $N_{rare}$ was the number of individuals in rare species, $F_i$ was the number of species with i observations, $C_{ACE}=1-F_1 N_{rare}$, and $$\gamma_{ACE}^2 = \max\left\{\frac{S_{rare}}{C_{ACE}} \frac{\sum_{i=1}^{10} i(i-1)F_i}{N_{rare}(N_{rare}-1)} - 1, 0\right\}$$

then $$S_{ACE} = S_{abund} + \frac{S_{rare}}{C_{ACE}} + \frac{F_1}{C_{ACE}}\gamma_{ACE}^2.$$

However, the samples used were non-homogeneous in that they were drawn at varying time points after an immune challenge, which may affect the antibody distribution, as compared to homogeneous samples. It was expected that such effects would be small, and so the estimators were still applied. More significantly, the coverage level just passed an inflection point (indicating the start of convergence towards an asymptote). In such cases, the actual diversities tended to be higher than the estimate values, and the estimators functioned as lower bounds on diversity. The re-sampled versions of these estimators are shown in FIGS. 12A-12D. Inflection points were observed for almost all curves, indicating approach towards an asymptote.

Similarly, the analogous incidence-based estimators Chao2, ICE, Jack1, Jack2 (Magurran, Supra) were used to estimate total blood diversity, using the multiple blood samples analogously to multiple quadrants in ecology. The same statistical considerations applied to these sets of estimators. The results are shown in FIG. 2E. The diversity estimation method of Arstila et al. (Arstila et al. (1999) *Science* 286:958) was also simulated using every possible V-J combination and every possible pseudo-spectratype peak. This method did not take statistical considerations into account a very large range of possible diversity estimates was expected. Indeed, a very broad distribution of values was obtained, though the mean value was still near the $10^6$ range (FIG. 2E).

Distribution of Fluctuations

Figure 20A:
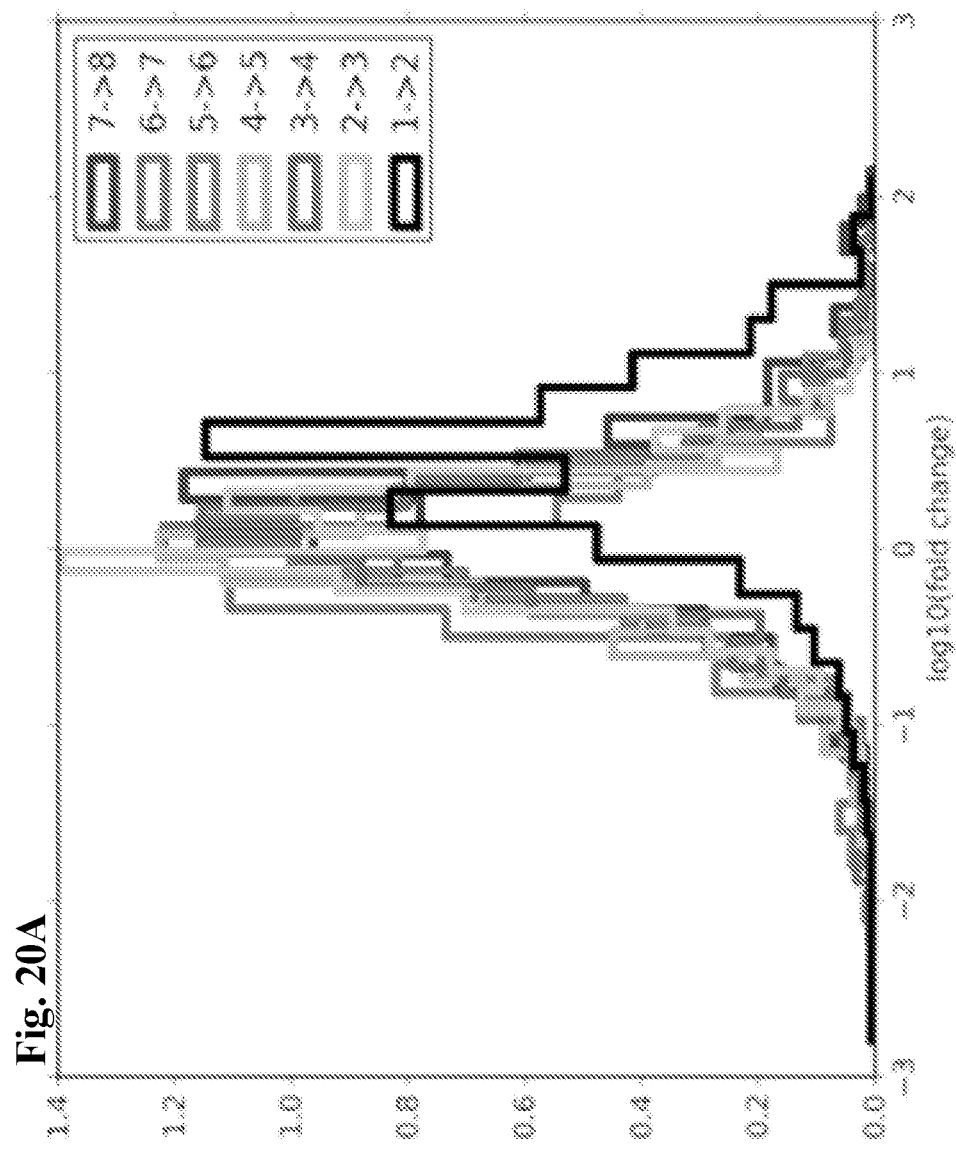
FIGS. 20A-20B depict (FIG. 20A) distribution of log(fold change) for each transition in time series that were positive at all 8 time points.
Figure 20B:
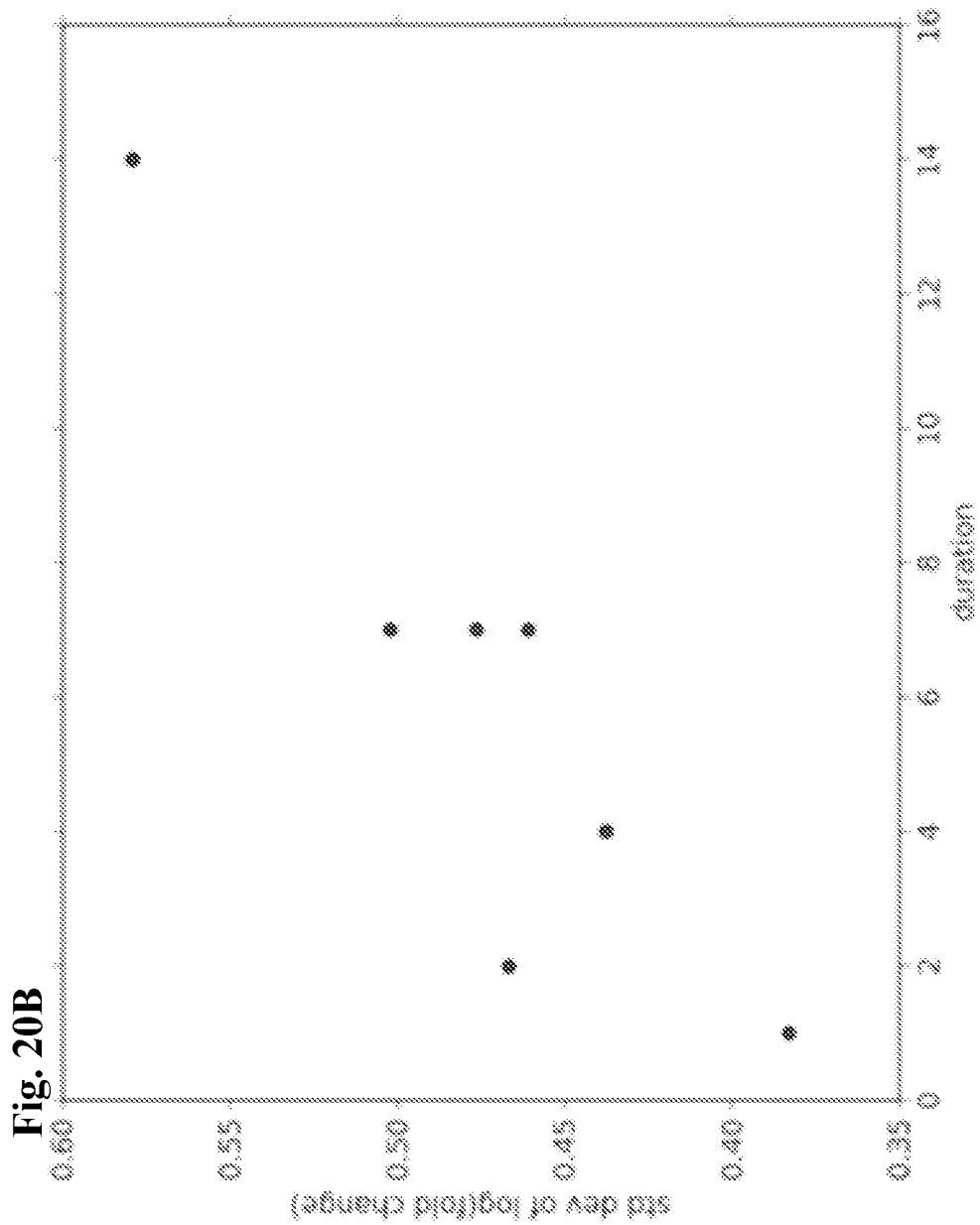

To characterize the dynamics of the antibody clones further, we analyzed the distribution of their typical fluctuations. For time series that were positive at all time points, the log-fold change from one time point was computed over the preceding time point. The distributions are shown in FIGS. 20A-20B. They appeared to be log-normally distributed and centered at zero. The −14 d time point distribution was off-center due to a sampling artifact. It was also expected that the variance of the distribution would be correlated with the duration of the time interval (i.e., longer durations lead to larger fluctuations). Indeed, FIGS. 20A-20B show a strong correlation, with a Pearson correlation coefficient of 0.91.

Pseudo-Spectratype Generation

For each time point, the count data was partitioned by V-J usage and then by CDR3 junction length. For each possible in-frame length (multiple of 3) the number of in-frame reads were computed versus out-of-frame reads that were one base too long or too short, and fitted this data to a Gaussian distribution. For each V-J combination, all such Gaussians were superposed and the curve renormalized to the total number of reads. Full pseudo-spectratypes are shown in FIG. 13. The use of Gaussians were for visualization purposes only.

Alignment to Specificity-Annotated IMGT/LIGM Database

The IMGT/LIGM database (Giudicelli et al. (2006) *Nucleic Acids Res*. 34:D781) contains about 9000 sequences with annotated specificities, 14 of which are specific for influenza hemagglutinin, 6 for hepatitis A, and 85 for hepatitis B. Though this represents a very small sample, the sequencing reads to this set of specificity-annotated sequences were aligned to search for highly identical sequences. To perform the alignments, the exonerate software package (Slater and Birney (2005) *BMC Bioinformatics* 6:31), which allows alignment using various alignment models, was used. Alignments were performed using either the full read or only the CDR3 junction, and using translated versions and/or nucleotide versions of the sequences. Because many background matches were expected (in the case of full read alignment), and due to the sensitivity of binding affinity to the exact amino acid sequence, the alignments were ranked by sequencing identity, and only matches that were almost completely identical were analyzed by hand. Examples of matches to influenza-specific or hepatitis-specific (FIGS. 21 and 22) antibodies were performed using full nucleotide sequence alignment. Poor alignment was observed at the CDR3 junction region, which is the most common form of misalignment. The best matching alignment was found by aligning translated junction regions only. An anti-digoxin antibody was successfully matched. The junction-only alignment (FIG. 23) and the full read alignment (FIG. 24) are shown.

Software Tools and Data Availability

The analysis software package used for the experiments described herein is available for download at the Worldwide Web Site: arep.med.harvard.edu/vdj, or the latest version can be pulled as a git repository from GitHub at the Worldwide Web Site: github.com/laserson/vdj. The software was implemented primarily in python with some C code used to increase performance. The NumPy (the Worldwide Web Site: numpy.scipy.org/) and SciPy (the Worldwide Web Site: scipy.org/) packages were also heavily relied upon for numerical calculations, and the matplotlib (the Worldwide Web Site: matplotlib.sourceforge.net/) package was relied upon for data visualization. The sequencing data is available for download in FASTA format at the Worldwide Web Site: arep.med.harvard.edu/vdj along with processed versions of it in XML format. The sequencing data will be submitted to the NCBI Short Read Archive, and to the international ImMunoGeneTics (IMGT) database for incorporation into Laboratoire d'ImmunoGénétique Moléculaire (LIGM).

Example V

Heavy and Light Chain Capture from a Unique Cell

Methods are provided to capture both the heavy and light chains of an antibody originating from a single, enabling the simultaneous capture of millions of cells at once (instead of prior arts of sorting one cell per well in a plate).

Small Oligo-Transfection of Single Cells

Two oligos, each presenting a complementary sequence to the heavy and light chain respectively, are partially annealed to each other through a universal sequence. This partial annealing bond is maintained in subsequent step and the use of locked nucleic acid (LNA) can be useful for this purpose. The oligos can also harbor phosphorothioates to protect the oligo from nucleases. Additionally, a distal or internal biotin can be included in one or both of the oligos, which will be used in recovery or the molecules downstream. This oligo linker is then transfected into lymphocytes samples using common transfection technologies such as TransIT®-Oligo Transfection Reagent (Minis Bio LLC) for example. The transfection component can also include RNase inhibitor as a precaution. The cells are then incubated at higher temperature so that annealing of the cell RNA that one which to capture is accomplished (can also be done with DNA). Ideally, the temperature is raised enough to favor melting of the targeted RNA secondary structure and to achieve specific annealing to the oligo linker by matching melting temperature as close as possible (generally near 65° C.), while the partial annealing of the two oligos is maintain due to the inherent sequence design (particularly with the use of LNA primers, where the annealing junction can be design to reach temperature above 90° C.). Following incubation annealing of the targeted RNAs, the cells can be chemically lysed and the oligo linker-target RNA molecule recovered through its biotin using a streptavidin coated magnetic bead (such as Dynabead M280 form Invitrogen, or other equivalent). One could also use any other solid substrate coated with streptavidin. The oligo linker 3' end can then be used directly for reverse transcription (using superscript III, Invitrogen, or other equivalent reverse transcriptase) of both the heavy and light chains, followed by second strand cDNA synthesis. The final molecule is amplified off the magnetic beads using distal primer with results in the recovery of a full ScFv composed of the heavy and light chains originating form a single cells, and this accomplished in millions of cells at once in the same reaction sample.

Bead Capture

In certain exemplary embodiments, a magnetic bead is coupled with a mixture of oligos complementary to the heavy and light chains but also harboring a universal sequence upstream (a non-magnetic bead will work, however magnetic beads facilitate downstream washes and recoveries). In certain aspects, covalent coupling chemistry or streptavidin-biotin linkages (e.g., if a biotin is added to the oligos during manufacturing) are used to produce oligo-beads. The oligo-bead is then either transfected into single cells using common transfection technologies, or liposome based transfection approaches (as long as the bead is small enough to be transfected), or the bead (or a few beads), is encapsulated inside an emulsion in the presence of a single lymphocyte. The cell is then lysed using heat denaturation or using freeze thaw cycles. In certain aspects, RNase inhibitors are added during the emulsification step. The emulsions are then either PCR amplified (assuming PCR and primer were also introduce during the emulsification), or the incubated at an optimal oligo hybridization temperature and/or salt concentration such that both heavy and light chains will anneal to their complementary sequence on the bead. The emulsions are then broken and the beads recovered. Unbound cell components and non-specific DNA or RNA are washed away and the resulting bead-RNA is subjected to reverse transcription (for RNA) or primer extension (for DNA), so that the bead now harbor the full heavy and light chains sequence of a same single cell. These beads can then be subjected to any of the described techniques to link both chains together prior sequencing, such as overlapping PCR (SOE-PCR), or using CRE-LOW recombination of both chains either in emulsion, or in a super diluted reaction. Cre-lox linking of single cell heavy and light chains has been demonstrated previously in formaldehyde cross-linked lymphocytes but with very poor efficiency (Chapal et al. (1992) *Biotechniques, PMID:* 9298226), whereas methods provided herein have coupled cross-linking to the process of high-throughput sequencing, thus enabling one of ordinary skill in the art the ability to survey large immune repertoire.

SOE-PCR Variation

SOE-PCR has never been coupled to the methods of high-throughput sequencing and analysis of large immune repertoire, but has instead always been limited to the study of a limited number of cells (such as conducted by Symphogen in their Symplex technology (Worldwide Web: symphogen.com/web/guest/symplex) described by Meijer (2006) *J. Mol. Biol., PMID:* 16563430, for example). Accordingly, multiple methods of SOE-PCR are provided that improve efficiency. These methods are used in single cell SOE-PCR by either capturing single cell in emulsion or by cross-linking cells in formaldehyde as described further herein. This allows for generation of single cell ScFv of millions of single cells in a single reaction volume, so that it can be coupled with high-throughput sequencing and analysis of immune repertoires.

Example VI

Expression and Functional Assay of Antibody and Nanobody Selected Candidates from High-Throughput Sequencing Analysis of a Human Immune Repertoire In Vitro Expression of Single Domain Antibody 1. A random colony from each clone was lifted by toothpick and inoculated into 5 mL of LB/Amp, and bacteria were incubated overnight at 37° C. in shaking at 225 rpm.

2. Bacteria were centrifuged at 4,700 g for 10 min, sup was discarded and pellets were used for miniprep (using a Qiagen miniprep kit).

3. Transcription reactions were set up: Nuclease free water 8 µL; 5× Transcription buffer 4 µL; NTP mix 4 µL; DNA template (~0.5 µg/mL) 2 µL; T7 RNA polymerase 2 µL; TOTAL 20 µL.

4. Reaction was incubated for 120 min at 32° C. The solutions became cloudy after this time, indicating efficient transcription (calcium precipitates).

5. Translation reactions were set up directly: Lysate for protein expression 12.5 µL; Accessory proteins 2.5 µL; Nuclease free water 3.75 µL; Salt Solution A 1 µL; Amino acids—Met 0.5 µL; Amino acids—Leu 0.5 µL; RNase inhibitor 1 µL; Energy mix 1.25 µL; RNA template from transcription reaction 2 µL; TOTAL 25 µL.

6. Translation reactions were incubated at 32° C. for 2 hours, then 2 µL of the transcription reaction was added.

7. The reaction was incubated for further 2 hours at 32° C., then spiked again with 1 µL of the transcription reaction and incubated for further 2 hours.

Proteins were Purified as Follows

1. The reaction was diluted with 28 µl, of 2× His binding buffer (40 mM phosphate, 1 M NaCl, 40 mM imidazole, pH 7.4).

2. Samples were cleaned on Vivaspin 0.2 µm columns to get rid of all debris and large complexes.

3. Ni-NTA sepharose resin (Amersham) was gently swirled for 5 minutes until all slurry was homogenous, then a total amount of (50 µL×(#samples+1)) was transferred to a 1.5 mL tube.

4. Resin was washed 3 times with 1× His binding buffer (20 mM phosphate, 0.5 M NaCl, 20 mM imidazole, pH 7.4) to remove ethanol and equilibrate resin.

5. 50 µL of the resin were added to each sample.

6. The samples were flipped overnight at 4° C.

7. Samples were washed 3 times with 150 µL of His binding buffer.

8. Proteins were eluted from resin in 100 µL of His elution buffer (20 mM phosphate, 0.5 M NaCl, 0.5 M imidazole, pH 7.4) by flipping at RT for 1 hour.

9. Resin was removed and samples were desalted using Vivaspin 5K as follows: a. Vivaspin 5K columns were equilibrated with 0.4 mL of PBS. b. 100 µL of sample were added to the column. c. Columns were placed in centrifuge with filter facing outwards, then centrifuged (15,000 g, 15 min). d. Flow-thru was discarded, and sample was resuspended in 0.4 mL of PBS and centrifuged again. e. Step d was repeated two additional times. f. Retentates (~50 µL average) were transferred to fresh tubes, sodium azide solution was added to a final concentration of 0.02% and the samples were stored at 4° C. Protein concentration and/or purity was evaluated using Nanodrop.

Gene Synthesis and Cloning Protocol

PCR amplify IDT gene synthesis using M13 forward and reverse primer

Assemble a reaction as follows (1 tube/13 tubes): ~50 ng/µl Gene synthesis (1 µl/—); dH₂O (34.6 µl/449.8 µl); 5× HF buffer (10 µl/130 µl); 15 µM primer 1* (1.7 µl/22.1 µl); 15 µM primer 2* (1.7 µl/22.1 µl); 25 mM dNTP (0.5 µl/6.5 µl); Phusion Hotstart (0.5 µl/6.5 µl); (49 µl/tube). Thermal cycle as follows: 9 to 12 cycles

| | |
|---|---|
| 1 | 98° C. for 30 sec |
| 2 | 98° C. for 10 seconds |
| 3 | 50° C. for 20 seconds |
| 4 | 72° C. for 20 seconds go to step 2, 25× |
| 5 | 72° C. for 5 min |
| 6 | 4° C. pause |

Qiagen purify, resuspend in 30111.

Double Digest with EcoRI-HF and NotI-HF

Assemble reaction as follows

| | 1 tubes | 13 tubes |
|---|---|---|
| H2O | 10.5 (to 50 µl) | 136.5 |
| DNA | 30 µl | — |
| 10×NEB buffer 4 | 5 µl | 65 |
| 100× BSA | 0.5 µl | 6.5 |
| NotI-HF | 2 µl | 26 |
| EcorI-HF | 2 µl | 26 |

Incubate at 37° C. for 15 min (20 µl/tubes). Heat inactivate at 65° C. for 20 min Qiagen purify, elute in 42 (will load 20 one gel); Nanodrop a few ~50 ng/µl. Extract using size select gels: Qiagen purify, elute in 30 µl; Nanodrop: ~9 ng/µ1.

Ligation into Thermo Expression Vector

Used 3:1 ratio inserts to vector Assembled reaction as follows (1 tube/14 tubes): H₂O (4 µl/56 µl); 2× Ligase buffer (10 µl/140 µl); Vector 50 ng/µ1 (2 µl (0.04 pmole)/28 µl); ~350 bp Inserts (9 ng/µl) (3 µl (0.12 pmole=30 ng)/–µl); Rapid ligase (1 µl/14 µl); (17 µl/tubes). Incubate at 22° C. for 30 min. Performed the cloning with X10 cells. Plated 2000 using beads, this morning plate were full, nice results. Recloned in NEB Shuffle T7 competent *E. coli* (at C3026H). Used mini prep, diluted 3-fold, used 1 µl (~80 ng) in 25 µl of *E. coli*. Grew midi batch of selected clones.

Picked one colony into 50 ml LB+1× Ampicillin, grew overnight at 30° C.

| clone ID | name of clone | synthesis ID | binding | large batch |
|---|---|---|---|---|
| IDT plate (yellow sticker row A) sampler un form left to right. | | | | |
| 1 | GMC_1688_Day1_2 | 1-IDT | | |
| 2 | GMC_1337_Day1_3 | 2-IDT | | |
| - | GMC_299_Day1_4 | 3-IDT | not done yet | |
| 3 | GMC_162_Day1_5 | 4-IDT | 10, 59 | X |
| 4 | GMC_961_Day7_2 | 5-IDT | | |
| 5 | GMC_1458_Day7_3 | 6-IDT | | |
| 6 | GMC_1494_Day7_4 | 7-IDT | 10, 59 | X |
| 7 | GMC_769_Day7_5 | 8-IDT | 59 | X |
| 8 | GMC_967_Day21_2 | 9-IDT | 59 | X |
| 9 | GMC_750_Day21_3 | 10-IDT | | |
| 10 | GMC_2629_Day21_4 | 11-IDT | 10, 59 | X |
| 11 | GMC_668_Day21_5 | 12-IDT | | |
| DNA2.0 plate (red sticker any well from 1 to 5) sampler un from top to down. | | | | |
| 12 | IDO_1_NEGCONT_BCELLTUMOR_optHEK1 | IDO1 | | |
| 13 | GMC_1687_Day1_1 | IDO2 | | |
| 14 | GMC_932_Day7_1 | IDO3 | 59 | X |
| 15 | GMC_393_Day7_6 | IDO4 | 10, 59 | X |
| 16 | GMC_376_Day21_1 | IDO5 | | |
| 17 | IDO_6_POSCONT_GFPMINIMIZER_optHEK1 | IDO6 | | X |

Redone

Recloned in T7 shuffle *E. coli*: 3, 6, 7, 8, 10, 12. Uses 2 µl of 13 dilution in 20 IA of T7 shuttle *E. coli* (NEB C3026H). Plated 200 µl on super large plate (too much, plenty of clone, try 100 ul next time). Grew one colony each in 5 ml of LB at 30° C. overnight. Used this a starter culture 500 µl for 50 ml LB+1000× ampi (50 mg/ml use at 1×). Grew for 3-4 hr, checked OD. Nanodrop. Cuvette: 0.3. Pedestal: 0.08 (nanodrop says that should be 10-fold lower than regular OD600). Kept some of 10 cell lysate for direct SPR testing.

Q8: How should I express my protein of interest in Shuffle? A8: For initial conditions we recommend using rich media at 30° C. Otherwise, overnight at 16° C. is possible. At 30° C. or 16° C., inoculate 1% overnight culture and grow cells at 30° C. for 3 hours until OD600~0.8 and then induce expression of protein for at least 5 hours at 30° C. or overnight at 16° C. If using 37° C., inoculate 1% overnight culture and grow cells for 2 hours at 37° C. until OD600 ~0.8 and then induce expression of protein for at least 6 hours at 37° C.

Protocol

Transformed expression plasmid into the T7 Express strain. Plated on antibiotic selection plates and incubate overnight at 37° C. Resuspended a single colony in 10 ml liquid culture with antibiotic. Incubated at 37° C. until OD600 reached 0.4-0.6. Induced with 40 µl of a 100 mM stock of IPTG (final concentration of 0.4 mM) and induced for 2 hours at 37° C. Checked for expression either by Coomassie stained protein gel, Western Blot or activity assay. Checked expression in both the total cell extract (soluble+insoluble) and the soluble fraction alone. For large scale, inoculated 1 L of liquid medium (with antibiotic) with a freshly grown colony or 10 ml of freshly grown culture. Incubated at 37° C. until OD600 reached 0.4-0.6. Added IPTG to 0.4 mM. Induced 2 hours at 37° C. or 15° C. overnight.

IPTG Induction

Cultures were grown for 4 hr total. IPTG was at 800 mM thus, added 25 µl to each 50 ml culture flask. Incubated for 6 hr at 30° C. (so stop it not before 8h30). Pelleted bacterial cells by centrifugation at 5,000×g for 10 minutes. (ultracentrifuge). Removed supernatant and stored at −80° C.

Procedure for Extracting Protein from Bacteria (B-PER Protocol from Thermo)

Optional: Add 2 µl of lysozyme and 2 µl of DNase I per 1 ml of B-PER Reagent. Add EDTA-free protease inhibitors. Add 4 ml of B-PER Reagent per gram of cell pellet. 0.5 g was obtained thus, add 2 ml. Pipetted the suspension up and down until it is homogeneous. Incubated 10-15 minutes at room temperature. Centrifuged lysate at 15,000×g for 5 minutes to separate soluble proteins from the insoluble proteins. Note: If a large percentage of over-expressed protein remains in the pellet, the protein of interest might be expressed in inclusion bodies. Either use the Inclusion Body Solubilization Reagent (Product No. 78115) or alter the expression conditions to minimize inclusion body formation.

Purification of His-Tag Using Ni-NTA Resin

For native conditions prepared the following buffers: Equilibration Buffer: 20 mM sodium phosphate, 300 mM sodium chloride (PBS) with 10 mM imidazole; pH 7.4; Wash Buffer: PBS with 25 mM imidazole; pH 7.4; Elution Buffer: PBS with 250 mM imidazole; pH 7.4.

Procedure for Purification of His-Tagged Proteins by Batch Method

The HisPur Ni-NTA Resin allows for purification strategy customization. Purification conditions can be scaled as needed. The procedure may be performed at room temperature or at 4° C. Added an appropriate amount of Ni-NTA resin to a tube. Centrifuged tube for 2 minutes at 700×g and carefully remove and discard the supernatant. Add two resin-bed volumes of Equilibration Buffer and mix until the resin is fully suspended. Centrifuged tube for 2 minutes at 700×g and carefully remove and discard buffer. Prepared sample by mixing protein extract with Equilibration Buffer so that the total volume equals two resin-bed volumes (instead added all component of equilibration buffer to sample so that sample is at 1×, then added 1 bed volume to resin, then added 650 µl of resin slurry to sample).

Added the prepared protein extract to the tube and mix on an end-over-end rotator for 60 minutes. Centrifuged the tube for 2 minutes at 700×g. If desired, save supernatant for downstream analysis. Washed the resin with two resin-bed volumes of Wash Buffer. Centrifuged the tube for 2 minutes at 700×g. If desired, save supernatant for downstream analysis. Repeated wash step and monitored supernatant by measuring its absorbance at 280 nm until baseline was reached. Eluted bound His-tagged proteins using one resin-bed volume of Elution Buffer. Centrifuged tube for 2 minutes at 700×g. Carefully removed and saved the supernatant. Repeated this step twice, saving each supernatant fraction in a separate tube. Monitored protein elution by measuring the absorbance of the fractions at 280 nm or by Coomassie Plus (Bradford) Assay Reagent (Product No. 23238) or Pierce® 660 nm Protein Assay (Product No. 22660). The eluted protein could be directly analyzed by SDS-PAGE. Note: To remove imidazole for downstream applications, used gel filtration (e.g., Thermo Scientific Zebra Spin Desalting Columns) or dialysis (e.g., Thermo Scientific Slide-A-Lyzer Dialysis Cassettes). Samples containing 6 M guanidine·HCl must be dialyzed against a buffer containing 8 M urea before SDS-PAGE analysis. The Thermo Scientific Pierce SDS-PAGE Sample Prep Kit (Product No. 89888) may also be used to remove guanidine.

Nanodrop phase A280

| Sample ID | Protein Conc. Mg/ml |
| --- | --- |
| bind lysate | 34.649 |
| Wash 1 | 5.319 |
| Wash 2 | 1.19 |
| Wash 3 | 0.343 |
| Elute 1 | 0.875 |
| Elute 2 | 0.308 |

Vivaspin clean up and concentrate. Tubes were centrifuged (15,000 g, 5 min) and supernatant was desalted by running on vivaspin 5K columns (15,000 g, 15 min), after each wash flow-thru was discarded and retentate was reconstituted to 0.5 mL with PBS, repeated 4 times. Average retentate volume after each wash was ~100 mL. Proteins were examined in Nanodrop. A280

Nanodrop phase A280

| Sample ID | Protein Conc. Mg/ml |
| --- | --- |
| 3 | 9.304 |
| 6 | 9.115 |
| 7 | 12.924 |
| 8 | 7.937 |

-continued

| Sample ID | Protein Conc. Mg/ml |
|---|---|
| 10 | 9.823 |
| 12 | 5.792 |

SDS-PAGE

| | Sample ID | µg/µl | dilute 1/10 or 1/5 | for 5 µg | to 6.5 h2o |
|---|---|---|---|---|---|
| 1 | Protein ladder NEB | | | | |
| 2 | bind lysate | 34.65 | 3.46 | 1.44 | 5.06 |
| 3 | Wash 1 | 5.32 | — | 0.94 | 5.56 |
| 4 | Wash 2 | 1.19 | — | 4.20 | 2.30 |
| 5 | Wash 3 | 0.34 | — | 14.58 | −8.08 |
| 6 | 3 | 9.30 | 1.86 | 2.69 | 3.81 |
| 7 | 6 | 9.12 | 1.82 | 2.74 | 3.76 |
| 8 | 7 | 12.92 | 2.58 | 1.93 | 4.57 |
| 9 | 8 | 7.94 | 1.59 | 3.15 | 3.35 |
| 10 | 10 | 9.82 | 1.96 | 2.55 | 3.95 |
| 11 | 12 | 5.79 | 1.16 | 4.32 | 2.18 |
| 12 | Inclusion | | | | |
| 13 | Pro inhib | | | | |

Figure 63:
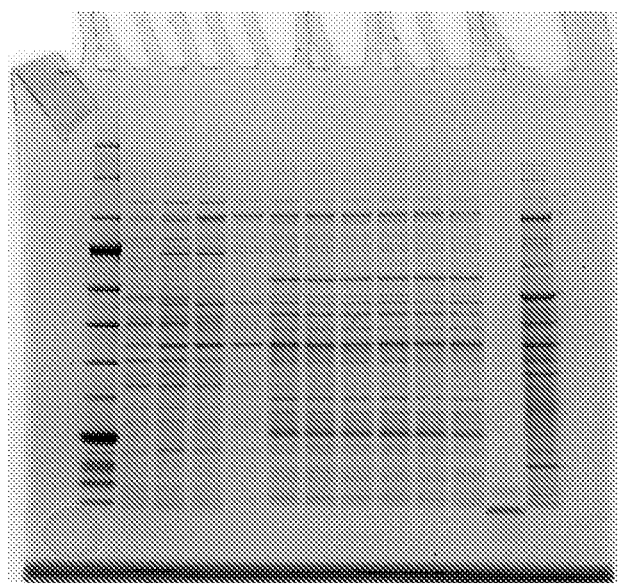
FIG. 63 depicts an SDS PAGE gel. 200 volts, ran for 45 minutes.
Figure 64:
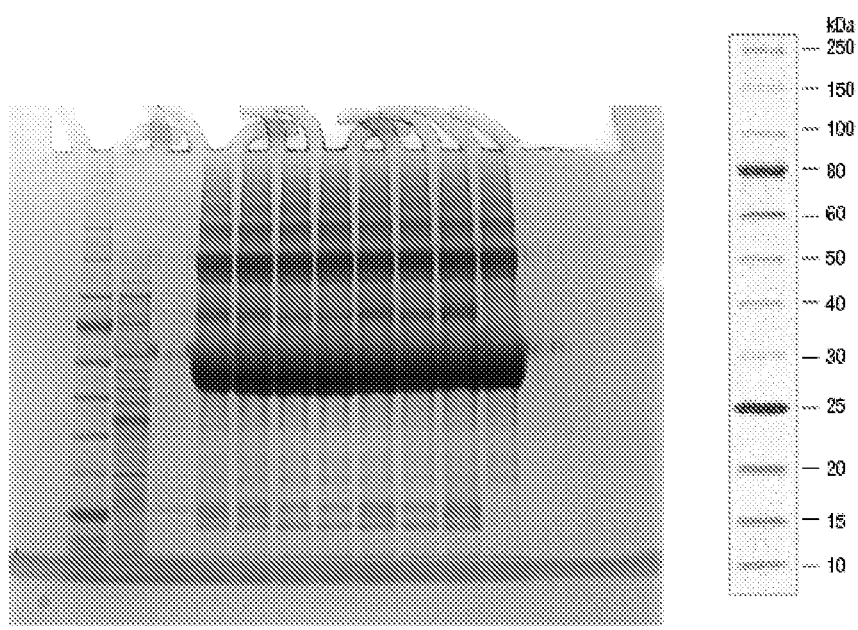
FIG. 64 depicts an SDS PAGE gel. 200 volts, ran for 30 minutes.

MOPS, 200 volt 45 minutes (FIGS. 63, 64)

SDS Take 2

Ran first batch of protein on, also loaded sample protein clone 3 post miltenyi his-tag second purification. MOPS, 200 volts, 30 minutes (should have done 45 minutes) (FIG. 95). Protein was in 0.5% BSA and 10% glycerol. Big stuff was BSA. 1, NEB ladder; 2, clone 6 Ni-NTA; 3, clone 2 post myltenyi; 4-11, Mi-NTA (+BSA)

Re-Clean and Concentrate DNA of Clone 393 (the Potential Neutralizer)

Pulled 3 wells, AMPure purified, resuspend in 15 µl H₂O. Nanodrop:500 ng/ul

In Vitro Translate (Thermo Human In Vitro Expression Kit)

Transcription

Will make 600 µl of final protein kit (20×25 µkit), thus need 40 µl of transcription reaction (s0 2 reaction worth).

| | 1 tube | 8 tubes |
|---|---|---|
| Nuclease-free Water | 8 | 16 |
| 5X Transcription Buffer | 4 | 8 |
| NTP Mix | 4 | 8 |
| Cloned DNA (500 ng/µl) | 2 | 4 |
| T7 RNA Polymerase | 2 | 4 |
| Total | 20 | 40 |

Gently mixed tubes and incubated for 60-75 minutes at 32° C.

Translation

Added the reagents in the order listed into a 1.5 or 0.5 ml RNase/DNase-free tube. For best results, incubated the Lysate with the Accessory Proteins for 5 minutes before adding subsequent components.

| | 1 tube | 20 tubes (in one 1.5 ml) |
|---|---|---|
| Lysate for Protein Expression | 12.5 | 250 |
| Accessory Proteins | 2.5 | 50 |
| Nuclease-free Water | 3.75 | 75 |
| Salt Solution A | 1 | 20 |
| Amino Acid minus Met | 0.5 | 10 |
| Amino Acid minus Leu | 0.5 | 10 |
| RNase Inhibitor (optional) | 1 | 20 |
| Energy Mix | 1.25 | 25 |
| Transcription Mix | 2 | 40 |
| Total | 25 | 500 |

Split in 5 tubes of 100 µl. Incubated at 30° C. on PCR for 4 hr, then 4° C. overnight Purification Test Split in 5 tubes of 95 µl: 1, lysate; 2, mylteniy (use 50 µl of beads in 500 µl of lysis buffer); 3, Invitrogen; 4, Cobalt Thermo; 5, Ni (Table 17).

TABLE 17

| # | description | | ug/ml or ng/ul | A280 | 260/280 | ug/ul | for 10 ug | dilution factor | | volume for 10 ug | water to 6.5 | |
|---|---|---|---|---|---|---|---|---|---|---|---|---|
| 1 | | in vitro lysate | 46297 | 46.297 | 1.6 | 46.30 | 0.22 | 10 | 4.63 | 2.16 | 4.34 |
| 2 | myltenyi | post bind | 186235 | 186.235 | 0.56 | 186.24 | 0.05 | 50 | 3.72 | 2.68 | 3.82 |
| 3 | | AB/Ag elution | 882 | 0.882 | 1.11 | 0.88 | 11.34 | 1 | 0.88 | 11.34 | 0.00 |
| 4 | | Invitrogen elution | 27 | 0.027 | 2.65 | 0.03 | 370.37 | 1 | 0.03 | 370.37 | 0.00 |
| 5 | | myltenyi SDS elution | 3390 | 3.39 | 0.71 | 3.39 | 2.95 | 1 | 3.39 | 2.95 | 3.55 |
| 6 | Invitrogen | post bind | 34384 | 34.384 | 1.65 | 34.38 | 0.29 | 10 | 3.44 | 2.91 | 3.59 |
| 7 | | Invitrogen elution | 837 | 0.837 | 1.79 | 0.84 | 11.95 | 1 | 0.84 | 11.95 | 0.00 |
| 8 | Cobalt thermo | post bind | 22703 | 22.703 | 1.73 | 22.70 | 0.44 | 10 | 2.27 | 4.40 | 2.10 |
| 9 | | elution 1 | 43 | 0.043 | 2.2 | 0.04 | 232.56 | 1 | 0.04 | 232.56 | 0.00 |
| 10 | | elution 2 | 0 | 0 | 82.49 | 0.00 | #DIV/0! | 1 | 0.00 | #DIV/0! | 0.00 |
| 11 | Ni-Nta nugen | post bind | 14513 | 14.513 | 1.66 | 14.51 | 0.69 | 5 | 2.90 | 3.45 | 3.05 |

TABLE 17-continued

| # | description | ug/ml or ng/ul | A280 | 260/280 | ug/ul | for 10 ug | dilution factor | volume for 10 ug | water to 6.5 |
|---|---|---|---|---|---|---|---|---|---|
| 12 | elution 1 | 833 | 0.833 | 1.4 | 0.83 | 12.00 | 1 | 0.83 | 12.00 | 0.00 |
| 13 | elution 2 | 417 | 0.417 | 1.64 | 0.42 | 23.98 | 1 | 0.42 | 23.98 | 0.00 |
| 14 | ladder | | | | | | | | |

Figure 65:
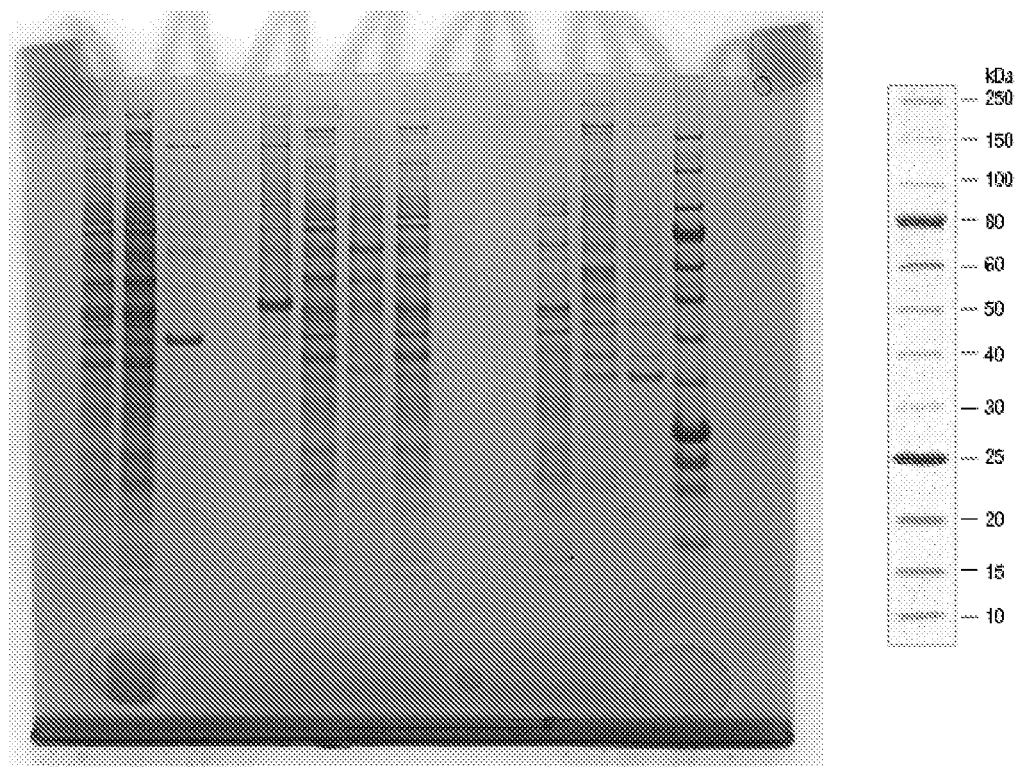
FIG. 65 depicts an SDS PAGE gel. Ran for 35 minutes, blue staining.

SDS page. MES buffer, run 35 minutes, simply blue staining (FIG. 65). The cloning may have put the His tag out of frame, but the protein is in frame.

Functional Assay Protocols

FACS Assay Preparation

1. Half of the protein samples were labeled with FITC as follows: a. ~20 µL of the protein sample was transferred to a 0.2 mL tube, and the volume was reconstituted to 100 µL with PBS (final concentration of protein was estimated to be 0.01 mg/mL); b. ~1 mg of FITC (Pierce) was dissolved in 1.5 mL of DMF; c. 1 µL of the FITC/DMF solution was added to the sample, and the tubes were incubated in the dark at RT for 30 min; d. Proteins were cleaned from excess FITC by Vivaspin 5K columns and washed 2 times with 0.4 mL PBS; e. Sodium azide was added to a final concentration of 0.02% and the samples (~20 µL) were stored at 4° C. until use.

2. HA proteins (Bris59, Bris10 and Flor04, purchased from Sino Biologicals, China) were biotinylated using EZ-Link-NHS-Biotin (Pierce) by incubation on ice for 1 hour and then cleaning on Vivaspin 10K columns, with 2 washes with 0.4 mL PBS.

3. The biotinylated HA proteins were used to coat Dynal streptavidin-coated magnetic beads by incubation in PBS (10 µL beads, 5 µL biotinylated protein, in 100 µL PBS total volume), with flipping, at RT for 1 hour.

4. Beads were washed 3 times with 100 µl, of bead assay buffer (0.1% BSA, 10% glycerol, 0.02% sodium azide in PBS, pH 7.4) using a magnet.

5. Finished beads were stored in 100 µL assay buffer at 4° C. until use.

FACS Assay 1. 1 µL of bead suspension (vortexed shortly before use) was mixed with 5 µL of antibody solution and 19 µL of FX buffer (0.1% BSA, 0.02% sodium azide in HBSS, pH 7.4) 30 min on ice (final antibody concentration ~10 µg/mL).

2. Samples were reconstituted with 25 µL cold FX buffer and analyzed by Accuri C6 flow cytometer.

QCM Measurements of Antibody/Antigen Binding

Crystals were coated with antibody a day prior to experiment as follows:

1. QCM gold crystals (purchased from Qsense) were coated with HS-PEG-NH$_2$ (from Nanocs) by incubating with 100 uL of a 5 mg/mL solution of HS-PEG-NH$_2$ in ultrapure water in a humid chamber, 1 hour at RT.

2. Crystals were washed gently with 0.5 mL of PBS.

3. 30 µL of antibody solution (~1.5 µg total protein) was mixed with 70 µL PBS containing 200 pmol of EDC and 200 pmol of sulfo-NHS (both from Pierce, sulfo-NHS is no weigh, mixed with 22 µL of ultrapure water prior to mixing), incubated at RT for 1 minute, then applied onto the crystal surface and incubated at RT for 1 hour in a humid chamber.

4. 1 µL of a 10 mg/mL solution of BSA was added and the liquid phase was mixed gently.

5. Humid chamber was moved to 4° C. for overnight storage without washing off antibody.

QCM Measurements were Performed on a Qsense E4 Instrument as Follows

1. PBS was flown through the cells at 0.1 mL/min until crystals were equilibrated (~30 minutes).

2. 2 mL of HA protein solutions (1 and 10 µg/mL) were flown through the cells switching back to PBS after sample is finished.

3. Crystals were washed with 0.1 M NaOH in between different concentrations.

Purification of E. coli Expressed Nanobodies

1. Cell pellets (supernatant thoroughly removed, pellets frozen at −20° C.) were resuspended in 1 mL lysis buffer (10 mM Tris-HCl pH 7.5, 1 mM EDTA, 0.05% Triton X-100, 5 µg/mL DNase I, 1× protease inhibitor cocktail from Pierce)

2. Suspensions were transferred to conical 15 mL tubes and sonicated by a standard probe sonicator, while kept on ice. Sonication parameters: [10 sec on+5 sec off]×4 pulses, 100% output.

3. Sonicates were centrifuged (4,800 g, 10 min, 4° C.) and supernatants were transferred to 1.5 mL tubes.

4. 4 mL (8 samples×0.5 mL/sample) of Ni-NTA sepharose resin (Amersham) were washed in a 15 mL tube to remove storage buffer (contains 20% ethanol), by 3 repeated centrifugations (500 g, 1 min) and washes with 10 mL His-binding buffer (20 mM phosphate, 0.5 M NaCl, 20 mM imidazole, pH 7.4), after the last wash, resin pellet was reconstituted with 4 mL of 2× His binding buffer.

5. 0.5 mL of resin were added to each sample and the tubes were rotated at 4° C. overnight.

6. Resin was washed two times with 1.5 mL of His binding buffer (30 min each wash, centrifugation 1000 g, 1 min).

7. After the final wash, resin bed was left wet (~0.6 mL) and stored overnight at 4° C.

8. 0.5 mL of His elution buffer (20 mM phosphate, 0.5 M NaCl, 0.5 M imidazole, pH 7.4) were added and the tubes were rotated overnight at 4° C.

9. Tubes were centrifuged (15,000 g, 5 min) and supernatant was desalted by running on vivaspin 5K columns (15,000 g, 15 min, after each wash flow-thru was discarded and retentate was reconstituted to 0.5 mL with PBS, repeated 4 times. Average retentate volume after each wash was ~100 µL).

10. Proteins were examined in Nanodrop.

11. 50 µL samples were taken for labeling.

Labeling of Nanobodies 1. 50 µL (~35 µg according to nanodrop) of each sample was mixed with 450 µL of 50 mM borate buffer pH 8.5.

2. Samples were cleaned on vivaspin 5K columns (15,000 g, 15 min, retentate ~20 µL). Calculated protein concentration (average in samples) after this step was ~1.5 mg/mL.

3. DyLight-649 (1 mg) was dissolved in 100 µL DMF, and 1 µL was added to each sample.

4. Tubes were incubated in the dark for 1 h at RT.

5. Labeled proteins were cleaned from excess dye by vivaspin 5K columns, with 3 washes with 470 µL PBS and one wash into 470 µL of 10 mM Tris buffer pH 7.5 to quench residual dye.

6. Calculated concentration in retentate (~20-25 µL each): 1.3-1.5 mg/mL.

Neutralization Assay

Flu Strains—Growth in A549 Cells and Immunotitration

1. The cells used were A549 human lung epithelial cells (Carcinoma). Cells were grown in 48-well plates in 0.4 mL medium (ATCC medium #F-12K+10% FBS+Pen/Strep). The cells were transferred to the plate following plating of A549 from a T75 culture flask [confluency>aspirate medium>1.3 mL of TrypLE or trypsin-EDTA>3-5 min at 37° C.>completed to 6 mL with medium>take 50 µL per well in a 48-well plate containing 0.35-0.4 mL medium].

2. At 80% confluency, infected cells with virus, by adding 10 µL of virus at the desired dilution, mix well using pipette.

3. Incubated at 37 for 24-48 h.

4. Aspirated medium, apply 100 µL TrypLE, incubate 5 min at 37° C.

5. Mixed well with pipette, take 200 µL of cells to a fresh u-shaped 96 well plate.

6. Fixed with formaldehyde, 2.5% final conc. On ice for at least 10 min.

7. Washed (centrifuged 3000 rpm, 3 min, 4° C.), resuspended in 100 µL of freezing-cold 100% methanol. Mixed well.

8. Incubated on ice for 10 min.

9. Added 100 µL cold FX buffer, spun again as in 7. Resuspend in 100 µL cold FX buffer.

10. Added 1 µL of FITC-conjugated anti-Influenza A nucleoprotein (from Millipore) per well, mixed well and incubated on ice for 60 min.

11. Spun as in 7, resuspended in 200 µL cold FX and spun again.

12. Resuspended in 200 µL cold FX, analyzed by FACS.

13. Determined titer as follows: Titer (FIU/µL)=D50×C/(2×V). D50: The concentration of virus at which 50% of the cells are infected (FITC+) C, Starting number of cells in the well (refer to Worldwide Web Site: invitrogen.com/etc/medialib/en/filelibrary/pdf.Par.4786.File.dat/Useful_Numbers_Y1447 2_Useful_Nmbrs.pdf for useful details); V, Volume of virus (in µL) used to infect the well Neutralization Assay 1. A549 cells at confluency 75% were incubated at 0.4 mL medium in 48 well plate. Nanobodies at various concentrations (50, 5, 0.5, 0.05 µg/mL, diluted in A549 medium) were added.

2. Immediately afterwards the cells were infected with Bris10 strain at MOI of ~33% (0.33) at a volume of 10 µL.

3. Cells were incubated for 24 h.

4. Medium was aspirated (and bleached). Cells were washed once with 0.5 mL HBSS.

5. 100 µL TrypLE was added and the plate was incubated at 37 deg. for 5 min.

6. Cells were aspirated into a 96 well plate and immediately fixed with formaldehyde as in step 6 in previous section.

Figure 67:
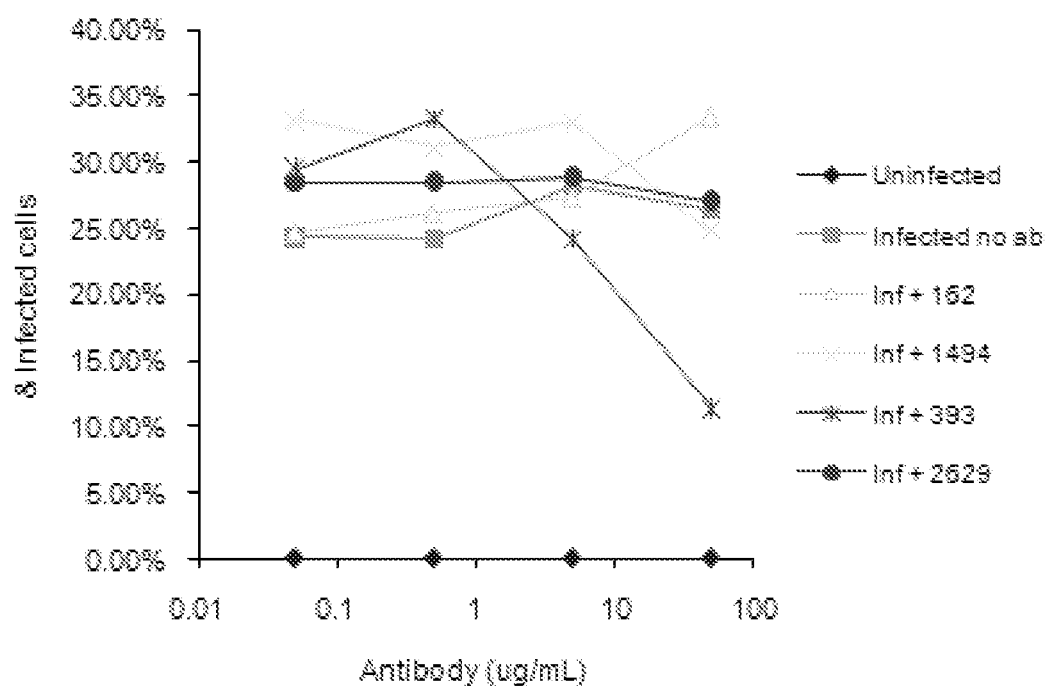
FIG. 67 graphically depicts neutralization results.

7. Protocol continued from step 6 in previous section. Neutralization results, FIGS. 66 and 67.

Example VII

Heavy and Light Chain Correlation

Initial Light Chain Analysis

Figure 46:
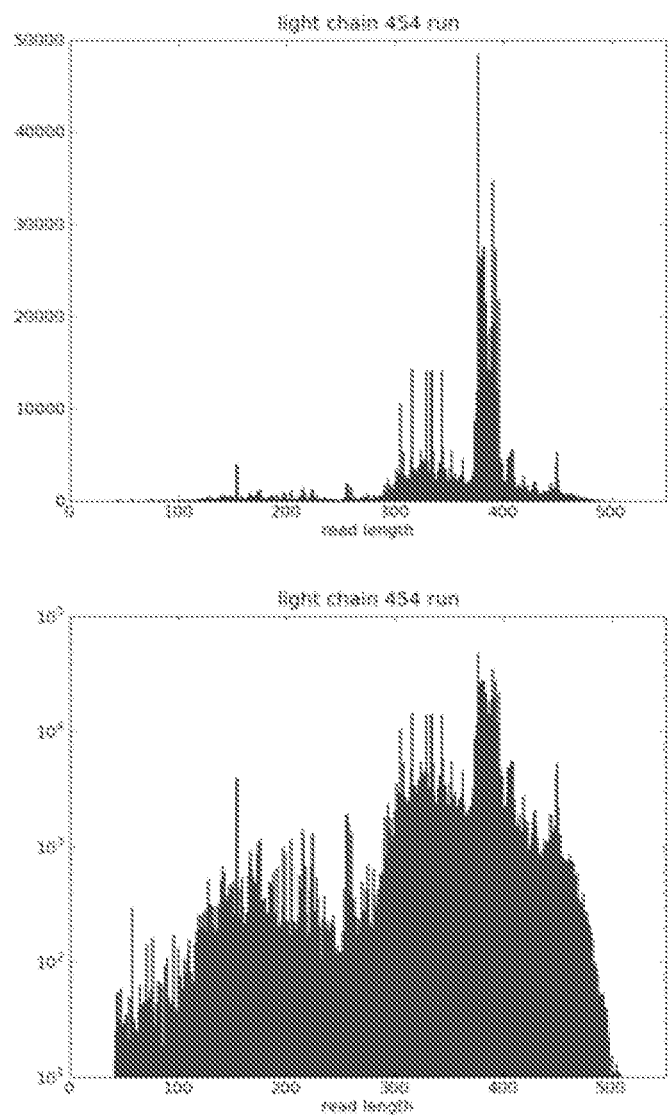
FIG. 46 depicts histograms of read lengths of light chains.

Light chain data was obtained from libraries made from a few time points of an experiment. Histograms of the read lengths are set forth at FIG. 46. There was a peak at 380 (expected), and a smaller aggregation around 325. 10 reads from each peak were randomly aligned. 7/10 from the 380 peak were light chains (all kappa). None of the 325 peaks were light chains or immune chains. They were random proteins that must have amplified. The cutoffs for size selection was 365-405.

VDJ Alignment/Classification and Clustering of Light Chain Data

Light chain data was taken through an initial pipeline. The contents of the README file in are set forth in the Table 4 below. The work was performed on orchestra. Symlinks were placed in the stable-data directory to the results.

Running the full pipeline on orchestra: These scripts were run when the vdj repository is at tag v1.3 The intermediate data is in the corresponding directory on orchestra: /home/u12/vdj-ome/analysis/20100810_light_chain_pipeline 1. fasta2vdjxml.py 2. size_select.py First I convert the fasta file to vdjxml, and, Size select the reads based on the readlen hist, 365-405, (from/home/u12/vdj-ome/stable-data/raw_light_chains): python ~/code/vdj/bin/fasta2vdjxml.py light_chains.20100802.fasta|python ~/code/vdj/bin/size_select.py--min 365 --max 405>light_chains.20100802.size365-405.vdjxml There are 496605 chains of the selected size in the file. 3. vdjxml2parts.py Split vdjxml into small chunks and place in working directory python ~/code/vdj/bin/vdjxml2parts.py--packetsize 10000 --basename ~/vdj-ome/analysis/light_chain_pipeline/data/light_chains.20100802. size365-405.vdj xml light_chains.20100802.size365-405.vdjxml Change directory to all the parts: cd ~/vdj-ome/analysis/light_chain_pipeline/data 4. barcode_id.py 5. coding_strand.py Identify barcodes for each read, and Determine whether we have the correct strand or not for FILE in light_chains.20100802.size365-405.vdjxml.*; do NAME.$ {FILE %. size*}".prealign.vdjxml."${FILE #*.vdjxml.*} bsub-qshared_2h -o pre-alignment.log "python ~/code/vdj/bin/barcode_id.py--barcodes ~/vdj-ome/stable-data/barcodes/454MID.barcodes.fasta $FILE|python ~/code/vdj/bin/coding_strand.py--locus IGK--locus IGL>$NAME" done #python ~/code/vdj/bin/barcode_id.py--barcodes ~/vdj-ome/stable-data/barcodes/454MID.barcodes.fasta #python ~/code/vdj/bin/coding_strand.py--locus IGK--locus IGL Some STATS: #Num of chains cat *prealign*|grep "<ImmuneChain>"|wc -1 496605 #Num with barcodes cat *prealign*|grep "<barcode>"|wc -1 486258 #Num that were reverse-complemented cat *prealign*|grep "revcomp"|wc -1 240928 #Barcode breakdown for NUM in 1 2 3 4 5 6 8 9; do cat *prealign*|grep "<barcode>0$NUM"|wc -1 done 01 71 0.015% 02 0 03 174550 35.9% 04 7 0.001% 05 142036 29.2% 06 0 08 169594 34.9% 09 0 6. align_vdj.py for FILE in light_chains 0.20100802.prealign.vdj xml.*; do NAME.$ {FILE %.prealign*}".vdjxml."${FILE #* .vdj xml.*} bsub-qshared_12h-o alignment.log python ~/code/vdj/bin/align_vdj.py--locus IGK--locus IGL $FILE $NAME done 7. cat_vdjxml.py python ~/code/vdj/bin/cat_vdjxml.py light_chains.20100802.vdjxml.*>light_chains.20100802. aligned.vdjxml Move processed data down one directory: my light_chains.20100802.aligned.vdjxml.. cd.. 8. filter_VJ.py python ~/code/vdj/bin/filter_VJ.py light_chains 0.20100802.aligned.vdj xml light_chains.20100802.VJ_filtered.vdjxml grep "<ImmuneChain>" light_chains.20100802.VJ_filtered.vdjxml|wc -1 356813 for NUM in 3 5 8; do grep "<barcode>0$NUM" light_chains.20100802.VJ_filtered.vdjxml|wc -1 done 03 131837 05 99618 08 117703 9. partition_VJ.py mkdir partitions python —/code/vdj/bin/partition_VJ.py--basename partitions/light_chains.20100802 light_chains.20100802.VJ_filtered.vdjxml cd partitions

How many chains in each partition? for FILE in light_chains.20100802.*.vdjxml; do grep "<ImmuneChain>" $FILE|wc −1 done|sort −n partial results: . . . 10021 11239 11285 12592 13451 13999 17935 10. cluster_cdr3.py for INFILE in light_chains.20100802.*.vdjxml; do VJID=${1NFILE#light_chains.20100802.} VJID=$ {VJID%.vdjxml} OUTFILE.$ {INFILE%.vdjxml}.clustered.vdjxml bsub-qshared_unlimited-o clustering.log python —/code/ydj/bin/cluster_cdr3.py--cut-off 4.5 --tag $VJID--linkage single $INFILE $OUTFILE done #How long did it take? grep "CPU" clustering.log|sort −n −k4 partial results: CPU time: 25.38 sec. CPU time: 29.70 sec. CPU time: 34.28 sec. CPU time: 42.63 sec. CPU time: 44.29 sec. CPU time: 46.46 sec. CPU time: 48.57 sec. CPU time: 57.70 sec. CPU time: 59.88 sec. 11. cat_vdjxml.py python —/code/vdj/bin/cat_vdjxml.py light_chains.20100802.*.clustered.vdjxml>../ light_chains.20100802.clustered.vdjxml cd.. #How many chains? grep "<ImmuneChain>" light_chains.20100802.clustered.vdjxml|wc −1 356813 #How many unique clones in total? grep "<clone>" light_chains.20100802.clustered.vdjxml|sort|uniq|wc −1 5009 #How many unique junctions in total? grep "<junction>" light_chains.20100802.clustered.vdjxml sort|uniq|wc −1 53880

Table 4.

Time Series and Clone Distribution of Light Chain Data

Figure 47:
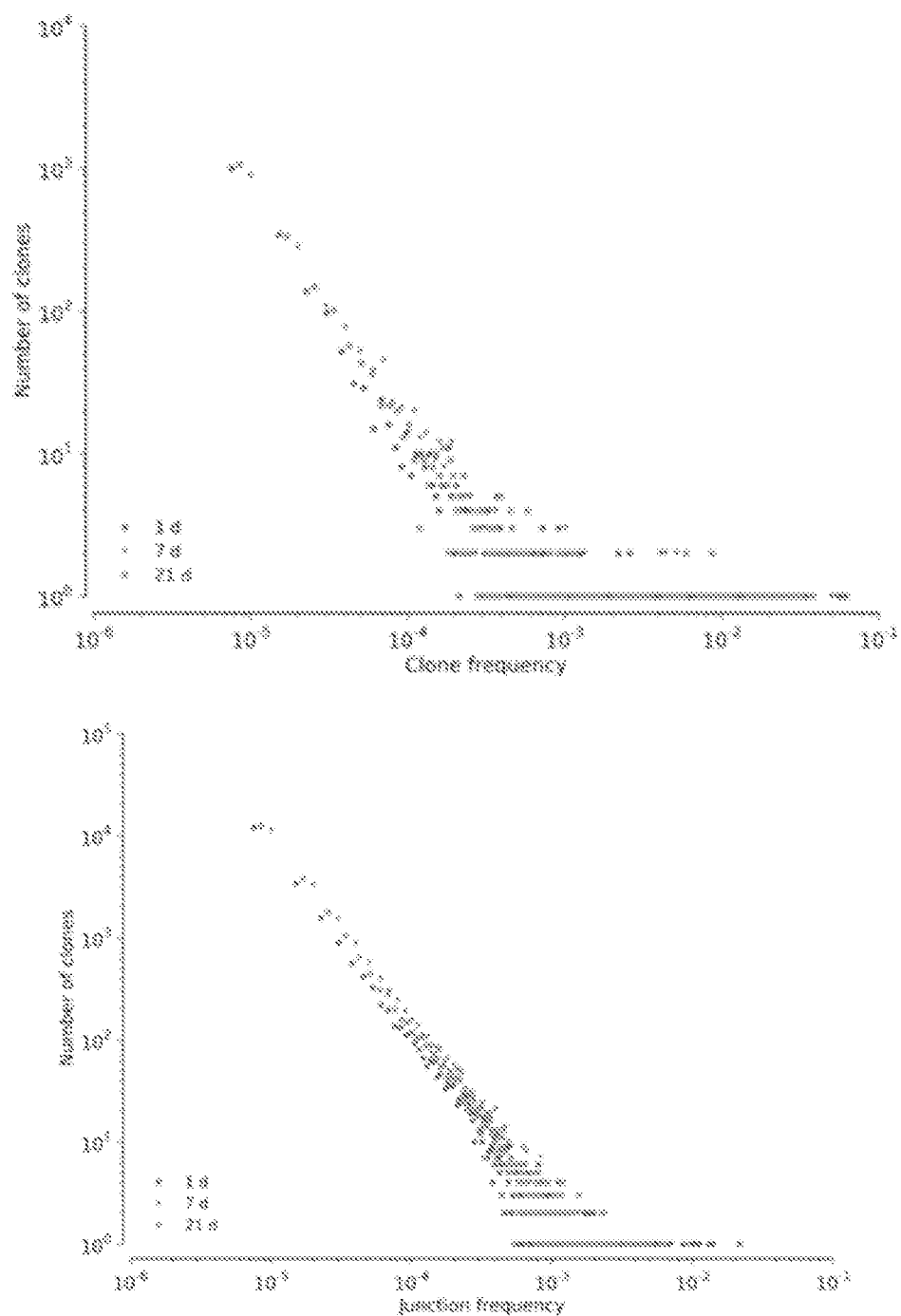
FIG. 47 depicts the distribution of junctions.
Figure 48:
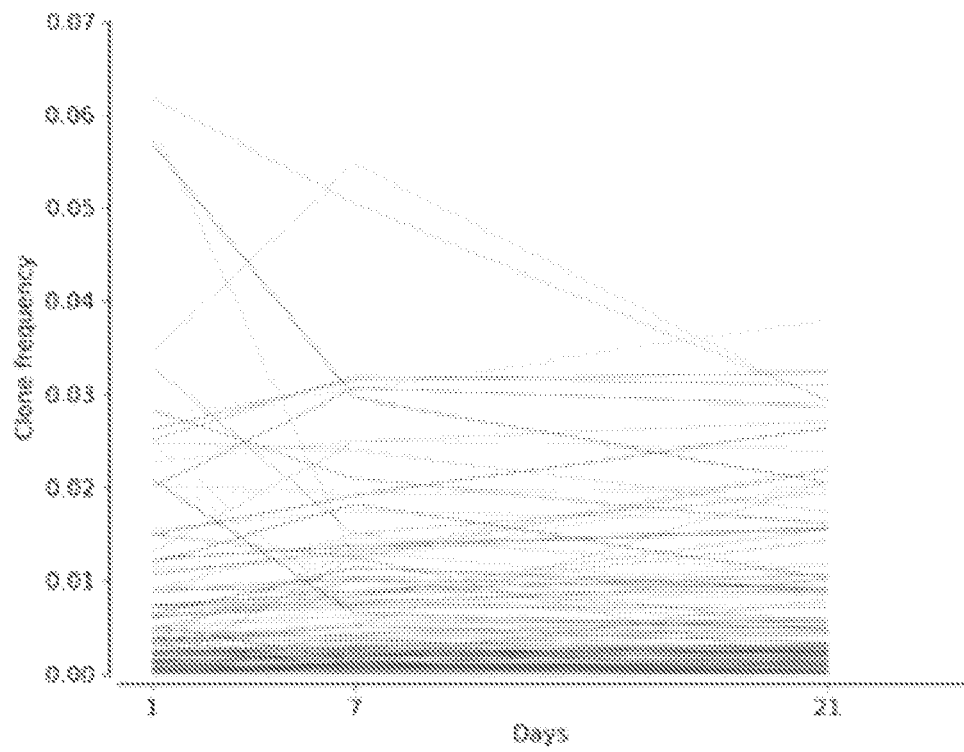
FIG. 48 depicts a clone time series.

Time series and clone frequency histograms were generated from the light chain data. There were only about 5000 clones. Without intending to be bound by scientific theory, it is possible that the cutoff value to define clones needs to be recalibrated for light chains. Without intending to be bound by scientific theory, lesser diversity may be expected since there is no D region. See FIGS. 47 and 48.

Light Chain Time Series Using Unique Junctions Instead of Clones

Figure 49:
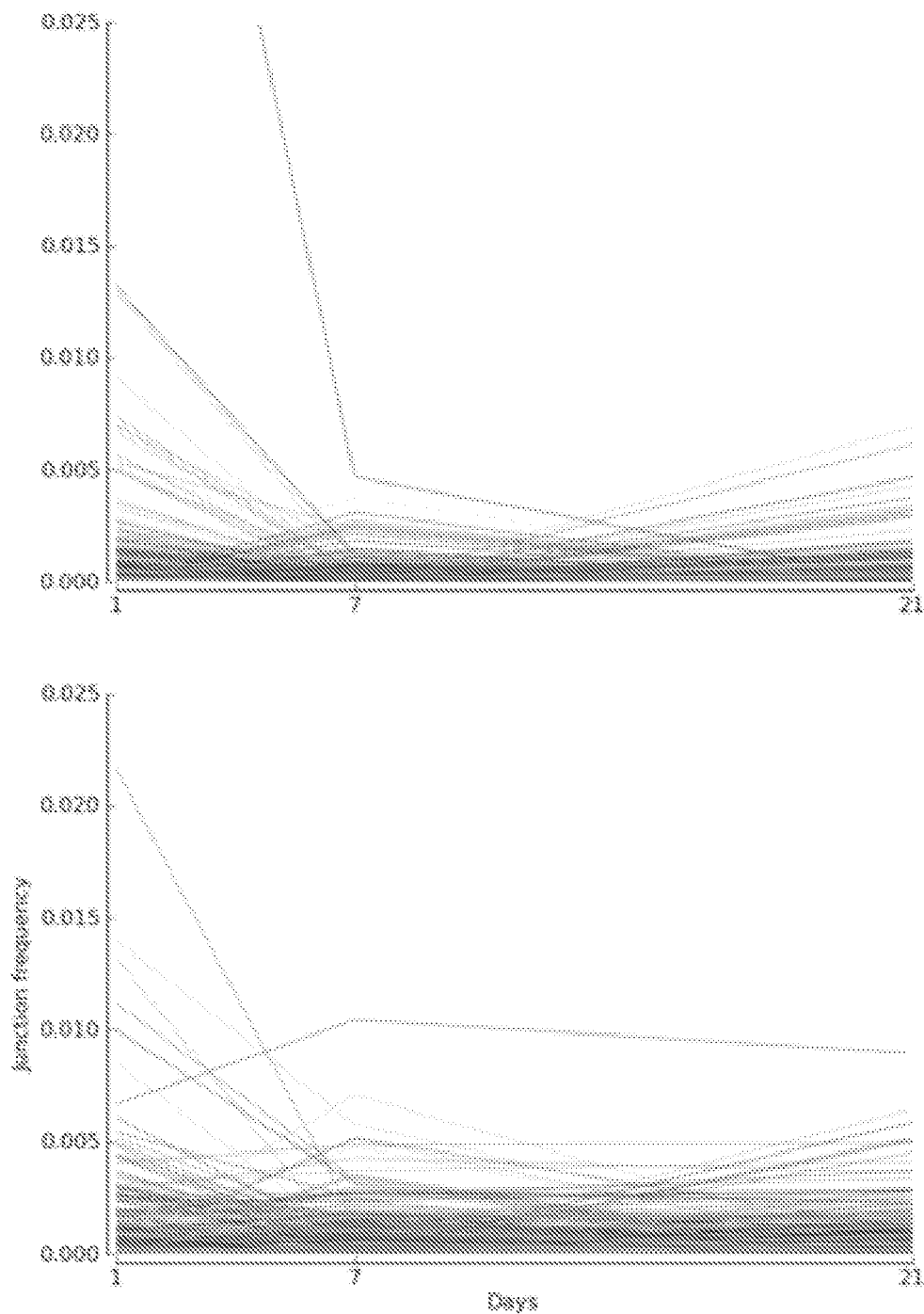
FIG. 49 depicts a time series for both heavy and light chains using unique junctions.

Because of a concern that the cluster definitions for heavy chains may not translate to light chains, time series figures were generated for both heavy and light chains using only unique junctions. A plot of the two is set forth at FIG. 49 (NOTE: heavy chains on top, light chains on bottom).

The top junction sequences are set for in the Table 5 below.

TABLE 5

```
heavy chain junctions: 1d
TGTGCGCAAACCGATAGCAGCAACTTAGACTACTACTACCACGGAATGGG
CGTCTGGTGTGCGAAAGGGGGAGATTGTGGTGGTGCTAGTTGCCCCCATT
TAGACTACTACTACTACGGTATGGACGTCTGGTGCGCGAGAGGGACGGGG
GGACCCTACGGTGACTATTATGGTGGTGCTTTTGATGTCTGGTGTGCGCA
AACCGATAGCACCAACTTAGACTTCTACTTCTACGGTTTGGACGACTGGT
GTGCGAGATCGGGGGATAGTTGGAGTCCTCCACAATTTGACTTCTGGTGT
GCGCAAACCGATAGCAGCCACATAGATTTCTACTACTATGGTATGGACGA
CTGGTGTGCGGTTCAAGATTGTAGTACTACCACCTGCTATCCTGCGAGTT
CCTACTACTACTATAACATGGGCGTCTGGTGTGCGGTTCAAGATTGTAGT
ACTACCACCTGTTATCCTGCGAGTTCCTACTACTACTACAACATGGGCGT
CTGGTGTGCGCAAACCGATAGCAGCCACATAGACTTCTACTACTACGGTA
TGGACGACTGGTGTGCGAGATCGGGGGATAGTTGGAGCCCTCCACAATTT
GACTTCTGG (SEQ ID NO: 834)

7d
TGTGCGCAAACCGATAGCAGCAACTTAGACTACTACTACCACGGAATGGG
CGTCTGGTGTGCGAGAGATGATCCATATTACGGCAGTATTGGTTATCGTA
TTGACTCCTGGTGTGCGAGAATCCCGCTAAGATCGAGTGGGACGCCTAC
TACTACGTATGGACGTCTGGTGTGCGAGATACCTTACCTGGAGATACTTT
GACTCCTGGTGTGCGAGAGTGTTCTCTAGTAGTGGTTATTACTACTACTTT
TGATTACTGGTGTGCAAGATCCCTCATTCTATATAGTGACTACATTGCCT
ACTGGTGTGCGAGGCAGTCAGGTAACCGAGGATTCGGTGACTCTTACTCC
TACTATTACTTCATGGACGTCTGGTGCGCGAGAACTTTGTATTCTCTGGT
AAAGTATAGTACTGGCTGGTACTACTTTGACTACTGGTGTGCGAGAACAA
ATGCTTTTCATATCTGGTGTGTAAGAGTTAAGGGTGGCATAGCAGCAGCT
GGTACCACTGCGGGGTACTTCGATCTCTGG (SEQ ID NO: 835)

21d
TGTGCGAGAGTACGGGGATATTGTAATGGTGGTAGCTGCTACTTTGACTA
CTGGTGTGCGAGAGAGAGGGCATTAGTGGGAGGTAGTACGACTCTCGGAT
ACTGGTGTGCGAGAGGCAGGGCTTCAACCTTTAAAGTCTACTATCACTAC
ATGGACTCTGGTGTGCGAGACATATGCGGGGTGGGAGCCCTAGTCAAACT
GCTTTTGATGTCTGGTGTGCGAGACATATGCGGGCTGGGAGTCCTAGTCA
AACTGCTTTTGATGTCTGGTGTGCGAGACATATGCGGGGTGGGAGTCCTA
GTCAAACTGCTTTTGATGTCTGGTGTGTGAAAGCGGTTTCGGGGTCGAAC
TACATCTTTGACTACTGGTGTGCGAGAGGCCGAGTGGGAGCTAAAGAGCC
GACCGTTTACTACTTTGACCACTGGTGTGCGAAAATTTTTGAGGCGAATT
TGGAAAACTACTGGTATGGTTTGGACGTCTGGTGTGCGAGACATCAGTAT
AATGTTGGTAACTCCTGGGCTTTTGATATCTGG (SEQ ID NO: 836)

light chain junctions: 1d
TGTCAACAGGCTAACAGTTTCCCGCTCACTTTCTGTCAATCACCAGACAG
CAGTGGTACTAATGAAGTCTTCTGTCAATCACCAGACAGCAGTGGTACTT
ATGAGTCTTCTGCGGAACATGGGATACCAGCCTGGGTACTAATTGGGTGT
TCTGCGGAACATGGGATACCAGCCTGAGAATTAATTGGGTGTTCTGTCAA
CAGTTTACTAATTTCCCGCTCACTTTCTGTCAACAGTATGGTAGTTCATG
GCGCACTTTTTGTCAGGCGTGGGACAGCAGCACTGTGGTATTCTGCGGAA
CATGGGATACCAGCCTGAGGATTAATTGGGTGTTCTGCTCAGCATGGGAC
AGCAGCCTCAGTGCTTGGGTGTTC (SEQ ID NO: 837)

7d
TGTCAGGCGTGGGACAGCAGCACTGTGGTATTCTGCTGCTCATATGCAGG
CAACTCTTATGTCTTTCTGTCAATCACCAGACAGCAGTGGTACTAATGAAG
TCTTCTGTCAGCAGTATGGTAGCTCACCTTGGACGTTCTGTCAGCAATAT
GGTAGCTCACCGACGTTCTGTAACTCCCGGGACAGCAGTGGTAACCATGT
GGTATTCTGTCAGCAGCGTAGCACCTGGCCTGCGACTTTCTGTCAGGTGT
GGGATAGTAGTAGTGATCATGTGGTATTCTGTCAATCAGCAGACAGCAGT
GGTACTTATGTGGTATTCTGCGGAGCGTGGGATAGCAGCCTGAGTGCTGT
GGTCTTC (SEQ ID NO: 838)

21d
TGTCAGGCGTGGGACAGCAGCACTGTGGTATTCTGTCAACAACATGGTAA
CTCACCGGTCACTTTCTGCTTCCTCTACTTTGATGGTCCTATAGTTTTCT
GTCAGCATTATCATACTCCACCGTACACTTTTTGCCAACAGTATAATACC
TGGTGGACATTCTGTTTACTCTATTATAATGGTGTCAGGGTGTTCTGTAA
CTCCCGGGACAGCAGTGGTAACCATGTGGTATTCTGCTGCTCATATGCAG
GTAGTAGCACTTTTGTCTTCTGTCAATCAGCAGACAGCAGTGGTACTTAT
GTGGTATTCTGCTCAGCATGGGACAGCAGCCTCAGTGCTTGGGTGTTC
(SEQ ID NO: 839)
```

Sequences corresponding to highest-expressed junctions from light chain and heavy chain time series are set forth in the Table 6 below. The script was pull_sequences.py and the output was manually put in sequences_highly_expressed-_junctions.fasta.

TABLE 6

```
>heavy_1d|FWMETYS01DQGF4|2
TTGTGGCTATTTTAAAAGGTGTCCAGTGTGACGTGCAGCTGGTGGAGTCT
GGGGGAGGCTTGGTACAGCCTGGGAAGTCCCTGAGACTCTCCTGTGCAGC
CTCTGGATTCACCTTTAGCAACTATGCCATGTCCTGGGTCCGCCAGGCTC
CAGGGAAGGGCCTGGAGTGGGTCTCAGGTATTAGTGGTAGTGGTGCTGCC
ACATACTACGCAGACTCCGTGAAGGGCCGGTTCACCATCTCCAGAGTCAA
TTCCAGGAACACGCTCCTTCTGCAAATGAACAGCCTGAGAGCCGAGGACA
CGGCCCTATATTACTGTGCGCAAACCGATAGCAGCAACTTAGACTACTAC
TACCACGGAATGGGCGTCTGGGGCCAAGGGACCACGGTCACCGTCTCCTC
AGCATCCCCGACCAGCCCCAAGG (SEQ ID NO: 840)

>heavy_1d|FWMETYS01A182M|2
TTGTGGCTATTTTAAAAGGTGTCCAGTGTGAGGTGCAGCTCTTGGAGTCT
GGGGGAGGCTTGGCACAGCCTGGGGGGTCCCTGAGACTCTCCTGGAGC
CTCTGGATTCACCTTTAGTAACTATGGCATGAGCTGGGTCCGCCAGGCTC
CAGGGAAGGGCTGGAGTGGGTCTCAGGTATTAGTGGTAGTGGTGCTAGT
ACATTCTACGCAGACTCCGTGAAGGGCCGGTTCACCATCTCCAGAGACAA
TTCCAAGAACACGCTGTATCTGCAAATGGACAGCCTGAGAGCCGAGGACA
CGGCCGTCTATTACTGTGCGAAAGGGGAAGTTGTGGTGCTAGTTGC
CCCCATTAGACTACTACTACTACGGTATGGACGTCTGGGGCCAAGGGAC
CACGGTCACCGTCTCCTCAGCATCCCCGACCAGCCCCAAGG (SEQ ID NO: 841)
```

TABLE 6-continued

>heavy_1d|FWMETYS01ESRCQ|2
CGGCTCCCAGATGGGTCCTGTCCCAGCTGCAGTTGCAGGAGTCGGGCCCA
GGAGTGGTGAAGCCTTCGGAGACCCTGTCCCTCACCTGCACTGTCTCTGG
TGGCTCCATCAGCACTAGCAGTTATTACTGGGGCTGGATCCGCCAGCCCC
CAGGGAAGGGGCTGGAGTGGATTGGGACTATCTATTCTAGTGGGGGCCCC
TACTACAACCCGTCCCTCAAGAGTCAAGTCGCCATATCCGTTGACAGTGC
CAAGAATCAATTCTCCCTGAAGGTGAACTCTATAATGCCGCAGACACGG
CTGTGTATTACTGCGCGAGAGGGACGGGGGGACCCTACGGTGACTATTAT
GGTGGTGCTTTTGATGTCTGGGGCCAAGGGAAAAGGGTCGCCGTCTCTTC
AGCATCCCCGACCAGCCCCAAGG (SEQ ID NO: 842)

>heavy_1d|FWMETYS01ALGIE|2
TTGTGGCTATTTTAAAAGGTGTCCAGTGTGAGGTGCGGCTGTTGGAGTCT
GGGGGAGGCTTAGTGCAGCCTGGGGGGTCCCTGAGACTCTCCTGTGCAGC
CTCTGGATTCACCTTTAGCAACTATGCCATGACCTGGGTCCGCCAGGCTC
CAGGGCAGGGGCTGGAGTGGGTCTCAGGAATTAGTGGTAGTGGTGCAAGC
ACATACTACGAAGACTCCGTGAAGGGCCGGTTCACCATCTCCAGACGAA
TTCCAAGAACACGCTGTATCTGCAAATGAATAGCCTGAGAGCCGAGGACA
CGGCCGTATACTACTGTGCGCAAACCGATAGCACCAACTTAGACTTCTAC
TTCTACGGTTTGGACGACTGGGGCCAAGGGACCACGGTCACCGTCTCCTC
AGCATCCCCGACCAGCCCCAAGG (SEQ ID NO: 843)

>heavy_1d|FWMETYS01EMQ99|2
CGGCTCCCAGATGGGTCCTGTCCCAGGTGCAGCTGCAGGAGTCGGGCCCA
GGACTGGTGAAGCCTTCGGAGACCCTGTCCCTCACCTGCCAAGGCCTCTAT
TGGCTCCGTCAGGAATTATTACTGGAGCTGGATCCGGCAGTCCCCCGGGA
AGGGACTGGAGTGGATTGCATATATCTTTCCCAATGGGAGGACCAGCCGC
AATCCCTCCCTCCAGAGTCGAGTCACCATATCAATTGACACACCCAAAAA
TCAGTTCTCCATGTTGCTGAGCTCTGCAGCCGCCGCAGACACGGCCGTCT
ATTACTGTGCGAGATCGGGGGATAGTTGGAGTCCTCCACAATTTGACTTC
TGGGGCCAGGGAATCCTAGTCACCGTCTCCTCAGCATCCCCGACCAGCCC
CAAGG (SEQ ID NO: 844)

>heavy_1d|FWMETYS01A36YN|2
TTGTGGCTATTTTAAAAGGTGTCCAGTGTGAGGTGCAGCTGTTGGAGTCT
GGGGGAGGCTTGGTGCAGCCTGGGGGGTCCCTGAGACTCTCCTGTGCAGC
CTCTGGATTCACGTTCAGCAACTATGCCATGAGCTGGGTCCGCCAGGCTC
CAGGGAAGGGGCTGGAGTGGGTCTCAGGAATGAGTGGTAGTGGTGCTAGC
ACATACTACGAAGACTCCGTGAAGGGCCGGTTCACCATCTCCAGAGACAA
TTCCAAGAACACGCTGTATCTGCAAATGAATAGCCTGAGAGCCGAGGACA
CGGCCGTATATTACTGTGCGCAAACCGATAGCAGCACATAGATTTCTAC
TACTATGGTATGGACGACTGGGGCCAAGGGACCACGGTCACCGTCTCCTC
AGCATCCCCGACCAGCCCCAAGG (SEQ ID NO: 845)

>heavy_1d|FWMETYS01A36AI|0
GCAGCAGCTACAGGTGTCCAGTCCCAGGTGCAGTTGGTGCAGTCTGGGGC
TGAGGTGAAGAGGCCTGGGTCCTCGGTGAAGGTCTCCTGCAAGGCTTCTG
GAGGCACCTTCAGCAACTATGCAATCAGCTGGGTGCGACAGGCCCCTGGA
CAAGGGCTTGAGTGGATGGGAGGGATCATCCCTACTTTTGGGACACCGAC
GTCACGCAGAAGTTCCAGGCCAGAGTCACGATTACCGCGGACGAATCTA
CGAGCACAGCCTACATGGAGCTGAGCAGCCTGAGATCTGAGGACACGGCC
GTCTATTGGTGTGCGGTTCAAGATTGTAGTACTACCACCTGCTATCCTGC
GAGTTCCTACTACTACTATAACATGGGCGTCTGGGGCAAAGGGACCACGG
TCACCGTCTCCTCAGCATCCCCGACCAGCCCCAAGG (SEQ ID NO:
846)

>heavy_1d|FWMETYS01BAHLT|2
CAGCAGCTACAGGTGTCCAGTCCCAGGTGCAGCTGGTGCAGTCTGGGGCT
GAGGTGAAGAGGCCTGGGTCCTCCGGTGAAGGTCTCCTGCCAGGCTTCTGG
AGGCACCTTCAGCAACTATGCTATCAGCTGGGTGCGACAGGCCCCTGGAC
AAGGGCTTGAGTGGATGGGAGGGATCATCCCTATGTTTGGTACACCAAAG
TACGCACAGCAGTTCCTGGACAGAGTCACGATAACGCGGACGAATCCAC
GAGTACAGCCTACATGGAGCTGAGCAGCCTGAGATCTGAGGACACGGCCG
TTTATTGGTGTGCGGTTCAAGATTGTAGTACTACCACCTGTTATCCTGCG
AGTTCCTACTACTACTACAACATGGGCGTCTGGGGCAAAGGGACCACGGT
CACCGTCTCCTCAGCATCCCCGACCAGCCCCAAGG (SEQ ID NO:
847)

>heavy_1d|FWMETYS01COGNO|0
GTGGCTATTTTAAAAGGTGTCCAGTGTGAGGTGCAGCTGTTGGAGTCTGG
GGGAGGCTTGGTGCAGCCTGGGGGGTCCCTGAGACTCTCCTGTGTAGCCT
CTGGATTCACCTTTAGCAACTATGCCATGAGCTGGGTCCGCCAGGCTCCA
GGGAAGGGGCTGGAGTGGGTCTCAGGAATTAGTGGTAGTGGTGCTAGCAC
ATACTACGAAGACTCCGTGAAGGGCCGGTTCACCATCTCCAGAGACAATT
CCAAGAACACGCTGTATCTGGACATGAATAGCCTGAGAGCCGAGGACACG
GCCGTATATTACTGTGCGCAAACCGATAGCAGCACATAGATTTCTACTA
CTACGGTATGGACGACTGGGGCCAAGGGACCACGGTCACCGTCTCCTCAG
CATCCCCGACCAGCCCCAAGG (SEQ ID NO: 848)

>heavy_1d|FWMETYS01B1GQ7|2
CGGCTCCCAGATGGGTCCTGTCCCAGGTGCAGCTGCAGGAGTCGGGCCCA
GGACTGGTGAAGCCTTCGGAGACCCTGTCCCTCACTTGCACTGTTTCTAG
TGGCTCCATCAGGATTACTACTGGAGCTGGATCCGGCAGACCCCAGGGA
AGGGACTGGAGTGGATTGGATATATCTTTTCCAATGGGAGGATCAAGTAC
AATTCCTCCCTCCAAGGTCGACTCACCATGTCACTAAACACGCCCGAGAA
TCAGTTCTCCCTGTGGCTGAGCTCTGTGACCGCCGCAGACACGGCCGTCT
ATTACTGTGCGGATCGGGGGGATAGTTGGAGCCCTCCACAATTTGACTTC
TGGGGCCAGGGAATCCTGGTCACCGTCTCCTCAGCATCCCCGACCAGCCC
CAAGG (SEQ ID NO: 849)

>heavy_21d|FWMETYS01ENDE7|2
TTGTGGCTATTTTAAAAGGTGTCCAGTGTGAGGTGCAGTTGTTGGAGTCT
GGGGGAGGCTTGGTACAGCCTGGGGGGTCCCTGAGACTCTCCTGTGCAGC
CTCTGGATTCACCTTTAACAACTATGCCACAAGCTGGGTCCGCCAGGCTC
CAGGGAAGGGGCTGGAGTGGGTCTCAACTATTAGTGGTGTTGGTGATACC
ACATACTACGCAGACTCCGTGAAGGGCCGGTTCACCATCTCCAGAGACAC
TTCCAAGAACACCCTGTATCTGCAAATGAACAGCCTGAGAGCCGAGGACA
CGGCCGAATATTACTGTGCGAGAGTACGGGGATATTGTAATGGTGGTAGC
TGCTACTTTGACTACTGGGGCCAGGGAACCCCGGTCACCGTCTCCTCAGG
GAGTGCATCCGCCCC (SEQ ID NO: 850)

>heavy_21d|FWMETYS01BI6DS|2
CAGCAGCCACAGGAGCCCACTCCCAGGTGCAACTGGTGCAGTCTGGGGCT
GAGGTGAAGAGGCCTGGGGCCTCAGTGAAGGTCTCCTGCAAGGCCTCTGG
ATACACCTTCACCGGCTACTATGTACACTGGGTGCGACAGGCCCCTGGAC
AAGGCTTGAGTGGATGGGATGGATCAACCCTAACAGTGGTGTCACAAAC
TACGCACAGAACTTTCAGGACAGGGTCACCATGACCAGGGACACGTCCAT
CAGCACAGCCTACATGGAGCTGACCAGGCTGAGATCTGACGACACGGCCC
TATATTACTGTGCAGAGAGAGGGCATTAGTGGGAGGTAGTACGACTCTC
GGATACTGGGGCCAGGGAACCCTGGTCACCGTCTCCTCAGGGAGTGCATC
CGCCCCAACCC (SEQ ID NO: 851)

>heavy_21d|FWMETYS01ASJFG|2
CGGCTCCCAGATGGGTCCTGTCCCAGGTGCAGTTACAGCAGTGGGGCGCA
GGACTGTTGAAGCCTTCGGAGACCCTGTCCCTCACCTGCGTTGTCTATGG
TGGGTCTTTCAGTCCTTATTACTGGAGCTGGATCCGCCAGACCCCAGGGA
AGGGGCTGGAGTGGATTGGGGAAATCAATCATAGTGGAAGCACCAACTAC
AACCCGTCCCTCAAGAGTCGAGTCTCCATATCACTAGACACGTCCAAGAA
TGAGTTCTCCCTGAGGCTGAACTCTGTGACCGCCGCGGACACGGCTGTGT
ATTACTGTGCGAGAGCAGGGCTTCAACCTTTAAAGTCTACTATCACTAC
ATGGACGTCTGGGGCAATGGGACCACGGTCACCGTCTCCTCAGCATCCCC
GACCAGCCCCAAGG (SEQ ID NO: 852)

>heavy_21d|FWMETYS01EEVTL|2
CGGCTCCCAGATGGGTCCTGTCCCAGGTGCAGCTGCAGGAGTCGGGCCCA
GGACTGGTGAAGCCTGCGGAGACCCTGTCCCTCACCTGCAATGTCTCTGG
TGGCTCCATGAGTAGTTACTACTGGAGCTGGATCCGGCAGCCCCAGGGA
AGGGACTGGAGTGGATCGGGTACATCCACTACAGGGGGACCACCAAATAC
AATCCCTCCCTCAAGAGTCGCGTCACCATATACAGACCTGTCCAAGAA
CCAGTTCTCCCTGAAACTGAGCTCTATGACCGCCGCAGATCGGCCAGAT
ATTACTGTGCGAGACATATGCGGGTGGGAGCCCTAGTCAAACTGCTTTT
GATGTCTGGGGCCAAGGGACAATGGTCACCGTCTCTTCAGCATCCCCGAC
CAGCCCCAAGG (SEQ ID NO: 853)

>heavy_21d|FWMETYS01BGHT7|2
CGGCTCCCAGATGGGTCCTGTCCCAGGTGCAGCTGCAGGAGTCGGGCCCA
GGACTGGTGAAGCCTTCGGAGACCCTGTCCCTCACCTGCAATGTCTCTGG
TGGCTCCATCAGTAGTTACTACTGGAGCTGGATCCGGCAGCCCCAGGGA
AGGCACTGGAGTGGATCGGGTATATCCACTACAGGGGGACTACCAAATAC
AATCCCTCCCTCAAGAGTCGCGTCACCATATCAGTAGACACGGCCATCT
ATTACTGTGCGAGACATATGCGGGCTGGGAGTCCTAGTCAAACTGCTTTT
GATGTCTGGGGCCAAGGGACAATGGTCACCGTCTCTTCAGCATCCCCGAC
CAGCCCCAAGG (SEQ ID NO: 854)

>heavy_21d|FWMETYS01DUYF3|2
CGGCTCCCAGATGGGTCCTGTCCCAGGTGCAGCTGCAGGAGTCGGGCCCA
GGACTGGTGAAGCCTTCGGGGACCCTGTCCCTCACCTGCAATGTCTCTGG
TGGCCCCATCAGTAGTTACTACTGGAGCTGGATCCGGCAGCCCCAGGGA
AGGGACTGGAGTGGATCGGGTATATTATTACAGGGGGACTACCAAATAC
AATCCCTCCCTCAAGAGTCGCGTCACCATATCAGTAGACATGTCCAAGAA
CCAGTTCTCCCTGAAACTGAGCTCTATGACCGCCGCAGATACGGCCATGT
ACTACTGTGCGAGACATATGCGGGTGGGAGTCCTAGTCAAACTGCTTTT
GATGTCTGGGGCCAAGGGACAATGGTCACCGTCTCTTCAGCATCCCCGAC
CAGCCCCAAGG (SEQ ID NO: 855)

TABLE 6-continued

>heavy_21d|FWMETYS01DI6U3|2
TTGTTGGCTATTTTAAAAGGTGTCCAGTGTGAGGTGCAGCTGTTGGAGTCT
GGGGGAGGCTTGATACAGCCTGGGGGGTCCCTGAGACTCTCCTGTGCAGC
CTCTGGATTCACCTTTAGCAAGTATGCCATGACCTGGGTCCGCCAGGCTC
CAGGGAAGGGCCTGGAGTGGGTCTCGACTATTAGTGGTAGTGCTACTGCC
ACATACTACGCAGACTCCGTGAAGGGCCGCTTCACCATCTCCAGAGACAA
TTCGAAGAACACGCTGTATCTGCAAATGAACAGCCTGAGAGCCGCGGACA
CGGCCGTTTATTACTGTGTGAAAGCGGTTTCGGGGTCGAACTACATCTTT
GACTACTGGGGCCAGGGAACCCAGGTCACCGTCTCCTCAGCATCCCCGAC
CAGCCCCAAGG (SEQ ID NO: 856)

>heavy_21d|FWMETYS01D3L49|2
TTGTTGGCTATTTTAAAAGGTGTCCAATGTGAGGTGCAACTGTTAGAATAT
GGGGGAGGCTTGGTACAGCCGGGGGGGTCCCTGAGACTCTCCTGTGAAGC
CTCTGGAATCCCCTTTAACAACTATGCCATGAGCTGGGTCCGCCAGGCTC
CAGGGAAGGGGCTGGAGTGGGTCTCAAGTATCAGTGGTAGTGGTAGTGGC
ACATATTACGGAGACTCCGTGAAGGGCCGGTTCACCATCTCCAGAGACAA
TTCCAAGAACACACTGTATCTGCAAATGAATAGCCTGAGAGCCGAGGACA
CGGCCGTATATTATTGTGCGAGAGGCCGAGTGGGAGCTAAAGAGCCGACC
GTTTACTACTTTGACCACTGGGGCCAGGGAACCCTGGTCACCGTCTCCTC
AGCATCCCCGACCAGCCCCAAGG (SEQ ID NO: 857)

>heavy_21d|FWMETYS01EOI8H|0
GTGGCTATTTTAAAAGGTGTCCAGTGTGAGGTGCAGCTGTTGGAGTCTGG
GGGAGGCTTGGTACAGCCTGGGGGGTCCTTGAGACTCTCCTGTGCAGCT
CTGGATTCACCTTCAGCAGCTATGCCATGAACTGGGTCCGCCTGCCTCCA
GGGATGGGGATGGAGAGCATCTCATCCATTAGTCGTAGTGGTGATAGAAC
ATACTACGCAGACTCCGTGAAGGGCCGGTTCACCATCTCCAGAGACAATT
CCAAGAACACGATGTATCTGGAAATGAACAGCCTGAGAGCCGAGGACACG
GCCGTATATTACTGTGCGAAAATTTTTGAGGCGAATTTGGAAAACTACTG
GTATGGTTTGGACGTCTGGGGCCAAGGGACCACGGTCACCGTCTCCTCAG
GGAGTGCATCCGCCCCAACCC (SEQ ID NO: 858)

>heavy_21d|FWMETYS01BIG98|2
CGGCTCCCAGATGGGTCCTGTCCCAGGTGCAGCTGCAGGAGTCGGGCCCA
GGACTGGTGAAGCCTTCGGAGACCCTGTCCCTCACCTGCGCTGTCTCTGG
TGCCTCCATTAAGTTACTATTGGAGCTGGATCCGGCTGCCCCCAGGGA
AGGGACTGGAGTGGATTGGGCATGTGTATCACAGTGGGAGCACCAGTTAC
AATCCCTCCCTCAAGAGTCGAGTCACCATATCAGTGGACACGTCCAAGAT
GCAGATCTCCCTGAGGCTGAACTCTGCGACTGCTGCGGACACGGCCGTGT
ATTACTGTGCGAGACATCAGTATAATGTTGGTAACTCCTGGGCTTTTGAT
ATCTGGGGCCAAGGGACAGTGGTCACCGTCTCTTCAGCATCCCCGACCAG
CCCCAAGG (SEQ ID NO: 859)

>heavy_7d|FWMETYS01DQGF4|2
TTGTGGCTATTTTAAAAGGTGTCCAGTGTGACGTGCAGCTGGTGGAGTCT
GGGGGAGGCTTGGTACAGCCTGGGAAGTCCCTGAGACTCTCCTGTGCAGC
CTCTGGATTCACCTTTAGCAACTATGCCATGTCCTGGGTCCGCCAGGCTC
CAGGGAAGGGCCTGGAGTGGGTCTCAGGTATTAGTGGTAGTGGTGCTGCC
ACATACTACGCAGACTCCGTGAAGGGCCGGTTCACCATCTCCAGAGACAA
TTCCAGGAACACGCTCCTTCTGCAAATGAACAGCCTGAGAGCCGAGGACA
CGGCCCTATATTACTGTGCGCAAACCGATAGCAGCAACTTAGACTACTAC
TACCACGGAATGGGCGTCTGGGGCCAAGGGACCACGGTCACCGTCTCCTC
AGCATCCCCGACCAGCCCCAAGG (SEQ ID NO: 860)

>heavy_7d|FWMETYS01EO8GA|2
CAGCAGCAACAGGTGCCCACTCCCAGGTTCAACTGGTGCAATCTGGAGCT
GAGGTGAAGAGGCCTGGGGCCTCAGTAAAGGTCTCCTGCACGGCTTCTGG
TTACACGTTTGACACTTATGGAGTCGGCTGGTTGCGACAGGCCCCTGGAC
AAGGGCTTGAGTGGATGGGCTGGATCAGCGGTGACAGTAGTCATACCAGA
TATGCAATGAGACTCCAGGGCAGAGTCACCATGACCACAGACTCATCCAC
GAGCACAGCCTACATGGAACTGAGGAGCCTGAGATCTGACGACACGGCCG
TCTATTACTGTGCGAGAGATGATCCATATTAGCAGTATTGGTTATCGT
ATTGACTCCTGGGGCCAGGGAACCCTGGTCACCGTCTCCTCAGCATCCCC
GACCAGCCCCAAGG (SEQ ID NO: 861)

>heavy_7d|FWMETYS02GPFII|2
CGGCTCCCAGATGGGTCCTGTCCCAGGTGCAACTGCAGGAGTCGGGCCCA
GGACTGGTGAAGCCTTCGGAGACCCTGTCCCTCACCTGCACTGTCTCTGG
TGGCTCCATCAGTAGTTACTACTTGAGCTGGATCCGGCAGCCCCAGGGA
AGGGGCTGGAGTGGATTGGGTATATCTATTACAGTGGGAGCACCAACTAC
AACCCCTCCCTCAAGAGTCGAGTCACCATATCAGTAGACACGTCCAAGAA
CCAGTTCTCCCTGAGGCTGAGCTCTGTGACCGCTGCGGACACGGCCGTGT
ATTACTGTGCGAGAATCCCGCTAAGATCGAGTGGGACGCCTACTACTAC
TACGGTATGGACGTCTGGGGCCAAGGGACCACGGTCACCGTCTCCTCAGG
GAGTGCATCCGCCCCAACCC (SEQ ID NO: 862)

>heavy_7d|FWMETYS01D3CAE|2
TTGTTGCTATATTTAGAAGGTGTCCAGTGTGAGGTGCAGTTGGTGGAGTCT
GGGGGAGGCTTGGTACAGCCTGGGGGGTCCCTGAGACTCTCCTGTGCAGC
CTCTGGATTCACTTTCAGTGGCTATAGCATGGACTGGGTCCGCCAGGCTC
CGGGGAAGGGGCTGGAGTGGGTTTCATTCATAAGTGATAATACTGGCAGT
CACATATACTACGCAGACTCTGTGAAGGGCCGATTCACCATCTCTAGAGA
CAATGCCGAGAACTCACTGTATCTACAAATGAACAGCCTGAGAGACGAGG
ACACGCTGTGTATTACTGTGCGAGAGACCTTACCTGGAGATACTTTGAC
TCCTGGGGCCATGGAGTCCTGGTCACCGTCTCCTCACGGAGTGCATCCGC
CCC (SEQ ID NO: 863)

>heavy_7d|FWMETYS01ASETU|2
TTGTTGCTATTTTAAAAGGTGTCCAGTGTGAGGTGCAGCTGGTGGAGTCT
GGAGGAGGCCTGATCCAGCCTGGGGGGTCCCTGAGACTCTCCTGTGCAGC
CTCTGGGTTCACCGTCAGTAGCAGCTACATGACCTGGGTCCGCCAGGCTC
CAGGGAAGGGGCTGGAGTGGGTCTCAGTTATTTATATGGTGGTACCACA
TACTACGCAGACTCCGTGAAGGGCCGATTCACCATCTCCAGAGACAATTC
CAAGAACACGCTGTATCTTCAAATGAACAGCCTGAGAGCCGAGGACACGG
CCGTGTATTACTGTGCGAGAGTGTTCTCTAGTAGTGGTTATTACTACTAC
TTTGATTACTGGGGCCAGGGAACCCTGGTCACCGTCTCCTCAGGGAGTGC
ATCCGCCCC (SEQ ID NO: 864)

>heavy_7d|FWMETYS01EL10A|2
CGGCTCCCAGATGGGTCCTGTCCCAGGTGCAGCTGCAGGAGTCGGGCCCA
GGACTGGTGAAGCCTTCGGAGACCCTGTCCCTCACCTGCACTGTCTCTGG
TGGCTCCATTAGTAGTTACTCCTGGAGCTGGATCCGGCAGTCCCCAGGGA
AGGGACTGGAGTGGATTGGGTCTACCTATTACAGTGGGAGCACCAACTAC
ACCAACTACAACCCCTCCCTCAAGAGTCGAGTCACCACATCAGTAGACAC
GTCCAAGAACCAGTTCTCCCTGGGCTGAACTCTGTGACCGCCGCGGACA
CGGCCATTTATTACTGTGCAAGATCCCTCATTCTATATAGTGACTACATT
GCCTACTGGGGCCAGGGAACCCTGGTCACCGTCTCCTCAGCATCCCCGAC
CAGCCCCAAGG (SEQ ID NO: 865)

>heavy_7d|FWMETYS01CU1FY|2
CAGCAGCAACAGGTGCCCGCTCCCAGGTTCAACTGATGCAGTCTGGAGCT
GAAGTGAGGAAGCCTGGGGCCTCAGTGACGGTCTCCTGCAAGACTTCTGG
TTACACCTTTACCTACTATGGTATCAGTTGGGTGCGACAGGCCCCTGGAC
AAGGCCTTGAGTGGATGGGATGGTTCAGCGCTTACAATGGTAAGACAAA
TATGCACAGAATCTCCAGGACAGAGTCACCATGACCAATTGACACATCCAC
GAGGACAGCCTACATGGAGTGAGGAGCCTGAGATCTGACGACACGGCCG
TATATTACTGTGCGAGGCAGTCAGGTAACCGAGGATTCGGTGACTCTTAC
TCCTACTATTACTTCATGGACGTCTGGGGCAAAGGGACCACGGTCACCGT
CGCCTCAGCATCCCCGACCAGCCCCAAGG (SEQ ID NO: 866)

>heavy_7d|FWMETYS01DFT1H|2
CGGCTCCCAGATGGGTCCTGTCCCAGGTGCAGCTACAGCAGTGGGGCGCA
GGACTGTTGAAGCCTTCGGAGACCCTGTCCCTCACCTGCGCTGTTTATGG
TGAGTCCTTCCGTGGTTACTCCTGGAGCTGGATCCGGCAGCCCCAGGGAA
AGGGGCTGGAGTGGATTGGGGAGATCAATCTTACTGGAAGCACCAACTAC
AACCCGTCCCTCAAGAGTCGGATCACCGTATCAATTGACCCGTCCAAGAC
TCAGTTCTCCCTGAAGCTGACCTCTGTGACCGCCGCGGGACACGGCTGTAT
ATTACTGCGCGAGAACTTTGTATTCTCTGGTAAAGTATAGTACTGGCTGG
TACTACTTTGACTACTGGGGCCAGGGAATCCTGGTCACCGTCTCCTCAGC
CTCCACCAAGGGCCCATCCG (SEQ ID NO: 867)

>heavy_7d|FWMETYS01DE08R|2
CGGCTCCCAGATGGGTCCTGTCCCAGGTGCAGCTGCAGGAGTCGGGCCCA
GGACTGGTGAAGCCTTCGGAGACTCTGTCCCTCACCTGCACTGTCTCTGG
TGACTCCATTAGTAGTGACTATTGGAGCTGGATCCGGCAGTCCCCAGGGA
AGGGACTGGAGTGGATTGGGTTTATTCAGTATACTGGGAGATCCCACTCC
AACCCCTCCCTCCAGAGTCGAGTCACCATATCATAGACGTCCAAGAA
CAACTTCTCCCTGAGGCTGACTCTGTGACCGCTGCGGACACGGCCGTGT
ATTATTGTGCGAGAACAAATGCTTTTCATATCTGGGGCCAAGGGACAATG
GTCACCGTCTCTTCAGGGAGTGCATCCGCCCC (SEQ ID NO: 868)

>heavy_7d|FWMETYS01BLJ3E|0
GTTGCTATATTAGAAGGTGTCCAGTGTGAGGTGCAGCTGGTGGAATCTGG
GGGAGGCTTAGTACAACCTGGGGGTTCGCTGAGACTCTCCTGTGCAGCCT
CTGGATTCACTTTCAGTGATTACGACATGCACTGGGTCCGCCAAGCTACA
GGAAAAGGTCTGAGTGGGTCTCAGCTATAGGAACTCTTGATGACACATA
CTATCCAGGCTCCGTGGAGGGCCGATTCACCGTCTCCAGAGACAATGCCA
GGGATTCCTTGTATCTTCAAATGAAGAGCCTCAGAGTCGCGGACACGGCT
GTATATTACTGTGTAAGAGTTAAGGGTGGACATAGCAGCAGCTGGTACCAC
TGCGGGGTACTTCGATCTCTGGGGCCGTGGCACCCTGGTCACTGTCTCCT
CAGGGAGTGCATCCGCCCCAACCC (SEQ ID NO: 869)

>light_1d|012171_0240_0412|2
TCTTCCCAGGTTCCAGATGCAGATCCAGATGACCCAGTCTCCGTCT
TCCGTGTCTGCATCTGTGGGAGACAGAGTCACCATCACTTGCCGGGCGAG
TCAGAGTCTTAGCGGCTTTTTAGCCTGGTATCAGCAGAAACAGGGAAAA
CCCCTAAGTTCCTGATCGATACTACCTCCATTTTGCAAAGTGGGGTCCCA
TCTAGATTCAGTGGCAGTGGATCTGGGACATTTTTCACTCTCACCATCAG
CAGCCTCCAGCCTGAAGATTTTGCAACTTACTATTGTCAACAGGCTAACA TABLE 6-continued GTTTCCCGCTCACTTTCGGCGAGGGACCAAGGTGGAGAGGAAACGAACT
GTGGCTGCACCATCTG (SEQ ID NO: 870)

>light_1d|016824_0202_0719|2
CTCACTGCACAGGCTCTGAGGCCTCCTATGAGCTGACACAGCCACCCTCG
GTGTCAGTGTCCCCAGGACAGACGGCCAGGATCACCTGCTCTGGAGATGC
ATTGCCAAAGCACTTTGCTTATTGGTACCAGCAGAAGCCAGGCCAGGCCC
CTGTACTGGTGATATATAAAGACACTGAGAGGCCCTCAGGGATCCCTGAG
CGATTCTCTGGCTCCAGCTCAGGGACAACAGTCACGTTGACCATCAGTGG
AGTCCAGGCAGAAGACGAGGCTGACTATTACTGTCAATCACCAGACAGCA
GTGGTACTAATGAAGTCTTCGGAACTGGGACCAAGGTCACCGTCCTAAGT
CAGCCCAAGGCCAACCCCACGGT (SEQ ID NO: 871)

>light_1d|025990_0147_0876|2
CTCACTGCACAGGCTCTGAGGCCTCCTATGAGCTGACACAGCCACCCTCG
GTGTCAGTGTCCCCAGGACAGACGGCCAGGATCACCTGCTCTGGAGATGC
ATTGCCAAAGCACTATGCTTATTGGTACCAGCAGAAGCCAGGCCAGGCCC
CTGTGTTGGTGATATATAAAGACAGTGAGAGGCCCTCAGGGATCCCTGAG
CGATTCTCTGGCTCCAGCTCAGGGACAACAGTCACGTTGACCATCAGTGG
AGTCCAGGCAGAAGACGAGGCTGACTATTACTGTCAATCACCAGACAGCA
GTGGTACTTATGAAGTCTTCGGAACTGGGACCAGGGTCACCGTCCTAGGT
CAGCCCAAGGCCAACCCCACTGT (SEQ ID NO: 872)

>light_1d|001721_0226_0129|2
CTCACTGCACAGGGTCCTGGGCCCAGTCTGTGTTGACGCAGCCGCCCTCA
GTGTCTGCGGCCCCAGGACAGAAGGTCACCATCTCCTGCTCTGGAAGCAG
CTCCAACATTGGCAAAAATTATGTATCCTGGTACCAGCATCTCCCAGGAA
CAGCCCCCAAACTCCTCATCTATGAAAATGATGAGCGACCCTCAGGGATT
CCTGACCGATTCTCTGGCTCCAAGTCTGGCACGTCAGCCACCCTGGGCAT
CACCGGACTCCAGACTGGGGACGAGGCCACTTATTTCTGCGGAACATGGG
ATACCAGCCTGGGTACTAATTGGGTGTTCGGCGGAGGGACCAAGCTGACC
GTCCTAGGTCAGCCCAAGGCTGCCCCCTCGGT (SEQ ID NO: 873)

>light_1d|035774_0389_0427|2
CTCACTGCACAGGGTCCTGGGCCCAGTCTGTGTTGACGCAGCCGCCCTCA
GTGTCTGCGGCCCCAGGACAGAAGGTCACCATCTCCTGCTCTGGAAGCAG
CTCCAACATTGGGAGTAATCGTGTATCCTGGTACCAGCAGCTCCCAGGAA
CAGCCCCCAAACTCCTCATCTATGAAAATAATGAGCGACCCTCAGGGATT
CCTGACCGATTCTCTGCCTCCAAGTCTGGCACGTCAGCCACCCTGGTCAT
CACCGGACTCCAGACTGGGGACGAGGCCGATTATTATTGCGGAACATGGG
ATACCAGCCTGAGAATTAATTGGGTGTTCGGCGGAGGGACCAAGCTGACC
GTCCTAGGTCAGCCCAAGGCTGCCCCCTCGGT (SEQ ID NO: 874)

>light_1d|007823_0201_0454|2
TCTGGCTCCCAGGTGCCAGATGTGACATCCTGTTGACCCAGTCTCCATCC
TTCCTGTCTGCAGCTGTAGGAAACAGAATCACCATTACTTGCCGGGCCAG
TCAGGGCATTAGTAGTTATTTAGCCTGGTTTCAGGAAAAAACCAGGGAAA
CCCCTAAACTCCTGATTTATGGTGCATCCATTTTGCAAAGTGGGGTCCCA
TCAAGGTTCAGCGGCAGTGGATCTGGGACAGAGTTCACTCTCACAATCAG
GAGCCTGCAGCCTGAAGATTTTGCAACTTATTACTGTCAACAGTTTACTA
ATTTCCCGCTCACTTTCGGCGAGGGACCAAGGTGGAGATCAAACGAACT
GTGGCTGCACCATCTG (SEQ ID NO: 875)

>light_1d|008086_0088_0336|1
ACTCTGGCTCACAGATACCACCGGAGAAATTGTGTTGACGCAGTCTCCAG
GCACCCTGTCTTTGTCTCCAGGGGAAAGAGCCACCCTCTCCTGCAGGGCC
AGTCAGAGAGTTAGCAGCAACTACTTAGCCTGGTACCAGCAGAAATCAGG
CCAGGCTCCCAGGCTCCTCATCTATAGTGCATCCCGCAGGGCCACTGGCA
TCCCAGACAGGTTCAGTGGCAGTGGGTCTGGGACAGACTTCACTCTCACC
ATCAGCAGACTGGAGCCTGAAGATTTTGCCGTGTATCACTGTCAACAGTA
TGGTAGTTCATGGCGCACTTTTGGCCAGGGGACCAAGGTGGAGATCAGAC
GAACTGTGGCTGCACCATCTG (SEQ ID NO: 876)

>light_1d|004730_0220_0168|2
CTTACTGCACAGGATCCGTGGCCTCCTATGAGCTGACTCAGCCACCCTCA
GTGTCCGTGTCCCCAGGACAGACAGCCAGCATCACCTGCTCTGGAGATAA
ATTGGGGATAAATATGCTTGCTATCAGCAGAAGCCAGGCCAGTCCC
CTGTGCTGGTCATCTATCAAGATAGCAAGCGGCCCTCAGGGATCCCTGAG
CGATTCTCTGGCTCCAACTCTGGGAACACAGCCACTCTGACCATCAGCGG
GACCCAGGCTATGGATGAGGCTGACTATTACTGTCAGGCGTGGGACAGCA
GCTGTGGTATTCGGCGGAGGGACCAAGCTGACCGTCCTAGGTCAGCCC
AAGGCTGCCCCCTCGGT (SEQ ID NO: 877)

>light_1d|018024_0239_0556|2
CTCACTGCACAGGGTCCTGGGCCCAGTCTGTGTTGACGCAGCCGCCCTCA
GTGTCTGCGGCCTCAGGACAGGAGGTCACCATCTCCTGCTCTGGAAGCAG
CTCCAACATTGGGAGTTATCGTGTATCCTGGTATCAGCACCTCCCAGGAA
CAGCCCCCAAACTCCTCATCTATGAAAATGATCAGCGACCCTCAGGGATT
CCTGACCGATTCTCTGGCTCCAAGTCTGGCACGTCAGCCACCCTGGTCAT
CACCGGACTCCTGACTGCGGACGAGGCCGATTATTACTGCGGAACATGGG TABLE 6-continued ATACCAGCCTGAGGATTAATTGGGTGTTCGGCGGAGGGACCAAGCTGACC
GTCCTAGGTCAGCCCAAGGCTGCCCCCTCGGT (SEQ ID NO: 878)

>light_1d|003754_0225_0116|1
CACTCACTCTGCAGTGTCAGTGGTCCAGGCAGGACTGACTCAGCCACCCT
CGGTGTCCAAGGACTTGAGACAGACCGCCACACTCACCTGCACTGGGAAC
AGCAACAATGTTGGCAACCTAGGAGCAGCTTGGCTGCAGCAGCACCAGGG
CCACCCTCCCACACTCCTATCCTACAGGGATAACAACCGGCCCTCAGGGA
TCTCAGAGAGATTCTCTGCATCCAGGTCAGGAAATACAGCCTCCCTGTCC
ATTACTGGACTCCAGCCTGACGACGAGGCTGACTATTACTGCTCAGCATG
GGACAGCAGCCTCAGTGCTTGGGTGTTCGGCGGAGGGACCAAGCTGACCG
TCCTAGGTCAGCCCAAGGCTGCCCCCTCGGT (SEQ ID NO: 879)

>light_21d|004730_0220_0168|2
CTTACTGCACAGGATCCGTGGCCTCCTATGAGCTGACTCAGCCACCCTCA
GTGTCCGTGTCCCCAGGACAGACAGCCAGCATCACCTGCTCTGGAGATAA
ATTGGGGATAAATATGCTTGCTATCAGCAGAAGCCAGGCCAGTCCC
CTGTGCTGGTCATCTATCAAGATAGCAAGCGGCCCTCAGGGATCCCTGAG
CGATTCTCTGGCTCCAACTCTGGGAACACAGCCACTCTGACCATCAGCGG
GACCCAGGCTATGGATGAGGCTGACTATTACTGTCAGGCGTGGGACAGCA
GCTGTGGTATTCGGCGGAGGGACCAAGCTGACCGTCCTAGGTCAGCCC
AAGGCTGCCCCCTCGGT (SEQ ID NO: 880)

>light_21d|010947_0053_0325|1
ACTCTGGCTCACAGATACCACCGGAGAGATTGTGTTGACGCAGTCTCCAA
GCACCCTGTCTTTCTCTCAGGAGAAAGAGCCACCCTCTCCTGCAGGGCC
AGTCAGATTATTACCAGCAGCTACTTAGCCTGGTACCAGCAGAAACCTGG
CCAGGCTCCCAGGCTCCTCATCTATGGTGGATCCAGCAGGGCCACTGGCA
TCCCAGACAGGTTAGTGGCAGTGGGGCTGGGACAGACTTCACGCTCACC
ATCAGCAGACTGGAGCCTGAAGATTTTGCAGTGTATTACTGTCAACAACA
TGGTAACTCACCGGTCACTTTCGGCGGAGGGACCAAGGTGGAGATCAAAG
GAACTGTGGCTGCACCATCTG (SEQ ID NO: 881)

>light_21d|016345_0101_0575|2
CTTGCTGCCCAGGGTCCAATTCCCAGGCTGTGGTGACTCAGGAGCCCTCA
CTGACTGTGTCCCCAGGAGGGACAGTCACTCTCACCTGTGGCTCCAGCAC
TGGAGCTGTCACCAGTGGTCATTATCCCTACTGGTTCCAGCAGAAGCCTG
GCCAAGCCCCCAGGACACTGATTTCTGATACAAGCAACAAATGTTCTTGG
ACCCCTGGCCGGTTCTCAGGCTCCCTCCTTGGGGGCAAAGCTGCCCTGAC
CCTTTCGGGTGCGCAGCCTGAGGATGAGGCTGACTATTATTGCTTCCTCT
ACTTTGATGGTCCTATAGTTTTCGGCGGAGGGACCAAGCTGACCGTCCTA
AGTCAGCCCAAGGCTGCCCCCTCGGT (SEQ ID NO: 882)

>light_21d|016683_0138_0575|0
CTCTGGATCTCTGGTGCCTACGGGGACATCGTGATGACCCAGTCTCCAGA
TTCCCTGGCTGTGTCTCTGGGCGAGAGGGCCACCATCAACTGCAAGTCCA
GCCAGAGTGTTTTGTGGGGCCCCAACAATAAGAACTACTTAGCTTGGTAC
CAGCAGAAACCAGGACAGTCTCCTAAGTTGCTCATTTACTGGGGATCTAC
CCGGAAATCCGGGGTCCCTGACCGATTCAGTGGCAGCGGGTCTGGGACAG
ATTTCACTCTCACCATCAGCAGCCTGCAGGCTGAAGATGTGGCAGTTTAT
TACTGTCAGCATTATCATACCACCGTACACTTTTGGCCAGGGGACCAA
GCTGGAGATCAAACGAACTGTGGCTGCACCATCTG (SEQ ID NO: 883)

>light_21d|014243_0165_0699|2
TCTGGGTCCCAGGTGCCAAATGTGTCGTCCAGATGACCCAGTCTCCTTCC
ACCCTGTCTGCATCTGTAGGAGACAGAGTCACCATCACTTGCCGGGCCAG
TGAGACTGTTGGACGTGGTTGGCCTGGTATCGGCAGAAACCAGGGAAAG
CCCCTAACCTCCTGATCTATGAGGCCTCTATTTTAGAAAGTGGGGTCCCA
TCGAGGTTCAGCGGCAGTGGATCTGGGACAGAGTTCACTCTCACCATCAG
CAGCCTGCAGCCTGATGATTTTGCAACTTATTACTGCCAACAGTATAATA
CCTGGTGGACATTCGGCCAAGGGACCAAGGTGGAAATCAAGCGAACTGTG
GCTGCACCATCTG (SEQ ID NO: 884)

>light_21d|007238_0089_0294|2
CTTGCTGCCCAGGGTCCAATTCCCAGGCTGTGGTGACTCAGGAGCCCTCA
CTGACTGTGTCCCCAGGAGGGACAGTCACTCTCACCTGTGGCTCCAGCAC
TGGAGCTGTCACCAGTGGTCATTATCCCTACTGGTTTCAGCAGAAGCTG
GCCAAGCCCCCAGGACACTGATGTATGATATAAGCATCAAACTGTCCTGG
ACCCCTGCCCGGTTCTCAGGCGCCCTCCTTGGGGGCAAAGCTGCCCTGAC
CCTTTCGGGTGCGCAGCCTGAGGATGAGGCTGAATATTATTGTTTACTCT
ATTATAATGGTCAGGGTGTTCGGCGGAGGGACCAAACTGACAGTCCTA
GGTCAGCCCAAGGCTGCCCCCTCGGT (SEQ ID NO: 885)

>light_21d|015152_0165_0715|1
CCTCACTCTTTGCATAGGTTCTGTGGTTTCTTCTGAGCTGACTCAGGACC
CTGCTGTGTCTGTGGCCTTGGGACAGACAGTCAGGATCACATGCCAAGGA
GACAGCCTCAGAAGCTATTATGCAAGCTGGTACCAGCAGAAGCCAGGACA
GGCCCCTGTACTTGTCATCTATGGTAAAAACAACCGGCCCTCAGGGATCC
CAGACCGATTCTCTGGCTCCAGCTCAGGAAACACAGCTTCCTTGACCATC TABLE 6-continued

```
>light_21d|003565_0121_0193|2
CTCGGGACACAGGGTCCTGGGCCCAGTCTGCCCTGACTCAGCCTGCCTCC
GTGTCTGGGTCTCCTGGACAGTCGATCACCATCTCCTGCACTGGAACCAG
CAGTGATGTTGGGAGATATAACCTTGTCTCCTGGTACCAACAACACCCAG
GCAAAGCCCCCAAATTCTTGATTTATGAGGTCAGTAAGGGGCCCTCAGGG
GTTTCTAATCGCTTCTCTGGCTCCAAGTCTGGCAACACGGCCTCCCTGAC
AATCTCTGGGCTCCAGGCTGAGGACGAGGCAGATTATTACTGCTGCTCAT
ATGCAGGTAGTAGCACTTTTGTCTTCGGAACTGGGACCACGGTCACCGTC
CTAGGTCAGCCCAAGGCCAACCCCACGGT (SEQ ID NO: 887)

>light_21d|010775_0076_0480|2
CTCACTGCACAGGCTCTGAGGCCTCCTATGAGCTGACACAGCCACCCTCG
GTGTCAGTGTCCCCAGGACAGACGGCCAGGATCACCTGCTCTGGAGATGC
ATTGCCAAAGCAATATGCTTATTGGTACCAGCAGAAGCCAGGCCAGGCCC
CTGTGCTGGTGATATATAAAGACAGTGAGAGGCCCTCAGGGATCCCTGAG
CGATTCTCTGGCTCCAGCTCAGGGACAACAGTCACGTTGACCATCAGTGG
AGTCCAGGCAGAAGACGAGGCTGACTATTACTGTCAATCAGCAGACAGCA
GTGGTACTTATGTGGTATTCGGCGGAGGGACCAAGCTGACCGTCCTAGGT
CAGCCCAAGGCTGCCCCCTCGGT (SEQ ID NO: 888)

>light_21d|003754_0225_0116|1
CACTCACTCTGCAGTGTCAGTGGTCCAGGCAGGACTGACTCAGCCACCCT
CGGTGTCCAAGGACTTGAGACAGACCGCCACACTCACCTGCACTGGGAAC
AGCAACAATGTTGGCAACCTAGGAGCAGCTTGGCTGCAGCAGCACCAGGG
CCACCCTCCCACACTCCTATCCTACAGGGATAACAACCGGCCCTCAGGGA
TCTCAGAGAGATTCTCTGCATCCAGGTCAGGAAATACAGCCTCCCTGTCC
ATTACTGGACTCCAGCCTGACGACGAGGCTGACTATTACTGCTCAGCATG
GGACAGCAGCCTCAGTGCTTGGGTGTTCGGCGGAGGGACCAAGCTGACCG
TCCTAGGTCAGCCCAAGGCTGCCCCCTCGGT (SEQ ID NO: 889)

>light_7d|004730_0220_0168|2
CTTACTGCACAGGATCCGTGGCCTCCTATGAGCTGACTCAGCCACCCTCA
GTGTCCGTGTCCCCAGGACAGACAGCCAGCATCACCTGCTCTGGAGATAA
ATTGGGGGATAAATATGCTTGCTGGTATCAGCAGAAGCCAGGCCAGTCCC
CTGTGCTGGTCATCTATCAAGATAGCAAGCGGCCCTCAGGGATCCCTGAG
CGATTCTCTGGCTCCAACTCTGGGAACACAGCCACTCTGACCATCAGCGG
GACCCAGGCTATGGATGAGGCTGACTATTACTGTCAGGCGTGGGACAGCA
GCACTGTGGTATTCGGCGGAGGGACCAAGCTGACCGTCCTAGGTCAGCCC
AAGGCTGCCCCCTCGGT (SEQ ID NO: 890)

>light_7d|016513_0160_0702|2
CTCAGGGCACAGGGTCCTGGGCTCAGTCTGCCCTGACTCAGCCTCGCTCA
GTGTCCGGGTCTCCTGGACAGTCAGTCACCATCTCCTGCACTGGAACCAG
CAGTGATGTTGGTAGTTATAACTATGTCTCCTGGTACCAACAGCACCCAG
GCAAAGCCCCCACACTCATGATTTATGATGTCACTAAGCGGCCCTCAGGG
GTCCTGATCGCTTCTCTGGCTCCAAGTCTGGCAACAGCCTCCCTGAC
CATCTCTGGGCTCCAGGCTGAGGATGAGGCTGATTATTACTGCTGCTCAT
ATGCAGGCAACTCTTATGTCTTCGGAACTGGGACCAAGGTCACCGTCCTA
GGTCAGCCCAAGGCCAACCCCACGGT (SEQ ID NO: 891)

>light_7d|016824_0202_0719|2
CTCACTGCACAGGCTCTGAGGCCTCCTATGAGCTGACACAGCCACCCTCG
GTGTCAGTGTCCCCAGGACAGACGGCCAGGATCACCTGCTCTGGAGATGC
ATTGCCAAAGCACTTTGCTTATTGGTACCAGCAGAAGCCAGGCCAGGCCC
CTGTACTGGTGATATATAAAGACACTGAGAGGCCCTCAGGGATCCCTGAG
CGATTCTCTGGCTCCAGCTCAGGGACAACAGTCACGTTGACCATCAGTGG
AGTCCAGGCAGAAGACGAGGCTGACTATTACTGTCAATCACCAGACAGCA
GTGGTACTAATGAAGTCTTCGGAACTGGGACCAAGGTCACCGTCCTAAGT
CAGCCCAAGGCCAACCCCACGGT (SEQ ID NO: 892)

>light_7d|076796_0530_0700|1
ACTCTGGCTCACAGATACCACCGGAGAAATTGTGTTGACGCAGTCTCCAG
GCACCCTGTCTTTGTCTCCAGGGGAAAGAGCCACCCTCTCCTGCAGGCCA
AGTCAGAGTGTTAGCAGCAGCTACTTAGCCTGGTACCAGCAGAAACCTGG
CCAGGCTCCCAGGCTCCTCATCTATGGTGCATCCAGCAGGGCCACTGGCA
TCCCAGACAGGTTCAGTGGCAGTGGGTCTGGGACAGACTTCACTCTCACC
ATCAGCAGACTGGAGCCTGAAGATTTTGCAGTGTATTACTGTCAGCAGTA
TGGTAGCTCACCTTGGACGTTCGGCCAAGGGACCAAGGTGGAAATCAAAC
GAACTGTGGCTGCACCATCTG (SEQ ID NO: 893)

>light_7d|006092_0191_0398|1
ACTCTGGCTCACAGATACCACCGGAGAAATTGTGTTGACGCAGTCTCCAG
GCACCCTGTCTTTGTCTCCAGGGGAAAGAGCCTTCCTCTCCTGCAGGGCC
AGTCAGACTGTTCCCAGCAGCTACTTAGCCTGGTACCAGCAGAGACCTGG
CCAAGTTCCCAGGCTCCTCATCTATGATGCATCCAGCAGGGCCACTGGCA
TCTCAGACAGGTTTAGTGGCAGTGGGTCTGGGACAGACTTCACTCTCACC
ATCAACACACTGGAGCCTGAAGATTCTGCTGTGTATTACTGTCAGCAATA
TGGTAGCTCACCGACGTTCGGCCAAGGGACCAAGGTGGAAATCAAACGAA
CTGTGGCTGCACCATCTG (SEQ ID NO: 894)

>light_7d|015152_0165_0715|1
CCTCACTCTTTGCATAGGTTCTGTGGTTTCTTCTGAGCTGACTCAGGACC
CTGCTGTGTCTGTGGCCTTGGGACAGACAGTCAGGATCACATGCCAAGGA
GACAGCCTCAGAAGCTATTATGCAAGCTGGTACCAGCAGAAGCCAGGACA
GGCCCCTGTACTTGTCATCTATGGTAAAAACAACCGGCCCTCAGGGATCC
CAGACCGATTCTCTGGCTCCAGCTCAGGAAACACAGCTTCCTTGACCATC
ACTGGGGCTCAGGCGGAAGATGAGGCTGACTATTACTGTAACTCCCGGGA
CAGCAGTGGTAACCATGTGGTATTCGGCGGAGGGACCAAGCTGACCGTCC
TAGGTCAGCCCAAGGCTGCCCCCTCGGT (SEQ ID NO: 895)

>light_7d|037667_0422_0484|1
ACTCTGGCTCACAGATACCACCGGAGAAATTGTGTTGACACAGTCTCCAG
CCACCCTGTCTTTGTCTCCAGGGGAAAGAGCCACCCTCTCCTGCAGGGCC
AGTCAGAGTGTTAGCACCTACTTAGCCTGGTACCAACAGAAACCTGGCCA
GCCTCCCAGACTCCTCATCTATGATGCATCCAACAGGGCCACTGGCATCC
CAGCCAGGTTCAGTGGCAGTGGGTCTGGGACAGACTTCACTCTCACCATC
AGCAGCCTAGAGCCTGAAGATTCTGCAGTTTATTACTGTCAGCAGCGTAG
CACCTGGCCTGCGACTTTCGGCCCTGGGACCAAAGTGGATATCAAACGAA
CTGTGGCTGCACCATCTG (SEQ ID NO: 896)

>light_7d|059523_0412_0968|2
CTCACTGCACAGGCTCTGTGACCTCCTATGTGCTGACTCAGCCACCCTCG
GTGTCAGTGGCCCCAGGAAAGACGGCCAGGATTACCTGTGGGGAAACAA
CATTGGAAGTAAAAGTGTGCACTGGTACCAGCAGAAGCCAGGCCAGGCCC
CTGTGCTGGTCGTCTATGATGATAGCGACCGGCCCTCAGGGATCCCTGAG
CGATTCTCTGGCTCCAACTCTGGGAACACGGCCACCCTGACCATCAGCAG
GGTCGAAGCCGGGGATGAGGCCGACTATTACTGTCAGGTGTGGGATAGTA
GTAGTGATCATGTGGTATTCGGCGGAGGGACCAAGCTGACCGTCCTAGGT
CAGCCCAAGGCTGCCCCCTCGGT (SEQ ID NO: 897)

>light_7d|010775_0076_0480|2
CTCACTGCACAGGCTCTGAGGCCTCCTATGAGCTGACACAGCCACCCTCG
GTGTCAGTGTCCCCAGGACAGACGGCCAGGATCACCTGCTCTGGAGATGC
ATTGCCAAAGCAATATGCTTATTGGTACCAGCAGAAGCCAGGCCAGGCCC
CTGTGCTGGTGATATATAAAGACAGTGAGAGGCCCTCAGGGATCCCTGAG
CGATTCTCTGGCTCCAGCTCAGGGACAACAGTCACGTTGACCATCAGTGG
AGTCCAGGCAGAAGACGAGGCTGACTATTACTGTCAATCAGCAGACAGCA
GTGGTACTTATGTGGTATTCGGCGGAGGGACCAAGCTGACCGTCCTAGGT
CAGCCCAAGGCTGCCCCCTCGGT (SEQ ID NO: 898)

>light_7d|030140_0479_0232|2
CTCACTGCACAGGGTCCTGGGCCCAGTCTGTGTATTGACGCAGCCGCCCTCA
GTGTCTGCAGCCCCAGGACAGAAGGTCACCATCTCCTGCTCTGGAAGCAC
CTCCAACATAGTTCATAATTTTGTATCGTGGTTCCAGCATCTCCCAGGAA
CAGCCCCCAAACTTCTCATATATGACAATAAGAGGCGGCCCTCAGGGATT
CCTGACCGATTCTCTGGCTCCAAGTCTGGCGCGTGCAGCCACCCTGGACAT
CACTGGACTCCAGACTGGGGACGAGGCCGATTATTACTGCGAGCGTGGG
ATAGCAGCCTGAGTGCTGTGGTCTTCGGCGGAGGGACCAAGCTGACCGTC
CTGGGTCAGCCCAAGGCTGCCCCCTCGGT (SEQ ID NO: 899)
```

The most highly expressed clones were manually matched to the original clones. Two of them don't match up perfectly. The names of the sequences include the reading frame (last field; 0, 1, or 2)

Figure 50:
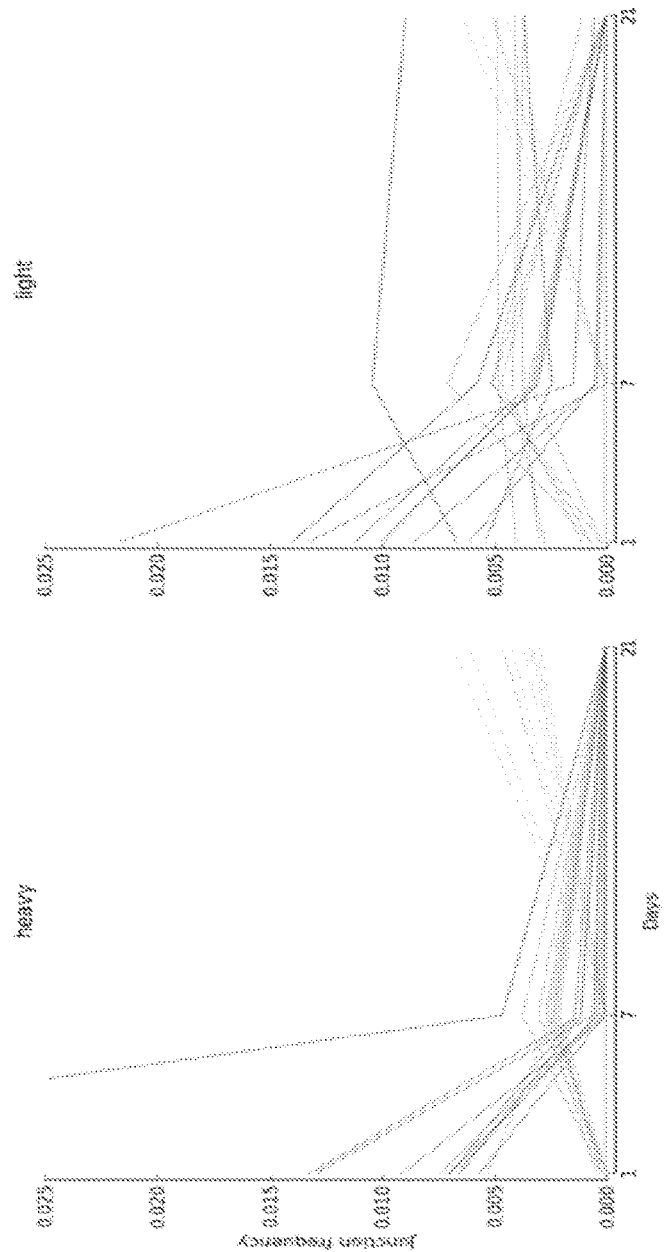
FIG. 50 depicts a re-plot time series of highly expressed heavy and light chain junctions.

To match the original synthesized heavy chains identified using highly-expressed clones with the new heavy chains identified via highly-expressed junctions, both sets of sequences and were analyzed with multiple sequence alignment (CLUSTAL) to determine how they paired. For the most part, they had identical sequence pairs, which was a consistent check that the two methods produced the same heavy chains. A re-plot of highly expressed time series for heavy and light chain junctions is set forth at FIG. 50.

Example VIII

Heavy Chain Immune Sequencing

Samples were concentrated using RNeasy kit from Qiagen, elute in 2×30 μl and nanodrop (See Table 7 below)

TABLE 7

| VDJ-ID | MID | vaccination sample | date | RNA concentration stock(ng/μl) prior DNase digestion | Volume for 8 μg DNase Digestion | Water to 150 μl |
|---|---|---|---|---|---|---|
| 1 | GMC 1 | −8 day | Dec. 7th 2009 | 91.71 | 87.23 | 62.77 |
| 2 | GMC 2 | −2 day | Dec. 13th 2009 | 75.6 | 105.82 | 44.18 |
| 3 | GMC 3 | −1 hr | Dec. 15th 2009 | 89.51 | 89.38 | 60.62 |
| 4 | GMC 4 | +1 hr | Dec. 15th 2009 | 96.87 | 82.58 | 67.42 |
| 5 | GMC 5 | +1 day | Dec. 16th 2009 | 117.3 | 68.20 | 81.80 |
| 6 | GMC 6 | +3 day | Dec. 18th 2009 | 90.22 | 88.67 | 61.33 |
| 7 | GMC 7 | +7 day | Dec. 22nd 2009 | 87.45 | 91.48 | 58.52 |
| 8 | GMC 8 | +14 day | Dec. 29th 2009 | 131.12 | 61.01 | 88.99 |
| 9 | GMC 9 | +21 day | Jan. 5th 2010 | 127.17 | 62.91 | 87.09 |
| 10 | GMC 10 | +28 day | Jan. 12th 2010 | 139.24 | 57.45 | 92.55 |
| 11 | IDO 1 | −8 day | Dec. 7th 2009 | 98.84 | 80.94 | 69.06 |
| 12 | IDO 2 | −2 day | Dec. 13th 2009 | 84.45 | 94.73 | 55.27 |
| 13 | IDO 3 | −1 hr | Dec. 15th 2009 | 72.56 | 110.25 | 39.75 |
| 14 | IDO 4 | +1 hr | Dec. 15th 2009 | 78.14 | 102.38 | 47.62 |
| 15 | IDO 5 | +1 day | Dec. 16th 2009 | 51 | 156.86 | −6.86 |
| 16 | IDO 6 | +3 day | Dec. 18th 2009 | 45.22 | 176.91 | −26.91 |
| 17 | IDO 7 | +7 day | Dec. 22nd 2009 | 101.42 | 78.88 | 71.12 |
| 18 | IDO 8 | +14 day | Dec. 29th 2009 | 109.09 | 73.33 | 76.67 |
| 19 | IDO 9 | +21 day | Jan. 5th 2010 | 127.49 | 62.75 | 87.25 |
| 20 | IDO 10 | +28 day | Jan. 12th 2010 | 89.01 | 89.88 | 60.12 |
| 21 | FV 1 | −8 day | Dec. 7th 2009 | 96.87 | 82.58 | 67.42 |
| 22 | FV 2 | −2 day | Dec. 13th 2009 | 127.13 | 62.93 | 87.07 |
| 23 | FV 3 | −1 hr | Dec. 15th 2009 | 115.25 | 69.41 | 80.59 |
| 24 | FV 4 | +1 hr | Dec. 15th 2009 | 136.05 | 58.80 | 91.20 |
| 25 | FV 5 | +1 day | Dec. 16th 2009 | 142.15 | 56.28 | 93.72 |
| 26 | FV 6 | +3 day | Dec. 18th 2009 | 113.49 | 70.49 | 79.51 |
| 27 | FV 7 | +7 day | Dec. 22nd 2009 | 91.81 | 87.14 | 62.86 |
| 28 | FV 8 | +14 day | Dec. 29th 2009 | 84.92 | 94.21 | 55.79 |
| 29 | FV 9 | +21 day | Jan. 5th 2010 | 131.06 | 61.04 | 88.96 |
| 30 | FV 10 | +28 day | Jan. 12th 2010 | 90.98 | 87.93 | 62.07 |

Vaccination and Blood Draw

Vaccine info: Seasonal flu 2010. Samples were extracted from 9 mL of blood from a single individual at various time points and processed using the leukolock kit (alternate protocol). Blood flow through was centrifuged, and plasma was saved and stored at −80° C. RBC fraction was saved and cross-linked in formaldehyde and store at 4° C.

RNA Extraction

Extracted RNA using the leukolock alternative protocol (trizol) with the following modifications: Conducted the total RNA extraction protocol which included small RNAs. Only vacuumed the first binding step, for each wash, centrifuged at maximum of 10,000×G. Eluted with 250 μl of dH$_2$O at 85° C., spun at max speed. Transferred RNA in solution without the little white pellet (probably some of the filter). Nanodropped the RNA, and stored at −80° C.

| | ng/μl | 260/280 | 260/230 | A260 | A280 |
|---|---|---|---|---|---|
| Average | 100.95 | 2.09 | 1.99 | 2.52 | 1.20 |

Protected RNA stock (bring to 10 mM Tris, 0.1 mM EDTA). To the 250 μl of RNA, added the following:

| | 1 tube | 50 tubes |
|---|---|---|
| 1M Tris-HCl | 2.5 μl | 125 μl |
| 50 mM EDTA | 0.5 μl (3 μl/tubes) | 25 μl |

Digest 8 μg with DNase and Concentrate

Conducted DNase digestion using Ambion TURBO DNA-free (AM1907) with the following modification. Added 0.1 volume (15 μl) 10×TURBO DNase Buffer and 1 μL TURBO DNase to the RNA, and mixed gently. Incubated at 37° C. for 20-30 min. Added resuspended DNase Inactivation Reagent (typically 0.1 volume) (15 μl) and mixed well. Incubated 5 min at room temperature, mixing occasionally. Centrifuged at 10,000×g for 5 min and transferred the RNA to a fresh tube. Conducted acid phenol and CHCl$_3$ extraction, followed by ethanol (EtOH) precipitation with NaOAc and glycoblue. Eluted in 500 of 10 mM Tris 0.1 mM EDTA, QC and stored at −80. This was repeated with 5 μg for sample 5 and 22 because RNA was too low (resuspend in 25 μl).

QC DNase treated RNA. Nanodrop Quantitation (see Table 8 below)

TABLE 8

| ID | Sample ID | ng/ul | 260/280 | 260/230 | for 500 ng | water to 7 μl |
|---|---|---|---|---|---|---|
| 1 | GMC 1 | 136.32 | 2.09 | 1.95 | 3.67 | 3.33 |
| 2 | GMC 2 | 132.63 | 2.12 | 1.98 | 3.77 | 3.23 |
| 3 | GMC 3 | 95.13 | 2.07 | 1.85 | 5.26 | 1.74 |
| 4 | GMC 4 | 96.39 | 2.08 | 1.89 | 5.19 | 1.81 |
| 5 | GMC 5 | 91.17 | 2 | 1.61 | 5.48 | 1.52 |
| 6 | GMC 6 | 131.56 | 2.03 | 1.89 | 3.80 | 3.20 |
| 7 | GMC 7 | 138.75 | 2.1 | 1.99 | 3.60 | 3.40 |
| 8 | GMC 8 | 120.75 | 2.09 | 1.92 | 4.14 | 2.86 |
| 9 | GMC 9 | 82.29 | 2.05 | 1.92 | 6.08 | 0.92 |
| 10 | GMC 10 | 87.76 | 2.08 | 1.85 | 5.70 | 1.30 |
| 11 | IDO 1 | 111.26 | 2.12 | 1.9 | 4.49 | 2.51 |
| 12 | IDO 2 | 119.51 | 2.11 | 1.9 | 4.18 | 2.82 |
| 13 | IDO 3 | 203.4 | 2.12 | 2.06 | 2.46 | 4.54 |
| 14 | IDO 4 | 190.66 | 2.11 | 2.04 | 2.62 | 4.38 |
| 15 | IDO 5 | 308.04 | 2.12 | 2.09 | 1.62 | 5.38 |
| 16 | IDO 6 | 311.67 | 2.13 | 2.12 | 1.60 | 5.40 |
| 17 | IDO 7 | 137.57 | 2.11 | 1.97 | 3.63 | 3.37 |
| 18 | IDO 8 | 155.92 | 2.1 | 1.99 | 3.21 | 3.79 |
| 19 | IDO 9 | 121.76 | 2.12 | 1.99 | 4.11 | 2.89 |
| 20 | IDO 10 | 159.76 | 2.11 | 1.95 | 3.13 | 3.87 |
| 21 | FV 1 | 112.87 | 2.09 | 1.91 | 4.43 | 2.57 |
| 22 | FV 2 | 83.53 | 2.03 | 1.67 | 5.99 | 1.01 |
| 23 | FV 3 | 95.56 | 2.08 | 1.87 | 5.23 | 1.77 |
| 24 | FV 4 | 84.47 | 2.1 | 1.85 | 5.92 | 1.08 |
| 25 | FV 5 | 95.18 | 2.12 | 1.9 | 5.25 | 1.75 |
| 26 | FV 6 | 100.07 | 2.11 | 1.9 | 5.00 | 2.00 |
| 27 | FV 7 | 113.7 | 2.1 | 1.89 | 4.40 | 2.60 |
| 28 | FV 8 | 182.87 | 2.12 | 2.05 | 2.73 | 4.27 |
| 29 | FV 9 | 86.99 | 2.09 | 1.83 | 5.75 | 1.25 |
| 30 | FV 10 | 128.91 | 2.11 | 1.91 | 3.88 | 3.12 |
| average | | 133.88 | 2.09 | 1.92 | | |

Primer mixing (See Table 9 below).

TABLE 9

| Primer type | plate date | plate stock | Well location | μl for each primer | μl H$_2$0 | Final mix |
|---|---|---|---|---|---|---|
| 5 × J IGH RT-PCR primer | 20080707 | | | | | 2 μM |
| 6 × J IGH PCR primer | 20080924 | 200 μM | Plate 1 A1-D7 | 20 μl each (100 μl total) | 880 μl | 4 μM (1000 μl) |
| 43x V IGH PCR primer | 20080924 | 20 0 μM | Plate 3 A1-A6 | 20 μl each (860 μl total) | 140 μl | 4 μM (1000 μl) |

Reverse Transcription
Assembled an RT reaction as follows:

|  | 1 tube | 35 tubes |
|---|---|---|
| H₂O (DEPC) | 0 µl (to 12 µl) | — |
| 2 µM Gene-specific primer (IGHC mix old) | 5 µl (5 pmole) | — |
| Total RNA | 7 µl (750 ng) | — |

Heated at 95° C. for 1 min. followed by 65° C. for 5 min and ice for 1 min.
Spun down and added the following:

|  | 1 tube | 35 tubes |
|---|---|---|
| 5× First strand buffer | 4 µl | 140 |
| 10 mM dNTP mix | 1 µl | 35 |
| 0.1M DTT | 1 µl | 35 |
| RnaseInh (Enzy) | 1 µl | 35 |
| Superscript III | 1 µl | 35 |
| Incubated at 55° C. for 60 min |  | (8 µl/tubes) |

Inactivated enzyme by heating at 70° C. for 15 min. Removed RNA/DNA hybrid by adding 1 µl of *E. coli* RNaseH. Incubated at 37° C. for 20 min, then ice.

Made a global master mix, then split across all samples (3×10 times point of 200 µl), then split each sample in 4×. Used half for PCR and kept other half as backup. Assembled a PCR test reaction as follows:

|  | 1t | 2x35t |
|---|---|---|
| dH₂O | 21.6 µl (to 50 µl) | 756 |
| cDNA | 5 µl | — |
| 5× HF buffer | 10 µl | 350 |
| dNTP (25 mM) | 0.4 µl | 14 |
| primer up (IGHV new-short) (4 µM) | 6.25 µl (25 pmole) | 218.75 |
| primer low (IGHC new-short) (4 µM) | 6.25 µl (25 pmole) | 218.75 |
| phusion | 0.5 µl | 17.5 |
| Added 90 PCR mix to 10 µl cDNA, split PCR reactions in 2 tube of 50, for each sample. |  |  |

Performed thermal cycling as follows:

| 1 | 98° C. for 1 min |
| 2 | 98° C. for 10 seconds |
| 3 | 62° C. for 20 seconds |
| 4 | 72° C. for 20 seconds go to step 2, 20× |
| 5 | 72° C. for 5 min |
| 6 | 4° C. pause |

Re-pooled each 2 reactions into 1. Added 41 of Exonuclease I (20 U/µl) to each tube and incubate at 37° C. for 20 min. AMPure XP purified ratio 1.8:1. Resuspend in 40 µl.
Conducted SPRI purification as follows:
Add the require amount of AMPure XP beads (1.8:1 ratio) to the DNA sample in buffer EB.
Vortex to mix
Incubate for 5 minutes at room temperature.
Magnet (MPC) for 5 minutes. Leave the tube of beads in the MPC during all wash steps
Remove the supernatant (keep in case of failure) and wash the beads twice with 500 µl of 70% ethanol, incubating for 30 sec each time.
Remove all the supernatant, quick spin, remove last drop and allow the AMPure beads to air dry completely (2 min).

Remove the tube from the MPC, add 40 µl of 10 mM Tris-HCl, 0.1 mM EDTA, pH 8.0 (or Qiagen's Buffer EB), and vortex for 30 sec to resuspend the beads, let sit for 3 min Magnet for 2 min and transfer supernatant to a new tube.

A diagnostic gel was run to check PCR efficiency. Ran 2 µl on a 2% Egel-X for 12 min.

Finalize Library

The following step was written to finalize all remaining library. The plate was ordered as set forth in the Table 10 below.

TABLE 10

| Library type (all heavy chains) | Row placement and BC info 1 = 13, etc. |
|---|---|
| Triple VDJ-HC GMC | A1-A10 |
| Triple VDJ-HC IDO | B1-B10 |
| Triple VDJ-HC FV | C1-C10 |
| RA | D1-D8 |
| HIV 1/2 | E1-E8 (5 progressor + 5 negative) BC; 1-2-3-4-5/ 6-7-8-9-10 |
| HIV 2/2 | F1-F7 (5 elite) BC; 1-2-3-4-5 |

Performed blunting reaction using Enzymatics End repair kit as follows:

|  | 1t | 60 |
|---|---|---|
| H₂O | 0 µl (to 25 µl) | 0 |
| Post PCR Purified DNA | 19 µl | — |
| 10× End repair buffer | 2.5 ul | 150 |
| 1 mM dNTP mix | 2.5 µl (0.1 mM) | 150 |
| enzyme mix (HC). | 1 µl | 60 |
| Incubated at 25° C. temperature for 30 min. (19/t). Heat inactivated at 75° C. for 20 min. |  |  |

A-tailed by adding the following directly to the mixture:

|  | 1t | 60t |
|---|---|---|
| H₂O | 20 µl (to 50 µl) | 1200 |
| Blunt DNA sample | 25 µl | — |
| 10 × Klenow buffer | 2.5 µl | 150 |
| 10 mM dATP | 0.5 µl | 30 |
| Klenow exo HC (3' to 5' exo minus) | 2 µl | 120 |
| Total reaction was now 50 ul (25/t) |  |  |

Incubated at 37° C. for 30 min. Heat inactivated at 75° C. for 20 min. Prepared 454 Y-adapters. 10 µl of 100 µM of each primer A and B+30 µl of (10 mM Tris 0.1 mM EDTA at 50 mM NaCl)) (each adapter are at 20 µM final). Incubated 95 for 3 min, ramp to 15 forever at 0.1° C./sec.

For Y adapter ligation, the following was add directly to the reaction:

|  | 1t | 2x30t |
|---|---|---|
| H₂O | 0 (add µl to 100 µl) | — |
| A-tailed DNA | 50 ul | — |
| 2 × Quick ligase buffer | 46 µl | 1380 |
| 20 µM adapter | 2 µl | — |
| T4 DNA ligase (quick) | 2 µl | 60 |
| Incubate PCR at 22° C. for 15 min. (48/t). Total reaction was then 100 µl. |  |  |

Figure 51:
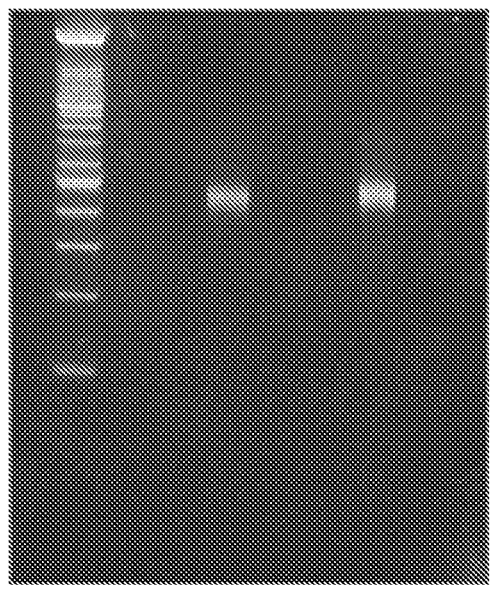
FIG. 51 depicts a gel showing Y adapter ligation.

Ampure was performed, and the substrate was eluted in 40 IA (using the liquidator). Library QC for pooling was tested on an HIV sample. Only the first 5 samples were tested (progressor) (FIG. 51).

Example IX

HIV VDJ

Samples are set forth in the Table 11 below.

TABLE 11

| Patient | Cohort | Date | HLA Type | Viral Load | Sex | DOB | Ethnicity |
|---|---|---|---|---|---|---|---|
| CR0744R | Progressor | Apr. 12, 2010 | A-0201 A-0301 B-3701 B-5201 C-0602 C-1202 | 4-12-10-31100 | M | 1970 | African American |
| CR0795Q | Progressor | Apr. 19, 2010 | A-0101 A-0201 B-2705 B-5101 C-0102 C-1502 | 4-19-10-61700 | M | 1964 | White |
| CR0216R | Progressor | Apr. 29, 2010 | A-0301 A-6801 B-1401 B-3801 C-0802 C-1203 | 4-29-10-86600 | F | 1963 | White |
| CR0778Z | Progressor | May 3, 2010 | A-3303 A-6801 B-0702 B-1503 C-0702 C1800 | 5-3-10-45700 | M | 1964 | African American |
| CR0757R | Progressor | May 6, 2010 | A-0201 A-2902 B-1501 B-4404 C-0102 C-1601 | 5-6-10-26300 | M | 1964 | White |
| CTR0147 | Elite Controller | Apr. 15, 2010 | A-0103 A-3201 B-3508 B-7301 C-0401 C-1505 | 4-18-10-<48 | M | 1953 | White |
| CTR24 | Elite Controller | Apr. 15, 2010 | A-0201 A-3001 B-1302 B-5701 C-0602 C-0602 | 4-15-10-<48 | F | 1954 | Biracial |
| 523507 | Elite Controller | May 14, 2010 | A-3002 A-2402 B-1801 B-5301 C-0401 C-1203 | 5-14-10-56 | M | 1962 | White |
| CTR174 | Elite Controller | Jun. 28, 2010 | A-0201 A-2301 B-5201 B-5801 C-0302 C-1601 | 2-18-10-<48 | M | 1961 | African American |
| FHCR0013E | Elite Controller | Jul. 1, 2010 | A-0301 A-1101 B-0702 B-3501 C-0401 C-0702 | 2-17-10-133 | M | 1947 | White |
| 924426 | HIV Negative | Apr. 7, 2010 | A-0201 A-0205 B-5701 B-5701 C-0602 C-0602 | 0 | | | |
| 714739 | HIV Negative | Apr. 7, 2010 | A-0101 A-0201 B-1801 B-5101 C-0602 C-1402 | 0 | | | |
| 564006 | HIV Negative | Apr. 7, 2010 | A-0201 A-0201 B-1801 B-3901 C-0501 C-1203 | 0 | | | |
| 084928 | HIV Negative | Apr. 6, 2010 | A-0201 A-0301 B-1401 B-1801 C-0501 C-0802 | 0 | | | |
| 039701 | HIV Negative | Apr. 6, 2010 | A-0201 A-3303 B-1501 B-5801 C-0302 C-0801 | 0 | | | |

Sample Acquisition

A fresh sample was obtained. 2 tubes of EDTA were prepared for each progressor, elite controller and HIV negative sample. Samples were processed immediately after receipt (ficolled. count cells). B Cell isolation was performed as follows:
1. Centrifuged cell suspension at 300×G for 10 min., aspirated supernatant.
2. Resuspended cell pellet in 80 μL of cold buffer per $10^7$ cells.
3. Buffer was a 1:20 dilution of MACS BSA stock solution with autoMACS rinsing solution. Degassed before use.
4. Added 20 μL of CD19 microbeads per $10^7$ cells.
5. Incubated for 15 minutes in the refrigerator (2-8° C.).
6. Washed cells by adding 1-2 mL of cold buffer per $10^7$ cells and centrifuge at 300×G for 10 min. aspirate supernatant.
7. Resuspended up to $10^8$ cells in 500 μL cold buffer
8. Placed MS column in a magnetic field and rinse the column with 500 μL of degassed buffer.
9. Added cell suspension.
10. Collected unlabeled cells that passed through and washed three times with 500 μL of buffer.
11. Removed column and placed in a new collection tube.
12. Added 1 mL of buffer and plunged out the magnetically labeled cells using the plunger.
13. Counted cells.
14. In a small centrifuge, centrifuged the CD19+ cells for 10 minutes at 9,000×G.
15. Aspirated the supernatant and added 300 μL of lysis buffer. Snap froze and stored at −80° C.

RNA Extraction

Used mirvana as per manufacturer protocol, eluted in 150 (did double phenol, phase was smaller on second run). QC nanodrop, too low, so EtOH ppt with glycoblue, elute in 20 ul, nanodrop. Dilute number 4 1:2. See Table 12 below.

TABLE 12

Used extra mix to make 5x FV1 (180 ng/ul . . . 1.67 ul RNA + 5.33 ul H₂O) for light chains and 5 for heavy chains.

| ID | ng/ul RNA | 260/280 | 260/230 | Total RNA | Volume for 150 ng | Water to 7 |
|---|---|---|---|---|---|---|
| 1 | 65.9 | 1.98 | 1.7 | 1252.1 | 2.276 | 4.724 |
| 2 | 32.4 | 1.92 | 1.33 | 615.6 | 4.630 | 2.370 |
| 3 | 26.1 | 2 | 1.48 | 495.9 | 5.747 | 1.253 |
| 4 | 216.1/ 120.6 | 2.03/ 1.97 | 2.05/ 1.58 | 4106/ 4583 | 1.244 | 5.756 |
| 5 | 103.4 | 2.02 | 1.93 | 1964.6 | 1.451 | 5.549 |
| 6 | 54.3 | 1.98 | 1.66 | 1031.7 | 2.762 | 4.238 |
| 7 | 89.9 | 2.02 | 1.89 | 1708.1 | 1.669 | 5.331 |
| 8 | 51.4 | 1.66 | 0.88 | 976.6 | 2.918 | 4.082 |
| 9 | 35.8 | 2.05 | 1.66 | 680.2 | 4.190 | 2.810 |
| 10 | 79.8 | 1.85 | 1.25 | 1516.2 | 1.880 | 5.120 |
| 11 | 104.4 | 1.96 | 1.62 | 1983.6 | 1.437 | 5.563 |
| 12 | 82.2 | 1.71 | 0.91 | 1561.8 | 1.825 | 5.175 |
| 13 | 154.8 | 1.97 | 1.72 | 2941.2 | 0.969 | 6.031 |
| 14 | 56.2 | 1.87 | 1.33 | 1067.8 | 2.669 | 4.331 |
| 15 | 84.4 | 1.8 | 1.06 | 1603.6 | 1.777 | 5.223 |

Sample 8 was concentrated by ethanol precipitation, resuspended in 20 μl, nanodrop=134.0. These were B cells RNA only, so there was no need for the same amount of starting RNA for VDJ research. In theory, lymphocytes represent 30% of PBMC, for which B cells represent 10%, accordingly 15 ng should be sufficient. 150 ng was used.

A reverse transcription (RT) reaction was assembled as follows:

|  | 2x 1 tube |
|---|---|
| $H_2O$ (DEPC) | 0 µl (to 12 µl) |
| 2 µM Gene-specific primer (heavy or light) | 5 µl (5 pmole) |
| Total RNA | 7 µl (150 ng) |

Heated at 95° C. for 1 min. followed by 65° C. for 5 min., then ice for 1 min.

| Spun down and the following was added: | 1 tube | 30 tubes |
|---|---|---|
| 5× First strand buffer | 4 µl | 120 |
| 10 mM dNTP mix | 1 µl | 30 |
| 0.1M DTT | 1 µl | 30 |
| RnaseInhibitor-Enzymatics | 1 µl | 30 |
| Superscript III | 1 µl | 30 |
| Incubated at 55° C. for 60 min |  | (8 µl/tubes) |

Inactivated enzyme by heating at 70° C. for 15 min. Removed RNA/DNA hybrid by adding 1 µl of *E. coli* RNaseH (Enzy). Incubated at 37° C. for 20 min., then ice. See Table 13 below.

TABLE 13

| Primer type | plate date | plate stock | Well location | ul for each primer | µl H20 | Final mix |
|---|---|---|---|---|---|---|
| 5 × J IGH RT-PCR primer | Tube order 5933901 |  |  | 20 ul*5 tubes | +400 ul | 4 µM* Dilute 1é2 before using |
| 6 × J IGH PCR primer | 20080924 | 200 µM | Plate 3 A1-A6 | 20 µl each (100 µl total) | 880 µl | 4 µM (1000 µl) |
| 43× V IGH PCR primer | 20080924 | 200 µM | Plate 1 A1-D7 | 20 µl each (860 µl total) | 140 µl | 4 µM (10000 µl) |

Assembled a PCR test reaction as follows:

|  | 1×× | × 2per sample × 15samples (45t) | (12t light chain) |
|---|---|---|---|
| $dH_2O$ | 21 µl (to 50 µl) | 945 (1084.46) | 252 (259.2) |
| cDNA | 5 µl | — | — |
| 5× HF buffer | 10 µl | 450 | 120 |
| dNTP (10 mM) (25 mM) | 1 µl (0.4) | 45 (18) | 12 (4.8) |
| primer up (IGHV new-short) (4 µM) | 6.25 µl (25 pmole) | 281.25 (225) | 75 |
| primer low (IGHC new-short) (4 µM) | 6.25 µl (25 pmole) | 281.25 (224) | 75 |
| phusion | 0.5 µl | 22.5 | 6 |

Added 90 PCR mix to 10 µl cDNA, split PCR reaction in 2 tubes of 50, for each sample. Was low on primer, so used bolded values.

Thermal cycled as follows:

| 1 | 98° C. for 1 min |
|---|---|
| 2 | 98° C. for 10 seconds |
| 6 | 62° C. for 20 seconds |
| 4 | 72° C. for 20 seconds go to step 2, 23× |
| 5 | 72° C. for 5 min |
| 6 | 4° C. pause |

Re-pooled each 2 reaction into 1. Added 2 µl of Exonuclease I (20 U/µl) to each tube and incubate at 37° C. for 20 min. AMPure XP purify ratio 1.8:1. Resuspend in 40 µl.

Conducted SPRI purification: Added the require amount of AMPure XP beads (1.8:1 ratio) to the DNA sample in buffer EB. Vortexed to mix. Incubated for 5 minutes at room temperature. Magnet (MPC) for 5 minutes. Left the tube of beads in the MPC during all wash steps. Removed the supernatant (kept in case of failure) and washed the beads twice with 500 µl of 70% ethanol, incubating for 30 sec each time. Removed all the supernatant, quick spun, removed last drop and allow the AMPure beads to air dry completely (2 min). Removed the tube from the MPC, added 40 IA of 10 mM Tris-HCl, 0.1 mM EDTA, pH 8.0 (or Qiagen's Buffer EB), and vortexed for 30 sec to resuspend the beads, let sit for 3 min., Magnet for 2 min. and transferred supernatant to a new tube.

Figure 52:
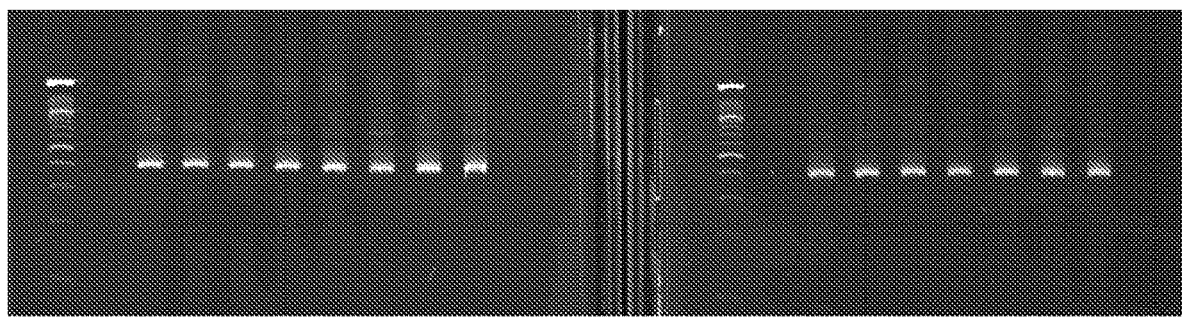
FIG. 52 depicts a diagnostic gel showing PCR efficiency.

A diagnostic gel was run to check PCR efficiency (FIG. 52). Ran 2 µl on a 2% Egel-X for 12 min.

Finalize Library

The following method was developed to finalize the remaining library.

Plate was ordered as follows in the Table 14 below.

TABLE 14

| Library type (all heavy chains) | Row placement and BC info 1 = 13, etc. |
|---|---|
| Triple VDJ-HC GMC | A1-A10 |
| Triple VDJ-HC IDO | B1-B10 |
| Triple VDJ-HC FV | C1-C10 |
| RA | D1-D8 |
| HIV 1/2 | E1-E8 (5 progresser + 5 negative) BC; 1-2-3-4-5/ 6-7-8-9-10 |
| HIV 2/2 | F1-F7 (5 elite) BC; 1-2-3-4-5 |

Performed blunting reaction using Enzymatics End repair kit as follows:

|  | 1t |  | 60 |
|---|---|---|---|
| H$_2$O | 0 μl (to 25 μl) |  | 0 |
| Post PCR Purified DNA | 19 μl |  | — |
| 10× End repair buffer | 2.5 μl |  | 150 |
| 1 mM dNTP mix | 2.5 μl | (0.1 mM) | 150 |
| enzyme mix (HC) | 1 μl |  | 60 |
| Incubated at 25° C. temperature for 30 min |  |  | (19/t) |

Heat inactivated at 75° C. for 20 min.
A-tailed by adding the following directly to the mixture:

|  | 1t | 60t |
|---|---|---|
| H$_2$O | 20 μl (to 50 μl) | 1200 |
| Blunt DNA sample | 25 μl | — |
| 10× Klenow buffer | 2.5 μl | 150 |
| 10 mM dATP | 0.5 μl | 30 |
| Klenow exo HC (3' to 5' exo minus) | 2 μl | 120 |
| Total rx is now 50 ul |  | (25/t) |
| Incubated at 37° C. for 30 min. Heat inactivated at 75° C. for 20 min. |  |  |

Prepared 454 Y-adapters: 10 μl of 100 μM of each primer A and B+30 μl of (10 mM Tris 0.1 mM EDTA at 50 mM NaCl)) (each adapter are at 20 μM final). Incubated 95° C. for 3 min, ramp to 15° C. forever at 0.1° C./see.

Y adapter ligation, added directly to the reaction as follow;

|  | 1t | 2x30t |
|---|---|---|
| H$_2$O | 0 (add μl to 100 μl) | — |
| A-tailed DNA | 50 μl | — |
| 2× Quick ligase buffer | 46 μl | 1380 |
| 20 μM adapter | 2 μl | — |
| T4 DNA ligase (quick) | 2 μl | 60 |
| Incubated on PCR at 22° C. for 15 min (48/t). Total reaction was now 100 μl. |  |  |

Ampure, elute in 40 ul (used the liquidator)
Library QC for Pooling
Test on HIV sample, test only first 5 samples (progressor). Nanodrop progressor sample. Dilute to 5 ng/ul. Nanodrop:

| 1 | 36.8 |
|---|---|
| 2 | 31.7 |
| 3 | 24.8 |
| 4 | 33.5 |
| 5 | 31.3 |

Diluted to 1 ng/μl using 10 mM Tris, 0.05% Tween 20. Diluted to 0.01 ng/μl (in 200 μl) in 10 mM Tris, 0.05% Tween 20, Prepared SYBR fast mix enough for triplicate run. Used 18 μl of mix, and added 2 μl of template to it.

|  | 1t | 20 |
|---|---|---|
| H$_2$O | 7.2 ul (to 20 ul) | 144 |
| 2× SYBR fast | 10 ul | 200 |
| 10 μm Primer up | 0.4 ul | 8 |
| 10 μm Primer low | 0.4 ul | 8 |
| 0.01 ng/ul DNA template | 2 ul | — |

Cycled:

| 95 | 1 min |  |
|---|---|---|
| 95 | 5 sec |  |
| 60 | 20 sec |  |
| 72 | 15 sec | tepest 40 time |

Prepared SYBR fast mix enough for triplicate run. Did 2 run, one set from the 0.01 ng sample, and one from the initial 5 ng/ul sample. Used 15 ul of mix, and add 5 ul of template to it. For 0.01 ng sample, used as follows:

| 0.01 ng volume to sue | Tris |
|---|---|
| 1.76 | 3.24 |
| 2.50 | 2.50 |
| 3.52 | 1.48 |
| 2.17 | 2.83 |
| 5.00 | 0.00 |

For the ~0.5 ng sample, the following dilution was performed down to a real 1 ng/μl and diluted 1/100 down to a real 0.01 ng/μl. Used 5 μl.

| Sample | dilution fold |
|---|---|
| 1 | 13.2 |
| 2 | 16.4 |
| 3 | 15.3 |
| 4 | 30.1 |
| 5 | 10.9 |

|  | 1t | 20 |
|---|---|---|
| H$_2$O | 4.2 ul (to 20 ul) | 84 |
| 2× SYBR fast | 10 ul | 200 |
| 10 μm Primer up | 0.4 ul | 8 |
| 10 μm Primer low | 0.4 ul | 8 |
| 0.01 or 5 ng/ul DNA template | 5 ul | — |

Plate Reader

Diluted sample as follows. Volume of H$_2$O added to volume 25 ul of sample to achieve same concentration of 250 nM.

| GMC | 26.95 | 11.56 | 8.99 | 9.23 | 15.31 | 10.02 | 10.67 | 0.22 | 14.69 | 14.23 |
|---|---|---|---|---|---|---|---|---|---|---|
| IDO | 11.40 | 12.94 | 8.58 | 9.95 | 11.15 | 11.05 | 26.07 | 8.04 | 11.02 | 10.27 |
| FV | 15.61 | 21.09 | 17.18 | 16.65 | 6.26 | 12.26 | 20.76 | 14.12 | 13.01 | 15.07 |
| RA | 7.58 | 6.95 | 8.50 | 7.51 | 8.94 | 5.92 | 9.59 | 6.97 |  |  |
| HIV | 45.28 | 23.65 | 21.59 | 29.23 | 23.86 | 27.46 | 29.26 | 29.74 | 34.51 | 28.37 |
| HIVelite | 37.04 | 29.70 | 27.82 | 34.51 | 37.93 |  |  |  |  |  |

GMC1, mixed 25 μl of each sample for a total of 30*10=300 μl. IDO1, mixed 30 μl. FV1, mixed 30 μl. RA, mixed first 4 at 35 μl and last 4 at 35 μl in separate batched, precipitated, and loaded on a gel to decide how to mix them together. HIV, pool equal ratio of each (40 μl), but did not mix elites samples with the combo neg+prog, these will be run with a gasket (so more read total for elite).

Qiagen prep+5 μl NaOAc (2 min wash), eluted in 30 μl, nanodrop.

| # | Sample ID | Nucleic Acid Conc. | 260/280 | 260/230 | total ng | μM |
|---|---|---|---|---|---|---|
| 1 | GMC | 16 | 2.01 | 1.98 | 480 | 1.39 |
| 2 | IDO | 25.7 | 1.93 | 1.87 | 771 | 2.22 |
| 3 | FV | 31.4 | 1.87 | 1.99 | 942 | 2.72 |
| 4 | RA1 | 8.4 | 1.95 | 2.02 | 252 | 0.73 |
| 5 | RA2 | 6.4 | 2.36 | 1.87 | 192 | 0.55 |
| 6 | HIV1 | 75.7 | 1.85 | 2.17 | 2271 | 6.55 |
| 7 | HIV2 | 37.9 | 1.87 | 2.18 | 1137 | 3.28 |
| 8 | HIV control | 22.4 | 1.95 | 1.99 | 672 | 1.94 |

Figure 53:
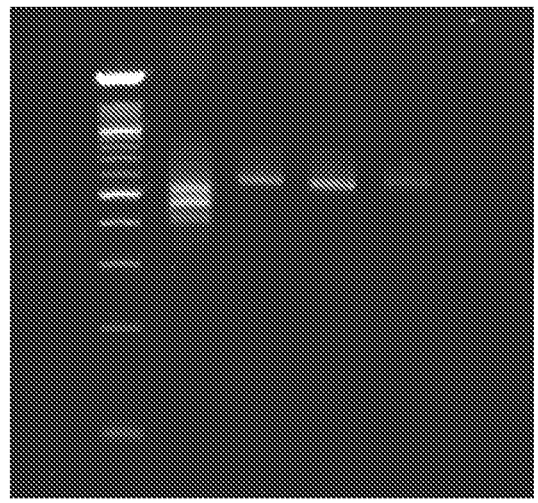
FIG. 53 depicts a gel showing a test pippin preparation with control sample number 8.

Tested pipin prep with control sample number 8; 475-525, 475-550, 500-575 (FIG. 53). Ran all sample on pippin prep. Split HIV1 in 2 runs, Extract 475-550. 1, GMC; 2, IDO; 3, FV; 4, HIV1/2 (FIG. 54).

Qubit Library HS dsDNA

Pooled both RA samples together and re Mapure because RA2 has nothing.

| no | ID | Qubit HS dsDNA | dilute to 5 ng/μl, take X μl | add Y H₂O | volume total |
|---|---|---|---|---|---|
| 1 | GMC | 8.44 | 3 | 2.064 | 5.064 |
| 2 | IDO | 7.99 | 3 | 1.794 | 4.794 |
| 3 | FV | 6.59 | 3 | 0.954 | 3.954 |
| 4 | RA1 | 6.59 | 3 | 0.954 | 3.954 |
| 5 | RA2 | | | pool with RA1 | |
| 6 | HIV1 | 49.8 | 3 | 26.88 | 29.88 |
| 7 | HIV2 | 25.2 | 3 | 12.12 | 15.12 |

Diluted 1/100 to 0.05 ng/ul. Load 1 ul on eGEL of each sample.

Run Real Time

Prepared SYBR fast mix enough for triplicate run. Use 18 ul of mix, and add 2 ul of template to it.

| | 1t | 20 |
|---|---|---|
| H₂O | 7.2 μl (to 20 μl) | 144 |
| 2× SYBR fast | 10 μl | 200 |
| 10 μm Primer up | 0.4 μl | 8 |
| 10 μm Primer low | 0.4 μl | 8 |
| 0.05 ng/ul DNA template | 2 μl | — |

Cycle

| | | |
|---|---|---|
| 95 | 1 min | |
| 95 | 5 sec | |
| 60 | 20 sec | |
| 72 | 15 sec | tepest 40 time |

Diluted all to 5 ng/μl using 13.5 μl of sample. Added H₂O to 13.5 μl of sample.

| 1 | 9.45 |
|---|---|
| 2 | 8.073 |
| 3 | 4.293 |
| 4 | 4.293 |
| 5 | 120.96 |
| 6 | 54.54 |

Shipped 15 μl to 454.

Example X

Emulsion PCR of Single Cell and Bead

| Oligonucleotide 5'-3' (ordered form IDT HPLC purified when applicable) | |
|---|---|
| PR1-F4-2BIO (1 mM) | /52-Bio/CCA CTA CGC CTC CGC TTT CCT CTC TAT GG (SEQ ID NO: 900) |
| PR1-R_Short (2 mM) | CTG CCC CGG GTT CCT CAT T (SEQ ID NO: 901) |

| Tube | beads | process |
|---|---|---|
| 1 | Dynabeads 1 μm myone C1 10 mg/ml | all wash with magnet |
| 2 | Dynabeads 1 μm myone C1 10 mg/ml | all wash by centrifugation (1 min max speed) |
| 3 | IBS 1 μm non-magnetic 10 mg/ml | all wash by centrifugation (1 min max speed) |

Bead-Loading with Emulsion Anchor Primer

Magneted or centrifuged beads during all steps according to assay setup table. Vortexed beads to resuspend and transferred 100 μl to 1.5 ml Ambion silicon tube. Washed twice with 200 μl of 2× bind and wash buffer (2×B&W). Resuspended beads in 100 μl of 2×B&W, add premixed anchor primer; 1 mM PR1-F4-2Bio (2 μl); H₂O (98 μl). Incubated on rotator for 20 min. Washed twice with 200 μl of 1×B&W. Washed once with 200 μl of TE. Resuspend beads in 1000 of TE and stored on rotator in cold room until used.

Emulsion PCR

| Prepared aqueous mix as follows: | 1 tube |
|---|---|
| dH₂O | 316.4 μl (to 800 μl) |
| 10× PCR buffer (Enzymatics) | 96 μl |
| 50 mM MgCl₂ | 242 μl |
| 25 mM dNTP mix | 135 μl |
| 2 mM PR1R-S | 6 μl |
| 30% (w/v) BSA (Sigma) | 1.6 μl |
| Library template* | 3 μl |

Vortexed thoroughly to mix. *for Library template, a 1:20 dilution of a 1 nM 280 bp human genomic library was used.

| Prepared oil mix: | 1 tube | 4 tubes (prep all in one 509 ml falcon) |
|---|---|---|
| Tegosoft DEC | 4.4 ml | 17.6 ml |
| mineral oil 1.2 ml | 4.8 ml | |
| ABIL WE09 | 425 μl | 1.7 ml |

Vortexed thoroughly, allowed to degas. Aliquoted 5.5 ml into 50 ml Teflon-coated aluminum falcon tubes.

Create emulsion. To the 800 µl PCR mix, 100 µl Enzymatics Taq (5 U/µl) was added, quickly vortexed and spun. 60 µl PR1F4 beads were immediately added, vortex quickly and spun. The total 960 µl was immediately transferred a to tube of oil, and vortexed for 2.25 min at 2200 rpm. The tube was placed into hydrocycler rack and the PCR program was started for overnight cycling.

Cycle as follows:
1—94° C. for 5 min
2—94° C. for 15 sec
3—58° C. for 30 sec (1 degree above to compensate hydrocycler setting)
4—70° C. for 75 sec
5—Got to 2 for 119×
6—72° C. for 2 min
7—Front cold tank (~10° C. forever)

Breaking Emulsion 22 ml isopropanol was added to each aluminum falcon tube, and the tubes were vortexed for 50 sec at 3000 rpm. The contents were transferred to a new 50 ml polypropylene falcon tube and centrifuged (touch 4000 rpm and stop). The supernatants were poured off (pellet stuck well to bottom). 30 ml isopropanol was added and the tubes were vortexed for 40 sec at 3000 rpm, centrifuged (touch 4000 rpm and stop), and the supernatant was poured off (pellet stuck well to bottom)

30 ml NXS buffer (10 mM Tris-HCl pH 8.0, 100 mM NaCl, 1% (v/v) Triton X-100, 1% (v/v) SDS) was added and the tubes were vortexed for 1.5 min at 3000 rpm (vortex more if pellet was still stuck at bottom), centrifuged (maintain 4000 rpm for 15 sec and stop), and the supernatant was pipetted (carefully since the pellet did not stick to the bottom very well this time). 100 µl of TE was added, and the pellet was resuspend by pipetting. The solution was transferred to a 1.5 siliconized Eppendorf tube, washed 1× with 200 µl NXS, washed 2× with 200 µl of TE, incubated for 5 min in 100 µl of 100 mM NaOH at RT, washed 1× with 120 µl of 100 mM NaOH, washed 2× with 150 µl TE, resuspended in 30 µl of TE and transferred to a new siliconized tube for storage.

Sequencing by Ligation Diagnostic of Beads

Sequencing by ligation of the minus one position was conducted using methods known in the art.

Capture Bead on Acrylamide Slide for SBL

An acrylamide bound-silane slide was prepared as follows:

| Beads in TE | 7 µl |
| 40% Acryl 19:1 | 1.25 µl |
| 5% TEMED | 0.5 µl |
| 0.5% APS | 0.75 µl |

This was put on a slide by half wicking under coverslip and sliding a coverslip on top and the slide was flipped upside down. The slide polymerized (~30 min, max 2 hr) and a dry circle formed (prepare wash 1 during this time). Removed coverslip and put slide in conical tube with TE (shake for 10 min)

Prepared wash 1:

| 1M Tri-HCl pH 7.5 | 10 ml |
| 2M KCl | 25 ml |
| 0.5M EDTA | 4 ml |
| 10% Triton X | 1 ml |

Prepared primer mix:

| 6× SSPE with 0.01% Triton X-100 | 100 µl |
| 1 mM anchor primer | 1 µl |

Removed slide from conical tube, dried white Teflon surface with Kimwipe, added 100 µl of anchor primer mix, incubated at 56° C. for 1 min., placed in conical tube with Wash 1, immediately changed to fresh Wash 1, incubated at RT for 5 min in Wash 1 with gentle agitation.

Prepared ligation mix as follow;

| $H_2O$ | 41 µl |
| 10× T4 DNA ligase buffer | 5 µl |
| Fluorescent nonamer mix | 4 µl |
| T4 DNA ligase (2 KU/µl) | 1 µl |

Figure 55:
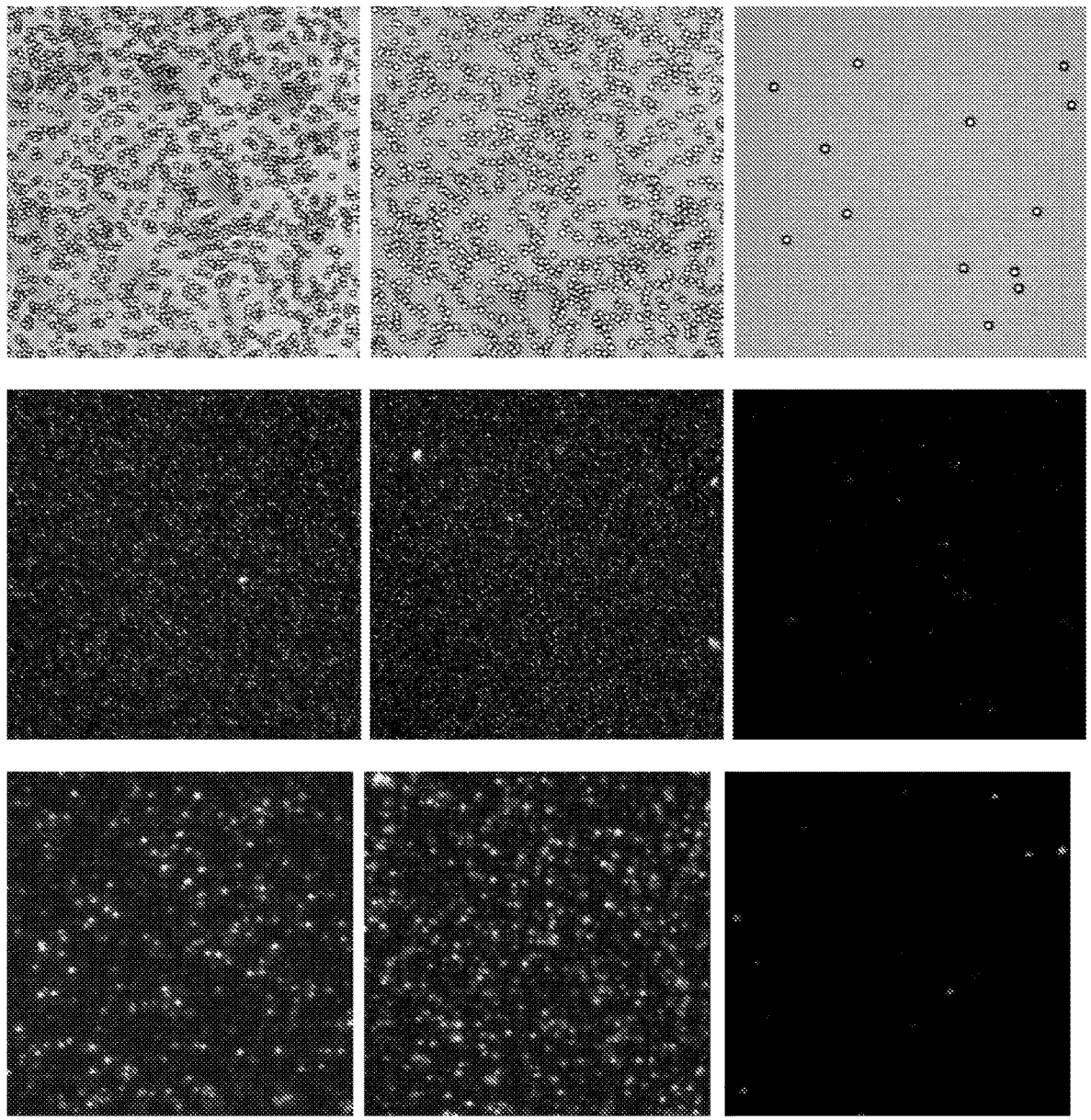
FIG. 55 depicts imaging data showing clonality of beads. All three assays demonstrated clonality, so emulsion of a human genomic library worked well, even when using a hydrocycler (which is a major time saving and technically facile solution). Top row: 20× white light, 200% zoom. Middle row: 20×, Cy5, Cy3, FITC color align. Bottom row: 20×, 200% zoom, Cy5, Cy3, FITC color align.
Figure 56:
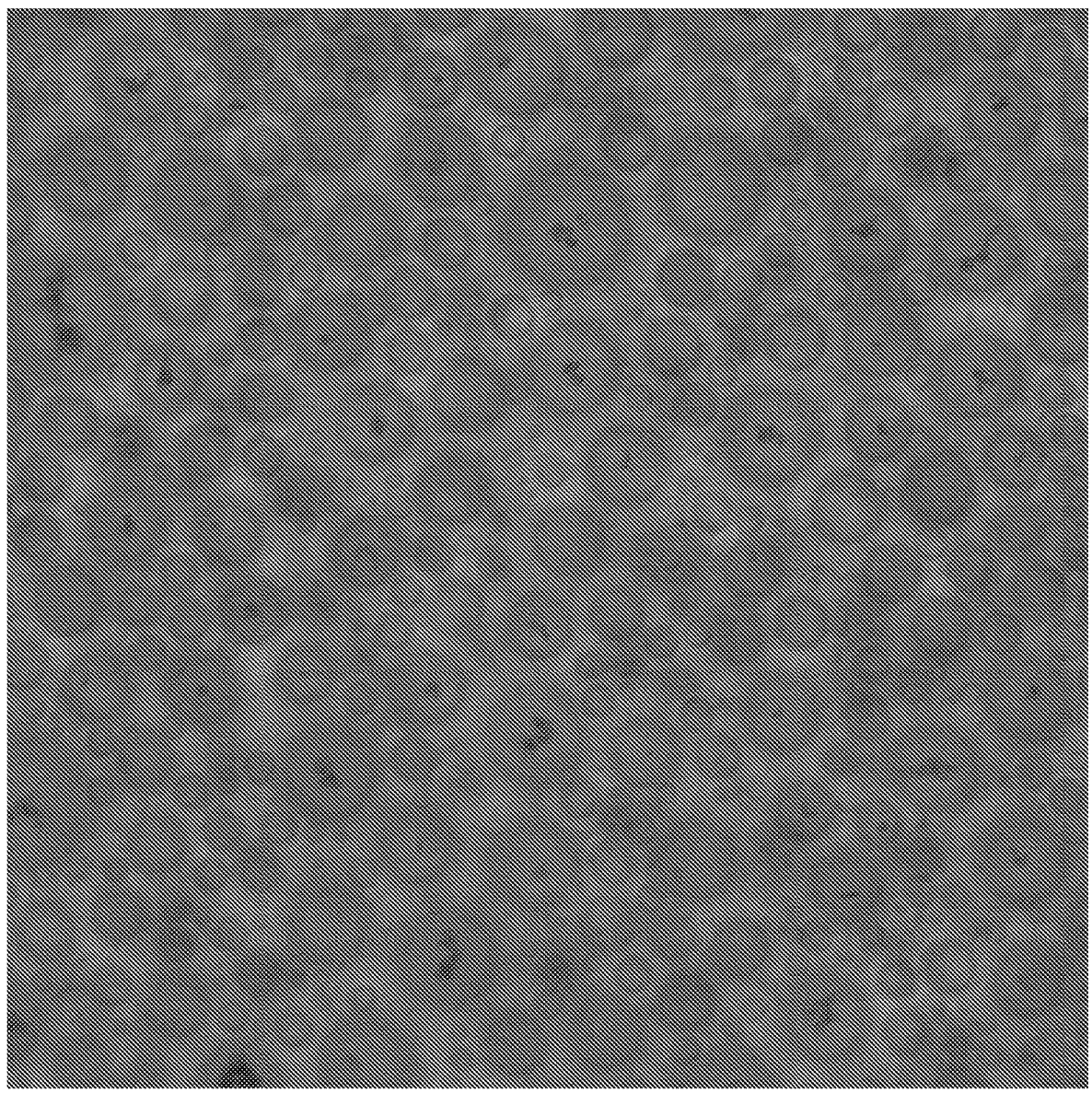
FIG. 56 depicts imaging data of a single cell post lysis and PCR with VDJ capturing beads.
Figure 57:
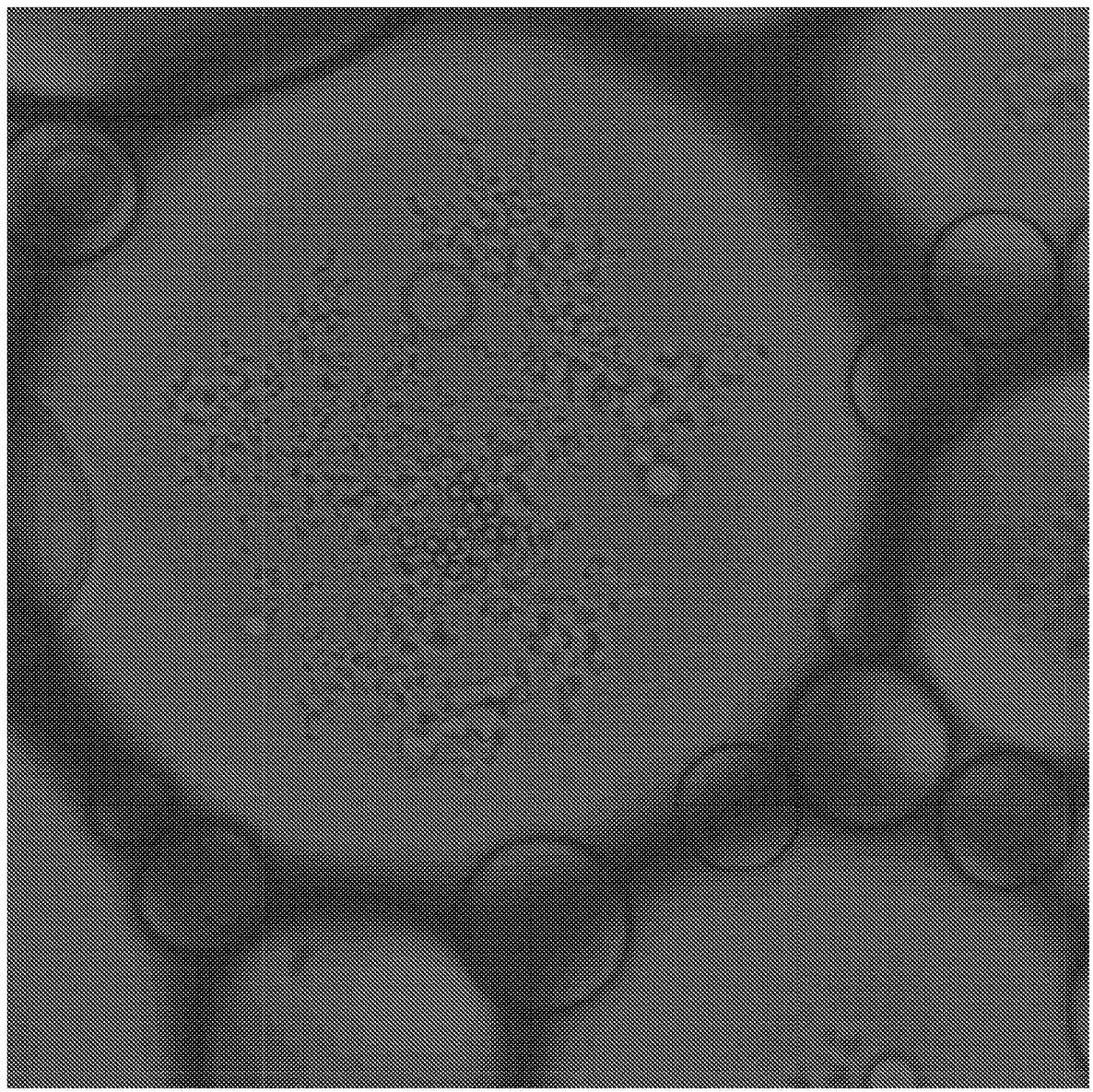
FIG. 57 depicts imaging data of PCR with VDJ capturing beads.

Removed slide from conical tube, dried white Teflon surface with Kimwipe, added 50 µl of ligation mix, incubated at 35° C. for 5 min., placed in conical tube with Wash 1, immediately changed to fresh Wash 1, incubated at RT for 5 min in Wash 1 with gentle agitation, changed Wash 1 for TE, and incubated with gentle agitation for 10 min to 2 hr. Imaged under microscope and analyzed imaging data (See FIGS. 55-57).

Example XI

Illumina VDJ

Objective

To develop a sample Illumina paired end sequencing protocol for immunoglobulin DNA.

Oligonucleotides

Primers were ordered having hotplate, standard desalting, first batch plain DNA compatible second section, with the proper Illumina adapter primary extension (not clustering) (Table 15). Plates were stocked at 200 µM

TABLE 15

| Ref # | Name | Pos | | TM |
|---|---|---|---|---|
| 50494259 | VDJ_IGHV_gDNA_01 | A1 | ACA GAA GTT CCA GGG CAG (SEQ ID NO: 902) | 54.62° C. |
| 50494263 | VDJ_IGHV_gDNA_02 | A2 | AGA CTC CAG GAA GGG CAG (SEQ ID NO: 903) | 56.48° C. |
| 50494264 | VDJ_IGHV_gDNA_03 | A3 | AGA CTC CAT GAA GGG CCA (SEQ ID NO: 904) | 55.89° C. |

TABLE 15-continued

| Ref # | Name | Pos | | TM |
|---|---|---|---|---|
| 50494265 | VDJ_IGHV_gDNA_04 | A4 | AGA CTC TGT GAA AGG CCG (SEQ ID NO: 905) | 54.53° C. |
| 50494266 | VDJ_IGHV_gDNA_05 | A5 | AGC ACA TCT CTG AAG ACC AG (SEQ ID NO: 906) | 54.19° C. |
| 50494267 | VDJ_IGHV_gDNA_06 | A6 | AGC ACA TCT CTG AAG AGC AG (SEQ ID NO: 907) | 54.46° C. |
| 50494268 | VDJ_IGHV_gDNA_07 | A7 | AGC ACG TCT CTG AAG AAC AG (SEQ ID NO: 908) | 54.53° C. |
| 50494269 | VDJ_IGHV_gDNA_08 | A8 | ATT ATG CAG TAT CTG TGA AAA GTC G (SEQ ID NO: 909) | 53.36° C. |
| 50494270 | VDJ_IGHV_gDNA_09 | A9 | CAG AAG CTC CAG GGC AG (SEQ ID NO: 910) | 55.68° C. |
| 50494260 | VDJ_IGHV_gDNA_10 | A10 | CAG ACT CTG TGA AGG GCA G (SEQ ID NO: 911) | 55.21° C. |
| 50494261 | VDJ_IGHV_gDNA_11 | A11 | CAG AGA AGT TCC AGG GCA G (SEQ ID NO: 912) | 55.28° C. |
| 50494262 | VDJ_IGHV_gDNA_12 | A12 | CAG GGC TTC ACA GGA CG (SEQ ID NO: 913) | 55.85° C. |
| 50494271 | VDJ_IGHV_gDNA_13 | B1 | CCC CTC CCT CAA GAG TCG (SEQ ID NO: 914) | 57.07° C. |
| 50494275 | VDJ_IGHV_gDNA_14 | B2 | CCC GTC CCT CAA GAG TCT (SEQ ID NO: 915) | 56.07° C. |
| 50494276 | VDJ_IGHV_gDNA_15 | B3 | CCG TCC CTC AAG AGT CG (SEQ ID NO: 916) | 54.86° C. |
| 50494277 | VDJ_IGHV_gDNA_16 | B4 | CCG TCC TTC AAG GGC CA (SEQ ID NO: 917) | 57.77° C. |
| 50494278 | VDJ_IGHV_gDNA_17 | B5 | CGC ACA GAA ATT CCA GGA CAG (SEQ ID NO: 918) | 56.24° C. |
| 50494279 | VDJ_IGHV_gDNA_18 | B6 | CGC ACA GAA GTT CCA GGA AAG (SEQ ID NO: 919) | 56.18° C. |
| 50494280 | VDJ_IGHV_gDNA_19 | B7 | CGC GTC TGT GAA AGG CAG (SEQ ID NO: 920) | 56.79° C. |
| 50494281 | VDJ_IGHV_gDNA_20 | B8 | GAC TCC GTG AAG GGC CG (SEQ ID NO: 921) | 58.62° C. |
| 50494282 | VDJ_IGHV_gDNA_21 | B9 | GAC TCA GTG AAG GGC CG (SEQ ID NO: 922) | 55.55° C. |
| 50494272 | VDJ_IGHV_gDNA_22 | B10 | GAC TCC GTG AAG GGC AG (SEQ ID NO: 923) | 55.55° C. |
| 50494273 | VDJ_IGHV_gDNA_23 | B11 | GAC TCT GTG AAG GGC CG (SEQ ID NO: 924) | 55.55° C. |
| 50494274 | VDJ_IGHV_gDNA_24 | B12 | GCA AAC TCT GTG AAG GGC AG (SEQ ID NO: 925) | 56.54° C. |
| 50494283 | VDJ_IGHV_gDNA_25 | C1 | GCA CAG AAG TTT CAG GGC AG (SEQ ID NO: 926) | 56.54° C. |
| 50494284 | VDJ_IGHV_gDNA_26 | C2 | GCA CCC GTG AAA GGC AG (SEQ ID NO: 927) | 57.09° C. |
| 50494285 | VDJ_IGHV_gDNA_27 | C3 | GCC CAT CTC TGA AGA GCA G (SEQ ID NO: 928) | 55.37° C. |
| 50494286 | VDJ_IGHV_gDNA_28 | C4 | GCG TCG GTG AAA GGC AG (SEQ ID NO: 929) | 56.97° C. |
| 50494287 | VDJ_IGHV_gDNA_29 | C5 | CTC CGT GAA GCG CCG (SEQ ID NO: 930) | 56.96° C. |

TABLE 15-continued

| Ref # | Name | Pos | | TM |
|---|---|---|---|---|
| 50494288 | VDJ_IGHV_gDNA_30 | C6 | TGC GTC TGT GAA AGG CAG (SEQ ID NO: 931) | 55.64° C. |
| 50494292 | VDJ_IGHJ_gDNA_01 | D1 | CTT ACC TGA GGA GAC GGT GAC C (SEQ ID NO: 932) | 58.73° C. |
| 50494293 | VDJ_IGHJ_gDNA_02 | D2 | CTC ACC TGA GGA GAC AGT GAC C (SEQ ID NO: 933) | 58.72° C. |
| 50494294 | VDJ_IGHJ_gDNA_03 | D3 | CTT ACC TGA AGA GAC GGT GAC C (SEQ ID NO: 934) | 56.83° C. |
| 50494295 | VDJ_IGHJ_gDNA_01IlluoverPE | D7 | CTC GGC ATT CCT GCT GAA CCG CTC TTC CGA TCT CTT ACC TGA GGA GAC GGT GAC C (SEQ ID NO: 935) | 71.88° C. |
| 50494296 | VDJ_IGHJ_gDNA_02IlluoverPE | D8 | CTC GGC ATT CCT GCT GAA CCG CTC TTC CGA TCT CTC ACC TGA GGA GAC AGT GAC C (SEQ ID NO: 936) | 71.90° C. |
| 50494297 | VDJ_IGHJ_gDNA_03IlluoverPE | D9 | CTC GGC ATT CCT GCT GAA CCG CTC TTC CGA TCT CTT ACC TGA AGA GAC GGT GAC C (SEQ ID NO: 937) | 71.28° C. |
| 50494298 | VDJ_IGHV_gDNA_01Illuover | E1 | ACA CTC TTT CCC TAC ACG ACG CTC TTC CGA TCT ACA GAA GTT CCA GGG CAG (SEQ ID NO: 938) | 69.95° C. |
| 50494302 | VDJ_IGHV_gDNA_02Illuover | E2 | ACA CTC TTT CCC TAC ACG ACG CTC TTC CGA TCT AGA CTC CAG GAA GGG CAG (SEQ ID NO: 939) | 70.46° C. |
| 50494303 | VDJ_IGHV_gDNA_03Illuover | E3 | ACA CTC TTT CCC TAC ACG ACG CTC TTC CGA TCT AGA CTC CAT GAA GGG CCA (SEQ ID NO: 940) | 70.54° C. |
| 50494304 | VDJ_IGHV_gDNA_04Illuover | E4 | ACA CTC TTT CCC TAC ACG ACG CTC TTC CGA TCT AGA CTC TGT GAA AGG CCG (SEQ ID NO: 941) | 69.81° C. |
| 50494305 | VDJ_IGHV_gDNA_05Illuover | E5 | ACA CTC TTT CCC TAC ACG ACG CTC TTC CGA TCT AGC ACA TCT CTG AAG ACC AG (SEQ ID NO: 942) | 69.24° C. |
| 50494306 | VDJ_IGHV_gDNA_06Illuover | E6 | ACA CTC TTT CCC TAC ACG ACG CTC TTC CGA TCT AGC ACA TCT CTG AAG AGC AG (SEQ ID NO: 943) | 69.30° C. |
| 50494307 | VDJ_IGHV_gDNA_07Illuover | E7 | ACA CTC TTT CCC TAC ACG ACG CTC TTC CGA TCT AGC ACG TCT CTG AAG AAC AG (SEQ ID NO: 944) | 69.25° C. |
| 50494308 | VDJ_IGHV_gDNA_08Illuover | E8 | ACA CTC TTT CCC TAC ACG ACG CTC TTC CGA TCT ATT ATG CAG TAT CTG TGA AAA GTC G (SEQ ID NO: 945) | 67.88° C. |
| 50494309 | VDJ_IGHV_gDNA_09Illuover | E9 | ACA CTC TTT CCC TAC ACG ACG CTC TTC CGA TCT CAG AAG CTC CAG GGC AG (SEQ ID NO: 946) | 71.06° C. |
| 50494299 | VDJ_IGHV_gDNA_10Illuover | E10 | ACA CTC TTT CCC TAC ACG ACG CTC TTC CGA TCT CAG ACT CTG TGA AGG CAG (SEQ ID NO: 947) | 70.35° C. |
| 50494300 | VDJ_IGHV_gDNA_11Illuover | E11 | ACA CTC TTT CCC TAC ACG ACG CTC TTC CGA TCT CAG AGA AGT TCC AGG CAG (SEQ ID NO: 948) | 70.42° C. |

TABLE 15-continued

| Ref # | Name | Pos | | TM |
|---|---|---|---|---|
| 50494301 | VDJ_IGHV_gDNA_12Illuover | E12 | ACA CTC TTT CCC TAC ACG ACG CTC TTC CGA TCT CAG GGC TTC ACA GGA CG (SEQ ID NO: 949) | 71.03° C. |
| 50494310 | VDJ_IGHV_gDNA_13Illuover | F1 | ACA CTC TTT CCC TAC ACG ACG CTC TTC CGA TCT CCC CTC CCT CAA GAG TCG (SEQ ID NO: 950) | 71.14° C. |
| 50494314 | VDJ_IGHV_gDNA_14Illuover | F2 | ACA CTC TTT CCC TAC ACG ACG CTC TTC CGA TCT CCC GTC CCT CAA GAG TCT (SEQ ID NO: 951) | 71.05° C. |
| 50494315 | VDJ_IGHV_gDNA_15Illuover | F3 | ACA CTC TTT CCC TAC ACG ACG CTC TTC CGA TCT CCG TCC CTC AAG AGT CG (SEQ ID NO: 952) | 70.66° C. |
| 50494316 | VDJ_IGHV_gDNA_16Illuover | F4 | ACA CTC TTT CCC TAC ACG ACG CTC TTC CGA TCT CCG TCC TTC CAA GGC CA (SEQ ID NO: 953) | 71.86° C. |
| 50494317 | VDJ_IGHV_gDNA_17Illuover | F5 | ACA CTC TTT CCC TAC ACG ACG CTC TTC CGA TCT CGC ACA GAA ATT CCA GGA CAG (SEQ ID NO: 954) | 70.19° C. |
| 50494318 | VDJ_IGHV_gDNA_18Illuover | F6 | ACA CTC TTT CCC TAC ACG ACG CTC TTC CGA TCT CGC ACA GAA GTT CCA GGA AAG (SEQ ID NO: 955) | 70.16° C. |
| 50494319 | VDJ_IGHV_gDNA_19Illuover | F7 | ACA CTC TTT CCC TAC ACG ACG CTC TTC CGA TCT CGC GTC TGT GAA AGG CAG (SEQ ID NO: 956) | 70.93° C. |
| 50494320 | VDJ_IGHV_gDNA_20Illuover | F8 | ACA CTC TTT CCC TAC ACG ACG CTC TTC CGA TCT GAC TCC GTG AAG GGC CG (SEQ ID NO: 957) | 71.82° C. |
| 50494321 | VDJ_IGHV_gDNA_21Illuover | F9 | ACA CTC TTT CCC TAC ACG ACG CTC TTC CGA TCT GAC TCA GTG AAG GGC CG (SEQ ID NO: 958) | 71.03° C. |
| 50494311 | VDJ_IGHV_gDNA_22Illuover | F10 | ACA CTC TTT CCC TAC ACG ACG CTC TTC CGA TCT GAC TCC GTG AAG GGC AG (SEQ ID NO: 959) | 71.03° C. |
| 50494312 | VDJ_IGHV_gDNA_23Illuover | F11 | ACA CTC TTT CCC TAC ACG ACG CTC TTC CGA TCT GAC TCT GTG AAG GGC CG (SEQ ID NO: 960) | 71.03° C. |
| 50494313 | VDJ_IGHV_gDNA_24Illuover | F12 | ACA CTC TTT CCC TAC ACG ACG CTC TTC CGA TCT GCA AAC TCT GTG AAG GGC AG (SEQ ID NO: 961) | 70.65° C. |
| 50494322 | VDJ_IGHV_gDNA_25Illuover | G1 | ACA CTC TTT CCC TAC ACG ACG CTC TTC CGA TCT GCA CAG AAG TTT CAG GGC AG (SEQ ID NO: 962) | 70.65° C. |
| 50494323 | VDJ_IGHV_gDNA_26Illuover | G2 | ACA CTC TTT CCC TAC ACG ACG CTC TTC CGA TCT GCA CCC GTG AAA GGC AG (SEQ ID NO: 963) | 71.50° C. |
| 50494324 | VDJ_IGHV_gDNA_27Illuover | G3 | ACA CTC TTT CCC TAC ACG ACG CTC TTC CGA TCT GCC CAT CTC TGA AGA GCA G (SEQ ID NO: 964) | 70.51° C. |
| 50494325 | VDJ_IGHV_gDNA_28Illuover | G4 | ACA CTC TTT CCC TAC ACG ACG CTC TTC CGA TCT GCG TCG GTG AAA GGC AG (SEQ ID NO: 965) | 71.35° C. |
| 50494326 | VDJ_IGHV_gDNA_29Illuover | G5 | ACA CTC TTT CCC TAC ACG ACG CTC TTC CGA TCT CTC CGT GAA GCG CCG (SEQ ID NO: 966) | 71.68° C. |

TABLE 15-continued

| Ref # Name | Pos | | TM |
|---|---|---|---|
| 50494327VDJ_IGHV_gDNA_30Illuover | G6 | ACA CTC TTT CCC TAC ACG ACG CTC TTC CGA TCT TGC GTC TGT GAA AGG CAG (SEQ ID NO: 967) | 70.40° C. |

Extract Genomic DNA

Extracted blood. PBMC extraction (ficoll), froze some in DMOS for eventual live pull down. Frozen cell stocks were used (3 vial, one for day 0-day 7 and day 21 total cell 5.5 million 70% viable). Extracted DNA (Agencourt kit; used 10× lysis mix+50 µl RNase cocktail; used bead binding at 50% volume, i.e., 300 µl of bead for 600 µl of solution). Nanodrop: 62.2 ng/µl (260/180 1.90, 280/230 2.0) total ~18 µg.

Primer Setup

Made a dilute plate at 5 µM each; 2 µl of each+78 µl of H$_2$O, but also to pooled tubes at 5 µM once pooled. V; 3 µl of each (90 µl total)+30 µl H$_2$O=120 µl at 5 µM. J; 2 µl of each (0.6 µl total)+74 µl H$_2$O=80 µl at 5 µM Individual Primer Testing Tested every primer one by one (non-Illumina overlap only): each V against a pool of all 3 J, (30 PCR reaction); each J against a pool of all V (3 PCR reaction).

Assembled a reaction as follows:

| | 1 tube | 5t | 35t |
|---|---|---|---|
| dH$_2$O | 9.8 µl (to 20 µl) | 49 | 343 |
| 62.2 ng/µl DNA | 1.60 µl 100 ng | 8 | 56 |
| 5× HF buffer | 4 µl 1× | 20 | 140 |
| 10 mM dNTP | 0.4 µl 0.2 µM | 2 | 14 |
| 5 µM primer v | 2 µl 0.5 µM | 10 | — |
| 5 µM primer J | 2 µl 0.5 µM | — | 70 |
| phusion hot start | 0.2 µl 0.02 U/µl (18 µl/tubes) | 1 | 7 |

Thermal cycled as follows:

| 1 | 98° C. for 1 min |
|---|---|
| 2 | 98° C. for 10 seconds |
| 3 | 55° C. for 30 seconds |
| 4 | 72° C. for 30 seconds go to step 2, 30× |
| 5 | 72° C. for 5 min |
| 6 | 4° C. pause |

Figure 58:
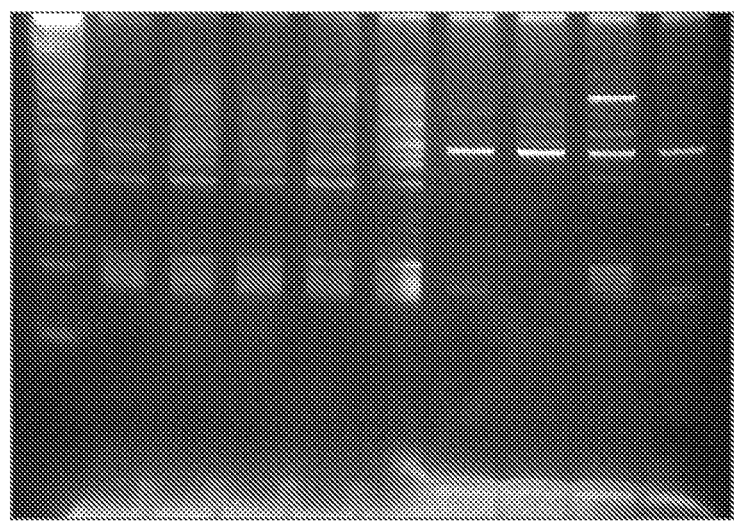
FIG. 58 depicts a gel showing individual primer testing. Lanes from left to right: 1,100 bp ladder; 2, full; 3, full-2; 4, J1; 5, J2; 6, J3; 7, V30; 8, V29; 9, V28; 10, V27.

Added 50 of 5× Novex buffer and load 6 µl on agarose gels (couldn't see anything). Ran 15 µl on 6% TBE, stain SYBR gold 12 min (FIG. 58)

Primer Setup Part 2

Plate (VDJ_gDNA_Apri102_10) was diluted at 400 µM. Diluted plates were made at 5 µM each: 2 µl for each V and J+158 µl of H$_2$O=160 µl, but also to pooled tubes at 5 µM once pooled. V; 2 µl of each (0.90 µl total)+70 µl H$_2$O=160 µl at 5 µM (well F1). J; 2 µl of each (=6 µl total)+154 µl H$_2$O=160 µl at 5 µM (well F2).

Individual Primer Testing

Tested every primer one by one (non-Illumina overlap only): each V against a pool of all 3 J, (45 PCR reaction); each J against a pool of all V (3 PCR reaction); and all V and J in one reaction (1 PCR reaction) (FIG. 59).

Assembled a reaction as follows:

Thermal cycling was as follows:

| | 1 tube | 5t (J and all) | 50t |
|---|---|---|---|
| dH$_2$O | 9.8 µl (to 20 µl) | 49 | 490 |
| 62.2 ng/µl DNA | 1.60 µl 100 ng | 8 | 80 |
| 5× HF buffer | 4 µl 1× | 20 | 140 |
| 10 mM dNTP | 0.4 µl 0.2 µM | 2 | 20 |
| 5 µM primer V | 2 µl 0.5 µM | 10 | — |
| 5 µM primer J | 2 µl 0.5 µM | — (10 all) | 100 |
| phusion hot start | 0.2 µl 0.02 U/µl (18 µl/tubes) | 1 | 10 |

| 1 | 98° C. for 1 min |
|---|---|
| 2 | 98° C. for 10 seconds |
| 3 | 58° C. for 20 seconds |
| 4 | 72° C. for 30 seconds go to step 2, 30× |
| 5 | 72° C. for 5 min |
| 6 | 4° C. pause |

With Illumina overhang (Table 16).

TABLE 16

| Reference Pos | Sequence Name | Sequence | Tm (50 mM NaCl) C |
|---|---|---|---|
| 51403096 A1 | Il_VDJ_IGHV_gDNA_trunc135_01 | ACA CTC TTT CCC TAC ACG ACG CTC TTC CGA TCT CCT GGA GTG GAT GGG GAT CA (SEQ ID NO: 968) | 71.5 |
| 51403097 A2 | Il_VDJ_IGHV_gDNA_trunc135_10 | ACA CTC TTT CCC TAC ACG ACG CTC TTC CGA TCT GGC TGG AGT GGG TCT CAG TT (SEQ ID NO: 969) | 71.7 |

TABLE 16-continued

| Reference Pos | Sequence Name | Sequence | Tm (50 mM NaCl) C |
|---|---|---|---|
| 51403098 A3 | Il_VDJ_IGHV_gDNA_trunc135_11 | ACA CTC TTT CCC TAC ACG ACG CTC TTC CGA TCT AGG GCT TGA GTG GAT GGG AC (SEQ ID NO: 970) | 70.9 |
| 51403099 A4 | Il_VDJ_IGHV_gDNA_trunc135_12 | ACA CTC TTT CCC TAC ACG ACG CTC TTC CGA TCT AGA GCT TGG GTG GAT GGG AC (SEQ ID NO: 971) | 70.9 |
| 51403100 A5 | Il_VDJ_IGHV_gDNA_trunc135_02 | ACA CTC TTT CCC TAC ACG ACG CTC TTC CGA TCT AAG GGC CTG GAG TGG GTT T (SEQ ID NO: 972) | 71.4 |
| 51403101 A6 | Il_VDJ_IGHV_gDNA_trunc135_03 | ACA CTC TTT CCC TAC ACG ACG CTC TTC CGA TCT CCT GGA GTG GAT TGG GTA CAT CT (SEQ ID NO: 973) | 70.7 |
| 51403102 A7 | Il_VDJ_IGHV_gDNA_trunc135_04 | ACA CTC TTT CCC TAC ACG ACG CTC TTC CGA TCT GGA AGG GGC TGG AGT GGA TT (SEQ ID NO: 974) | 71.8 |
| 51403103 A8 | Il_VDJ_IGHV_gDNA_trunc135_05 | ACA CTC TTT CCC TAC ACG ACG CTC TTC CGA TCT AGG GTC TGG AGT GGG TCT CA (SEQ ID NO: 975) | 71.1 |
| 51403104 A9 | Il_VDJ_IGHV_gDNA_trunc135_06 | ACA CTC TTT CCC TAC ACG ACG CTC TTC CGA TCT CTG GAG TGG CTT GCA CAC A (SEQ ID NO: 976) | 71.5 |
| 51403105 A10 | Il_VDJ_IGHV_gDNA_trunc135_07 | ACA CTC TTT CCC TAC ACG ACG CTC TTC CGA TCT CTG GAG TGG ATG GGG AGG ATT (SEQ ID NO: 977) | 71.2 |
| 51403106 A11 | Il_VDJ_IGHV_gDNA_trunc135_08 | ACA CTC TTT CCC TAC ACG ACG CTC TTC CGA TCT AAA GGC CCT GGA GTG GCT T (SEQ ID NO: 978) | 71.4 |
| 51403107 A12 | Il_VDJ_IGHV_gDNA_trunc135_09 | ACA CTC TTT CCC TAC ACG ACG CTC TTC CGA TCT CCT GGA GTG GCT TGC ACT CA (SEQ ID NO: 979) | 71.8 |
| 51403108 B1 | Il_VDJ_IGHV_gDNA_trunc135_13 | ACA CTC TTT CCC TAC ACG ACG CTC TTC CGA TCT AGG GCT TGA GTG GAT GGG AG (SEQ ID NO: 980) | 70.8 |
| 51403109 B2 | Il_VDJ_IGHV_gDNA_trunc135_22 | ACA CTC TTT CCC TAC ACG ACG CTC TTC CGA TCT CAG GGA AGG GAC TGG AAT ATG TTT C (SEQ ID NO: 981) | 69.8 |

TABLE 16-continued

| Reference Pos | Sequence Name | Sequence | Tm (50 mM NaCl) C |
|---|---|---|---|
| 51403110 B3 | Il_VDJ_IGHV_gDNA_trunc135_23 | ACA CTC TTT CCC TAC ACG ACG CTC TTC CGA TCT GGA AAG GGC TGG AGT GGG TT (SEQ ID NO: 982) | 72.0 |
| 51403111 B4 | Il_VDJ_IGHV_gDNA_trunc135_24 | ACA CTC TTT CCC TAC ACG ACG CTC TTC CGA TCT GAG TGG GTC TCT CTT ATT AGT TGG GA (SEQ ID NO: 983) | 69.8 |
| 51403112 B5 | Il_VDJ_IGHV_gDNA_trunc135_14 | ACA CTC TTT CCC TAC ACG ACG CTC TTC CGA TCT GCT GGA GTG GGT CTC ATC CA (SEQ ID NO: 984) | 71.6 |
| 51403113 B6 | Il_VDJ_IGHV_gDNA_trunc135_15 | ACA CTC TTT CCC TAC ACG ACG CTC TTC CGA TCT GGG CTG GAG TGG GTA GGT TT (SEQ ID NO: 985) | 71.8 |
| 51403114 B7 | Il_VDJ_IGHV_gDNA_trunc135_16 | ACA CTC TTT CCC TAC ACG ACG CTC TTC CGA TCT GTT GGC CGT ACT AGA AAC AAA GCT (SEQ ID NO: 986) | 70.2 |
| 51403115 B8 | Il_VDJ_IGHV_gDNA_trunc135_17 | ACA CTC TTT CCC TAC ACG ACG CTC TTC CGA TCT CTG GAG TGG GTA TCG GGT GT (SEQ ID NO: 987) | 71.4 |
| 51403116 B9 | Il_VDJ_IGHV_gDNA_trunc135_18 | ACA CTC TTT CCC TAC ACG ACG CTC TTC CGA TCT GAG TGG ATG GGA TTG GTG TGC (SEQ ID NO: 988) | 71.0 |
| 51403117 B10 | Il_VDJ_IGHV_gDNA_trunc135_19 | ACA CTC TTT CCC TAC ACG ACG CTC TTC CGA TCT CTT GAG TGG ATG GGA GGT TTT GAT C (SEQ ID NO: 989) | 69.9 |
| 51403118 B11 | Il_VDJ_IGHV_gDNA_trunc135_20 | ACA CTC TTT CCC TAC ACG ACG CTC TTC CGA TCT AGG CTT GAG TGG ATG GGA TGG (SEQ ID NO: 990) | 70.7 |
| 51403119 B12 | Il_VDJ_IGHV_gDNA_trunc135_21 | ACA CTC TTT CCC TAC ACG ACG CTC TTC CGA TCT CCT GGA GTG GCT TGC TCA CA (SEQ ID NO: 991) | 71.8 |
| 51403120 C1 | Il_VDJ_IGHV_gDNA_trunc135_25 | ACA CTC TTT CCC TAC ACG ACG CTC TTC CGA TCT AGT GGG TGG CAG TTA TAT GGT ATG A (SEQ ID NO: 992) | 69.5 |
| 51403121 C2 | Il_VDJ_IGHV_gDNA_trunc135_34 | ACA CTC TTT CCC TAC ACG ACG CTC TTC CGA TCT TGA GTG GAT AGG ATG GAT CGT CG (SEQ ID NO: 993) | 69.9 |

TABLE 16-continued

| Reference Pos | Sequence Name | Sequence | Tm (50 mM NaCl) C |
|---|---|---|---|
| 51403122 C3 | I1_VDJ_IGHV_gDNA_trunc135_35 | ACA CTC TTT CCC TAC ACG ACG CTC TTC CGA TCT GGG TTG GCC GTA TTA AAA GCA AAA C (SEQ ID NO: 994) | 70.0 |
| 51403123 C4 | I1_VDJ_IGHV_gDNA_trunc135_36 | ACA CTC TTT CCC TAC ACG ACG CTC TTC CGA TCT ACT GGA GTG GAT TGG GTA CAT CTA TT (SEQ ID NO: 995) | 69.3 |
| 51403124 C5 | I1_VDJ_IGHV_gDNA_trunc135_26 | ACA CTC TTT CCC TAC ACG ACG CTC TTC CGA TCT AGG GCT TGA GTG GAT GGG AA (SEQ ID NO: 996) | 70.9 |
| 51403125 C6 | I1_VDJ_IGHV_gDNA_trunc135_27 | ACA CTC TTT CCC TAC ACG ACG CTC TTC CGA TCT CTG GAG TGG ATT GGG TAC ATC TAT CA (SEQ ID NO: 997) | 69.9 |
| 51403126 C7 | I1_VDJ_IGHV_gDNA_trunc135_28 | ACA CTC TTT CCC TAC ACG ACG CTC TTC CGA TCT CGC TTG AGT GGA TGG GAT GG (SEQ ID NO: 998) | 71.1 |
| 51403127 C8 | I1_VDJ_IGHV_gDNA_trunc135_29 | ACA CTC TTT CCC TAC ACG ACG CTC TTC CGA TCT GGG TGG CCA ACA TAA AGC AAG A (SEQ ID NO: 999) | 71.0 |
| 51403128 C9 | I1_VDJ_IGHV_gDNA_trunc135_30 | ACA CTC TTT CCC TAC ACG ACG CTC TTC CGA TCT GGG ACT GGA GTG GAT TGG GT (SEQ ID NO: 1000) | 71.7 |
| 51403129 C10 | I1_VDJ_IGHV_gDNA_trunc135_31 | ACA CTC TTT CCC TAC ACG ACG CTC TTC CGA TCT GCT AGA GTG GGT GGC AGT TAT ATC A (SEQ ID NO: 1001) | 70.2 |
| 51403130 C11 | I1_VDJ_IGHV_gDNA_trunc135_32 | ACA CTC TTT CCC TAC ACG ACG CTC TTC CGA TCT CTT GAG TGG ATG GGA TGG ATG AAC (SEQ ID NO: 1002) | 70.1 |
| 51403131 C12 | I1_VDJ_IGHV_gDNA_trunc135_33 | ACA CTC TTT CCC TAC ACG ACG CTC TTC CGA TCT AGT GGG TCT CAG CTA TTA GTG GTA G (SEQ ID NO: 1003) | 69.2 |
| 51403132 D1 | I1_VDJ_IGHV_gDNA_trunc135_37 | ACA CTC TTT CCC TAC ACG ACG CTC TTC CGA TCT GCT GGA GTG GGT CTC TGG TA (SEQ ID NO: 1004) | 71.4 |
| 51403133 D2 | I1_VDJ_IGHV_gDNA_trunc135_38 | ACA CTC TTT CCC TAC ACG ACG CTC TTC CGA TCT GCT GGT GTG GGT CTC ACG TA (SEQ ID NO: 1005) | 71.5 |

TABLE 16-continued

| Reference Pos | Sequence Name | Sequence | Tm (50 mM NaCl)C |
|---|---|---|---|
| 51403134 D3 | Il_VDJ_IGHV_gDNA_trunc135_39 | ACA CTC TTT CCC TAC ACG ACG CTC TTC CGA TCT GAG TGG GTC TCA GGT ATT AGT TGG A (SEQ ID NO: 1006) | 70.1 |
| 51403135 D4 | Il_VDJ_IGHV_gDNA_trunc135_40 | ACA CTC TTT CCC TAC ACG ACG CTC TTC CGA TCT CAG GAA AAG GTC TGG AGT GGG T (SEQ ID NO: 1007) | 71.1 |
| 51403136 D5 | Il_VDJ_IGHV_gDNA_trunc135_41 | ACA CTC TTT CCC TAC ACG ACG CTC TTC CGA TCT TGG AGT GGG TGG CAG TTA TAT CA (SEQ ID NO: 1008) | 70.2 |
| 51403137 D6 | Il_VDJ_IGHV_gDNA_trunc135_42 | ACA CTC TTT CCC TAC ACG ACG CTC TTC CGA TCT GGG ACT GGA GTG GGT TC ATA CA (SEQ ID NO: 1009) | 70.9 |
| 51403138 D7 | Il_VDJ_IGHV_gDNA_trunc135_43 | ACA CTC TTT CCC TAC ACG ACG CTC TTC CGA TCT AGG GCT TGA GTG GAT GGG ATG(SEQ ID NO: 1010) | 70.7 |
| 51403139 D8 | Il_VDJ_IGHV_gDNA_trunc135_44 | ACA CTC TTT CCC TAC ACG ACG CTC TTC CGA TCT AGG GAA AGG GCT AGA GTT GGT AG (SEQ ID NO: 1011) | 69.8 |
| 51403140 D9 | Il_VDJ_IGHV_gDNA_trunc135_45 | ACA CTC TTT CCC TAC ACG ACG CTC TTC CGA TCT TCC CCA TCG AGA GGC TTT GA (SEQ ID NO: 1012) | 71.6 |
| 51403141 E1 | Il_VDJ_IGHJ_gDNA_01 | CTC GGC ATT CCT GCT GAA CCG CTC TTC CGA TCT CTT ACC TGA GGA GAC GGT GAC C (SEQ ID NO: 1013) | 71.9 |
| 51403142 E2 | Il_VDJ_IGHJ_gDNA_02 | CTC GGC ATT CCT GCT GAA CCG CTC TTC CGA TCT CTC ACC TGA GGA GAC AGT GAC C (SEQ ID NO: 1014) | 71.9 |
| 51403143 E3 | Il_VDJ_IGHJ_gDNA_03 | CTC GGC ATT CCT GCT GAA CCG CTC TTC CGA TCT CTT ACC TGA AGA GAC GGT GAC C (SEQ ID NO: 1015) | 71.3 |

Primer Setup Part 2

Plate (VD.UDNA_Apri123_10_illumina) was diluted at 400 µM. Plates were supplied at 10 nM, resuspend all oligos in 25 µl each. They were not tested one by one, instead overall band intensity was tested, and also to pooled tubes at 5 µM once pooled. V; 2 µl of each (=90 µl total)+70 µl H₂O=160 µl at 5 µM (well F1). J; 2 µl of each (=6 µl total)+154 µl H₂O=160 µl at 5 µM (well F2)

combined Illumina primer overlap testing

Assembled a reaction as follows:

|  | 1 tube | 4 tubes |
|---|---|---|
| dH₂O | 14.42 µl (to 25 µl) | 57.68 |
| 180 ng/µl DNA | 0.83 µl 150 ng | 3.33 |
| 5× HF buffer | 5 µl 1× | 20 |
| 10 mM dNTP | 0.5 µl 0.2 µM | 2 |
| 5 µM primer V | 2 µl 0.5 µM | 8 |
| 5 µM primer J | 2 µl 0.5 µM | 8 |
| phusion hot start | 0.25 µl 0.02 U/µl | 1 |
|  | (25 µl/tubes) |  |

Thermal cycle was performed as follows:

| 1 | 98° C. for 1 min |
| 2 | 98° C. for 10 seconds |
| 3 | 58° C. for 20 seconds |
| 4 | 72° C. for 20 seconds go to step 2, 30× |
| 5 | 72° C. for 5 min |
| 6 | 4° C. pause |

Qiagen purified, eluted in 3411. Nanodrop

| 1 | 70 ng/µl | no overhang |
| 2 | 128 ng/µl | Illumina overhang |
| 3 | 90 ng/µl | Illumina overhang, Veraseq |

Figure 60:
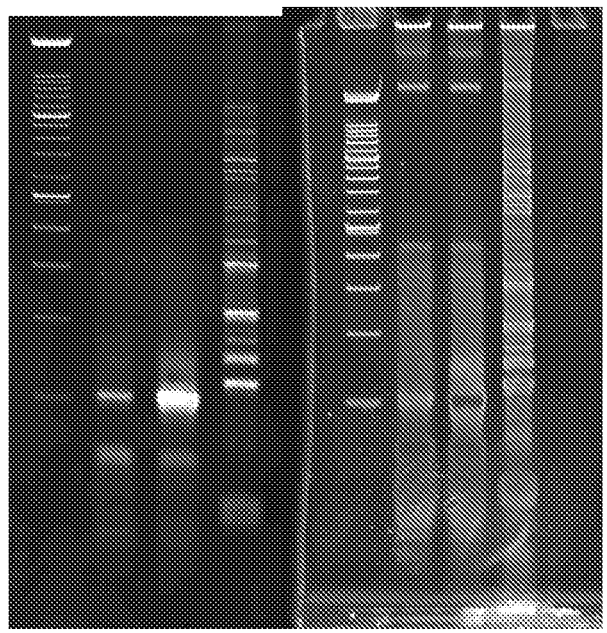
FIG. 60 depicts a gel showing combined Illumina primer overlap testing.

To 6 µl, added 6 µl of 2× blue juice and loaded 6 µl. Ran 2×6 µl on 6% TBE (20 min), stained half with ethidium bromide (EtBr) and SYBR gold 12 min. Inversed loading (so number 3 is Phusion with primer no-overhang) (FIG. 60).

Assembled a reaction as follows:

|  | 1 tube | 5t |
|---|---|---|
| dH₂O | 10.85 µl (to 20 µl) | 54.25 |
| 180 ng/µl DNA | 0.55 µl 100 ng | — |
| 5× HF buffer | 4 µl 1× | 20 |
| 10 mM dNTP | 0.4 µl 0.2 µM | 2 |
| 5 µM primer V | 2 µl 0.5 µM | — |
| 5 µM primer J | 2 µl 0.5 µM | — |
| phusion hot start | 0.2 µl 0.02 U/µl | 1 |
|  | (15.45 µl/tubes) |  |

Figure 61:
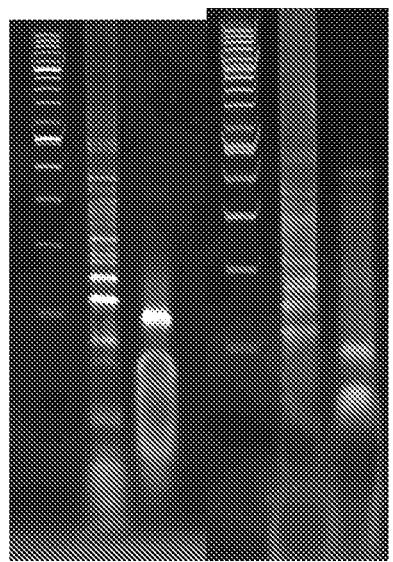
FIG. 61 depicts a gel showing an assembly.

Thermal cycling performed as follows (FIG. 61):

| 1 | 98° C. for 1 min |
| 2 | 98° C. for 10 seconds |
| 3 | 55° C. for 30 seconds |
| 4 | 72° C. for 30 seconds go to step 2, 30× |
| 5 | 72° C. for 5 min |
| 6 | 4° C. pause |

Repeated with cDNA of 62 ng/µl and coriel DNA (dilute 1:5). Tried from FV1 cDNA (RT-PCR done as in heavy chain 454 sequencing).

Assembled a reaction as follow:

|  | 1 tube |
|---|---|
| dH2O | 6.4 µl (to 20 µl) |
| cDNA | 5 µl 100 ng |
| 5 HF buffer | 4 µl 1× |
| 10 mM dNTP | 0.4 µl 0.2 µM |
| 5 µM primer V | 2 µl 0.5 µM |
| 5 µM primer J | 2 µl 0.5 µM |
| phusion hot start | 0.2 µl 0.02 U/µl |
|  | (18 µl/tubes) |

Thermal cycling performed as follows:

| 1 | 98° C. for 1 min |
| 2 | 98° C. for 10 seconds |
| 3 | 58° C. for 20 seconds |
| 4 | 72° C. for 20 seconds go to step 2, 25× |
| 5 | 72° C. for 5 min |
| 6 | 4° C. pause |

Figure 62:
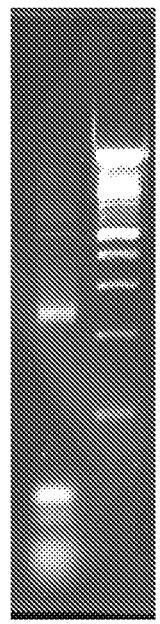
FIG. 62 depicts a gel showing cDNA and coriel DNA.

Loaded 5 µl on 6% TBE gel, ran 25 min, stained with 10 µl EtBr 15 min (FIG. 62).

Example XII

Rheumatoid Arthritis Immune Sequencing

Sample information is set forth in Table 17.

TABLE 17

| CCP + RA Specimen ID | Sp type | Sp Des | Diagnosis | Gender | Age | RF | RF date | RF highest | RF highest date | CCP | CCP date | CCP highest | CCP highest date | CRP | CRP date |
|---|---|---|---|---|---|---|---|---|---|---|---|---|---|---|---|
| DL-SF-0306 | SF | knee | RA | F | 63 | 48 | Jun. 2, 2011 | 59 | Aug. 4, 2008 | >100 | Jun. 2, 2011 | >100 | Jun. 2, 2011 | 11.6 | Jun. 2, 2011 |
| DL-SF-0331 | SF | knee | RA | F | 59 | 173 | Sep. 14, 2009 | 173 | Sep. 14, 2009 | >100 | Sep. 14, 2009 | >100 | Sep. 14, 2009 |  |  |

TABLE 17-continued

| | | | | | | | | | | | | | | | |
|---|---|---|---|---|---|---|---|---|---|---|---|---|---|---|---|
| DL-SF-0263 | SF | knee | Psoriatic | M | 26 | 48 | Apr. 3, 2009 | 48 | Mar. 12, 2009 | >100 | Mar. 12, 2009 | >100 | Mar. 12, 2009 | | |
| DL-SF-0375 | SF | knee | RA + Sec OA | M | 60 | 154 | Oct. 3, 2007 | 233 | May 2, 2004 | >100 | Oct. 3, 2007 | >100 | Oct. 3, 2007 | 82.6 | Oct. 3, 2007 |

| Non-RA Specimen ID | Sp type | Sp Des | Diagnosis | Gender | Age | RF | RF date | RF highest | CCP | CCP date | CCP highest | RF highest date | CRP | CRP date |
|---|---|---|---|---|---|---|---|---|---|---|---|---|---|---|
| DL-SF-0291 | SF | knee | OA | M | 0 | | | | | | | | | |
| DL-SF-0237 | SF | knee | OA | M | 0 | | | | | | | | | |
| DL-SF-0313 | SF | knee | Gout | F | 73 | | | | | | | | | |
| DL-SF-0264 | SF | knee | OA | F | 77 | | | | | | | | | |

RNA Extraction

Used Mirvana as per manufacturer protocol. QC nanodrop. Diluted all to 250 ng/µl (Table 18).

TABLE 18

| ID | ng/ul RNA | 260/280 | 260/230 | 1/3 dilution | Volume for 500 ul | Water to 7 |
|---|---|---|---|---|---|---|
| 1 | 768.6 | 2.06 | 1.4 | 260.6 | 1.92 | 5.08 |
| 2 | 644.7 | 2.09 | 2.05 | 213.1 | 2.35 | 4.65 |
| 3 | 349.3 | 2.07 | 2.05 | 112.0 | 4.46 | 2.54 |
| 4 | 181.7 | 2.04 | 1.7 | — | 2.75 | 4.25 |
| 5 | 434.6 | 2.1 | 1.11 | 141.6 | 3.53 | 3.47 |
| 6 | 1071.3 | 2.09 | 1.59 | 360.4 | 1.39 | 5.61 |
| 7 | 597 | 2.04 | 1.82 | 199.2 | 2.51 | 4.49 |
| 8 | 18.7/134.0 | 1.88 | 1.13 | — | 3.73 | 3.27 |

Concentrated sample 8 by EtOH precipitation, resuspended in 20 ml, nanodrop=134.0. Reverse transcription. Proceeded as follows for RT-PCR:

| | 2× 1 tube |
|---|---|
| H₂O (DEPC) | 0 µl (to 12 µl) |
| 2 µM Gene-specific primer (IGHC K and L) | 5 (5 pmole) |
| Total RNA | 7 µl (500 ng) |

Heated at 95° C. for 1 min. followed by 65° C. for 5 min., than ice for 1 min. Spun down and added the following:

| | 1 tube | 10 tubes |
|---|---|---|
| 5× First strand buffer | 4 µl | 40 |
| 10 mM dNTP mix | 1 µl | 10 |
| 0.1M DTT | 1 µl | 10 |
| RNase Inhibitor-Enzy | 1 µl | 10 |
| Superscript III | 1 µl | 10 |

Incubated at 55° C. for 60 min. (8 µl/tubes). Inactivated enzyme by heating at 70° C. for 15 min. Removed RNA/DNA hybrid by adding 1 µl of *E. coli* RNaseH. Incubated at 37° C. for 20 min., then ice. Assembled PCR reaction as follows (used half for PCR, kept other half as backup):

| | 1× | ×2 per sample × 12 samples (16t) |
|---|---|---|
| dH₂O | 21 µl (to 50 ul) | 420 |
| cDNA | 5 µl | — |
| 5× HF buffer | 10 µl | 240 |
| dNTP(10 mM) | 1 µl | 24 |
| primer up (IGHV new-short) (4 µM) | 6.25 µl (25 pmole) | 150 |
| primer low (IGHC new-short) (4 µM) | 6.25 µl (25 pmole) | 150 |
| phusion | 0.5 µl | 12 |

Added 45 ml to 5 IA twice for each cDNA sample. Thermal cycled as follows:

| | |
|---|---|
| 1 | 98° C. for 1 min. |
| 2 | 98° C. for 10 seconds |
| 3 | 62° C. for 20 seconds |
| 4 | 72° C. for 20 seconds went to step 2, 23× |
| 5 | 72° C. for 5 min. |
| 6 | 4° C. pause |

Pooled both tubes together (total 100 µl). Added 2 µl of Exonuclease I (20 U/µl) to each 100 µl tube and incubated at 37° C. for 20 min. AMPure XP purified, ratio 1.8:1. Resuspended in 40 µl, transferred to PCR strip. Conducted SPRI purification as follows:

Added the require amount of AMPure XP beads (1.8:1 ratio) to the DNA sample in buffer EB.
Vortexed to mix.
Incubated for 5 minutes at room temperature.
Magnet (MPC) for 5 minutes. Left the tube of beads in the MPC during all wash steps.
Removed the supernatant (kept in case of failure) and washed the beads twice with 500 µl of 70% ethanol, incubating for 30 sec. each time.
Removed all the supernatant, quick spun, removed last drop and allowed the AMPure beads to air dry completely (2 min.).
Removed the tube from the MPC, added 40 µl of 10 mM Tris-HCl, 0.1 mM EDTA, pH 8.0 (or Qiagen's Buffer EB), and vortexed for 30 sec. to resuspend the beads, let sit for 3 min. Magnet for 2 min. and transfer supernatant to a new tube.

Figure 68:
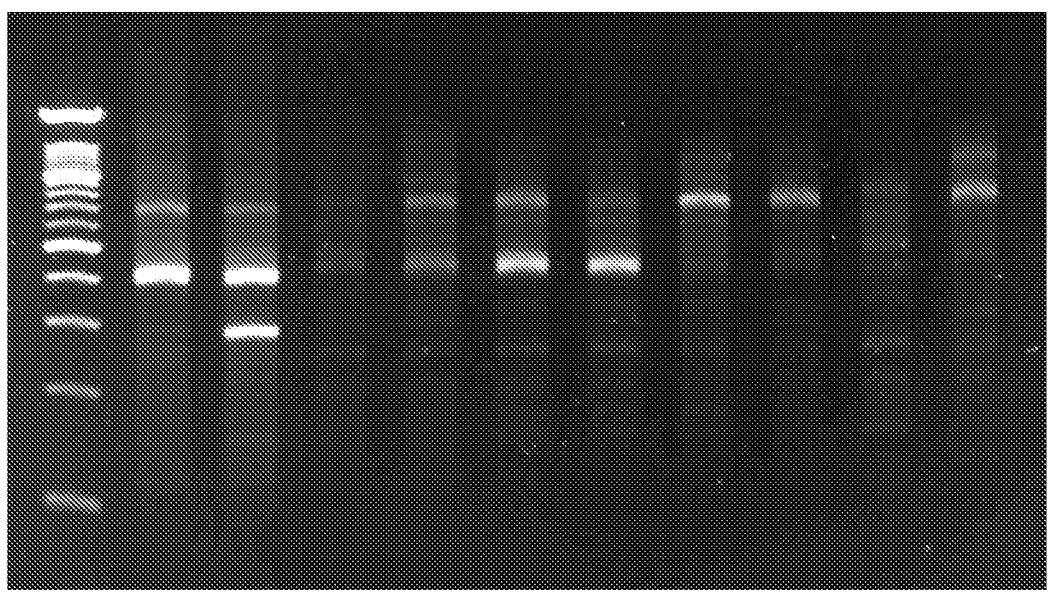
FIG. 68 depicts a diagnostic gel used to confirm PCR efficiency.

A diagnostic gel was used to check PCR efficiency. 2 µl was run on a 2% Egel-X for 12 min. (FIG. 68). Blunting reactions were performed using Enzymatics End repair kit as follows:

|  | 1t | 12t |
| --- | --- | --- |
| H₂O | 0 µl (to 50 µl) | 0 |
| Purified DNA | 38 µl | — |
| 10× End repair buffer | 5 µl | 60 |
| 1 mM dNTP mix | 5 µl | 60 |
| enzyme mix. | 5 µl | 60 |

Figure 69:
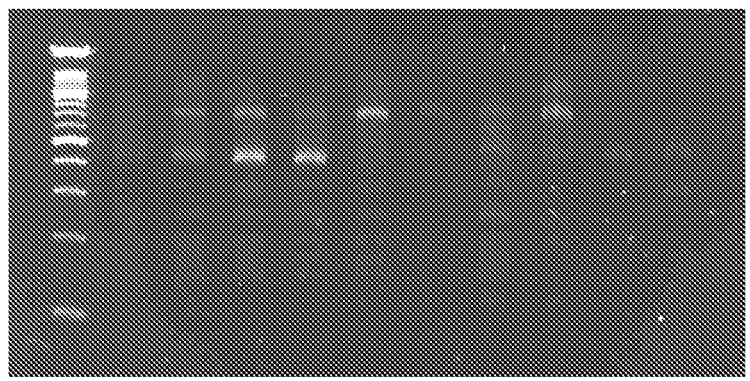
FIG. 69 depicts a diagnostic gel used to confirm efficiency of blunting and ampure beads.

Incubated at 25° C. temperature for 30 min. Heat inactivated at 75° C. for 20 min. AMPure XP purified, ratio 1.8:1. Resuspended in 37 IA (kept non-bind volume as backup). Saved 2 µl of each sample for gel diagnostic. A diagnostic gel was run to check efficiency of blunting and ampure beads. 2 µl of sample was run on a 2% Egel-X for 12 mM. (FIG. 69). AMPure purified to remove all dNTP, eluted in 44 µl. E Gel diagnostic 2 µl. Tested the following steps on one sample only: (sample 10 FV1, the one with the extra band at 275 bp).

A-Tailing—FV1 Sample Only

Klenow exo—"A" and "T" tailing. The following reaction mix was prepared:

| H₂O | 42 µl (to 50 µl) |
| --- | --- |
| DNA sample | 41 µl |
| 10× Klenow buffer | 5 µl |
| 10 mM dATP | 1 µl |
| Klenow exo (3' to 5' exo minus) | 3 µl |

Figure 70:
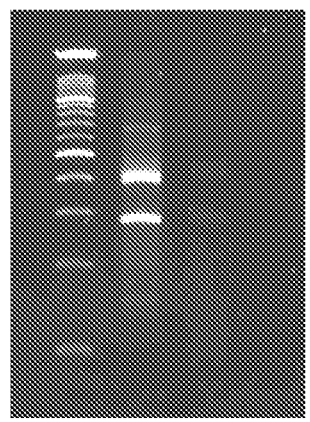
FIG. 70 depicts a diagnostic gel used to confirm AMPure efficiency.

Incubated for 30 minutes at 37° C. AMPure purified, eluted in 26 µl. Ran on diagnostic gel (FIG. 70). Ln 1 post A-tail, 1n2, second round of AMPure of supernatant non-bind post end it. Everything looked fine. Without intending to be bound by scientific theory, the previous gel bands of FV1 (samples 9 and 10), were probably faint from bad gel loading.

Y Adaptor Ligation

Self annealed 454 oligo into adapter A and B together. Followed 454 protocol (10 µl of 100 µM of each primer+30 µl of (10 mM Tris, 0.1 mM EDTA at 50 mM NaCl)) (each adapter was at 20 µM final), 95° C. for 3 min., ramp to 15° C. forever at 0.1° C./sec.

Ligation of rapid 454 Y adapter as follows (kept 2 µl of DNA on the side for gel comparison):

|  | 1 tube |
| --- | --- |
| H₂O | 0 µl (to 50 µl) |
| 2× Quick ligase buffer | 25 µl |
| VDJ DNA | 23 µl |
| 20 µM adapter | 1 µl |
| T4 DNA ligase (quick) | 2 µl |

Incubated on PCR at 22° C. for 15 min. AMPure XP purified, ratio 1.8:1. Resuspended in 25 µl. Ran sample on a diagnostic gel.

Tested all combined reactions, like in the 454 rapid protocol. Used sample 9 (FV1 for this), pretended endit was not done yet (cause need buffer in the mixture). Performed blunting reaction using Enzymatics End repair kit as follows (simultaneous Endit and A-tailing):

|  | 1 tube |
| --- | --- |
| H₂O | 0 µl (to 50 µl) |
| Purified DNA | 40 µl |
| 10× End repair buffer | 5 µl |
| 1 mM dNTP mix | 5 µl |
| enzyme mix. | 2 µl (T4 pol + PNK) |
| TAQ polymerase | 2 µl |

Incubated at 25° C. temperature for 20 min., then 72° C. for 20 min., then 4° C. hold. Y adapter ligation, add directly to the reaction as follows:

| Endit A-tailed DNA | 50 µl |
| --- | --- |
| 2× Quick ligase buffer | 50 µl |
| 20 µM adapter | 1 µl |
| T4 DNA ligase (quick) | 2 µl |

Figure 71:
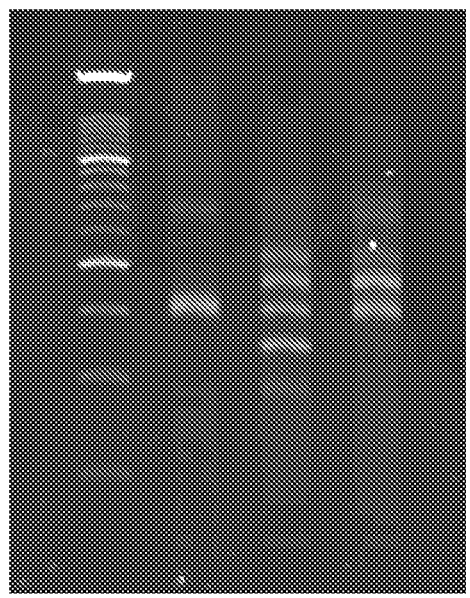
FIG. 71 depicts a diagnostic gel used to confirm combined reaction efficiency.

Incubated on PCR at 22° C. for 15 min. (total volume was at 107 µl) so 1.8 ampure=193 AMPure XP purified, ratio 1.8:1. Resuspended in 25 µl. Performed diagnostic gel on sample (FIG. 71), 2% egel, ran 16 min. Lane 1, marker; lane 2, pre-ligation control; lane 3, Kienow A tail; lane 4, Taq A tail.

The extra bands in lane 2 were the RNase H non-specific bands that got ligated. Now the question was to know if ligation will show one Y adapter vs. 2 Y adapters. Primer A 41 nt, primer B 43 nt=total 84. Without intending to be bound by scientific theory, this would mean that the first band would be proper ligation and the other one above would be something else because the final product is 100 bp or more, unless the FAM is causing this migration pattern. But ideally a phospho primer set, follow in PCR by a cycle of TAQ, would probably be the way to go . . . but phusion would compete for A tail of Taq. Test ligation of Y adapter on forever ladder test a few sizes. (no a-tailing concern here). Then test Taq A tailing sequential vs. mixed with the blunt ending.

PCR Test

Used primers (Table 19) that amplified the final product, so only double adapter ligation should get amplified exponentially. Started with a 1/10 dilution, did PCR of 15 cycles and see what happen on gel.

TABLE 19

| Reference | Purification | Sequence Name | Sequence | Tm |
| --- | --- | --- | --- | --- |
| 53164334 | Standard Desalting | 454 rapid top PCR | CCA TCT CAT CCC TGC GTG TCT CC (SEQ ID NO: 1016) | 61.4 |
| 53164335 | Standard Desalting | 454 rapid low PCR | CCT ATC CCC TGT GTG CCT TGA GAG (SEQ ID NO: 1017) | 60.9 |

Assembles a PCR test reaction as follows:

|  | 1× | 5× |
| --- | --- | --- |
| dH₂O | 15.75 μl (to 25 μl) | 78.75 |
| 1/10 dilution of DNA | 1 μl | — |
| 5× HF buffer | 5 μl | 25 |
| dNTP(10 mM) | 0.5 μl | 2.5 |
| primer up 10 μM | 1.25 | 6.25 |
| primer low 10 μM | 1.25 | 6.25 |
| phusion | 0.25 μl | 1.25 |

Thermal cycled as follows:

| 1 | 98° C. for 1 min. |
| --- | --- |
| 2 | 98° C. for 10 seconds |
| 3 | 65° C. for 20 seconds |
| 4 | 72° C. for 20 seconds went to step 2, 15x |
| 5 | 72° C. for 5 min. |
| 6 | 4° C. pause |

Figure 72:
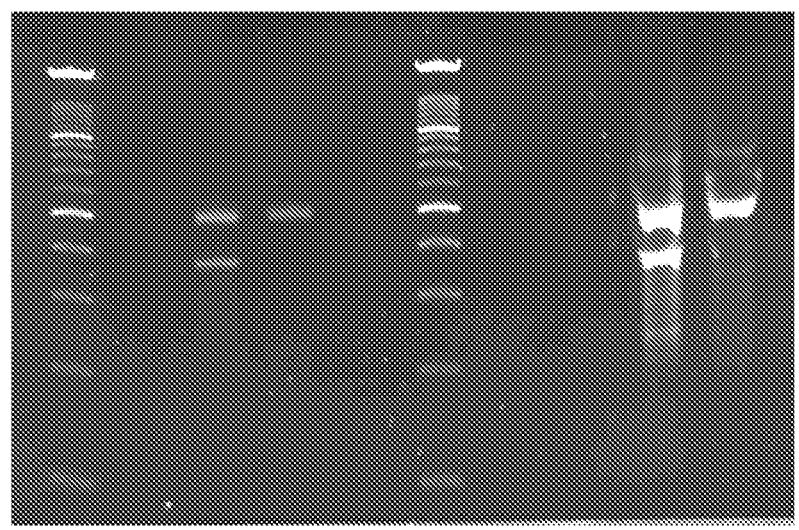
FIG. 72 depicts a diagnostic gel used to confirm PCR efficiency using primers that amplify the final product.

Loaded 2 μl and 20 μl samples on 2% ex gel and ran for 16 min. (FIG. 72). Sample 1, pre-ligation control; sample 2, Klenow A tail; sample 3, Taq A tail; sample 4, no template PCR control. Without intending to be bound by scientific theory, it appeared that the upper band was the correct one, the absence of FAM there would make it migrate slightly lower. An extraction would confirm once and for all, but the resulting enrichment looked very nice. (Re-ordered the primer with a 5' FAM on top primer and both HPLC purified.)

Performed a pippin prep extraction test. Band extraction pattern was as follows:

| 1 | 475 | 450-500 |  |
| --- | --- | --- | --- |
| 2 | 500 | 475-525 | nicely done |
| 3 | 538 | 500-575 |  |
| 4 | 500 | 460-540 | 100 bp ladder (7 μl pippin) extract 500 bp |

Loaded 20 μl of resulting elution chamber (60-80 μl) on 2% exgel (FIG. 73. Left panel pre-pippin; right panel, post-pippin. Lane 1, control FV-μ1 VDJ, HC purified. Validated PCR extraction. 1. negative control FV-μ1 (used 1 μl). 2. 475-525 (hypo:one Y adapter only). 3. 500-550 (hypo: 2 Y adapter).

Assembled a PCR test reaction as follow

|  | 1× | 4 |
| --- | --- | --- |
| dH₂O | 11.7 5 μl (to 25 μl) | 47 |
| pipin elution dilution of DNA | 5 μl | — |
| 5× HF buffer | 5 μl | 20 |
| dNTP (10 mM) | 0.5 μl | 2 |
| primer up 10 μM | 1.25 | 5 |
| primer low 10 μM | 1.25 | 5 |
| phusion | 0.25 μl | 1 |

Thermal cycled as follows (20 μl/tube):

| 1 | 98° C. for 1 min. |
| --- | --- |
| 2 | 98° C. for 10 seconds |
| 3 | 65° C. for 20 seconds |
| 4 | 72° C. for 20 seconds went to step 2, 15x |
| 5 | 72° C. for 5 min. |
| 6 | 4° C. pause |

Figure 74:
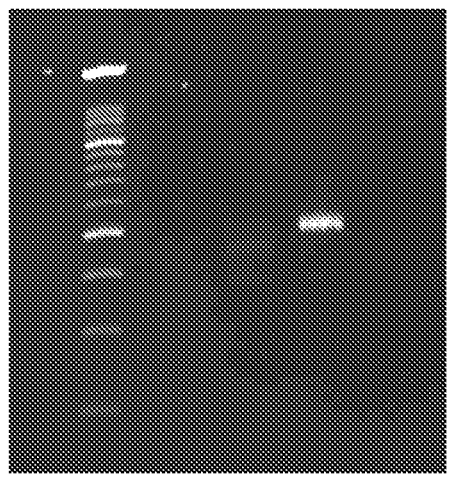
FIG. 74 depicts a diagnostic gel used to confirm PCR efficiency.

Loaded 2 μl and 20 μl samples on an ex gel, ran 16 min. (FIG. 74).

Optimize A-Tailing

Tried adding Klenow or Taq right after blunt ending (no cleanup), with an excess of dATP and fresh buffer. Then combined with or without cleanup prior ligation. Used post-ligation sample for initial testing. Two good-sized bands were obtained to evaluate efficiency: 1, Klenow–lig; 2, Klenow–clean+lig; 3, Taq lig; 4, Taq clean+lig; 5, bst largefrag lig; 6, bst largefrag clean+lig.

Used one of FV1 heavy chain, post PCR, post cleanup. Split reaction in 6 for testing. Performed blunting reaction using Enzymatics End repair kit as follows (use only half of PCR product maybe?):

|  | 1t | 8 |
| --- | --- | --- |
| H₂O | 0 μl (to 25 μl) | 104 |
| Purified DNA | 19 μl (6 DNA + 13 water) | — |
| 10× End repair buffer | 2.5 μl | 20 |
| 1 mM dNTP mix | 2.5 μl (0.1 mM) | 20 |
| enzyme mix (HC) | 1 μl | 8 |

Incubated at 25° C. temperature for 30 min. (19/t). Heat inactivated at 75° C. for 20 min. A-tailed by adding the following directly to the mixture (also did with TAQ and BST with proper buffers):

|  | 1t | 2t |
| --- | --- | --- |
| H₂O | 20 μl (add 25 to 50 μl) | 40 |
| Blunt DNA sample | 25 μl | 50 |
| 10× Klenow buffer | 2.5 μl | 5 |
| 10 mM dATP | 0.5 μl | 1 |
| Klenow exo HC (3' to 5' exo minus) | 2 μl | 4 |

Total reaction was now 50 μl. Klenow, incubated at 37° C. for 30 min., heat inactivated at 75° C. for 20 min. Taq, incubated at 72° C. for 30 min. BST, incubated at 65° C. for 30 min., heat inactivated at 80° C. for 10 min. Split each reaction in 2 tubes of 50. Apure XP purified half of each reaction, eluted in 50 ul. The other half was run directly in the ligation.

Y adapter ligation. The following were add directly to the reaction:

|  | 1t | 7t |
| --- | --- | --- |
| H₂O | 0 (add μl to 100 μl) | — |
| A-tailed DNA | 50 μl | — |
| 2× Quick ligase buffer | 46 μl | 322 |
| 20 μM adapter | 2 μl | 14 |
| T4 DNA ligase (quick) | 2 μl | 14 |

Figure 75:
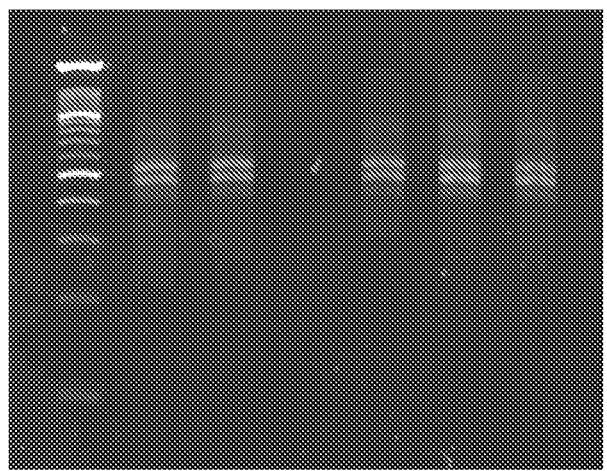
FIG. 75 depicts a diagnostic gel used to confirm ligation efficiency.

Incubated on PCR at 22° C. for 15 min. Total reaction was then 100 μl. Ampure, 1.8 ratio. Eluted in 25 μl (FIG. 75).

Pippin Prep Test 2 (Loading Quantity)

Pooled all samples. Nanodrop: 25 ng/μ1 ratio were way high (FAM?). Load on pippin prep at different quantity. Kept some to run as negative control. Extract range 475 to 550. Loaded on pippin nanodrop post-pippin. Sample 1, 2.5 μl; sample 2, 5; sample 3, 10; sample 4, 20; sample 5, ref. Ampure XP, eluted in 20 μl. Nanodrop all 0. Loaded 5 μl on 2% e-gel ex (FIG. 76). Did not look like the correct size was extracted. Without intending to be bound by scientific theory, this may be due to the fact that 475-550 was used instead of 475-525.

Finalize Library

The following protocol was designed to finalize remaining library. Plate was setup as follows (Table 20):

TABLE 20

| Library type (all heavy chains) | Row placement and BC info 1 = 13, etc. |
|---|---|
| Triple VDJ-HC GMC | A1-A10 |
| Triple VDJ-HC IDO | B1-B10 |
| Triple VDJ-HC FV | C1-C10 |
| RA | D1-D8 |
| HIV 1/2 | E1-E8 (5 progressor + 5 negative) BC; 1-2-3-4-5/6-7-8-9-10 |
| HIV 2/2 | F1-F7 (5 elite) BC; 1-2-3-4-5 |

Perform blunting reaction using Enzymatics End repair kit as follows (use only half of PCR product maybe):

|  | 1t | 60 |
|---|---|---|
| H₂O | 0 µl (to 25 µl) | 0 |
| Post PCR Purified DNA | 19 µl | — |
| 10× End repair buffer | 2.5 µl | 150 |
| 1 mM dNTP mix | 2.5 µl (0.1 mM) | 150 |
| enzyme mix (HC) | 1 µl | 60 |

Incubated at 25° C. temperature for 30 min. (19/t). Heat inactivated at 75° C. for 20 min. A-tailed by adding the following directly to the mixture:

|  | 1t | 60t |
|---|---|---|
| H₂O | 20 µl (to 50 µl) | 1200 |
| Blunt DNA sample | 25 µl | — |
| 10× Klenow buffer | 2.5 µl | 150 |
| 10 mM dATP | 0.5 µl | 30 |
| Klenow exo HC (3' to 5' exo minus) | 2 µl | 120 |

Total reaction was then 50 µl (25/t). Incubated at 37° C. for 30 min. Heat inactivated at 75° C. for 20 min.

Prepared 454 Y-adapters. 10 µl of 100 µM of each primer A and B+30 µl of (10 mM Tris, 0.1 mM EDTA at 50 mM NaCl)) (each adapter was at 20 µM final). Incubated at 95° C. for 3 min., ramp to 15° C. forever at 0.1° C./sec.

Y adapter ligation. The following was added directly to the reaction:

|  | 1t | 2×30t |
|---|---|---|
| H₂O | 0 (add µl to 100 µl) | — |
| A-tailed DNA | 50 µl | — |
| 2× Quick ligase buffer | 46 µl | 1380 |
| 20 µM adapter | 2 µl | — |
| T4 DNA ligase (quick) | 2 µl | 60 |

Incubated on PCR at 22° C. for 15 min. (48/t). Total reaction was then 100 µl. Ampured, eluted in 40 µl (used the liquidator). Library QC for pooling. Tested on HIV sample, tested only first 5 samples (progressor).

Example XIII sets forth ScFv primers. Example XIV sets forth methods of SOE-PCR and ScFV generation from single cells. Example XV sets forth VDJome analysis methods.

Example XIII

ScFv Primers

A strategy for nested PCR was devised. Primers used were the same primers used for the original VDJ-ome project. (See VDJ-ome_Primers for more detail on their design.) The primers were ordered on two plates. The Excel files for IDT were: Media: _left.xls, and Media: _right_RT.xls.

Mixing experiments were performed. The plates were ordered at 200 µM. The individual tubes were ordered LabReady at 100 µM. For plates, to make 2.5 µM each primer, 1 µL stock was added into 80 µL total volume of each primer. For tubes, to make 2.5 µM each primer, 2 µL stock was added into 80 µL total volume of each primer. Note, the IGHV, IGK/LV, IGHC, IHKJLC were four different primer mixes.

Gateway cloning primers were prepared, which are the "outer" primers with attB tags added on for Gateway cloning.

The attB primer sequences are:

```
>20100505_IGHV_left_attB1_1
                                     (SEQ ID NO: 216)
ggggacaagtttgtacaaaaaagcaggcttcGAGGTGCAGCTGGTGGAGT

CCG

>20100505_IGHV_left_attB1_2
                                     (SEQ ID NO: 217)
ggggacaagtttgtacaaaaaagcaggcttcGAGGTGCAGCTGGTGGAGT

CTGG

>20100505_IGHV_left_attB1_3
                                     (SEQ ID NO: 218)
ggggacaagtttgtacaaaaaagcaggettcCAGGTCACCTTGAGGGAGT

CTGGTCC

>20100505_IGHV_left_attB1_4
                                     (SEQ ID NO: 219)
ggggacaagtttgtacaaaaaagcaggcttcCAGGTTCAGCTGTTGCAGC

CTGG

>20100505_IGHV_left_attB1_5
                                     (SEQ ID NO: 220)
ggggacaagtttgtacaaaaaagcaggcttcCAGGTGCAGCTACAGCAGT

GGGG

>20100505_IGHV_left_attB1_6
                                     (SEQ ID NO: 221)
ggggacaagtttgtacaaaaaagcaggcttcCAGGTGCAGCTGGTGCAAT

CTGG

>20100505_IGHV_left_attB1_7
                                     (SEQ ID NO: 222)
ggggacaagtttgtacaaaaaagcaggettcCAGGTCACCTTGAAGGAGT

CTGGTCC

>20100505_IGHV_left_attB1_8
                                     (SEQ ID NO: 223)
ggggacaagtttgtacaaaaaagcaggcttcCAGGTCCAGCTGGTACAGT

CTGGG

>20100505_IGHV_left_attB1_9
                                     (SEQ ID NO: 224)
ggggacaagtttgtacaaaaaagcaggcttcCAGGACCAGTTGGTGCAGT

CTGGG
```

-continued

>20100505_IGHV_left_attB1_10
(SEQ ID NO: 225)
ggggacaagtttgtacaaaaaagcaggcttcCAGGTGCAGCTGGTGGAGT
CTGG >20100505_IGHV_left_attB1_11
(SEQ ID NO: 226)
ggggacaagtttgtacaaaaaagcaggcttcCAGATGCAGCTGGTGCAGT
CTGG >20100505_IGHV_left_attB1_12
(SEQ ID NO: 227)
ggggacaagtttgtacaaaaaagcaggcttcCAAATGCAGCTGGTGCAGT
CTGGG >20100505_IGHV_left_attB1_13
(SEQ ID NO: 228)
ggggacaagtttgtacaaaaaagcaggcttcGAAGTGCAGCTGGTGGAGT
CTGGG >20100505_IGHV_left_attB1_14
(SEQ ID NO: 229)
ggggacaagtttgtacaaaaaagcaggcttcCAGGTGCAGCTGGTGCAGT
CTG >20100505_IGHV_left_attB1_15
(SEQ ID NO: 230)
ggggacaagtttgtacaaaaaagcaggcttcGAGGATCAGCTGGTGGAGT
CTGGG >20100505_IGHV_left_attB1_16
(SEQ ID NO: 231)
ggggacaagtttgtacaaaaaagcaggcttcGAGGTCCAGCTGGTACAGT
CTGGG >20100505_IGHV_left_attB1_17
(SEQ ID NO: 232)
ggggacaagtttgtacaaaaaagcaggcttcCAGCTGCAGCTGCAGGAGT
CC >20100505_IGHV_left_attB1_18
(SEQ ID NO: 233)
ggggacaagtttgtacaaaaaagcaggcttcGAGGTGCAGCTGGTGGAGT
CTGG >20100505_IGHV_left_attB1_19
(SEQ ID NO: 234)
ggggacaagtttgtacaaaaaagcaggcttcCAGGTGCAGCTGGTGCAGT
CTG >20100505_IGHV_left_attB1_20
(SEQ ID NO: 235)
ggggacaagtttgtacaaaaaagcaggcttcCAGGTACAGCTGCAGCAGT
CAGGT >20100505_IGHV_left_attB1_21
(SEQ ID NO: 236)
ggggacaagtttgtacaaaaaagcaggcttcGAGATGCAGCTGGTGGAGT
CTGGG >20100505_IGHV_left_attB1_22
(SEQ ID NO: 237)
ggggacaagtttgtacaaaaaagcaggcttcGAGGTGCATCTGGTGGAGT
CTGGG >20100505_IGHV_left_attB1_23
(SEQ ID NO: 238)
ggggacaagtttgtacaaaaaagcaggcttcGAGGTGCAGCTGGTGGAGT
CTGG >20100505_IGHV_left_attB1_24
(SEQ ID NO: 239)
ggggacaagtttgtacaaaaaagcaggcttcGAGGTGCAGCTGGTGGAGT
CTGG >20100505_IGHV_left_attB1_25
(SEQ ID NO: 240)
ggggacaagtttgtacaaaaaagcaggcttcCAGGTCCAACTGGTGTAGT
CTGGAGC >20100505_IGHV_left_attB1_26
(SEQ ID NO: 241)
ggggacaagtttgtacaaaaaagcaggcttcGAGGTGCAGCTGGTGCAGT
CTG >20100505_IGHV_left_attB1_27
(SEQ ID NO: 242)
ggggacaagtttgtacaaaaaagcaggcttcGAGGTGCAGCTGGTGGAGT
CTCG >20100505_IGHV_left_attB1_28
(SEQ ID NO: 243)
ggggacaagtttgtacaaaaaagcaggcttcGAGGTTCAGCTGGTGCAGT
CTGGG >20100505_IGHV_left_attB1_29
(SEQ ID NO: 244)
ggggacaagtttgtacaaaaaagcaggcttcCAGGTGCAGCTGGTGCAGT
CTG >20100505_IGHV_left_attB1_30
(SEQ ID NO: 245)
ggggacaagtttgtacaaaaaagcaggcttcGAAGTGCAGCTGGTGCAGT
CTGG >20100505_IGHV_left_attB1_31
(SEQ ID NO: 246)
ggggacaagtttgtacaaaaaagcaggcttcGAGGTGGAGCTGATAGAGT
CCATAGA >20100505_IGHV_left_attB1_32
(SEQ ID NO: 247)
ggggacaagtttgtacaaaaaagcaggcttcACAGTGCAGCTGGTGGAGT
CTGG >20100505_IGHV_left_attB1_33
(SEQ ID NO: 248)
ggggacaagtttgtacaaaaaagcaggcttcGAGGTGCAGCTGGAGGAGT
CTGG >20100505_IGHV_left_attB1_34
(SEQ ID NO: 249)
ggggacaagtttgtacaaaaaagcaggcttcGAGGTACAGCTGGTGGAGT
CTGAAGA >20100505_IGHV_left_attB1_35
(SEQ ID NO: 250)
ggggacaagtttgtacaaaaaagcaggcttcCAGGTGCAGCTGCAGGAGT
CG

```
>20100505_IGHV_left_attB1_36
                                 (SEQ ID NO: 251)
ggggacaagtttgtacaaaaaagcaggcttcGAGGTGCAGCTGTTGGAGT

CTGGG

>20100505_IGHV_left_attB1_37
                                 (SEQ ID NO: 252)
ggggacaagtttgtacaaaaaagcaggcttcCAGGTGCAGCTGGGGCAGT

C

>20100505_IGHV_left_attB1_38
                                 (SEQ ID NO: 253)
ggggacaagtttgtacaaaaaagcaggcttcCAGCTGCAGCTGCAGGAGT

CG

>20100505_IGHV_left_attB1_39
                                 (SEQ ID NO: 254)
ggggacaagtttgtacaaaaaagcaggcttcCAGGTTCAGCTGGTGCAGT

CTGGA

>20100505_IGHV_left_attB1_40
                                 (SEQ ID NO: 255)
ggggacaagtttgtacaaaaaagcaggcttcGAGGTGCAGCTGGTAGAGT

CTGGG

>20100505_IGHV_left_attB1_41
                                 (SEQ ID NO: 256)
ggggacaagtttgtacaaaaaagcaggcttcCAGGTCCAGCTTGTGCAGT

CTGGG

>20100505_IGHV_left_attB1_42
                                 (SEQ ID NO: 257)
ggggacaagtttgtacaaaaaagcaggcttcGAGGTGCAGCTGTTGCAGT

CTGC

>20100505_IGHV_left_attB1_43
                                 (SEQ ID NO: 258)
ggggacaagtttgtacaaaaaagcaggcttcGAGGTACAACTGGTGGAGT

CTGGGGG

>20100505_IGHV_left_attB1_44
                                 (SEQ ID NO: 259)
ggggacaagtttgtacaaaaaagcaggcttcCAGATCACCTTGAAGGAGT

CTGGTCC

>20100505_IGHV_left_attB1_45
                                 (SEQ ID NO: 260)
ggggacaagtttgtacaaaaaagcaggcttcCAGGTACAGCTGATGCAGT

CTGGGG

>20100505_IGKJ_right_attB2_1
                                 (SEQ ID NO: 261)
ggggaccactttgtacaagaaagctgggtcTTTGATCTCCACCTTGGTCC

CTCCGC

>20100505_IGKJ_right_attB2_2
                                 (SEQ ID NO: 262)
ggggaccactttgtacaagaaagctgggtcTTTGATCTCCAGCTTGGTCC

CCTGG

>20100505_IGKJ_right_attB2_3
                                 (SEQ ID NO: 263)
ggggaccactttgtacaagaaagctgggtcTTTGATATCCACTTTGGTCC

CAGGGC

>20100505_IGKJ_right_attB2_4
                                 (SEQ ID NO: 264)
ggggaccactttgtacaagaaagctgggtcTTTGATTTCCACCTTGGTCC

CTTGGC

>20100505_IGKJ_right_attB2_5
                                 (SEQ ID NO: 265)
ggggaccactttgtacaagaaagctgggtcTTTAATCTCCAGTCGTGTCC

CTTGGC

>20100505_IGLJ_right_attB2_1
                                 (SEQ ID NO: 266)
ggggaccactttgtacaagaaagctgggtcGAGGACGGTCACCTTGGTGC

CA

>20100505_IGLJ_right_attB2_2
                                 (SEQ ID NO: 267)
ggggaccactttgtacaagaaagctgggtcTAGGACGGTCAGCTTGGTCC

CTCC

>20100505_IGLJ_right_attB2_3
                                 (SEQ ID NO: 268)
ggggaccactttgtacaagaaagctgggtcGAGGACGGTCAGCTGGGTGC

C

>20100505_IGLJ_right_attB2_4
                                 (SEQ ID NO: 269)
ggggaccactttgtacaagaaagctgggtcTAAAATGATCAGCTGGGTTC

CTCCAC

>20100505_IGLJ_right_attB2_5
                                 (SEQ ID NO: 270)
ggggaccactttgtacaagaaagctgggtcTAGGACGGTGACCTTGGTCC

CAGT

>20100505_IGLJ_right_attB2_6
                                 (SEQ ID NO: 271)
ggggaccactttgtacaagaaagctgggtcTAGGACGGTCAGCTCGGTCC

CC
```

The linker primers only (note truncation of one of them to match Tm):

```
>attB1_left (Tm: 61.7)
                                 (SEQ ID NO: 343)
GGGGACAAGTTTGTACAAAAAAGCAGGCTTC >attB2_right (Tm: 62.8)
                                 (SEQ ID NO: 344)
GGGGACCACTTTGTACAAGAAAGCTGGG
```

All primers were ordered at 200 μM. Mixes were made to 2.5 μM for each primer. Per 80 μL mix, stock of each primer was added (diluted in Tris-HCl)

scFv-USER sequences were as follows:

```
>20100826_scFv_USER_VH1/2for
                                 (SEQ ID NO: 272)
gttaggUGAGGAGACRGTGACCAGGGTG >20100826_scFv_USER_VH4/5for
                                 (SEQ ID NO: 273)
gttaggUGAGGAGACGGTGACCAGGGTT >20100826_scFv_USER_VH3for
                                 (SEQ ID NO: 274)
gttaggUGAAGAGACGGTGACCATTGT
```

-continued

>20100826_scFv_USER_VH6for
(SEQ ID NO: 275)
gttaggUGAGGAGACGGTGACCGTGGTCC

>20100826_scFv_USER_VL1back
(SEQ ID NO: 276)
gggatcuCAGTCTGTSBTGACGCAGCCGCC

>20100826_scFv_USER_VL3back
(SEQ ID NO: 277)
gggatcuTCCTATGWGCTGACWCAGCCAC

>20100826_scFv_USER_VL38back
(SEQ ID NO: 278)
gggatcuTCCTATGAGCTGAYRCAGCYACC

>20100826_scFv_USER_VL4back
(SEQ ID NO: 279)
gggatcuCAGCCTGTGCTGACTCARYC

>20100826_scFv_USER_VL7/8back
(SEQ ID NO: 280)
gggatcuCAGDCTGTGGTGACYCAGGAGCC

>20100826_scFv_USER_VL9back
(SEQ ID NO: 281)
gggatcuCAGCCWGKGCTGACTCAGCCMCC

>20100826_scFv_USER_VL11back
(SEQ ID NO: 282)
gggatcuTCCTCTGAGCTGASTCAGGASCC

>20100826_scFv_USER_VL13back
(SEQ ID NO: 283)
gggatcuCAGTCTGYYCTGAYTCAGCCT

>20100826_scFv_USER_VL15back
(SEQ ID NO: 284)
gggatcuAATTTTATGCTGACTCAGCCCC

>20100826_scFv_USER_VK1back
(SEQ ID NO: 285)
gggatcuGACATCCRGDTGACCCAGTCTCC

>20100826_scFv_USER_VK2backts
(SEQ ID NO: 286)
gggatcuGAAATTGTRWTGACRCAGTCTCC

>20100826_scFv_USER_VK9back
(SEQ ID NO: 287)
gggatcuGATATTGTGMTGACBCAGWCTCC

>20100826_scFv_USER_VK12back
(SEQ ID NO: 288)
gggatcuGAAACGACACTCACGCAGTCTC

>20100826_scFv_linker_upper_PEDS_11_405_LLA4_term_
(SEQ ID NO: 345)
TAGCGCGAGCCACAGTGGTTCTGCTCCGAATACTAGTTCTGCTCCGGGAT
CT >20100826_scFv_linker_lower_PEDS_11_405_LLA4_term_
(SEQ ID NO: 346)
TGGAGCAGAACTAGTATTCGGAGCAGAACCACTGTGGCTCGCGCTGTTAG
Gt USER sequences were as follows:

>20100827_USER_VH1/2for
(SEQ ID NO: 289)
agtctagUGAGGAGACRGTGACCAGGGTG

>20100827_USER_VH4/5for
(SEQ ID NO: 290)
agtctagUGAGGAGACGGTGACCAGGGTT

>20100827_USER_VH3for
(SEQ ID NO: 291)
agtctagUGAAGAGACGGTGACCATTGT

>20100827_USER_VH6for
(SEQ ID NO: 292)
agtctagUGAGGAGACGGTGACCGTGGCC

>20100827_USER_VL1back
(SEQ ID NO: 293)
actagacuCAGTCTGTSBTGACGCAGCCGCC

>20100827_USER_VL3back
(SEQ ID NO: 294)
actagacuTCCTATGWGCTGACWCAGCCAC

>20100827_USER_VL38back
(SEQ ID NO: 295)
actagacuTCCTATGAGCTGAYRCAGCYACC

>20100827_USER_VL4back
(SEQ ID NO: 296)
actagacuCAGCCTGTGCTGACTCARYC

>20100827_USER_VL7/8back
(SEQ ID NO: 297)
actagacuCAGDCTGTGGTGACYCAGGAGCC

>20100827_USER_VL9back
(SEQ ID NO: 298)
actagacuCAGCCWGKGCTGACTCAGCCMCC

>20100827_USER_VL11back
(SEQ ID NO: 299)
actagacuTCCTCTGAGCTGASTCAGGASCC

>20100827_USER_VL13back
(SEQ ID NO: 300)
actagacuCAGTCTGYYCTGAYTCAGCCT

>20100827_USER_VL15back
(SEQ ID NO: 301)
actagacuAATTTTATGCTGACTCAGCCCC

>20100827_USER_VK1back
(SEQ ID NO: 302)
actagacuGACATCCRGDTGACCCAGTCTCC

>20100827_USER_VK2backts
(SEQ ID NO: 303)
actagacuGAAATTGTRWTGACRCAGTCTCC

>20100827_USER_VK9back
(SEQ ID NO: 304)
actagacuGATATTGTGMTGACBCAGWCTCC

>20100827_USER_VK12back
(SEQ ID NO: 305)
actagacuGAAACGACACTCACGCAGTCTC

The scFv linker portions were ordered in individual tubes. Note: to order deoxyuridine, the IDT code used was: /ideoxyU/

20100826_scFv_USER_VH1/2for
(SEQ ID NO: 306)
gttagg/ideoxyU/GAGGAGACRGTGACCAGGGTG 20100826_scFv_USER_VH4/5for
(SEQ ID NO: 307)
gttagg/ideoxyU/GAGGAGACGGTGACCAGGGTT 20100826_scFv_USER_VH3for
(SEQ ID NO: 308)
gttagg/ideoxyU/GAAGAGACGGTGACCATTGT

```
20100826_scFv_USER_VH6for
                                     (SEQ ID NO: 309)
gttagg/ideoxyU/GAGGAGACGGTGACCGTGGTCC 20100826_scFv_USER_VL1back
                                     (SEQ ID NO: 310)
gggatc/ideoxyU/CAGTCTGTSBTGACGCAGCCGCC 20100826_scFv_USER_VL3back
                                     (SEQ ID NO: 311)
gggatc/ideoxyU/TCCTATGWGCTGACWCAGCCAC 20100826_scFv_USER_VL38back
                                     (SEQ ID NO: 312)
gggatc/ideoxyU/TCCTATGAGCTGAYRCAGCYACC 20100826_scFv_USER_VL4back
                                     (SEQ ID NO: 313)
gggatc/ideoxyU/CAGCCTGTGCTGACTCARYC 20100826_scFv_USER_VL7/8back
                                     (SEQ ID NO: 314)
gggatc/ideoxyU/CAGDCTGTGGTGACYCAGGAGCC 20100826_scFv_USER_VL9back
                                     (SEQ ID NO: 315)
gggatc/ideoxyU/CAGCCWGKGCTGACTCAGCCMCC 20100826_scFv_USER_VL11back
                                     (SEQ ID NO: 316)
gggatc/ideoxyU/TCCTCTGAGCTGASTCAGGASCC 20100826_scFv_USER_VL13back
                                     (SEQ ID NO: 317)
gggatc/ideoxyU/CAGTCTGYYCTGAYTCAGCCT 20100826_scFv_USER_VL15back
                                     (SEQ ID NO: 318)
gggatc/ideoxyU/AATTTTATGCTGACTCAGCCCC 20100826_scFv_USER_VK1back
                                     (SEQ ID NO: 319)
gggatc/ideoxyU/GACATCCRGDTGACCCAGTCTCC 20100826_scFv_USER_VK2backts
                                     (SEQ ID NO: 320)
gggatc/ideoxyU/GAAATTGTRWTGACRCAGTCTCC 20100826_scFv_USER_VK9back
                                     (SEQ ID NO: 321)
gggatc/ideoxyU/GATATTGTGMTGACBCAGWCTCC 20100826_scFv_USER_VK12back
                                     (SEQ ID NO: 322)
gggatc/ideoxyU/GAAACGACACTCACGCAGTCTC 20100827_USER_VH1/2for
                                     (SEQ ID NO: 323)
agtctag/ideoxyU/GAGGAGACRGTGACCAGGGTG 20100827_USER_VH4/5for
                                     (SEQ ID NO: 324)
agtctag/ideoxyU/GAGGAGACGGTGACCAGGGTT 20100827_USER_VH3for
                                     (SEQ ID NO: 325)
agtctag/ideoxyU/GAAGAGACGGTGACCATTGT 20100827_USER_VH6for
                                     (SEQ ID NO: 326)
agtctag/ideoxyU/GAGGAGACGGTGACCGTGGTCC 20100827_USER_VL1back
                                     (SEQ ID NO: 327)
actagac/ideoxyU/CAGTCTGTSBTGACGCAGCCGCC 20100827_USER_VL3back
                                     (SEQ ID NO: 328)
actagac/ideoxyU/TCCTATGWGCTGACWCAGCCAC 20100827_USER_VL38back
                                     (SEQ ID NO: 329)
actagac/ideoxyU/TCCTATGAGCTGAYRCAGCYACC 20100827_USER_VL4back
                                     (SEQ ID NO: 330)
actagac/ideoxyU/CAGCCTGTGCTGACTCARYC 20100827_USER_VL7/8back
                                     (SEQ ID NO: 331)
actagac/ideoxyU/CAGDCTGTGGTGACYCAGGAGCC 20100827_USER_VL9back
                                     (SEQ ID NO: 332)
actagac/ideoxyU/CAGCCWGKGCTGACTCAGCCMCC 20100827_USER_VL11back
                                     (SEQ ID NO: 333)
actagac/ideoxyU/TCCTCTGAGCTGASTCAGGASCC 20100827_USER_VL13back
                                     (SEQ ID NO: 334)
actagac/ideoxyU/CAGTCTGYYCTGAYTCAGCCT 20100827_USER_VL15back
                                     (SEQ ID NO: 335)
actagac/ideoxyU/AATTTTATGCTGACTCAGCCCC 20100827_USER_VK1back
                                     (SEQ ID NO: 336)
actagac/ideoxyU/GACATCCRGDTGACCCAGTCTCC 20100827_USER_VK2backts
                                     (SEQ ID NO: 337)
actagac/ideoxyU/GAAATTGTRWTGACRCAGTCTCC 20100827_USER_VK9back
                                     (SEQ ID NO: 338)
actagac/ideoxyU/GATATTGTGMTGACBCAGWCTCC 20100827_USER_VK12back
                                     (SEQ ID NO: 339)
actagac/ideoxyU/GAAACGACACTCACGCAGTCTC
``` scFv linker sequences were ordered from LabReady as 100 μM in pH 8 TE. The primers in the plate were at 200 μM, so they must be mixed and diluted. A 2.5 μM mix was made for each primer. Since they are 200 μM, we divided by 80. Per 80 μL total, put in 1 μL of each primer. Put K and L primers together. Made tubes with Tris-HCl first:

| Tube | Initial Tris-HCl per 80 μL |
|---|---|
| A | 76 |
| B | 67 |
| E | 76 |
| F | 67 |

Linker was:

```
>PEDS_11_405_LLA4
                                     (SEQ ID NO: 340)
CCTAACAGCGCGAGCCACAGTGGTTCTGCTCCGAATACTAGTTCTGCTCC

GGGATCC
```

The overlap was:

```
VL
                                     (SEQ ID NO: 341)
ACAGTGGTTCTGCTCCGAATACTAGTTCTGCTCCGGGATCCGAAATTGTG

TTGACGCAGTCTCCAGC
```

-continued

VH (SEQ ID NO: 342)
CTGGTGCCAGTGGCAGAGGAGTGGATTGTCGCGCTCGGTGTCACCAAGAC

GAGGCTTATGATC

| Primer target | Number of primers |
|---|---|
| IGHV (VH/heavy left) | 45 |
| IGHJ (VH/heavy right) | 8 |
| IGK/LV (VL/light left) | 68 |
| IGK/LJ (VL/light right) | 11 |

Sequences

>20100505_IGHV_left_1 (SEQ ID NO: 347)
GAGGTGCAGCTGGTGGAGTCCG

>20100505_IGHV_left_2 (SEQ ID NO: 348)
GAGGTGCAGCTGGTGGAGTCTGG

>20100505_IGHV_left_3 (SEQ ID NO: 349)
CAGGTCACCTTGAGGGAGTCTGGTCC

>20100505_IGHV_left_4 (SEQ ID NO: 350)
CAGGTTCAGCTGTTGCAGCCTGG

>20100505_IGHV_left_5 (SEQ ID NO: 351)
CAGGTGCAGCTACAGCAGTGGGG

>20100505_IGHV_left_6 (SEQ ID NO: 352)
CAGGTGCAGCTGGTGCAATCTGG

>20100505_IGHV_left_7 (SEQ ID NO: 353)
CAGGTCACCTTGAAGGAGTCTGGTCC

>20100505_IGHV_left_8 (SEQ ID NO: 354)
CAGGTCCAGCTGGTACAGTCTGGG

>20100505_IGHV_left_9 (SEQ ID NO: 355)
CAGGACCAGTTGGTGCAGTCTGGG

>20100505_IGHV_left_10 (SEQ ID NO: 356)
CAGGTGCAGCTGGTGGAGTCTGG

>20100505_IGHV_left_11 (SEQ ID NO: 357)
CAGATGCAGCTGGTGCAGTCTGG

>20100505_IGHV_left_12 (SEQ ID NO: 358)
CAAATGCAGCTGGTGCAGTCTGGG

>20100505_IGHV_left_13 (SEQ ID NO: 359)
GAAGTGCAGCTGGTGGAGTCTGGG

>20100505_IGHV_left_14 (SEQ ID NO: 360)
CAGGTGCAGCTGGTGCAGTCTG

>20100505_IGHV_left_15 (SEQ ID NO: 361)
GAGGATCAGCTGGTGGAGTCTGGG

>20100505_IGHV_left_16 (SEQ ID NO: 362)
GAGGTCCAGCTGGTACAGTCTGGG

>20100505_IGHV_left_17 (SEQ ID NO: 363)
CAGCTGCAGCTGCAGGAGTCC

>20100505_IGHV_left_18 (SEQ ID NO: 364)
GAGGTGCAGCTGGTGGAGTCTGG

>20100505_IGHV_left_19 (SEQ ID NO: 365)
CAGGTGCAGCTGGTGCAGTCTG

>20100505_IGHV_left_20 (SEQ ID NO: 366)
CAGGTACAGCTGCAGCAGTCAGGT

>20100505_IGHV_left_21 (SEQ ID NO: 367)
GAGATGCAGCTGGTGGAGTCTGGG

>20100505_IGHV_left_22 (SEQ ID NO: 368)
GAGGTGCATCTGGTGGAGTCTGGG

>20100505_IGHV_left_23 (SEQ ID NO: 369)
GAGGTGCAGCTGGTGGAGTCTGG

>20100505_IGHV_left_24 (SEQ ID NO: 370)
GAGGTGCAGCTGGTGGAGTCTGG

>20100505_IGHV_left_25 (SEQ ID NO: 371)
CAGGTCCAACTGGTGTAGTCTGGAGC

>20100505_IGHV_left_26 (SEQ ID NO: 372)
GAGGTGCAGCTGGTGCAGTCTG

>20100505_IGHV_left_27 (SEQ ID NO: 373)
GAGGTGCAGCTGGTGGAGTCTCG

>20100505_IGHV_left_28 (SEQ ID NO: 374)
GAGGTTCAGCTGGTGCAGTCTGGG

>20100505_IGHV_left_29 (SEQ ID NO: 375)
CAGGTGCAGCTGGTGCAGTCTG

>20100505_IGHV_left_30 (SEQ ID NO: 376)
GAAGTGCAGCTGGTGCAGTCTGG

>20100505_IGHV_left_31 (SEQ ID NO: 377)
GAGGTGGAGCTGATAGAGTCCATAGA

>20100505_IGHV_left_32 (SEQ ID NO: 378)
ACAGTGCAGCTGGTGGAGTCTGG

>20100505_IGHV_left_33 (SEQ ID NO: 379)
GAGGTGCAGCTGGAGGAGTCTGG

>20100505_IGHV_left_34 (SEQ ID NO: 380)
GAGGTACAGCTGGTGGAGTCTGAAGA

>20100505_IGHV_left_35 (SEQ ID NO: 381)
CAGGTGCAGCTGCAGGAGTCG

-continued

>20100505_IGHV_left_36
(SEQ ID NO: 382)
GAGGTGCAGCTGTTGGAGTCTGGG

>20100505_IGHV_left_37
(SEQ ID NO: 383)
CAGGTGCAGCTGGGGCAGTC

>20100505_IGHV_left_38
(SEQ ID NO: 384)
CAGCTGCAGCTGCAGGAGTCG

>20100505_IGHV_left_39
(SEQ ID NO: 385)
CAGGTTCAGCTGGTGCAGTCTGGA

>20100505_IGHV_left_40
(SEQ ID NO: 386)
GAGGTGCAGCTGGTAGAGTCTGGG

>20100505_IGHV_left_41
(SEQ ID NO: 387)
CAGGTCCAGCTTGTGCAGTCTGGG

>20100505_IGHV_left_42
(SEQ ID NO: 388)
GAGGTGCAGCTGTTGCAGTCTGC

>20100505_IGHV_left_43
(SEQ ID NO: 389)
GAGGTACAACTGGTGGAGTCTGGGGG

>20100505_IGHV_left_44
(SEQ ID NO: 390)
CAGATCACCTTGAAGGAGTCTGGTCC

>20100505_IGHV_left_45
(SEQ ID NO: 391)
CAGGTACAGCTGATGCAGTCTGGGG

>20100505_IGHJ_right_1_SOE_PEDS_11_405_LLA4
(SEQ ID NO: 392)
CTAGTATTCGGAGCAGAACCACTGTGGCTCGCGCTGTTAGGTGAGGAGAC

GGTGACCGTGGTC

>20100505_IGHJ_right_2_SOE_PEDS_11_405_LLA4
(SEQ ID NO: 393)
CTAGTATTCGGAGCAGAACCACTGTGGCTCGCGCTGTTAGGTGAGGAGAC

AGTGACCAGGGTGCC

>20100505_IGHJ_right_3_SOE_PEDS_11_405_LLA4
(SEQ ID NO: 394)
CTAGTATTCGGAGCAGAACCACTGTGGCTCGCGCTGTTAGGTGATGTGGC

TGCGGTCTCAGGG

>20100505_IGHJ_right_4_SOE_PEDS_11_405_LLA4
(SEQ ID NO: 395)
CTAGTATTCGGAGCAGAACCACTGTGGCTCGCGCTGTTAGGTGAGGAGAC

GGTGACCAGGGTTCC

>20100505_IGHJ_right_5_SOE_PEDS_11_405_LLA4
(SEQ ID NO: 396)
CTAGTATTCGGAGCAGAACCACTGTGGCTCGCGCTGTTAGGGACCCCTCA

GAAGCCAGACCACC

>20100505_IGHJ_right_6_SOE_PEDS_11_405_LLA4
(SEQ ID NO: 397)
CTAGTATTCGGAGCAGAACCACTGTGGCTCGCGCTGTTAGGTGAGGAGAC

GGTGACCAGGGTGC

>20100505_IGHJ_right_7_SOE_PEDS_11_405_LLA4
(SEQ ID NO: 398)
CTAGTATTCGGAGCAGAACCACTGTGGCTCGCGCTGTTAGGGACGTTCCC

AGGGAGACGGTGT

-continued

>20100505_IGHJ_right_8_SOE_PEDS_11_405_LLA4
(SEQ ID NO: 399)
CTAGTATTCGGAGCAGAACCACTGTGGCTCGCGCTGTTAGGTGAAGAGAC

GGTGACCATTGTCCCTT

>20100505_IGKV_left_1_SOE_PEDS_11_405_LLA4
(SEQ ID NO: 400)
ACAGTGGTTCTGCTCCGAATACTAGTTCTGCTCCGGGATCCGAAATTGTG

TTGACGCAGTCTCCAGC

>20100505_IGKV_left_2_SOE_PEDS_11_405_LLA4
(SEQ ID NO: 401)
ACAGTGGTTCTGCTCCGAATACTAGTTCTGCTCCGGGATCCGAAATTGTG

TTGACGCAGTCTCCAGG

>20100505_IGKV_left_3_SOE_PEDS_11_405_LLA4
(SEQ ID NO: 402)
ACAGTGGTTCTGCTCCGAATACTAGTTCTGCTCCGGGATCCGCCATCCAG

TTGACCCAGTCTCCA

>20100505_IGKV_left_4_SOE_PEDS_11_405_LLA4
(SEQ ID NO: 403)
ACAGTGGTTCTGCTCCGAATACTAGTTCTGCTCCGGGATCCGACATCCAG

ATGACTCAGCCTCCATC

>20100505_IGKV_left_5_SOE_PEDS_11_405_LLA4
(SEQ ID NO: 404)
ACAGTGGTTCTGCTCCGAATACTAGTTCTGCTCCGGGATCCGAAACGACA

CTCACGCAGTCTCCAGC

>20100505_IGKV_left_6_SOE_PEDS_11_405_LLA4
(SEQ ID NO: 405)
ACAGTGGTTCTGCTCCGAATACTAGTTCTGCTCCGGGATCCGACATCCAG

ATGACCCAGTCTCCATC

>20100505_IGKV_left_7_SOE_PEDS_11_405_LLA4
(SEQ ID NO: 406)
ACAGTGGTTCTGCTCCGAATACTAGTTCTGCTCCGGGATCCGACATCCAG

GTGACCCAGTCTCCATC

>20100505_IGKV_left_8_SOE_PEDS_11_405_LLA4
(SEQ ID NO: 407)
ACAGTGGTTCTGCTCCGAATACTAGTTCTGCTCCGGGATCCGACATTGTG

ATGACCCAGACTCCACT

>20100505_IGKV_left_9_SOE_PEDS_11_405_LLA4
(SEQ ID NO: 408)
ACAGTGGTTCTGCTCCGAATACTAGTTCTGCTCCGGGATCCGACATCGTG

ATGACCCAGTCTCCAGA

>20100505_IGKV_left_10_SOE_PEDS_11_405_LLA4
(SEQ ID NO: 409)
ACAGTGGTTCTGCTCCGAATACTAGTTCTGCTCCGGGATCCGCCATCCGG

ATGACCCAGTCTCC

>20100505_IGKV_left_11_SOE_PEDS_11_405_LLA4
(SEQ ID NO: 410)
ACAGTGGTTCTGCTCCGAATACTAGTTCTGCTCCGGGATCCGATGTTGTG

ATGACACAGTCTCCAGC

>20100505_IGKV_left_12_SOE_PEDS_11_405_LLA4
(SEQ ID NO: 411)
ACAGTGGTTCTGCTCCGAATACTAGTTCTGCTCCGGGATCCGATATTGTG

ATGACCCAGCATCTGCT

-continued

\>20100505_IGKV_left_13_SOE_PEDS_11_405_LLA4
(SEQ ID NO: 412)
ACAGTGGTTCTGCTCCGAATACTAGTTCTGCTCCGGGATCCGAAATAGTG

ATGACGCAGTCTCCAGC

\>20100505_IGKV_left_14_SOE_PEDS_11_405_LLA4
(SEQ ID NO: 413)
ACAGTGGTTCTGCTCCGAATACTAGTTCTGCTCCGGGATCCGATATTGTG

ATGACCCAGACTCCACC

\>20100505_IGKV_left_15_SOE_PEDS_11_405_LLA4
(SEQ ID NO: 414)
ACAGTGGTTCTGCTCCGAATACTAGTTCTGCTCCGGGATCCGACATCCAG

ATGATCCAGTCTCCATC

\>20100505_IGKV_left_16_SOE_PEDS_11_405_LLA4
(SEQ ID NO: 415)
ACAGTGGTTCTGCTCCGAATACTAGTTCTGCTCCGGGATCCGAAATTGTG

TTGACACAGTCTCCAGC

\>20100505_IGKV_left_17_SOE_PEDS_11_405_LLA4
(SEQ ID NO: 416)
ACAGTGGTTCTGCTCCGAATACTAGTTCTGCTCCGGGATCCGATATTGTG

ATGACTCAGTCTCCACT

\>20100505_IGKV_left_18_SOE_PEDS_11_405_LLA4
(SEQ ID NO: 417)
ACAGTGGTTCTGCTCCGAATACTAGTTCTGCTCCGGGATCCGCCATCCGG

ATGACCCAGTCTCC

\>20100505_IGKV_left_19_SOE_PEDS_11_405_LLA4
(SEQ ID NO: 418)
ACAGTGGTTCTGCTCCGAATACTAGTTCTGCTCCGGGATCCAACATCCAG

ATGACCCAGTCTCCATC

\>20100505_IGKV_left_20_SOE_PEDS_11_405_LLA4
(SEQ ID NO: 419)
ACAGTGGTTCTGCTCCGAATACTAGTTCTGCTCCGGGATCCGAAATTGTA

ATGACACAGTCTCCAGC

\>20100505_IGKV_left_21_SOE_PEDS_11_405_LLA4
(SEQ ID NO: 420)
ACAGTGGTTCTGCTCCGAATACTAGTTCTGCTCCGGGATCCGAAATTGTA

ATGACACAGTCTCCACC

\>20100505_IGKV_left_22_SOE_PEDS_11_405_LLA4
(SEQ ID NO: 421)
ACAGTGGTTCTGCTCCGAATACTAGTTCTGCTCCGGGATCCGATGTTGTG

ATGACTCAGTCTCCACT

\>20100505_IGKV_left_23_SOE_PEDS_11_405_LLA4
(SEQ ID NO: 422)
ACAGTGGTTCTGCTCCGAATACTAGTTCTGCTCCGGGATCCGACATTGTG

CTGACCCAGTCTCCAGC

\>20100505_IGKV_left_24_SOE_PEDS_11_405_LLA4
(SEQ ID NO: 423)
ACAGTGGTTCTGCTCCGAATACTAGTTCTGCTCCGGGATCCGACATCCAG

ATGACCCAGTCTCCTTC

\>20100505_IGKV_left_25_SOE_PEDS_11_405_LLA4
(SEQ ID NO: 424)
ACAGTGGTTCTGCTCCGAATACTAGTTCTGCTCCGGGATCCGAAATTGTG

CTGACTCAGTCTCCAGA

\>20100505_IGKV_left_26_SOE_PEDS_11_405_LLA4
(SEQ ID NO: 425)
ACAGTGGTTCTGCTCCGAATACTAGTTCTGCTCCGGGATCCGAGATTGTG

ATGACCCAGACTCCACT

\>20100505_IGKV_left_27_SOE_PEDS_11_405_LLA4
(SEQ ID NO: 426)
ACAGTGGTTCTGCTCCGAATACTAGTTCTGCTCCGGGATCCGCCATCCAG

ATGACCCAGTCTCCATC

\>20100505_IGKV_left_28_SOE_PEDS_11_405_LLA4
(SEQ ID NO: 427)
ACAGTGGTTCTGCTCCGAATACTAGTTCTGCTCCGGGATCCGACATCCAG

TTGACCCAGTCTCCATC

\>20100505_IGKV_left_29_SOE_PEDS_11_405_LLA4
(SEQ ID NO: 428)
ACAGTGGTTCTGCTCCGAATACTAGTTCTGCTCCGGGATCCGATATTGTG

ATGACCCAGACTCCACT

\>20100505_IGKV_left_30_SOE_PEDS_11_405_LLA4
(SEQ ID NO: 429)
ACAGTGGTTCTGCTCCGAATACTAGTTCTGCTCCGGGATCCGTCATCTGG

ATGACCCAGTCTCCATC

\>20100505_IGKV_left_31_SOE_PEDS_11_405_LLA4
(SEQ ID NO: 430)
ACAGTGGTTCTGCTCCGAATACTAGTTCTGCTCCGGGATCCGACATCCAG

ATGACCCAGCCTCCATC

\>20100505_IGKV_left_32_SOE_PEDS_11_405_LLA4
(SEQ ID NO: 431)
ACAGTGGTTCTGCTCCGAATACTAGTTCTGCTCCGGGATCCGAAATTGTG

TTGACACAGTCTCCAGG

\>20100505_IGKJ_right_1
(SEQ ID NO: 432)
TTTGATCTCCACCTTGGTCCCTCCGC

\>20100505_IGKJ_right_2
(SEQ ID NO: 433)
TTTGATCTCCAGCTTGGTCCCCTGG

\>20100505_IGKJ_right_3
(SEQ ID NO: 434)
TTTGATATCCACTTTGGTCCCAGGGC

\>20100505_IGKJ_right_4
(SEQ ID NO: 435)
TTTGATTTCCACCTTGGTCCCTTGGC

\>20100505_IGKJ_right_5
(SEQ ID NO: 436)
TTTAATCTCCAGTCGTGTCCCTTGGC

\>20100505_IGLV_left_1_SOE_PEDS_11_405_LLA4
(SEQ ID NO: 437)
ACAGTGGTTCTGCTCCGAATACTAGTTCTGCTCCGGGATCCCAGTCTGCC

CTGATTCAGCCTCCC

\>20100505_IGLV_left_2_SOE_PEDS_11_405_LLA4
(SEQ ID NO: 438)
ACAGTGGTTCTGCTCCGAATACTAGTTCTGCTCCGGGATCCCTGCCTGTG

CTGACTCAGCCCC

>20100505_IGLV_left_3_SOE_PEDS_11_405_LLA4
(SEQ ID NO: 439)
ACAGTGGTTCTGCTCCGAATACTAGTTCTGCTCCGGGATCCCAGCCTGTG

CTGACTCAGCCAC

>20100505_IGLV_left_4_SOE_PEDS_11_405_LLA4
(SEQ ID NO: 440)
ACAGTGGTTCTGCTCCGAATACTAGTTCTGCTCCGGGATCCTCTTCTGAG

CTGACTCAGGACCCTGC

>20100505_IGLV_left_5_SOE_PEDS_11_405_LLA4
(SEQ ID NO: 441)
ACAGTGGTTCTGCTCCGAATACTAGTTCTGCTCCGGGATCCCAATCTGCC

CTGACTCAGCCTCCT

>20100505_IGLV_left_6_SOE_PEDS_11_405_LLA4
(SEQ ID NO: 442)
ACAGTGGTTCTGCTCCGAATACTAGTTCTGCTCCGGGATCCTCCTATGAG

CTGACACAGCCACCC

>20100505_IGLV_left_7_SOE_PEDS_11_405_LLA4
(SEQ ID NO: 443)
ACAGTGGTTCTGCTCCGAATACTAGTTCTGCTCCGGGATCCCGGCCCGTG

CTGACTCAGC

>20100505_IGLV_left_8_SOE_PEDS_11_405_LLA4
(SEQ ID NO: 444)
ACAGTGGTTCTGCTCCGAATACTAGTTCTGCTCCGGGATCCCAGCCTGTG

CTGACTCAATCATCCTC

>20100505_IGLV_left_9_SOE_PEDS_11_405_LLA4
(SEQ ID NO: 445)
ACAGTGGTTCTGCTCCGAATACTAGTTCTGCTCCGGGATCCTCCTCTGAG

CTGAGTCAGGAGCCT

>20100505_IGLV_left_10_SOE_PEDS_11_405_LLA4
(SEQ ID NO: 446)
ACAGTGGTTCTGCTCCGAATACTAGTTCTGCTCCGGGATCCCAGTCTGCC

CTGACTCAGCCTCC

>20100505_IGLV_left_11_SOE_PEDS_11_405_LLA4
(SEQ ID NO: 447)
ACAGTGGTTCTGCTCCGAATACTAGTTCTGCTCCGGGATCCCAGTCTGTG

TTGACGCAGCCGC

>20100505_IGLV_left_12_SOE_PEDS_11_405_LLA4
(SEQ ID NO: 448)
ACAGTGGTTCTGCTCCGAATACTAGTTCTGCTCCGGGATCCCAGGCAGGG

CTGACTCAGCCA

>20100505_IGLV_left_13_SOE_PEDS_11_405_LLA4
(SEQ ID NO: 449)
ACAGTGGTTCTGCTCCGAATACTAGTTCTGCTCCGGGATCCCAGTCTGTG

TTGACGCAGCCGC

>20100505_IGLV_left_14_SOE_PEDS_11_405_LLA4
(SEQ ID NO: 450)
ACAGTGGTTCTGCTCCGAATACTAGTTCTGCTCCGGGATCCCAGTCTGTG

CTGACTCAGCCACCC

>20100505_IGLV_left_15_SOE_PEDS_11_405_LLA4
(SEQ ID NO: 451)
ACAGTGGTTCTGCTCCGAATACTAGTTCTGCTCCGGGATCCTCCTATGAG

CTGACTCAGCCACTCTC

>20100505_IGLV_left_16_SOE_PEDS_11_405_LLA4
(SEQ ID NO: 452)
ACAGTGGTTCTGCTCCGAATACTAGTTCTGCTCCGGGATCCCAGCCTGTG

CTGACTCAGCCAAC

>20100505_IGLV_left_17_SOE_PEDS_11_405_LLA4
(SEQ ID NO: 453)
ACAGTGGTTCTGCTCCGAATACTAGTTCTGCTCCGGGATCCTCCTATGAG

CTGACACAGCCACCC

>20100505_IGLV_left_18_SOE_PEDS_11_405_LLA4
(SEQ ID NO: 454)
ACAGTGGTTCTGCTCCGAATACTAGTTCTGCTCCGGGATCCTCCTATGAG

CTGACACAGCCATCCTC

>20100505_IGLV_left_19_SOE_PEDS_11_405_LLA4
(SEQ ID NO: 455)
ACAGTGGTTCTGCTCCGAATACTAGTTCTGCTCCGGGATCCCAGCCTGTG

CTGACTCAGCCAAC

>20100505_IGLV_left_20_SOE_PEDS_11_405_LLA4
(SEQ ID NO: 456)
ACAGTGGTTCTGCTCCGAATACTAGTTCTGCTCCGGGATCCTCCTATGAG

CTGACACAGCTACCCTC

>20100505_IGLV_left_21_SOE_PEDS_11_405_LLA4
(SEQ ID NO: 457)
ACAGTGGTTCTGCTCCGAATACTAGTTCTGCTCCGGGATCCCAGCCTGTG

CTGACTCAGCCATCT

>20100505_IGLV_left_22_SOE_PEDS_11_405_LLA4
(SEQ ID NO: 458)
ACAGTGGTTCTGCTCCGAATACTAGTTCTGCTCCGGGATCCTCCTCTGGG

CCAACTCAGGTGC

>20100505_IGLV_left_23_SOE_PEDS_11_405_LLA4
(SEQ ID NO: 459)
ACAGTGGTTCTGCTCCGAATACTAGTTCTGCTCCGGGATCCTCCTATGAG

CTGACTCAGCCACCCT

>20100505_IGLV_left_24_SOE_PEDS_11_405_LLA4
(SEQ ID NO: 460)
ACAGTGGTTCTGCTCCGAATACTAGTTCTGCTCCGGGATCCCAGACTGTG

GTGACCCAGGAGCC

>20100505_IGLV_left_25_SOE_PEDS_11_405_LLA4
(SEQ ID NO: 461)
ACAGTGGTTCTGCTCCGAATACTAGTTCTGCTCCGGGATCCCAGTCTGCC

CTGACTCAGCCTGC

>20100505_IGLV_left_26_SOE_PEDS_11_405_LLA4
(SEQ ID NO: 462)
ACAGTGGTTCTGCTCCGAATACTAGTTCTGCTCCGGGATCCAATTTTATG

CTGACTCAGCCCCACTC

>20100505_IGLV_left_27_SOE_PEDS_11_405_LLA4
(SEQ ID NO: 463)
ACAGTGGTTCTGCTCCGAATACTAGTTCTGCTCCGGGATCCTCCTATGAG

CTGATGCAGCCACCC

>20100505_IGLV_left_28_SOE_PEDS_11_405_LLA4
(SEQ ID NO: 464)
ACAGTGGTTCTGCTCCGAATACTAGTTCTGCTCCGGGATCCCAGGCTGTG

GTGACTCAGGAGCC

-continued

>20100505_IGLV_left_29_SOE_PEDS_11_405_LLA4
(SEQ ID NO: 465)
ACAGTGGTTCTGCTCCGAATACTAGTTCTGCTCCGGGATCCCAGCTTGTG
CTGACTCAATCGCCC >20100505_IGLV_left_30_SOE_PEDS_11_405_LLA4
(SEQ ID NO: 466)
ACAGTGGTTCTGCTCCGAATACTAGTTCTGCTCCGGGATCCCAGACTGTG
GTGACTCAGGAGCCC >20100505_IGLV_left_31_SOE_PEDS_11_405_LLA4
(SEQ ID NO: 467)
ACAGTGGTTCTGCTCCGAATACTAGTTCTGCTCCGGGATCCTCCTATGAG
CTGACTCAGCCACACTC >20100505_IGLV_left_32_SOE_PEDS_11_405_LLA4
(SEQ ID NO: 468)
ACAGTGGTTCTGCTCCGAATACTAGTTCTGCTCCGGGATCCCAGGCTGTG
CTGACTCAGCCG >20100505_IGLV_left_33_SOE_PEDS_11_405_LLA4
(SEQ ID NO: 469)
ACAGTGGTTCTGCTCCGAATACTAGTTCTGCTCCGGGATCCTCCTATGTG
CTGACTCAGCCACCC >20100505_IGLV_left_34_SOE_PEDS_11_405_LLA4
(SEQ ID NO: 470)
ACAGTGGTTCTGCTCCGAATACTAGTTCTGCTCCGGGATCCCAGTCTGCC
CTGACTCAGCCTCG >20100505_IGLV_left_35_SOE_PEDS_11_405_LLA4
(SEQ ID NO: 471)
ACAGTGGTTCTGCTCCGAATACTAGTTCTGCTCCGGGATCCCAGTCTGTT
CTGACTCAGCCTCGCT >20100505_IGLV_left_36_SOE_PEDS_11_405_LLA4
(SEQ ID NO: 472)
ACAGTGGTTCTGCTCCGAATACTAGTTCTGCTCCGGGATCCCAGTCTGTG
CTGACGCAGCCG >20100505_IGLJ_right_1
(SEQ ID NO: 473)
GAGGACGGTCACCTTGGTGCCA >20100505_IGLJ_right_2
(SEQ ID NO: 474)
TAGGACGGTCAGCTTGGTCCCTCC >20100505_IGLJ_right_3
(SEQ ID NO: 475)
GAGGACGGTCAGCTGGGTGCC >20100505_IGLJ_right_4
(SEQ ID NO: 476)
TAAAATGATCAGCTGGGTTCCTCCAC >20100505_IGLJ_right_5
(SEQ ID NO: 477)
TAGGACGGTGACCTTGGTCCCAGT >20100505_IGLJ_right_6
(SEQ ID NO: 478)
TAGGACGGTCAGCTCGGTCCCC SOE_PEDS_11_405_LLA4 primers were made. Made 2.5 μM mix of each primer. Since they are 200 μM, we must divide by 80. Per 80 μL total, put in 1 μL of each primer. Made tubes with Tris-HCl first:

| Tube | Initial buffer per 80 μL |
|------|--------------------------|
| A    | 18                       |
| B    | 17                       |
| C    | 72                       |
| D    | 4                        |
| E    | 4                        |
| F    | 4                        |
| G    | 69                       |
| H    |                          |

Then using a multichannel, pipette 1 μL per 80 of each column was pipetted into the tubes. Then tubes were combined as follows: A-FB, C, D+E+F, G.

The $T_m$ was designed for 62° C.

| Primer target | Number of primers |
|---------------|-------------------|
| IGHV (VH/heavy left) | 45 |
| IGHJ (VH/heavy right) | 8 |
| IGK/LV (VL/light left) | 68 |
| IGK/LJ (VL/light right) | 11 |

Sequences

>20100505_IGHV_left_1
(SEQ ID NO: 479)
GAGGTGCAGCTGGTGGAGTCCG

>20100505_IGHV_left_2
(SEQ ID NO: 480)
GAGGTGCAGCTGGTGGAGTCTGG

>20100505_IGHV_left_3
(SEQ ID NO: 481)
CAGGTCACCTTGAGGGAGTCTGGTCC

>20100505_IGHV_left_4
(SEQ ID NO: 482)
CAGGTTCAGCTGTTGCAGCCTGG

>20100505_IGHV_left_5
(SEQ ID NO: 483)
CAGGTGCAGCTACAGCAGTGGGG

>20100505_IGHV_left_6
(SEQ ID NO: 484)
CAGGTGCAGCTGGTGCAATCTGG

>20100505_IGHV_left_7
(SEQ ID NO: 485)
CAGGTCACCTTGAAGGAGTCTGGTCC

>20100505_IGHV_left_8
(SEQ ID NO: 486)
CAGGTCCAGCTGGTACAGTCTGGG

>20100505_IGHV_left_9
(SEQ ID NO: 487)
CAGGACCAGTTGGTGCAGTCTGGG

>20100505_IGHV_left_10
(SEQ ID NO: 488)
CAGGTGCAGCTGGTGGAGTCTGG

>20100505_IGHV_left_11
(SEQ ID NO: 489)
CAGATGCAGCTGGTGCAGTCTGG

>20100505_IGHV_left_12
(SEQ ID NO: 490)
CAAATGCAGCTGGTGCAGTCTGGG

-continued

>20100505_IGHV_left_13
(SEQ ID NO: 491)
GAAGTGCAGCTGGTGGAGTCTGGG

>20100505_IGHV_left_14
(SEQ ID NO: 492)
CAGGTGCAGCTGGTGCAGTCTG

>20100505_IGHV_left_15
(SEQ ID NO: 493)
GAGGATCAGCTGGTGGAGTCTGGG

>20100505_IGHV_left_16
(SEQ ID NO: 494)
GAGGTCCAGCTGGTACAGTCTGGG

>20100505_IGHV_left_17
(SEQ ID NO: 495)
CAGCTGCAGCTGCAGGAGTCC

>20100505_IGHV_left_18
(SEQ ID NO: 496)
GAGGTGCAGCTGGTGGAGTCTGG

>20100505_IGHV_left_19
(SEQ ID NO: 497)
CAGGTGCAGCTGGTGCAGTCTG

>20100505_IGHV_left_20
(SEQ ID NO: 498)
CAGGTACAGCTGCAGCAGTCAGGT

>20100505_IGHV_left_21
(SEQ ID NO: 499)
GAGATGCAGCTGGTGGAGTCTGGG

>20100505_IGHV_left_22
(SEQ ID NO: 500)
GAGGTGCATCTGGTGGAGTCTGGG

>20100505_IGHV_left_23
(SEQ ID NO: 501)
GAGGTGCAGCTGGTGGAGTCTGG

>20100505_IGHV_left_24
(SEQ ID NO: 502)
GAGGTGCAGCTGGTGGAGTCTGG

>20100505_IGHV_left_25
(SEQ ID NO: 503)
CAGGTCCAACTGGTGTAGTCTGGAGC

>20100505_IGHV_left_26
(SEQ ID NO: 504)
GAGGTGCAGCTGGTGCAGTCTG

>20100505_IGHV_left_27
(SEQ ID NO: 505)
GAGGTGCAGCTGGTGGAGTCTCG

>20100505_IGHV_left_28
(SEQ ID NO: 506)
GAGGTTCAGCTGGTGCAGTCTGGG

>20100505_IGHV_left_29
(SEQ ID NO: 507)
CAGGTGCAGCTGGTGCAGTCTG

>20100505_IGHV_left_30
(SEQ ID NO: 508)
GAAGTGCAGCTGGTGCAGTCTGG

>20100505_IGHV_left_31
(SEQ ID NO: 509)
GAGGTGGAGCTGATAGAGTCCATAGA

>20100505_IGHV_left_32
(SEQ ID NO: 510)
ACAGTGCAGCTGGTGGAGTCTGGG

>20100505_IGHV_left_33
(SEQ ID NO: 511)
GAGGTGCAGCTGGAGGAGTCTGG

>20100505_IGHV_left_34
(SEQ ID NO: 512)
GAGGTACAGCTGGTGGAGTCTGAAGA

>20100505_IGHV_left_35
(SEQ ID NO: 513)
CAGGTGCAGCTGCAGGAGTCG

>20100505_IGHV_left_36
(SEQ ID NO: 514)
GAGGTGCAGCTGTTGGAGTCTGGG

>20100505_IGHV_left_37
(SEQ ID NO: 515)
CAGGTGCAGCTGGGGCAGTC

>20100505_IGHV_left_38
(SEQ ID NO: 516)
CAGCTGCAGCTGCAGGAGTCG

>20100505_IGHV_left_39
(SEQ ID NO: 517)
CAGGTTCAGCTGGTGCAGTCTGGA

>20100505_IGHV_left_40
(SEQ ID NO: 518)
GAGGTGCAGCTGGTAGAGTCTGGG

>20100505_IGHV_left_41
(SEQ ID NO: 519)
CAGGTCCAGCTTGTGCAGTCTGGG

>20100505_IGHV_left_42
(SEQ ID NO: 520)
GAGGTGCAGCTGTTGCAGTCTGC

>20100505_IGHV_left_43
(SEQ ID NO: 521)
GAGGTACAACTGGTGGAGTCTGGGGG

>20100505_IGHV_left_44
(SEQ ID NO: 522)
CAGATCACCTTGAAGGAGTCTGGTCC

>20100505_IGHV_left_45
(SEQ ID NO: 523)
CAGGTACAGCTGATGCAGTCTGGGG

>20100505_IGHJ_right_1
(SEQ ID NO: 524)
TGAGGAGACGGTGACCGTGGTC

>20100505_IGHJ_right_2
(SEQ ID NO: 525)
TGAGGAGACAGTGACCAGGGTGCC

>20100505_IGHJ_right_3
(SEQ ID NO: 526)
TGATGTGGCTGCGGTCTCAGGG

>20100505_IGHJ_right_4
(SEQ ID NO: 527)
TGAGGAGACGGTGACCAGGGTTCC

>20100505_IGHJ_right_5
(SEQ ID NO: 528)
GACCCCTCAGAAGCCAGACCACC

>20100505_IGHJ_right_6
(SEQ ID NO: 529)
TGAGGAGACGGTGACCAGGGTGC

-continued

>20100505_IGHJ_right_7
(SEQ ID NO: 530)
GACGTTCCCAGGGAGACGGTGT

>20100505_IGHJ_right_8
(SEQ ID NO: 531)
TGAAGAGACGGTGACCATTGTCCCTT

>20100505_IGKV_left_1
(SEQ ID NO: 532)
GAAATTGTGTTGACGCAGTCTCCAGC

>20100505_IGKV_left_2
(SEQ ID NO: 533)
GAAATTGTGTTGACGCAGTCTCCAGG

>20100505_IGKV_left_3
(SEQ ID NO: 534)
GCCATCCAGTTGACCCAGTCTCCA

>20100505_IGKV_left_4
(SEQ ID NO: 535)
GACATCCAGATGACTCAGCCTCCATC

>20100505_IGKV_left_5
(SEQ ID NO: 536)
GAAACGACACTCACGCAGTCTCCAGC

>20100505_IGKV_left_6
(SEQ ID NO: 537)
GACATCCAGATGACCCAGTCTCCATC

>20100505_IGKV_left_7
(SEQ ID NO: 538)
GACATCCAGGTGACCCAGTCTCCATC

>20100505_IGKV_left_8
(SEQ ID NO: 539)
GACATTGTGATGACCCAGACTCCACT

>20100505_IGKV_left_9
(SEQ ID NO: 540)
GACATCGTGATGACCCAGTCTCCAGA

>20100505_IGKV_left_10
(SEQ ID NO: 541)
GCCATCCGGATGACCCAGTCTCC

>20100505_IGKV_left_11
(SEQ ID NO: 542)
GATGTTGTGATGACACAGTCTCCAGC

>20100505_IGKV_left_12
(SEQ ID NO: 543)
GATATTGTGATGACCCAGCATCTGCT

>20100505_IGKV_left_13
(SEQ ID NO: 544)
GAAATAGTGATGACGCAGTCTCCAGC

>20100505_IGKV_left_14
(SEQ ID NO: 545)
GATATTGTGATGACCCAGACTCCACC

>20100505_IGKV_left_15
(SEQ ID NO: 546)
GACATCCAGATGATCCAGTCTCCATC

>20100505_IGKV_left_16
(SEQ ID NO: 547)
GAAATTGTGTTGACACAGTCTCCAGC

>20100505_IGKV_left_17
(SEQ ID NO: 548)
GATATTGTGATGACTCAGTCTCCACT

>20100505_IGKV_left_18
(SEQ ID NO: 549)
GCCATCCGGATGACCCAGTCTCC

>20100505_IGKV_left_19
(SEQ ID NO: 550)
AACATCCAGATGACCCAGTCTCCATC

>20100505_IGKV_left_20
(SEQ ID NO: 551)
GAAATTGTAATGACACAGTCTCCAGC

>20100505_IGKV_left_21
(SEQ ID NO: 552)
GAAATTGTAATGACACAGTCTCCACC

>20100505_IGKV_left_22
(SEQ ID NO: 553)
GATGTTGTGATGACTCAGTCTCCACT

>20100505_IGKV_left_23
(SEQ ID NO: 554)
GACATTGTGCTGACCCAGTCTCCAGC

>20100505_IGKV_left_24
(SEQ ID NO: 555)
GACATCCAGATGACCCAGTCTCCTTC

>20100505_IGKV_left_25
(SEQ ID NO: 556)
GAAATTGTGCTGACTCAGTCTCCAGA

>20100505_IGKV_left_26
(SEQ ID NO: 557)
GAGATTGTGATGACCCAGACTCCACT

>20100505_IGKV_left_27
(SEQ ID NO: 558)
GCCATCCAGATGACCCAGTCTCCATC

>20100505_IGKV_left_28
(SEQ ID NO: 559)
GACATCCAGTTGACCCAGTCTCCATC

>20100505_IGKV_left_29
(SEQ ID NO: 560)
GATATTGTGATGACCCAGACTCCACT

>20100505_IGKV_left_30
(SEQ ID NO: 561)
GTCATCTGGATGACCCAGTCTCCATC

>20100505_IGKV_left_31
(SEQ ID NO: 562)
GACATCCAGATGACCCAGCCTCCATC

>20100505_IGKV_left_32
(SEQ ID NO: 563)
GAAATTGTGTTGACACAGTCTCCAGG

>20100505_IGLV_left_1
(SEQ ID NO: 564)
CAGTCTGCCCTGATTCAGCCTCCC

>20100505_IGLV_left_2
(SEQ ID NO: 565)
CTGCCTGTGCTGACTCAGCCCC

>20100505_IGLV_left_3
(SEQ ID NO: 566)
CAGCCTGTGCTGACTCAGCCAC

>20100505_IGLV_left_4
(SEQ ID NO: 567)
TCTTCTGAGCTGACTCAGGACCCTGC

>20100505_IGLV_left_5
(SEQ ID NO: 568)
CAATCTGCCCTGACTCAGCCTCCT

```
>20100505_IGLV_left_6
                                          (SEQ ID NO: 569)
TCCTATGAGCTGACACAGCCACCC >20100505_IGLV_left_7
                                          (SEQ ID NO: 570)
CGGCCCGTGCTGACTCAGC >20100505_IGLV_left_8
                                          (SEQ ID NO: 571)
CAGCCTGTGCTGACTCAATCATCCTC >20100505_IGLV_left_9
                                          (SEQ ID NO: 572)
TCCTCTGAGCTGAGTCAGGAGCCT >20100505_IGLV_left_10
                                          (SEQ ID NO: 573)
CAGTCTGCCCTGACTCAGCCTCC >20100505_IGLV_left_11
                                          (SEQ ID NO: 574)
CAGTCTGTGTTGACGCAGCCGC >20100505_IGLV_left_12
                                          (SEQ ID NO: 575)
CAGGCAGGGCTGACTCAGCCA >20100505_IGLV_left_13
                                          (SEQ ID NO: 576)
CAGTCTGTGTTGACGCAGCCGC >20100505_IGLV_left_14
                                          (SEQ ID NO: 577)
CAGTCTGTGCTGACTCAGCCACCC >20100505_IGLV_left_15
                                          (SEQ ID NO: 578)
TCCTATGAGCTGACTCAGCCACTCTC >20100505_IGLV_left_16
                                          (SEQ ID NO: 579)
CAGCCTGTGCTGACTCAGCCAAC >20100505_IGLV_left_17
                                          (SEQ ID NO: 580)
TCCTATGAGCTGACACAGCCACCC >20100505_IGLV_left_18
                                          (SEQ ID NO: 581)
TCCTATGAGCTGACACAGCCATCCTC >20100505_IGLV_left_19
                                          (SEQ ID NO: 582)
CAGCCTGTGCTGACTCAGCCAAC >20100505_IGLV_left_20
                                          (SEQ ID NO: 583)
TCCTATGAGCTGACACAGCTACCCTC >20100505_IGLV_left_21
                                          (SEQ ID NO: 584)
CAGCCTGTGCTGACTCAGCCATCT >20100505_IGLV_left_22
                                          (SEQ ID NO: 585)
TCCTCTGGGCCAACTCAGGTGC >20100505_IGLV_left_23
                                          (SEQ ID NO: 586)
TCCTATGAGCTGACTCAGCCACCCT >20100505_IGLV_left_24
                                          (SEQ ID NO: 587)
CAGACTGTGGTGACCCAGGAGCC >20100505_IGLV_left_25
                                          (SEQ ID NO: 588)
CAGTCTGCCCTGACTCAGCCTGC >20100505_IGLV_left_26
                                          (SEQ ID NO: 589)
AATTTTATGCTGACTCAGCCCCACTC >20100505_IGLV_left_27
                                          (SEQ ID NO: 590)
TCCTATGAGCTGATGCAGCCACCC >20100505_IGLV_left_28
                                          (SEQ ID NO: 591)
CAGGCTGTGGTGACTCAGGAGCC >20100505_IGLV_left_29
                                          (SEQ ID NO: 592)
CAGCTTGTGCTGACTCAATCGCCC >20100505_IGLV_left_30
                                          (SEQ ID NO: 593)
CAGACTGTGGTGACTCAGGAGCCC >20100505_IGLV_left_31
                                          (SEQ ID NO: 594)
TCCTATGAGCTGACTCAGCCACACTC >20100505_IGLV_left_32
                                          (SEQ ID NO: 595)
CAGGCTGTGCTGACTCAGCCG >20100505_IGLV_left_33
                                          (SEQ ID NO: 596)
TCCTATGTGCTGACTCAGCCACCC >20100505_IGLV_left_34
                                          (SEQ ID NO: 597)
CAGTCTGCCCTGACTCAGCCTCG >20100505_IGLV_left_35
                                          (SEQ ID NO: 598)
CAGTCTGTTCTGACTCAGCCTCGCT >20100505_IGLV_left_36
                                          (SEQ ID NO: 599)
CAGTCTGTGCTGACGCAGCCG >20100505_IGKJ_right_1
                                          (SEQ ID NO: 600)
TTTGATCTCCACCTTGGTCCCTCCGC >20100505_IGKJ_right_2
                                          (SEQ ID NO: 601)
TTTGATCTCCAGCTTGGTCCCCTGG >20100505_IGKJ_right_3
                                          (SEQ ID NO: 602)
TTTGATATCCACTTTGGTCCCAGGGC >20100505_IGKJ_right_4
                                          (SEQ ID NO: 603)
TTTGATTTCCACCTTGGTCCCTTGGC >20100505_IGKJ_right_5
                                          (SEQ ID NO: 604)
TTTAATCTCCAGTCGTGTCCCTTGGC >20100505_IGLJ_right_1
                                          (SEQ ID NO: 605)
GAGGACGGTCACCTTGGTGCCA >20100505_IGLJ_right_2
                                          (SEQ ID NO: 606)
TAGGACGGTCAGCTTGGTCCCTCC >20100505_IGLJ_right_3
                                          (SEQ ID NO: 607)
GAGGACGGTCAGCTGGGTGCC
```

-continued

>20100505_IGLJ_right_4
(SEQ ID NO: 608)
TAAAATGATCAGCTGGGTTCCTCCAC

>20100505_IGLJ_right_5
(SEQ ID NO: 609)
TAGGACGGTGACCTTGGTCCCAGT

>20100505_IGLJ_right_6
(SEQ ID NO: 610]
TAGGACGGTCAGCTCGGTCCCC

Primers were made. Made 2.5 µM mix in each primer. Since they are 200 µM, we must divide by 80. Per 80 µL total, put in 1 µL of each primer. Made tubes with Tris-HCl first:

| Tube | Initial buffer per 80 µL |
|---|---|
| A | 18 |
| B | 17 |
| C | 72 |
| D | 4 |
| E | 4 |
| F | 4 |
| G | 69 |
| H | |

Using a multichannel, 1 µL per 80 of each column was pipetted into the tubes. Then the tubes were combined as follows: A+B, C, D+E+F, G.

SOE_PEDS_11_405_LLA4 Primers were made.

Linker is:

>PEDS_11_405_LLA4
(SEQ ID NO: 611)
CCTAACAGCGCGAGCCACAGTGGTTCTGCTCCGAATACTAGTTCTGCTCC
GGGATCC

Example overlap is:

VL
(SEQ ID NO: 612)
ACAGTGGTTCTGCTCCGAATACTAGTTCTGCTCCGGGATCCCAGTCTGTG
TTGACGCAGCCGCC

VH
(SEQ ID NO: 613)
CCTGGTGCCAGTGGCAGAGGAGTGGATTGTCGCGCTCGGTGTCACCAAGA
CGAGGCTTATGATC

| Primer target | Number of primers |
|---|---|
| IGHV (VH/heavy left) | 22 |
| IGHJ (VH/heavy right) | 5 |
| IGK/LV (VL/light left) | 76 |
| IGK/LJ (VL/light right) | 10 |

Sequences

>20100329_VH4back|1
(SEQ ID NO: 614)
CAGGTGCAGCTGCAGGAGTCCG

>20100329_VH4back|2
(SEQ ID NO: 615)
CAGGTGCAGCTGCAGGAGTCGG

>20100329_VH5back|1
(SEQ ID NO: 616)
CAGGTACAGCTGCAGCAGTCA

>20100329_VH6back|1
(SEQ ID NO: 617)
CAGGTGCAGCTACAGCAGTGGG

>20100329_VH10back|1
(SEQ ID NO: 618)
GAGGTGCAGCTGGTGGAGACC

>20100329_VH10back|2
(SEQ ID NO: 619)
GAGGTGCAGCTGGTGGAGACT

>20100329_VH10back|3
(SEQ ID NO: 620)
GAGGTGCAGCTGGTGGAGTCC

>20100329_VH10back|4
(SEQ ID NO: 621)
GAGGTGCAGCTGGTGGAGTCT

>20100329_VH10back|5
(SEQ ID NO: 622)
GAGGTGCAGCTGTTGGAGACC

>20100329_VH10back|6
(SEQ ID NO: 623)
GAGGTGCAGCTGTTGGAGACT

>20100329_VH10back|7
(SEQ ID NO: 624)
GAGGTGCAGCTGTTGGAGTCC

>20100329_VH10back|8
(SEQ ID NO: 625)
GAGGTGCAGCTGTTGGAGTCT

>20100329_VH12back|1
(SEQ ID NO: 626)
CAGGTCCAGCTGGTACAGTCTGG

>20100329_VH12back|2
(SEQ ID NO: 627)
CAGGTCCAGCTGGTGCAGTCTGG

>20100329_VH12back|3
(SEQ ID NO: 628)
CAGGTCCAGCTTGTACAGTCTGG

>20100329_VH12back|4
(SEQ ID NO: 629)
CAGGTCCAGCTTGTGCAGTCTGG

>20100329_VH14back|1
(SEQ ID NO: 630)
CAGATCACCTTGAAGGAGTCTG

>20100329_VH14back|2
(SEQ ID NO: 631)
CAGGTCACCTTGAAGGAGTCTG

-continued

>20100329_VH22back|1
(SEQ ID NO: 632)
CAGGTGCAGCTGGTGCAATCTGG

>20100329_VH22back|2
(SEQ ID NO: 633)
CAGGTGCAGCTGGTGCAGTCTGG

>20100329_VH22back|3
(SEQ ID NO: 634)
CAGGTGCAGCTGGTGGAATCTGG

>20100329_VH22back|4
(SEQ ID NO: 635)
CAGGTGCAGCTGGTGGAGTCTGG

>20100329_VH1/2for|1_SOE_PEDS_11_405_LLA4
(SEQ ID NO: 636)
CTAGTATTCGGAGCAGAACCACTGTGGCTCGCGCTGTTAGGTGAGGAGAC

AGTGACCAGGGTG

>20100329_VH1/2for|2_SOE_PEDS_11_405_LLA4
(SEQ ID NO: 637)
CTAGTATTCGGAGCAGAACCACTGTGGCTCGCGCTGTTAGGTGAGGAGAC

GGTGACCAGGGTG

>20100329_VH4/5for|1_SOE_PEDS_11_405_LLA4
(SEQ ID NO: 638)
CTAGTATTCGGAGCAGAACCACTGTGGCTCGCGCTGTTAGGTGAGGAGAC

GGTGACCAGGGTT

>20100329_VH3for|1_SOE_PEDS_11_405_LLA4
(SEQ ID NO: 639)
CTAGTATTCGGAGCAGAACCACTGTGGCTCGCGCTGTTAGGTGAAGAGAC

GGTGACCATTGT

>20100329_VH6for|1_SOE_PEDS_11_405_LLA4
(SEQ ID NO: 640)
CTAGTATTCGGAGCAGAACCACTGTGGCTCGCGCTGTTAGGTGAGGAGAC

GGTGACCGTGGTCC

>20100329_VL1back|1_SOE_PEDS_11_405_LLA4
(SEQ ID NO: 641)
ACAGTGGTTCTGCTCCGAATACTAGTTCTGCTCCGGGATCCCAGTCTGTC

CTGACGCAGCCGCC

>20100329_VL1back|2_SOE_PEDS_11_405_LLA4
(SEQ ID NO: 642)
ACAGTGGTTCTGCTCCGAATACTAGTTCTGCTCCGGGATCCCAGTCTGTC

GTGACGCAGCCGCC

>20100329_VL1back|3_SOE_PEDS_11_405_LLA4
(SEQ ID NO: 643)
ACAGTGGTTCTGCTCCGAATACTAGTTCTGCTCCGGGATCCCAGTCTGTC

TTGACGCAGCCGCC

>20100329_VL1back|4_SOE_PEDS_11_405_LLA4
(SEQ ID NO: 644)
ACAGTGGTTCTGCTCCGAATACTAGTTCTGCTCCGGGATCCCAGTCTGTG

CTGACGCAGCCGCC

>20100329_VL1back|5_SOE_PEDS_11_405_LLA4
(SEQ ID NO: 645)
ACAGTGGTTCTGCTCCGAATACTAGTTCTGCTCCGGGATCCCAGTCTGTG

GTGACGCAGCCGCC

>20100329_VL1back|6_SOE_PEDS_11_405_LLA4
(SEQ ID NO: 646)
ACAGTGGTTCTGCTCCGAATACTAGTTCTGCTCCGGGATCCCAGTCTGTG

TTGACGCAGCCGCC

-continued

>20100329_VL3back|1_SOE_PEDS_11_405_LLA4
(SEQ ID NO: 647)
ACAGTGGTTCTGCTCCGAATACTAGTTCTGCTCCGGGATCCTCCTATGAG

CTGACACAGCCAC

>20100329_VL3back|2_SOE_PEDS_11_405_LLA4
(SEQ ID NO: 648)
ACAGTGGTTCTGCTCCGAATACTAGTTCTGCTCCGGGATCCTCCTATGAG

CTGACTCAGCCAC

>20100329_VL3back|3_SOE_PEDS_11_405_LLA4
(SEQ ID NO: 649)
ACAGTGGTTCTGCTCCGAATACTAGTTCTGCTCCGGGATCCTCCTATGTG

CTGACACAGCCAC

>20100329_VL3back|4_SOE_PEDS_11_405_LLA4
(SEQ ID NO: 650)
ACAGTGGTTCTGCTCCGAATACTAGTTCTGCTCCGGGATCCTCCTATGTG

CTGACTCAGCCAC

>20100329_VL38back|1_SOE_PEDS_11_405_LLA4
(SEQ ID NO: 651)
ACAGTGGTTCTGCTCCGAATACTAGTTCTGCTCCGGGATCCTCCTATGAG

CTGACACAGCCACC

>20100329_VL38back|2_SOE_PEDS_11_405_LLA4
(SEQ ID NO: 652)
ACAGTGGTTCTGCTCCGAATACTAGTTCTGCTCCGGGATCCTCCTATGAG

CTGACACAGCTACC

>20100329_VL38back|3_SOE_PEDS_11_405_LLA4
(SEQ ID NO: 653)
ACAGTGGTTCTGCTCCGAATACTAGTTCTGCTCCGGGATCCTCCTATGAG

CTGACGCAGCCACC

>20100329_VL38back|4_SOE_PEDS_11_405_LLA4
(SEQ ID NO: 654)
ACAGTGGTTCTGCTCCGAATACTAGTTCTGCTCCGGGATCCTCCTATGAG

CTGACGCAGCTACC

>20100329_VL38back|5_SOE_PEDS_11_405_LLA4
(SEQ ID NO: 655)
ACAGTGGTTCTGCTCCGAATACTAGTTCTGCTCCGGGATCCTCCTATGAG

CTGATACAGCCACC

>20100329_VL38back|6_SOE_PEDS_11_405_LLA4
(SEQ ID NO: 656)
ACAGTGGTTCTGCTCCGAATACTAGTTCTGCTCCGGGATCCTCCTATGAG

CTGATACAGCTACC

>20100329_VL38back|7_SOE_PEDS_11_405_LLA4
(SEQ ID NO: 657)
ACAGTGGTTCTGCTCCGAATACTAGTTCTGCTCCGGGATCCTCCTATGAG

CTGATGCAGCCACC

>20100329_VL38back|8_SOE_PEDS_11_405_LLA4
(SEQ ID NO: 658)
ACAGTGGTTCTGCTCCGAATACTAGTTCTGCTCCGGGATCCTCCTATGAG

CTGATGCAGCTACC

>20100329_VL4back|1_SOE_PEDS_11_405_LLA4
(SEQ ID NO: 659)
ACAGTGGTTCTGCTCCGAATACTAGTTCTGCTCCGGGATCCCAGCCTGTG

CTGACTCAACC

```
>20100329_VL4back|2_SOE_PEDS_11_405_LLA4
                          (SEQ ID NO: 660)
ACAGTGGTTCTGCTCCGAATACTAGTTCTGCTCCGGGATCCCAGCCTGTG

CTGACTCAATC

>20100329_VL4back|3_SOE_PEDS_11_405_LLA4
                          (SEQ ID NO: 661)
ACAGTGGTTCTGCTCCGAATACTAGTTCTGCTCCGGGATCCCAGCCTGTG

CTGACTCAGCC

>20100329_VL4back|4_SOE_PEDS_11_405_LLA4
                          (SEQ ID NO: 662)
ACAGTGGTTCTGCTCCGAATACTAGTTCTGCTCCGGGATCCCAGCCTGTG

CTGACTCAGTC

>20100329_VL7/8back|1_SOE_PEDS_11_405_LLA4
                          (SEQ ID NO: 663)
ACAGTGGTTCTGCTCCGAATACTAGTTCTGCTCCGGGATCCCAGACTGTG

GTGACCCAGGAGCC

>20100329_VL7/8back|2_SOE_PEDS_11_405_LLA4
                          (SEQ ID NO: 664)
ACAGTGGTTCTGCTCCGAATACTAGTTCTGCTCCGGGATCCCAGACTGTG

GTGACTCAGGAGCC

>20100329_VL7/8back|3_SOE_PEDS_11_405_LLA4
                          (SEQ ID NO: 665)
ACAGTGGTTCTGCTCCGAATACTAGTTCTGCTCCGGGATCCCAGGCTGTG

GTGACCCAGGAGCC

>20100329_VL7/8back|4_SOE_PEDS_11_405_LLA4
                          (SEQ ID NO: 666)
ACAGTGGTTCTGCTCCGAATACTAGTTCTGCTCCGGGATCCCAGGCTGTG

GTGACTCAGGAGCC

>20100329_VL7/8back|5_SOE_PEDS_11_405_LLA4
                          (SEQ ID NO: 667)
ACAGTGGTTCTGCTCCGAATACTAGTTCTGCTCCGGGATCCCAGTCTGTG

GTGACCCAGGAGCC

>20100329_VL7/8back|6_SOE_PEDS_11_405_LLA4
                          (SEQ ID NO: 668)
ACAGTGGTTCTGCTCCGAATACTAGTTCTGCTCCGGGATCCCAGTCTGTG

GTGACTCAGGAGCC

>20100329_VL9back|1_SOE_PEDS_11_405_LLA4
                          (SEQ ID NO: 669)
ACAGTGGTTCTGCTCCGAATACTAGTTCTGCTCCGGGATCCCAGCCAGGG

CTGACTCAGCCACC

>20100329_VL9back|2_SOE_PEDS_11_405_LLA4
                          (SEQ ID NO: 670)
ACAGTGGTTCTGCTCCGAATACTAGTTCTGCTCCGGGATCCCAGCCAGGG

CTGACTCAGCCCCC

>20100329_VL9back|3_SOE_PEDS_11_405_LLA4
                          (SEQ ID NO: 671)
ACAGTGGTTCTGCTCCGAATACTAGTTCTGCTCCGGGATCCCAGCCAGTG

CTGACTCAGCCACC

>20100329_VL9back|4_SOE_PEDS_11_405_LLA4
                          (SEQ ID NO: 672)
ACAGTGGTTCTGCTCCGAATACTAGTTCTGCTCCGGGATCCCAGCCAGTG

CTGACTCAGCCCCC

>20100329_VL9back|5_SOE_PEDS_11_405_LLA4
                          (SEQ ID NO: 673)
ACAGTGGTTCTGCTCCGAATACTAGTTCTGCTCCGGGATCCCAGCCTGGG

CTGACTCAGCCACC

>20100329_VL9back|6_SOE_PEDS_11_405_LLA4
                          (SEQ ID NO: 674)
ACAGTGGTTCTGCTCCGAATACTAGTTCTGCTCCGGGATCCCAGCCTGGG

CTGACTCAGCCCCC

>20100329_VL9back|7_SOE_PEDS_11_405_LLA4
                          (SEQ ID NO: 675)
ACAGTGGTTCTGCTCCGAATACTAGTTCTGCTCCGGGATCCCAGCCTGTG

CTGACTCAGCCACC

>20100329_VL9back|8_SOE_PEDS_11_405_LLA4
                          (SEQ ID NO: 676)
ACAGTGGTTCTGCTCCGAATACTAGTTCTGCTCCGGGATCCCAGCCTGTG

CTGACTCAGCCCCC

>20100329_VL11back|1_SOE_PEDS_11_405_LLA4
                          (SEQ ID NO: 677)
ACAGTGGTTCTGCTCCGAATACTAGTTCTGCTCCGGGATCCTCCTCTGAG

CTGACTCAGGACCC

>20100329_VL11back|2_SOE_PEDS_11_405_LLA4
                          (SEQ ID NO: 678)
ACAGTGGTTCTGCTCCGAATACTAGTTCTGCTCCGGGATCCTCCTCTGAG

CTGACTCAGGAGCC

>20100329_VL11back|3_SOE_PEDS_11_405_LLA4
                          (SEQ ID NO: 679)
ACAGTGGTTCTGCTCCGAATACTAGTTCTGCTCCGGGATCCTCCTCTGAG

CTGAGTCAGGACCC

>20100329_VL11back|4_SOE_PEDS_11_405_LLA4
                          (SEQ ID NO: 680)
ACAGTGGTTCTGCTCCGAATACTAGTTCTGCTCCGGGATCCTCCTCTGAG

CTGAGTCAGGAGCC

>20100329_VL13back|1_SOE_PEDS_11_405_LLA4
                          (SEQ ID NO: 681)
ACAGTGGTTCTGCTCCGAATACTAGTTCTGCTCCGGGATCCCAGTCTGCC

CTGACTCAGCCT

>20100329_VL13back|2_SOE_PEDS_11_405_LLA4
                          (SEQ ID NO: 682)
ACAGTGGTTCTGCTCCGAATACTAGTTCTGCTCCGGGATCCCAGTCTGCC

CTGATTCAGCCT

>20100329_VL13back|3_SOE_PEDS_11_405_LLA4
                          (SEQ ID NO: 683)
ACAGTGGTTCTGCTCCGAATACTAGTTCTGCTCCGGGATCCCAGTCTGCT

CTGACTCAGCCT

>20100329_VL13back|4_SOE_PEDS_11_405_LLA4
                          (SEQ ID NO: 684)
ACAGTGGTTCTGCTCCGAATACTAGTTCTGCTCCGGGATCCCAGTCTGCT

CTGATTCAGCCT

>20100329_VL13back|5_SOE_PEDS_11_405_LLA4
                          (SEQ ID NO: 685)
ACAGTGGTTCTGCTCCGAATACTAGTTCTGCTCCGGGATCCCAGTCTGTC

CTGACTCAGCCT
```

-continued

>20100329_VL13back|6_SOE_PEDS_11_405_LLA4
(SEQ ID NO: 686)
ACAGTGGTTCTGCTCCGAATACTAGTTCTGCTCCGGGATCCCAGTCTGTC

CTGATTCAGCCT

>20100329_VL13back|7_SOE_PEDS_11_405_LLA4
(SEQ ID NO: 687)
ACAGTGGTTCTGCTCCGAATACTAGTTCTGCTCCGGGATCCCAGTCTGTT

CTGACTCAGCCT

>20100329_VL13back|8_SOE_PEDS_11_405_LLA4
(SEQ ID NO: 688)
ACAGTGGTTCTGCTCCGAATACTAGTTCTGCTCCGGGATCCCAGTCTGTT

CTGATTCAGCCT

>20100329_VL15back|1_SOE_PEDS_11_405_LLA4
(SEQ ID NO: 689)
ACAGTGGTTCTGCTCCGAATACTAGTTCTGCTCCGGGATCCAATTTTATG

CTGACTCAGCCCC

>20100329_VK1back|1_SOE_PEDS_11_405_LLA4
(SEQ ID NO: 690)
ACAGTGGTTCTGCTCCGAATACTAGTTCTGCTCCGGGATCCGACATCCAG

ATGACCCAGTCTCC

>20100329_VK1back|2_SOE_PEDS_11_405_LLA4
(SEQ ID NO: 691)
ACAGTGGTTCTGCTCCGAATACTAGTTCTGCTCCGGGATCCGACATCCAG

GTGACCCAGTCTCC

>20100329_VK1back|3_SOE_PEDS_11_405_LLA4
(SEQ ID NO: 692)
ACAGTGGTTCTGCTCCGAATACTAGTTCTGCTCCGGGATCCGACATCCAG

TTGACCCAGTCTCC

>20100329_VK1back|4_SOE_PEDS_11_405_LLA4
(SEQ ID NO: 693)
ACAGTGGTTCTGCTCCGAATACTAGTTCTGCTCCGGGATCCGACATCCGG

ATGACCCAGTCTCC

>20100329_VK1back|5_SOE_PEDS_11_405_LLA4
(SEQ ID NO: 694)
ACAGTGGTTCTGCTCCGAATACTAGTTCTGCTCCGGGATCCGACATCCGG

GTGACCCAGTCTCC

>20100329_VK1back|6_SOE_PEDS_11_405_LLA4
(SEQ ID NO: 695)
ACAGTGGTTCTGCTCCGAATACTAGTTCTGCTCCGGGATCCGACATCCGG

TTGACCCAGTCTCC

>20100329_VK2backts|1_SOE_PEDS_11_405_LLA4
(SEQ ID NO: 696)
ACAGTGGTTCTGCTCCGAATACTAGTTCTGCTCCGGGATCCGAAATTGTA

ATGACACAGTCTCC

>20100329_VK2backts|2_SOE_PEDS_11_405_LLA4
(SEQ ID NO: 697)
ACAGTGGTTCTGCTCCGAATACTAGTTCTGCTCCGGGATCCGAAATTGTA

ATGACGCAGTCTCC

>20100329_VK2backts|3_SOE_PEDS_11_405_LLA4
(SEQ ID NO: 698)
ACAGTGGTTCTGCTCCGAATACTAGTTCTGCTCCGGGATCCGAAATTGTA

TTGACACAGTCTCC

>20100329_VK2backts|4_SOE_PEDS_11_405_LLA4
(SEQ ID NO: 699)
ACAGTGGTTCTGCTCCGAATACTAGTTCTGCTCCGGGATCCGAAATTGTA

TTGACGCAGTCTCC

>20100329_VK2backts|5_SOE_PEDS_11_405_LLA4
(SEQ ID NO: 700)
ACAGTGGTTCTGCTCCGAATACTAGTTCTGCTCCGGGATCCGAAATTGTG

ATGACACAGTCTCC

>20100329_VK2backts|6_SOE_PEDS_11_405_LLA4
(SEQ ID NO: 701)
ACAGTGGTTCTGCTCCGAATACTAGTTCTGCTCCGGGATCCGAAATTGTG

ATGACGCAGTCTCC

>20100329_VK2backts|7_SOE_PEDS_11_405_LLA4
(SEQ ID NO: 702)
ACAGTGGTTCTGCTCCGAATACTAGTTCTGCTCCGGGATCCGAAATTGTG

TTGACACAGTCTCC

>20100329_VK2backts|8_SOE_PEDS_11_405_LLA4
(SEQ ID NO: 703)
ACAGTGGTTCTGCTCCGAATACTAGTTCTGCTCCGGGATCCGAAATTGTG

TTGACGCAGTCTCC

>20100329_VK9back|1_SOE_PEDS_11_405_LLA4
(SEQ ID NO: 704)
ACAGTGGTTCTGCTCCGAATACTAGTTCTGCTCCGGGATCCGATATTGTG

ATGACCCAGACTCC

>20100329_VK9back|2_SOE_PEDS_11_405_LLA4
(SEQ ID NO: 705)
ACAGTGGTTCTGCTCCGAATACTAGTTCTGCTCCGGGATCCGATATTGTG

ATGACCCAGTCTCC

>20100329_VK9back|3_SOE_PEDS_11_405_LLA4
(SEQ ID NO: 706)
ACAGTGGTTCTGCTCCGAATACTAGTTCTGCTCCGGGATCCGATATTGTG

ATGACGCAGACTCC

>20100329_VK9back|4_SOE_PEDS_11_405_LLA4
(SEQ ID NO: 707)
ACAGTGGTTCTGCTCCGAATACTAGTTCTGCTCCGGGATCCGATATTGTG

ATGACGCAGTCTCC

>20100329_VK9back|5_SOE_PEDS_11_405_LLA4
(SEQ ID NO: 708)
ACAGTGGTTCTGCTCCGAATACTAGTTCTGCTCCGGGATCCGATATTGTG

ATGACTCAGACTCC

>20100329_VK9back|6_SOE_PEDS_11_405_LLA4
(SEQ ID NO: 709)
ACAGTGGTTCTGCTCCGAATACTAGTTCTGCTCCGGGATCCGATATTGTG

ATGACTCAGTCTCC

>20100329_VK9back|7_SOE_PEDS_11_405_LLA4
(SEQ ID NO: 710)
ACAGTGGTTCTGCTCCGAATACTAGTTCTGCTCCGGGATCCGATATTGTG

CTGACCCAGACTCC

>20100329_VK9back|8_SOE_PEDS_11_405_LLA4
(SEQ ID NO: 711)
ACAGTGGTTCTGCTCCGAATACTAGTTCTGCTCCGGGATCCGATATTGTG

CTGACCCAGTCTCC

-continued

```
>20100329_VK9back|9_SOE_PEDS_11_405_LLA4
                                   (SEQ ID NO: 712)
ACAGTGGTTCTGCTCCGAATACTAGTTCTGCTCCGGGATCCGATATTGTG

CTGACGCAGACTCC

>20100329_VK9back|10_SOE_PEDS_11_405_LLA4
                                   (SEQ ID NO: 713)
ACAGTGGTTCTGCTCCGAATACTAGTTCTGCTCCGGGATCCGATATTGTG

CTGACGCAGTCTCC

>20100329_VK9back|11_SOE_PEDS_11_405_LLA4
                                   (SEQ ID NO: 714)
ACAGTGGTTCTGCTCCGAATACTAGTTCTGCTCCGGGATCCGATATTGTG

CTGACTCAGACTCC

>20100329_VK9back|12_SOE_PEDS_11_405_LLA4
                                   (SEQ ID NO: 715)
ACAGTGGTTCTGCTCCGAATACTAGTTCTGCTCCGGGATCCGATATTGTG

CTGACTCAGTCTCC

>20100329_VK12back|1_SOE_PEDS_11_405_LLA4
                                   (SEQ ID NO: 716)
ACAGTGGTTCTGCTCCGAATACTAGTTCTGCTCCGGGATCCGAAACGACA

CTCACGCAGTCTC

>20100329_VL1/2for|1
                                   (SEQ ID NO: 717)
TAGGACGGTCACCTTGGTCC >20100329_VL1/2for|2
                                   (SEQ ID NO: 718)
TAGGACGGTCAGCTTGGTCC >20100329_VL1/2for|3
                                   (SEQ ID NO: 719)
TAGGACGGTGACCTTGGTCC >20100329_VL1/2for|4
                                   (SEQ ID NO: 720)
TAGGACGGTGAGCTTGGTCC >20100329_VL7for|1
                                   (SEQ ID NO: 721)
GAGGACGGTCAGCTGGGTGC >20100329_VK1for|1
                                   (SEQ ID NO: 722)
TTTGATTTCCACCTTGGTCC >20100329_VK2/4for|1
                                   (SEQ ID NO: 723)
TTTGATCTCCACCTTGGTCC >20100329_VK2/4for|2
                                   (SEQ ID NO: 724)
TTTGATCTCCAGCTTGGTCC >20100329_VK3for|1
                                   (SEQ ID NO: 725)
TTTGATATCCACTTTGGTCC >20100329_VK5for|1
                                   (SEQ ID NO: 726)
TTTAATCTCCAGTCGTGTCC
```

Primers were ordered from IDT in IDTE pH 8 at 200 µM concentration. Media: _SOE_PEDS_11_405_LLA4.xls. 2.5 µM mix was made for each primer. Since they were 200 µM, we must divide by 80. Per 80 µl, total, put in 1 µL of each primer. Made tubes with Tris-HCl first:

| Tube | Initial buffer per 80 µL |
|------|--------------------------|
| A    | 58                       |
| B    | 75                       |
| C    | 1                        |
| D    | 1                        |
| E    | 1                        |
| F    | 1                        |
| G    | 35                       |
| H    | 35                       |

Using a multichannel, 1 µL per 80 of each column was pipetted into the tubes. The tubes were combined as follows: A, B, C+D+E+F, G+H.

SOE_PNAS_85_5879_GRS3 primers were made.

scFv linker sequence:

```
>(G_4 S)_3 scFv linker from Huston
et al., PNAS 85: 5879
                                   (SEQ ID NO: 727)
GGTGGCGGTGGCTCGGGCGGTGGTGGGTCGGGTGGCGGCGGATCT
```

The counts were:

| Primer target          | Number of primers |
|------------------------|-------------------|
| IGHV (VH/heavy left)   | 7                 |
| IGHJ (VH/heavy right)  | 4                 |
| IGK/LV (VL/light left) | 13                |
| IGK/LJ (VL/light right)| 6                 |

The primers are below. "Back" are the 5' primers (to the left) and "for" are the 3' primers (to the right).

```
>20100329_VH4back
                                   (SEQ ID NO: 728)
CAGGTGCAGCTGCAGGAGTCSG >20100329_VH5back
                                   (SEQ ID NO: 729)
CAGGTACAGCTGCAGCAGTCA >20100329_VH6back
                                   (SEQ ID NO: 730)
CAGGTGCAGCTACAGCAGTGGG >20100329_VH10back
                                   (SEQ ID NO: 731)
GAGGTGCAGCTGKTGGAGWCY >20100329_VH12back
                                   (SEQ ID NO: 732)
CAGGTCCAGCTKGTRCAGTCTGG >20100329_VH14back
                                   (SEQ ID NO: 733)
CAGRTCACCTTGAAGGAGTCTG >20100329_VH22back
                                   (SEQ ID NO: 734)
CAGGTGCAGCTGGTGSARTCTGG >20100329_VH1/2for_SOE
                                   (SEQ ID NO: 735)
CCCGACCCACCACCGCCCGAGCCACCGCCACCTGAGGAGACRGTGACCAG
GGTG >20100329_VH4/5for_SOE
                                   (SEQ ID NO: 736)
CCCGACCCACCACCGCCCGAGCCACCGCCACCTGAGGAGACGGTGACCAG
GGTT
```

-continued

>20100329_VH3for_SOE
(SEQ ID NO: 737)
CCCGACCCACCACCGCCCGAGCCACCGCCACCTGAAGAGACGGTGACCAT
TGT >20100329_VH6for_SOE
(SEQ ID NO: 738)
CCCGACCCACCACCGCCCGAGCCACCGCCACCTGAGGAGACGGTGACCGT
GGTCC >20100329_VL1back_SOE
(SEQ ID NO: 739)
CGGGCGGTGGTGGGTCGGGTGGCGGCGGATCTCAGTCTGTSBTGACGCAG
CCGCC >20100329_VL3back_SOE
(SEQ ID NO: 740)
CGGGCGGTGGTGGGTCGGGTGGCGGCGGATCTTCCTATGWGCTGACWCA
GCCAC >20100329_VL38back_SOE
(SEQ ID NO: 741)
CGGGCGGTGGTGGGTCGGGTGGCGGCGGATCTTCCTATGAGCTGAYRCAG
CYACC >20100329_VL4back_SOE
(SEQ ID NO: 742)
CGGGCGGTGGTGGGTCGGGTGGCGGCGGATCTCAGCCTGTGCTGACTCAR
YC >20100329_VL7/8back_SOE
(SEQ ID NO: 743)
CGGGCGGTGGTGGGTCGGGTGGCGGCGGATCTCAGDCTGTGGTGACYCAG
GAGCC >20100329_VL9back_SOE
(SEQ ID NO: 744)
CGGGCGGTGGTGGGTCGGGTGGCGGCGGATCTCAGCCWGKGCTGACTCA
GCCMCC >20100329_VL11back_SOE
(SEQ ID NO: 745)
CGGGCGGTGGTGGGTCGGGTGGCGGCGGATCTTCCTCTGAGCTGASTCAG
GASCC >20100329_VL13back_SOE
(SEQ ID NO: 746)
CGGGCGGTGGTGGGTCGGGTGGCGGCGGATCTCAGTCTGYYCTGAYTCAG
CCT >20100329_VL15back_SOE
(SEQ ID NO: 747)
CGGGCGGTGGTGGGTCGGGTGGCGGCGGATCTAATTTTATGCTGACTCAG
CCCC >20100329_VL1/2fo
(SEQ ID NO: 748)
TAGGACGGTSASCTTGGTCC >20100329_VL7for
(SEQ ID NO: 749)
GAGGACGGTCAGCTGGGTGC >20100329_VK1back_SOE
(SEQ ID NO: 750)
CGGGCGGTGGTGGGTCGGGTGGCGGCGGATCTGACATCCRGDTGACCCAG
TCTCC >20100329_VK2backts_SOE
(SEQ ID NO: 751)
CGGGCGGTGGTGGGTCGGGTGGCGGCGGATCTGAAATTGTRWTGACRCAG
TCTCC >20100329_VK9back_SOE
(SEQ ID NO: 752)
CGGGCGGTGGTGGGTCGGGTGGCGGCGGATCTGATATTGTGMTGACBCAG
WCTCC >20100329_VK12back_SOE
(SEQ ID NO: 753)
CGGGCGGTGGTGGGTCGGGTGGCGGCGGATCTGAAACGACACTCACGCAG
TCTC >20100329_VK1for
(SEQ ID NO: 754)
TTTGATTTCCACCTTGGTCC >20100329_VK2/4for
(SEQ ID NO: 755)
TTTGATCTCCASCTTGGTCC >20100329_VK3for
(SEQ ID NO: 756)
TTTGATATCCACTTTGGTCC >20100329_VK5fo
(SEQ ID NO: 757)
TTTAATCTCCAGTCGTGTCC The IDT plate was arranged as follows:

| Well Position | Name | Sequence |
|---|---|---|
| A1 | 20100329_VH4back | CAGGTGCAGCTGCAGGAGTCSG (SEQ ID NO: 758) |
| A2 | 20100329_VH5back | CAGGTACAGCTGCAGCAGTCA (SEQ ID NO: 759) |
| A3 | 20100329_VH6back | CAGGTGCAGCTACAGCAGTGGG (SEQ ID NO: 760) |
| A4 | 20100329_VH10back | GAGGTGCAGCTGKTGGAGWCY (SEQ ID NO: 761) |
| A5 | 20100329_VH12back | CAGGTCCAGCTKGTRCAGTCTGG (SEQ ID NO: 762) |
| A6 | 20100329_VH14back | CAGRTCACCTTGAAGGAGTCTG (SEQ ID NO: 763) |
| A7 | 20100329_VH22back | CAGGTGCAGCTGGTGSARTCTGG (SEQ ID NO: 764) |
| B1 | 20100329_VH1/2for_SOE | CCCGACCCACCACCGCCCGAGCCACCGCCACCTGAGGAGACRGTGACCAGGGTG (SEQ ID NO: 765) |

-continued

| Well Position | Name | Sequence |
|---|---|---|
| B2 | 20100329_VH4/5for_SOE | CCCGACCCACCACCGCCCGAGCCACCGCCACCTGA GGAGACGGTGACCAGGGTT (SEQ ID NO: 766) |
| B3 | 20100329_VH3for_SOE | CCCGACCCACCACCGCCCGAGCCACCGCCACCTGA AGAGACGGTGACCATTGT (SEQ ID NO: 767) |
| B4 | 20100329_VH6for_SOE | CCCGACCCACCACCGCCCGAGCCACCGCCACCTGA GGAGACGGTGACCGTGGTCC (SEQ ID NO: 768) |
| C1 | 20100329_VL1back_SOE | CGGGCGGTGGTGGGTCGGGTGGCGGCGGATCTCAG TCTGTSBTGACGCAGCCGCC (SEQ ID NO: 769) |
| C2 | 20100329_VL3back_SOE | CGGGCGGTGGTGGGTCGGGTGGCGGCGGATCTTCC TATGWGCTGACWCAGCCAC (SEQ ID NO: 770) |
| C3 | 20100329_VL38back_SOE | CGGGCGGTGGTGGGTCGGGTGGCGGCGGATCTTCC TATGAGCTGAYRCAGCYACC (SEQ ID NO: 771) |
| C4 | 20100329_VL4back_SOE | CGGGCGGTGGTGGGTCGGGTGGCGGCGGATCTCAG CCTGTGCTGACTCARYC (SEQ ID NO: 772) |
| C5 | 20100329_VL7/8back_SOE | CGGGCGGTGGTGGGTCGGGTGGCGGCGGATCTCAG DCTGTGGTGACYCAGGAGCC (SEQ ID NO: 773) |
| C6 | 20100329_VL9back_SOE | CGGGCGGTGGTGGGTCGGGTGGCGGCGGATCTCAG CCWGKGCTGACTCAGCCMCC (SEQ ID NO: 774) |
| C7 | 20100329_VL11back_SOE | CGGGCGGTGGTGGGTCGGGTGGCGGCGGATCTTCC TCTGAGCTGASTCAGGASCC (SEQ ID NO: 775) |
| C8 | 20100329_VL13back_SOE | CGGGCGGTGGTGGGTCGGGTGGCGGCGGATCTCAG TCTGYYCTGAYTCAGCCT (SEQ ID NO: 776) |
| C9 | 20100329_VL15back_SOE | CGGGCGGTGGTGGGTCGGGTGGCGGCGGATCTAAT TTTATGCTGACTCAGCCCC (SEQ ID NO: 777) |
| D1 | 20100329_VL1/2for | TAGGACGGTSASCTTGGTCC (SEQ ID NO: 778) |
| D2 | 20100329_VL7for | GAGGACGGTCAGCTGGGTGC (SEQ ID NO: 779) |
| E1 | 20100329_VK1back_SOE | CGGGCGGTGGTGGGTCGGGTGGCGGCGGATCTGAC ATCCRGDTGACCCAGTCTCC (SEQ ID NO: 780) |
| E2 | 20100329_VK2backts_SOE | CGGGCGGTGGTGGGTCGGGTGGCGGCGGATCTGAA ATTGTRWTGACRCAGTCTCC (SEQ ID NO: 781) |
| E3 | 20100329_VK9back_SOE | CGGGCGGTGGTGGGTCGGGTGGCGGCGGATCTGAT ATTGTGMTGACBCAGWCTCC (SEQ ID NO: 782) |
| E4 | 20100329_VK12back_SOE | CGGGCGGTGGTGGGTCGGGTGGCGGCGGATCTGAA ACGACACTCACGCAGTCTC (SEQ ID NO: 783) |
| F1 | 20100329_VK1for | TTTGATTTCCACCTTGGTCC (SEQ ID NO: 784) |
| F2 | 20100329_VK2/4for | TTTGATCTCCASCTTGGTCC (SEQ ID NO: 785) |
| F3 | 20100329_VK3for | TTTGATATCCACTTTGGTCC (SEQ ID NO: 786) |
| F4 | 20100329_VK5for | TTTAATCTCCAGTCGTGTCC (SEQ ID NO: 787) |

"Linker primers" were ordered that were only complementary to the linker.

(SEQ ID NO: 788)
5' CGGGCGGTGGTGGGTCGGGTGGCGGCGGATCTCAGTCTGTSBTGACGCAGCCGCC (SEQ ID NO: 789)
3' TGGGACCAGTGGCAGAGGAGTCCACCGCCACCGAGCCCGCCACCACCAGCCC

>VHfor_SOE_linker
(SEQ ID NO: 790)
CCCGACCCACCACCGCCCG

>VLback_SOE_linker
(SEQ ID NO: 791)
CGGGCGGTGGTGGGTCGGG

>20100329_VH1/2for
(SEQ ID NO: 792)
TGAGGAGACRGTGACCAGGGTG

-continued

>20100329_VH4/5for (SEQ ID NO: 793)
TGAGGAGACGGTGACCAGGGTT

>20100329_VH3for (SEQ ID NO: 794)
TGAAGAGACGGTGACCATTGT

>20100329_VH6for (SEQ ID NO: 795)
TGAGGAGACGGTGACCGTGGTCC

>20100329_VL1back (SEQ ID NO: 796)
CAGTCTGTSBTGACGCAGCCGCC

>20100329_VL3back (SEQ ID NO: 797)
TCCTATGWGCTGACWCAGCCAC

>20100329_VL38back (SEQ ID NO: 798)
TCCTATGAGCTGAYRCAGCYACC

>20100329_VL4back (SEQ ID NO: 799)
CAGCCTGTGCTGACTCARYC

>20100329_VL7/8back (SEQ ID NO: 800)
CAGDCTGTGGTGACYCAGGAGCC

>20100329_VL9back (SEQ ID NO: 801)
CAGCCWGKGCTGACTCAGCCMCC

>20100329_VL11back (SEQ ID NO: 802)
TCCTCTGAGCTGASTCAGGASCC

>20100329_VL13back (SEQ ID NO: 803)
CAGTCTGYYCTGAYTCAGCCT

>20100329_VL15back (SEQ ID NO: 804)
AATTTTATGCTGACTCAGCCCC

>20100329_VK1back (SEQ ID NO: 805)
GACATCCRGDTGACCCAGTCTCC

>20100329_VK2backts (SEQ ID NO: 806)
GAAATTGTRWTGACRCAGTCTCC

>20100329_VK9back (SEQ ID NO: 807)
GATATTGTGMTGACBCAGWCTCC

>20100329_VK12back (SEQ ID NO: 808)
GAAACGACACTCACGCAGTCTC

These were arranged in the plate as follows:

| Well Position | Name | Sequence |
|---|---|---|
| A1 | 20100329_VH1/2for | TGAGGAGACRGTGACCAGGGTG (SEQ ID NO: 810) |
| A2 | 20100329_VH4/5for | TGAGGAGACGGTGACCAGGGTT (SEQ ID NO: 811) |
| A3 | 20100329_VH3for | TGAAGAGACGGTGACCATTGT (SEQ ID NO: 812) |
| A4 | 20100329_VH6for | TGAGGAGACGGTGACCGTGGTCC (SEQ ID NO: 813) |
| C1 | 20100329_VL1back | CAGTCTGTSBTGACGCAGCCGCC (SEQ ID NO: 814) |
| C2 | 20100329_VL3back | TCCTATGWGCTGACWCAGCCAC (SEQ ID NO: 815) |
| C3 | 20100329_VL38back | TCCTATGAGCTGAYRCAGCYACC (SEQ ID NO: 816) |
| C4 | 20100329_VL4back | CAGCCTGTGCTGACTCARYC (SEQ ID NO: 817) |
| C5 | 20100329_VL7/8back | CAGDCTGTGGTGACYCAGGAGCC (SEQ ID NO: 818) |
| C6 | 20100329_VL9back | CAGCCWGKGCTGACTCAGCCMCC (SEQ ID NO: 819) |
| C7 | 20100329_VL11back | TCCTCTGAGCTGASTCAGGASCC (SEQ ID NO: 820) |
| C8 | 20100329_VL13back | CAGTCTGYYCTGAYTCAGCCT (SEQ ID NO: 821) |
| C9 | 20100329_VL15back | AATTTTATGCTGACTCAGCCCC (SEQ ID NO: 822) |
| E1 | 20100329_VK1back | GACATCCRGDTGACCCAGTCTCC (SEQ ID NO: 823) |
| E2 | 20100329_VK2backts | GAAATTGTRWTGACRCAGTCTCC (SEQ ID NO: 824) |
| E3 | 20100329_VK9back | GATATTGTGMTGACBCAGWCTCC (SEQ ID NO: 825) |
| E4 | 20100329_VK12back | GAAACGACACTCACGCAGTCTC (SEQ ID NO: 826) |
| H6 | garbage 1 | ACGTATGCATGCTAG (SEQ ID NO: 827) |

| Well Position | Name | Sequence |
|---|---|---|
| H7 | garbage 2 | ACGTATGCAGTCTAG (SEQ ID NO: 828) |
| H8 | garbage 3 | ACCCGTGCATGCTAG (SEQ ID NO: 829) |
| H9 | garbage 4 | GGTTATGCATGCTAG (SEQ ID NO: 830) |
| H10 | garbage 5 | ACGTATGCAGACTAG (SEQ ID NO: 831) |
| H11 | garbage 6 | ACGTATGCATTTTAG (SEQ ID NO: 832) |
| H12 | garbage 7 | ACGTATGGGTGCTAG (SEQ ID NO: 833) |

Example XIV

SOE-PCR and ScFV Generation in Single Cells

SOE VDJ (Heavy and Light Chain Pairing)

Used extra mix to make 5× FV1 (180 ng/ul . . . 1.67 ulRNA+5.33 ul H$_2$O) for light chains and 5 for heavy chains. Reverse transcription proceeded as follows for RT-PCR. Five tubes were used for heavy chain reactions and 5 tubes were used for light chain reactions (mix shown here was used because this was done at the same time as HIV VDJ).

| 1.1 Assembled an RT reaction as follows: | 2x 1 tube |
|---|---|
| H$_2$O (DEPC) | 0 µl (to 12 µl) |
| 2 µM Gene-specific primer(heavy or light) | 5 ul (5 pmole) |
| Total RNA | 7 µl (150 ng) |

Heated at 95° C. for 1 min followed by 65° C. for 5 min, than ice for 1 min. Spun down and added the following:

| | 1 tube | 30 tubes |
|---|---|---|
| 5× First strand buffer | 4 µl | 120 |
| 10 mM dNTP mix | 1 µl | 30 |
| 0.1M DTT | 1 µl | 30 |
| RnaseInhibitor-Enzymatics | 1 µl | 30 |
| Superscript III | 1 µl | 30 |
| Incubated at 55° C. for 60 min | | (8 µl/tubes) |

Inactivated enzyme by heating at 70° C. for 15 min. Removed RNA/DNA hybrid by adding 1 µl of *E. coli* RNaseH (Enzy). Incubated at 37° C. for 20 min, then ice.

Assembled PCR reaction as follows: Used half for PCR kept other half as backup (extra amount made because done in parallel with HIV-VDJ project). Assembled a PCR test reaction as follows:

| | 1× | x2per sample x 15samples (45t) | (12t light chain) |
|---|---|---|---|
| dH$_2$O | 21 µl (to 50 µl) | 945 (1084.46) | 252 (259.2) |
| cDNA | 5 µl | — | — |
| 5× HF buffer | 10 µl | 450 | 120 |
| dNTP (10 mM) (25 mM) | 1 µl (0.4) | 45 (18) | 12 (4.8) |
| primer up (IGHV new-short) (4 µM) | 6.25 µl (25 pmole) | 281.25 (225) | 75 |
| primer low (IGHC new-short) (4 µM) | 6.25 µl (25 pmole) | 281.25 (224) | 75 |
| phusion | 0.5 µl | 22.5 | 6 |

Added 90 PCR mix to 10 ul cDNA, split PCR reaction in 2 tubes of 50 for each sample. Was low on primer, so did number in red.

Thermal cycled as follows:

| 1 | 98° C. for 1 min |
| 2 | 98° C. for 10 seconds |
| 3 | 62° C. for 20 seconds |
| 4 | 72° C. for 20 seconds go to step 2, 23× |
| 5 | 72° C. for 5 min |
| 6 | 4° C. pause |

Repooled each 2 reactions into 1. Added 2 µl of Exonucleasel (20 U/µl) to each tube and incubated at 37° C. for 20 minutes. AMPure XP purified using a 1.8:1 ratio. Resuspended in 40 ul (lower if possible).

Conducted SPRI purification as follows: Added the require amount of AMPure XP beads (1.8:1 ratio) to the DNA sample in buffer EB. Vortexed to mix. Incubated for 5 minutes at room temperature. Magnet (MPC) for 5 minutes. Leave the tube of beads in the MPC during all wash steps. Remove the supernatant (kept in case of failure) and washed the beads twice with 500 µl of 70% ethanol, incubating for 30 sec each time. Removed all the supernatant, performed quick spin, removed last drop and allowed the AMPure beads to air dry completely (2 min). Removed the tube from the MPC, added 40 µl of 10 mM Tris-HCl, 0.1 mM EDTA, pH 8.0 (or Qiagen's Buffer EB), and vortexed for 30 sec to resuspend the beads, let sit for 3 min Magnet for 2 min and transfer supernatant to a new tube.

Figure 77:
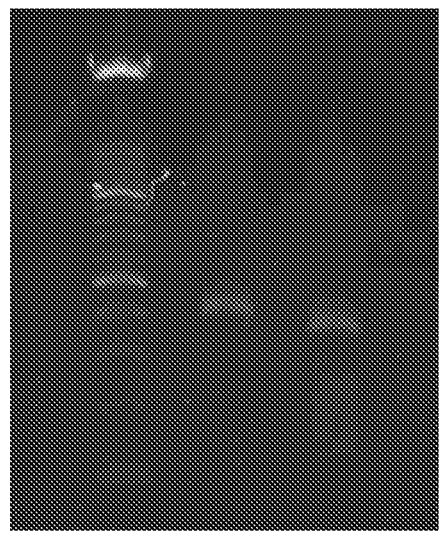
FIG. 77-FIG. 92 depict results on diagnostic gels according to certain embodiments of the invention.

Ran a diagnostic gel to check PCR efficiency. Ran 2 ul on a 2% Egel-X for 12 min. VH=410 bp, VL=360 bp. Pool all 5 tubes. re-concentrated with ampure down to 60 ul so that it could be loaded across 2 lanes on the pippin prep. (FIG. 77)

Performed Phusion PCR of SOE LLA4 primers from cDNA. Made a master mix of the following components:

|  | 4.1x master mix |
| --- | --- |
| dH₂O | 11 | 45.1 |
| 5× HF buffer (det. free) | 4 | 16.4 |
| 10 mM dNTP | 0.4 | 1.64 |
| cDNA | 4 | 16.4 |
| Phusion Hot Start | 0.2 | 0.82 |
| Total | 19.6 | |

Figure 78:
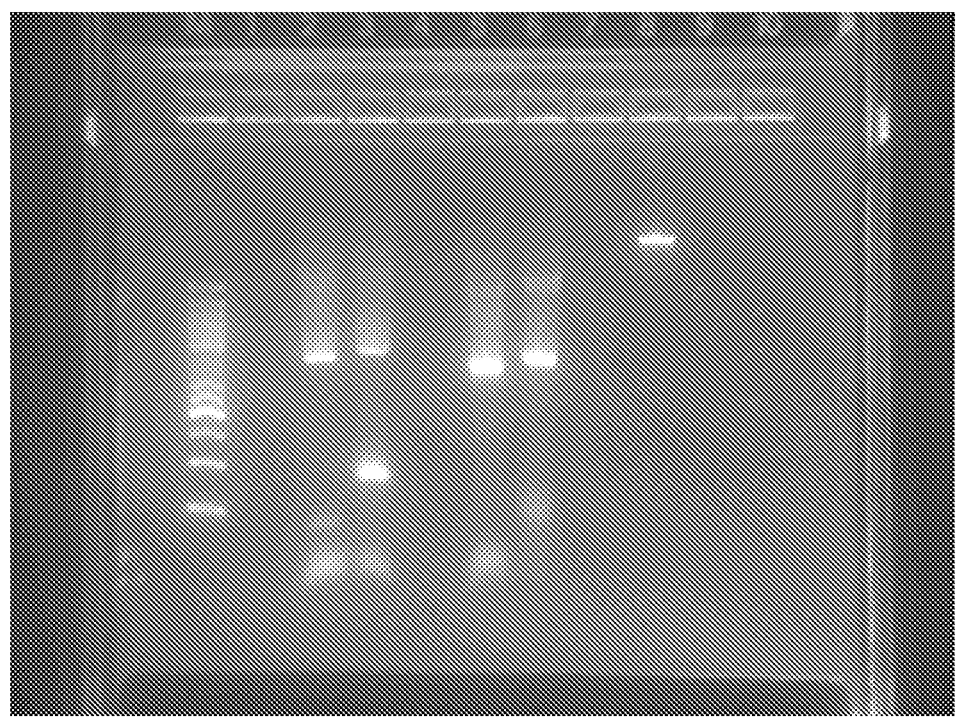

Aliquoted 19.6 µL into 4 PCR tubes. Added 0.2 µl, of each appropriate primer, as follows (8 different primer mixes total):
1. VH primers
2. LLA4 SOE VII primers
3. VL primers
4. LLA4 SOE VL primers Cycling was performed as follows:
1. 98° C., 30 s
2. 98° C., 10 s
3. 65° C., 30 s
4. 72° C., 30 s
5. Goto 2, 29×
6. 72° C., 5 min
7. 4° C., forever A 2% E-gel EX was run for 10 minutes, and was loaded in the following order: (FIG. 78)

| Lane | Sample | Amount |
| --- | --- | --- |
| M | NEB 50 bp ladder | 1 µL in 20 |
| 1 | | |
| 2 | VH PCR | 10 µL in 20 |
| 3 | VH LLA4 SOE PCR | 10 µL in 20 |
| 4 | | |
| 5 | VL PCR | 10 µL in 20 |
| 6 | VL LLA4 SOE PCR | 10 µL in 20 |
| 7 | | |
| 8 | Billy's sample | |
| 9 | | |
| 10 | | |

Gradient PCR of LLA4 primers with Phusion from cDNA. The following two master mixes were generated:

|  | VH master (4.1x) | VL master (4.1x) |
| --- | --- | --- |
| dH₂O | 11 | 45.1 | 45.1 |
| 5× HF buff (det. free) | 4 | 16.4 | 16.4 |
| 10 mM dNTP | 0.4 | 1.64 | 1.64 |
| Primer 1 | 0.2 | 0.82 | 0.82 |
| Primer 2 | 0.2 | 0.82 | 0.82 |
| cDNA | 4 | 16.4 | 16.4 |
| Phusion Hot Start | 0.2 | 0.82 | 0.82 |
| Total | 20 | | |

20 µL of each mix was aliquoted into 4 tubes of a PCR strip, using tubes 1, 3, 5, 7. The strips were placed in positions 3-10 of the gradient block. The gradient temperatures were:
1. 64.9° C.
2. 66.9° C.
3. 70.0° C.
4. 72.5° C.

Figure 79:
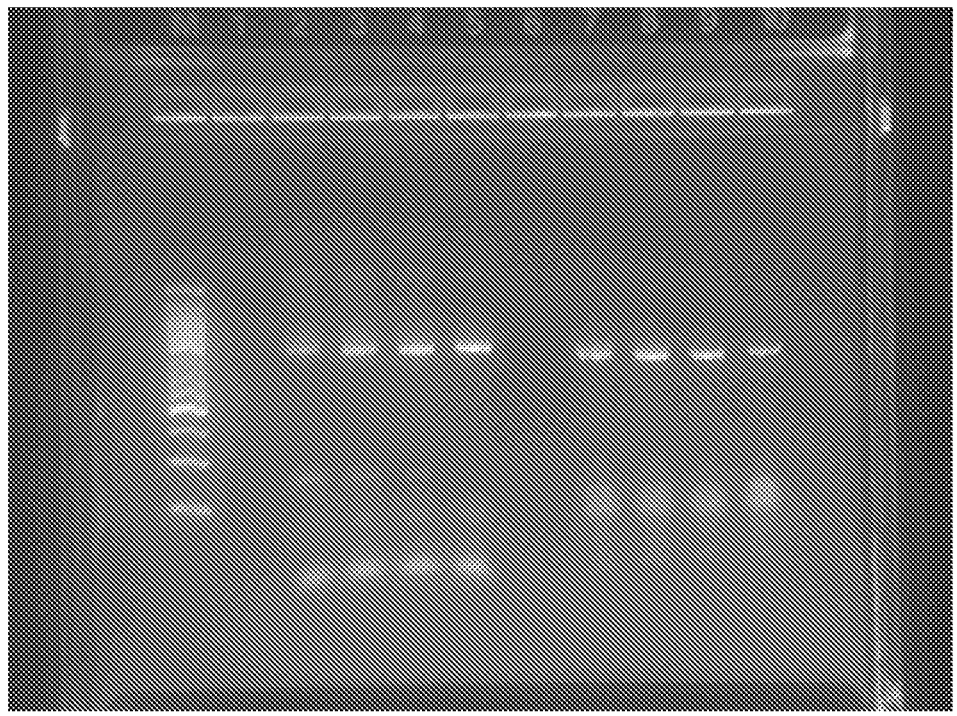

Cycling was:
1. 98° C., 30 s
2. 98° C., 10 s
3. Grad 64° C.-74° C. (machine set), 30 s
4. 72° C., 30 s
5. Goto 2, 24×
6. 4° C., forever A 2% E-gel EX was run for 10 min and was loaded as follows: (FIG. 79)

| Lane | Sample | Amount |
| --- | --- | --- |
| M | NEB 50 bp ladder | 1 µL in 20 |
| 1 | | |
| 2 | VH (gradient) 64.9° C. | 10 µL in 20 |
| 3 | VH (gradient) 66.9° C. | 10 µL in 20 |
| 4 | VH (gradient) 70.0° C. | 10 µL in 20 |
| 5 | VH (gradient) 72.5° C. | 10 µL in 20 |
| 6 | | |
| 7 | VL (gradient) 64.9° C. | 10 µL in 20 |
| 8 | VL (gradient) 66.9° C. | 10 µL in 20 |
| 9 | VL (gradient) 70.0° C. | 10 µL in 20 |
| 10 | VL (gradient) 72.5° C. | 10 µL in 20 |

Kapa 2G Robust PCR with LLA4 from cDNA. The Kapa 2G Robust enzyme was used to determine if it performed better using the same primer set than Phusion. Without intending to be bound by scientific theory, it was believes that Kapa has no exo activity, and that the primer dimer band may require exo in order to form robustly, so perhaps this will help avoid it. The following reactions were mixed in separate PCR tubes:

|  | VH neg control | VH | VL neg control | VL |
| --- | --- | --- | --- | --- |
| dH₂O | 19 | 15 | 19 | 15 |
| Kapa 2G buffer A | 5 | 5 | 5 | 5 |
| dNTP 10 mM | 0.5 | 0.5 | 0.5 | 0.5 |
| Primer 1 | 0.2 | 0.2 | 0.2 | 0.2 |
| Primer 2 | 0.2 | 0.2 | 0.2 | 0.2 |
| cDNA | 0 | 4 | 0 | 4 |
| Kapa 2G Robust | 0.1 | 0.1 | 0.1 | 0.1 |
| Total | 25 | 25 | 25 | 25 |

Figure 80:
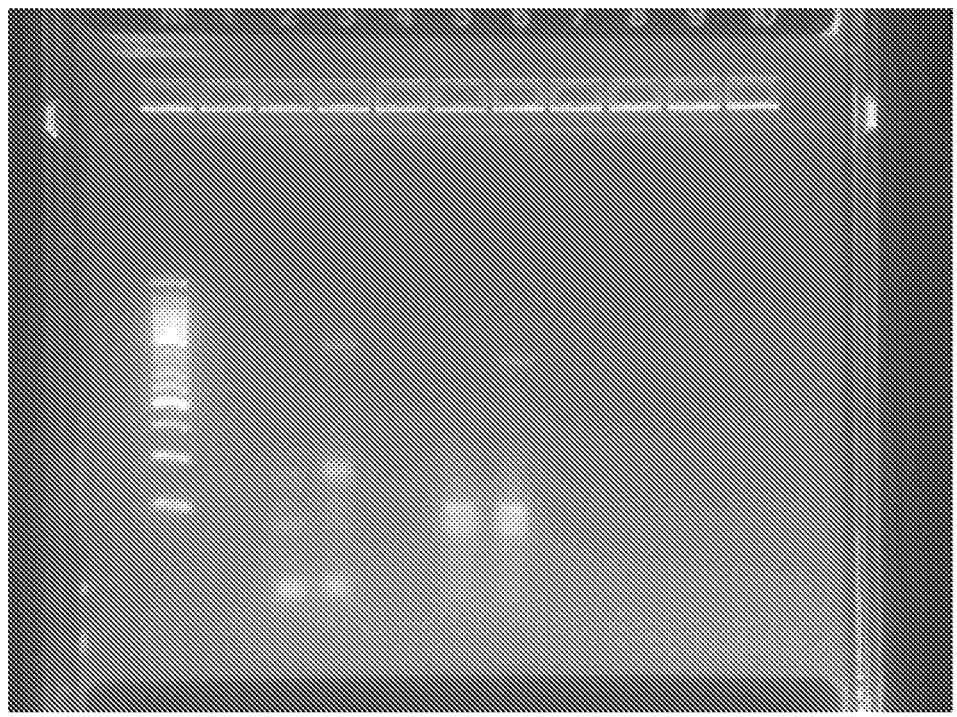

Cycling was performed as follows:
1. 95° C., 1 min
2. 95° C., 20 s
3. 65° C., 20 s
4. 72° C., 30 s
5. Goto 2, 24×
6. 4° C., forever A 2% E-gel EX was run and was loaded in the order shown below: (FIG. 80)

| Lane | Sample | Amount |
| --- | --- | --- |
| M | NEB 50 bp ladder | 1 µL in 20 |
| 1 | | |
| 2 | VH neg control | 10 µL in 20 |
| 3 | VH | 10 µL in 20 |
| 4 | | |
| 5 | VL neg control | 10 µL in 20 |
| 6 | VL | 10 µL in 20 |

Heavy/light chain clone matching. Heavy and light chain candidates were manually matched for synthesis. Further notes are present in the spreadsheet herein. Phusion PCR using different numbers of cycles was performed to determine whether reducing the number of cycles more would help the PCRs. The reactions were mixed as follows:

|  |  | VH master (5.2x) | VL master (5.2x) |
|---|---|---|---|
| dH$_2$O | 11 | 57.2 | 57.2 |
| HF buffer (det. free buff) | 4 | 20.8 | 20.8 |
| 10 mM dNTP | 0.4 | 2.08 | 2.08 |
| Primer 1 | 0.2 | 1.04 | 1.04 |
| Primer 2 | 0.2 | 1.04 | 1.04 |
| cDNA | 4 | 20.8 | 20.8 |
| Phusion Hot Start | 0.2 | 1.04 | 1.04 |

Note: one of the cDNA samples ran out, so two different cDNA samples were used (i.e., VH and VL). 20 µL was aliquoted into 5 PCR tubes for each of VH and VL. The PCR tubes are were apart and loaded onto a thermocycler. Different amounts of cycling were tested: 9, 13, 17, 21 and 25 cycles. After 9 cycles, one of the tubes was removed for each of VH and VL, and an additional tube was removed every 4 cycles thereafter till the last tube did 25 cycles.

Figure 81:
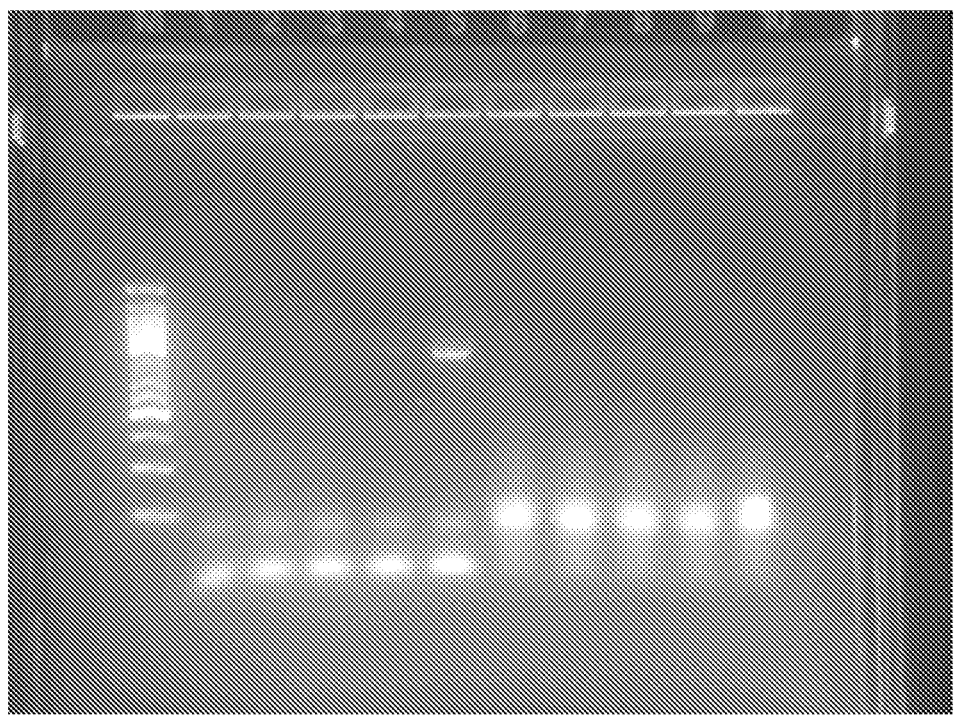

The cycling was performed as follows:
1. 98° C., 30 s
2. 98° C., 10 s
3. 72° C., 30 s
4. Goto 2, 8×
5. 20° C., forever (pull tube)
6. 98° C., 10 s
7. 72° C., 30 s
8. Goto 6, 3×
9. Goto 5, 3×
10. 4° C., forever A 2% E-gel EX was run for 10 minutes and was loaded as shown below: (FIG. 81)

| Lane | Sample | Amount |
|---|---|---|
| M | NEB 50 bp ladder | 1 µL in 20 |
| 1 | VH 9 cycles | 10 µL in 20 |
| 2 | VH 13 cycles | 10 µL in 20 |
| 3 | VH 17 cycles | 10 µL in 20 |
| 4 | VH 21 cycles | 10 µL in 20 |
| 5 | VH 25 cycles | 10 µL in 20 |
| 6 | VL 9 cycles | 10 µL in 20 |
| 7 | VL 13 cycles | 10 µL in 20 |
| 8 | VL 17 cycles | 10 µL in 20 |
| 9 | VL 21 cycles | 10 µL in 20 |
| 10 | VL 25 cycles | 10 µL in 20 | cDNA synthesis was performed using SuperScript III. RNA labeled PBMC RNA was used. The whole tube was used (which is why somewhat less RNA was used than in the previous cDNA synthesis). The following mixes were made:

|  | (correct) | 16.5x master mix | actual mix |
|---|---|---|---|
| total RNA (PBMC) (70 ng/µL) | 5 | 82.5 | 66 |
| random hexamers | 1 | 16.5 | 16.5 |
| 10 mM dNTP | 1 | 16.5 | 16.5 |
| DEPC H$_2$O | 3 | 49.5 | 72 |

Note: The actual mix was over diluted because instead of adding 16.5 µL water, 22.5 µL water was added. 10 µL of this mix was aliquoted into 16 PCR tubes. The tubes were incubated at 65° C. for 5 minutes, followed by 4° C. for greater than one minute. Meanwhile, the following mix was made:

|  |  | 16.5x master |
|---|---|---|
| 10× RT buffer | 2 | 33 |
| 25 mM MgCl$_2$ | 4 | 66 |
| 0.1M DTT | 2 | 33 |
| RNaseOUT (40 U/µL) | 1 | 16.5 |
| SuperScript III (200 U/µL) | 1 | 16.5 |

10 µL was aliquoted into each tube, which were then incubated as follows: 25° C. for 10 minutes, 50° C. for 50 minutes, 85° C. for 5 minutes, and then chilled on ice. All 16 reactions into a single Eppendorf tube. 16 µL of RNase H was added, and the reaction was and incubated at 37° C. for 20 minutes.

A primer concentration gradient was determined for Phusion PCR from cDNA. One of the final optimizations that was perform before moving on to the cross-linking was to determine optimal primer concentrations. A primer concentration gradient was performed to check for secondary products and efficiency. The following master mix was generated (VH and VL could be together because primers were be added separately).

|  |  | 16.5x master |
|---|---|---|
| dH$_2$O | 0.2 | 3.3 |
| HF buffer (det. free) | 4 | 66 |
| 10 mM dNTP | 0.4 | 6.6 |
| cDNA | 4 | 66 |
| Phusion hot start | 0.2 | 3.3 |

8.8 µL was aliquoted into each of 16 PCR tubes (8 VH, 8 VL). The primers were added as follows:

| Tube | Primer concentration (nM; each primer) | Primer mix volume | dH$_2$O volume |
|---|---|---|---|
| 1 | 12.5 | 0.1 | 5.5 |
| 2 | 25 | 0.2 | 5.4 |
| 3 | 40 | 0.32 | 5.28 |
| 4 | 70 | 0.56 | 5.04 |
| 5 | 125 | 1 | 4.6 |
| 6 | 250 | 2 | 3.6 |
| 7 | 500 | 4 | 1.6 |
| 8 | 700 | 5.6 | 0 |

Note that the amounts added were for each primer mix, so that each individual tube required 4 pipetting steps (right primer+water, left primer+water).

Figure 82:
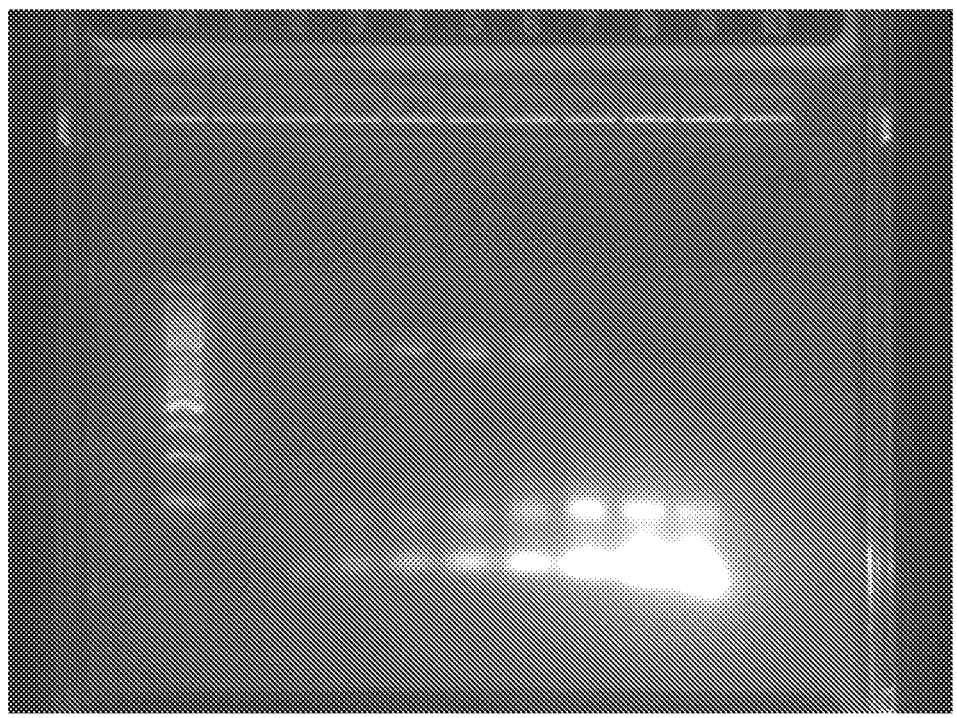

Cycling was performed as follows:
1. 98° C., 30 s
2. 98° C., 10 s
3. 72° C., 30 s
4. Goto 2, 24×
5. 4° C., forever A 2% E-gel EX was run and was loaded as shown below: (FIG. 82)

| Lane | Sample | Amount |
|---|---|---|
| M | NEB 50 bp ladder | 1 µL in 20 |
| 1 |  |  |
| 2 | VH 12.5 nM | 10 µL in 20 |
| 3 | VH 25 nM | 10 µL in 20 |
| 4 | VH 40 nM | 10 µL in 20 |

-continued

| Lane | Sample | Amount |
|---|---|---|
| 5 | VH 70 nM | 10 µL in 20 |
| 6 | VH 125 nM | 10 µL in 20 |
| 7 | VH 250 nM | 10 µL in 20 |
| 8 | VH 500 nM | 10 µL in 20 |
| 9 | VH 700 nM | 10 µL in 20 |
| 10 | | |

The VH PCR showed a clear maximum of produced product. It was a bit difficult to see any secondary products (without intending to be bound by scientific theory, this was probably because of the slightly reduced number of cycles), but it appeared that the optimal amount was probably 40-70 nM of each primer (0.32-0.56 µL primer mix at 2.5 µM each primer).

PCRs were performed for gel purification of VH and VL chains. PCR was performed using SOE primers and USER primers to gel extract the material. The following reactions were prepared:

| LLA4 (SOE) primers | VH | VL |
|---|---|---|
| dH₂O | 11 | 11 |
| HF buffer (det. free) | 4 | 4 |
| dNTP 10 mM | 0.4 | 0.4 |
| Primer 1 | 0.2 | 0.2 |
| Primer 2 | 0.2 | 0.2 |
| cDNA | 4 | 4 |
| Phusion | 0.2 | 0.2 |

| USER primers | VH | VL |
|---|---|---|
| dH₂O | 14.4 | 14.4 |
| Buffer A (5×) | 5 | 5 |
| dNTP 10 mM ea | 0.5 | 0.5 |
| Primer 1 | 0.5 | 0.5 |
| Primer 2 | 0.5 | 0.5 |
| Ligation reaction | 4 | 4 |
| Kapa 2G Robust | 0.1 | 0.1 |

Figure 83:

Cycling was performed as follows:
LLA4 SOE
1. 98° C., 30 s
2. 98° C., 10 s
3. 67° C., 30 s
4. 72° C., 30 s
5. Goto 2, 24×
6. 4° C., forever
USER
1. 95° C., 1 min
2. 95° C., 10 s
3. 55° C., 30 s
4. 72° C., 15 s
5. Goto 2, 4×
6. 95° C., 10 s
7. 60° C., 30 s
8. 72° C., 15 s
9. Goto 6, 19×
10. 4° C., forever During the extraction, the approximately 450 bp bands were cut out and purified using the Qiagen MinElute kit. The DNA was eluted using 10 µL of EB buffer. Afterwards 9 µL Tris-HCl was added to each tube. A 2% E-gel EX was run for 10 minutes and was loaded as follows: (FIG. 83)

| Lane | Sample | Amount |
|---|---|---|
| M | NEB 50 bp ladder | 1.25 µL in 25 |
| 1 | | |
| 2 | SOE VH | 20 µL in 25 |
| 3 | | |
| 4 | SOE VL | 20 µL in 25 |
| 5 | | |
| 6 | USER VH | 20 µL in 25 |
| 7 | | |
| 8 | USER VL | 20 µL in 25 |
| 9 | | |
| 10 | | |

Linked VH/VL was assembled from size-selected immune chains via SOE-PCR or USER/T4 ligase. SOE-PCR assembly was performed. The following was mixed (Note: did not add the primers. They were be added after the first 5 cycles of PCR. The VH amplicons shown here are the LLA4 SOE primed amplicons.

| | |
|---|---|
| dH₂O | 13 |
| HF buffer (det. free) | 4 |
| dNTP 10 mM | 0.4 |
| Primer 1 | (0.2) |
| Primer 2 | (0.2) |
| VH amplicon | 1 |
| VL amplicon | 1 |
| Phusion | 0.2 |

Cycling was performed as follows:
1. 98° C., 30 s
2. 98° C., 10 s
3. 67° C., 30 s
4. 72° C., 30 s
5. Goto 2, 4×
6. 16° C., forever (added primer here)
7. 98° C., 10 s
8. 67° C., 30 s
9. 72° C., 30 s
10. Goto 7, 24×
11. 4° C., forever USER/T4 ligase reactions were performed (Note: The amplicons used here were the 0827 primed amplicons for USER digestion (no scFv)). USER digestion—the following components were combined and then incubated at 37° C. for 30 minutes: 3 µL VH amplicon, 3 µL VL amplicon, 4 µL dH₂O, 0.5 µL UDG (Enzymatics), and 0.5 µL Endo VIII (Enzymatics). Ligation reaction—To the digestion reaction, the following was added and then incubated at 16° C. for 30 minutes followed by 65° C. for 10 minutes: 7 µL dH₂O, 1 µL 10× T4 ligase buffer, and 14 T4 ligase (NEB).

PCR amplification of linked product was performed using the following PCR mix:

| | |
|---|---|
| dH₂O | 13.4 |
| Buffer A (5×) | 5 |
| dNTP 10 mM ea | 0.5 |

| | |
|---|---|
| Primer 1 | 0.5 |
| Primer 2 | 0.5 |
| Ligation reaction | 5 |
| Kapa 2G Robust | 0.1 |

Figure 84:
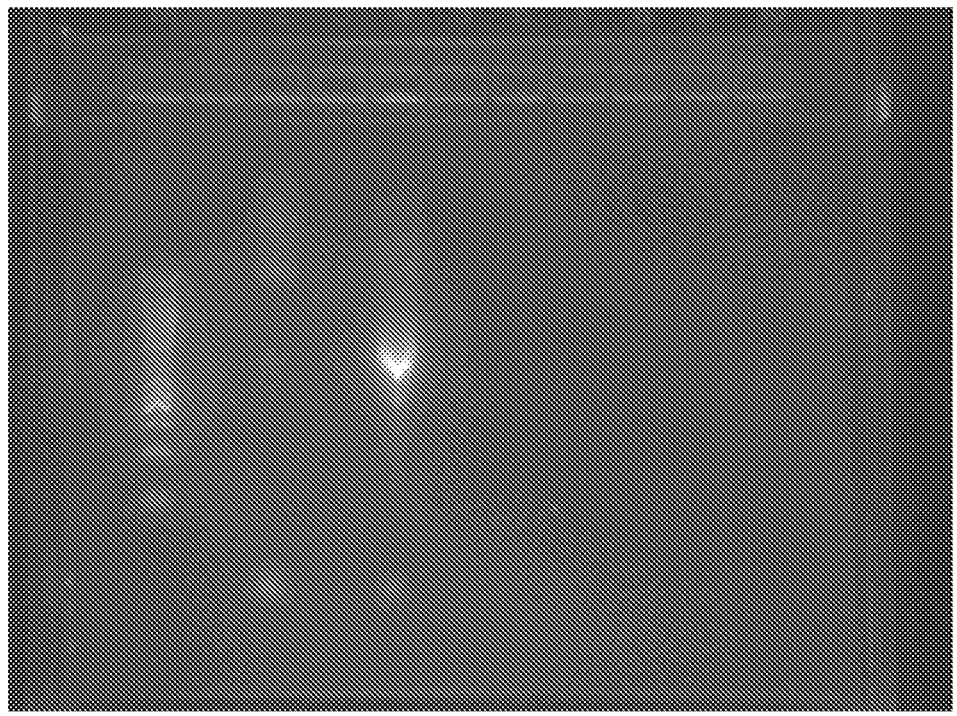

Cycling was performed as follows:
1. 95° C., 1 min
2. 95° C., 10 s
3. 55° C., 30 s
4. 72° C., 15 s
5. Goto 2, 4×
6. 95° C., 10 s
7. 60° C., 30 s
8. 72° C., 15 s
9. Goto 6, 19×
10. 4° C., forever A 2% E-gel EX was run for 10 minutes and was loaded as follows: (FIG. 84)

| Lane | Sample | Amount |
|---|---|---|
| M | NEB 50 bp ladder | 1 µL in 20 |
| 1 | | |
| 2 | SOE-PCR | 10 µL in 20 |
| 3 | | |
| 4 | USER/T4 ligation | 10 µL in 20 |

Images (long and short exposure):

Multistep PCR of VH and VL was performed. An attempt to obtain scFvs using serial PCR reactions was performed using different primer sets. Control PCR with original primers was performed. The following was mixed (note, separate primers for Kappa and Lambda chains):

| | VH | VL |
|---|---|---|
| dH₂O | 11.15 | 10.9 |
| HF buff. (det. free; 5×) | 4 | 4 |
| dNTP (10 mM ea) | 0.4 | 0.4 |
| Primer 1 (4 µM ea) | 0.125 | 0.125 × 2 (K and L chains) |
| Primer 2 (4 µM ea) | 0.125 | 0.125 × 2 (K and L chains) |
| cDNA | 4 | 4 |
| Phusion | 0.2 | 0.2 |

Cycling was performed as follows:
1. 98° C., 1 min
2. 98° C., 10 s
3. 62° C., 20 s
4. 72° C., 20 s
5. Goto 2, 24×
6. 4° C., forever Multistep PCR was performed.

PCR A

First PCR was performed using the original PCR outer primers. The following was mixed (Heavy and Light chains were amplified together):

| | VH + VK + VL |
|---|---|
| dH₂O | 10.65 |
| HF buff. (det. free; 5×) | 4 |
| dNTP (10 mM ea) | 0.4 |
| Primer (4 µM ea) | 0.125 × 6 (all loci) |
| cDNA | 4 |
| Phusion | 0.2 |

Cycling was performed as follows:
1. 98° C., 1 min
2. 98° C., 10 s
3. 62° C., 20 s
4. 72° C., 20 s
5. Goto 2, 9×
6. 4° C., forever 1 µL Exo I was added and the mixture was and incubated for 37° C. at 30 minutes, followed by 80° C. for 20 minutes.

PCR B & C

Inner nested PCR was performed using the original primers. Both the non-SOE and SOE versions were used just to test the PCR reactions. The following was mixed:

| | non-SOE PCR B | SOE (LLA4) PCR C |
|---|---|---|
| dH₂O | 13.6 | 13.6 |
| HF buff. (det. free; 5×) | 4 | 4 |
| dNTP (10 mM ea) | 0.4 | 0.4 |
| Primer (2.5 µM ea) | 0.2 × 4 (VH + VL) | 0.2 × 4 (VH + VL) |
| PCR A | 1 | 1 |
| Phusion | 0.2 | 0.2 |

Cycling was performed as follows:
1. 98° C., 30 s
2. 98° C., 10 s
3. 67° C., 30 s
4. 72° C., 30 s
5. Goto 2, 9×
6. 4° C., forever 1 µL Exo I was added, and the reaction was incubated at 37° C. for 30 minutes, followed by 80° C. for 20 minutes.

PCR D

The SOE LLA4 tags were added to PCR B. the following was mixed:

| | 0505 SOE (LLA4) PCR D |
|---|---|
| dH₂O | 13.6 |
| HF buff. (det. free; 5×) | 4 |
| dNTP (10 mM ea) | 0.4 |
| Primer (2.5 µM ea) | 0.2 × 4 (VH + VL) |
| PCR B | 1 |
| Phusion | 0.2 |

Cycling was as follows:
1. 98° C., 30 s
2. 98° C., 10 s
3. 67° C., 30 s
4. 72° C., 30 s 5. Goto 2, 9×
6. 4° C., forever 1 µL Exo I was added, and the mixture was incubated at 37° C. for 30 minutes followed by 80° C. for 20 minutes. The rest was performed another day Overlap extension cycling was performed, which is some cycling with no primer to get SOE scFv fragments. To PCR reactions C and D, add the following was added:

| | |
|---|---|
| dNTP (10 mM ea) | 0.2 |
| Phusion | 0.4 |

Cycling was as follows:
1. 98° C., 30 s
2. 98° C., 10 s
3. 62° C., 30 s
4. 72° C., 30 s
5. Goto 2, 9×
6. 4° C., forever Final outer PCR was performed, which is the final PCR to amplify up the scFv. 25 cycles were done here. To the above cycled reactions, the following was added (Note, only the "outer primers" were added):

| | |
|---|---|
| VH left primer 2.5 µM | 0.2 |
| VL right primer 2.5 µM | 0.2 |

Figure 85:
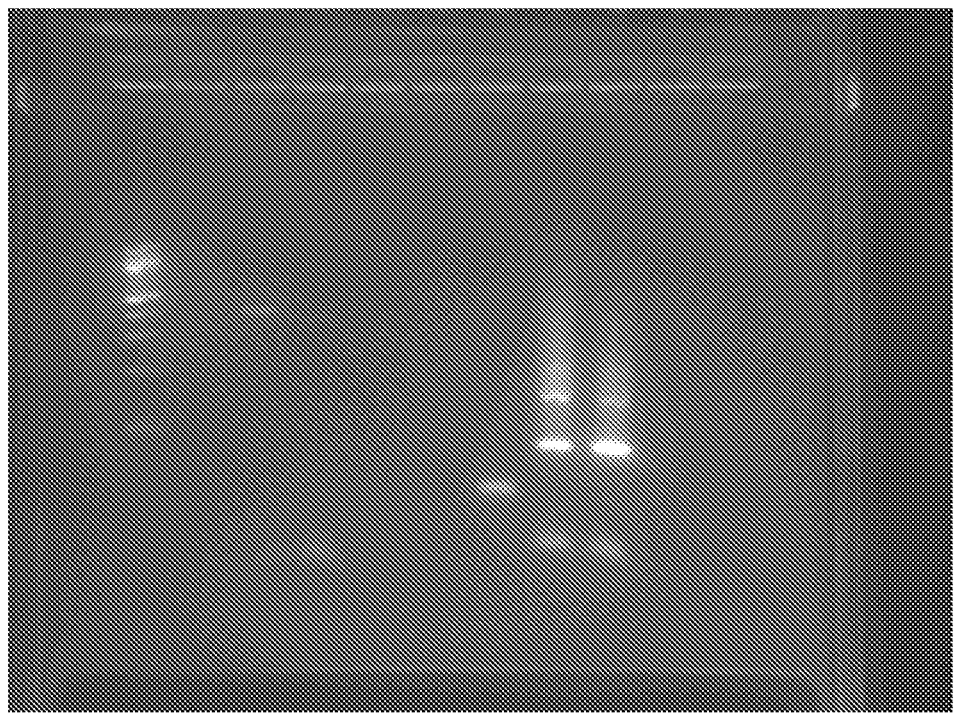

Cycling was performed as follows:
1. 98° C., 30 s
2. 98° C., 10 s
3. 67° C., 30 s
4. 72° C., 30 s
5. Goto 2, 24×
6. 4° C., forever A 2% EX E-gel was run for 10 minutes, and was loaded as follows: (FIG. 85)

| Lane | Sample | Amount |
|---|---|---|
| M | NEB 100 bp ladder | 1 µL in 20 |
| 1 | | |
| 2 | VH control PCR | 10 µL in 20 |
| 3 | VL control PCR | 10 µL in 20 |
| 4 | | |
| 5 | PCR A | 10 µL in 20 |
| 6 | PCR B | 10 µL in 20 |
| 7 | PCR C (final) | 10 µL in 20 |
| 8 | PCR D (final) | 10 µL in 20 |

Full cDNA→scFv pipeline was performed with reduced cycles. PCR was performed with from cDNA with primers.
PCR A
The following was mixed (the primers are the primers)

| | VH | VL | VH + VL |
|---|---|---|---|
| dH$_2$O | 11.15 | 10.9 | 10.65 |
| HF buff. (det. free; 5×) | 4 | 4 | 4 |
| dNTP (10 mM ea) | 0.4 | 0.4 | 0.4 |
| Primer (4 µM ea) | 0.125 × 2 | 0.125 × 4 (K + L) | 0.125 × 6 (all loci) |
| cDNA | 4 | 4 | 4 |
| Phusion | 0.2 | 0.2 | 0.2 |

Cycling was performed as follows:
1. 98° C., 30 s
2. 98° C., 10 s
3. 60° C., 30 s
4. 72° C., 30 s
5. Goto 2, 14×
6. 10° C., forever 1 µL Exo I was added, and the reaction was incubated at 37° C. for 30 minutes followed by 80° C. for 20 minutes. PCR was performed from PCR A using SOE attB primers.
PCR B
The following was mixed (Note the primers were the SOE-attB primers):

| | VH | VL | VH + VL |
|---|---|---|---|
| dH$_2$O | 14.5 | 14.5 | 14.1 |
| HF buff. (det. free; 5×) | 4 | 4 | 4 |
| dNTP (10 mM ea) | 0.4 | 0.4 | 0.4 |
| Primer (2.5 µM ea) | 0.2 × 2 | 0.2 × 2 | 0.2 × 4 |
| PCR A | 0.5 | 0.5 | 0.5 |
| Phusion | 0.2 | 0.2 | 0.2 |

Cycling was performed as follows:
1. 98° C., 30 s
2. 98° C., 10 s
3. 65° C., 30 s
4. 72° C., 30 s
5. Goto 2, 14×
6. 10° C., forever 1 µL Exo I was added, and the reaction was incubated at 37° C. for 30 minutes, followed by 80° C. for 20 minutes. The remainder of the experiment was finished the following day. PCR was performed from PCR B using attB universal primers.
PCR C
The individual VH and VL reactions must now be combined to get scFvs. This combined reaction was labeled "VH/VL sep." The following was mixed:

| | VH/VL sep. | VH + VL |
|---|---|---|
| dH$_2$O | 12.4 | 12.9 |
| HF buff. (det. free; 5×) | 4 | 4 |
| dNTP (10 mM ea) | 0.4 | 0.4 |
| PCR B | 0.5 × 2 (VH and VL) | 0.5 |
| Phusion | 0.2 | 0.2 |
| Total | 18 | 18 |

Figure 86:
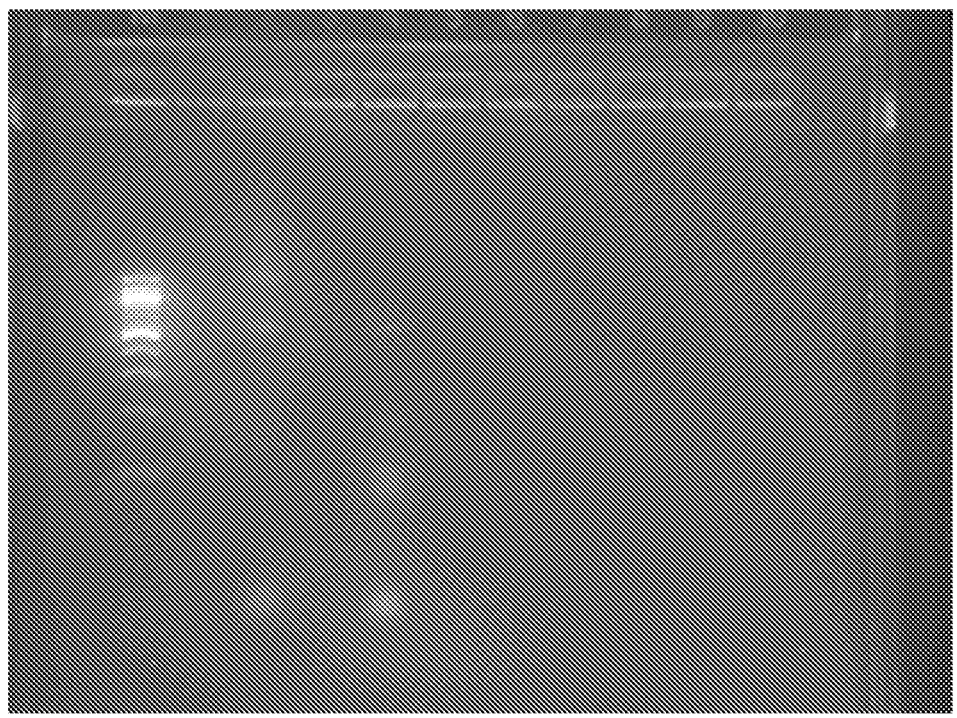

1 µL each 10 µM universal attB primers was added at pause point.
Cycling was as follows:
1. 98° C., 30 s
2. 98° C., 10 s
3. 67° C., 30 s
4. 72° C., 30 s
5. Goto 2, 9×
6. 10° C., forever Primer was added, followed by:
7. 98° C., 30 s
8. 98° C., 10 s
9. 63° C., 30 s
10. 72° C., 30 s
11. Goto 8, 21×
12. 10° C., forever A 2% E-gel EX was run for 10 minutes, and was loaded as follows: (FIG. 86)

| Lane | Sample | Amount |
|---|---|---|
| M | NEB 100 bp ladder | 1 μL in 20 |
| 1 | | |
| 2 | VH/VL sep. | 10 μL in 20 |
| 3 | | |
| 4 | VH + VL | 10 μL in 20 |

Example XV

VDJome Analysis Methods

Light chain library preparation was performed on samples of day 1, 7 and 21 only.

Sample ID

Sample were extracted from 9 mL of blood from a single individual at various time point and processed using the Leukolock extraction kit from Ambion. The samples were concentrated using RNeasy kit form Qiagen, and eluted in 2×30 μl and nanodropped.

Light chain, the real deal

Used original sample Or second batch

| ID | | for 500 ng | water to 7 | for 500 ng | water to 7 |
|---|---|---|---|---|---|
| 3 | 90.57 ng/ul | 5.52 | 1.48 | 2.0 | 5 |
| 5 | 84.74 ng/ul | 5.9 | 1.1 | 2.16 | 4.84 |
| 7 | 71.89 ng/ul | 6.96 | 0 | 2.7 | 4.3 |
| FV1 | 180 ng/ul | 2.78 | 4.22 | | |

| ID | MID | vaccination sample | concentration (ng/μl) | 260/280 | Vol for 500 ng | H2O for 9.5 μl |
|---|---|---|---|---|---|---|
| 1 | 1 | -n | 84.28 | 2.13 | 8.93 | 0.57 |
| 2 | 2 | 0 | 63.15 | 2.12 | 7.92 | 1.58 |
| 3 | 3 | 24 hr | 90.57 | 2.13 | 5.52 | 3.98 |
| 4 | 4 | 3 days | 94.84 | 2.15 | 5.27 | 4.23 |
| 5 | 5 | 7 days | 84.74 | 2.14 | 5.90 | 3.60 |
| 6 | 6 | 14 days | 72.97 | 2.13 | 6.85 | 2.65 |
| 7 | 8 | 21 days | 71.89 | 2.14 | 6.96 | 2.54 |
| 8 | 9 | 28 days | 79.11 | 2.17 | 6.32 | 3.18 |
| 9 | 10 | FV test sample | 133.09 | 2.16 | 3.75 | 5.75 |

Then samples were concentrated using RNeasy kit form Qiagen, eluted in 2×30 μl and nanodrop.

| VDJ-ID | MID | vaccination sample | concentration (ng/μl) | Bioanalyzer-RNA nano | RIN | Vol for 1000 ng | H2O for 9.5 μl |
|---|---|---|---|---|---|---|---|
| 1 | 1 | -n | 128.32 | 128 | 7.20 | 7.79 | 1.71 |
| 2 | 2 | 0 | 167.18 | 163 | 6.10 | 5.98 | 3.52 |
| 3 | 3 | 24 hr | 251.42 | 287 | 7.20 | 3.98 | 5.52 |
| 4 | 4 | 3 days | 263.68 | 200 | 6.60 | 3.79 | 5.71 |
| 5 | 5 | 7 days | 231.84 | 235 | 8.90 | 4.31 | 5.19 |
| 6 | 6 | 14 days | 193.86 | 165 | 7.70 | 5.16 | 4.34 |
| 7 | 8 | 21 days | 185.23 | 186 | 7.60 | 5.40 | 4.1 |
| 8 | 9 | 28 days | 193.29 | 156 | 6.30 | 5.17 | 4.33 |

| Tube | ID | notes |
|---|---|---|
| 1 | old-3 | |
| 2 | old-5 | |
| 3 | old-7 | barely anything 1ul maybe |
| 4 | FV1 | |
| 5 | rneasy-3 | |
| 6 | rneasy-5 | |
| 7 | rneasy-7 | |

Reverse transcription was performed (RT-PCR). An RT reaction was performed as follows:

| | 2× 1 tube |
|---|---|
| H2O (DEPC) | 0 μl (to 12 μl) |
| 2 μM Gene-specific primer (IGHC K and L) | 5 (5 pmole) |
| Total RNA | 7 μl (500 ng) |

Heated at 95° C. for 1 minutes followed by 65° C. for 5 minutes, then ice for 1 minute. The reaction was spun down and the following was added, followed by incubation at 55° C. for 60 min:

| | 1 tube | 9 tubes |
|---|---|---|
| 5× First strand buffer | 4 μl | 36 |
| 10 mM dNTP mix | 1 μl | 9 |
| 0.1M DTT | 1 μl | 9 |
| RnaseInhibitor-Enzy | 1 μl | 9 |
| Superscript III | 1 μl | 9 |
| | | (8 μl/tubes) |

Enzyme was inactivated by heating at 70° C. for 15 minutes. RNA/DNA hybrids were removed by adding 1 μl of *E. coli* RNaseH (Enzy), incubated at 37° C. for 20 minutes, then placed on ice. The PCR reaction was assembled as follows (half was used for PCR and half was kept as backup. A PCR test reaction was performed as follows (90 PCR mix was added to 10 ul cDNA, then split in 2 tube of 50 for each sample):

| | 1× | ×2 per sample × 7 samples (16t) |
|---|---|---|
| dH₂O | 21 μl (to 50 μl) | 336 |
| cDNA | 5 μl | — |
| 5× HF buffer | 10 μl | 160 |
| dNTP(10 mM) | 1 μl | 16 |
| primer up (IGHV new-short) (4 μM) | 6.25 μl (25 pmole) | 100 (50 of each K and L) |
| primer low (IGHC new-short) (4 μM) | 6.25 μl (25 pmole) | 100 |
| phusion | 0.5 μl | 8 |

Figure 87:
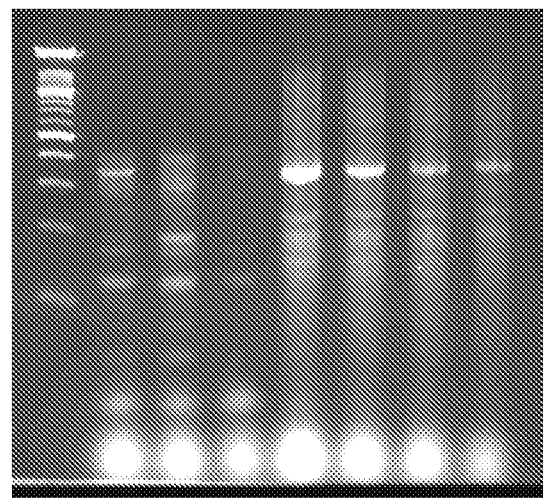

4.2 Thermal cycling was performed as follows (after which time the samples were frozen): (FIG. 87)

| 1 | 98° C. for 1 min |
|---|---|
| 2 | 98° C. for 10 seconds |
| 3 | 62° C. for 20 seconds |
| 4 | 72° C. for 20 seconds go to step 2, 23× |
| 5 | 72° C. for 5 min |
| 6 | 4° C. pause |

A diagnostic gel was run to check PCR efficiency. (A 2% Egel-X was run for 11 minutes.) 2 μl of ExonucleaseI (20

U/µl) was added to each tube and incubated at 37° C. for 20 min (did 20 min). AMPure XP purified at a ratio of 1.8:1. Resuspended in 40 ul (kept non-bind volume as backup). Save 2 ul of each sample was saved for gel diagnostic.

SPRI purification was conducted as follows: Added the require amount of AMPure XP beads (1.8:1 ratio) to the DNA sample in buffer EB. Vortexed to mix. Incubated for 5 minutes at room temperature. Magnet (MPC) for 5 minutes. Left the tube of beads in the MPC during all wash steps. Removed the supernatant (kept in case of failure) and washed the beads twice with 500 µl of 70% ethanol, incubating for 30 seconds each time. Removed all the supernatant, quick spun, removed last drop and allowed the AMPure beads to air dry completely (2 minutes). Removed the tube from the MPC, added 40 µl of 10 mM Tris-HCl, 0.1 mM EDTA, pH 8.0 (or Qiagen's Buffer EB), and vortexed for 30 sec to resuspend the beads, let sit for 3 minutes, Magnet for 2 minutes, and transferred supernatant to a new tube.

Figure 88:
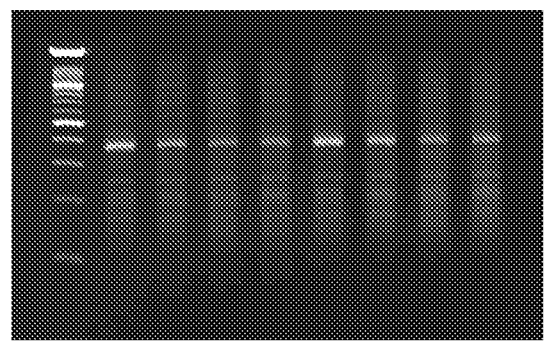

A diagnostic gel was run to check efficiency of AMPure beads. 2 ul was run on a 2% Egel-X for 12 minutes. The first 4 lanes looked good. (FIG. 88)

Blunting reactions were performed using Enzymatics End repair kit as follows:

|  | 1t |
| --- | --- |
| H$_2$O | 0 µl (to 50 µl) |
| Purified DNA | 38 µl |
| 10× End repair buffer | 5 ul |
| 1 mM dNTP mix | 5 µl |
| enzyme mix. | 5 µl |

Figure 89:
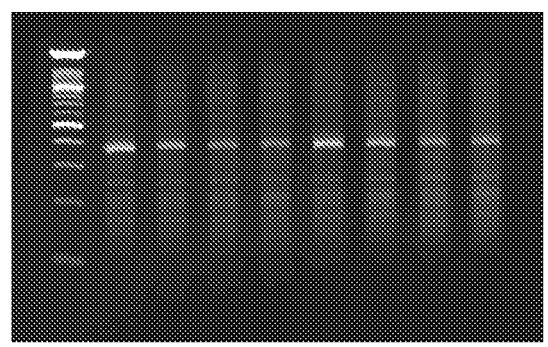

The reaction was incubated at 25° C. temperature for 30 minutes, followed by heat inactivation at 75° C. for 20 minutes. The reaction was AMPure XP purified to a ratio of 1.8:1, and resuspended in 37 ul (kept non-bind volume as backup). 2 ul of each sample was saved for gel diagnostic. A diagnostic gel was run to check efficiency of blunting and ampure beads): 2 ul was run on a 2% Egel-X for 12 minutes. The last 4 lanes looked good. (FIG. 89)

Adaptor ligation (with 25× excess) was performed. 454 oligo was self-annealed into adapter A and B together. The 454 protocol was followed (10 µl of 100 µM of each primer+300 of (10 mM Tris 0.1 mM EDTA at 50 mM NaCl)) (each adapter was at 20 µM final), 95° C. for 3 min, ramp to 15 forever at 0.1° C./sec. Adapter A MID 3-5-8 and adapter B only were prepared.

Ligation of adapter 454-A and 454-B (454 use a 15:1 ratio of adapter DNA) was performed as followed by incubation at 22° C. for 30 minutes:

|  | 1t |
| --- | --- |
| H2O | 10 µl (to 100 µl) |
| 2× Quick ligase buffer | 50 µl |
| VDJ DNA | 35 µl (~1.25 pmole at 400 bp) |
| 20 µM 454-A | 1.5 µl (~30 pmole) |
| 20 µM 454-B | 1.5 µl (~30 pmole) |
| T4 DNA ligase (quick) | 2 µl |

The reaction was AMPure XP purified to a ratio of 1.8:1, and then resuspended in 37 ul.

Figure 90:
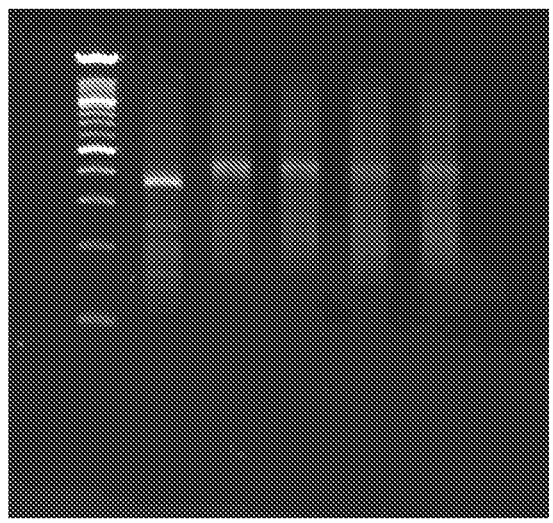

A diagnostic gel was run (2 ul on a 2% Egel-X for 12 minutes). 100 bp ladder, lane 1-FV1 pre ligation; lanes 2-5 post ligation, post purification. (FIG. 90)

A fill-in reaction was performed. If using BST, an A-tail was present at the 3' ends. In a microcentrifuge tube, the following reagents were added in the order indicated, and mixed (followed by incubation at 30° C. for 10 minutes, then 60° C. for 15 minutes (thermocycler), and heat inactivation at 80° C. for 15 minutes):

|  | 1t | 5t |
| --- | --- | --- |
| H$_2$O | 5.5 (to 50 µl) | 27.5 |
| DNA | 35 | — |
| 10× Thermopol buffer I | 2.5 µl | 12.5 |
| 10× Phi29 buffer | 2.5 | 12.5 |
| 100× BSA (10 mg/ml) | 0.5 | 2.5 |
| 10 mM dNTP Mix | 1 µl (0.2 mM) | 5 |
| Bst Polymerase (8 U/µl) | 2 µl | 10 |
| Phi29 | 1 ul | 5 |

The reactions were AMPure XP purified to a ratio of 1.8:1, and resuspend in 30 ul.

Figure 91:
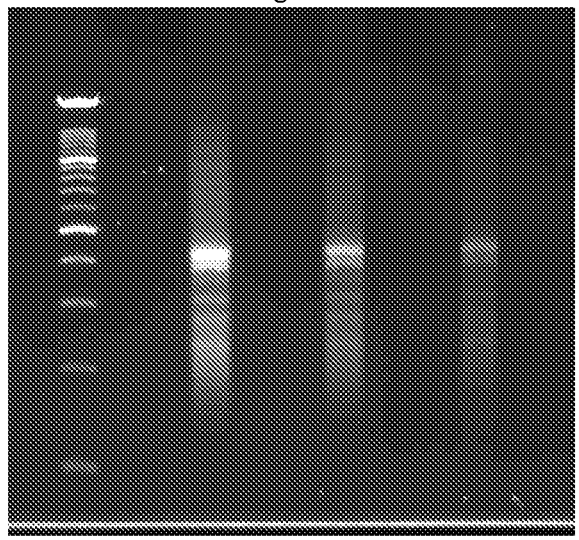

Gel extraction was performed on a heavy chain-ligated library. Loading capacity was tested with FV1 sample only, loaded 10 ul 5 ul and 2.5 ul (space between each lane). A 2% e-gel ex was run for 15 min. Other samples were loaded across 3 lanes (10 ul/lanes). Qiagen buffer gel extraction kit was used (melt band at room temp on thermo mixer), and the samples were eluted in 17 ul (using mini-elute columns). (FIG. 91)

QC and pooling were performed. Nanodrop: the number was weird (230 is real high). 4 ul of TE was added and the samples were AMPure XP purified with a ratio of 1.8:1. The samples were resuspended in 20 ul (remagnet manually in PCR tube). A diagnostic gel was run (2% e gel ex 11 min, 2 ul each sample) (sage ladder, 100 bp ladder, 25 bp ladder, VDJ samples). All samples were diluted to the same concentration of lowest ng/ul.

| Sample | volumeS | waterQbit | water gel |
| --- | --- | --- | --- |
| 24 hr | 12 ul | 2.43 | 1.56 |
| 7 days | 12 ul | 0 | 0 |
| 21 days | 12 ul | 1.91 | 2.11 |

Figure 92:
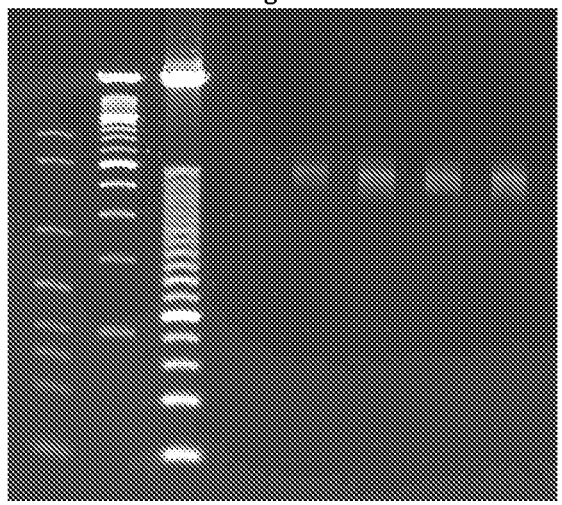

12 ul of each sample were mixed together, and the stored at −20. (FIG. 92)

Nanodrop Qubit dsDNA HS area density

| ID | ng/ul |  |  |
| --- | --- | --- | --- |
| FV1 | 6.4 | 9.84 |  |
| 24 hr | 7.6 | 16.6 | 18.0 = 15.6 |
| 7 days | 7.9 | 13.8 | 15.9 = 13.8 |
| 21 days | 9.1 | 16.0 | 18.7 = 16.23 |

Example XVI

Primer Design Software Code

The Primer Design Software Code is attached in the computer program listing appendix, whose contents are expressly incorporated herein by reference in their entirety for all purposes.

What is claimed is:

1. A method comprising:
   a) linking a polynucleotide sequence encoding a heavy chain variable region (VH) and a polynucleotide sequence encoding a light chain variable region (VL) from a single lymphocyte from a first biological sample from a subject, thereby forming first paired sequences; and performing high-throughput sequencing of the first paired sequences, thereby forming a first reference library of paired sequence reads,
   b) linking a polynucleotide sequence encoding a heavy chain variable region (VH) and a polynucleotide sequence encoding a light chain variable region (VL) from a single lymphocyte from a second biological sample from the subject, thereby forming second paired sequences; and performing high-throughput sequencing of the second paired sequences, thereby forming a second reference library of paired sequence reads, wherein the first biological sample is or has been obtained before an immune response of the subject and the second biological sample is or has been obtained during or after the immune response of the subject, and c) comparing the paired sequence reads of the first reference library and the second reference library.

2. The method of claim 1, further comprising purifying and performing high-throughput sequencing for additional samples obtained over a time course.

3. The method of claim 1, further comprising administering an agent to the subject before obtaining the second biological sample from the subject.

4. The method of claim 3, wherein the agent is an antigen, a vaccine, a drug, a small molecule, a biologic, or any combination thereof.

5. The method of claim 1, wherein the first and/or second biological sample is blood, saliva, synovial fluid, cultured cells, a tissue section, or a biopsy.

6. The method of claim 1, further comprising binning the paired sequence reads according to at least their V segment and J segment to form VDJ clones, and determining clone frequency of the VDJ clones.

7. The method of claim 6, wherein a coefficient of variation for replicate comparisons of about 0.5 occurs at VDJ clone frequencies of $<10^{-4}$-$10^{-3}$.

8. The method of claim 1, wherein the comparing comprises comparing the level of expression of one or more paired sequences in the first and second reference libraries.

9. The method of claim 3, wherein, following the comparing, the method further comprises altering administration of the agent to the subject.

10. The method of claim 8, further comprising correlating the subject's T cell receptor usage with the subject's MHC type to diagnose a disease or disorder.

11. The method of claim 8, wherein the subject is afflicted with an infection, an autoimmune disorder, a cellular proliferative disorder, or any combination thereof.

12. The method of claim 11, further comprising determining the prognosis for treating the disease or disorder.

13. The method of claim 1, wherein the high-throughput sequencing of the first paired sequences and the high-throughput sequencing of the second paired sequences are performed simultaneously.

14. The method of claim 1, wherein the high-throughput sequencing of the first paired sequences and high-throughput sequencing of the second paired sequences are performed at separate times.

* * * * *

SEQUENCE LISTING

<160> NUMBER OF SEQ ID NOS: 1017

<210> SEQ ID NO 1
<211> LENGTH: 54
<212> TYPE: DNA
<213> ORGANISM: Homo sapiens

<400> SEQUENCE: 1
tgtgcgagag agggctacgg tgactaccgt tactactacg gtatggacgt ctgg      54

<210> SEQ ID NO 2
<211> LENGTH: 54
<212> TYPE: DNA
<213> ORGANISM: Homo sapiens

<400> SEQUENCE: 2
tgtgcgagag agggctacgg tgactaccgt tactactacg gtatggacgt ctgg      54

<210> SEQ ID NO 3
<211> LENGTH: 54
<212> TYPE: DNA
<213> ORGANISM: Homo sapiens

<400> SEQUENCE: 3
tgtgcgagag agggctacgg tgactaccgt tactactacg gtatggacgt ctgg      54

<210> SEQ ID NO 4
<211> LENGTH: 54
<212> TYPE: DNA
<213> ORGANISM: Homo sapiens

<400> SEQUENCE: 4
tgtgcgagag agggctacgg tgactaccgt tactactacg gtatggacgt ctgg      54

<210> SEQ ID NO 5
<211> LENGTH: 51
<212> TYPE: DNA
<213> ORGANISM: Homo sapiens

<400> SEQUENCE: 5
tgtgcgagag aggactacgg tgactacgtc tactacggta tggacgtctg g         51

<210> SEQ ID NO 6
<211> LENGTH: 51
<212> TYPE: DNA
<213> ORGANISM: Homo sapiens

<400> SEQUENCE: 6
tgtgcgagag ggtactacgg tgactacggc cactacggta tggacgtctg g         51

<210> SEQ ID NO 7
<211> LENGTH: 57
<212> TYPE: DNA
<213> ORGANISM: Homo sapiens
<220> FEATURE:
<221> NAME/KEY: misc_feature
<222> LOCATION: (22)..(22)
<223> OTHER INFORMATION: n is a, c, g, or t

<400> SEQUENCE: 7
tgtgcggcag ttcccccccc tnagggaacg acattttggg gtgcttttga gatctgg   57

<210> SEQ ID NO 8
<211> LENGTH: 58

```
<212> TYPE: DNA
<213> ORGANISM: Homo sapiens
<220> FEATURE:
<221> NAME/KEY: misc_feature
<222> LOCATION: (22)..(22)
<223> OTHER INFORMATION: n is a, c, g, or t

<400> SEQUENCE: 8
tgtgcggcag ttcccccccc tnagggaacg acatttnggg gtgcttttg agatctgg      58

<210> SEQ ID NO 9
<211> LENGTH: 59
<212> TYPE: DNA
<213> ORGANISM: Homo sapiens

<400> SEQUENCE: 9
tgtgcggcag ttcccccccc tcagggaacg acatttttgg ggtgctttttt gagatctgg   59

<210> SEQ ID NO 10
<211> LENGTH: 58
<212> TYPE: DNA
<213> ORGANISM: Homo sapiens

<400> SEQUENCE: 10
tgtgcggcag ttcccccccc tcagggaacg acattttggg gtgcttttg agatctgg      58

<210> SEQ ID NO 11
<211> LENGTH: 58
<212> TYPE: DNA
<213> ORGANISM: Homo sapiens

<400> SEQUENCE: 11
tgtgcggcag ttcccccccc ctcagggaac gacattttgg ggtgcttttg agatctgg     58

<210> SEQ ID NO 12
<211> LENGTH: 53
<212> TYPE: DNA
<213> ORGANISM: Homo sapiens

<400> SEQUENCE: 12
tgtgcggcag ttccccccct caggaacgac atttgggtgc ttttgagatc tgg           53

<210> SEQ ID NO 13
<211> LENGTH: 56
<212> TYPE: DNA
<213> ORGANISM: Homo sapiens

<400> SEQUENCE: 13
tgtgcggcag ttccccccct cagggaacga catttggggg tgcttttgag atctgg        56

<210> SEQ ID NO 14
<211> LENGTH: 56
<212> TYPE: DNA
<213> ORGANISM: Homo sapiens

<400> SEQUENCE: 14
tgtgcggcag ttccccccct cagggaacga catttggggg tgcttttgag atctgg        56

<210> SEQ ID NO 15
<211> LENGTH: 56
<212> TYPE: DNA
<213> ORGANISM: Homo sapiens

<400> SEQUENCE: 15
```
tgtgcggcag ttcccccct cagggaacga catttttgggg tgcttttgag atctgg    56

<210> SEQ ID NO 16
<211> LENGTH: 56
<212> TYPE: DNA
<213> ORGANISM: Homo sapiens

<400> SEQUENCE: 16
tgtgcggcag ttcccccct cagggaacga catttttgggg tgcttttgag atctgg    56

<210> SEQ ID NO 17
<211> LENGTH: 56
<212> TYPE: DNA
<213> ORGANISM: Homo sapiens

<400> SEQUENCE: 17
tgtgcggcag ttcccccct cagggaacga catttttgggg tgcttttgag atctgg    56

<210> SEQ ID NO 18
<211> LENGTH: 56
<212> TYPE: DNA
<213> ORGANISM: Homo sapiens

<400> SEQUENCE: 18
tgtgcggcag ttcccccct cagggaacga catttttgggg tgcttttgag atctgg    56

<210> SEQ ID NO 19
<211> LENGTH: 57
<212> TYPE: DNA
<213> ORGANISM: Homo sapiens

<400> SEQUENCE: 19
tgtgcggcag ttccccccc tcagggaacg acatttttggg gtgcttttga gatctgg    57

<210> SEQ ID NO 20
<211> LENGTH: 57
<212> TYPE: DNA
<213> ORGANISM: Homo sapiens

<400> SEQUENCE: 20
tgtgcggcag ttccccccc tcagggaacg acatttttggg gtgcttttga gatctgg    57

<210> SEQ ID NO 21
<211> LENGTH: 57
<212> TYPE: DNA
<213> ORGANISM: Homo sapiens

<400> SEQUENCE: 21
tgtgcggcag ttccccccc tcagggaacg acatttttggg gtgcttttga gatctgg    57

<210> SEQ ID NO 22
<211> LENGTH: 55
<212> TYPE: DNA
<213> ORGANISM: Homo sapiens

<400> SEQUENCE: 22
tgtgcggcag ttcccccctc agggaacgac attttggggt gctttgaga tctgg    55

<210> SEQ ID NO 23
<211> LENGTH: 57
<212> TYPE: DNA
<213> ORGANISM: Homo sapiens

<400> SEQUENCE: 23
tgtgcggcag ttcccccccc tcagggaacg acattttggg gtgcttttga gatctgg        57

<210> SEQ ID NO 24
<211> LENGTH: 59
<212> TYPE: DNA
<213> ORGANISM: Homo sapiens

<400> SEQUENCE: 24
tgtgcggcag ttcccccccc tcagggaacg acattttggg ggtgcttttt gagatctgg       59

<210> SEQ ID NO 25
<211> LENGTH: 58
<212> TYPE: DNA
<213> ORGANISM: Homo sapiens

<400> SEQUENCE: 25
tgtgcggcag ttcccccccc tcagggaacg acatttggg gtgcttttg agatctgg          58

<210> SEQ ID NO 26
<211> LENGTH: 57
<212> TYPE: DNA
<213> ORGANISM: Homo sapiens

<400> SEQUENCE: 26
tgtgcggcag ttcccccccc tcagggaacg acattttggg gtgcttttga gatctgg        57

<210> SEQ ID NO 27
<211> LENGTH: 57
<212> TYPE: DNA
<213> ORGANISM: Homo sapiens

<400> SEQUENCE: 27
tgtgcggcag ttcccccccc tcagggaacg acattttggg gtgcttttga gatctgg        57

<210> SEQ ID NO 28
<211> LENGTH: 58
<212> TYPE: DNA
<213> ORGANISM: Homo sapiens

<400> SEQUENCE: 28
tgtgcggcag ttcccccccc tcagggaacg acattttggg gtgcttttg agatctgg         58

<210> SEQ ID NO 29
<211> LENGTH: 58
<212> TYPE: DNA
<213> ORGANISM: Homo sapiens

<400> SEQUENCE: 29
tgtgcggcag ttcccccccc tcagggaacg acattttggg gtgcttttg agatctgg         58

<210> SEQ ID NO 30
<211> LENGTH: 57
<212> TYPE: DNA
<213> ORGANISM: Homo sapiens

<400> SEQUENCE: 30
tgtgcggcag ttcccccccc tccagggaac gacatttggg gtgcttttga gatctgg        57

<210> SEQ ID NO 31
<211> LENGTH: 40
<212> TYPE: DNA
<213> ORGANISM: Homo sapiens

```
<400> SEQUENCE: 31
tgtgcgacgg tgggagttcc ccaccggttt tgatatctgg                         40

<210> SEQ ID NO 32
<211> LENGTH: 42
<212> TYPE: DNA
<213> ORGANISM: Homo sapiens

<400> SEQUENCE: 32
tgtgcgacgg tgggacgttc ccctaccggt tttgatatct gg                      42

<210> SEQ ID NO 33
<211> LENGTH: 39
<212> TYPE: DNA
<213> ORGANISM: Homo sapiens

<400> SEQUENCE: 33
tgtgcgacgg tgggagttcc caccggtttt gatatctgg                          39

<210> SEQ ID NO 34
<211> LENGTH: 38
<212> TYPE: DNA
<213> ORGANISM: Homo sapiens

<400> SEQUENCE: 34
tgtgcgacgg tgggagttcc cacggttttg atatctgg                           38

<210> SEQ ID NO 35
<211> LENGTH: 39
<212> TYPE: DNA
<213> ORGANISM: Homo sapiens

<400> SEQUENCE: 35
tgtgcgacgg tgggagttcc caccggtttt gatatctgg                          39

<210> SEQ ID NO 36
<211> LENGTH: 39
<212> TYPE: DNA
<213> ORGANISM: Homo sapiens

<400> SEQUENCE: 36
tgtgcgacgg tgggagttcc caccggtttt gatatctgg                          39

<210> SEQ ID NO 37
<211> LENGTH: 39
<212> TYPE: DNA
<213> ORGANISM: Homo sapiens

<400> SEQUENCE: 37
tgtgcgacgg tgggagttcc caccggtttt gatatctgg                          39

<210> SEQ ID NO 38
<211> LENGTH: 39
<212> TYPE: DNA
<213> ORGANISM: Homo sapiens

<400> SEQUENCE: 38
tgtgcgacgg tgggagttcc caccggtttt gatatctgg                          39

<210> SEQ ID NO 39
<211> LENGTH: 39
<212> TYPE: DNA
<213> ORGANISM: Homo sapiens
```

-continued

```
<400> SEQUENCE: 39
tgtgcgacgg tgggagttcc caccggtttt gatatctgg                              39

<210> SEQ ID NO 40
<211> LENGTH: 39
<212> TYPE: DNA
<213> ORGANISM: Homo sapiens

<400> SEQUENCE: 40
tgtgcgacgg tgggagttcc caccggtttt gatatctgg                              39

<210> SEQ ID NO 41
<211> LENGTH: 39
<212> TYPE: DNA
<213> ORGANISM: Homo sapiens

<400> SEQUENCE: 41
tgtgcgacgg tgggagttcc caccggtttt gatatctgg                              39

<210> SEQ ID NO 42
<211> LENGTH: 39
<212> TYPE: DNA
<213> ORGANISM: Homo sapiens

<400> SEQUENCE: 42
tgtgcgacgg tgggagttcc caccggtttt gatatctgg                              39

<210> SEQ ID NO 43
<211> LENGTH: 39
<212> TYPE: DNA
<213> ORGANISM: Homo sapiens

<400> SEQUENCE: 43
tgtgcgacgg tgggagttcc caccggtttt gatatctgg                              39

<210> SEQ ID NO 44
<211> LENGTH: 39
<212> TYPE: DNA
<213> ORGANISM: Homo sapiens

<400> SEQUENCE: 44
tgtgcgacgg tgggagttcc caccggtttt gatatctgg                              39

<210> SEQ ID NO 45
<211> LENGTH: 39
<212> TYPE: DNA
<213> ORGANISM: Homo sapiens

<400> SEQUENCE: 45
tgtgcgacgg tgggagttcc caccggtttt gatatctgg                              39

<210> SEQ ID NO 46
<211> LENGTH: 39
<212> TYPE: DNA
<213> ORGANISM: Homo sapiens

<400> SEQUENCE: 46
tgtgcgacgg tgggagttcc caccggtttt gatatctgg                              39

<210> SEQ ID NO 47
<211> LENGTH: 39
<212> TYPE: DNA
```

```
<213> ORGANISM: Homo sapiens

<400> SEQUENCE: 47
tgtgcgacgg tgggagttcc caccggtttt gatatctgg                            39

<210> SEQ ID NO 48
<211> LENGTH: 39
<212> TYPE: DNA
<213> ORGANISM: Homo sapiens

<400> SEQUENCE: 48
tgtgcgacgg tgggagttcc caccggtttt gatatctgg                            39

<210> SEQ ID NO 49
<211> LENGTH: 39
<212> TYPE: DNA
<213> ORGANISM: Homo sapiens

<400> SEQUENCE: 49
tgtgcgacgg tgggagttcc caccggtttt gatatctgg                            39

<210> SEQ ID NO 50
<211> LENGTH: 40
<212> TYPE: DNA
<213> ORGANISM: Homo sapiens

<400> SEQUENCE: 50
tgtgcgacgg tgggagttct caccggtttt tgatatctgg                           40

<210> SEQ ID NO 51
<211> LENGTH: 38
<212> TYPE: DNA
<213> ORGANISM: Homo sapiens

<400> SEQUENCE: 51
tgtgcgacgg tgggagttcc accggttttg atatctgg                             38

<210> SEQ ID NO 52
<211> LENGTH: 38
<212> TYPE: DNA
<213> ORGANISM: Homo sapiens

<400> SEQUENCE: 52
tgtgcgacgg tgggaattcc accggttttg atatctgg                             38

<210> SEQ ID NO 53
<211> LENGTH: 40
<212> TYPE: DNA
<213> ORGANISM: Homo sapiens

<400> SEQUENCE: 53
tgtgcgacgg tgggagttcc caccggtttt tgatatctgg                           40

<210> SEQ ID NO 54
<211> LENGTH: 40
<212> TYPE: DNA
<213> ORGANISM: Homo sapiens

<400> SEQUENCE: 54
tgtgcgacgg tgggagttcc caccggtttt tgatatctgg                           40

<210> SEQ ID NO 55
<211> LENGTH: 40
```

<212> TYPE: DNA
<213> ORGANISM: Homo sapiens

<400> SEQUENCE: 55
tgtgcgacgg tgggagttcc caccggtttt tgatatctgg    40

<210> SEQ ID NO 56
<211> LENGTH: 40
<212> TYPE: DNA
<213> ORGANISM: Homo sapiens

<400> SEQUENCE: 56
tgtgcgacgg tgggagttcc caccggtttt tgatatctgg    40

<210> SEQ ID NO 57
<211> LENGTH: 40
<212> TYPE: DNA
<213> ORGANISM: Homo sapiens

<400> SEQUENCE: 57
tgtgcgacgg tgggagttcc caccggtttt tgatatctgg    40

<210> SEQ ID NO 58
<211> LENGTH: 40
<212> TYPE: DNA
<213> ORGANISM: Homo sapiens

<400> SEQUENCE: 58
tgtgcgacgg tgggagttcc caccggtttt tgatatctgg    40

<210> SEQ ID NO 59
<211> LENGTH: 40
<212> TYPE: DNA
<213> ORGANISM: Homo sapiens

<400> SEQUENCE: 59
tgtgcgacgg tgggagttcc caccggtttt tgatatctgg    40

<210> SEQ ID NO 60
<211> LENGTH: 39
<212> TYPE: DNA
<213> ORGANISM: Homo sapiens

<400> SEQUENCE: 60
tgtgcgacgg tgggagttcc caccggtttt gatatctgg    39

<210> SEQ ID NO 61
<211> LENGTH: 39
<212> TYPE: DNA
<213> ORGANISM: Homo sapiens

<400> SEQUENCE: 61
tgtgcgacgg tgggagttcc caccggtttt gatatctgg    39

<210> SEQ ID NO 62
<211> LENGTH: 39
<212> TYPE: DNA
<213> ORGANISM: Homo sapiens

<400> SEQUENCE: 62
tgtgcgacgg tgggagttcc caccggtttt gatatctgg    39

<210> SEQ ID NO 63

```
<211> LENGTH: 39
<212> TYPE: DNA
<213> ORGANISM: Homo sapiens

<400> SEQUENCE: 63
tgtgcgacgg tgggagttcc caccggtttt gatatctgg                              39

<210> SEQ ID NO 64
<211> LENGTH: 39
<212> TYPE: DNA
<213> ORGANISM: Homo sapiens

<400> SEQUENCE: 64
tgtgcgacgg tgggagttcc caccggtttt gatatctgg                              39

<210> SEQ ID NO 65
<211> LENGTH: 39
<212> TYPE: DNA
<213> ORGANISM: Homo sapiens

<400> SEQUENCE: 65
tgtgcgacgg tgggagttcc caccggtttt gatatctgg                              39

<210> SEQ ID NO 66
<211> LENGTH: 39
<212> TYPE: DNA
<213> ORGANISM: Homo sapiens

<400> SEQUENCE: 66
tgtgcgacgg tgggagttcc caccggtttt gatatctgg                              39

<210> SEQ ID NO 67
<211> LENGTH: 39
<212> TYPE: DNA
<213> ORGANISM: Homo sapiens

<400> SEQUENCE: 67
tgtgcgacgg tgggagttcc caccggtttt gatatctgg                              39

<210> SEQ ID NO 68
<211> LENGTH: 39
<212> TYPE: DNA
<213> ORGANISM: Homo sapiens

<400> SEQUENCE: 68
tgtgcgacgg tgggagttcc caccggtttt gatatctgg                              39

<210> SEQ ID NO 69
<211> LENGTH: 39
<212> TYPE: DNA
<213> ORGANISM: Homo sapiens

<400> SEQUENCE: 69
tgtgcgacgg tgggagttcc caccggtttt gatatctgg                              39

<210> SEQ ID NO 70
<211> LENGTH: 39
<212> TYPE: DNA
<213> ORGANISM: Homo sapiens

<400> SEQUENCE: 70
tgtgcgacgg tgggagttcc caccggtttt gatatctgg                              39
```

```
<210> SEQ ID NO 71
<211> LENGTH: 39
<212> TYPE: DNA
<213> ORGANISM: Homo sapiens

<400> SEQUENCE: 71
tgtgcgacgg tgggagttcc caccggtttt gatatctgg                        39

<210> SEQ ID NO 72
<211> LENGTH: 39
<212> TYPE: DNA
<213> ORGANISM: Homo sapiens

<400> SEQUENCE: 72
tgtgcgacgg tgggagttcc caccggtttt gatatctgg                        39

<210> SEQ ID NO 73
<211> LENGTH: 39
<212> TYPE: DNA
<213> ORGANISM: Homo sapiens

<400> SEQUENCE: 73
tgtgcgacgg tgggagttcc caccggtttt gatatctgg                        39

<210> SEQ ID NO 74
<211> LENGTH: 39
<212> TYPE: DNA
<213> ORGANISM: Homo sapiens

<400> SEQUENCE: 74
tgtgcgacgg tgggagttcc caccggtttt gatatctgg                        39

<210> SEQ ID NO 75
<211> LENGTH: 39
<212> TYPE: DNA
<213> ORGANISM: Homo sapiens

<400> SEQUENCE: 75
tgtgcgacgg tgggagttcc caccggtttt gatatctgg                        39

<210> SEQ ID NO 76
<211> LENGTH: 39
<212> TYPE: DNA
<213> ORGANISM: Homo sapiens

<400> SEQUENCE: 76
tgtgcgacgg tgggagttcc caccggtttt gatatctgg                        39

<210> SEQ ID NO 77
<211> LENGTH: 39
<212> TYPE: DNA
<213> ORGANISM: Homo sapiens

<400> SEQUENCE: 77
tgtgcgacgg tgggagttcc caccggtttt gatatctgg                        39

<210> SEQ ID NO 78
<211> LENGTH: 39
<212> TYPE: DNA
<213> ORGANISM: Homo sapiens

<400> SEQUENCE: 78
tgtgcgacgg tgggagttcc caccggtttt gatatctgg                        39
```

```
<210> SEQ ID NO 79
<211> LENGTH: 38
<212> TYPE: DNA
<213> ORGANISM: Homo sapiens

<400> SEQUENCE: 79
tgtgcgacgg tggagttccc accggttttg atatctgg                              38

<210> SEQ ID NO 80
<211> LENGTH: 38
<212> TYPE: DNA
<213> ORGANISM: Homo sapiens

<400> SEQUENCE: 80
tgtgcgacgg tggagttccc accggttttg atatctgg                              38

<210> SEQ ID NO 81
<211> LENGTH: 38
<212> TYPE: DNA
<213> ORGANISM: Homo sapiens

<400> SEQUENCE: 81
tgtgcgacgg tggagttccc accggttttg atatctgg                              38

<210> SEQ ID NO 82
<211> LENGTH: 39
<212> TYPE: DNA
<213> ORGANISM: Homo sapiens

<400> SEQUENCE: 82
tgtgcgacgg tgggagttcc caccggtttt gatatctgg                             39

<210> SEQ ID NO 83
<211> LENGTH: 39
<212> TYPE: DNA
<213> ORGANISM: Homo sapiens

<400> SEQUENCE: 83
tgtgcgacgg tgggagttcc caccggtttt gatatctgg                             39

<210> SEQ ID NO 84
<211> LENGTH: 39
<212> TYPE: DNA
<213> ORGANISM: Homo sapiens

<400> SEQUENCE: 84
tgtgcgacgg tgggagttcc caccggtttt gatatctgg                             39

<210> SEQ ID NO 85
<211> LENGTH: 39
<212> TYPE: DNA
<213> ORGANISM: Homo sapiens

<400> SEQUENCE: 85
tgtgcgacgg tgggagttcc caccggtttt gatatctgg                             39

<210> SEQ ID NO 86
<211> LENGTH: 39
<212> TYPE: DNA
<213> ORGANISM: Homo sapiens

<400> SEQUENCE: 86
tgtgcgacgg tgggagttcc caccggtttt gatatctgg                             39
```

<210> SEQ ID NO 87
<211> LENGTH: 39
<212> TYPE: DNA
<213> ORGANISM: Homo sapiens

<400> SEQUENCE: 87
tgtgcgacgg tgggagttcc caccggtttt gatatctgg                              39

<210> SEQ ID NO 88
<211> LENGTH: 39
<212> TYPE: DNA
<213> ORGANISM: Homo sapiens

<400> SEQUENCE: 88
tgtgcgacgg tgggagttcc caccggtttt gatatctgg                              39

<210> SEQ ID NO 89
<211> LENGTH: 39
<212> TYPE: DNA
<213> ORGANISM: Homo sapiens

<400> SEQUENCE: 89
tgtgcgacgg tgggagttcc caccggtttt gatatctgg                              39

<210> SEQ ID NO 90
<211> LENGTH: 39
<212> TYPE: DNA
<213> ORGANISM: Homo sapiens

<400> SEQUENCE: 90
tgtgcgacgg tgggagttcc caccggtttt gatatctgg                              39

<210> SEQ ID NO 91
<211> LENGTH: 39
<212> TYPE: DNA
<213> ORGANISM: Homo sapiens

<400> SEQUENCE: 91
tgtgcgacgg tgggagttcc caccggtttt gatatctgg                              39

<210> SEQ ID NO 92
<211> LENGTH: 39
<212> TYPE: DNA
<213> ORGANISM: Homo sapiens

<400> SEQUENCE: 92
tgtgcgacgg tgggagttcc caccggtttt gatatctgg                              39

<210> SEQ ID NO 93
<211> LENGTH: 39
<212> TYPE: DNA
<213> ORGANISM: Homo sapiens

<400> SEQUENCE: 93
tgtgcgacgg tgggagttcc caccggtttt gatatctgg                              39

<210> SEQ ID NO 94
<211> LENGTH: 39
<212> TYPE: DNA
<213> ORGANISM: Homo sapiens

<400> SEQUENCE: 94
tgtgcgacgg tgggagttcc caccggtttt gatatctgg                                39

<210> SEQ ID NO 95
<211> LENGTH: 39
<212> TYPE: DNA
<213> ORGANISM: Homo sapiens

<400> SEQUENCE: 95
tgtgcgacgg tgggagttcc caccggtttt gatatctgg                                39

<210> SEQ ID NO 96
<211> LENGTH: 39
<212> TYPE: DNA
<213> ORGANISM: Homo sapiens

<400> SEQUENCE: 96
tgtgcgacgg tgggagttcc caccggtttt gatatctgg                                39

<210> SEQ ID NO 97
<211> LENGTH: 39
<212> TYPE: DNA
<213> ORGANISM: Homo sapiens

<400> SEQUENCE: 97
tgtgcgacgg tgggagttcc caccggtttt gatatctgg                                39

<210> SEQ ID NO 98
<211> LENGTH: 39
<212> TYPE: DNA
<213> ORGANISM: Homo sapiens

<400> SEQUENCE: 98
tgtgcgacgg tgggagttcc caccggtttt gatatctgg                                39

<210> SEQ ID NO 99
<211> LENGTH: 39
<212> TYPE: DNA
<213> ORGANISM: Homo sapiens

<400> SEQUENCE: 99
tgtgcgacgg tgggagttcc caccggtttt gatatctgg                                39

<210> SEQ ID NO 100
<211> LENGTH: 39
<212> TYPE: DNA
<213> ORGANISM: Homo sapiens

<400> SEQUENCE: 100
tgtgcgacgg tgggagttcc caccggtttt gatatctgg                                39

<210> SEQ ID NO 101
<211> LENGTH: 39
<212> TYPE: DNA
<213> ORGANISM: Homo sapiens

<400> SEQUENCE: 101
tgtgcgacgg tgggagttcc caccggtttt gatatctgg                                39

<210> SEQ ID NO 102
<211> LENGTH: 39
<212> TYPE: DNA
<213> ORGANISM: Homo sapiens

<400> SEQUENCE: 102
tgtgcgacgg tgggagttcc caccggtttt gatatctgg        39

<210> SEQ ID NO 103
<211> LENGTH: 39
<212> TYPE: DNA
<213> ORGANISM: Homo sapiens

<400> SEQUENCE: 103
tgtgcgacgg tgggagttcc caccggtttt gatatctgg        39

<210> SEQ ID NO 104
<211> LENGTH: 39
<212> TYPE: DNA
<213> ORGANISM: Homo sapiens

<400> SEQUENCE: 104
tgtgcgacgg tgggagttcc caccggtttt gatatctgg        39

<210> SEQ ID NO 105
<211> LENGTH: 39
<212> TYPE: DNA
<213> ORGANISM: Homo sapiens

<400> SEQUENCE: 105
tgtgcgacgg tgggagttcc caccggtttt gatatctgg        39

<210> SEQ ID NO 106
<211> LENGTH: 39
<212> TYPE: DNA
<213> ORGANISM: Homo sapiens

<400> SEQUENCE: 106
tgtgcgacgg tgggagttcc caccggtttt gatatctgg        39

<210> SEQ ID NO 107
<211> LENGTH: 39
<212> TYPE: DNA
<213> ORGANISM: Homo sapiens

<400> SEQUENCE: 107
tgtgcgacgg tgggagttcc caccggtttt gatatctgg        39

<210> SEQ ID NO 108
<211> LENGTH: 39
<212> TYPE: DNA
<213> ORGANISM: Homo sapiens

<400> SEQUENCE: 108
tgtgcgacgg tgggagttcc caccggtttt gatatctgg        39

<210> SEQ ID NO 109
<211> LENGTH: 39
<212> TYPE: DNA
<213> ORGANISM: Homo sapiens

<400> SEQUENCE: 109
tgtgcgacgg tgggagttcc caccggtttt gatatctgg        39

<210> SEQ ID NO 110
<211> LENGTH: 39
<212> TYPE: DNA
<213> ORGANISM: Homo sapiens

```
<400> SEQUENCE: 110
tgtgcgacgg tgggagttcc caccggtttt gatatctgg           39

<210> SEQ ID NO 111
<211> LENGTH: 39
<212> TYPE: DNA
<213> ORGANISM: Homo sapiens

<400> SEQUENCE: 111
tgtgcgacgg tgggagttcc caccggtttt gatatctgg           39

<210> SEQ ID NO 112
<211> LENGTH: 39
<212> TYPE: DNA
<213> ORGANISM: Homo sapiens

<400> SEQUENCE: 112
tgtgcgacgg tgggagttcc caccggtttt gatatctgg           39

<210> SEQ ID NO 113
<211> LENGTH: 39
<212> TYPE: DNA
<213> ORGANISM: Homo sapiens

<400> SEQUENCE: 113
tgtgcgacgg tgggagttcc caccggtttt gatatctgg           39

<210> SEQ ID NO 114
<211> LENGTH: 39
<212> TYPE: DNA
<213> ORGANISM: Homo sapiens

<400> SEQUENCE: 114
tgtgcgacgg tgggagttcc caccggtttt gatatctgg           39

<210> SEQ ID NO 115
<211> LENGTH: 39
<212> TYPE: DNA
<213> ORGANISM: Homo sapiens

<400> SEQUENCE: 115
tgtgcgacgg tgggagttcc caccggtttt gatatctgg           39

<210> SEQ ID NO 116
<211> LENGTH: 39
<212> TYPE: DNA
<213> ORGANISM: Homo sapiens

<400> SEQUENCE: 116
tgtgcgacgg tgggagttcc caccggtttt gatatctgg           39

<210> SEQ ID NO 117
<211> LENGTH: 39
<212> TYPE: DNA
<213> ORGANISM: Homo sapiens

<400> SEQUENCE: 117
tgtgcgacgg tgggagttcc caccggtttt gatatctgg           39

<210> SEQ ID NO 118
<211> LENGTH: 39
<212> TYPE: DNA
<213> ORGANISM: Homo sapiens
```

-continued

```
<400> SEQUENCE: 118
tgtgcgacgg tgggagttcc caccggtttt gatatctgg                    39

<210> SEQ ID NO 119
<211> LENGTH: 39
<212> TYPE: DNA
<213> ORGANISM: Homo sapiens

<400> SEQUENCE: 119
tgtgcgacgg tgggagttcc caccggtttt gatatctgg                    39

<210> SEQ ID NO 120
<211> LENGTH: 39
<212> TYPE: DNA
<213> ORGANISM: Homo sapiens

<400> SEQUENCE: 120
tgtgcgacgg tgggagttcc caccggtttt gatatctgg                    39

<210> SEQ ID NO 121
<211> LENGTH: 39
<212> TYPE: DNA
<213> ORGANISM: Homo sapiens

<400> SEQUENCE: 121
tgtgcgacgg tgggagttcc caccggtttt gatatctgg                    39

<210> SEQ ID NO 122
<211> LENGTH: 40
<212> TYPE: DNA
<213> ORGANISM: Homo sapiens

<400> SEQUENCE: 122
tgtgcgacgg tgggagttcc ctaccggttt tgatatctgg                   40

<210> SEQ ID NO 123
<211> LENGTH: 40
<212> TYPE: DNA
<213> ORGANISM: Homo sapiens

<400> SEQUENCE: 123
tgtgcgacgg tgggagttcc ctaccggttt tgatatctgg                   40

<210> SEQ ID NO 124
<211> LENGTH: 40
<212> TYPE: DNA
<213> ORGANISM: Homo sapiens

<400> SEQUENCE: 124
tgtgcgacgg tgggagttcc ctaccggttt tgatatctgg                   40

<210> SEQ ID NO 125
<211> LENGTH: 40
<212> TYPE: DNA
<213> ORGANISM: Homo sapiens

<400> SEQUENCE: 125
tgtgcgacgg tgggagttcc ctaccggttt tgatatctgg                   40

<210> SEQ ID NO 126
<211> LENGTH: 38
<212> TYPE: DNA
```

<213> ORGANISM: Homo sapiens

<400> SEQUENCE: 126
tgtgcgacgg tgggagttcc caccggtttg atatctgg        38

<210> SEQ ID NO 127
<211> LENGTH: 41
<212> TYPE: DNA
<213> ORGANISM: Homo sapiens

<400> SEQUENCE: 127
tgtgcgacgg tgggagttcc cctaccggtt ttgatatctg g        41

<210> SEQ ID NO 128
<211> LENGTH: 41
<212> TYPE: DNA
<213> ORGANISM: Homo sapiens

<400> SEQUENCE: 128
tgtgcgacgg tgggagttcc cctaccggtt ttgatatctg g        41

<210> SEQ ID NO 129
<211> LENGTH: 43
<212> TYPE: DNA
<213> ORGANISM: Homo sapiens

<400> SEQUENCE: 129
tgtgcgacgg gtgggacgtt cccctaccgg ttttgatatc tgg        43

<210> SEQ ID NO 130
<211> LENGTH: 39
<212> TYPE: DNA
<213> ORGANISM: Homo sapiens

<400> SEQUENCE: 130
tgtgcgacgg tgggacttcc caccgctttt gatttctgg        39

<210> SEQ ID NO 131
<211> LENGTH: 40
<212> TYPE: DNA
<213> ORGANISM: Homo sapiens

<400> SEQUENCE: 131
tgtgcgacgg tgggagttcc caccggtttt gattatcgtg        40

<210> SEQ ID NO 132
<211> LENGTH: 42
<212> TYPE: DNA
<213> ORGANISM: Homo sapiens

<400> SEQUENCE: 132
tgtgcgacgg tgggacgttc ccctaccggt tttgatatcg tg        42

<210> SEQ ID NO 133
<211> LENGTH: 18
<212> TYPE: DNA
<213> ORGANISM: artificial
<220> FEATURE:
<223> OTHER INFORMATION: Reverse transcription primer
<220> FEATURE:
<221> NAME/KEY: misc_feature
<222> LOCATION: (5)..(5)
<223> OTHER INFORMATION: wherein Y is C or T

<400> SEQUENCE: 133
agggygccag ggggaaga                                                    18

<210> SEQ ID NO 134
<211> LENGTH: 19
<212> TYPE: DNA
<213> ORGANISM: artificial
<220> FEATURE:
<223> OTHER INFORMATION: Reverse transcription primer

<400> SEQUENCE: 134
ggagacgagg gggaaaagg                                                   19

<210> SEQ ID NO 135
<211> LENGTH: 18
<212> TYPE: DNA
<213> ORGANISM: artificial
<220> FEATURE:
<223> OTHER INFORMATION: Reverse transcription primer

<400> SEQUENCE: 135
cagcgggaag accttggg                                                    18

<210> SEQ ID NO 136
<211> LENGTH: 18
<212> TYPE: DNA
<213> ORGANISM: artificial
<220> FEATURE:
<223> OTHER INFORMATION: Reverse transcription primer

<400> SEQUENCE: 136
cacatccgga gccttggt                                                    18

<210> SEQ ID NO 137
<211> LENGTH: 19
<212> TYPE: DNA
<213> ORGANISM: artificial
<220> FEATURE:
<223> OTHER INFORMATION: Reverse transcription primer

<400> SEQUENCE: 137
tcaaggggaa gacggatgg                                                   19

<210> SEQ ID NO 138
<211> LENGTH: 18
<212> TYPE: DNA
<213> ORGANISM: artificial
<220> FEATURE:
<223> OTHER INFORMATION: PCR primer

<400> SEQUENCE: 138
ccgatgggcc cttggtgg                                                    18

<210> SEQ ID NO 139
<211> LENGTH: 18
<212> TYPE: DNA
<213> ORGANISM: artificial
<220> FEATURE:
<223> OTHER INFORMATION: PCR primer

<400> SEQUENCE: 139
cggatgggcc cttggtgg                                                    18

<210> SEQ ID NO 140
<211> LENGTH: 18
<212> TYPE: DNA

```
<213> ORGANISM: artificial
<220> FEATURE:
<223> OTHER INFORMATION: PCR primer

<400> SEQUENCE: 140
gggttggggc ggatgcac                                                 18

<210> SEQ ID NO 141
<211> LENGTH: 18
<212> TYPE: DNA
<213> ORGANISM: artificial
<220> FEATURE:
<223> OTHER INFORMATION: PCR primer

<400> SEQUENCE: 141
ccttggggct ggtcgggg                                                 18

<210> SEQ ID NO 142
<211> LENGTH: 18
<212> TYPE: DNA
<213> ORGANISM: artificial
<220> FEATURE:
<223> OTHER INFORMATION: PCR primer

<400> SEQUENCE: 142
catccggagc cttggtgg                                                 18

<210> SEQ ID NO 143
<211> LENGTH: 18
<212> TYPE: DNA
<213> ORGANISM: artificial
<220> FEATURE:
<223> OTHER INFORMATION: PCR primer

<400> SEQUENCE: 143
cggatgggct ctgtgtgg                                                 18

<210> SEQ ID NO 144
<211> LENGTH: 18
<212> TYPE: DNA
<213> ORGANISM: artificial
<220> FEATURE:
<223> OTHER INFORMATION: PCR primer

<400> SEQUENCE: 144
gagcagcgac aggtgccc                                                 18

<210> SEQ ID NO 145
<211> LENGTH: 18
<212> TYPE: DNA
<213> ORGANISM: artificial
<220> FEATURE:
<223> OTHER INFORMATION: PCR primer

<400> SEQUENCE: 145
cagcagccac aggtgccc                                                 18

<210> SEQ ID NO 146
<211> LENGTH: 19
<212> TYPE: DNA
<213> ORGANISM: artificial
<220> FEATURE:
<223> OTHER INFORMATION: PCR primer

<400> SEQUENCE: 146
gcagcagcta caggtgtcc                                                19
```

<210> SEQ ID NO 147
<211> LENGTH: 18
<212> TYPE: DNA
<213> ORGANISM: artificial
<220> FEATURE:
<223> OTHER INFORMATION: PCR primer

<400> SEQUENCE: 147
ctgtagcacc aggtgccc                                               18

<210> SEQ ID NO 148
<211> LENGTH: 19
<212> TYPE: DNA
<213> ORGANISM: artificial
<220> FEATURE:
<223> OTHER INFORMATION: PCR primer

<400> SEQUENCE: 148
gctgtagctc caggtgctc                                              19

<210> SEQ ID NO 149
<211> LENGTH: 18
<212> TYPE: DNA
<213> ORGANISM: artificial
<220> FEATURE:
<223> OTHER INFORMATION: PCR primer

<400> SEQUENCE: 149
cagcaccaac aggtgccc                                               18

<210> SEQ ID NO 150
<211> LENGTH: 18
<212> TYPE: DNA
<213> ORGANISM: artificial
<220> FEATURE:
<223> OTHER INFORMATION: PCR primer
<220> FEATURE:
<221> NAME/KEY: misc_feature
<222> LOCATION: (13)..(13)
<223> OTHER INFORMATION: wherein N is G, A, T or C

<400> SEQUENCE: 150
cagcagccac agntgcct                                               18

<210> SEQ ID NO 151
<211> LENGTH: 18
<212> TYPE: DNA
<213> ORGANISM: artificial
<220> FEATURE:
<223> OTHER INFORMATION: PCR primer

<400> SEQUENCE: 151
cagcagctac aagtgccc                                               18

<210> SEQ ID NO 152
<211> LENGTH: 18
<212> TYPE: DNA
<213> ORGANISM: artificial
<220> FEATURE:
<223> OTHER INFORMATION: PCR primer

<400> SEQUENCE: 152
cagcagccac aggagccc                                               18

<210> SEQ ID NO 153

```
<211> LENGTH: 18
<212> TYPE: DNA
<213> ORGANISM: artificial
<220> FEATURE:
<223> OTHER INFORMATION: PCR primer

<400> SEQUENCE: 153
cagcagccac aggtgtcc                                              18

<210> SEQ ID NO 154
<211> LENGTH: 18
<212> TYPE: DNA
<213> ORGANISM: artificial
<220> FEATURE:
<223> OTHER INFORMATION: PCR primer

<400> SEQUENCE: 154
cagcagctac aggcaccc                                              18

<210> SEQ ID NO 155
<211> LENGTH: 16
<212> TYPE: DNA
<213> ORGANISM: artificial
<220> FEATURE:
<223> OTHER INFORMATION: PCR primer

<400> SEQUENCE: 155
cctgtttttg gtgccc                                                16

<210> SEQ ID NO 156
<211> LENGTH: 18
<212> TYPE: DNA
<213> ORGANISM: artificial
<220> FEATURE:
<223> OTHER INFORMATION: PCR primer

<400> SEQUENCE: 156
tggcagcacc aggcgccc                                              18

<210> SEQ ID NO 157
<211> LENGTH: 18
<212> TYPE: DNA
<213> ORGANISM: artificial
<220> FEATURE:
<223> OTHER INFORMATION: PCR primer

<400> SEQUENCE: 157
tcatagctgc aggtgccc                                              18

<210> SEQ ID NO 158
<211> LENGTH: 18
<212> TYPE: DNA
<213> ORGANISM: artificial
<220> FEATURE:
<223> OTHER INFORMATION: PCR primer

<400> SEQUENCE: 158
ctgtcccgtc ctgggtct                                              18

<210> SEQ ID NO 159
<211> LENGTH: 19
<212> TYPE: DNA
<213> ORGANISM: artificial
<220> FEATURE:
<223> OTHER INFORMATION: PCR primer

<400> SEQUENCE: 159
```

-continued

| | |
|---|---|
| accatccctt catgggtct | 19 |

<210> SEQ ID NO 160
<211> LENGTH: 18
<212> TYPE: DNA
<213> ORGANISM: artificial
<220> FEATURE:
<223> OTHER INFORMATION: PCR primer

<400> SEQUENCE: 160

| | |
|---|---|
| ccaccccttc ctgggtct | 18 |

<210> SEQ ID NO 161
<211> LENGTH: 24
<212> TYPE: DNA
<213> ORGANISM: artificial
<220> FEATURE:
<223> OTHER INFORMATION: PCR primer

<400> SEQUENCE: 161

| | |
|---|---|
| ttctgtgcta tattaaagct gtcc | 24 |

<210> SEQ ID NO 162
<211> LENGTH: 24
<212> TYPE: DNA
<213> ORGANISM: artificial
<220> FEATURE:
<223> OTHER INFORMATION: PCR primer

<400> SEQUENCE: 162

| | |
|---|---|
| ttgttgctat tttaaaggt gtcc | 24 |

<210> SEQ ID NO 163
<211> LENGTH: 23
<212> TYPE: DNA
<213> ORGANISM: artificial
<220> FEATURE:
<223> OTHER INFORMATION: PCR primer

<400> SEQUENCE: 163

| | |
|---|---|
| cgttgctctt ttaagaggtg tcc | 23 |

<210> SEQ ID NO 164
<211> LENGTH: 24
<212> TYPE: DNA
<213> ORGANISM: artificial
<220> FEATURE:
<223> OTHER INFORMATION: PCR primer

<400> SEQUENCE: 164

| | |
|---|---|
| ttgttgctat ttttaaaggt gtcc | 24 |

<210> SEQ ID NO 165
<211> LENGTH: 24
<212> TYPE: DNA
<213> ORGANISM: artificial
<220> FEATURE:
<223> OTHER INFORMATION: PCR primer

<400> SEQUENCE: 165

| | |
|---|---|
| ttgttgctat attagaaggt gtcc | 24 |

<210> SEQ ID NO 166
<211> LENGTH: 19
<212> TYPE: DNA

```
<213> ORGANISM: artificial
<220> FEATURE:
<223> OTHER INFORMATION: PCR primer

<400> SEQUENCE: 166
gctattttaa aaggtgtcc                                              19

<210> SEQ ID NO 167
<211> LENGTH: 24
<212> TYPE: DNA
<213> ORGANISM: artificial
<220> FEATURE:
<223> OTHER INFORMATION: PCR primer

<400> SEQUENCE: 167
ttgttgctat tttagaaggt gtcc                                        24

<210> SEQ ID NO 168
<211> LENGTH: 24
<212> TYPE: DNA
<213> ORGANISM: artificial
<220> FEATURE:
<223> OTHER INFORMATION: PCR primer

<400> SEQUENCE: 168
ttgtggctat tttaaaaggt gtcc                                        24

<210> SEQ ID NO 169
<211> LENGTH: 24
<212> TYPE: DNA
<213> ORGANISM: artificial
<220> FEATURE:
<223> OTHER INFORMATION: PCR primer

<400> SEQUENCE: 169
ttgttgttat tttacaaggt gtcc                                        24

<210> SEQ ID NO 170
<211> LENGTH: 24
<212> TYPE: DNA
<213> ORGANISM: artificial
<220> FEATURE:
<223> OTHER INFORMATION: PCR primer

<400> SEQUENCE: 170
ttcctgctat tttaaaaggt gtcc                                        24

<210> SEQ ID NO 171
<211> LENGTH: 24
<212> TYPE: DNA
<213> ORGANISM: artificial
<220> FEATURE:
<223> OTHER INFORMATION: PCR primer

<400> SEQUENCE: 171
ttgctgctat tttaaaaggt gtcc                                        24

<210> SEQ ID NO 172
<211> LENGTH: 24
<212> TYPE: DNA
<213> ORGANISM: artificial
<220> FEATURE:
<223> OTHER INFORMATION: PCR primer

<400> SEQUENCE: 172
ttttggctat tttaaaaggt gtcc                                        24
```

```
<210> SEQ ID NO 173
<211> LENGTH: 24
<212> TYPE: DNA
<213> ORGANISM: artificial
<220> FEATURE:
<223> OTHER INFORMATION: PCR primer

<400> SEQUENCE: 173
ttgtggctaa aataaaaggt gtcc                                              24

<210> SEQ ID NO 174
<211> LENGTH: 24
<212> TYPE: DNA
<213> ORGANISM: artificial
<220> FEATURE:
<223> OTHER INFORMATION: PCR primer

<400> SEQUENCE: 174
ttgttgctat aataaaaggt gtcc                                              24

<210> SEQ ID NO 175
<211> LENGTH: 24
<212> TYPE: DNA
<213> ORGANISM: artificial
<220> FEATURE:
<223> OTHER INFORMATION: PCR primer

<400> SEQUENCE: 175
ttgctggtat tttaaaaggt gtcc                                              24

<210> SEQ ID NO 176
<211> LENGTH: 24
<212> TYPE: DNA
<213> ORGANISM: artificial
<220> FEATURE:
<223> OTHER INFORMATION: PCR primer

<400> SEQUENCE: 176
ttgttggtat tttaaaaggt gtcc                                              24

<210> SEQ ID NO 177
<211> LENGTH: 18
<212> TYPE: DNA
<213> ORGANISM: artificial
<220> FEATURE:
<223> OTHER INFORMATION: PCR primer

<400> SEQUENCE: 177
cagctcccag atgggtcc                                                    18

<210> SEQ ID NO 178
<211> LENGTH: 18
<212> TYPE: DNA
<213> ORGANISM: artificial
<220> FEATURE:
<223> OTHER INFORMATION: PCR primer

<400> SEQUENCE: 178
cggctcccag atgggtcc                                                    18

<210> SEQ ID NO 179
<211> LENGTH: 18
<212> TYPE: DNA
<213> ORGANISM: artificial
<220> FEATURE:
```

<223> OTHER INFORMATION: PCR primer

<400> SEQUENCE: 179
gctcccagat gtgggtcc                                                 18

<210> SEQ ID NO 180
<211> LENGTH: 20
<212> TYPE: DNA
<213> ORGANISM: artificial
<220> FEATURE:
<223> OTHER INFORMATION: PCR primer

<400> SEQUENCE: 180
ggctgttctc caaggagtct                                               20

<210> SEQ ID NO 181
<211> LENGTH: 20
<212> TYPE: DNA
<213> ORGANISM: artificial
<220> FEATURE:
<223> OTHER INFORMATION: PCR primer

<400> SEQUENCE: 181
cctccacagt gagtgagtct                                               20

<210> SEQ ID NO 182
<211> LENGTH: 23
<212> TYPE: DNA
<213> ORGANISM: artificial
<220> FEATURE:
<223> OTHER INFORMATION: PCR primer

<400> SEQUENCE: 182
cctagctatt ctccaaggag tct                                           23

<210> SEQ ID NO 183
<211> LENGTH: 18
<212> TYPE: DNA
<213> ORGANISM: artificial
<220> FEATURE:
<223> OTHER INFORMATION: PCR primer

<400> SEQUENCE: 183
gcctcccatg gggtgtcc                                                 18

<210> SEQ ID NO 184
<211> LENGTH: 18
<212> TYPE: DNA
<213> ORGANISM: artificial
<220> FEATURE:
<223> OTHER INFORMATION: PCR primer

<400> SEQUENCE: 184
gggcctccat gggtgtcc                                                 18

<210> SEQ ID NO 185
<211> LENGTH: 18
<212> TYPE: DNA
<213> ORGANISM: artificial
<220> FEATURE:
<223> OTHER INFORMATION: PCR primer

<400> SEQUENCE: 185
cagcagcaac aggtgccc                                                 18

```
<210> SEQ ID NO 186
<211> LENGTH: 19
<212> TYPE: DNA
<213> ORGANISM: artificial
<220> FEATURE:
<223> OTHER INFORMATION: PCR primer

<400> SEQUENCE: 186
gcagcagcaa caggtacct                                                    19

<210> SEQ ID NO 187
<211> LENGTH: 40
<212> TYPE: DNA
<213> ORGANISM: Artificial
<220> FEATURE:
<223> OTHER INFORMATION: Construction oligonucleotide

<400> SEQUENCE: 187
ccatctcatc cctgcgtgtc tccgactcag acgagtgcgt                              40

<210> SEQ ID NO 188
<211> LENGTH: 40
<212> TYPE: DNA
<213> ORGANISM: Artificial
<220> FEATURE:
<223> OTHER INFORMATION: Construction oligonucleotide

<400> SEQUENCE: 188
ccatctcatc cctgcgtgtc tccgactcag acgctcgaca                              40

<210> SEQ ID NO 189
<211> LENGTH: 40
<212> TYPE: DNA
<213> ORGANISM: Artificial
<220> FEATURE:
<223> OTHER INFORMATION: Construction oligonucleotide

<400> SEQUENCE: 189
ccatctcatc cctgcgtgtc tccgactcag agacgcactc                              40

<210> SEQ ID NO 190
<211> LENGTH: 40
<212> TYPE: DNA
<213> ORGANISM: Artificial
<220> FEATURE:
<223> OTHER INFORMATION: Construction oligonucleotide

<400> SEQUENCE: 190
ccatctcatc cctgcgtgtc tccgactcag agcactgtag                              40

<210> SEQ ID NO 191
<211> LENGTH: 40
<212> TYPE: DNA
<213> ORGANISM: Artificial
<220> FEATURE:
<223> OTHER INFORMATION: Construction oligonucleotide

<400> SEQUENCE: 191
ccatctcatc cctgcgtgtc tccgactcag atcagacacg                              40

<210> SEQ ID NO 192
<211> LENGTH: 40
<212> TYPE: DNA
<213> ORGANISM: Artificial
<220> FEATURE:
<223> OTHER INFORMATION: Construction oligonucleotide
```

```
<400> SEQUENCE: 192
ccatctcatc cctgcgtgtc tccgactcag atatcgcgag                          40

<210> SEQ ID NO 193
<211> LENGTH: 40
<212> TYPE: DNA
<213> ORGANISM: Artificial
<220> FEATURE:
<223> OTHER INFORMATION: Construction oligonucleotide

<400> SEQUENCE: 193
ccatctcatc cctgcgtgtc tccgactcag ctcgcgtgtc                          40

<210> SEQ ID NO 194
<211> LENGTH: 40
<212> TYPE: DNA
<213> ORGANISM: Artificial
<220> FEATURE:
<223> OTHER INFORMATION: Construction oligonucleotide

<400> SEQUENCE: 194
ccatctcatc cctgcgtgtc tccgactcag tagtatcagc                          40

<210> SEQ ID NO 195
<211> LENGTH: 40
<212> TYPE: DNA
<213> ORGANISM: Artificial
<220> FEATURE:
<223> OTHER INFORMATION: Construction oligonucleotide

<400> SEQUENCE: 195
ccatctcatc cctgcgtgtc tccgactcag tctctatgcg                          40

<210> SEQ ID NO 196
<211> LENGTH: 22
<212> TYPE: DNA
<213> ORGANISM: Artificial
<220> FEATURE:
<223> OTHER INFORMATION: Construction oligonucleotide

<400> SEQUENCE: 196
acgcactcgt ctgagtcgga ga                                             22

<210> SEQ ID NO 197
<211> LENGTH: 22
<212> TYPE: DNA
<213> ORGANISM: Artificial
<220> FEATURE:
<223> OTHER INFORMATION: Construction oligonucleotide

<400> SEQUENCE: 197
tgtcgagcgt ctgagtcgga ga                                             22

<210> SEQ ID NO 198
<211> LENGTH: 22
<212> TYPE: DNA
<213> ORGANISM: Artificial
<220> FEATURE:
<223> OTHER INFORMATION: Construction oligonucleotide

<400> SEQUENCE: 198
gagtgcgtct ctgagtcgga ga                                             22

<210> SEQ ID NO 199
<211> LENGTH: 22
```

```
<212> TYPE: DNA
<213> ORGANISM: Artificial
<220> FEATURE:
<223> OTHER INFORMATION: Construction oligonucleotide

<400> SEQUENCE: 199
ctacagtgct ctgagtcgga ga                                              22

<210> SEQ ID NO 200
<211> LENGTH: 22
<212> TYPE: DNA
<213> ORGANISM: Artificial
<220> FEATURE:
<223> OTHER INFORMATION: Construction oligonucleotide

<400> SEQUENCE: 200
cgtgtctgat ctgagtcgga ga                                              22

<210> SEQ ID NO 201
<211> LENGTH: 22
<212> TYPE: DNA
<213> ORGANISM: Artificial
<220> FEATURE:
<223> OTHER INFORMATION: Construction oligonucleotide

<400> SEQUENCE: 201
ctcgcgatat ctgagtcgga ga                                              22

<210> SEQ ID NO 202
<211> LENGTH: 22
<212> TYPE: DNA
<213> ORGANISM: Artificial
<220> FEATURE:
<223> OTHER INFORMATION: Construction oligonucletide

<400> SEQUENCE: 202
gacacgcgag ctgagtcgga ga                                              22

<210> SEQ ID NO 203
<211> LENGTH: 22
<212> TYPE: DNA
<213> ORGANISM: Artificial
<220> FEATURE:
<223> OTHER INFORMATION: Construction oligonucleotide

<400> SEQUENCE: 203
gctgatacta ctgagtcgga ga                                              22

<210> SEQ ID NO 204
<211> LENGTH: 22
<212> TYPE: DNA
<213> ORGANISM: Artificial
<220> FEATURE:
<223> OTHER INFORMATION: Construction oligonucleotide

<400> SEQUENCE: 204
cgcatagaga ctgagtcgga ga                                              22

<210> SEQ ID NO 205
<211> LENGTH: 30
<212> TYPE: DNA
<213> ORGANISM: Artificial
<220> FEATURE:
<223> OTHER INFORMATION: Construction oligonucleotide

<400> SEQUENCE: 205
```

<210> SEQ ID NO 206
<211> LENGTH: 12
<212> TYPE: DNA
<213> ORGANISM: Artificial
<220> FEATURE:
<223> OTHER INFORMATION: Construction oligonucleotide

<400> SEQUENCE: 206

```
ctgagactgc ca                                                         12
```

<210> SEQ ID NO 207
<211> LENGTH: 390
<212> TYPE: DNA
<213> ORGANISM: Hepatitis B virus

<400> SEQUENCE: 207

```
cgcgttgctc ttttaagagg tgtccagtgt caggtgcagc tggtggagtc tgggggaggc      60
gtggtccagc ctgggaggtc cctgagactc tcctgtgcag cctctggatt caccttcagt     120
agctatggca tgcactgggt ccgccaggct ccaggcaagg gctggagtg gtggcagtt      180
atatcatatg atggaagtaa taatactat gcagactccg tgaagggccg attcaccatc      240
tccagagaca attccaagaa cacgctgtat ctgcaaatga acagcctgag agctgaggac     300
acggctgtgt attactgtgc gagagaactt actatggttc ggggagttcc tgactactgg     360
ggccagggaa ccctggtcac cgtctcctca                                     390
```

<210> SEQ ID NO 208
<211> LENGTH: 396
<212> TYPE: DNA
<213> ORGANISM: Hepatitis B virus

<400> SEQUENCE: 208

```
ctcgttgctc ttttaagagg tgtccagtgt caggtgcagc tggtggagtc tgggggaggc      60
gtggtccagc ctgggaggtc cctgagactc tcctgtgcag cctctggatt caccttcagt     120
aggtatggca tgcactgggt ccgccaggct ccaggcaagg gctggagtg gtggcagtg      180
atatcatatg atggaagtaa taatggtat gcagactccg tgaagggccg attcaccatc      240
tccagagaca attccaagaa cactctgttt ctgcaaatgc acagcctgag agctgcggac     300
acgggtgtat attactgtgc gaaagatcaa ctttactttg gttcgcagag tcccgggcac     360
tactgggtcc agggaacccct ggtcaccgtc tcctca                             396
```

<210> SEQ ID NO 209
<211> LENGTH: 399
<212> TYPE: DNA
<213> ORGANISM: Hepatitis B virus

<400> SEQUENCE: 209

```
tgcgtcgttg ctcttttaag aggtgtccag tgtcaggtgc agctggtgga gtctggggga      60
ggcgtggtcc agcctgggag gtccctgaga ctctcctgtg cagcctctgg attcaccttc     120
agtagctatg gcatgcactg gtccgccag gctccaggca aggggctgga gtgggtggca     180
gttatatcat atgatggaag taataaatac tatgcagact ccgtgaaggg ccgattcacc     240
atctccagag acaattccaa gaacacgctg tatctgcaaa tgaacagcct gagagctgag     300
gacacggctg tgtattactg tgcgaaagat ctggcctact atggttcggg gagttattac     360
gactactggg gccagggaac cctggtcacc gtctcctca                            399
```

<210> SEQ ID NO 210
<211> LENGTH: 399
<212> TYPE: DNA
<213> ORGANISM: Hepatitis B virus

<400> SEQUENCE: 210

```
ttcctcgttg ctcttttaag aggtgtccag tgtcaggtgc agctggtgga gtctggggga      60
ggcgtggtcc agcctgggag gtccctgaga ctctcctgtg cagcctctgg attcaccttc     120
agtaggtatg gcatgcactg ggtccgccag gctccaggca aggggctgga gtgggtggca     180
gtgatatcat atgatggaag taataaatgg tatgcagact ccgtgaaggg ccgattcacc     240
atctccagag acaattccaa gaacactctg tttctgcaaa tgcacagcct gagagctgcg     300
gacacgggtg tatattactg tgcgaaagat caactttact ttggttcgca gagtcccggg     360
cactactggg tccagggaac cctggtcacc gtctcctca                            399
```

<210> SEQ ID NO 211
<211> LENGTH: 9
<212> TYPE: PRT
<213> ORGANISM: Hepatitis B virus

<400> SEQUENCE: 211

Cys Ala Arg Gln Thr Phe Asp Tyr Trp
1               5

<210> SEQ ID NO 212
<211> LENGTH: 282
<212> TYPE: DNA
<213> ORGANISM: Hepatitis B virus

<400> SEQUENCE: 212

```
tctctgaaga tctcctgtaa gggttctgga tacagcttta ccagctactg gatcggctgg      60
gtgcgccaga tgcccgggaa aggcctggag tggatgggga tcatctatcc tggtgactct     120
gataccagat acagcccgtc cttccaaggc caggtcacca tctcagccga caagtccatc     180
agcaccgcct acctgcagtg gagcagcctg aaggcctcgg acaccgccat gtattactgt     240
gcgagacaga cttttgacta ctggggccag ggaaccctgg tc                        282
```

<210> SEQ ID NO 213
<211> LENGTH: 346
<212> TYPE: DNA
<213> ORGANISM: Hepatitis B virus

<400> SEQUENCE: 213

```
tctctgaaga tctcctgtaa gggttctgga tacagcttta ccaactactg gatcggctgg      60
gtgcgccaga tgcccgggaa aggcctggag tggatgggga tcatctatcc tggtgactct     120
gataccagat acagcccgtc cttccaaggc caggtcacca tctcagccga caagtccatc     180
agcaccgcct acctgcagtg gagcagcctg aaggcctcgg acaccgccat gtattactgt     240
gcgagacaga cttttgctgc agtggagcag cctgaaggcc tcggacaccg ccatgtatta     300
ctgtgcgaga caaactttg actactgggg ccagggaacc ctggtc                    346
```

<210> SEQ ID NO 214
<211> LENGTH: 94
<212> TYPE: PRT
<213> ORGANISM: Hepatitis B virus

<400> SEQUENCE: 214

```
Ser Leu Lys Ile Ser Cys Lys Gly Ser Gly Tyr Ser Phe Thr Ser Tyr
1               5                   10                  15

Trp Ile Gly Trp Val Arg Gln Met Pro Gly Lys Gly Leu Glu Trp Met
            20                  25                  30

Gly Ile Ile Tyr Pro Gly Asp Ser Asp Thr Arg Tyr Ser Pro Ser Phe
            35                  40                  45

Gln Gly Gln Val Thr Ile Ser Ala Asp Lys Ser Ile Ser Thr Ala Tyr
    50                  55                  60

Leu Gln Trp Ser Ser Leu Lys Ala Ser Asp Thr Ala Met Tyr Tyr Cys
65                  70                  75                  80

Ala Arg Gln Thr Phe Asp Tyr Trp Gly Gln Gly Thr Leu Val
                85                  90
```

<210> SEQ ID NO 215
<211> LENGTH: 94
<212> TYPE: PRT
<213> ORGANISM: Hepatitis B virus

<400> SEQUENCE: 215

```
Ser Leu Lys Ile Ser Cys Lys Gly Ser Gly Tyr Ser Phe Thr Asn Tyr
1               5                   10                  15

Trp Ile Gly Trp Val Arg Gln Met Pro Gly Lys Gly Leu Glu Trp Met
            20                  25                  30

Gly Ile Ile Tyr Pro Gly Asp Ser Asp Thr Arg Tyr Ser Pro Ser Phe
            35                  40                  45

Gln Gly Gln Val Thr Ile Ser Ala Asp Lys Ser Ile Ser Thr Ala Tyr
    50                  55                  60

Leu Gln Trp Ser Ser Leu Lys Ala Ser Asp Thr Ala Met Tyr Tyr Cys
65                  70                  75                  80

Ala Arg Gln Thr Phe Asp Tyr Trp Gly Gln Gly Thr Leu Val
                85                  90
```

<210> SEQ ID NO 216
<211> LENGTH: 50
<212> TYPE: DNA
<213> ORGANISM: Artificial
<220> FEATURE:
<223> OTHER INFORMATION: PCR primer

<400> SEQUENCE: 216
gggacaagtt tgtcaaaaag caggcttcga ggtgcagctg gtggagtccg            50

<210> SEQ ID NO 217
<211> LENGTH: 51
<212> TYPE: DNA
<213> ORGANISM: Artificial
<220> FEATURE:
<223> OTHER INFORMATION: PCR primer

<400> SEQUENCE: 217
gggacaagtt tgtcaaaaag caggcttcga ggtgcagctg gtggagtctg g          51

<210> SEQ ID NO 218
<211> LENGTH: 56
<212> TYPE: DNA
<213> ORGANISM: Artificial
<220> FEATURE:
<223> OTHER INFORMATION: PCR primer

<400> SEQUENCE: 218

-continued gggacaagtt tgtacaaaaa agcaggcttc caggtcacct tgagggagtc tggtcc    56

<210> SEQ ID NO 219
<211> LENGTH: 51
<212> TYPE: DNA
<213> ORGANISM: Artificial
<220> FEATURE:
<223> OTHER INFORMATION: PCR primer

<400> SEQUENCE: 219
gggacaagtt tgtcaaaaag caggcttcca ggttcagctg ttgcagcctg g    51

<210> SEQ ID NO 220
<211> LENGTH: 51
<212> TYPE: DNA
<213> ORGANISM: Artificial
<220> FEATURE:
<223> OTHER INFORMATION: PCR primer

<400> SEQUENCE: 220
gggacaagtt tgtcaaaaag caggcttcca ggtgcagcta cagcagtggg g    51

<210> SEQ ID NO 221
<211> LENGTH: 51
<212> TYPE: DNA
<213> ORGANISM: Artificial
<220> FEATURE:
<223> OTHER INFORMATION: PCR primer

<400> SEQUENCE: 221
gggacaagtt tgtcaaaaag caggcttcca ggtgcagctg gtgcaatctg g    51

<210> SEQ ID NO 222
<211> LENGTH: 56
<212> TYPE: DNA
<213> ORGANISM: Artificial
<220> FEATURE:
<223> OTHER INFORMATION: PCR primer

<400> SEQUENCE: 222
gggacaagtt tgtacaaaaa agcaggcttc caggtcacct tgaaggagtc tggtcc    56

<210> SEQ ID NO 223
<211> LENGTH: 52
<212> TYPE: DNA
<213> ORGANISM: Artificial
<220> FEATURE:
<223> OTHER INFORMATION: PCR primer

<400> SEQUENCE: 223
gggacaagtt tgtcaaaaag caggcttcca ggtccagctg gtacagtctg gg    52

<210> SEQ ID NO 224
<211> LENGTH: 52
<212> TYPE: DNA
<213> ORGANISM: Artificial
<220> FEATURE:
<223> OTHER INFORMATION: PCR primer

<400> SEQUENCE: 224
gggacaagtt tgtcaaaaag caggcttcca ggaccagttg gtgcagtctg gg    52

<210> SEQ ID NO 225
<211> LENGTH: 53
<212> TYPE: DNA
<213> ORGANISM: Artificial

```
<220> FEATURE:
<223> OTHER INFORMATION: PCR primer

<400> SEQUENCE: 225
gggacaagtt tgtacaaaaa agcaggcttc caggtgcagc tggtggagtc tgg         53

<210> SEQ ID NO 226
<211> LENGTH: 52
<212> TYPE: DNA
<213> ORGANISM: Artificial
<220> FEATURE:
<223> OTHER INFORMATION: PCR primer

<400> SEQUENCE: 226
ggggacaagt ttgtcaaaaa gcaggcttcc agatgcagct ggtgcagtct gg          52

<210> SEQ ID NO 227
<211> LENGTH: 52
<212> TYPE: DNA
<213> ORGANISM: Artificial
<220> FEATURE:
<223> OTHER INFORMATION: PCR primer

<400> SEQUENCE: 227
gggacaagtt tgtcaaaaag caggcttcca atgcagctg gtgcagtctg gg           52

<210> SEQ ID NO 228
<211> LENGTH: 52
<212> TYPE: DNA
<213> ORGANISM: Artificial
<220> FEATURE:
<223> OTHER INFORMATION: PCR primer

<400> SEQUENCE: 228
gggacaagtt tgtcaaaaag caggcttcga agtgcagctg gtggagtctg gg          52

<210> SEQ ID NO 229
<211> LENGTH: 53
<212> TYPE: DNA
<213> ORGANISM: Artificial
<220> FEATURE:
<223> OTHER INFORMATION: PCR primer

<400> SEQUENCE: 229
ggggacaagt ttgtacaaaa aagcaggctt ccaggtgcag ctggtgcagt ctg         53

<210> SEQ ID NO 230
<211> LENGTH: 52
<212> TYPE: DNA
<213> ORGANISM: Artificial
<220> FEATURE:
<223> OTHER INFORMATION: PCR primer

<400> SEQUENCE: 230
gggacaagtt tgtcaaaaag caggcttcga ggatcagctg gtggagtctg gg          52

<210> SEQ ID NO 231
<211> LENGTH: 52
<212> TYPE: DNA
<213> ORGANISM: Artificial
<220> FEATURE:
<223> OTHER INFORMATION: PCR primer

<400> SEQUENCE: 231
gggacaagtt tgtcaaaaag caggcttcga ggtccagctg gtacagtctg gg          52
```

<210> SEQ ID NO 232
<211> LENGTH: 51
<212> TYPE: DNA
<213> ORGANISM: Artificial
<220> FEATURE:
<223> OTHER INFORMATION: PCr primer

<400> SEQUENCE: 232
gggacaagtt tgtacaaaaa agcaggcttc cagctgcagc tgcaggagtc c         51

<210> SEQ ID NO 233
<211> LENGTH: 51
<212> TYPE: DNA
<213> ORGANISM: Artificial
<220> FEATURE:
<223> OTHER INFORMATION: PCR primer

<400> SEQUENCE: 233
gggacaagtt tgtcaaaaag caggcttcga ggtgcagctg gtggagtctg g         51

<210> SEQ ID NO 234
<211> LENGTH: 50
<212> TYPE: DNA
<213> ORGANISM: Artificial
<220> FEATURE:
<223> OTHER INFORMATION: PCR primer

<400> SEQUENCE: 234
gggacaagtt tgtcaaaaag caggcttcca ggtgcagctg gtgcagtctg          50

<210> SEQ ID NO 235
<211> LENGTH: 52
<212> TYPE: DNA
<213> ORGANISM: Artificial
<220> FEATURE:
<223> OTHER INFORMATION: PCR primer

<400> SEQUENCE: 235
gggacaagtt tgtcaaaaag caggcttcca ggtacagctg cagcagtcag gt        52

<210> SEQ ID NO 236
<211> LENGTH: 55
<212> TYPE: DNA
<213> ORGANISM: Artificial
<220> FEATURE:
<223> OTHER INFORMATION: PCR primer

<400> SEQUENCE: 236
ggggacaagt ttgtacaaaa aagcaggctt cgagatgcag ctggtggagt ctggg     55

<210> SEQ ID NO 237
<211> LENGTH: 52
<212> TYPE: DNA
<213> ORGANISM: Artificial
<220> FEATURE:
<223> OTHER INFORMATION: PCR primer

<400> SEQUENCE: 237
gggacaagtt tgtcaaaaag caggcttcga ggtgcatctg gtggagtctg gg        52

<210> SEQ ID NO 238
<211> LENGTH: 51
<212> TYPE: DNA
<213> ORGANISM: Artificial
<220> FEATURE:
<223> OTHER INFORMATION: PCR primer

```
<400> SEQUENCE: 238
gggacaagtt tgtcaaaaag caggcttcga ggtgcagctg gtggagtctg g          51

<210> SEQ ID NO 239
<211> LENGTH: 53
<212> TYPE: DNA
<213> ORGANISM: Artificial
<220> FEATURE:
<223> OTHER INFORMATION: PCR primer

<400> SEQUENCE: 239
gggacaagtt tgtacaaaaa agcaggcttc gaggtgcagc tgtggagtc tgg         53

<210> SEQ ID NO 240
<211> LENGTH: 56
<212> TYPE: DNA
<213> ORGANISM: Artificial
<220> FEATURE:
<223> OTHER INFORMATION: PCR primer

<400> SEQUENCE: 240
gggacaagtt tgtacaaaaa agcaggcttc caggtccaac tggtgtagtc tggagc     56

<210> SEQ ID NO 241
<211> LENGTH: 52
<212> TYPE: DNA
<213> ORGANISM: Artificial
<220> FEATURE:
<223> OTHER INFORMATION: PCR primer

<400> SEQUENCE: 241
gggacaagtt tgtacaaaaa agcaggcttc gaggtgcagc tggtgcagtc tg         52

<210> SEQ ID NO 242
<211> LENGTH: 52
<212> TYPE: DNA
<213> ORGANISM: Artificial
<220> FEATURE:
<223> OTHER INFORMATION: PCR primer

<400> SEQUENCE: 242
gggacaagtt tgtacaaaaa gcaggcttcg aggtgcagct ggtggagtct cg         52

<210> SEQ ID NO 243
<211> LENGTH: 54
<212> TYPE: DNA
<213> ORGANISM: Artificial
<220> FEATURE:
<223> OTHER INFORMATION: PCR primer

<400> SEQUENCE: 243
gggacaagtt tgtacaaaaa agcaggcttc gaggttcagc tggtgcagtc tggg       54

<210> SEQ ID NO 244
<211> LENGTH: 51
<212> TYPE: DNA
<213> ORGANISM: Artificial
<220> FEATURE:
<223> OTHER INFORMATION: PCR primer

<400> SEQUENCE: 244
gggacaagtt tgtcaaaaaa gcaggcttcc aggtgcagct ggtgcagtct g          51

<210> SEQ ID NO 245
```

```
<211> LENGTH: 52
<212> TYPE: DNA
<213> ORGANISM: Artificial
<220> FEATURE:
<223> OTHER INFORMATION: PCR primer

<400> SEQUENCE: 245
gggacaagtt tgtacaaaaa gcaggcttcg aagtgcagct ggtgcagtct gg         52

<210> SEQ ID NO 246
<211> LENGTH: 56
<212> TYPE: DNA
<213> ORGANISM: Artificial
<220> FEATURE:
<223> OTHER INFORMATION: PCR primer

<400> SEQUENCE: 246
gggacaagtt tgtacaaaaa agcaggcttc gaggtggagc tgatagagtc cataga     56

<210> SEQ ID NO 247
<211> LENGTH: 52
<212> TYPE: DNA
<213> ORGANISM: Artificial
<220> FEATURE:
<223> OTHER INFORMATION: PCR primer

<400> SEQUENCE: 247
gggacaagtt tgtcaaaaaa gcaggcttca cagtgcagct ggtggagtct gg         52

<210> SEQ ID NO 248
<211> LENGTH: 52
<212> TYPE: DNA
<213> ORGANISM: Artificial
<220> FEATURE:
<223> OTHER INFORMATION: PCR primer

<400> SEQUENCE: 248
gggacaagtt tgtacaaaaa gcaggcttcg aggtgcagct ggaggagtct gg         52

<210> SEQ ID NO 249
<211> LENGTH: 55
<212> TYPE: DNA
<213> ORGANISM: Artificial
<220> FEATURE:
<223> OTHER INFORMATION: PCR primer

<400> SEQUENCE: 249
gggacaagtt tgtcaaaaaa gcaggcttcg aggtacagct ggtggagtct gaaga      55

<210> SEQ ID NO 250
<211> LENGTH: 51
<212> TYPE: DNA
<213> ORGANISM: Artificial
<220> FEATURE:
<223> OTHER INFORMATION: PCR primer

<400> SEQUENCE: 250
gggacaagtt tgtacaaaaa agcaggcttc caggtgcagc tgcaggagtc g          51

<210> SEQ ID NO 251
<211> LENGTH: 52
<212> TYPE: DNA
<213> ORGANISM: Artificial
<220> FEATURE:
<223> OTHER INFORMATION: PCR primer

<400> SEQUENCE: 251
```
gggacaagtt tgtcaaaaag caggcttcga ggtgcagctg ttggagtctg gg    52

<210> SEQ ID NO 252
<211> LENGTH: 50
<212> TYPE: DNA
<213> ORGANISM: Artificial
<220> FEATURE:
<223> OTHER INFORMATION: PCR primer

<400> SEQUENCE: 252
gggacaagtt tgtacaaaaa agcaggcttc caggtgcagc tggggcagtc    50

<210> SEQ ID NO 253
<211> LENGTH: 51
<212> TYPE: DNA
<213> ORGANISM: Artificial
<220> FEATURE:
<223> OTHER INFORMATION: PCR primer

<400> SEQUENCE: 253
gggacaagtt tgtacaaaaa agcaggcttc cagctgcagc tgcaggagtc g    51

<210> SEQ ID NO 254
<211> LENGTH: 54
<212> TYPE: DNA
<213> ORGANISM: Artificial
<220> FEATURE:
<223> OTHER INFORMATION: PCR primer

<400> SEQUENCE: 254
gggacaagtt tgtacaaaaa agcaggcttc caggttcagc tggtgcagtc tgga    54

<210> SEQ ID NO 255
<211> LENGTH: 54
<212> TYPE: DNA
<213> ORGANISM: Artificial
<220> FEATURE:
<223> OTHER INFORMATION: PCR primer

<400> SEQUENCE: 255
gggacaagtt tgtacaaaaa agcaggcttc gaggtgcagc tggtagagtc tggg    54

<210> SEQ ID NO 256
<211> LENGTH: 52
<212> TYPE: DNA
<213> ORGANISM: Artificial
<220> FEATURE:
<223> OTHER INFORMATION: PCR primer

<400> SEQUENCE: 256
gggacaagtt tgtcaaaaag caggcttcca ggtccagctt gtgcagtctg gg    52

<210> SEQ ID NO 257
<211> LENGTH: 53
<212> TYPE: DNA
<213> ORGANISM: Artificial
<220> FEATURE:
<223> OTHER INFORMATION: PCR primer

<400> SEQUENCE: 257
gggacaagtt tgtacaaaaa agcaggcttc gaggtgcagc tgttgcagtc tgc    53

<210> SEQ ID NO 258
<211> LENGTH: 56
<212> TYPE: DNA

```
<213> ORGANISM: Artificial
<220> FEATURE:
<223> OTHER INFORMATION: PCR primer

<400> SEQUENCE: 258
gggacaagtt tgtacaaaaa agcaggcttc gaggtacaac tggtggagtc tggggg        56

<210> SEQ ID NO 259
<211> LENGTH: 56
<212> TYPE: DNA
<213> ORGANISM: Artificial
<220> FEATURE:
<223> OTHER INFORMATION: PCR primer

<400> SEQUENCE: 259
gggacaagtt tgtacaaaaa agcaggcttc cagatcacct tgaaggagtc tggtcc        56

<210> SEQ ID NO 260
<211> LENGTH: 55
<212> TYPE: DNA
<213> ORGANISM: Artificial
<220> FEATURE:
<223> OTHER INFORMATION: PCR primer

<400> SEQUENCE: 260
gggacaagtt tgtacaaaaa agcaggcttc caggtacagc tgatgcagtc tgggg         55

<210> SEQ ID NO 261
<211> LENGTH: 55
<212> TYPE: DNA
<213> ORGANISM: Artificial
<220> FEATURE:
<223> OTHER INFORMATION: PCR primer

<400> SEQUENCE: 261
gggaccactt tgtacaagaa agctgggtct tgatctcca ccttggtccc tccgc          55

<210> SEQ ID NO 262
<211> LENGTH: 55
<212> TYPE: DNA
<213> ORGANISM: Artificial
<220> FEATURE:
<223> OTHER INFORMATION: PCR primer

<400> SEQUENCE: 262
ggggaccact tgtacaagaa aagctgggtc tttgatctcc agcttggtcc cctgg         55

<210> SEQ ID NO 263
<211> LENGTH: 55
<212> TYPE: DNA
<213> ORGANISM: Artificial
<220> FEATURE:
<223> OTHER INFORMATION: PCR primer

<400> SEQUENCE: 263
gggaccactt tgtacaagaa agctgggtct tgatatcca ctttggtccc agggc          55

<210> SEQ ID NO 264
<211> LENGTH: 55
<212> TYPE: DNA
<213> ORGANISM: Artificial
<220> FEATURE:
<223> OTHER INFORMATION: PCR primer

<400> SEQUENCE: 264
gggaccactt tgtacaagaa agctgggtct tgatttcca ccttggtccc ttggc          55
```

<210> SEQ ID NO 265
<211> LENGTH: 55
<212> TYPE: DNA
<213> ORGANISM: Artificial
<220> FEATURE:
<223> OTHER INFORMATION: PCR primer

<400> SEQUENCE: 265
gggaccactt tgtacaagaa agctgggtct ttaatctcca gtcgtgtccc ttggc          55

<210> SEQ ID NO 266
<211> LENGTH: 51
<212> TYPE: DNA
<213> ORGANISM: Artificial
<220> FEATURE:
<223> OTHER INFORMATION: PCR primer

<400> SEQUENCE: 266
gggaccactt tgtacaagaa agctgggtcg aggacggtca ccttggtgcc a              51

<210> SEQ ID NO 267
<211> LENGTH: 54
<212> TYPE: DNA
<213> ORGANISM: Artificial
<220> FEATURE:
<223> OTHER INFORMATION: PCR primer

<400> SEQUENCE: 267
ggggaccact tgtacaaga aagctgggtc taggacggtc agcttggtcc ctcc            54

<210> SEQ ID NO 268
<211> LENGTH: 51
<212> TYPE: DNA
<213> ORGANISM: Artificial
<220> FEATURE:
<223> OTHER INFORMATION: PCR primer

<400> SEQUENCE: 268
ggggaccact tgtacaaga aagctgggtc gaggacggtc agctgggtgc c               51

<210> SEQ ID NO 269
<211> LENGTH: 56
<212> TYPE: DNA
<213> ORGANISM: Artificial
<220> FEATURE:
<223> OTHER INFORMATION: PCR primer

<400> SEQUENCE: 269
ggggaccact tgtacaaga aagctgggtc taaaatgatc agctgggttc ctccac          56

<210> SEQ ID NO 270
<211> LENGTH: 54
<212> TYPE: DNA
<213> ORGANISM: Artificial
<220> FEATURE:
<223> OTHER INFORMATION: PCR primer

<400> SEQUENCE: 270
ggggaccact tgtacaaga aagctgggtc taggacggtg accttggtcc cagt            54

<210> SEQ ID NO 271
<211> LENGTH: 51
<212> TYPE: DNA
<213> ORGANISM: Artificial
<220> FEATURE:

<223> OTHER INFORMATION: PCR primer

<400> SEQUENCE: 271 gggaccact ttgtacaaga agctgggtct aggacggtca gctcggtccc c        51

<210> SEQ ID NO 272
<211> LENGTH: 28
<212> TYPE: DNA
<213> ORGANISM: Artificial
<220> FEATURE:
<223> OTHER INFORMATION: PCR primer

<400> SEQUENCE: 272
gttaggugag gagacrgtga ccagggtg        28

<210> SEQ ID NO 273
<211> LENGTH: 28
<212> TYPE: DNA
<213> ORGANISM: Artificial
<220> FEATURE:
<223> OTHER INFORMATION: PCR primer

<400> SEQUENCE: 273
gttaggugag gagacggtga ccagggtt        28

<210> SEQ ID NO 274
<211> LENGTH: 27
<212> TYPE: DNA
<213> ORGANISM: Artificial
<220> FEATURE:
<223> OTHER INFORMATION: PCR primer

<400> SEQUENCE: 274
gttaggugaa gagacggtga ccattgt        27

<210> SEQ ID NO 275
<211> LENGTH: 29
<212> TYPE: DNA
<213> ORGANISM: Artificial
<220> FEATURE:
<223> OTHER INFORMATION: PCR primer

<400> SEQUENCE: 275
gttaggugag gagacggtga ccgtggtcc        29

<210> SEQ ID NO 276
<211> LENGTH: 30
<212> TYPE: DNA
<213> ORGANISM: Artificial
<220> FEATURE:
<223> OTHER INFORMATION: PCR primer

<400> SEQUENCE: 276
gggatcucag tctgtsbtga cgcagccgcc        30

<210> SEQ ID NO 277
<211> LENGTH: 29
<212> TYPE: DNA
<213> ORGANISM: Artificial
<220> FEATURE:
<223> OTHER INFORMATION: PCR primer

<400> SEQUENCE: 277
gggatcutcc tatgwgctga cwcagccac        29

```
<210> SEQ ID NO 278
<211> LENGTH: 30
<212> TYPE: DNA
<213> ORGANISM: Artificial
<220> FEATURE:
<223> OTHER INFORMATION: PCR primer

<400> SEQUENCE: 278
gggatcutcc tatgagctga yrcagcyacc                                   30

<210> SEQ ID NO 279
<211> LENGTH: 27
<212> TYPE: DNA
<213> ORGANISM: Artificial
<220> FEATURE:
<223> OTHER INFORMATION: PCR primer

<400> SEQUENCE: 279
gggatcucag cctgtgctga ctcaryc                                      27

<210> SEQ ID NO 280
<211> LENGTH: 29
<212> TYPE: DNA
<213> ORGANISM: Artificial
<220> FEATURE:
<223> OTHER INFORMATION: PCR primer

<400> SEQUENCE: 280
ggatcucagd ctgtggtgac ycaggagcc                                    29

<210> SEQ ID NO 281
<211> LENGTH: 30
<212> TYPE: DNA
<213> ORGANISM: Artificial
<220> FEATURE:
<223> OTHER INFORMATION: PCR primer

<400> SEQUENCE: 281
gggatcucag ccwgkgctga ctcagccmcc                                   30

<210> SEQ ID NO 282
<211> LENGTH: 30
<212> TYPE: DNA
<213> ORGANISM: Artificial
<220> FEATURE:
<223> OTHER INFORMATION: PCR primer

<400> SEQUENCE: 282
gggatcutcc tctgagctga stcaggascc                                   30

<210> SEQ ID NO 283
<211> LENGTH: 28
<212> TYPE: DNA
<213> ORGANISM: Artificial
<220> FEATURE:
<223> OTHER INFORMATION: PCR primer

<400> SEQUENCE: 283
gggatcucag tctgyyctga ytcagcct                                     28

<210> SEQ ID NO 284
<211> LENGTH: 29
<212> TYPE: DNA
<213> ORGANISM: Artificial
<220> FEATURE:
<223> OTHER INFORMATION: PCR primer
```

```
<400> SEQUENCE: 284
gggatcuaat tttatgctga ctcagcccc                                29

<210> SEQ ID NO 285
<211> LENGTH: 30
<212> TYPE: DNA
<213> ORGANISM: Artificial
<220> FEATURE:
<223> OTHER INFORMATION: PCR primer

<400> SEQUENCE: 285
gggatcugac atccrgdtga cccagtctcc                               30

<210> SEQ ID NO 286
<211> LENGTH: 30
<212> TYPE: DNA
<213> ORGANISM: Artificial
<220> FEATURE:
<223> OTHER INFORMATION: PCR primer

<400> SEQUENCE: 286
gggatcugaa attgtrwtga crcagtctcc                               30

<210> SEQ ID NO 287
<211> LENGTH: 30
<212> TYPE: DNA
<213> ORGANISM: Artificial
<220> FEATURE:
<223> OTHER INFORMATION: PCR primer

<400> SEQUENCE: 287
gggatcugat attgtgmtga cbcagwctcc                               30

<210> SEQ ID NO 288
<211> LENGTH: 29
<212> TYPE: DNA
<213> ORGANISM: Artificial
<220> FEATURE:
<223> OTHER INFORMATION: PCR primer

<400> SEQUENCE: 288
gggatcugaa acgacactca cgcagtctc                                29

<210> SEQ ID NO 289
<211> LENGTH: 29
<212> TYPE: DNA
<213> ORGANISM: Artificial
<220> FEATURE:
<223> OTHER INFORMATION: PCR primer

<400> SEQUENCE: 289
agtctaguga ggagacrgtg accagggtg                                29

<210> SEQ ID NO 290
<211> LENGTH: 29
<212> TYPE: DNA
<213> ORGANISM: Artificial
<220> FEATURE:
<223> OTHER INFORMATION: PCR primer

<400> SEQUENCE: 290
agtctaguga ggagacggtg accagggtt                                29

<210> SEQ ID NO 291
<211> LENGTH: 28
```

<212> TYPE: DNA
<213> ORGANISM: Artificial
<220> FEATURE:
<223> OTHER INFORMATION: PCR primer

<400> SEQUENCE: 291
agtctaguga agagacggtg accattgt                                  28

<210> SEQ ID NO 292
<211> LENGTH: 30
<212> TYPE: DNA
<213> ORGANISM: Artificial
<220> FEATURE:
<223> OTHER INFORMATION: PCR primer

<400> SEQUENCE: 292
agtctaguga ggagacggtg accgtggtcc                                30

<210> SEQ ID NO 293
<211> LENGTH: 31
<212> TYPE: DNA
<213> ORGANISM: Artificial
<220> FEATURE:
<223> OTHER INFORMATION: PCR primer

<400> SEQUENCE: 293
actagacuca gtctgtsbtg acgcagccgc c                              31

<210> SEQ ID NO 294
<211> LENGTH: 30
<212> TYPE: DNA
<213> ORGANISM: Artificial
<220> FEATURE:
<223> OTHER INFORMATION: PCR primer

<400> SEQUENCE: 294
actagacutc ctatgwgctg acwcagccac                                30

<210> SEQ ID NO 295
<211> LENGTH: 31
<212> TYPE: DNA
<213> ORGANISM: Artificial
<220> FEATURE:
<223> OTHER INFORMATION: PCR primer

<400> SEQUENCE: 295
actagacutc ctatgagctg ayrcagcyac c                              31

<210> SEQ ID NO 296
<211> LENGTH: 28
<212> TYPE: DNA
<213> ORGANISM: Artificial
<220> FEATURE:
<223> OTHER INFORMATION: PCR primer

<400> SEQUENCE: 296
actagacuca gcctgtgctg actcaryc                                  28

<210> SEQ ID NO 297
<211> LENGTH: 31
<212> TYPE: DNA
<213> ORGANISM: Artificial
<220> FEATURE:
<223> OTHER INFORMATION: PCR primer

<400> SEQUENCE: 297
actagacuca gdctgtggtg acycaggagc c         31

<210> SEQ ID NO 298
<211> LENGTH: 31
<212> TYPE: DNA
<213> ORGANISM: Artificial
<220> FEATURE:
<223> OTHER INFORMATION: PCR primer

<400> SEQUENCE: 298
actagacuca gccwgkgctg actcagccmc c         31

<210> SEQ ID NO 299
<211> LENGTH: 31
<212> TYPE: DNA
<213> ORGANISM: Artificial
<220> FEATURE:
<223> OTHER INFORMATION: PCR primer

<400> SEQUENCE: 299
actagacutc ctctgagctg astcaggasc c         31

<210> SEQ ID NO 300
<211> LENGTH: 29
<212> TYPE: DNA
<213> ORGANISM: Artificial
<220> FEATURE:
<223> OTHER INFORMATION: PCR primer

<400> SEQUENCE: 300
actagacuca gtctgyyctg aytcagcct            29

<210> SEQ ID NO 301
<211> LENGTH: 30
<212> TYPE: DNA
<213> ORGANISM: Artificial
<220> FEATURE:
<223> OTHER INFORMATION: PCR primer

<400> SEQUENCE: 301
actagacuaa ttttatgctg actcagcccc           30

<210> SEQ ID NO 302
<211> LENGTH: 31
<212> TYPE: DNA
<213> ORGANISM: Artificial
<220> FEATURE:
<223> OTHER INFORMATION: PCR primer

<400> SEQUENCE: 302
actagacuga catccrgdtg acccagtctc c         31

<210> SEQ ID NO 303
<211> LENGTH: 31
<212> TYPE: DNA
<213> ORGANISM: Artificial
<220> FEATURE:
<223> OTHER INFORMATION: PCR primer

<400> SEQUENCE: 303
actagacuga aattgtrwtg acrcagtctc c         31

<210> SEQ ID NO 304
<211> LENGTH: 31
<212> TYPE: DNA
<213> ORGANISM: Artificial

```
-continued

<220> FEATURE:
<223> OTHER INFORMATION: PCR primer

<400> SEQUENCE: 304
actagacuga tattgtgmtg acbcagwctc c                              31

<210> SEQ ID NO 305
<211> LENGTH: 30
<212> TYPE: DNA
<213> ORGANISM: Artificial
<220> FEATURE:
<223> OTHER INFORMATION: PCR primer

<400> SEQUENCE: 305
actagacuga aacgacactc acgcagtctc                                30

<210> SEQ ID NO 306
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 306
gttaggugag gagacrgtga ccagggtg                                  28

<210> SEQ ID NO 307
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 307
gttaggugag gagacggtga ccagggtt                                  28

<210> SEQ ID NO 308
<211> LENGTH: 27
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 308
gttaggugaa gagacggtga ccattgt                                   27

<210> SEQ ID NO 309
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine
```

<400> SEQUENCE: 309
gttaggugag gagacggtga ccgtggtcc                               29

<210> SEQ ID NO 310
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 310
gggatcucag tctgtsbtga cgcagccgcc                              30

<210> SEQ ID NO 311
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 311
gggatcutcc tatgwgctga cwcagccac                               29

<210> SEQ ID NO 312
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 312
gggatcutcc tatgagctga yrcagcyacc                              30

<210> SEQ ID NO 313
<211> LENGTH: 27
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 313
gggatcucag cctgtgctga ctcaryc                                 27

<210> SEQ ID NO 314
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 314
gggatcucag dctgtggtga cycaggagcc					30

<210> SEQ ID NO 315
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 315
gggatcucag ccwgkgctga ctcagccmcc					30

<210> SEQ ID NO 316
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 316
gggatcutcc tctgagctga stcaggascc					30

<210> SEQ ID NO 317
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 317
gggatcucag tctgyyctga ytcagcct					28

<210> SEQ ID NO 318
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: wherein u is deoxyuridine

<400> SEQUENCE: 318
gggatcuaat tttatgctga ctcagcccc					29

<210> SEQ ID NO 319
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)

<223> OTHER INFORMATION: u is deoxyuridine

<400> SEQUENCE: 319
gggatcugac atccrgdtga cccagtctcc                30

<210> SEQ ID NO 320
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 320
gggatcugaa attgtrwtga crcagtctcc                30

<210> SEQ ID NO 321
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 321
gggatcugat attgtgmtga cbcagwctcc                30

<210> SEQ ID NO 322
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (7)..(7)
<223> OTHER INFORMATION: u is deoxyuridine

<400> SEQUENCE: 322
gggatcugaa acgacactca cgcagtctc                 29

<210> SEQ ID NO 323
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 323
agtctaguga ggagacrgtg accagggtg                 29

<210> SEQ ID NO 324
<211> LENGTH: 29
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 324
agtctaguga ggagacggtg accagggtt                                29

<210> SEQ ID NO 325
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 325
agtctaguga agagacggtg accattgt                                 28

<210> SEQ ID NO 326
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 326
agtctaguga ggagacggtg accgtggtcc                               30

<210> SEQ ID NO 327
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 327
actagacuca gtctgtsbtg acgcagccgc c                             31

<210> SEQ ID NO 328
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 328
actagacutc ctatgwgctg acwcagccac                               30

<210> SEQ ID NO 329
<211> LENGTH: 31
<212> TYPE: DNA
<213> ORGANISM: Artificial
<220> FEATURE:
<223> OTHER INFORMATION: PCR primer
<220> FEATURE:

<221> NAME/KEY: misc
<222> LOCATION: (8)..(8)
<223> OTHER INFORMATION: u is deoxyuridine

<400> SEQUENCE: 329
actagacutc ctatgagctg ayrcagcyac c                              31

<210> SEQ ID NO 330
<211> LENGTH: 28
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 330
actagacuca gcctgtgctg actcaryc                                  28

<210> SEQ ID NO 331
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 331
actagacuca gdctgtggtg acycaggagc c                              31

<210> SEQ ID NO 332
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 332
actagacuca gccwgkgctg actcagccmc c                              31

<210> SEQ ID NO 333
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 333
actagacutc ctctgagctg astcaggasc c                              31

<210> SEQ ID NO 334
<211> LENGTH: 29
<212> TYPE: DNA
<213> ORGANISM: Artificial
<220> FEATURE:
<223> OTHER INFORMATION: PCR primer

```
<220> FEATURE:
<221> NAME/KEY: misc
<222> LOCATION: (8)..(8)
<223> OTHER INFORMATION: u is deoxyuridine

<400> SEQUENCE: 334
actagacuca gtctgyyctg aytcagcct                                  29

<210> SEQ ID NO 335
<211> LENGTH: 30
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 335
actagacuaa ttttatgctg actcagcccc                                 30

<210> SEQ ID NO 336
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 336
actagacuga catccrgdtg acccagtctc c                               31

<210> SEQ ID NO 337
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 337
actagacuga aattgtrwtg acrcagtctc c                               31

<210> SEQ ID NO 338
<211> LENGTH: 31
<212> TYPE: DNA
<213> ORGANISM: Artificial
<220> FEATURE:
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 338
actagacuga tattgtgmtg acbcagwctc c                               31

<210> SEQ ID NO 339
<211> LENGTH: 30
<212> TYPE: DNA
<213> ORGANISM: Artificial
<220> FEATURE:
```

```
<223> OTHER INFORMATION: PCR primer
<220> FEATURE:
<221> NAME/KEY: misc
<222> LOCATION: (8)..(8)
<223> OTHER INFORMATION: u is deoxyuridine

<400> SEQUENCE: 339
actagacuga aacgacactc acgcagtctc                              30

<210> SEQ ID NO 340
<211> LENGTH: 56
<212> TYPE: DNA
<213> ORGANISM: Artificial
<220> FEATURE:
<223> OTHER INFORMATION: PCR primer

<400> SEQUENCE: 340
ctaacagcgc gagccacagt ggttctgctc cgaatactag ttctgctccg ggatcc   56

<210> SEQ ID NO 341
<211> LENGTH: 61
<212> TYPE: DNA
<213> ORGANISM: Artificial
<220> FEATURE:
<223> OTHER INFORMATION: PCR primer

<400> SEQUENCE: 341
acagtggttc tgctccgaat actagttctg ctccgggatc cgaaattgtg ttgacgcagt  60
c                                                                 61

<210> SEQ ID NO 342
<211> LENGTH: 63
<212> TYPE: DNA
<213> ORGANISM: Artificial
<220> FEATURE:
<223> OTHER INFORMATION: PCR primer

<400> SEQUENCE: 342
ctggtgccag tggcagagga gtggattgtc gcgctcggtg tcaccaagac gaggcttatg  60
atc                                                               63

<210> SEQ ID NO 343
<211> LENGTH: 30
<212> TYPE: DNA
<213> ORGANISM: Artificial
<220> FEATURE:
<223> OTHER INFORMATION: PCR primer

<400> SEQUENCE: 343
gggacaagtt tgtacaaaaa agcaggcttc                              30

<210> SEQ ID NO 344
<211> LENGTH: 27
<212> TYPE: DNA
<213> ORGANISM: Artificial
<220> FEATURE:
<223> OTHER INFORMATION: PCR primer

<400> SEQUENCE: 344
gggaccactt tgtacaagaa agctggg                                 27

<210> SEQ ID NO 345
<211> LENGTH: 51
<212> TYPE: DNA
<213> ORGANISM: Artificial
```

<220> FEATURE:
<223> OTHER INFORMATION: PCR primer

<400> SEQUENCE: 345
agcgcgagcc acagtggttc tgctccgaat actagttctg ctccgggatc t    51

<210> SEQ ID NO 346
<211> LENGTH: 51
<212> TYPE: DNA
<213> ORGANISM: Artificial
<220> FEATURE:
<223> OTHER INFORMATION: PCR primer

<400> SEQUENCE: 346
ggagcagaac tagtattcgg agcagaacca ctgtggctcg cgctgttagg t    51

<210> SEQ ID NO 347
<211> LENGTH: 22
<212> TYPE: DNA
<213> ORGANISM: Artificial
<220> FEATURE:
<223> OTHER INFORMATION: PCR primer

<400> SEQUENCE: 347
gaggtgcagc tggtggagtc cg    22

<210> SEQ ID NO 348
<211> LENGTH: 23
<212> TYPE: DNA
<213> ORGANISM: Artificial
<220> FEATURE:
<223> OTHER INFORMATION: PCR primer

<400> SEQUENCE: 348
gaggtgcagc tggtggagtc tgg    23

<210> SEQ ID NO 349
<211> LENGTH: 26
<212> TYPE: DNA
<213> ORGANISM: Artificial
<220> FEATURE:
<223> OTHER INFORMATION: PCR primer

<400> SEQUENCE: 349
caggtcacct tgagggagtc tggtcc    26

<210> SEQ ID NO 350
<211> LENGTH: 23
<212> TYPE: DNA
<213> ORGANISM: Artificial
<220> FEATURE:
<223> OTHER INFORMATION: PCR primer

<400> SEQUENCE: 350
caggttcagc tgttgcagcc tgg    23

<210> SEQ ID NO 351
<211> LENGTH: 23
<212> TYPE: DNA
<213> ORGANISM: Artificial
<220> FEATURE:
<223> OTHER INFORMATION: PCR primer

<400> SEQUENCE: 351
caggtgcagc tacagcagtg ggg    23

```
<210> SEQ ID NO 352
<211> LENGTH: 23
<212> TYPE: DNA
<213> ORGANISM: Artificial
<220> FEATURE:
<223> OTHER INFORMATION: PCR primer

<400> SEQUENCE: 352
caggtgcagc tggtgcaatc tgg                                              23

<210> SEQ ID NO 353
<211> LENGTH: 26
<212> TYPE: DNA
<213> ORGANISM: Artificial
<220> FEATURE:
<223> OTHER INFORMATION: PCR primer

<400> SEQUENCE: 353
caggtcacct tgaaggagtc tggtcc                                           26

<210> SEQ ID NO 354
<211> LENGTH: 24
<212> TYPE: DNA
<213> ORGANISM: Artificial
<220> FEATURE:
<223> OTHER INFORMATION: PCR primer

<400> SEQUENCE: 354
caggtccagc tggtacagtc tggg                                             24

<210> SEQ ID NO 355
<211> LENGTH: 24
<212> TYPE: DNA
<213> ORGANISM: Artificial
<220> FEATURE:
<223> OTHER INFORMATION: PCR primer

<400> SEQUENCE: 355
caggaccagt tggtgcagtc tggg                                             24

<210> SEQ ID NO 356
<211> LENGTH: 23
<212> TYPE: DNA
<213> ORGANISM: Artificial
<220> FEATURE:
<223> OTHER INFORMATION: PCR primer

<400> SEQUENCE: 356
caggtgcagc tggtggagtc tgg                                              23

<210> SEQ ID NO 357
<211> LENGTH: 23
<212> TYPE: DNA
<213> ORGANISM: Artificial
<220> FEATURE:
<223> OTHER INFORMATION: PCR primer

<400> SEQUENCE: 357
cagatgcagc tggtgcagtc tgg                                              23

<210> SEQ ID NO 358
<211> LENGTH: 24
<212> TYPE: DNA
<213> ORGANISM: Artificial
<220> FEATURE:
<223> OTHER INFORMATION: PCR primer
```

```
<400> SEQUENCE: 358
caaatgcagc tggtgcagtc tggg                                    24

<210> SEQ ID NO 359
<211> LENGTH: 24
<212> TYPE: DNA
<213> ORGANISM: Artificial
<220> FEATURE:
<223> OTHER INFORMATION: PCR primer

<400> SEQUENCE: 359
caagtgcagc tggtggagtc tggg                                    24

<210> SEQ ID NO 360
<211> LENGTH: 22
<212> TYPE: DNA
<213> ORGANISM: Artificial
<220> FEATURE:
<223> OTHER INFORMATION: PCR primer

<400> SEQUENCE: 360
caggtgcagc tggtgcagtc tg                                      22

<210> SEQ ID NO 361
<211> LENGTH: 24
<212> TYPE: DNA
<213> ORGANISM: Artificial
<220> FEATURE:
<223> OTHER INFORMATION: PCR primer

<400> SEQUENCE: 361
gaggatcagc tggtggagtc tggg                                    24

<210> SEQ ID NO 362
<211> LENGTH: 24
<212> TYPE: DNA
<213> ORGANISM: Artificial
<220> FEATURE:
<223> OTHER INFORMATION: PCR primer

<400> SEQUENCE: 362
gaggtccagc tggtacagtc tggg                                    24

<210> SEQ ID NO 363
<211> LENGTH: 21
<212> TYPE: DNA
<213> ORGANISM: Artificial
<220> FEATURE:
<223> OTHER INFORMATION: PCR sequence

<400> SEQUENCE: 363
gagctgcagc tgcaggagtc c                                       21

<210> SEQ ID NO 364
<211> LENGTH: 23
<212> TYPE: DNA
<213> ORGANISM: Artificial
<220> FEATURE:
<223> OTHER INFORMATION: PCR primer

<400> SEQUENCE: 364
gaggtgcagc tggtggagtc tgg                                     23

<210> SEQ ID NO 365
```

```
<211> LENGTH: 22
<212> TYPE: DNA
<213> ORGANISM: Artificial
<220> FEATURE:
<223> OTHER INFORMATION: PCR primer

<400> SEQUENCE: 365
caggtgcagc tggtgcagtc tg                                         22

<210> SEQ ID NO 366
<211> LENGTH: 24
<212> TYPE: DNA
<213> ORGANISM: Artificial
<220> FEATURE:
<223> OTHER INFORMATION: PCR primer

<400> SEQUENCE: 366
caggtacagc tgcagcagtc aggt                                       24

<210> SEQ ID NO 367
<211> LENGTH: 24
<212> TYPE: DNA
<213> ORGANISM: Artificial
<220> FEATURE:
<223> OTHER INFORMATION: PCR primer

<400> SEQUENCE: 367
gagatgcagc tggtggagtc tggg                                       24

<210> SEQ ID NO 368
<211> LENGTH: 24
<212> TYPE: DNA
<213> ORGANISM: Artificial
<220> FEATURE:
<223> OTHER INFORMATION: PCR primer

<400> SEQUENCE: 368
gaggtgcatc tggtggagtc tggg                                       24

<210> SEQ ID NO 369
<211> LENGTH: 23
<212> TYPE: DNA
<213> ORGANISM: Artificial
<220> FEATURE:
<223> OTHER INFORMATION: PCR primer

<400> SEQUENCE: 369
gaggtgcagc tggtggagtc tgg                                        23

<210> SEQ ID NO 370
<211> LENGTH: 23
<212> TYPE: DNA
<213> ORGANISM: Artificial
<220> FEATURE:
<223> OTHER INFORMATION: PCR primer

<400> SEQUENCE: 370
gaggtgcagc tggtggagtc tgg                                        23

<210> SEQ ID NO 371
<211> LENGTH: 26
<212> TYPE: DNA
<213> ORGANISM: Artificial
<220> FEATURE:
<223> OTHER INFORMATION: PCR primer

<400> SEQUENCE: 371
```

-continued

```
caggtccaac tggtgtagtc tggagc                                    26

<210> SEQ ID NO 372
<211> LENGTH: 22
<212> TYPE: DNA
<213> ORGANISM: Artificial
<220> FEATURE:
<223> OTHER INFORMATION: PCR primer

<400> SEQUENCE: 372
gaggtgcagc tggtgcagtc tg                                        22

<210> SEQ ID NO 373
<211> LENGTH: 23
<212> TYPE: DNA
<213> ORGANISM: Artificial
<220> FEATURE:
<223> OTHER INFORMATION: PCR primer

<400> SEQUENCE: 373
gaggtgcagc tggtggagtc tcg                                       23

<210> SEQ ID NO 374
<211> LENGTH: 24
<212> TYPE: DNA
<213> ORGANISM: Artificial
<220> FEATURE:
<223> OTHER INFORMATION: PCR primer

<400> SEQUENCE: 374
gaggttcagc tggtgcagtc tggg                                      24

<210> SEQ ID NO 375
<211> LENGTH: 22
<212> TYPE: DNA
<213> ORGANISM: Artificial
<220> FEATURE:
<223> OTHER INFORMATION: PCR primer

<400> SEQUENCE: 375
caggtgcagc tggtgcagtc tg                                        22

<210> SEQ ID NO 376
<211> LENGTH: 23
<212> TYPE: DNA
<213> ORGANISM: Artificial
<220> FEATURE:
<223> OTHER INFORMATION: PCR primer

<400> SEQUENCE: 376
gaagtgcagc tggtgcagtc tgg                                       23

<210> SEQ ID NO 377
<211> LENGTH: 26
<212> TYPE: DNA
<213> ORGANISM: Artificial
<220> FEATURE:
<223> OTHER INFORMATION: PCR primer

<400> SEQUENCE: 377
gaggtggagc tgatagagtc cataga                                    26

<210> SEQ ID NO 378
<211> LENGTH: 23
<212> TYPE: DNA
```

```
<213> ORGANISM: Artificial
<220> FEATURE:
<223> OTHER INFORMATION: PCR primer

<400> SEQUENCE: 378
acagtgcagc tggtggagtc tgg                                          23

<210> SEQ ID NO 379
<211> LENGTH: 23
<212> TYPE: DNA
<213> ORGANISM: Artificial
<220> FEATURE:
<223> OTHER INFORMATION: PCR primer

<400> SEQUENCE: 379
gaggtgcagc tggaggagtc tgg                                          23

<210> SEQ ID NO 380
<211> LENGTH: 26
<212> TYPE: DNA
<213> ORGANISM: Artificial
<220> FEATURE:
<223> OTHER INFORMATION: PCR primer

<400> SEQUENCE: 380
gaggtacagc tggtggagtc tgaaga                                       26

<210> SEQ ID NO 381
<211> LENGTH: 21
<212> TYPE: DNA
<213> ORGANISM: Artificial
<220> FEATURE:
<223> OTHER INFORMATION: PCR primer

<400> SEQUENCE: 381
caggtgcagc tgcaggagtc g                                            21

<210> SEQ ID NO 382
<211> LENGTH: 24
<212> TYPE: DNA
<213> ORGANISM: Artificial
<220> FEATURE:
<223> OTHER INFORMATION: PCR primer

<400> SEQUENCE: 382
gaggtgcagc tgttggagtc tggg                                         24

<210> SEQ ID NO 383
<211> LENGTH: 20
<212> TYPE: DNA
<213> ORGANISM: Artificial
<220> FEATURE:
<223> OTHER INFORMATION: PCR primer

<400> SEQUENCE: 383
caggtgcagc tggggcagtc                                              20

<210> SEQ ID NO 384
<211> LENGTH: 21
<212> TYPE: DNA
<213> ORGANISM: Artificial
<220> FEATURE:
<223> OTHER INFORMATION: PCR primer

<400> SEQUENCE: 384
cagctgcagc tgcaggagtc g                                            21
```

<210> SEQ ID NO 385
<211> LENGTH: 24
<212> TYPE: DNA
<213> ORGANISM: Artificial
<220> FEATURE:
<223> OTHER INFORMATION: PCR primer

<400> SEQUENCE: 385
caggttcagc tggtgcagtc tgga                                          24

<210> SEQ ID NO 386
<211> LENGTH: 24
<212> TYPE: DNA
<213> ORGANISM: Artificial
<220> FEATURE:
<223> OTHER INFORMATION: PCR primer

<400> SEQUENCE: 386
gaggtgcagc tggtagagtc tggg                                          24

<210> SEQ ID NO 387
<211> LENGTH: 24
<212> TYPE: DNA
<213> ORGANISM: Artificial
<220> FEATURE:
<223> OTHER INFORMATION: PCR primer

<400> SEQUENCE: 387
caggtccagc ttgtgcagtc tggg                                          24

<210> SEQ ID NO 388
<211> LENGTH: 23
<212> TYPE: DNA
<213> ORGANISM: Artificial
<220> FEATURE:
<223> OTHER INFORMATION: PCR primer

<400> SEQUENCE: 388
gaggtgcagc tgttgcagtc tgc                                           23

<210> SEQ ID NO 389
<211> LENGTH: 26
<212> TYPE: DNA
<213> ORGANISM: Artificial
<220> FEATURE:
<223> OTHER INFORMATION: PCR primer

<400> SEQUENCE: 389
gaggtacaac tggtggagtc tgggggg                                       26

<210> SEQ ID NO 390
<211> LENGTH: 26
<212> TYPE: DNA
<213> ORGANISM: Artificial
<220> FEATURE:
<223> OTHER INFORMATION: PCR primer

<400> SEQUENCE: 390
cagatcacct tgaaggagtc tggtcc                                        26

<210> SEQ ID NO 391
<211> LENGTH: 25
<212> TYPE: DNA
<213> ORGANISM: Artificial
<220> FEATURE:

<223> OTHER INFORMATION: PCR primer

<400> SEQUENCE: 391
caggtacagc tgatgcagtc tgggg                                    25

<210> SEQ ID NO 392
<211> LENGTH: 63
<212> TYPE: DNA
<213> ORGANISM: Artificial
<220> FEATURE:
<223> OTHER INFORMATION: PCR primer

<400> SEQUENCE: 392
ctagtattcg gagcagaacc actgtggctc gcgctgttag gtgaggagac ggtgaccgtg    60
gtc                                                            63

<210> SEQ ID NO 393
<211> LENGTH: 65
<212> TYPE: DNA
<213> ORGANISM: Artificial
<220> FEATURE:
<223> OTHER INFORMATION: PCR primer

<400> SEQUENCE: 393
ctagtattcg gagcagaacc actgtggctc gcgctgttag gtgaggagac agtgaccagg    60
gtgcc                                                          65

<210> SEQ ID NO 394
<211> LENGTH: 63
<212> TYPE: DNA
<213> ORGANISM: Artificial
<220> FEATURE:
<223> OTHER INFORMATION: PCR primer

<400> SEQUENCE: 394
ctagtattcg gagcagaacc actgtggctc gcgctgttag gtgatgtggc tgcggtctca    60
ggg                                                            63

<210> SEQ ID NO 395
<211> LENGTH: 64
<212> TYPE: DNA
<213> ORGANISM: Artificial
<220> FEATURE:
<223> OTHER INFORMATION: PCR primer

<400> SEQUENCE: 395
tagtattcgg agcagaacca ctgtggctcg cgctgttagg tgaggagacg gtgaccaggg    60
ttcc                                                           64

<210> SEQ ID NO 396
<211> LENGTH: 64
<212> TYPE: DNA
<213> ORGANISM: Artificial
<220> FEATURE:
<223> OTHER INFORMATION: PCR primer

<400> SEQUENCE: 396
ctagtattcg gagcagaacc actgtggctc gcgctgttag ggaccctca gaagccagac    60 cacc                                                           64

<210> SEQ ID NO 397
<211> LENGTH: 64

```
<212> TYPE: DNA
<213> ORGANISM: Artificial
<220> FEATURE:
<223> OTHER INFORMATION: PCR primer

<400> SEQUENCE: 397
ctagtattcg gagcagaacc actgtggctc gcgctgttag gtgaggagac ggtgaccagg      60
gtgc                                                                  64

<210> SEQ ID NO 398
<211> LENGTH: 63
<212> TYPE: DNA
<213> ORGANISM: Artificial
<220> FEATURE:
<223> OTHER INFORMATION: PCR primer

<400> SEQUENCE: 398
ctagtattcg gagcagaacc actgtggctc gcgctgttag ggacgttccc agggagacgg      60
tgt                                                                   63

<210> SEQ ID NO 399
<211> LENGTH: 67
<212> TYPE: DNA
<213> ORGANISM: Artificial
<220> FEATURE:
<223> OTHER INFORMATION: PCR primer

<400> SEQUENCE: 399
ctagtattcg gagcagaacc actgtggctc gcgctgttag gtgaagagac ggtgaccatt      60
gtccctt                                                               67

<210> SEQ ID NO 400
<211> LENGTH: 67
<212> TYPE: DNA
<213> ORGANISM: Artificial
<220> FEATURE:
<223> OTHER INFORMATION: PCR primer

<400> SEQUENCE: 400
acagtggttc tgctccgaat actagttctg ctccgggatc cgaaattgtg ttgacgcagt      60
ctccagc                                                               67

<210> SEQ ID NO 401
<211> LENGTH: 67
<212> TYPE: DNA
<213> ORGANISM: Artificial
<220> FEATURE:
<223> OTHER INFORMATION: PCR primer

<400> SEQUENCE: 401
acagtggttc tgctccgaat actagttctg ctccgggatc cgaaattgtg ttgacgcagt      60
ctccagg                                                               67

<210> SEQ ID NO 402
<211> LENGTH: 65
<212> TYPE: DNA
<213> ORGANISM: Artificial
<220> FEATURE:
<223> OTHER INFORMATION: PCR primer

<400> SEQUENCE: 402
acagtggttc tgctccgaat actagttctg ctccgggatc cgccatccag ttgacccagt      60
``` ctcca                                                                65

<210> SEQ ID NO 403
<211> LENGTH: 67
<212> TYPE: DNA
<213> ORGANISM: Artificial
<220> FEATURE:
<223> OTHER INFORMATION: PCR primer

<400> SEQUENCE: 403
acagtggttc tgctccgaat actagttctg ctccgggatc cgacatccag atgactcagc    60
ctccatc                                                              67

<210> SEQ ID NO 404
<211> LENGTH: 67
<212> TYPE: DNA
<213> ORGANISM: Artificial
<220> FEATURE:
<223> OTHER INFORMATION: PCR primer

<400> SEQUENCE: 404
acagtggttc tgctccgaat actagttctg ctccgggatc cgaaacgaca ctcacgcagt    60
ctccagc                                                              67

<210> SEQ ID NO 405
<211> LENGTH: 67
<212> TYPE: DNA
<213> ORGANISM: Artificial
<220> FEATURE:
<223> OTHER INFORMATION: PCR primer

<400> SEQUENCE: 405
acagtggttc tgctccgaat actagttctg ctccgggatc cgacatccag atgacccagt    60
ctccatc                                                              67

<210> SEQ ID NO 406
<211> LENGTH: 67
<212> TYPE: DNA
<213> ORGANISM: Artificial
<220> FEATURE:
<223> OTHER INFORMATION: PCR primer

<400> SEQUENCE: 406
acagtggttc tgctccgaat actagttctg ctccgggatc cgacatccag gtgacccagt    60
ctccatc                                                              67

<210> SEQ ID NO 407
<211> LENGTH: 67
<212> TYPE: DNA
<213> ORGANISM: Artificial
<220> FEATURE:
<223> OTHER INFORMATION: PCR primer

<400> SEQUENCE: 407
acagtggttc tgctccgaat actagttctg ctccgggatc cgacattgtg atgacccaga    60
ctccact                                                              67

<210> SEQ ID NO 408
<211> LENGTH: 67
<212> TYPE: DNA
<213> ORGANISM: Artificial
<220> FEATURE:
<223> OTHER INFORMATION: PCR primer

```
<400> SEQUENCE: 408
acagtggttc tgctccgaat actagttctg ctccgggatc cgacatcgtg atgacccagt    60
ctccaga                                                              67

<210> SEQ ID NO 409
<211> LENGTH: 64
<212> TYPE: DNA
<213> ORGANISM: Artificial
<220> FEATURE:
<223> OTHER INFORMATION: PCR primer

<400> SEQUENCE: 409
acagtggttc tgctccgaat actagttctg ctccgggatc cgccatccgg atgacccagt    60
ctcc                                                                 64

<210> SEQ ID NO 410
<211> LENGTH: 67
<212> TYPE: DNA
<213> ORGANISM: Artificial
<220> FEATURE:
<223> OTHER INFORMATION: PCR primer

<400> SEQUENCE: 410
acagtggttc tgctccgaat actagttctg ctccgggatc cgatgttgtg atgacacagt    60
ctccagc                                                              67

<210> SEQ ID NO 411
<211> LENGTH: 67
<212> TYPE: DNA
<213> ORGANISM: Artificial
<220> FEATURE:
<223> OTHER INFORMATION: PCR primer

<400> SEQUENCE: 411
acagtggttc tgctccgaat actagttctg ctccgggatc cgatattgtg atgacccagc    60
atctgct                                                              67

<210> SEQ ID NO 412
<211> LENGTH: 67
<212> TYPE: DNA
<213> ORGANISM: Artificial
<220> FEATURE:
<223> OTHER INFORMATION: PCR primer

<400> SEQUENCE: 412
acagtggttc tgctccgaat actagttctg ctccgggatc cgaaatagtg atgacgcagt    60
ctccagc                                                              67

<210> SEQ ID NO 413
<211> LENGTH: 67
<212> TYPE: DNA
<213> ORGANISM: Artificial
<220> FEATURE:
<223> OTHER INFORMATION: PCR primer

<400> SEQUENCE: 413
acagtggttc tgctccgaat actagttctg ctccgggatc cgatattgtg atgacccaga    60
ctccacc                                                              67

<210> SEQ ID NO 414
```

```
<211> LENGTH: 67
<212> TYPE: DNA
<213> ORGANISM: Artificial
<220> FEATURE:
<223> OTHER INFORMATION: PCR primer

<400> SEQUENCE: 414
acagtggttc tgctccgaat actagttctg ctccgggatc cgacatccag atgatccagt    60
ctccatc                                                              67

<210> SEQ ID NO 415
<211> LENGTH: 67
<212> TYPE: DNA
<213> ORGANISM: Artificial
<220> FEATURE:
<223> OTHER INFORMATION: PCR primer

<400> SEQUENCE: 415
acagtggttc tgctccgaat actagttctg ctccgggatc cgaaattgtg ttgacacagt    60
ctccagc                                                              67

<210> SEQ ID NO 416
<211> LENGTH: 67
<212> TYPE: DNA
<213> ORGANISM: Artificial
<220> FEATURE:
<223> OTHER INFORMATION: PCR primer

<400> SEQUENCE: 416
acagtggttc tgctccgaat actagttctg ctccgggatc cgatattgtg atgactcagt    60
ctccact                                                              67

<210> SEQ ID NO 417
<211> LENGTH: 64
<212> TYPE: DNA
<213> ORGANISM: Artificial
<220> FEATURE:
<223> OTHER INFORMATION: PCR primer

<400> SEQUENCE: 417
acagtggttc tgctccgaat actagttctg ctccgggatc cgccatccgg atgacccagt    60
ctcc                                                                 64

<210> SEQ ID NO 418
<211> LENGTH: 67
<212> TYPE: DNA
<213> ORGANISM: Artificial
<220> FEATURE:
<223> OTHER INFORMATION: PCR primer

<400> SEQUENCE: 418
acagtggttc tgctccgaat actagttctg ctccgggatc caacatccag atgacccagt    60
ctccatc                                                              67

<210> SEQ ID NO 419
<211> LENGTH: 67
<212> TYPE: DNA
<213> ORGANISM: Artificial
<220> FEATURE:
<223> OTHER INFORMATION: PCR primer

<400> SEQUENCE: 419
acagtggttc tgctccgaat actagttctg ctccgggatc cgaaattgta atgacacagt    60
```

```
ctccagc                                                              67

<210> SEQ ID NO 420
<211> LENGTH: 67
<212> TYPE: DNA
<213> ORGANISM: Artificial
<220> FEATURE:
<223> OTHER INFORMATION: PCR primer

<400> SEQUENCE: 420
acagtggttc tgctccgaat actagttctg ctccgggatc cgaaattgta atgacacagt     60
ctccacc                                                              67

<210> SEQ ID NO 421
<211> LENGTH: 67
<212> TYPE: DNA
<213> ORGANISM: Artificial
<220> FEATURE:
<223> OTHER INFORMATION: PCR primer

<400> SEQUENCE: 421
acagtggttc tgctccgaat actagttctg ctccgggatc cgatgttgtg atgactcagt     60
ctccact                                                              67

<210> SEQ ID NO 422
<211> LENGTH: 67
<212> TYPE: DNA
<213> ORGANISM: Artificial
<220> FEATURE:
<223> OTHER INFORMATION: PCR primer

<400> SEQUENCE: 422
acagtggttc tgctccgaat actagttctg ctccgggatc cgacattgtg ctgacccagt     60
ctccagc                                                              67

<210> SEQ ID NO 423
<211> LENGTH: 67
<212> TYPE: DNA
<213> ORGANISM: Artificial
<220> FEATURE:
<223> OTHER INFORMATION: PCR primer

<400> SEQUENCE: 423
acagtggttc tgctccgaat actagttctg ctccgggatc cgacatccag atgacccagt     60
ctccttc                                                              67

<210> SEQ ID NO 424
<211> LENGTH: 67
<212> TYPE: DNA
<213> ORGANISM: Artificial
<220> FEATURE:
<223> OTHER INFORMATION: PCR primer

<400> SEQUENCE: 424
acagtggttc tgctccgaat actagttctg ctccgggatc cgaaattgtg ctgactcagt     60
ctccaga                                                              67

<210> SEQ ID NO 425
<211> LENGTH: 67
<212> TYPE: DNA
<213> ORGANISM: Artificial
<220> FEATURE:
```

```
<223> OTHER INFORMATION: PCR primer

<400> SEQUENCE: 425
acagtggttc tgctccgaat actagttctg ctccgggatc cgagattgtg atgacccaga    60
ctccact                                                              67

<210> SEQ ID NO 426
<211> LENGTH: 67
<212> TYPE: DNA
<213> ORGANISM: Artificial
<220> FEATURE:
<223> OTHER INFORMATION: PCR primer

<400> SEQUENCE: 426
acagtggttc tgctccgaat actagttctg ctccgggatc cgccatccag atgacccagt    60
ctccatc                                                              67

<210> SEQ ID NO 427
<211> LENGTH: 67
<212> TYPE: DNA
<213> ORGANISM: Artificial
<220> FEATURE:
<223> OTHER INFORMATION: PCR primer

<400> SEQUENCE: 427
acagtggttc tgctccgaat actagttctg ctccgggatc cgacatccag ttgacccagt    60
ctccatc                                                              67

<210> SEQ ID NO 428
<211> LENGTH: 67
<212> TYPE: DNA
<213> ORGANISM: Artificial
<220> FEATURE:
<223> OTHER INFORMATION: PCR primer

<400> SEQUENCE: 428
acagtggttc tgctccgaat actagttctg ctccgggatc cgatattgtg atgacccaga    60
ctccact                                                              67

<210> SEQ ID NO 429
<211> LENGTH: 67
<212> TYPE: DNA
<213> ORGANISM: Artificial
<220> FEATURE:
<223> OTHER INFORMATION: PCR primer

<400> SEQUENCE: 429
acagtggttc tgctccgaat actagttctg ctccgggatc cgtcatctgg atgacccagt    60
ctccatc                                                              67

<210> SEQ ID NO 430
<211> LENGTH: 67
<212> TYPE: DNA
<213> ORGANISM: Artificial
<220> FEATURE:
<223> OTHER INFORMATION: PCR primer

<400> SEQUENCE: 430
acagtggttc tgctccgaat actagttctg ctccgggatc cgacatccag atgacccagc    60
ctccatc                                                              67
```

<210> SEQ ID NO 431
<211> LENGTH: 67
<212> TYPE: DNA
<213> ORGANISM: Artificial
<220> FEATURE:
<223> OTHER INFORMATION: PCR primer

<400> SEQUENCE: 431
acagtggttc tgctccgaat actagttctg ctccgggatc cgaaattgtg ttgacacagt    60
ctccagg                                                              67

<210> SEQ ID NO 432
<211> LENGTH: 26
<212> TYPE: DNA
<213> ORGANISM: Artificial
<220> FEATURE:
<223> OTHER INFORMATION: PCR primer

<400> SEQUENCE: 432
tttgatctcc accttggtcc ctccgc                                         26

<210> SEQ ID NO 433
<211> LENGTH: 25
<212> TYPE: DNA
<213> ORGANISM: Artificial
<220> FEATURE:
<223> OTHER INFORMATION: PCR primer

<400> SEQUENCE: 433
tttgatctcc agcttggtcc cctgg                                          25

<210> SEQ ID NO 434
<211> LENGTH: 26
<212> TYPE: DNA
<213> ORGANISM: Artificial
<220> FEATURE:
<223> OTHER INFORMATION: PCR primer

<400> SEQUENCE: 434
tttgatatcc actttggtcc cagggc                                         26

<210> SEQ ID NO 435
<211> LENGTH: 26
<212> TYPE: DNA
<213> ORGANISM: Artificial
<220> FEATURE:
<223> OTHER INFORMATION: PCR primer

<400> SEQUENCE: 435
tttgatttcc accttggtcc cttggc                                         26

<210> SEQ ID NO 436
<211> LENGTH: 26
<212> TYPE: DNA
<213> ORGANISM: Artificial
<220> FEATURE:
<223> OTHER INFORMATION: PCR primer

<400> SEQUENCE: 436
tttaatctcc agtcgtgtcc cttggc                                         26

<210> SEQ ID NO 437
<211> LENGTH: 65
<212> TYPE: DNA
<213> ORGANISM: Artificial
<220> FEATURE:

<223> OTHER INFORMATION: PCR primer

<400> SEQUENCE: 437
acagtggttc tgctccgaat actagttctg ctccgggatc ccagtctgcc ctgattcagc    60
ctccc    65

<210> SEQ ID NO 438
<211> LENGTH: 63
<212> TYPE: DNA
<213> ORGANISM: Artificial
<220> FEATURE:
<223> OTHER INFORMATION: PCR primer

<400> SEQUENCE: 438
acagtggttc tgctccgaat actagttctg ctccgggatc cctgcctgtg ctgactcagc    60
ccc    63

<210> SEQ ID NO 439
<211> LENGTH: 63
<212> TYPE: DNA
<213> ORGANISM: Artificial
<220> FEATURE:
<223> OTHER INFORMATION: PCR primer

<400> SEQUENCE: 439
acagtggttc tgctccgaat actagttctg ctccgggatc ccagcctgtg ctgactcagc    60
cac    63

<210> SEQ ID NO 440
<211> LENGTH: 67
<212> TYPE: DNA
<213> ORGANISM: Artificial
<220> FEATURE:
<223> OTHER INFORMATION: PCR primer

<400> SEQUENCE: 440
acagtggttc tgctccgaat actagttctg ctccgggatc ctcttctgag ctgactcagg    60
accctgc    67

<210> SEQ ID NO 441
<211> LENGTH: 65
<212> TYPE: DNA
<213> ORGANISM: Artificial
<220> FEATURE:
<223> OTHER INFORMATION: PCR primer

<400> SEQUENCE: 441
acagtggttc tgctccgaat actagttctg ctccgggatc ccaatctgcc ctgactcagc    60
ctcct    65

<210> SEQ ID NO 442
<211> LENGTH: 65
<212> TYPE: DNA
<213> ORGANISM: Artificial
<220> FEATURE:
<223> OTHER INFORMATION: PCR primer

<400> SEQUENCE: 442
acagtggttc tgctccgaat actagttctg ctccgggatc ctcctatgag ctgacacagc    60
caccc    65

-continued

```
<210> SEQ ID NO 443
<211> LENGTH: 60
<212> TYPE: DNA
<213> ORGANISM: Artificial
<220> FEATURE:
<223> OTHER INFORMATION: PCR primer

<400> SEQUENCE: 443
acagtggttc tgctccgaat actagttctg ctccgggatc ccggcccgtg ctgactcagc    60

<210> SEQ ID NO 444
<211> LENGTH: 67
<212> TYPE: DNA
<213> ORGANISM: Artificial
<220> FEATURE:
<223> OTHER INFORMATION: PCR primer

<400> SEQUENCE: 444
acagtggttc tgctccgaat actagttctg ctccgggatc ccagcctgtg ctgactcaat    60
catcctc                                                              67

<210> SEQ ID NO 445
<211> LENGTH: 65
<212> TYPE: DNA
<213> ORGANISM: Artificial
<220> FEATURE:
<223> OTHER INFORMATION: PCR primer

<400> SEQUENCE: 445
acagtggttc tgctccgaat actagttctg ctccgggatc ctcctctgag ctgagtcagg    60
agcct                                                                65

<210> SEQ ID NO 446
<211> LENGTH: 64
<212> TYPE: DNA
<213> ORGANISM: Artificial
<220> FEATURE:
<223> OTHER INFORMATION: PCR primer

<400> SEQUENCE: 446
acagtggttc tgctccgaat actagttctg ctccgggatc ccagtctgcc ctgactcagc    60
ctcc                                                                 64

<210> SEQ ID NO 447
<211> LENGTH: 63
<212> TYPE: DNA
<213> ORGANISM: Artificial
<220> FEATURE:
<223> OTHER INFORMATION: PCR primer

<400> SEQUENCE: 447
acagtggttc tgctccgaat actagttctg ctccgggatc ccagtctgtg ttgacgcagc    60
cgc                                                                  63

<210> SEQ ID NO 448
<211> LENGTH: 62
<212> TYPE: DNA
<213> ORGANISM: Artificial
<220> FEATURE:
<223> OTHER INFORMATION: PCR primer

<400> SEQUENCE: 448
acagtggttc tgctccgaat actagttctg ctccgggatc ccaggcaggg ctgactcagc    60
``` ca                                                                62

<210> SEQ ID NO 449
<211> LENGTH: 63
<212> TYPE: DNA
<213> ORGANISM: Artificial
<220> FEATURE:
<223> OTHER INFORMATION: PCR primer

<400> SEQUENCE: 449
acagtggttc tgctccgaat actagttctg ctccgggatc ccagtctgtg ttgacgcagc    60
cgc                                                               63

<210> SEQ ID NO 450
<211> LENGTH: 65
<212> TYPE: DNA
<213> ORGANISM: Artificial
<220> FEATURE:
<223> OTHER INFORMATION: PCR primer

<400> SEQUENCE: 450
acagtggttc tgctccgaat actagttctg ctccgggatc ccagtctgtg ctgactcagc    60
caccc                                                             65

<210> SEQ ID NO 451
<211> LENGTH: 67
<212> TYPE: DNA
<213> ORGANISM: Artificial
<220> FEATURE:
<223> OTHER INFORMATION: PCR primer

<400> SEQUENCE: 451
acagtggttc tgctccgaat actagttctg ctccgggatc ctcctatgag ctgactcagc    60
cactctc                                                           67

<210> SEQ ID NO 452
<211> LENGTH: 64
<212> TYPE: DNA
<213> ORGANISM: Artificial
<220> FEATURE:
<223> OTHER INFORMATION: PCR primer

<400> SEQUENCE: 452
acagtggttc tgctccgaat actagttctg ctccgggatc ccagcctgtg ctgactcagc    60
caac                                                              64

<210> SEQ ID NO 453
<211> LENGTH: 65
<212> TYPE: DNA
<213> ORGANISM: Artificial
<220> FEATURE:
<223> OTHER INFORMATION: PCR primer

<400> SEQUENCE: 453
acagtggttc tgctccgaat actagttctg ctccgggatc ctcctatgag ctgacacagc    60
caccc                                                             65

<210> SEQ ID NO 454
<211> LENGTH: 67
<212> TYPE: DNA
<213> ORGANISM: Artificial
<220> FEATURE:
<223> OTHER INFORMATION: PCR primer

```
<400> SEQUENCE: 454
acagtggttc tgctccgaat actagttctg ctccgggatc ctcctatgag ctgacacagc    60
catcctc                                                              67

<210> SEQ ID NO 455
<211> LENGTH: 64
<212> TYPE: DNA
<213> ORGANISM: Artificial
<220> FEATURE:
<223> OTHER INFORMATION: PCR primer

<400> SEQUENCE: 455
acagtggttc tgctccgaat actagttctg ctccgggatc ccagcctgtg ctgactcagc    60
caac                                                                 64

<210> SEQ ID NO 456
<211> LENGTH: 67
<212> TYPE: DNA
<213> ORGANISM: Artificial
<220> FEATURE:
<223> OTHER INFORMATION: PCR primer

<400> SEQUENCE: 456
acagtggttc tgctccgaat actagttctg ctccgggatc ctcctatgag ctgacacagc    60
tacccctc                                                             67

<210> SEQ ID NO 457
<211> LENGTH: 65
<212> TYPE: DNA
<213> ORGANISM: Artificial
<220> FEATURE:
<223> OTHER INFORMATION: PCR primer

<400> SEQUENCE: 457
acagtggttc tgctccgaat actagttctg ctccgggatc ccagcctgtg ctgactcagc    60
catct                                                                65

<210> SEQ ID NO 458
<211> LENGTH: 63
<212> TYPE: DNA
<213> ORGANISM: Artificial
<220> FEATURE:
<223> OTHER INFORMATION: PCR primer

<400> SEQUENCE: 458
acagtggttc tgctccgaat actagttctg ctccgggatc ctcctctggg ccaactcagg    60
tgc                                                                  63

<210> SEQ ID NO 459
<211> LENGTH: 66
<212> TYPE: DNA
<213> ORGANISM: Artificial
<220> FEATURE:
<223> OTHER INFORMATION: PCR primer

<400> SEQUENCE: 459
acagtggttc tgctccgaat actagttctg ctccgggatc ctcctatgag ctgactcagc    60
caccct                                                               66

<210> SEQ ID NO 460
```

```
<211> LENGTH: 64
<212> TYPE: DNA
<213> ORGANISM: Artificial
<220> FEATURE:
<223> OTHER INFORMATION: PCR primer

<400> SEQUENCE: 460
acagtggttc tgctccgaat actagttctg ctccgggatc ccagactgtg gtgacccagg     60
agcc                                                                  64

<210> SEQ ID NO 461
<211> LENGTH: 64
<212> TYPE: DNA
<213> ORGANISM: Artificial
<220> FEATURE:
<223> OTHER INFORMATION: PCR primer

<400> SEQUENCE: 461
acagtggttc tgctccgaat actagttctg ctccgggatc ccagtctgcc ctgactcagc     60
ctgc                                                                  64

<210> SEQ ID NO 462
<211> LENGTH: 67
<212> TYPE: DNA
<213> ORGANISM: Artificial
<220> FEATURE:
<223> OTHER INFORMATION: PCR primer

<400> SEQUENCE: 462
acagtggttc tgctccgaat actagttctg ctccgggatc caattttatg ctgactcagc     60
cccactc                                                               67

<210> SEQ ID NO 463
<211> LENGTH: 65
<212> TYPE: DNA
<213> ORGANISM: Artificial
<220> FEATURE:
<223> OTHER INFORMATION: PCR primer

<400> SEQUENCE: 463
acagtggttc tgctccgaat actagttctg ctccgggatc ctcctatgag ctgatgcagc     60
caccc                                                                 65

<210> SEQ ID NO 464
<211> LENGTH: 64
<212> TYPE: DNA
<213> ORGANISM: Artificial
<220> FEATURE:
<223> OTHER INFORMATION: PCR primer

<400> SEQUENCE: 464
acagtggttc tgctccgaat actagttctg ctccgggatc ccaggctgtg gtgactcagg     60
agcc                                                                  64

<210> SEQ ID NO 465
<211> LENGTH: 65
<212> TYPE: DNA
<213> ORGANISM: Artificial
<220> FEATURE:
<223> OTHER INFORMATION: PCR primer

<400> SEQUENCE: 465
acagtggttc tgctccgaat actagttctg ctccgggatc ccagcttgtg ctgactcaat     60
```

```
cgccc                                                                 65

<210> SEQ ID NO 466
<211> LENGTH: 65
<212> TYPE: DNA
<213> ORGANISM: Artificial
<220> FEATURE:
<223> OTHER INFORMATION: PCR primer

<400> SEQUENCE: 466
acagtggttc tgctccgaat actagttctg ctccgggatc ccagactgtg gtgactcagg     60
agccc                                                                 65

<210> SEQ ID NO 467
<211> LENGTH: 67
<212> TYPE: DNA
<213> ORGANISM: Artificial
<220> FEATURE:
<223> OTHER INFORMATION: PCR primer

<400> SEQUENCE: 467
acagtggttc tgctccgaat actagttctg ctccgggatc ctcctatgag ctgactcagc     60
cacactc                                                               67

<210> SEQ ID NO 468
<211> LENGTH: 62
<212> TYPE: DNA
<213> ORGANISM: Artificial
<220> FEATURE:
<223> OTHER INFORMATION: PCR primer

<400> SEQUENCE: 468
acagtggttc tgctccgaat actagttctg ctccgggatc ccaggctgtg ctgactcagc     60
cg                                                                    62

<210> SEQ ID NO 469
<211> LENGTH: 65
<212> TYPE: DNA
<213> ORGANISM: Artificial
<220> FEATURE:
<223> OTHER INFORMATION: PCR primer

<400> SEQUENCE: 469
acagtggttc tgctccgaat actagttctg ctccgggatc ctcctatgtg ctgactcagc     60
caccc                                                                 65

<210> SEQ ID NO 470
<211> LENGTH: 64
<212> TYPE: DNA
<213> ORGANISM: Artificial
<220> FEATURE:
<223> OTHER INFORMATION: PCR primer

<400> SEQUENCE: 470
acagtggttc tgctccgaat actagttctg ctccgggatc ccagtctgcc ctgactcagc     60
ctcg                                                                  64

<210> SEQ ID NO 471
<211> LENGTH: 66
<212> TYPE: DNA
<213> ORGANISM: Artificial
<220> FEATURE:
```

-continued

<223> OTHER INFORMATION: PCR primer

<400> SEQUENCE: 471
acagtggttc tgctccgaat actagttctg ctccgggatc ccagtctgtt ctgactcagc    60
ctcgct    66

<210> SEQ ID NO 472
<211> LENGTH: 62
<212> TYPE: DNA
<213> ORGANISM: Artificial
<220> FEATURE:
<223> OTHER INFORMATION: PCR primer

<400> SEQUENCE: 472
acagtggttc tgctccgaat actagttctg ctccgggatc ccagtctgtg ctgacgcagc    60
cg    62

<210> SEQ ID NO 473
<211> LENGTH: 22
<212> TYPE: DNA
<213> ORGANISM: Artificial
<220> FEATURE:
<223> OTHER INFORMATION: PCR primer

<400> SEQUENCE: 473
gaggacggtc accttggtgc ca    22

<210> SEQ ID NO 474
<211> LENGTH: 24
<212> TYPE: DNA
<213> ORGANISM: Artificial
<220> FEATURE:
<223> OTHER INFORMATION: PCR primer

<400> SEQUENCE: 474
taggacggtc agcttggtcc ctcc    24

<210> SEQ ID NO 475
<211> LENGTH: 21
<212> TYPE: DNA
<213> ORGANISM: Artificial
<220> FEATURE:
<223> OTHER INFORMATION: PCR primer

<400> SEQUENCE: 475
gaggacggtc agctgggtgc c    21

<210> SEQ ID NO 476
<211> LENGTH: 26
<212> TYPE: DNA
<213> ORGANISM: Artificial
<220> FEATURE:
<223> OTHER INFORMATION: PCR primer

<400> SEQUENCE: 476
taaaatgatc agctgggttc ctccac    26

<210> SEQ ID NO 477
<211> LENGTH: 24
<212> TYPE: DNA
<213> ORGANISM: Artificial
<220> FEATURE:
<223> OTHER INFORMATION: PCR primer

<400> SEQUENCE: 477

```
taggacggtg accttggtcc cagt                                          24

<210> SEQ ID NO 478
<211> LENGTH: 22
<212> TYPE: DNA
<213> ORGANISM: Artificial
<220> FEATURE:
<223> OTHER INFORMATION: PCR primer

<400> SEQUENCE: 478
taggacggtc agctcggtcc cc                                            22

<210> SEQ ID NO 479
<211> LENGTH: 22
<212> TYPE: DNA
<213> ORGANISM: Artificial
<220> FEATURE:
<223> OTHER INFORMATION: PCR primer

<400> SEQUENCE: 479
gaggtgcagc tggtggagtc cg                                            22

<210> SEQ ID NO 480
<211> LENGTH: 23
<212> TYPE: DNA
<213> ORGANISM: Artificial
<220> FEATURE:
<223> OTHER INFORMATION: PCR primer

<400> SEQUENCE: 480
gaggtgcagc tggtggagtc tgg                                           23

<210> SEQ ID NO 481
<211> LENGTH: 26
<212> TYPE: DNA
<213> ORGANISM: Artificial
<220> FEATURE:
<223> OTHER INFORMATION: PCR primer

<400> SEQUENCE: 481
caggtcacct tgagggagtc tggtcc                                        26

<210> SEQ ID NO 482
<211> LENGTH: 23
<212> TYPE: DNA
<213> ORGANISM: Artificial
<220> FEATURE:
<223> OTHER INFORMATION: PCR primer

<400> SEQUENCE: 482
caggttcagc tgttgcagcc tgg                                           23

<210> SEQ ID NO 483
<211> LENGTH: 24
<212> TYPE: DNA
<213> ORGANISM: Artificial
<220> FEATURE:
<223> OTHER INFORMATION: PCR primer

<400> SEQUENCE: 483
ctaggtgcag ctacagcagt gggg                                          24

<210> SEQ ID NO 484
<211> LENGTH: 23
<212> TYPE: DNA
```

-continued

```
<213> ORGANISM: Artificial
<220> FEATURE:
<223> OTHER INFORMATION: PCR primer

<400> SEQUENCE: 484
caggtgcagc tggtgcaatc tgg                                              23

<210> SEQ ID NO 485
<211> LENGTH: 26
<212> TYPE: DNA
<213> ORGANISM: Artificial
<220> FEATURE:
<223> OTHER INFORMATION: PCR primer

<400> SEQUENCE: 485
caggtcacct tgaaggagtc tggtcc                                           26

<210> SEQ ID NO 486
<211> LENGTH: 25
<212> TYPE: DNA
<213> ORGANISM: Artificial
<220> FEATURE:
<223> OTHER INFORMATION: PCR primer

<400> SEQUENCE: 486
ctaggtccag ctggtacagt ctggg                                            25

<210> SEQ ID NO 487
<211> LENGTH: 24
<212> TYPE: DNA
<213> ORGANISM: Artificial
<220> FEATURE:
<223> OTHER INFORMATION: PCR primer

<400> SEQUENCE: 487
caggaccagt tggtgcagtc tggg                                             24

<210> SEQ ID NO 488
<211> LENGTH: 23
<212> TYPE: DNA
<213> ORGANISM: Artificial
<220> FEATURE:
<223> OTHER INFORMATION: PCR primer

<400> SEQUENCE: 488
caggtgcagc tggtggagtc tgg                                              23

<210> SEQ ID NO 489
<211> LENGTH: 23
<212> TYPE: DNA
<213> ORGANISM: Artificial
<220> FEATURE:
<223> OTHER INFORMATION: PCR primer

<400> SEQUENCE: 489
cagatgcagc tggtgcagtc tgg                                              23

<210> SEQ ID NO 490
<211> LENGTH: 25
<212> TYPE: DNA
<213> ORGANISM: Artificial
<220> FEATURE:
<223> OTHER INFORMATION: PCR primer

<400> SEQUENCE: 490
ctaaatgcag ctggtgcagt ctggg                                            25
```

<210> SEQ ID NO 491
<211> LENGTH: 24
<212> TYPE: DNA
<213> ORGANISM: Artificial
<220> FEATURE:
<223> OTHER INFORMATION: PCR primer

<400> SEQUENCE: 491
gaagtgcagc tggtggagtc tggg                                              24

<210> SEQ ID NO 492
<211> LENGTH: 22
<212> TYPE: DNA
<213> ORGANISM: Artificial
<220> FEATURE:
<223> OTHER INFORMATION: PCR primer

<400> SEQUENCE: 492
caggtgcagc tggtgcagtc tg                                                22

<210> SEQ ID NO 493
<211> LENGTH: 24
<212> TYPE: DNA
<213> ORGANISM: Artificial
<220> FEATURE:
<223> OTHER INFORMATION: PCR primer

<400> SEQUENCE: 493
gaggatcagc tggtggagtc tggg                                              24

<210> SEQ ID NO 494
<211> LENGTH: 24
<212> TYPE: DNA
<213> ORGANISM: Artificial
<220> FEATURE:
<223> OTHER INFORMATION: PCR primer

<400> SEQUENCE: 494
gaggtccagc tggtacagtc tggg                                              24

<210> SEQ ID NO 495
<211> LENGTH: 21
<212> TYPE: DNA
<213> ORGANISM: Artificial
<220> FEATURE:
<223> OTHER INFORMATION: PCR primer

<400> SEQUENCE: 495
cagctgcagc tgcaggagtc c                                                 21

<210> SEQ ID NO 496
<211> LENGTH: 23
<212> TYPE: DNA
<213> ORGANISM: Artificial
<220> FEATURE:
<223> OTHER INFORMATION: PCR primer

<400> SEQUENCE: 496
gaggtgcagc tggtggagtc tgg                                               23

<210> SEQ ID NO 497
<211> LENGTH: 23
<212> TYPE: DNA
<213> ORGANISM: Artificial
<220> FEATURE:

<223> OTHER INFORMATION: PCR primer

<400> SEQUENCE: 497
ctaggtgcag ctggtgcagt ctg                                              23

<210> SEQ ID NO 498
<211> LENGTH: 24
<212> TYPE: DNA
<213> ORGANISM: Artificial
<220> FEATURE:
<223> OTHER INFORMATION: PCR primer

<400> SEQUENCE: 498
caggtacagc tgcagcagtc aggt                                             24

<210> SEQ ID NO 499
<211> LENGTH: 24
<212> TYPE: DNA
<213> ORGANISM: Artificial
<220> FEATURE:
<223> OTHER INFORMATION: PCR primer

<400> SEQUENCE: 499
gagatgcagc tggtggagtc tggg                                             24

<210> SEQ ID NO 500
<211> LENGTH: 24
<212> TYPE: DNA
<213> ORGANISM: Artificial
<220> FEATURE:
<223> OTHER INFORMATION: PCR primer

<400> SEQUENCE: 500
gaggtgcatc tggtggagtc tggg                                             24

<210> SEQ ID NO 501
<211> LENGTH: 23
<212> TYPE: DNA
<213> ORGANISM: Artificial
<220> FEATURE:
<223> OTHER INFORMATION: PCR primer

<400> SEQUENCE: 501
gaggtgcagc tggtggagtc tgg                                              23

<210> SEQ ID NO 502
<211> LENGTH: 23
<212> TYPE: DNA
<213> ORGANISM: Artificial
<220> FEATURE:
<223> OTHER INFORMATION: PCR primer

<400> SEQUENCE: 502
gaggtgcagc tggtggagtc tgg                                              23

<210> SEQ ID NO 503
<211> LENGTH: 26
<212> TYPE: DNA
<213> ORGANISM: Artificial
<220> FEATURE:
<223> OTHER INFORMATION: PCR primer

<400> SEQUENCE: 503
caggtccaac tggtgtagtc tggagc                                           26

```
<210> SEQ ID NO 504
<211> LENGTH: 22
<212> TYPE: DNA
<213> ORGANISM: Artificial
<220> FEATURE:
<223> OTHER INFORMATION: PCR primer

<400> SEQUENCE: 504
gaggtgcagc tggtgcagtc tg                                              22

<210> SEQ ID NO 505
<211> LENGTH: 23
<212> TYPE: DNA
<213> ORGANISM: Artificial
<220> FEATURE:
<223> OTHER INFORMATION: PCR primer

<400> SEQUENCE: 505
gaggtgcagc tggtggagtc tcg                                             23

<210> SEQ ID NO 506
<211> LENGTH: 24
<212> TYPE: DNA
<213> ORGANISM: Artificial
<220> FEATURE:
<223> OTHER INFORMATION: PCR primer

<400> SEQUENCE: 506
gaggttcagc tggtgcagtc tggg                                            24

<210> SEQ ID NO 507
<211> LENGTH: 22
<212> TYPE: DNA
<213> ORGANISM: Artificial
<220> FEATURE:
<223> OTHER INFORMATION: PCR primer

<400> SEQUENCE: 507
caggtgcagc tggtgcagtc tg                                              22

<210> SEQ ID NO 508
<211> LENGTH: 23
<212> TYPE: DNA
<213> ORGANISM: Artificial
<220> FEATURE:
<223> OTHER INFORMATION: PCR primer

<400> SEQUENCE: 508
gaagtgcagc tggtgcagtc tgg                                             23

<210> SEQ ID NO 509
<211> LENGTH: 26
<212> TYPE: DNA
<213> ORGANISM: Artificial
<220> FEATURE:
<223> OTHER INFORMATION: PCR primer

<400> SEQUENCE: 509
gaggtggagc tgatagagtc cataga                                          26

<210> SEQ ID NO 510
<211> LENGTH: 23
<212> TYPE: DNA
<213> ORGANISM: Artificial
<220> FEATURE:
<223> OTHER INFORMATION: PCR primer
```

<400> SEQUENCE: 510
acagtgcagc tggtggagtc tgg                                   23

<210> SEQ ID NO 511
<211> LENGTH: 23
<212> TYPE: DNA
<213> ORGANISM: Artificial
<220> FEATURE:
<223> OTHER INFORMATION: PCR primer

<400> SEQUENCE: 511
gaggtgcagc tggaggagtc tgg                                   23

<210> SEQ ID NO 512
<211> LENGTH: 26
<212> TYPE: DNA
<213> ORGANISM: Artificial
<220> FEATURE:
<223> OTHER INFORMATION: PCR primer

<400> SEQUENCE: 512
gaggtacagc tggtggagtc tgaaga                                26

<210> SEQ ID NO 513
<211> LENGTH: 21
<212> TYPE: DNA
<213> ORGANISM: Artificial
<220> FEATURE:
<223> OTHER INFORMATION: PCR primer

<400> SEQUENCE: 513
caggtgcagc tgcaggagtc g                                     21

<210> SEQ ID NO 514
<211> LENGTH: 24
<212> TYPE: DNA
<213> ORGANISM: Artificial
<220> FEATURE:
<223> OTHER INFORMATION: PCR primer

<400> SEQUENCE: 514
gaggtgcagc tgttggagtc tggg                                  24

<210> SEQ ID NO 515
<211> LENGTH: 20
<212> TYPE: DNA
<213> ORGANISM: Artificial
<220> FEATURE:
<223> OTHER INFORMATION: PCR primer

<400> SEQUENCE: 515
caggtgcagc tggggcagtc                                       20

<210> SEQ ID NO 516
<211> LENGTH: 21
<212> TYPE: DNA
<213> ORGANISM: Artificial
<220> FEATURE:
<223> OTHER INFORMATION: PCR primer

<400> SEQUENCE: 516
cagctgcagc tgcaggagtc g                                     21

<210> SEQ ID NO 517
<211> LENGTH: 24

```
<212> TYPE: DNA
<213> ORGANISM: Artificial
<220> FEATURE:
<223> OTHER INFORMATION: PCR primer

<400> SEQUENCE: 517
caggttcagc tggtgcagtc tgga                                    24

<210> SEQ ID NO 518
<211> LENGTH: 24
<212> TYPE: DNA
<213> ORGANISM: Artificial
<220> FEATURE:
<223> OTHER INFORMATION: PCR primer

<400> SEQUENCE: 518
gaggtgcagc tggtagagtc tggg                                    24

<210> SEQ ID NO 519
<211> LENGTH: 24
<212> TYPE: DNA
<213> ORGANISM: Artificial
<220> FEATURE:
<223> OTHER INFORMATION: PCR primer

<400> SEQUENCE: 519
caggtccagc ttgtgcagtc tggg                                    24

<210> SEQ ID NO 520
<211> LENGTH: 23
<212> TYPE: DNA
<213> ORGANISM: Artificial
<220> FEATURE:
<223> OTHER INFORMATION: PCR primer

<400> SEQUENCE: 520
gaggtgcagc tgttgcagtc tgc                                     23

<210> SEQ ID NO 521
<211> LENGTH: 26
<212> TYPE: DNA
<213> ORGANISM: Artificial
<220> FEATURE:
<223> OTHER INFORMATION: PCR primer

<400> SEQUENCE: 521
gaggtacaac tggtggagtc tggggg                                  26

<210> SEQ ID NO 522
<211> LENGTH: 26
<212> TYPE: DNA
<213> ORGANISM: Artificial
<220> FEATURE:
<223> OTHER INFORMATION: PCR primer

<400> SEQUENCE: 522
cagatcacct tgaaggagtc tggtcc                                  26

<210> SEQ ID NO 523
<211> LENGTH: 25
<212> TYPE: DNA
<213> ORGANISM: Artificial
<220> FEATURE:
<223> OTHER INFORMATION: PCR primer

<400> SEQUENCE: 523
```

```
caggtacagc tgatgcagtc tgggg                                              25

<210> SEQ ID NO 524
<211> LENGTH: 22
<212> TYPE: DNA
<213> ORGANISM: Artificial
<220> FEATURE:
<223> OTHER INFORMATION: PCR primer

<400> SEQUENCE: 524
tgaggagacg gtgaccgtgg tc                                                 22

<210> SEQ ID NO 525
<211> LENGTH: 24
<212> TYPE: DNA
<213> ORGANISM: Artificial
<220> FEATURE:
<223> OTHER INFORMATION: PCR primer

<400> SEQUENCE: 525
tgaggagaca gtgaccaggg tgcc                                               24

<210> SEQ ID NO 526
<211> LENGTH: 22
<212> TYPE: DNA
<213> ORGANISM: Artificial
<220> FEATURE:
<223> OTHER INFORMATION: PCR primer

<400> SEQUENCE: 526
tgatgtggct gcggtctcag gg                                                 22

<210> SEQ ID NO 527
<211> LENGTH: 24
<212> TYPE: DNA
<213> ORGANISM: Artificial
<220> FEATURE:
<223> OTHER INFORMATION: PCR primer

<400> SEQUENCE: 527
tgaggagacg gtgaccaggg ttcc                                               24

<210> SEQ ID NO 528
<211> LENGTH: 23
<212> TYPE: DNA
<213> ORGANISM: Artificial
<220> FEATURE:
<223> OTHER INFORMATION: PCR primer

<400> SEQUENCE: 528
gacccctcag aagccagacc acc                                                23

<210> SEQ ID NO 529
<211> LENGTH: 23
<212> TYPE: DNA
<213> ORGANISM: Artificial
<220> FEATURE:
<223> OTHER INFORMATION: PCR primer

<400> SEQUENCE: 529
tgaggagacg gtgaccaggg tgc                                                23

<210> SEQ ID NO 530
<211> LENGTH: 22
<212> TYPE: DNA
<213> ORGANISM: Artificial
```

```
<220> FEATURE:
<223> OTHER INFORMATION: PCR primer

<400> SEQUENCE: 530
gacgttccca gggagacggt gt                                              22

<210> SEQ ID NO 531
<211> LENGTH: 26
<212> TYPE: DNA
<213> ORGANISM: Artificial
<220> FEATURE:
<223> OTHER INFORMATION: PCR primer

<400> SEQUENCE: 531
tgaagagacg gtgaccattg tccctt                                          26

<210> SEQ ID NO 532
<211> LENGTH: 26
<212> TYPE: DNA
<213> ORGANISM: Artificial
<220> FEATURE:
<223> OTHER INFORMATION: PCR primer

<400> SEQUENCE: 532
gaaattgtgt tgacgcagtc tccagc                                          26

<210> SEQ ID NO 533
<211> LENGTH: 26
<212> TYPE: DNA
<213> ORGANISM: Artificial
<220> FEATURE:
<223> OTHER INFORMATION: PCR primer

<400> SEQUENCE: 533
gaaattgtgt tgacgcagtc tccagg                                          26

<210> SEQ ID NO 534
<211> LENGTH: 24
<212> TYPE: DNA
<213> ORGANISM: Artificial
<220> FEATURE:
<223> OTHER INFORMATION: PCR primer

<400> SEQUENCE: 534
gccatccagt tgacccagtc tcca                                            24

<210> SEQ ID NO 535
<211> LENGTH: 26
<212> TYPE: DNA
<213> ORGANISM: Artificial
<220> FEATURE:
<223> OTHER INFORMATION: PCR primer

<400> SEQUENCE: 535
gacatccaga tgactcagcc tccatc                                          26

<210> SEQ ID NO 536
<211> LENGTH: 26
<212> TYPE: DNA
<213> ORGANISM: Artificial
<220> FEATURE:
<223> OTHER INFORMATION: PCR primer

<400> SEQUENCE: 536
gaaacgacac tcacgcagtc tccagc                                          26
```

<210> SEQ ID NO 537
<211> LENGTH: 26
<212> TYPE: DNA
<213> ORGANISM: Artificial
<220> FEATURE:
<223> OTHER INFORMATION: PCR primer

<400> SEQUENCE: 537
gacatccaga tgacccagtc tccatc        26

<210> SEQ ID NO 538
<211> LENGTH: 26
<212> TYPE: DNA
<213> ORGANISM: Artificial
<220> FEATURE:
<223> OTHER INFORMATION: PCR primer

<400> SEQUENCE: 538
gacatccagg tgacccagtc tccatc        26

<210> SEQ ID NO 539
<211> LENGTH: 26
<212> TYPE: DNA
<213> ORGANISM: Artificial
<220> FEATURE:
<223> OTHER INFORMATION: PCR primer

<400> SEQUENCE: 539
gacattgtga tgacccagac tccact        26

<210> SEQ ID NO 540
<211> LENGTH: 26
<212> TYPE: DNA
<213> ORGANISM: Artificial
<220> FEATURE:
<223> OTHER INFORMATION: PCR primer

<400> SEQUENCE: 540
gacatcgtga tgacccagtc tccaga        26

<210> SEQ ID NO 541
<211> LENGTH: 23
<212> TYPE: DNA
<213> ORGANISM: Artificial
<220> FEATURE:
<223> OTHER INFORMATION: PCR primer

<400> SEQUENCE: 541
gccatccgga tgacccagtc tcc        23

<210> SEQ ID NO 542
<211> LENGTH: 26
<212> TYPE: DNA
<213> ORGANISM: Artificial
<220> FEATURE:
<223> OTHER INFORMATION: PCR primer

<400> SEQUENCE: 542
gatgttgtga tgacacagtc tccagc        26

<210> SEQ ID NO 543
<211> LENGTH: 26
<212> TYPE: DNA
<213> ORGANISM: Artificial
<220> FEATURE:
<223> OTHER INFORMATION: PCR primer

```
<400> SEQUENCE: 543
gatattgtga tgacccagca tctgct                                          26

<210> SEQ ID NO 544
<211> LENGTH: 26
<212> TYPE: DNA
<213> ORGANISM: Artificial
<220> FEATURE:
<223> OTHER INFORMATION: PCR primer

<400> SEQUENCE: 544
gaaatagtga tgacgcagtc tccagc                                          26

<210> SEQ ID NO 545
<211> LENGTH: 26
<212> TYPE: DNA
<213> ORGANISM: Artificial
<220> FEATURE:
<223> OTHER INFORMATION: PCR primer

<400> SEQUENCE: 545
gatattgtga tgacccagac tccacc                                          26

<210> SEQ ID NO 546
<211> LENGTH: 27
<212> TYPE: DNA
<213> ORGANISM: Artificial
<220> FEATURE:
<223> OTHER INFORMATION: PCR primer

<400> SEQUENCE: 546
gcacatccag atgatccagt ctccatc                                         27

<210> SEQ ID NO 547
<211> LENGTH: 26
<212> TYPE: DNA
<213> ORGANISM: Artificial
<220> FEATURE:
<223> OTHER INFORMATION: PCR primer

<400> SEQUENCE: 547
gaaattgtgt tgacacagtc tccagc                                          26

<210> SEQ ID NO 548
<211> LENGTH: 26
<212> TYPE: DNA
<213> ORGANISM: Artificial
<220> FEATURE:
<223> OTHER INFORMATION: PCR primer

<400> SEQUENCE: 548
gatattgtga tgactcagtc tccact                                          26

<210> SEQ ID NO 549
<211> LENGTH: 23
<212> TYPE: DNA
<213> ORGANISM: Artificial
<220> FEATURE:
<223> OTHER INFORMATION: PCR primer

<400> SEQUENCE: 549
gccatccgga tgacccagtc tcc                                             23

<210> SEQ ID NO 550
```

```
<211> LENGTH: 26
<212> TYPE: DNA
<213> ORGANISM: Artificial
<220> FEATURE:
<223> OTHER INFORMATION: PCR primer

<400> SEQUENCE: 550
aacatccaga tgacccagtc tccatc                                              26

<210> SEQ ID NO 551
<211> LENGTH: 26
<212> TYPE: DNA
<213> ORGANISM: Artificial
<220> FEATURE:
<223> OTHER INFORMATION: PCR primer

<400> SEQUENCE: 551
gaaattgtaa tgacacagtc tccagc                                              26

<210> SEQ ID NO 552
<211> LENGTH: 26
<212> TYPE: DNA
<213> ORGANISM: Artificial
<220> FEATURE:
<223> OTHER INFORMATION: PCR primer

<400> SEQUENCE: 552
gaaattgtaa tgacacagtc tccacc                                              26

<210> SEQ ID NO 553
<211> LENGTH: 26
<212> TYPE: DNA
<213> ORGANISM: Artificial
<220> FEATURE:
<223> OTHER INFORMATION: PCR primer

<400> SEQUENCE: 553
gatgttgtga tgactcagtc tccact                                              26

<210> SEQ ID NO 554
<211> LENGTH: 26
<212> TYPE: DNA
<213> ORGANISM: Artificial
<220> FEATURE:
<223> OTHER INFORMATION: PCR primer

<400> SEQUENCE: 554
gacattgtgc tgacccagtc tccagc                                              26

<210> SEQ ID NO 555
<211> LENGTH: 26
<212> TYPE: DNA
<213> ORGANISM: Artificial
<220> FEATURE:
<223> OTHER INFORMATION: PCR primer

<400> SEQUENCE: 555
gacatccaga tgacccagtc tccttc                                              26

<210> SEQ ID NO 556
<211> LENGTH: 26
<212> TYPE: DNA
<213> ORGANISM: Artificial
<220> FEATURE:
<223> OTHER INFORMATION: PCR primer

<400> SEQUENCE: 556
```
gaaattgtgc tgactcagtc tccaga 26

<210> SEQ ID NO 557
<211> LENGTH: 26
<212> TYPE: DNA
<213> ORGANISM: Artificial
<220> FEATURE:
<223> OTHER INFORMATION: PCR primer

<400> SEQUENCE: 557
gagattgtga tgacccagac tccact 26

<210> SEQ ID NO 558
<211> LENGTH: 26
<212> TYPE: DNA
<213> ORGANISM: Artificial
<220> FEATURE:
<223> OTHER INFORMATION: PCR primer

<400> SEQUENCE: 558
gccatccaga tgacccagtc tccatc 26

<210> SEQ ID NO 559
<211> LENGTH: 26
<212> TYPE: DNA
<213> ORGANISM: Artificial
<220> FEATURE:
<223> OTHER INFORMATION: PCR primer

<400> SEQUENCE: 559
gacatccagt tgacccagtc tccatc 26

<210> SEQ ID NO 560
<211> LENGTH: 26
<212> TYPE: DNA
<213> ORGANISM: Artificial
<220> FEATURE:
<223> OTHER INFORMATION: PCR primer

<400> SEQUENCE: 560
gatattgtga tgacccagac tccact 26

<210> SEQ ID NO 561
<211> LENGTH: 26
<212> TYPE: DNA
<213> ORGANISM: Artificial
<220> FEATURE:
<223> OTHER INFORMATION: PCR primer

<400> SEQUENCE: 561
gtcatctgga tgacccagtc tccatc 26

<210> SEQ ID NO 562
<211> LENGTH: 26
<212> TYPE: DNA
<213> ORGANISM: Artificial
<220> FEATURE:
<223> OTHER INFORMATION: PCR primer

<400> SEQUENCE: 562
gacatccaga tgacccagcc tccatc 26

<210> SEQ ID NO 563
<211> LENGTH: 26
<212> TYPE: DNA

```
<213> ORGANISM: Artificial
<220> FEATURE:
<223> OTHER INFORMATION: PCR primer

<400> SEQUENCE: 563
gaaattgtgt tgacacagtc tccagg                                        26

<210> SEQ ID NO 564
<211> LENGTH: 24
<212> TYPE: DNA
<213> ORGANISM: Artificial
<220> FEATURE:
<223> OTHER INFORMATION: PCR primer

<400> SEQUENCE: 564
cagtctgccc tgattcagcc tccc                                          24

<210> SEQ ID NO 565
<211> LENGTH: 22
<212> TYPE: DNA
<213> ORGANISM: Artificial
<220> FEATURE:
<223> OTHER INFORMATION: PCR primer

<400> SEQUENCE: 565
ctgcctgtgc tgactcagcc cc                                            22

<210> SEQ ID NO 566
<211> LENGTH: 22
<212> TYPE: DNA
<213> ORGANISM: Artificial
<220> FEATURE:
<223> OTHER INFORMATION: PCR primer

<400> SEQUENCE: 566
cagcctgtgc tgactcagcc ac                                            22

<210> SEQ ID NO 567
<211> LENGTH: 26
<212> TYPE: DNA
<213> ORGANISM: Artificial
<220> FEATURE:
<223> OTHER INFORMATION: PCR primer

<400> SEQUENCE: 567
tcttctgagc tgactcagga ccctgc                                        26

<210> SEQ ID NO 568
<211> LENGTH: 24
<212> TYPE: DNA
<213> ORGANISM: Artificial
<220> FEATURE:
<223> OTHER INFORMATION: PCR primer

<400> SEQUENCE: 568
caatctgccc tgactcagcc tcct                                          24

<210> SEQ ID NO 569
<211> LENGTH: 24
<212> TYPE: DNA
<213> ORGANISM: Artificial
<220> FEATURE:
<223> OTHER INFORMATION: PCR primer

<400> SEQUENCE: 569
tcctatgagc tgacacagcc accc                                          24
```

```
<210> SEQ ID NO 570
<211> LENGTH: 19
<212> TYPE: DNA
<213> ORGANISM: Artificial
<220> FEATURE:
<223> OTHER INFORMATION: PCR primer

<400> SEQUENCE: 570
cggcccgtgc tgactcagc                                                 19

<210> SEQ ID NO 571
<211> LENGTH: 26
<212> TYPE: DNA
<213> ORGANISM: Artificial
<220> FEATURE:
<223> OTHER INFORMATION: PCR primer

<400> SEQUENCE: 571
cagcctgtgc tgactcaatc atcctc                                         26

<210> SEQ ID NO 572
<211> LENGTH: 24
<212> TYPE: DNA
<213> ORGANISM: Artificial
<220> FEATURE:
<223> OTHER INFORMATION: PCR primer

<400> SEQUENCE: 572
tcctctgagc tgagtcagga gcct                                           24

<210> SEQ ID NO 573
<211> LENGTH: 23
<212> TYPE: DNA
<213> ORGANISM: Artificial
<220> FEATURE:
<223> OTHER INFORMATION: PCR primer

<400> SEQUENCE: 573
cagtctgccc tgactcagcc tcc                                            23

<210> SEQ ID NO 574
<211> LENGTH: 22
<212> TYPE: DNA
<213> ORGANISM: Artificial
<220> FEATURE:
<223> OTHER INFORMATION: PCR primer

<400> SEQUENCE: 574
cagtctgtgt tgacgcagcc gc                                             22

<210> SEQ ID NO 575
<211> LENGTH: 21
<212> TYPE: DNA
<213> ORGANISM: Artificial
<220> FEATURE:
<223> OTHER INFORMATION: PCR primer

<400> SEQUENCE: 575
caggcagggc tgactcagcc a                                              21

<210> SEQ ID NO 576
<211> LENGTH: 22
<212> TYPE: DNA
<213> ORGANISM: Artificial
<220> FEATURE:
```

<223> OTHER INFORMATION: PCR primer

<400> SEQUENCE: 576
cagtctgtgt tgacgcagcc gc                                              22

<210> SEQ ID NO 577
<211> LENGTH: 24
<212> TYPE: DNA
<213> ORGANISM: Artificial
<220> FEATURE:
<223> OTHER INFORMATION: PCR primer

<400> SEQUENCE: 577
cagtctgtgc tgactcagcc accc                                            24

<210> SEQ ID NO 578
<211> LENGTH: 26
<212> TYPE: DNA
<213> ORGANISM: Artificial
<220> FEATURE:
<223> OTHER INFORMATION: PCR primer

<400> SEQUENCE: 578
tcctatgagc tgactcagcc actctc                                          26

<210> SEQ ID NO 579
<211> LENGTH: 23
<212> TYPE: DNA
<213> ORGANISM: Artificial
<220> FEATURE:
<223> OTHER INFORMATION: PCR primer

<400> SEQUENCE: 579
cagcctgtgc tgactcagcc aac                                             23

<210> SEQ ID NO 580
<211> LENGTH: 24
<212> TYPE: DNA
<213> ORGANISM: Artificial
<220> FEATURE:
<223> OTHER INFORMATION: PCR primer

<400> SEQUENCE: 580
tcctatgagc tgacacagcc accc                                            24

<210> SEQ ID NO 581
<211> LENGTH: 26
<212> TYPE: DNA
<213> ORGANISM: Artificial
<220> FEATURE:
<223> OTHER INFORMATION: PCR primer

<400> SEQUENCE: 581
tcctatgagc tgacacagcc atcctc                                          26

<210> SEQ ID NO 582
<211> LENGTH: 23
<212> TYPE: DNA
<213> ORGANISM: Artificial
<220> FEATURE:
<223> OTHER INFORMATION: PCR primer

<400> SEQUENCE: 582
cagcctgtgc tgactcagcc aac                                             23

```
<210> SEQ ID NO 583
<211> LENGTH: 26
<212> TYPE: DNA
<213> ORGANISM: Artificial
<220> FEATURE:
<223> OTHER INFORMATION: PCR primer

<400> SEQUENCE: 583
tcctatgagc tgacacagct accctc                                          26

<210> SEQ ID NO 584
<211> LENGTH: 24
<212> TYPE: DNA
<213> ORGANISM: Artificial
<220> FEATURE:
<223> OTHER INFORMATION: PCR primer

<400> SEQUENCE: 584
cagcctgtgc tgactcagcc atct                                            24

<210> SEQ ID NO 585
<211> LENGTH: 22
<212> TYPE: DNA
<213> ORGANISM: Artificial
<220> FEATURE:
<223> OTHER INFORMATION: PCR primer

<400> SEQUENCE: 585
tcctctgggc caactcaggt gc                                              22

<210> SEQ ID NO 586
<211> LENGTH: 25
<212> TYPE: DNA
<213> ORGANISM: Artificial
<220> FEATURE:
<223> OTHER INFORMATION: PCR primer

<400> SEQUENCE: 586
tcctatgagc tgactcagcc accct                                           25

<210> SEQ ID NO 587
<211> LENGTH: 23
<212> TYPE: DNA
<213> ORGANISM: Artificial
<220> FEATURE:
<223> OTHER INFORMATION: PCR primer

<400> SEQUENCE: 587
cagactgtgg tgacccagga gcc                                             23

<210> SEQ ID NO 588
<211> LENGTH: 23
<212> TYPE: DNA
<213> ORGANISM: Artificial
<220> FEATURE:
<223> OTHER INFORMATION: PCR primer

<400> SEQUENCE: 588
cagtctgccc tgactcagcc tgc                                             23

<210> SEQ ID NO 589
<211> LENGTH: 25
<212> TYPE: DNA
<213> ORGANISM: Artificial
<220> FEATURE:
<223> OTHER INFORMATION: PCR primer
```

```
<400> SEQUENCE: 589
attttatgct gactcagccc cactc                                        25

<210> SEQ ID NO 590
<211> LENGTH: 24
<212> TYPE: DNA
<213> ORGANISM: Artificial
<220> FEATURE:
<223> OTHER INFORMATION: PCR primer

<400> SEQUENCE: 590
tcctatgagc tgatgcagcc accc                                         24

<210> SEQ ID NO 591
<211> LENGTH: 23
<212> TYPE: DNA
<213> ORGANISM: Artificial
<220> FEATURE:
<223> OTHER INFORMATION: PCR primer

<400> SEQUENCE: 591
caggctgtgg tgactcagga gcc                                          23

<210> SEQ ID NO 592
<211> LENGTH: 24
<212> TYPE: DNA
<213> ORGANISM: Artificial
<220> FEATURE:
<223> OTHER INFORMATION: PCR primer

<400> SEQUENCE: 592
cagcttgtgc tgactcaatc gccc                                         24

<210> SEQ ID NO 593
<211> LENGTH: 24
<212> TYPE: DNA
<213> ORGANISM: Artificial
<220> FEATURE:
<223> OTHER INFORMATION: PCR primer

<400> SEQUENCE: 593
cagactgtgg tgactcagga gccc                                         24

<210> SEQ ID NO 594
<211> LENGTH: 26
<212> TYPE: DNA
<213> ORGANISM: Artificial
<220> FEATURE:
<223> OTHER INFORMATION: PCR primer

<400> SEQUENCE: 594
tcctatgagc tgactcagcc acactc                                       26

<210> SEQ ID NO 595
<211> LENGTH: 21
<212> TYPE: DNA
<213> ORGANISM: Artificial
<220> FEATURE:
<223> OTHER INFORMATION: PCR primer

<400> SEQUENCE: 595
caggctgtgc tgactcagcc g                                            21

<210> SEQ ID NO 596
<211> LENGTH: 24
```

<212> TYPE: DNA
<213> ORGANISM: Artificial
<220> FEATURE:
<223> OTHER INFORMATION: PCR primer

<400> SEQUENCE: 596
tcctatgtgc tgactcagcc accc                                      24

<210> SEQ ID NO 597
<211> LENGTH: 23
<212> TYPE: DNA
<213> ORGANISM: Artificial
<220> FEATURE:
<223> OTHER INFORMATION: PCR primer

<400> SEQUENCE: 597
cagtctgccc tgactcagcc tcg                                       23

<210> SEQ ID NO 598
<211> LENGTH: 25
<212> TYPE: DNA
<213> ORGANISM: Artificial
<220> FEATURE:
<223> OTHER INFORMATION: PCR primer

<400> SEQUENCE: 598
cagtctgttc tgactcagcc tcgct                                     25

<210> SEQ ID NO 599
<211> LENGTH: 21
<212> TYPE: DNA
<213> ORGANISM: Artificial
<220> FEATURE:
<223> OTHER INFORMATION: PCR primer

<400> SEQUENCE: 599
cagtctgtgc tgacgcagcc g                                         21

<210> SEQ ID NO 600
<211> LENGTH: 26
<212> TYPE: DNA
<213> ORGANISM: Artificial
<220> FEATURE:
<223> OTHER INFORMATION: PCR primer

<400> SEQUENCE: 600
tttgatctcc accttggtcc ctccgc                                    26

<210> SEQ ID NO 601
<211> LENGTH: 25
<212> TYPE: DNA
<213> ORGANISM: Artificial
<220> FEATURE:
<223> OTHER INFORMATION: PCR primer

<400> SEQUENCE: 601
tttgatctcc agcttggtcc cctgg                                     25

<210> SEQ ID NO 602
<211> LENGTH: 26
<212> TYPE: DNA
<213> ORGANISM: Artificial
<220> FEATURE:
<223> OTHER INFORMATION: PCR primer

<400> SEQUENCE: 602

```
tttgatatcc actttggtcc cagggc                                              26

<210> SEQ ID NO 603
<211> LENGTH: 26
<212> TYPE: DNA
<213> ORGANISM: Artificial
<220> FEATURE:
<223> OTHER INFORMATION: PCR primer

<400> SEQUENCE: 603
tttgatttcc accttggtcc cttggc                                              26

<210> SEQ ID NO 604
<211> LENGTH: 26
<212> TYPE: DNA
<213> ORGANISM: Artificial
<220> FEATURE:
<223> OTHER INFORMATION: PCR primer

<400> SEQUENCE: 604
tttaatctcc agtcgtgtcc cttggc                                              26

<210> SEQ ID NO 605
<211> LENGTH: 22
<212> TYPE: DNA
<213> ORGANISM: Artificial
<220> FEATURE:
<223> OTHER INFORMATION: PCR primer

<400> SEQUENCE: 605
gaggacggtc accttggtgc ca                                                  22

<210> SEQ ID NO 606
<211> LENGTH: 24
<212> TYPE: DNA
<213> ORGANISM: Artificial
<220> FEATURE:
<223> OTHER INFORMATION: PCR primer

<400> SEQUENCE: 606
taggacggtc agcttggtcc ctcc                                                24

<210> SEQ ID NO 607
<211> LENGTH: 21
<212> TYPE: DNA
<213> ORGANISM: Artificial
<220> FEATURE:
<223> OTHER INFORMATION: PCR primer

<400> SEQUENCE: 607
gaggacggtc agctgggtgc c                                                   21

<210> SEQ ID NO 608
<211> LENGTH: 26
<212> TYPE: DNA
<213> ORGANISM: Artificial
<220> FEATURE:
<223> OTHER INFORMATION: PCR primer

<400> SEQUENCE: 608
taaaatgatc agctgggttc ctccac                                              26

<210> SEQ ID NO 609
<211> LENGTH: 24
<212> TYPE: DNA
<213> ORGANISM: Artificial
```

```
<220> FEATURE:
<223> OTHER INFORMATION: PCR primer

<400> SEQUENCE: 609
taggacggtg accttggtcc cagt                                          24

<210> SEQ ID NO 610
<211> LENGTH: 22
<212> TYPE: DNA
<213> ORGANISM: Artificial
<220> FEATURE:
<223> OTHER INFORMATION: PCR primer

<400> SEQUENCE: 610
taggacggtc agctcggtcc cc                                            22

<210> SEQ ID NO 611
<211> LENGTH: 56
<212> TYPE: DNA
<213> ORGANISM: Artificial
<220> FEATURE:
<223> OTHER INFORMATION: PCR primer

<400> SEQUENCE: 611
ctaacagcgc gagccacagt ggttctgctc cgaatactag ttctgctccg ggatcc       56

<210> SEQ ID NO 612
<211> LENGTH: 60
<212> TYPE: DNA
<213> ORGANISM: Artificial
<220> FEATURE:
<223> OTHER INFORMATION: PCR primer

<400> SEQUENCE: 612
acagtggttc tgctccgaat actagttctg ctccgggatc ccagtctgtg ttgacgcagc   60

<210> SEQ ID NO 613
<211> LENGTH: 64
<212> TYPE: DNA
<213> ORGANISM: Artificial
<220> FEATURE:
<223> OTHER INFORMATION: PCR primer

<400> SEQUENCE: 613
cctggtgcca gtggcagagg agtggattgt cgcgctcggt gtcaccaaga cgaggcttat   60
gatc                                                                64

<210> SEQ ID NO 614
<211> LENGTH: 22
<212> TYPE: DNA
<213> ORGANISM: Artificial
<220> FEATURE:
<223> OTHER INFORMATION: PCR primer

<400> SEQUENCE: 614
caggtgcagc tgcaggagtc cg                                            22

<210> SEQ ID NO 615
<211> LENGTH: 22
<212> TYPE: DNA
<213> ORGANISM: Artificial
<220> FEATURE:
<223> OTHER INFORMATION: PCR primer

<400> SEQUENCE: 615
```

-continued caggtgcagc tgcaggagtc gg    22

<210> SEQ ID NO 616
<211> LENGTH: 21
<212> TYPE: DNA
<213> ORGANISM: Artificial
<220> FEATURE:
<223> OTHER INFORMATION: PCR primer

<400> SEQUENCE: 616
caggtacagc tgcagcagtc a    21

<210> SEQ ID NO 617
<211> LENGTH: 22
<212> TYPE: DNA
<213> ORGANISM: Artificial
<220> FEATURE:
<223> OTHER INFORMATION: PCR primer

<400> SEQUENCE: 617
caggtgcagc tacagcagtg gg    22

<210> SEQ ID NO 618
<211> LENGTH: 21
<212> TYPE: DNA
<213> ORGANISM: Artificial
<220> FEATURE:
<223> OTHER INFORMATION: PCR primer

<400> SEQUENCE: 618
gaggtgcagc tggtggagac c    21

<210> SEQ ID NO 619
<211> LENGTH: 21
<212> TYPE: DNA
<213> ORGANISM: Artificial
<220> FEATURE:
<223> OTHER INFORMATION: PCR primer

<400> SEQUENCE: 619
gaggtgcagc tggtggagac t    21

<210> SEQ ID NO 620
<211> LENGTH: 21
<212> TYPE: DNA
<213> ORGANISM: Artificial
<220> FEATURE:
<223> OTHER INFORMATION: PCR primer

<400> SEQUENCE: 620
gaggtgcagc tggtggagtc c    21

<210> SEQ ID NO 621
<211> LENGTH: 21
<212> TYPE: DNA
<213> ORGANISM: Artificial
<220> FEATURE:
<223> OTHER INFORMATION: PCR primer

<400> SEQUENCE: 621
gaggtgcagc tggtggagtc t    21

<210> SEQ ID NO 622
<211> LENGTH: 21
<212> TYPE: DNA
<213> ORGANISM: Artificial

```
<220> FEATURE:
<223> OTHER INFORMATION: PCR primer

<400> SEQUENCE: 622
gaggtgcagc tgttggagac c                                            21

<210> SEQ ID NO 623
<211> LENGTH: 21
<212> TYPE: DNA
<213> ORGANISM: Artificial
<220> FEATURE:
<223> OTHER INFORMATION: PCR primer

<400> SEQUENCE: 623
gaggtgcagc tgttggagac t                                            21

<210> SEQ ID NO 624
<211> LENGTH: 21
<212> TYPE: DNA
<213> ORGANISM: Artificial
<220> FEATURE:
<223> OTHER INFORMATION: PCR primer

<400> SEQUENCE: 624
gaggtgcagc tgttggagtc c                                            21

<210> SEQ ID NO 625
<211> LENGTH: 21
<212> TYPE: DNA
<213> ORGANISM: Artificial
<220> FEATURE:
<223> OTHER INFORMATION: PCR primer

<400> SEQUENCE: 625
gaggtgcagc tgttggagtc t                                            21

<210> SEQ ID NO 626
<211> LENGTH: 23
<212> TYPE: DNA
<213> ORGANISM: Artificial
<220> FEATURE:
<223> OTHER INFORMATION: PCR primer

<400> SEQUENCE: 626
caggtccagc tggtacagtc tgg                                          23

<210> SEQ ID NO 627
<211> LENGTH: 23
<212> TYPE: DNA
<213> ORGANISM: Artificial
<220> FEATURE:
<223> OTHER INFORMATION: PCR primer

<400> SEQUENCE: 627
caggtccagc tggtgcagtc tgg                                          23

<210> SEQ ID NO 628
<211> LENGTH: 23
<212> TYPE: DNA
<213> ORGANISM: Artificial
<220> FEATURE:
<223> OTHER INFORMATION: PCR primer

<400> SEQUENCE: 628
caggtccagc ttgtacagtc tgg                                          23
```

```
<210> SEQ ID NO 629
<211> LENGTH: 23
<212> TYPE: DNA
<213> ORGANISM: Artificial
<220> FEATURE:
<223> OTHER INFORMATION: PCR primer

<400> SEQUENCE: 629
caggtccagc ttgtgcagtc tgg                                                 23

<210> SEQ ID NO 630
<211> LENGTH: 22
<212> TYPE: DNA
<213> ORGANISM: Artificial
<220> FEATURE:
<223> OTHER INFORMATION: PCR primer

<400> SEQUENCE: 630
cagatcacct tgaaggagtc tg                                                  22

<210> SEQ ID NO 631
<211> LENGTH: 22
<212> TYPE: DNA
<213> ORGANISM: Artificial
<220> FEATURE:
<223> OTHER INFORMATION: PCR primer

<400> SEQUENCE: 631
caggtcacct tgaaggagtc tg                                                  22

<210> SEQ ID NO 632
<211> LENGTH: 23
<212> TYPE: DNA
<213> ORGANISM: Artificial
<220> FEATURE:
<223> OTHER INFORMATION: PCR primer

<400> SEQUENCE: 632
caggtgcagc tggtgcaatc tgg                                                 23

<210> SEQ ID NO 633
<211> LENGTH: 23
<212> TYPE: DNA
<213> ORGANISM: Artificial
<220> FEATURE:
<223> OTHER INFORMATION: PCR primer

<400> SEQUENCE: 633
caggtgcagc tggtgcagtc tgg                                                 23

<210> SEQ ID NO 634
<211> LENGTH: 23
<212> TYPE: DNA
<213> ORGANISM: Artificial
<220> FEATURE:
<223> OTHER INFORMATION: PCR primer

<400> SEQUENCE: 634
caggtgcagc tggtggaatc tgg                                                 23

<210> SEQ ID NO 635
<211> LENGTH: 23
<212> TYPE: DNA
<213> ORGANISM: Artificial
<220> FEATURE:
<223> OTHER INFORMATION: PCR primer
```

-continued

<400> SEQUENCE: 635
caggtgcagc tggtggagtc tgg                                        23

<210> SEQ ID NO 636
<211> LENGTH: 63
<212> TYPE: DNA
<213> ORGANISM: Artificial
<220> FEATURE:
<223> OTHER INFORMATION: PCR primer

<400> SEQUENCE: 636
ctagtattcg gagcagaacc actgtggctc gcgctgttag gtgaggagac agtgaccagg    60
gtg                                                                63

<210> SEQ ID NO 637
<211> LENGTH: 63
<212> TYPE: DNA
<213> ORGANISM: Artificial
<220> FEATURE:
<223> OTHER INFORMATION: PCR primer

<400> SEQUENCE: 637
ctagtattcg gagcagaacc actgtggctc gcgctgttag gtgaggagac ggtgaccagg    60
gtg                                                                63

<210> SEQ ID NO 638
<211> LENGTH: 63
<212> TYPE: DNA
<213> ORGANISM: Artificial
<220> FEATURE:
<223> OTHER INFORMATION: PCR primer

<400> SEQUENCE: 638
ctagtattcg gagcagaacc actgtggctc gcgctgttag gtgaggagac ggtgaccagg    60
gtt                                                                63

<210> SEQ ID NO 639
<211> LENGTH: 62
<212> TYPE: DNA
<213> ORGANISM: Artificial
<220> FEATURE:
<223> OTHER INFORMATION: PCR primer

<400> SEQUENCE: 639
ctagtattcg gagcagaacc actgtggctc gcgctgttag gtgaagagac ggtgaccatt    60
gt                                                                 62

<210> SEQ ID NO 640
<211> LENGTH: 64
<212> TYPE: DNA
<213> ORGANISM: Artificial
<220> FEATURE:
<223> OTHER INFORMATION: PCR primer

<400> SEQUENCE: 640
ctagtattcg gagcagaacc actgtggctc gcgctgttag gtgaggagac ggtgaccgtg    60
gtcc                                                               64

<210> SEQ ID NO 641
<211> LENGTH: 64
<212> TYPE: DNA

```
<213> ORGANISM: Artificial
<220> FEATURE:
<223> OTHER INFORMATION: PCR primer

<400> SEQUENCE: 641
acagtggttc tgctccgaat actagttctg ctccgggatc ccagtctgtc ctgacgcagc    60
cgcc                                                                 64

<210> SEQ ID NO 642
<211> LENGTH: 64
<212> TYPE: DNA
<213> ORGANISM: Artificial
<220> FEATURE:
<223> OTHER INFORMATION: PCR primer

<400> SEQUENCE: 642
acagtggttc tgctccgaat actagttctg ctccgggatc ccagtctgtc gtgacgcagc    60
cgcc                                                                 64

<210> SEQ ID NO 643
<211> LENGTH: 64
<212> TYPE: DNA
<213> ORGANISM: Artificial
<220> FEATURE:
<223> OTHER INFORMATION: PCR primer

<400> SEQUENCE: 643
acagtggttc tgctccgaat actagttctg ctccgggatc ccagtctgtc ttgacgcagc    60
cgcc                                                                 64

<210> SEQ ID NO 644
<211> LENGTH: 64
<212> TYPE: DNA
<213> ORGANISM: Artificial
<220> FEATURE:
<223> OTHER INFORMATION: PCR primer

<400> SEQUENCE: 644
acagtggttc tgctccgaat actagttctg ctccgggatc ccagtctgtg ctgacgcagc    60
cgcc                                                                 64

<210> SEQ ID NO 645
<211> LENGTH: 64
<212> TYPE: DNA
<213> ORGANISM: Artificial
<220> FEATURE:
<223> OTHER INFORMATION: PCR primer

<400> SEQUENCE: 645
acagtggttc tgctccgaat actagttctg ctccgggatc ccagtctgtg gtgacgcagc    60
cgcc                                                                 64

<210> SEQ ID NO 646
<211> LENGTH: 64
<212> TYPE: DNA
<213> ORGANISM: Artificial
<220> FEATURE:
<223> OTHER INFORMATION: PCR primer

<400> SEQUENCE: 646
acagtggttc tgctccgaat actagttctg ctccgggatc ccagtctgtg ttgacgcagc    60
cgcc                                                                 64
```

<210> SEQ ID NO 647
<211> LENGTH: 63
<212> TYPE: DNA
<213> ORGANISM: Artificial
<220> FEATURE:
<223> OTHER INFORMATION: PCR primer

<400> SEQUENCE: 647
acagtggttc tgctccgaat actagttctg ctccgggatc ctcctatgag ctgacacagc    60
cac    63

<210> SEQ ID NO 648
<211> LENGTH: 63
<212> TYPE: DNA
<213> ORGANISM: Artificial
<220> FEATURE:
<223> OTHER INFORMATION: PCR primer

<400> SEQUENCE: 648
acagtggttc tgctccgaat actagttctg ctccgggatc ctcctatgag ctgactcagc    60
cac    63

<210> SEQ ID NO 649
<211> LENGTH: 63
<212> TYPE: DNA
<213> ORGANISM: Artificial
<220> FEATURE:
<223> OTHER INFORMATION: PCR primer

<400> SEQUENCE: 649
acagtggttc tgctccgaat actagttctg ctccgggatc ctcctatgtg ctgacacagc    60
cac    63

<210> SEQ ID NO 650
<211> LENGTH: 63
<212> TYPE: DNA
<213> ORGANISM: Artificial
<220> FEATURE:
<223> OTHER INFORMATION: PCR primer

<400> SEQUENCE: 650
acagtggttc tgctccgaat actagttctg ctccgggatc ctcctatgtg ctgactcagc    60
cac    63

<210> SEQ ID NO 651
<211> LENGTH: 64
<212> TYPE: DNA
<213> ORGANISM: Artificial
<220> FEATURE:
<223> OTHER INFORMATION: PCR primer

<400> SEQUENCE: 651
acagtggttc tgctccgaat actagttctg ctccgggatc ctcctatgag ctgacacagc    60
cacc    64

<210> SEQ ID NO 652
<211> LENGTH: 64
<212> TYPE: DNA
<213> ORGANISM: Artificial
<220> FEATURE:
<223> OTHER INFORMATION: PCR primer

```
<400> SEQUENCE: 652
acagtggttc tgctccgaat actagttctg ctccgggatc ctcctatgag ctgacacagc    60
tacc                                                                64

<210> SEQ ID NO 653
<211> LENGTH: 64
<212> TYPE: DNA
<213> ORGANISM: Artificial
<220> FEATURE:
<223> OTHER INFORMATION: PCR primer

<400> SEQUENCE: 653
acagtggttc tgctccgaat actagttctg ctccgggatc ctcctatgag ctgacgcagc    60
cacc                                                                64

<210> SEQ ID NO 654
<211> LENGTH: 64
<212> TYPE: DNA
<213> ORGANISM: Artificial
<220> FEATURE:
<223> OTHER INFORMATION: PCR primer

<400> SEQUENCE: 654
acagtggttc tgctccgaat actagttctg ctccgggatc ctcctatgag ctgacgcagc    60
tacc                                                                64

<210> SEQ ID NO 655
<211> LENGTH: 64
<212> TYPE: DNA
<213> ORGANISM: Artificial
<220> FEATURE:
<223> OTHER INFORMATION: PCR primer

<400> SEQUENCE: 655
acagtggttc tgctccgaat actagttctg ctccgggatc ctcctatgag ctgatacagc    60
cacc                                                                64

<210> SEQ ID NO 656
<211> LENGTH: 64
<212> TYPE: DNA
<213> ORGANISM: Artificial
<220> FEATURE:
<223> OTHER INFORMATION: PCR primer

<400> SEQUENCE: 656
acagtggttc tgctccgaat actagttctg ctccgggatc ctcctatgag ctgatacagc    60
tacc                                                                64

<210> SEQ ID NO 657
<211> LENGTH: 64
<212> TYPE: DNA
<213> ORGANISM: Artificial
<220> FEATURE:
<223> OTHER INFORMATION: PCR primer

<400> SEQUENCE: 657
acagtggttc tgctccgaat actagttctg ctccgggatc ctcctatgag ctgatgcagc    60
cacc                                                                64

<210> SEQ ID NO 658
<211> LENGTH: 64
```

```
<212> TYPE: DNA
<213> ORGANISM: Artificial
<220> FEATURE:
<223> OTHER INFORMATION: PCR primer

<400> SEQUENCE: 658
acagtggttc tgctccgaat actagttctg ctccgggatc ctcctatgag ctgatgcagc    60
tacc                                                                 64

<210> SEQ ID NO 659
<211> LENGTH: 61
<212> TYPE: DNA
<213> ORGANISM: Artificial
<220> FEATURE:
<223> OTHER INFORMATION: PCR primer

<400> SEQUENCE: 659
acagtggttc tgctccgaat actagttctg ctccgggatc ccagcctgtg ctgactcaac    60
c                                                                    61

<210> SEQ ID NO 660
<211> LENGTH: 61
<212> TYPE: DNA
<213> ORGANISM: Artificial
<220> FEATURE:
<223> OTHER INFORMATION: PCR primer

<400> SEQUENCE: 660
acagtggttc tgctccgaat actagttctg ctccgggatc ccagcctgtg ctgactcaat    60
c                                                                    61

<210> SEQ ID NO 661
<211> LENGTH: 60
<212> TYPE: DNA
<213> ORGANISM: Artificial
<220> FEATURE:
<223> OTHER INFORMATION: PCR primer

<400> SEQUENCE: 661
cagtggttct gctccgaata ctagttctgc tccgggatcc cagcctgtgc tgactcagcc    60

<210> SEQ ID NO 662
<211> LENGTH: 61
<212> TYPE: DNA
<213> ORGANISM: Artificial
<220> FEATURE:
<223> OTHER INFORMATION: PCR primer

<400> SEQUENCE: 662
acagtggttc tgctccgaat actagttctg ctccgggatc ccagcctgtg ctgactcagt    60
c                                                                    61

<210> SEQ ID NO 663
<211> LENGTH: 64
<212> TYPE: DNA
<213> ORGANISM: Artificial
<220> FEATURE:
<223> OTHER INFORMATION: PCR primer

<400> SEQUENCE: 663
acagtggttc tgctccgaat actagttctg ctccgggatc ccagactgtg gtgacccagg    60
agcc                                                                 64
```

<210> SEQ ID NO 664
<211> LENGTH: 64
<212> TYPE: DNA
<213> ORGANISM: Artificial
<220> FEATURE:
<223> OTHER INFORMATION: PCR primer

<400> SEQUENCE: 664
acagtggttc tgctccgaat actagttctg ctccgggatc ccagactgtg gtgactcagg    60
agcc    64

<210> SEQ ID NO 665
<211> LENGTH: 64
<212> TYPE: DNA
<213> ORGANISM: Artificial
<220> FEATURE:
<223> OTHER INFORMATION: PCR primer

<400> SEQUENCE: 665
acagtggttc tgctccgaat actagttctg ctccgggatc ccaggctgtg gtgacccagg    60
agcc    64

<210> SEQ ID NO 666
<211> LENGTH: 64
<212> TYPE: DNA
<213> ORGANISM: Artificial
<220> FEATURE:
<223> OTHER INFORMATION: PCR primer

<400> SEQUENCE: 666
acagtggttc tgctccgaat actagttctg ctccgggatc ccaggctgtg gtgactcagg    60
agcc    64

<210> SEQ ID NO 667
<211> LENGTH: 64
<212> TYPE: DNA
<213> ORGANISM: Artificial
<220> FEATURE:
<223> OTHER INFORMATION: PCR primer

<400> SEQUENCE: 667
acagtggttc tgctccgaat actagttctg ctccgggatc ccagtctgtg gtgacccagg    60
agcc    64

<210> SEQ ID NO 668
<211> LENGTH: 64
<212> TYPE: DNA
<213> ORGANISM: Artificial
<220> FEATURE:
<223> OTHER INFORMATION: PCR primer

<400> SEQUENCE: 668
acagtggttc tgctccgaat actagttctg ctccgggatc ccagtctgtg gtgactcagg    60
agcc    64

<210> SEQ ID NO 669
<211> LENGTH: 64
<212> TYPE: DNA
<213> ORGANISM: Artificial
<220> FEATURE:
<223> OTHER INFORMATION: PCR primer

<400> SEQUENCE: 669

```
acagtggttc tgctccgaat actagttctg ctccgggatc ccagccaggg ctgactcagc    60
cacc                                                                 64
```

<210> SEQ ID NO 670
<211> LENGTH: 64
<212> TYPE: DNA
<213> ORGANISM: Artificial
<220> FEATURE:
<223> OTHER INFORMATION: PCR primer

<400> SEQUENCE: 670

```
acagtggttc tgctccgaat actagttctg ctccgggatc ccagccaggg ctgactcagc    60
cccc                                                                 64
```

<210> SEQ ID NO 671
<211> LENGTH: 64
<212> TYPE: DNA
<213> ORGANISM: Artificial
<220> FEATURE:
<223> OTHER INFORMATION: PCR primer

<400> SEQUENCE: 671

```
acagtggttc tgctccgaat actagttctg ctccgggatc ccagccagtg ctgactcagc    60
cacc                                                                 64
```

<210> SEQ ID NO 672
<211> LENGTH: 64
<212> TYPE: DNA
<213> ORGANISM: Artificial
<220> FEATURE:
<223> OTHER INFORMATION: PCR primer

<400> SEQUENCE: 672

```
acagtggttc tgctccgaat actagttctg ctccgggatc ccagccagtg ctgactcagc    60
cccc                                                                 64
```

<210> SEQ ID NO 673
<211> LENGTH: 64
<212> TYPE: DNA
<213> ORGANISM: Artificial
<220> FEATURE:
<223> OTHER INFORMATION: PCR primer

<400> SEQUENCE: 673

```
acagtggttc tgctccgaat actagttctg ctccgggatc ccagcctggg ctgactcagc    60
cacc                                                                 64
```

<210> SEQ ID NO 674
<211> LENGTH: 64
<212> TYPE: DNA
<213> ORGANISM: Artificial
<220> FEATURE:
<223> OTHER INFORMATION: PCR primer

<400> SEQUENCE: 674

```
acagtggttc tgctccgaat actagttctg ctccgggatc ccagcctggg ctgactcagc    60
cccc                                                                 64
```

<210> SEQ ID NO 675
<211> LENGTH: 64
<212> TYPE: DNA

```
<213> ORGANISM: Artificial
<220> FEATURE:
<223> OTHER INFORMATION: PCR primer

<400> SEQUENCE: 675
acagtggttc tgctccgaat actagttctg ctccgggatc ccagcctgtg ctgactcagc    60
cacc                                                                  64

<210> SEQ ID NO 676
<211> LENGTH: 64
<212> TYPE: DNA
<213> ORGANISM: Artificial
<220> FEATURE:
<223> OTHER INFORMATION: PCR primer

<400> SEQUENCE: 676
acagtggttc tgctccgaat actagttctg ctccgggatc ccagcctgtg ctgactcagc    60
cccc                                                                  64

<210> SEQ ID NO 677
<211> LENGTH: 64
<212> TYPE: DNA
<213> ORGANISM: Artificial
<220> FEATURE:
<223> OTHER INFORMATION: PCR primer

<400> SEQUENCE: 677
acagtggttc tgctccgaat actagttctg ctccgggatc ctcctctgag ctgactcagg    60
accc                                                                  64

<210> SEQ ID NO 678
<211> LENGTH: 64
<212> TYPE: DNA
<213> ORGANISM: Artificial
<220> FEATURE:
<223> OTHER INFORMATION: PCR primer

<400> SEQUENCE: 678
acagtggttc tgctccgaat actagttctg ctccgggatc ctcctctgag ctgactcagg    60
agcc                                                                  64

<210> SEQ ID NO 679
<211> LENGTH: 64
<212> TYPE: DNA
<213> ORGANISM: Artificial
<220> FEATURE:
<223> OTHER INFORMATION: PCR primer

<400> SEQUENCE: 679
acagtggttc tgctccgaat actagttctg ctccgggatc ctcctctgag ctgagtcagg    60
accc                                                                  64

<210> SEQ ID NO 680
<211> LENGTH: 64
<212> TYPE: DNA
<213> ORGANISM: Artificial
<220> FEATURE:
<223> OTHER INFORMATION: PCR primer

<400> SEQUENCE: 680
acagtggttc tgctccgaat actagttctg ctccgggatc ctcctctgag ctgagtcagg    60
agcc                                                                  64
```

<210> SEQ ID NO 681
<211> LENGTH: 62
<212> TYPE: DNA
<213> ORGANISM: Artificial
<220> FEATURE:
<223> OTHER INFORMATION: PCR primer

<400> SEQUENCE: 681
acagtggttc tgctccgaat actagttctg ctccgggatc ccagtctgcc ctgactcagc    60
ct                                                                   62

<210> SEQ ID NO 682
<211> LENGTH: 62
<212> TYPE: DNA
<213> ORGANISM: Artificial
<220> FEATURE:
<223> OTHER INFORMATION: PCR primer

<400> SEQUENCE: 682
acagtggttc tgctccgaat actagttctg ctccgggatc ccagtctgcc ctgattcagc    60
ct                                                                   62

<210> SEQ ID NO 683
<211> LENGTH: 62
<212> TYPE: DNA
<213> ORGANISM: Artificial
<220> FEATURE:
<223> OTHER INFORMATION: PCR primer

<400> SEQUENCE: 683
acagtggttc tgctccgaat actagttctg ctccgggatc ccagtctgct ctgactcagc    60
ct                                                                   62

<210> SEQ ID NO 684
<211> LENGTH: 62
<212> TYPE: DNA
<213> ORGANISM: Artificial
<220> FEATURE:
<223> OTHER INFORMATION: PCR primer

<400> SEQUENCE: 684
acagtggttc tgctccgaat actagttctg ctccgggatc ccagtctgct ctgattcagc    60
ct                                                                   62

<210> SEQ ID NO 685
<211> LENGTH: 62
<212> TYPE: DNA
<213> ORGANISM: Artificial
<220> FEATURE:
<223> OTHER INFORMATION: PCR primer

<400> SEQUENCE: 685
acagtggttc tgctccgaat actagttctg ctccgggatc ccagtctgtc ctgactcagc    60
ct                                                                   62

<210> SEQ ID NO 686
<211> LENGTH: 62
<212> TYPE: DNA
<213> ORGANISM: Artificial
<220> FEATURE:
<223> OTHER INFORMATION: PCR primer

```
<400> SEQUENCE: 686
acagtggttc tgctccgaat actagttctg ctccgggatc ccagtctgtc ctgattcagc    60
ct                                                                  62

<210> SEQ ID NO 687
<211> LENGTH: 62
<212> TYPE: DNA
<213> ORGANISM: Artificial
<220> FEATURE:
<223> OTHER INFORMATION: PCR primer

<400> SEQUENCE: 687
acagtggttc tgctccgaat actagttctg ctccgggatc ccagtctgtt ctgactcagc    60
ct                                                                  62

<210> SEQ ID NO 688
<211> LENGTH: 62
<212> TYPE: DNA
<213> ORGANISM: Artificial
<220> FEATURE:
<223> OTHER INFORMATION: PCR primer

<400> SEQUENCE: 688
acagtggttc tgctccgaat actagttctg ctccgggatc ccagtctgtt ctgattcagc    60
ct                                                                  62

<210> SEQ ID NO 689
<211> LENGTH: 63
<212> TYPE: DNA
<213> ORGANISM: Artificial
<220> FEATURE:
<223> OTHER INFORMATION: PCR primer

<400> SEQUENCE: 689
acagtggttc tgctccgaat actagttctg ctccgggatc caattttatg ctgactcagc    60
ccc                                                                 63

<210> SEQ ID NO 690
<211> LENGTH: 64
<212> TYPE: DNA
<213> ORGANISM: Artificial
<220> FEATURE:
<223> OTHER INFORMATION: PCR primer

<400> SEQUENCE: 690
acagtggttc tgctccgaat actagttctg ctccgggatc cgacatccag atgacccagt    60
ctcc                                                                64

<210> SEQ ID NO 691
<211> LENGTH: 64
<212> TYPE: DNA
<213> ORGANISM: Artificial
<220> FEATURE:
<223> OTHER INFORMATION: PCR primer

<400> SEQUENCE: 691
acagtggttc tgctccgaat actagttctg ctccgggatc cgacatccag gtgacccagt    60
ctcc                                                                64

<210> SEQ ID NO 692
<211> LENGTH: 64
```

```
<212> TYPE: DNA
<213> ORGANISM: Artificial
<220> FEATURE:
<223> OTHER INFORMATION: PCR primer

<400> SEQUENCE: 692
acagtggttc tgctccgaat actagttctg ctccgggatc cgacatccag ttgacccagt    60
ctcc                                                                  64

<210> SEQ ID NO 693
<211> LENGTH: 64
<212> TYPE: DNA
<213> ORGANISM: Artificial
<220> FEATURE:
<223> OTHER INFORMATION: PCR primer

<400> SEQUENCE: 693
acagtggttc tgctccgaat actagttctg ctccgggatc cgacatccgg atgacccagt    60
ctcc                                                                  64

<210> SEQ ID NO 694
<211> LENGTH: 64
<212> TYPE: DNA
<213> ORGANISM: Artificial
<220> FEATURE:
<223> OTHER INFORMATION: PCR primer

<400> SEQUENCE: 694
acagtggttc tgctccgaat actagttctg ctccgggatc cgacatccgg gtgacccagt    60
ctcc                                                                  64

<210> SEQ ID NO 695
<211> LENGTH: 64
<212> TYPE: DNA
<213> ORGANISM: Artificial
<220> FEATURE:
<223> OTHER INFORMATION: PCR primer

<400> SEQUENCE: 695
acagtggttc tgctccgaat actagttctg ctccgggatc cgacatccgg ttgacccagt    60
ctcc                                                                  64

<210> SEQ ID NO 696
<211> LENGTH: 64
<212> TYPE: DNA
<213> ORGANISM: Artificial
<220> FEATURE:
<223> OTHER INFORMATION: PCR primer

<400> SEQUENCE: 696
acagtggttc tgctccgaat actagttctg ctccgggatc cgaaattgta atgacacagt    60
ctcc                                                                  64

<210> SEQ ID NO 697
<211> LENGTH: 64
<212> TYPE: DNA
<213> ORGANISM: Artificial
<220> FEATURE:
<223> OTHER INFORMATION: PCR primer

<400> SEQUENCE: 697
acagtggttc tgctccgaat actagttctg ctccgggatc cgaaattgta atgacgcagt    60
```

| ctcc | 64 |

<210> SEQ ID NO 698
<211> LENGTH: 64
<212> TYPE: DNA
<213> ORGANISM: Artificial
<220> FEATURE:
<223> OTHER INFORMATION: PCR primer

<400> SEQUENCE: 698

| acagtggttc tgctccgaat actagttctg ctccgggatc cgaaattgta ttgacacagt | 60 |
| ctcc | 64 |

<210> SEQ ID NO 699
<211> LENGTH: 64
<212> TYPE: DNA
<213> ORGANISM: Artificial
<220> FEATURE:
<223> OTHER INFORMATION: PCR primer

<400> SEQUENCE: 699

| acagtggttc tgctccgaat actagttctg ctccgggatc cgaaattgta ttgacgcagt | 60 |
| ctcc | 64 |

<210> SEQ ID NO 700
<211> LENGTH: 64
<212> TYPE: DNA
<213> ORGANISM: Artificial
<220> FEATURE:
<223> OTHER INFORMATION: PCR primer

<400> SEQUENCE: 700

| acagtggttc tgctccgaat actagttctg ctccgggatc cgaaattgtg atgacacagt | 60 |
| ctcc | 64 |

<210> SEQ ID NO 701
<211> LENGTH: 64
<212> TYPE: DNA
<213> ORGANISM: Artificial
<220> FEATURE:
<223> OTHER INFORMATION: PCR primer

<400> SEQUENCE: 701

| acagtggttc tgctccgaat actagttctg ctccgggatc cgaaattgtg atgacgcagt | 60 |
| ctcc | 64 |

<210> SEQ ID NO 702
<211> LENGTH: 64
<212> TYPE: DNA
<213> ORGANISM: Artificial
<220> FEATURE:
<223> OTHER INFORMATION: PCR primer

<400> SEQUENCE: 702

| acagtggttc tgctccgaat actagttctg ctccgggatc cgaaattgtg ttgacacagt | 60 |
| ctcc | 64 |

<210> SEQ ID NO 703
<211> LENGTH: 64
<212> TYPE: DNA
<213> ORGANISM: Artificial
<220> FEATURE:
<223> OTHER INFORMATION: PCR primer

```
<400> SEQUENCE: 703
acagtggttc tgctccgaat actagttctg ctccgggatc cgaaattgtg ttgacgcagt    60
ctcc                                                                 64

<210> SEQ ID NO 704
<211> LENGTH: 64
<212> TYPE: DNA
<213> ORGANISM: Artificial
<220> FEATURE:
<223> OTHER INFORMATION: PCR primer

<400> SEQUENCE: 704
acagtggttc tgctccgaat actagttctg ctccgggatc cgaaattgtg ttgacgcagt    60
ctcc                                                                 64

<210> SEQ ID NO 705
<211> LENGTH: 64
<212> TYPE: DNA
<213> ORGANISM: Artificial
<220> FEATURE:
<223> OTHER INFORMATION: PCR primer

<400> SEQUENCE: 705
acagtggttc tgctccgaat actagttctg ctccgggatc cgatattgtg atgacccagt    60
ctcc                                                                 64

<210> SEQ ID NO 706
<211> LENGTH: 64
<212> TYPE: DNA
<213> ORGANISM: Artificial
<220> FEATURE:
<223> OTHER INFORMATION: PCR primer

<400> SEQUENCE: 706
acagtggttc tgctccgaat actagttctg ctccgggatc cgatattgtg atgacgcaga    60
ctcc                                                                 64

<210> SEQ ID NO 707
<211> LENGTH: 64
<212> TYPE: DNA
<213> ORGANISM: Artificial
<220> FEATURE:
<223> OTHER INFORMATION: PCR primer

<400> SEQUENCE: 707
acagtggttc tgctccgaat actagttctg ctccgggatc cgatattgtg atgacgcagt    60
ctcc                                                                 64

<210> SEQ ID NO 708
<211> LENGTH: 64
<212> TYPE: DNA
<213> ORGANISM: Artificial
<220> FEATURE:
<223> OTHER INFORMATION: PCR primer

<400> SEQUENCE: 708
acagtggttc tgctccgaat actagttctg ctccgggatc cgatattgtg atgactcaga    60
ctcc                                                                 64

<210> SEQ ID NO 709
```

```
<211> LENGTH: 64
<212> TYPE: DNA
<213> ORGANISM: Artificial
<220> FEATURE:
<223> OTHER INFORMATION: PCR primer

<400> SEQUENCE: 709
acagtggttc tgctccgaat actagttctg ctccgggatc cgatattgtg atgactcagt      60
ctcc                                                                  64

<210> SEQ ID NO 710
<211> LENGTH: 64
<212> TYPE: DNA
<213> ORGANISM: Artificial
<220> FEATURE:
<223> OTHER INFORMATION: PCR primer

<400> SEQUENCE: 710
acagtggttc tgctccgaat actagttctg ctccgggatc cgatattgtg ctgacccaga      60
ctcc                                                                  64

<210> SEQ ID NO 711
<211> LENGTH: 64
<212> TYPE: DNA
<213> ORGANISM: Artificial
<220> FEATURE:
<223> OTHER INFORMATION: PCR primer

<400> SEQUENCE: 711
acagtggttc tgctccgaat actagttctg ctccgggatc cgatattgtg ctgacccagt      60
ctcc                                                                  64

<210> SEQ ID NO 712
<211> LENGTH: 64
<212> TYPE: DNA
<213> ORGANISM: Artificial
<220> FEATURE:
<223> OTHER INFORMATION: PCR primer

<400> SEQUENCE: 712
acagtggttc tgctccgaat actagttctg ctccgggatc cgatattgtg ctgacgcaga      60
ctcc                                                                  64

<210> SEQ ID NO 713
<211> LENGTH: 64
<212> TYPE: DNA
<213> ORGANISM: Artificial
<220> FEATURE:
<223> OTHER INFORMATION: PCR primer

<400> SEQUENCE: 713
acagtggttc tgctccgaat actagttctg ctccgggatc cgatattgtg ctgacgcagt      60
ctcc                                                                  64

<210> SEQ ID NO 714
<211> LENGTH: 64
<212> TYPE: DNA
<213> ORGANISM: Artificial
<220> FEATURE:
<223> OTHER INFORMATION: PCR primer

<400> SEQUENCE: 714
acagtggttc tgctccgaat actagttctg ctccgggatc cgatattgtg ctgactcaga      60
```

```
ctcc                                                            64

<210> SEQ ID NO 715
<211> LENGTH: 64
<212> TYPE: DNA
<213> ORGANISM: Artificial
<220> FEATURE:
<223> OTHER INFORMATION: PCR primer

<400> SEQUENCE: 715
acagtggttc tgctccgaat actagttctg ctccgggatc cgatattgtg ctgactcagt    60
ctcc                                                            64

<210> SEQ ID NO 716
<211> LENGTH: 63
<212> TYPE: DNA
<213> ORGANISM: Artificial
<220> FEATURE:
<223> OTHER INFORMATION: PCR primer

<400> SEQUENCE: 716
acagtggttc tgctccgaat actagttctg ctccgggatc cgaaacgaca ctcacgcagt    60
ctc                                                             63

<210> SEQ ID NO 717
<211> LENGTH: 20
<212> TYPE: DNA
<213> ORGANISM: Artificial
<220> FEATURE:
<223> OTHER INFORMATION: PCR primer

<400> SEQUENCE: 717
taggacggtc accttggtcc                                                20

<210> SEQ ID NO 718
<211> LENGTH: 20
<212> TYPE: DNA
<213> ORGANISM: Artificial
<220> FEATURE:
<223> OTHER INFORMATION: PCR primer

<400> SEQUENCE: 718
taggacggtc agcttggtcc                                                20

<210> SEQ ID NO 719
<211> LENGTH: 20
<212> TYPE: DNA
<213> ORGANISM: Artificial
<220> FEATURE:
<223> OTHER INFORMATION: PCR primer

<400> SEQUENCE: 719
taggacggtg accttggtcc                                                20

<210> SEQ ID NO 720
<211> LENGTH: 20
<212> TYPE: DNA
<213> ORGANISM: Artificial
<220> FEATURE:
<223> OTHER INFORMATION: PCR primer

<400> SEQUENCE: 720
taggacggtg agcttggtcc                                                20
```

```
<210> SEQ ID NO 721
<211> LENGTH: 20
<212> TYPE: DNA
<213> ORGANISM: Artificial
<220> FEATURE:
<223> OTHER INFORMATION: PCR primer

<400> SEQUENCE: 721
taggacggtc agctgggtgc                                                 20

<210> SEQ ID NO 722
<211> LENGTH: 20
<212> TYPE: DNA
<213> ORGANISM: Artificial
<220> FEATURE:
<223> OTHER INFORMATION: PCR primer

<400> SEQUENCE: 722
tttgatttcc accttggtcc                                                 20

<210> SEQ ID NO 723
<211> LENGTH: 20
<212> TYPE: DNA
<213> ORGANISM: Artificial
<220> FEATURE:
<223> OTHER INFORMATION: PCR primer

<400> SEQUENCE: 723
tttgatctcc accttggtcc                                                 20

<210> SEQ ID NO 724
<211> LENGTH: 20
<212> TYPE: DNA
<213> ORGANISM: Artificial
<220> FEATURE:
<223> OTHER INFORMATION: PCR primer

<400> SEQUENCE: 724
tttgatctcc agcttggtcc                                                 20

<210> SEQ ID NO 725
<211> LENGTH: 20
<212> TYPE: DNA
<213> ORGANISM: Artificial
<220> FEATURE:
<223> OTHER INFORMATION: PCR primer

<400> SEQUENCE: 725
tttgatatcc actttggtcc                                                 20

<210> SEQ ID NO 726
<211> LENGTH: 20
<212> TYPE: DNA
<213> ORGANISM: Artificial
<220> FEATURE:
<223> OTHER INFORMATION: PCR primer

<400> SEQUENCE: 726
tttaatctcc agtcgtgtcc                                                 20

<210> SEQ ID NO 727
<211> LENGTH: 45
<212> TYPE: DNA
<213> ORGANISM: Artificial
<220> FEATURE:
<223> OTHER INFORMATION: PCR primer
```

<400> SEQUENCE: 727
ggtggcggtg gctcgggcgg tggtgggtcg ggtggcggcg gatct    45

<210> SEQ ID NO 728
<211> LENGTH: 22
<212> TYPE: DNA
<213> ORGANISM: Artificial
<220> FEATURE:
<223> OTHER INFORMATION: PCR primer

<400> SEQUENCE: 728
caggtgcagc tgcaggagtc sg    22

<210> SEQ ID NO 729
<211> LENGTH: 21
<212> TYPE: DNA
<213> ORGANISM: Artificial
<220> FEATURE:
<223> OTHER INFORMATION: PCR primer

<400> SEQUENCE: 729
caggtacagc tgcagcagtc a    21

<210> SEQ ID NO 730
<211> LENGTH: 22
<212> TYPE: DNA
<213> ORGANISM: Artificial
<220> FEATURE:
<223> OTHER INFORMATION: PCR primer

<400> SEQUENCE: 730
caggtgcagc tacagcagtg gg    22

<210> SEQ ID NO 731
<211> LENGTH: 21
<212> TYPE: DNA
<213> ORGANISM: Artificial
<220> FEATURE:
<223> OTHER INFORMATION: PCR primer

<400> SEQUENCE: 731
gaggtgcagc tgktggagwc y    21

<210> SEQ ID NO 732
<211> LENGTH: 23
<212> TYPE: DNA
<213> ORGANISM: Artificial
<220> FEATURE:
<223> OTHER INFORMATION: PCR primer

<400> SEQUENCE: 732
caggtccagc tkgtrcagtc tgg    23

<210> SEQ ID NO 733
<211> LENGTH: 22
<212> TYPE: DNA
<213> ORGANISM: Artificial
<220> FEATURE:
<223> OTHER INFORMATION: PCR primer

<400> SEQUENCE: 733
cagrtcacct tgaaggagtc tg    22

<210> SEQ ID NO 734

```
<211> LENGTH: 23
<212> TYPE: DNA
<213> ORGANISM: Artificial
<220> FEATURE:
<223> OTHER INFORMATION: PCR primer

<400> SEQUENCE: 734
caggtgcagc tggtgsartc tgg                                              23

<210> SEQ ID NO 735
<211> LENGTH: 54
<212> TYPE: DNA
<213> ORGANISM: Artificial
<220> FEATURE:
<223> OTHER INFORMATION: PCR primer

<400> SEQUENCE: 735
cccgacccac caccgcccga gccaccgcca cctgaggaga crgtgaccag ggtg            54

<210> SEQ ID NO 736
<211> LENGTH: 54
<212> TYPE: DNA
<213> ORGANISM: Artificial
<220> FEATURE:
<223> OTHER INFORMATION: PCR primer

<400> SEQUENCE: 736
cccgacccac caccgcccga gccaccgcca cctgaggaga cggtgaccag ggtt            54

<210> SEQ ID NO 737
<211> LENGTH: 53
<212> TYPE: DNA
<213> ORGANISM: Artificial
<220> FEATURE:
<223> OTHER INFORMATION: PCR primer

<400> SEQUENCE: 737
cccgacccac caccgcccga gccaccgcca cctgaagaga cggtgaccat tgt             53

<210> SEQ ID NO 738
<211> LENGTH: 55
<212> TYPE: DNA
<213> ORGANISM: Artificial
<220> FEATURE:
<223> OTHER INFORMATION: PCR primer

<400> SEQUENCE: 738
cccgacccac caccgcccga gccaccgcca cctgaggaga cggtgaccgt ggtcc           55

<210> SEQ ID NO 739
<211> LENGTH: 55
<212> TYPE: DNA
<213> ORGANISM: Artificial
<220> FEATURE:
<223> OTHER INFORMATION: PCR primer

<400> SEQUENCE: 739
cgggcggtgg tgggtcgggt ggcggcggat ctcagtctgt sbtgacgcag ccgcc           55

<210> SEQ ID NO 740
<211> LENGTH: 54
<212> TYPE: DNA
<213> ORGANISM: Artificial
<220> FEATURE:
<223> OTHER INFORMATION: PCR primer

<400> SEQUENCE: 740
```

```
cgggcggtgg tgggtcgggt ggcggcggat cttcctatgw gctgacwcag ccac          54
```

<210> SEQ ID NO 741
<211> LENGTH: 55
<212> TYPE: DNA
<213> ORGANISM: Artificial
<220> FEATURE:
<223> OTHER INFORMATION: PCR primer

<400> SEQUENCE: 741

```
cgggcggtgg tgggtcgggt ggcggcggat cttcctatga gctgayrcag cyacc         55
```

<210> SEQ ID NO 742
<211> LENGTH: 52
<212> TYPE: DNA
<213> ORGANISM: Artificial
<220> FEATURE:
<223> OTHER INFORMATION: PCR primer

<400> SEQUENCE: 742

```
cgggcggtgg tgggtcgggt ggcggcggat ctcagcctgt gctgactcar yc            52
```

<210> SEQ ID NO 743
<211> LENGTH: 55
<212> TYPE: DNA
<213> ORGANISM: Artificial
<220> FEATURE:
<223> OTHER INFORMATION: PCR primer

<400> SEQUENCE: 743

```
cgggcggtgg tgggtcgggt ggcggcggat ctcagdctgt ggtgacycag gagcc         55
```

<210> SEQ ID NO 744
<211> LENGTH: 55
<212> TYPE: DNA
<213> ORGANISM: Artificial
<220> FEATURE:
<223> OTHER INFORMATION: PCR primer

<400> SEQUENCE: 744

```
cgggcggtgg tgggtcgggt ggcggcggat ctcagccwgk gctgactcag ccmcc         55
```

<210> SEQ ID NO 745
<211> LENGTH: 55
<212> TYPE: DNA
<213> ORGANISM: Artificial
<220> FEATURE:
<223> OTHER INFORMATION: PCR primer

<400> SEQUENCE: 745

```
cgggcggtgg tgggtcgggt ggcggcggat cttcctctga gctgastcag gascc         55
```

<210> SEQ ID NO 746
<211> LENGTH: 53
<212> TYPE: DNA
<213> ORGANISM: Artificial
<220> FEATURE:
<223> OTHER INFORMATION: PCR primer

<400> SEQUENCE: 746

```
cgggcggtgg tgggtcgggt ggcggcggat ctcagtctgy yctgaytcag cct           53
```

<210> SEQ ID NO 747
<211> LENGTH: 54
<212> TYPE: DNA

```
<213> ORGANISM: Artificial
<220> FEATURE:
<223> OTHER INFORMATION: PCR primer

<400> SEQUENCE: 747
cgggcggtgg tgggtcgggt ggcggcggat ctaattttat gctgactcag cccc        54

<210> SEQ ID NO 748
<211> LENGTH: 19
<212> TYPE: DNA
<213> ORGANISM: Artificial
<220> FEATURE:
<223> OTHER INFORMATION: PCR primer

<400> SEQUENCE: 748
aggacggtsa scttggtcc                                               19

<210> SEQ ID NO 749
<211> LENGTH: 19
<212> TYPE: DNA
<213> ORGANISM: Artificial
<220> FEATURE:
<223> OTHER INFORMATION: PCR primer

<400> SEQUENCE: 749
aggacggtca gctgggtgc                                               19

<210> SEQ ID NO 750
<211> LENGTH: 55
<212> TYPE: DNA
<213> ORGANISM: Artificial
<220> FEATURE:
<223> OTHER INFORMATION: PCR primer

<400> SEQUENCE: 750
cgggcggtgg tgggtcgggt ggcggcggat ctgacatccr gdtgacccag tctcc       55

<210> SEQ ID NO 751
<211> LENGTH: 55
<212> TYPE: DNA
<213> ORGANISM: Artificial
<220> FEATURE:
<223> OTHER INFORMATION: PCR primer

<400> SEQUENCE: 751
cgggcggtgg tgggtcgggt ggcggcggat ctgaaattgt rwtgacrcag tctcc       55

<210> SEQ ID NO 752
<211> LENGTH: 55
<212> TYPE: DNA
<213> ORGANISM: Artificial
<220> FEATURE:
<223> OTHER INFORMATION: PCR primer

<400> SEQUENCE: 752
cgggcggtgg tgggtcgggt ggcggcggat ctgatattgt gmtgacbcag wctcc       55

<210> SEQ ID NO 753
<211> LENGTH: 54
<212> TYPE: DNA
<213> ORGANISM: Artificial
<220> FEATURE:
<223> OTHER INFORMATION: PCR primer

<400> SEQUENCE: 753
cgggcggtgg tgggtcgggt ggcggcggat ctgaaacgac actcacgcag tctc        54
```

<210> SEQ ID NO 754
<211> LENGTH: 20
<212> TYPE: DNA
<213> ORGANISM: Artificial
<220> FEATURE:
<223> OTHER INFORMATION: PCR primer

<400> SEQUENCE: 754
tttgatttcc accttggtcc                                              20

<210> SEQ ID NO 755
<211> LENGTH: 20
<212> TYPE: DNA
<213> ORGANISM: Artificial
<220> FEATURE:
<223> OTHER INFORMATION: PCR primer

<400> SEQUENCE: 755
tttgatctcc ascttggtcc                                              20

<210> SEQ ID NO 756
<211> LENGTH: 20
<212> TYPE: DNA
<213> ORGANISM: Artificial
<220> FEATURE:
<223> OTHER INFORMATION: PCR primer

<400> SEQUENCE: 756
tttgatatcc actttggtcc                                              20

<210> SEQ ID NO 757
<211> LENGTH: 20
<212> TYPE: DNA
<213> ORGANISM: Artificial
<220> FEATURE:
<223> OTHER INFORMATION: PCR primer

<400> SEQUENCE: 757
tttaatctcc agtcgtgtcc                                              20

<210> SEQ ID NO 758
<211> LENGTH: 22
<212> TYPE: DNA
<213> ORGANISM: Artificial
<220> FEATURE:
<223> OTHER INFORMATION: PCR primer

<400> SEQUENCE: 758
caggtgcagc tgcaggagtc sg                                           22

<210> SEQ ID NO 759
<211> LENGTH: 21
<212> TYPE: DNA
<213> ORGANISM: Artificial
<220> FEATURE:
<223> OTHER INFORMATION: PCR primer

<400> SEQUENCE: 759
caggtacagc tgcagcagtc a                                            21

<210> SEQ ID NO 760
<211> LENGTH: 22
<212> TYPE: DNA
<213> ORGANISM: Artificial
<220> FEATURE:

-continued

<223> OTHER INFORMATION: PCR primer

<400> SEQUENCE: 760
caggtgcagc tacagcagtg gg                                            22

<210> SEQ ID NO 761
<211> LENGTH: 21
<212> TYPE: DNA
<213> ORGANISM: Artificial
<220> FEATURE:
<223> OTHER INFORMATION: PCR primer

<400> SEQUENCE: 761
gaggtgcagc tgktggagwc y                                             21

<210> SEQ ID NO 762
<211> LENGTH: 23
<212> TYPE: DNA
<213> ORGANISM: Artificial
<220> FEATURE:
<223> OTHER INFORMATION: PCR primer

<400> SEQUENCE: 762
caggtccagc tkgtrcagtc tgg                                           23

<210> SEQ ID NO 763
<211> LENGTH: 22
<212> TYPE: DNA
<213> ORGANISM: Artificial
<220> FEATURE:
<223> OTHER INFORMATION: PCR primer

<400> SEQUENCE: 763
cagrtcacct tgaaggagtc tg                                            22

<210> SEQ ID NO 764
<211> LENGTH: 23
<212> TYPE: DNA
<213> ORGANISM: Artificial
<220> FEATURE:
<223> OTHER INFORMATION: PCR primer

<400> SEQUENCE: 764
caggtgcagc tggtgsartc tgg                                           23

<210> SEQ ID NO 765
<211> LENGTH: 54
<212> TYPE: DNA
<213> ORGANISM: Artificial
<220> FEATURE:
<223> OTHER INFORMATION: PCR primer

<400> SEQUENCE: 765
cccgacccac caccgcccga gccaccgcca cctgaggaga crgtgaccag ggtg          54

<210> SEQ ID NO 766
<211> LENGTH: 54
<212> TYPE: DNA
<213> ORGANISM: Artificial
<220> FEATURE:
<223> OTHER INFORMATION: PCR primer

<400> SEQUENCE: 766
cccgacccac caccgcccga gccaccgcca cctgaggaga cggtgaccag ggtt          54

```
<210> SEQ ID NO 767
<211> LENGTH: 53
<212> TYPE: DNA
<213> ORGANISM: Artificial
<220> FEATURE:
<223> OTHER INFORMATION: PCR primer

<400> SEQUENCE: 767
cccgacccac caccgcccga gccaccgcca cctgaagaga cggtgaccat tgt          53

<210> SEQ ID NO 768
<211> LENGTH: 55
<212> TYPE: DNA
<213> ORGANISM: Artificial
<220> FEATURE:
<223> OTHER INFORMATION: PCR primer

<400> SEQUENCE: 768
cccgacccac caccgcccga gccaccgcca cctgaggaga cggtgaccgt ggtcc        55

<210> SEQ ID NO 769
<211> LENGTH: 55
<212> TYPE: DNA
<213> ORGANISM: Artificial
<220> FEATURE:
<223> OTHER INFORMATION: PCR primer

<400> SEQUENCE: 769
cgggcggtgg tgggtcgggt ggcggcggat ctcagtctgt sbtgacgcag ccgcc        55

<210> SEQ ID NO 770
<211> LENGTH: 54
<212> TYPE: DNA
<213> ORGANISM: Artificial
<220> FEATURE:
<223> OTHER INFORMATION: PCR primer

<400> SEQUENCE: 770
cgggcggtgg tgggtcgggt ggcggcggat cttcctatgw gctgacwcag ccac         54

<210> SEQ ID NO 771
<211> LENGTH: 55
<212> TYPE: DNA
<213> ORGANISM: Artificial
<220> FEATURE:
<223> OTHER INFORMATION: PCR primer

<400> SEQUENCE: 771
cgggcggtgg tgggtcgggt ggcggcggat cttcctatga gctgayrcag cyacc        55

<210> SEQ ID NO 772
<211> LENGTH: 52
<212> TYPE: DNA
<213> ORGANISM: Artificial
<220> FEATURE:
<223> OTHER INFORMATION: PCR primer

<400> SEQUENCE: 772
cgggcggtgg tgggtcgggt ggcggcggat ctcagcctgt gctgactcar yc           52

<210> SEQ ID NO 773
<211> LENGTH: 55
<212> TYPE: DNA
<213> ORGANISM: Artificial
<220> FEATURE:
<223> OTHER INFORMATION: PCR primer
```

<400> SEQUENCE: 773
cgggcggtgg tgggtcgggt ggcggcggat ctcagdctgt ggtgacycag gaggc    55

<210> SEQ ID NO 774
<211> LENGTH: 55
<212> TYPE: DNA
<213> ORGANISM: Artificial
<220> FEATURE:
<223> OTHER INFORMATION: PCR primer

<400> SEQUENCE: 774
cgggcggtgg tgggtcgggt ggcggcggat ctcagccwgk gctgactcag ccmcc    55

<210> SEQ ID NO 775
<211> LENGTH: 55
<212> TYPE: DNA
<213> ORGANISM: Artificial
<220> FEATURE:
<223> OTHER INFORMATION: PCR primer

<400> SEQUENCE: 775
cgggcggtgg tgggtcgggt ggcggcggat cttcctctga gctgastcag gascc    55

<210> SEQ ID NO 776
<211> LENGTH: 53
<212> TYPE: DNA
<213> ORGANISM: Artificial
<220> FEATURE:
<223> OTHER INFORMATION: PCR primer

<400> SEQUENCE: 776
cgggcggtgg tgggtcgggt ggcggcggat ctcagtctgy yctgaytcag cct    53

<210> SEQ ID NO 777
<211> LENGTH: 54
<212> TYPE: DNA
<213> ORGANISM: Artificial
<220> FEATURE:
<223> OTHER INFORMATION: PCR primer

<400> SEQUENCE: 777
cgggcggtgg tgggtcgggt ggcggcggat ctaattttat gctgactcag cccc    54

<210> SEQ ID NO 778
<211> LENGTH: 20
<212> TYPE: DNA
<213> ORGANISM: Artificial
<220> FEATURE:
<223> OTHER INFORMATION: PCR primer

<400> SEQUENCE: 778
taggacggts ascttggtcc    20

<210> SEQ ID NO 779
<211> LENGTH: 20
<212> TYPE: DNA
<213> ORGANISM: Artificial
<220> FEATURE:
<223> OTHER INFORMATION: PCR primer

<400> SEQUENCE: 779
gaggacggtc agctgggtgc    20

<210> SEQ ID NO 780
<211> LENGTH: 55

```
<212> TYPE: DNA
<213> ORGANISM: Artificial
<220> FEATURE:
<223> OTHER INFORMATION: PCR primer

<400> SEQUENCE: 780
cgggcggtgg tgggtcgggt ggcggcggat ctgacatccr gdtgacccag tctcc       55

<210> SEQ ID NO 781
<211> LENGTH: 55
<212> TYPE: DNA
<213> ORGANISM: Artificial
<220> FEATURE:
<223> OTHER INFORMATION: PCR primer

<400> SEQUENCE: 781
cgggcggtgg tgggtcgggt ggcggcggat ctgaaattgt rwtgacrcag tctcc       55

<210> SEQ ID NO 782
<211> LENGTH: 55
<212> TYPE: DNA
<213> ORGANISM: Artificial
<220> FEATURE:
<223> OTHER INFORMATION: PCR primer

<400> SEQUENCE: 782
cgggcggtgg tgggtcgggt ggcggcggat ctgatattgt gmtgacbcag wctcc       55

<210> SEQ ID NO 783
<211> LENGTH: 55
<212> TYPE: DNA
<213> ORGANISM: Artificial
<220> FEATURE:
<223> OTHER INFORMATION: PCR primer

<400> SEQUENCE: 783
cgggcggtgg tgggtcgggt ggcggcggat ctgaaacgac actcacgcag tcctc       55

<210> SEQ ID NO 784
<211> LENGTH: 20
<212> TYPE: DNA
<213> ORGANISM: Artificial
<220> FEATURE:
<223> OTHER INFORMATION: PCR primer

<400> SEQUENCE: 784
tttgatttcc accttggtcc                                              20

<210> SEQ ID NO 785
<211> LENGTH: 20
<212> TYPE: DNA
<213> ORGANISM: Artificial
<220> FEATURE:
<223> OTHER INFORMATION: PCR primer

<400> SEQUENCE: 785
tttgatctcc ascttggtcc                                              20

<210> SEQ ID NO 786
<211> LENGTH: 20
<212> TYPE: DNA
<213> ORGANISM: Artificial
<220> FEATURE:
<223> OTHER INFORMATION: PCR primer

<400> SEQUENCE: 786
```

```
tttgatatcc actttggtcc                                        20

<210> SEQ ID NO 787
<211> LENGTH: 20
<212> TYPE: DNA
<213> ORGANISM: Artificial
<220> FEATURE:
<223> OTHER INFORMATION: PCR primer

<400> SEQUENCE: 787
tttaatctcc agtcgtgtcc                                        20

<210> SEQ ID NO 788
<211> LENGTH: 55
<212> TYPE: DNA
<213> ORGANISM: Artificial
<220> FEATURE:
<223> OTHER INFORMATION: PCR primer

<400> SEQUENCE: 788
cgggcggtgg tgggtcgggt ggcggcggat ctcagtctgt sbtgacgcag ccgcc    55

<210> SEQ ID NO 789
<211> LENGTH: 54
<212> TYPE: DNA
<213> ORGANISM: Artificial
<220> FEATURE:
<223> OTHER INFORMATION: PCR primer

<400> SEQUENCE: 789
ttgggaccag tggcagagga gtccaccgcc accgagcccg ccaccaccca gccc     54

<210> SEQ ID NO 790
<211> LENGTH: 19
<212> TYPE: DNA
<213> ORGANISM: Artificial
<220> FEATURE:
<223> OTHER INFORMATION: PCR primer

<400> SEQUENCE: 790
cccgacccac caccgcccg                                         19

<210> SEQ ID NO 791
<211> LENGTH: 19
<212> TYPE: DNA
<213> ORGANISM: Artificial
<220> FEATURE:
<223> OTHER INFORMATION: PCR primer

<400> SEQUENCE: 791
cgggcggtgg tgggtcggg                                         19

<210> SEQ ID NO 792
<211> LENGTH: 22
<212> TYPE: DNA
<213> ORGANISM: Artificial
<220> FEATURE:
<223> OTHER INFORMATION: PCR primer

<400> SEQUENCE: 792
tgaggagacr gtgaccaggg tg                                     22

<210> SEQ ID NO 793
<211> LENGTH: 22
<212> TYPE: DNA
<213> ORGANISM: Artificial
```

<220> FEATURE:
<223> OTHER INFORMATION: PCR primer

<400> SEQUENCE: 793
tgaggagacg gtgaccaggg tt					22

<210> SEQ ID NO 794
<211> LENGTH: 21
<212> TYPE: DNA
<213> ORGANISM: Artificial
<220> FEATURE:
<223> OTHER INFORMATION: PCR primer

<400> SEQUENCE: 794
tgaagagacg gtgaccattg t					21

<210> SEQ ID NO 795
<211> LENGTH: 23
<212> TYPE: DNA
<213> ORGANISM: Artificial
<220> FEATURE:
<223> OTHER INFORMATION: PCR primer

<400> SEQUENCE: 795
tgaggagacg gtgaccgtgg tcc					23

<210> SEQ ID NO 796
<211> LENGTH: 23
<212> TYPE: DNA
<213> ORGANISM: Artificial
<220> FEATURE:
<223> OTHER INFORMATION: PCR primer

<400> SEQUENCE: 796
cagtctgtsb tgacgcagcc gcc					23

<210> SEQ ID NO 797
<211> LENGTH: 22
<212> TYPE: DNA
<213> ORGANISM: Artificial
<220> FEATURE:
<223> OTHER INFORMATION: PCR primer

<400> SEQUENCE: 797
tcctatgwgc tgacwcagcc ac					22

<210> SEQ ID NO 798
<211> LENGTH: 23
<212> TYPE: DNA
<213> ORGANISM: Artificial
<220> FEATURE:
<223> OTHER INFORMATION: PCR primer

<400> SEQUENCE: 798
tcctatgagc tgayrcagcy acc					23

<210> SEQ ID NO 799
<211> LENGTH: 20
<212> TYPE: DNA
<213> ORGANISM: Artificial
<220> FEATURE:
<223> OTHER INFORMATION: PCR primer

<400> SEQUENCE: 799
cagcctgtgc tgactcaryc					20

<210> SEQ ID NO 800
<211> LENGTH: 23
<212> TYPE: DNA
<213> ORGANISM: Artificial
<220> FEATURE:
<223> OTHER INFORMATION: PCR primer

<400> SEQUENCE: 800
cagdctgtgg tgacycagga gcc                                              23

<210> SEQ ID NO 801
<211> LENGTH: 23
<212> TYPE: DNA
<213> ORGANISM: Artificial
<220> FEATURE:
<223> OTHER INFORMATION: PCR primer

<400> SEQUENCE: 801
cagccwgkgc tgactcagcc mcc                                              23

<210> SEQ ID NO 802
<211> LENGTH: 23
<212> TYPE: DNA
<213> ORGANISM: Artificial
<220> FEATURE:
<223> OTHER INFORMATION: PCR primer

<400> SEQUENCE: 802
tcctctgagc tgastcagga scc                                              23

<210> SEQ ID NO 803
<211> LENGTH: 21
<212> TYPE: DNA
<213> ORGANISM: Artificial
<220> FEATURE:
<223> OTHER INFORMATION: PCR primer

<400> SEQUENCE: 803
cagtctgyyc tgaytcagcc t                                                21

<210> SEQ ID NO 804
<211> LENGTH: 22
<212> TYPE: DNA
<213> ORGANISM: Artificial
<220> FEATURE:
<223> OTHER INFORMATION: PCR primer

<400> SEQUENCE: 804
aattttatgc tgactcagcc cc                                               22

<210> SEQ ID NO 805
<211> LENGTH: 23
<212> TYPE: DNA
<213> ORGANISM: Artificial
<220> FEATURE:
<223> OTHER INFORMATION: PCR primer

<400> SEQUENCE: 805
gacatccrgd tgacccagtc tcc                                              23

<210> SEQ ID NO 806
<211> LENGTH: 23
<212> TYPE: DNA
<213> ORGANISM: Artificial
<220> FEATURE:
<223> OTHER INFORMATION: PCR primer

```
<400> SEQUENCE: 806
gaaattgtrw tgacrcagtc tcc                                            23

<210> SEQ ID NO 807
<211> LENGTH: 23
<212> TYPE: DNA
<213> ORGANISM: Artificial
<220> FEATURE:
<223> OTHER INFORMATION: PCR primer

<400> SEQUENCE: 807
gatattgtgm tgacbcagwc tcc                                            23

<210> SEQ ID NO 808
<211> LENGTH: 22
<212> TYPE: DNA
<213> ORGANISM: Artificial
<220> FEATURE:
<223> OTHER INFORMATION: PCR primer

<400> SEQUENCE: 808
gaaacgacac tcacgcagtc tc                                             22

<210> SEQ ID NO 809
<211> LENGTH: 22
<212> TYPE: DNA
<213> ORGANISM: Artificial
<220> FEATURE:
<223> OTHER INFORMATION: PCR primer

<400> SEQUENCE: 809
gaaacgacac tcacgcagtc tc                                             22

<210> SEQ ID NO 810
<211> LENGTH: 22
<212> TYPE: DNA
<213> ORGANISM: Artificial
<220> FEATURE:
<223> OTHER INFORMATION: PCR primer

<400> SEQUENCE: 810
tgaggagacr gtgaccaggg tg                                             22

<210> SEQ ID NO 811
<211> LENGTH: 22
<212> TYPE: DNA
<213> ORGANISM: Artificial
<220> FEATURE:
<223> OTHER INFORMATION: PCR primer

<400> SEQUENCE: 811
tgaggagacg gtgaccaggg tt                                             22

<210> SEQ ID NO 812
<211> LENGTH: 21
<212> TYPE: DNA
<213> ORGANISM: Artificial
<220> FEATURE:
<223> OTHER INFORMATION: PCR primer

<400> SEQUENCE: 812
tgaagagacg gtgaccattg t                                              21

<210> SEQ ID NO 813
```

```
<211> LENGTH: 23
<212> TYPE: DNA
<213> ORGANISM: Artificial
<220> FEATURE:
<223> OTHER INFORMATION: PCR primer

<400> SEQUENCE: 813
tgaggagacg gtgaccgtgg tcc                                              23

<210> SEQ ID NO 814
<211> LENGTH: 23
<212> TYPE: DNA
<213> ORGANISM: Artificial
<220> FEATURE:
<223> OTHER INFORMATION: PCR primer

<400> SEQUENCE: 814
cagtctgtsb tgacgcagcc gcc                                              23

<210> SEQ ID NO 815
<211> LENGTH: 22
<212> TYPE: DNA
<213> ORGANISM: Artificial
<220> FEATURE:
<223> OTHER INFORMATION: PCR primer

<400> SEQUENCE: 815
tcctatgwgc tgacwcagcc ac                                               22

<210> SEQ ID NO 816
<211> LENGTH: 23
<212> TYPE: DNA
<213> ORGANISM: Artificial
<220> FEATURE:
<223> OTHER INFORMATION: PCR primer

<400> SEQUENCE: 816
tcctatgagc tgayrcagcy acc                                              23

<210> SEQ ID NO 817
<211> LENGTH: 20
<212> TYPE: DNA
<213> ORGANISM: Artificial
<220> FEATURE:
<223> OTHER INFORMATION: PCR primer

<400> SEQUENCE: 817
cagcctgtgc tgactcaryc                                                  20

<210> SEQ ID NO 818
<211> LENGTH: 23
<212> TYPE: DNA
<213> ORGANISM: Artificial
<220> FEATURE:
<223> OTHER INFORMATION: PCR primer

<400> SEQUENCE: 818
cagdctgtgg tgacycagga gcc                                              23

<210> SEQ ID NO 819
<211> LENGTH: 23
<212> TYPE: DNA
<213> ORGANISM: Artificial
<220> FEATURE:
<223> OTHER INFORMATION: PCR primer

<400> SEQUENCE: 819
```

```
cagccwgkgc tgactcagcc mcc                                        23

<210> SEQ ID NO 820
<211> LENGTH: 23
<212> TYPE: DNA
<213> ORGANISM: Artificial
<220> FEATURE:
<223> OTHER INFORMATION: PCR primer

<400> SEQUENCE: 820
tcctctgagc tgastcagga scc                                        23

<210> SEQ ID NO 821
<211> LENGTH: 21
<212> TYPE: DNA
<213> ORGANISM: Artificial
<220> FEATURE:
<223> OTHER INFORMATION: PCR primer

<400> SEQUENCE: 821
cagtctgyyc tgaytcagcc t                                          21

<210> SEQ ID NO 822
<211> LENGTH: 22
<212> TYPE: DNA
<213> ORGANISM: Artificial
<220> FEATURE:
<223> OTHER INFORMATION: PCR primer

<400> SEQUENCE: 822
aattttatgc tgactcagcc cc                                         22

<210> SEQ ID NO 823
<211> LENGTH: 23
<212> TYPE: DNA
<213> ORGANISM: Artificial
<220> FEATURE:
<223> OTHER INFORMATION: PCR primer

<400> SEQUENCE: 823
gacatccrgd tgacccagtc tcc                                        23

<210> SEQ ID NO 824
<211> LENGTH: 23
<212> TYPE: DNA
<213> ORGANISM: Artificial
<220> FEATURE:
<223> OTHER INFORMATION: PCR primer

<400> SEQUENCE: 824
gaaattgtrw tgacrcagtc tcc                                        23

<210> SEQ ID NO 825
<211> LENGTH: 23
<212> TYPE: DNA
<213> ORGANISM: Artificial
<220> FEATURE:
<223> OTHER INFORMATION: PCR primer

<400> SEQUENCE: 825
gatattgtgm tgacbcagwc tcc                                        23

<210> SEQ ID NO 826
<211> LENGTH: 22
<212> TYPE: DNA
```

```
<213> ORGANISM: Artificial
<220> FEATURE:
<223> OTHER INFORMATION: PCR primer

<400> SEQUENCE: 826
gaaacgacac tcacgcagtc tc                                              22

<210> SEQ ID NO 827
<211> LENGTH: 15
<212> TYPE: DNA
<213> ORGANISM: Artificial
<220> FEATURE:
<223> OTHER INFORMATION: PCR primer

<400> SEQUENCE: 827
acgtatgcat gctag                                                      15

<210> SEQ ID NO 828
<211> LENGTH: 15
<212> TYPE: DNA
<213> ORGANISM: Artificial
<220> FEATURE:
<223> OTHER INFORMATION: PCR primer

<400> SEQUENCE: 828
acgtatgcag tctag                                                      15

<210> SEQ ID NO 829
<211> LENGTH: 15
<212> TYPE: DNA
<213> ORGANISM: Artificial
<220> FEATURE:
<223> OTHER INFORMATION: PCR primer

<400> SEQUENCE: 829
acccgtgcat gctag                                                      15

<210> SEQ ID NO 830
<211> LENGTH: 15
<212> TYPE: DNA
<213> ORGANISM: Artificial
<220> FEATURE:
<223> OTHER INFORMATION: PCR primer

<400> SEQUENCE: 830
ggttatgcat gctag                                                      15

<210> SEQ ID NO 831
<211> LENGTH: 15
<212> TYPE: DNA
<213> ORGANISM: Artificial
<220> FEATURE:
<223> OTHER INFORMATION: PCR primer

<400> SEQUENCE: 831
acgtatgcag actag                                                      15

<210> SEQ ID NO 832
<211> LENGTH: 15
<212> TYPE: DNA
<213> ORGANISM: Artificial
<220> FEATURE:
<223> OTHER INFORMATION: PCR primer

<400> SEQUENCE: 832
acgtatgcat tttag                                                      15
```

<210> SEQ ID NO 833
<211> LENGTH: 15
<212> TYPE: DNA
<213> ORGANISM: Artificial
<220> FEATURE:
<223> OTHER INFORMATION: PCR primer

<400> SEQUENCE: 833
acgtatgggt gctag                                                        15

<210> SEQ ID NO 834
<211> LENGTH: 609
<212> TYPE: DNA
<213> ORGANISM: Homo sapiens

<400> SEQUENCE: 834
tgtgcgcaaa ccgatagcag caacttagac tactactacc acggaatggg cgtctggtgt       60
gcgaaagggg gagattgtgg tggtgctagt tgcccccatt tagactacta ctactacggt      120
atggacgtct ggtgcgcgag agggacgggg ggaccctacg gtgactatta tggtggtgct      180
tttgatgtct ggtgtgcgca aaccgatagc accaacttag acttctactt ctacggtttg      240
gacgactggt gtgcgagatc ggggatagt tggagtcctc cacaatttga cttctggtgt       300
gcgcaaaccg atagcagcca catagatttc tactactatg gtatggacga ctggtgtgcg      360
gttcaagatt gtagtactac cacctgctat cctgcgagtt cctactacta ctataacatg      420
ggcgtctggt gtgcggttca agattgtagt actaccacct gttatcctgc gagttcctac      480
tactactaca acatgggcgt ctggtgtgcg caaaccgata gcagccacat agacttctac      540
tactacggta tggacgactg gtgtgcgaga tcgggggata gttggagccc tccacaattt      600
gacttctgg                                                              609

<210> SEQ ID NO 835
<211> LENGTH: 534
<212> TYPE: DNA
<213> ORGANISM: Homo sapiens

<400> SEQUENCE: 835
tgtgcgcaaa ccgatagcag caacttagac tactactacc acggaatggg cgtctggtgt       60
gcgagagatg atccatatta cggcagtatt ggttatcgta ttgactcctg gtgtgcgaga      120
atccccgcta agatcgagtg ggacgcctac tactactacg gtatggacgt ctggtgtgcg      180
agagacctta cctggagata ctttgactcc tggtgtgcga gagtgttctc tagtagtggt      240
tattactact actttgatta ctggtgtgca agatccctca ttctatatag tgactacatt      300
gcctactggt gtgcgaggca gtcaggtaac cgaggattcg gtgactctta ctcctactat      360
tacttcatgg acgtctggtg cgcgagaact ttgtattctc tggtaaagta tagtactggc      420
tggtactact ttgactactg gtgtgcgaga acaaatgctt ttcatatctg gtgtgtaaga      480
gttaagggtg gcatagcagc agctggtacc actgcggggt acttcgatct ctgg            534

<210> SEQ ID NO 836
<211> LENGTH: 534
<212> TYPE: DNA
<213> ORGANISM: Homo sapiens

<400> SEQUENCE: 836
tgtgcgagag tacggggata ttgtaatggt ggtagctgct actttgacta ctggtgtgcg       60

```
agagagaggg cattagtggg aggtagtacg actctcggat actggtgtgc gagaggcagg    120
gcttcaacct ttaaagtcta ctatcactac atggacgtct ggtgtgcgag acatatgcgg    180
ggtgggagcc ctagtcaaac tgcttttgat gtctggtgtg cgagacatat gcgggctggg    240
agtcctagtc aaactgcttt tgatgtctgg tgtgcgagac atatgcgggg tgggagtcct    300
agtcaaactg cttttgatgt ctggtgtgtg aaagcggttt cggggtcgaa ctacatcttt    360
gactactggt gtgcgagagg ccgagtggga gctaaagagc cgaccgttta ctactttgac    420
cactggtgtg cgaaaatttt tgaggcgaat ttggaaaact actggtatgg tttggacgtc    480
tggtgtgcga gacatcagta taatgttggt aactcctggg cttttgatat ctgg         534

<210> SEQ ID NO 837
<211> LENGTH: 375
<212> TYPE: DNA
<213> ORGANISM: Homo sapiens

<400> SEQUENCE: 837
tgtcaacagg ctaacagttt cccgctcact ttctgtcaat caccagacag cagtggtact     60
aatgaagtct tctgtcaatc accagacagc agtggtactt atgaagtctt ctgcggaaca    120
tgggatacca gcctgggtac taattgggtg ttctgcggaa catgggatac cagcctgaga    180
attaattggg tgttctgtca acagtttact aatttcccgc tcactttctg tcaacagtat    240
ggtagttcat ggcgcacttt tgtcaggcg tgggacagca gcactgtggt attctgcgga    300
acatgggata ccagcctgag gattaattgg gtgttctgct cagcatggga cagcagcctc    360
agtgctgggt gttc                                                      375

<210> SEQ ID NO 838
<211> LENGTH: 357
<212> TYPE: DNA
<213> ORGANISM: Homo sapiens

<400> SEQUENCE: 838
tgtcaggcgt gggacagcag cactgtggta ttctgctgct catatgcagg caactcttat     60
gtcttctgtc aatcaccaga cagcagtggt actaatgaag tcttctgtca gcagtatggt    120
agctcacctt ggacgttctg tcagcaatat ggtagctcac cgacgttctg taactcccgg    180
gacagcagtg gtaaccatgt ggtattctgt cagcagcgta gcacctggcc tgcgactttc    240
tgtcaggtgt gggatagtag tagtgatcat gtggtattct gtcaatcagc agacagcagt    300
ggtacttatg tggtattctg cggagcgtgg gatagcagcc tgagtgctgt ggtcttc      357

<210> SEQ ID NO 839
<211> LENGTH: 348
<212> TYPE: DNA
<213> ORGANISM: Homo sapiens

<400> SEQUENCE: 839
tgtcaggcgt gggacagcag cactgtggta ttctgtcaac acatggtaa ctcaccggtc      60 actttctgct tcctctactt tgatggtcct atagttttct gtcagcatta tcatactcca    120
ccgtacactt tttgccaaca gtataatacc tggtggacat tctgtttact ctattataat    180
ggtgtcaggg tgttctgtaa ctcccgggac agcagtggta accatgtggt attctgctgc    240
tcatatgcag gtagtagcac ttttgtcttc tgtcaatcag cagacagcag tggtacttat    300
gtggtattct gctcagcatg ggacagcagc ctcagtgctt gggtgttc                 348
```

<210> SEQ ID NO 840
<211> LENGTH: 423
<212> TYPE: DNA
<213> ORGANISM: Homo sapiens

<400> SEQUENCE: 840

```
ttgtggctat tttaaaaggt gtccagtgtg acgtgcagct ggtggagtct gggggaggct    60
tggtacagcc tgggaagtcc ctgagactct cctgtgcagc ctctggattc acctttagca   120
actatgccat gtcctgggtc cgccaggctc agggaaggg cctggagtgg gtctcaggta    180
ttagtggtag tggtgctgcc acatactacg cagactccgt gaagggccgg ttcaccatct   240
ccagagtcaa ttccaggaac acgctccttc tgcaaatgaa cagcctgaga gccgaggaca   300
cggccctata ttactgtgcg caaaccgata gcagcaactt agactactac taccacggaa   360
tgggcgtctg gggccaaggg accacggtca ccgtctcctc agcatccccg accagcccca   420
agg                                                                 423
```

<210> SEQ ID NO 841
<211> LENGTH: 441
<212> TYPE: DNA
<213> ORGANISM: Homo sapiens

<400> SEQUENCE: 841

```
ttgtggctat tttaaaaggt gtccagtgtg aggtgcagct cttggagtct gggggaggct    60
tggcacagcc tggggggtcc ctgagactct cctgtggagc ctctggattc acctttagta   120
actatggcat gacctgggtc cgccaggctc agggaaggg gctggagtgg gtctcaggta    180
ttagtggtag tggtgctagt acattctacg cagactccgt gaagggccgg ttcaccatct   240
ccagagacaa ttccaagaac acgctgtatc tgcaaatgga cagcctgaga gccgaggaca   300
cggccgtcta ttactgtgcg aaaggggag attgtggtgg tgctagttgc ccccatttag    360
actactacta ctacggtatg gacgtctggg gccaagggac cacggtcacc gtctcctcag   420
catccccgac cagccccaag g                                             441
```

<210> SEQ ID NO 842
<211> LENGTH: 423
<212> TYPE: DNA
<213> ORGANISM: Homo sapiens

<400> SEQUENCE: 842

```
cggctcccag atgggtcctg tcccagctgc agttgcagga gtcgggccca ggagtggtga    60
agccttcgga gaccctgtcc ctcacctgca ctgtctctgg tggctccatc agcactagca   120
gttattactg gggctggatc cgccagcccc cagggaaggg gctggagtgg attgggacta   180
tctattctag tggggctcc tactacaacc cgtccctcaa gagtcaagtc gccatatccg    240
ttgacatgtc caagaatcaa ttctccctga aggtgaactc tataatcgcc gcagacacgg   300
ctgtgtatta ctgcgcgaga gggacggggg gaccctacgg tgactattat ggtggtgctt   360
ttgatgtctg gggccaaggg aaaagggtcg ccgtctcttc agcatccccg accagcccca   420
agg                                                                 423
```

<210> SEQ ID NO 843
<211> LENGTH: 423
<212> TYPE: DNA
<213> ORGANISM: Homo sapiens

<400> SEQUENCE: 843

```
ttgtggctat tttaaaaggt gtccagtgtg aggtgcggct gttggagtct ggggaggct      60 tagtgcagcc tggggggtcc ctgagactct cctgtgcagc ctctggattc acctttagca    120
actatgccat gacctgggtc cgccaggctc cagggcaggg gctggagtgg gtctcaggaa    180
ttagtggtag tggtgcaagc acatactacg aagactccgt gaagggccgg ttcaccatct    240
ccagacagaa ttccaagaac acgctgtatc tgcaaatgaa tagcctgaga gccgaggaca    300
cggccgtata ctactgtgcg caaaccgata gcaccaactt agacttctac ttctacggtt    360
tggacgactg gggccaaggg accacggtca ccgtctcctc agcatccccg accagcccca    420
agg                                                                  423

<210> SEQ ID NO 844
<211> LENGTH: 405
<212> TYPE: DNA
<213> ORGANISM: Homo sapiens

<400> SEQUENCE: 844
cggctcccag atgggtcctg tcccaggtgc agctgcagga gtcgggccca ggactggtga     60
agccttcgga gaccctgtcc ctcacctgca agtttctat tggctccgtc aggaattatt    120
actggagctg gatccggcag tccccgggaa agggactgga gtggattgca tatatctttc    180
ccaatgggag gaccagccgc aatccctccc tccagagtcg agtcaccata tcaattgaca    240
cacccaaaaa tcagttctcc atgttgctga gctctgcgac cgccgcagac acggccgtct    300
attactgtgc gagatcgggg gatagttgga gtcctccaca atttgacttc tggggccagg    360
gaatcctagt caccgtctcc tcagcatccc cgaccagccc caagg                    405

<210> SEQ ID NO 845
<211> LENGTH: 345
<212> TYPE: DNA
<213> ORGANISM: Homo sapiens

<400> SEQUENCE: 845
ccctgagact ctcctgtgca gcctctggat tcacgttcag caactatgcc atgagctggg     60
tccgccaggc tccagggaag gggctggagt gggtctcagg aatgagtggt agtggtgcta    120
gcacatacta cgaagactcc gtgaagggcc ggttcaccat ctccagagac aattccaaga    180
acacgctgta tctgcaaatg aatagcctga gagccgagga cacggccgta tattactgtg    240
cgcaaaccga tagcagccac atagatttct actactatgg tatggacgac tggggccaag    300
ggaccacggt caccgtctcc tcagcatccc cgaccagccc caagg                    345

<210> SEQ ID NO 846
<211> LENGTH: 436
<212> TYPE: DNA
<213> ORGANISM: Homo sapiens

<400> SEQUENCE: 846
gcagcagcta caggtgtcca gtcccaggtg cagttggtgc agtctggggc tgaggtgaag     60
aggcctgggt cctcggtgaa ggtctcctgc aaggcttctg gaggcacctt cagcaactat    120
gcaatcagct gggtgcgaca ggcccctgga caagggcttg agtggatggg agggatcatc    180 cctactttg gacaccgac gtacgcacag aagttccagg ccagagtcac gattaccgcg    240
gacgaatcta cgagcacagc ctacatggag ctgagcagcc tgagatctga ggacacggcc    300
gtctattggt gtgcggttca agattgtagt actaccacct gctatcctgc gagttcctac    360
tactactata acatgggcgt ctggggcaaa gggaccacgg tcaccgtctc ctcagcatcc    420
```

```
ccgaccagcc ccaagg                                                    436

<210> SEQ ID NO 847
<211> LENGTH: 435
<212> TYPE: DNA
<213> ORGANISM: Homo sapiens

<400> SEQUENCE: 847
cagcagctac aggtgtccag tcccaggtgc agctggtgca gtctggggct gaggtgaaga    60
ggcctgggtc ctcggtgaag gtctcctgcc aggcttctgg aggcaccttc agcaactatg   120
ctatcagctg ggtgcgacag gcccctggac aagggcttga gtggatggga gggatcatcc   180
ctatgtttgg tacaccaaag tacgcacagc agttcctgga cagagtcacg ataaccgcgg   240
acgaatccac gagtacagcc tacatggagc tgagcagcct gagatctgcg acatggccg    300 tttattggtg tgcggttcaa gattgtagta ctaccacctg ttatcctgcg agttcctact   360
actactacaa catgggcgtc tggggcaaag gaccacggt caccgtctcc tcagcatccc    420
cgaccagccc caagg                                                    435

<210> SEQ ID NO 848
<211> LENGTH: 421
<212> TYPE: DNA
<213> ORGANISM: Homo sapiens

<400> SEQUENCE: 848
gtggctattt taaaaggtgt ccagtgtgag gtgcagctgt tggagtctgg gggaggcttg    60
gtgcagcctg gggggtccct gagactctcc tgtgtagcct ctggattcac ctttagcaac   120
tatgccatga gctgggtccg ccaggctcca gggaaggggc tggagtgggt ctcaggaatt   180
agtggtagtg gtgctagcac atactacgaa gactccgtga agggccggtt caccatctcc   240
agagacaatt ccaagaacac gctgtatctg gacatgaata gcctgagagc cgaggacacg   300
gccgtatatt actgtgcgca aaccgatagc agccacatag acttctacta ctacggtatg   360
gacgactggg gccaagggac cacggtcacc gtctcctcag catccccgac cagccccaag   420
g                                                                  421

<210> SEQ ID NO 849
<211> LENGTH: 405
<212> TYPE: DNA
<213> ORGANISM: Homo sapiens

<400> SEQUENCE: 849
cggctcccag atgggtcctg tcccaggtgc agctgcagga gtcgggccca ggactggtga    60
agccttcgga gaccctgtcc ctcacttgca ctgtttctag tggctccatc aggaattact   120
actggagctg gatccggcag accccaggga agggactgga gtggattgga tatatctttt   180
ccaatgggag gatcaagtac aattcctccc tccaaggtcg actcaccatg tcactaaaca   240
cgcccgagaa tcagttctcc ctgtggctga gctctgtgac cgccgcagac acggccgtct   300
attactgtgc gagatcgggg gatagttgga gccctccaca atttgacttc tggggccagg   360
gaatcctggt caccgtctcc tcagcatccc cgaccagccc caagg                   405

<210> SEQ ID NO 850
<211> LENGTH: 415
<212> TYPE: DNA
<213> ORGANISM: Homo sapiens
```

<400> SEQUENCE: 850

```
ttgtggctat tttaaaaggt gtccagtgtg aggtgcagtt gttggagtct ggggggaggct    60
tggtacagcc tgggggtcc ctgagactct cctgtgcagc ctctggattc acctttaaca   120
actatgccac aagctgggtc cgccaggctc cagggaaggg gctggagtgg gtctcaacta   180
ttagtggtgt tggtgatacc acatactacg caaattccgt gaagggccgg ttcaccatct   240
ccagagacac ttccaagaac accctgtatc tgcaaatgaa cagcctgaga gccgaggaca   300
cggccgaata ttactgtgcg agagtacggg gatattgtaa tggtggtagc tgctactttg   360
actactgggg ccagggaacc ccggtcaccg tctcctcagg gagtgcatcc gcccc         415
```

<210> SEQ ID NO 851
<211> LENGTH: 411
<212> TYPE: DNA
<213> ORGANISM: Homo sapiens

<400> SEQUENCE: 851

```
cagcagccac aggagcccac tcccaggtgc aactggtgca gtctggggct gaggtgaaga    60
ggcctggggc ctcagtgaag gtctcctgca aggcctctgg atacaccttc accggctact   120
atgtacactg ggtgcgacag gcccctggac aaggtcttga gtggatggga tggatcaacc   180
ctaacagtgg tgtcacaaac tacgcacaga actttcagga cagggtcacc atgaccaggg   240
acacgtccat cagcacagcc tacatggagc tgaccaggct gagatctgac gacacggccc   300
tatattactg tgcgagagag agggcattag tgggaggtag tacgactctc ggatactggg   360
gccagggaac cctggtcacc gtctcctcag ggagtgcatc cgccccaacc c             411
```

<210> SEQ ID NO 852
<211> LENGTH: 414
<212> TYPE: DNA
<213> ORGANISM: Homo sapiens

<400> SEQUENCE: 852

```
cggctcccag atgggtcctg tcccaggtgc agttacagca gtggggcgca ggactgttga    60
agccttcgga gaccctgtcc ctcacctgcg ttgtctatgg tgggtctttc agtccttatt   120
actggagctg gatccgccag accccaggga aggggctgga gtggattggg gaaatcaatc   180
atagtggaag caccaactac aacccgtccc tcaagagtcg agtctccata tcactagaca   240
cgtccaagaa tgagttctcc ctgaggctga actctctgac cgccgcggac acggctgtgt   300
attactgtgc gagaggcagg gcttcaacct ttaaagtcta ctatcactac atggacgtct   360
ggggcaatgg gaccacggtc accgtctcct cagcatcccc gaccagcccc aagg          414
```

<210> SEQ ID NO 853
<211> LENGTH: 411
<212> TYPE: DNA
<213> ORGANISM: Homo sapiens

<400> SEQUENCE: 853

```
cggctcccag atgggtcctg tcccaggtgc agctgcagga gtcgggccca ggactggtga    60
agcctgcgga gaccctgtcc ctcacctgca atgtctctgg tggctccatg agtagttact   120
actggagctg gatccggcag ccccagggaa agggactgga gtggatcggg tacatccact   180
acagggggac caccaaatac aatccctccc tcaagagtcg cgtcaccata tcaatagacc   240
tgtccaagaa ccagttctcc ctgaaactga gctctatgac cgccgcagat acggccagtt   300
attactgtgc gagacatatg cggggtggga gccctagtca aactgctttt gatgtctggg   360
```

```
gccaagggac aatggtcacc gtctcttcag catccccgac cagccccaag g          411
```

<210> SEQ ID NO 854
<211> LENGTH: 411
<212> TYPE: DNA
<213> ORGANISM: Homo sapiens

<400> SEQUENCE: 854

```
cggctcccag atgggtcctg tcccaggtgc agctgcagga gtcgggccca ggactggtga   60
agccttcgga gaccctgtcc ctcacctgca atgtctctgg tggctccatc agtagttact  120
actggagctg gatccggcag ccccagggaa ggcactgga gtggatcggg tatatccact   180
acaggggac  taccaaatac aatccctccc tcaagagtcg cgtcaccata tcagtagaca  240
tgtccaagaa ccagttctcc ctgaagctga gctctatgac cgccgcagat acggccatct  300
attactgtgc gagacatatg cgggctggga gtcctagtca aactgctttt gatgtctggg  360
gccaagggac aatggtcacc gtctcttcag catccccgac cagccccaag g           411
```

<210> SEQ ID NO 855
<211> LENGTH: 411
<212> TYPE: DNA
<213> ORGANISM: Homo sapiens

<400> SEQUENCE: 855

```
cggctcccag atgggtcctg tcccaggtgc agctgcagga gtcgggccca ggactggtga   60
agccttcggg gaccctgtcc ctcacctgca atgtctctgg tggcccccatc agtagttact 120
actggagctg gatccggcag ccccccaggga agggactgga gtggatcggc tatatctatt 180
acaggggac  taccaaatac aatccctccc tcaagagtcg cgtcaccata tcagtagaca  240
tgtccaagaa ccagttctcc ctgaacctga gctctatgac cgccgcagat acggccatgt  300
actactgtgc gagacatatg cggggtggga gtcctagtca aactgctttt gatgtctggg  360
gccaagggac aatggtcacc gtctcttcag catccccgac cagccccaag g           411
```

<210> SEQ ID NO 856
<211> LENGTH: 411
<212> TYPE: DNA
<213> ORGANISM: Homo sapiens

<400> SEQUENCE: 856

```
ttgtggctat tttaaaaggt gtccagtgtg aggtgcagct gttggagtct gggggaggct   60
tgatacagcc tggggggtcc ctgagactct cctgtgcagc ctctggattc acctttagca  120
agtatgccat gacctgggtc cgccaggctc cagggaaggg cctggagtgg gtctcgacta  180
ttagtggtag tgctactgcc acatactacg cagactccgt gaagggccgc ttcaccatct  240
ccagagacaa ttcgaagaac acgctgtatc tgcaaatgaa cagcctgaga gccgcggaca  300
cggccgttta ttactgtgtg aaagcggttt cggggtcgaa ctacatcttt gactactggg  360
gccagggaac ccaggtcacc gtctcctcag catccccgac cagccccaag g           411
```

<210> SEQ ID NO 857
<211> LENGTH: 423
<212> TYPE: DNA
<213> ORGANISM: Homo sapiens

<400> SEQUENCE: 857

```
ttgtggctat tttaaaaggt gtccaatgtg aggtgcaact gttagaatat gggggaggct   60
```

```
tggtacagcc ggggggtcc ctgagactct cctgtgaagc ctctggaatc cccttttaaca      120 actatgccat gagctgggtc cgccaggctc cagggaaggg gctggagtgg gtctcaagta      180
tcagtggtag tggtagtggc acatattacg gagactccgt gaagggccgg ttcaccatct      240
ccagagacaa ttccaagaac acactgtatc tgcaaatgaa tagcctgaga gccgaggaca      300
cggccgtata ttattgtgcg agaggccgag tgggagctaa agagccgacc gtttactact      360
ttgaccactg gggccaggga accctggtca ccgtctcctc agcatccccg accagcccca      420
agg                                                                    423

<210> SEQ ID NO 858
<211> LENGTH: 421
<212> TYPE: DNA
<213> ORGANISM: Homo sapiens

<400> SEQUENCE: 858
gtggctattt taaaaggtgt ccagtgtgag gtgcagctgt tggagtctgg gggaggcttg      60
gtacagcctg gggggtcctt gagactctcc tgtgcagcct ctggattcac cttcagcagc      120
tatgccatga actgggtccg cctgcctcca gggatgggga tggagagcat ctcatccatt      180
agtcgtagtg gtgatagaac atactacgca gactccgtga agggccggtt caccatctcc      240
agagacaatt ccaagaacac gatgtatctg gaaatgaaca gcctgagagc cgaagacacg      300
gccgtatatt actgtgcgaa aattttgag gcgaatttgg aaaactactg gtatggtttg      360
gacgtctggg gccaagggac cacggtcacc gtctcctcag ggagtgcatc cgccccaacc      420
c                                                                      421

<210> SEQ ID NO 859
<211> LENGTH: 408
<212> TYPE: DNA
<213> ORGANISM: Homo sapiens

<400> SEQUENCE: 859
cggctcccag atgggtcctg tcccaggtgc agctgcagga gtcgggccca ggactggtga      60
agccttcgga gaccctgtcc ctcacctgcg ctgtctctgg tgcctccatt agaagttact      120
attggagctg gatccggctg ccccaggga agggactgga gtggattggg catgtgtatc      180
acagtgggag caccagttac aatccctccc tcaagagtcg agtcaccata tcagtggaca      240
cgtccaagat gcagatctcc ctgaggctga actctgcgac tgctgcggac acggccgtgt      300
attactgtgc gagacatcag tataatgttg gtaactcctg gcttttgat atctggggcc      360 aagggacagt ggtcaccgtc tcttcagcat ccccgaccag ccccaagg                   408

<210> SEQ ID NO 860
<211> LENGTH: 423
<212> TYPE: DNA
<213> ORGANISM: Homo sapiens

<400> SEQUENCE: 860
ttgtggctat tttaaaaggt gtccagtgtg acgtgcagct ggtggagtct gggggaggct      60
tggtacagcc tggaagtcc ctgagactct cctgtgcagc ctctggattc accttagca       120 actatgccat gtcctgggtc cgccaggctc cagggaaggg cctggagtgg gtctcaggta     180
ttagtggtag tggtgctgcc acatactacg cagactccgt gaagggccgg ttcaccatct     240
ccagagtcaa ttccaggaac acgctccttc tgcaaatgaa cagcctgaga gccgaggaca     300
cggccctata ttactgtgcg caaaccgata gcagcaactt agactactac taccacggaa    360
```

```
tgggcgtctg gggccaaggg accacggtca ccgtctcctc agcatccccg accagcccca    420
agg                                                                 423

<210> SEQ ID NO 861
<211> LENGTH: 414
<212> TYPE: DNA
<213> ORGANISM: Homo sapiens

<400> SEQUENCE: 861
cagcagcaac aggtgcccac tcccaggttc aactggtgca atctggagct gaggtgaaga    60
ggcctggggc ctcagtaaag gtctcctgca cggcttctgg ttacacgttt gacacttatg   120
gagtcagctg gttgcgacag gcccctggac aagggcttga gtggatgggc tggatcagcg   180
gtgacagtag tcataccaga tatgcaatga gactccaggg cagagtcacc atgaccacag   240
actcatccac gagcacagcc tacatggaac tgaggagcct gagatctgac gacacggccg   300
tctattactg tgcgagagat gatccatatt acggcagtat tggttatcgt attgactcct   360
ggggccaggg aaccctggtc accgtctcct cagcatcccc gaccagcccc aagg         414

<210> SEQ ID NO 862
<211> LENGTH: 415
<212> TYPE: DNA
<213> ORGANISM: Homo sapiens

<400> SEQUENCE: 862
cggctcccag atgggtcctg tcccaggtgc aactgcagga gtcgggccca ggactggtga    60
agccttcgga gaccctgtcc ctcacctgca ctgtctctgg tggctccatc agtagttact   120
acttgagctg gatccggcag cccccaggga aggggctgga gtggattggg tatatctatt   180
acagtgggag caccaactac aacccctccc tcaagagtcg agtcaccata tcagtagaca   240
cgtccaagaa ccagttctcc ctgaggctga gctctgtgac cgctgcggac acggccgtgt   300
attactgtgc gagaatcccc gctaagatcg agtgggacgc ctactactac tacggtatgg   360
acgtctgggg ccaagggacc acggtcaccg tctcctcagg gagtgcatcc gcccc        415

<210> SEQ ID NO 863
<211> LENGTH: 403
<212> TYPE: DNA
<213> ORGANISM: Homo sapiens

<400> SEQUENCE: 863
ttgttgctat tttagaaggt gtccagtgtg aggtgcagtt ggtggagtct gggggaggct    60
tggtacagcc tggggggtcc ctgagactct cctgtgcagc ctctggattc actttcagtg   120
gctatagcat ggactgggtc cgccaggctc cggggaaggg gctggagtgg gtttcattca   180
taagtgataa tactggcagt cacatatact acgcagactc tgtgaagggc cgattcacca   240
tctctagaga caatgccgag aactcactgt atctacaaat gaacagcctg agagacgagg   300
acacggctgt gtattactgt gcgagagacc ttacctggag atactttgac tcctggggcc   360
atggagtcct ggtcaccgtc tcctcacgga gtgcatccgc ccc                     403

<210> SEQ ID NO 864
<211> LENGTH: 409
<212> TYPE: DNA
<213> ORGANISM: Homo sapiens

<400> SEQUENCE: 864
```

```
ttgttgctat tttaaaaggt gtccagtgtg aggtgcagct ggtggagtct ggaggaggcc      60
tgatccagcc tggggggtcc ctgagactct cctgtgcagc ctctgggttc accgtcagta    120
gcagctacat gacctgggtc cgccaggctc agggaaggg gctggagtgg gtctcagtta    180
tttatagtgg tggtaccaca tactacgcag actccgtgaa gggccgattc accatctcca    240
gagacaattc caagaacacg ctgtatcttc aaatgaacag cctgagagcc gaggacacgg    300
ccgtgtatta ctgtgcgaga gtgttctcta gtagtggtta ttactactac tttgattact    360
ggggccaggg aaccctggtc accgtctcct cagggagtgc atccgcccc                409

<210> SEQ ID NO 865
<211> LENGTH: 411
<212> TYPE: DNA
<213> ORGANISM: Homo sapiens

<400> SEQUENCE: 865
cggctcccag atgggtcctg tcccaggtgc agctgcagga gtcgggccca ggactggtga     60
agccttcgga gaccctgtcc ctcacctgca ctgtctctgg tggctccatt agtagttact    120
cctggagctg gatccggcag tccccaggga agggactgga gtggattggg tctacctatt    180
acagtgggag caccaactac accaactaca acccctccct caagagtcga gtcaccacat    240
cagtagacac gtccaagaac cagttgtccc tggggctgaa ctctgtgacc gcagcggaca    300
cggccattta ttactgtgca agatccctca ttctatatag tgactacatt gcctactggg    360
gccagggaac cctggtcacc gtctcctcag catccccgac cagccccaag g            411

<210> SEQ ID NO 866
<211> LENGTH: 429
<212> TYPE: DNA
<213> ORGANISM: Homo sapiens

<400> SEQUENCE: 866
cagcagcaac aggtgcccgc tcccaggttc aactgatgca gtctggagct gaagtgagga     60
agcctggggc ctcagtgacg gtctcctgca agacttctgg ttacacctt acctactatg    120 gtatcagttg ggtgcgacag gcccctggac aaggccttga gtggatggga tggttcagcg    180
cttacaatgg taagacaaaa tatgcacaga atctccagga cagagtcacc atgacaattg    240
acacatccac gaggacagcc tacatggagc tgaggagcct gagatctgac gacacggccg    300
tatattactg tgcgaggcag tcaggtaacc gaggattcgg tgactcttac tcctactatt    360
acttcatgga cgtctggggc aaagggacca cggtcaccgt cgcctcagca tccccgacca    420
gccccaagg                                                             429

<210> SEQ ID NO 867
<211> LENGTH: 420
<212> TYPE: DNA
<213> ORGANISM: Homo sapiens

<400> SEQUENCE: 867
cggctcccag atgggtcctg tcccaggtgc agctacagca gtggggcgca ggactgttga     60
agccttcgga gaccctgtcc ctcacctgcg ctgtttatgg tgagtccttc cgtggttact    120
cctggagctg gatccggcag cccccaggga aggggctgga gtggattggt gaaatcaatc    180
ttactggaag caccaactac aacccgtccc tcaagagtcg gatcaccgta tcaattgacc    240
cgtccaagac tcagttctcc ctgaagctga cctctgtgac cgccgcggac acggctgtat    300
attactgcgc gagaactttg tattctctgg taaagtatag tactggctgg tactactttg    360
```

```
actactgggg ccagggaatc ctggtcaccg tctcctcagc ctccaccaag ggcccatccg      420
```

<210> SEQ ID NO 868
<211> LENGTH: 382
<212> TYPE: DNA
<213> ORGANISM: Homo sapiens

<400> SEQUENCE: 868

```
cggctcccag atgggtcctg tcccaggtgc agctgcagga gtcgggccca ggactggtga       60
agccttcgga gactctgtcc ctcacctgca ctgtctctgg tgactccatt agtagtgact      120
attggagctg gatccggcag tccccaggga agggactgga gtggattggg tttattcagt      180
atactgggag atcccactcc aacccctccc tccagagtcg agtcaccata tcactagaca      240
cgtccaagaa caacttctcc ctgaggctga cctctgtgac cgctgcggac acggccgtgt      300
attattgtgc gagaacaaat gcttttcata tctggggcca agggacaatg gtcaccgtct      360
cttcagggag tgcatccgcc cc                                               382
```

<210> SEQ ID NO 869
<211> LENGTH: 424
<212> TYPE: DNA
<213> ORGANISM: Homo sapiens

<400> SEQUENCE: 869

```
gttgctatat tagaaggtgt ccagtgtgag gtgcagctgg tggaatctgg gggaggctta       60
gtacaacctg ggggttcgct gagactctcc tgtgcagcct ctggattcac tttcagtgat      120
tacgacatgc actgggtccg ccaagctaca ggaaaaggtc tggagtgggt ctcagctata      180
ggaactcttg atgacacata ctatccaggc tccgtggagg gccgattcac cgtctccaga      240
gacaatgcca gggattcctt gtatcttcaa atgaagagcc tcagagtcgc ggacacggct      300
gtatattact gtgtaagagt taagggtggc atagcagcag ctggtaccac tgcggggtac      360
ttcgatctct ggggccgtgg caccctggtc actgtctcct caggagtgc atccgcccca      420
accc                                                                   424
```

<210> SEQ ID NO 870
<211> LENGTH: 366
<212> TYPE: DNA
<213> ORGANISM: Homo sapiens

<400> SEQUENCE: 870

```
tctggttccc aggttccaga tgcgacatcc agatgaccca gtctccgtct tccgtgtctg       60
catctgtggg ggacagagtc accatcactt gccgggcgag tcagagtctt agcggctttt      120
tagcctggta tcagcagaaa ccagggaaag cccctaagtt cctgatcgat actacctcca      180
ttttgcaaag tggggtccca tctagattca gtggcagtgg atctgggaca ttttcactc       240
tcaccatcag cagcctccag cctgaagatt ttgcaactta ctattgtcaa caggctaaca      300
gtttcccgct cactttcggc ggagggacca aggtggagag gaaacgaact gtggctgcac      360
catctg                                                                 366
```

<210> SEQ ID NO 871
<211> LENGTH: 373
<212> TYPE: DNA
<213> ORGANISM: Homo sapiens

<400> SEQUENCE: 871

```
ctcactgcac aggctctgag gcctcctatg agctgacaca gccaccctcg gtgtcagtgt    60
ccccaggaca gacggccagg atcacctgct ctggagatgc attgccaaag cactttgctt    120
attggtacca gcagaagcca ggccaggccc ctgtactggt gatatataaa gacactgaga    180
ggccctcagg gatccctgag cgattctctg gctccagctc agggacaaca gtcacgttga    240
ccatcagtgg agtccaggca gaagacgagg ctgactatta ctgtcaatca ccagacagca    300
gtggtactaa tgaagtcttc ggaactggga ccaaggtcac cgtcctaagt cagcccaagg    360
ccaaccccac ggt                                                       373
```

<210> SEQ ID NO 872
<211> LENGTH: 373
<212> TYPE: DNA
<213> ORGANISM: Homo sapiens

<400> SEQUENCE: 872

```
ctcactgcac aggctctgag gcctcctatg agctgacaca gccaccctcg gtgtcagtgt    60
ccccaggaca gacggccagg atcacctgct ctggagatgc attgccaaag cactatgctt    120
attggtacca gcagaagcca ggccaggccc ctgtgttggt gatatataaa gacagtgaga    180
ggccctcagg gatccctgag cgattctctg gctccagctc agggacaaca gtcacgttga    240
ccatcagtgg agtccaggca gaagacgagg ctgactatta ctgtcaatca ccagacagca    300
gtggtactta tgaagtcttc ggaactggga ccagggtcac cgtcctaggt cagcccaagg    360
ccaaccccac tgt                                                       373
```

<210> SEQ ID NO 873
<211> LENGTH: 382
<212> TYPE: DNA
<213> ORGANISM: Homo sapiens

<400> SEQUENCE: 873

```
ctcactgcac agggtcctgg gcccagtctg tgttgacgca gccgccctca gtgtctgcgg    60
ccccaggaca gaaggtcacc atctcctgct ctggaagcag ctccaacatt ggcaaaaatt    120
atgtatcctg gtaccagcat ctcccaggaa cagccccaa actcctcatc tatgaaaatg    180
atgagcgacc ctcagggatt cctgaccgat tctctggctc caagtatggc acgtcagcca    240
ccctgggcat caccggactc cagactgggg acgaggccac ttatttctgc ggaacatggg    300
ataccagcct gggtactaat tgggtgttcg gcggagggac caagctgacc gtcctaggtc    360
agcccaaggc tgccccctcg gt                                             382
```

<210> SEQ ID NO 874
<211> LENGTH: 382
<212> TYPE: DNA
<213> ORGANISM: Homo sapiens

<400> SEQUENCE: 874

```
ctcactgcac agggtcctgg gcccagtctg tgttgacgca gccgccctca gtgtctgcgg    60
ccccaggaca gaaggtcacc atctcctgct ctggaagcag ctccaacatt gggagtaatc    120
gtgtatcctg gtaccagcag ctcccaggaa cagccccaa actcctcatc tatgaaaata    180
atgagcgacc ctcagggatt cctgaccgat tctctgcctc caagtctggc acgtcagcca    240
ccctggtcat caccggactc cagactgggg acgaggccga ttattattgc ggaacatggg    300
ataccagcct gagaattaat tgggtgttcg gcggagggac caagctgacc gtcctaggtc    360
agcccaaggc tgccccctcg gt                                             382
```

<210> SEQ ID NO 875
<211> LENGTH: 366
<212> TYPE: DNA
<213> ORGANISM: Homo sapiens

<400> SEQUENCE: 875

| | | | | | | |
|---|---|---|---|---|---|---|
| tctggctccc | aggtgccaga | tgtgacatcc | tgttgaccca | gtctccatcc | ttcctgtctg | 60 |
| cagctgtagg | aaacagaatc | accattactt | gccgggccag | tcagggcatt | agtagttatt | 120 |
| tagcctggtt | tcaggaaaaa | ccagggaaag | cccctaaact | cctgatttat | ggtgcatcca | 180 |
| ttttgcaaag | tggggtccca | tcaaggttca | gcggcagtgg | atctgggaca | gagttcactc | 240 |
| tcacaatcag | gagcctgcag | cctgaagatt | ttgcaactta | ttactgtcaa | cagtttacta | 300 |
| atttcccgct | cactttcggc | ggagggacca | aggtggagat | caaacgaact | gtggctgcac | 360 |
| catctg | | | | | | 366 |

<210> SEQ ID NO 876
<211> LENGTH: 371
<212> TYPE: DNA
<213> ORGANISM: Homo sapiens

<400> SEQUENCE: 876

| | | | | | | |
|---|---|---|---|---|---|---|
| actctggctc | acagatacca | ccggagaaat | tgtgttgacg | cagtctccag | gcaccctgtc | 60 |
| tttgtctcca | ggggaaagag | ccaccctctc | ctgcagggcc | agtcagagag | ttagcagcaa | 120 |
| ctacttagcc | tggtaccagc | agaaatcagg | ccaggctccc | aggctcctca | tctatagtgc | 180 |
| atcccgcagg | gccactggca | tcccagacag | gttcagtggc | agtgggtctg | ggacagactt | 240 |
| cactctcacc | atcagcagac | tggagcctga | agattttgcc | gtgtatcact | gtcaacagta | 300 |
| tggtagttca | tggcgcactt | ttggccaggg | gaccaaggtg | gagatcagac | gaactgtggc | 360 |
| tgcaccatct | g | | | | | 371 |

<210> SEQ ID NO 877
<211> LENGTH: 367
<212> TYPE: DNA
<213> ORGANISM: Homo sapiens

<400> SEQUENCE: 877

| | | | | | | |
|---|---|---|---|---|---|---|
| cttactgcac | aggatccgtg | gcctcctatg | agctgactca | gccaccctca | gtgtccgtgt | 60 |
| ccccaggaca | gacagccagc | atcacctgct | ctggagataa | attgggggat | aaatatgctt | 120 |
| gctggtatca | gcagaagcca | ggccagtccc | ctgtgctggt | catctatcaa | gatagcaagc | 180 |
| ggccctcagg | gatccctgag | cgattctctg | gctccaactc | tgggaacaca | gccactctga | 240 |
| ccatcagcgg | gacccaggct | atggatgagg | ctgactatta | ctgtcaggcg | tgggacagca | 300 |
| gcactgtggt | attcggcgga | gggaccaagc | tgaccgtcct | aggtcagccc | aaggctgccc | 360 |
| cctcggt | | | | | | 367 |

<210> SEQ ID NO 878
<211> LENGTH: 382
<212> TYPE: DNA
<213> ORGANISM: Homo sapiens

<400> SEQUENCE: 878

| | | | | | | |
|---|---|---|---|---|---|---|
| ctcactgcac | agggtcctgg | gcccagtctg | tgttgacgca | gccgccctca | gtgtctgcgg | 60 |
| cctcaggaca | ggaggtcacc | atctcctgct | ctggaagcag | ctccaacatt | gggagttatc | 120 |

```
gtgtatcctg gtatcagcac ctcccaggaa cagcccccaa actcctcatc tatgaaaatg    180
atcagcgacc ctcagggatt cctgaccgat tctctggctc caagtctggc acgtcagcca    240
ccctggtcat caccggactc ctgactgcgg acgaggccga ttattactgc ggaacatggg    300
ataccagcct gaggattaat tgggtgttcg gcggagggac caagctgacc gtcctaggtc    360
agcccaaggc tgcccctcg gt                                              382

<210> SEQ ID NO 879
<211> LENGTH: 381
<212> TYPE: DNA
<213> ORGANISM: Homo sapiens

<400> SEQUENCE: 879
cactcactct gcagtgtcag tggtccaggc aggactgact cagccaccct cggtgtccaa    60
ggacttgaga cagaccgcca cactcacctg cactgggaac agcaacaatg ttggcaacct    120
aggagcagct tggctgcagc agcaccaggg ccaccctccc acactcctat cctacaggga    180
taacaaccgg ccctcaggga tctcagagag attctctgca tccaggtcag gaaatacagc    240
ctccctgtcc attactggac tccagcctga cgacgaggct gactattact gctcagcatg    300
ggacagcagc ctcagtgctt gggtgttcgg cggagggacc aagctgaccg tcctaggtca    360
gcccaaggct gccccctcgg t                                              381

<210> SEQ ID NO 880
<211> LENGTH: 367
<212> TYPE: DNA
<213> ORGANISM: Homo sapiens

<400> SEQUENCE: 880
cttactgcac aggatccgtg gcctcctatg agctgactca gccaccctca gtgtccgtgt    60
ccccaggaca gacagccagc atcacctgct ctggagataa attgggggat aaatatgctt    120
gctggtatca gcagaagcca ggccagtccc ctgtgctggt catctatcaa gatagcaagc    180
ggccctcagg gatccctgag cgattctctg gctccaactc tgggaacaca gccactctga    240
ccatcagcgg gacccaggct atggatgagg ctgactatta ctgtcaggcg tgggacagca    300
gcactgtggt attcggcgga gggaccaagc tgaccgtcct aggtcagccc aaggctgccc    360
cctcggt                                                              367

<210> SEQ ID NO 881
<211> LENGTH: 371
<212> TYPE: DNA
<213> ORGANISM: Homo sapiens

<400> SEQUENCE: 881
actctggctc acagatacca ccggagagat tgtgttgacg cagtctccaa gcaccctgtc    60
tttctctcca ggagaaagag ccaccctctc ctgcagggcc agtcagatta ttaccagcag    120
ctacttagcc tggtaccagc agaaacctgg ccaggctccc aggctcctca tctatggtgg    180
atccagcagg gccactggca tcccaaacag gtttagtggc agtggggctg ggacagactt    240
cacgctcacc atcagcagac tggagcctga agatttttgca gtgtattact gtcaacaaca    300
tggtaactca ccggtcactt tcggcggagg gaccaaggtg gagatcaaag gaactgtggc    360
tgcaccatct g                                                          371

<210> SEQ ID NO 882
<211> LENGTH: 376
```

<212> TYPE: DNA
<213> ORGANISM: Homo sapiens

<400> SEQUENCE: 882
cttgctgccc agggtccaat tcccaggctg tggtgactca ggagccctca ctgactgtgt      60
ccccaggagg gacagtcact ctcacctgtg gctccagcac tggagctgtc accagtggtc     120
attatcccta ctggttccag cagaagcctg gccaagcccc caggacactg atttctgata     180
caagcaacaa atgttcttgg acccctggcc ggttctcagg ctccctcctt gggggcaaag     240
ctgccctgac cctttcgggt gcgcagcctg aggatgaggc tgactattat tgcttcctct     300
actttgatgg tcctatagtt ttcggcggag ggaccaagct gaccgtccta agtcagccca     360
aggctgcccc ctcggt                                                    376

<210> SEQ ID NO 883
<211> LENGTH: 385
<212> TYPE: DNA
<213> ORGANISM: Homo sapiens

<400> SEQUENCE: 883
ctctggatct ctggtgccta cggggacatc gtgatgaccc agtctccaga ttccctggct      60
gtgtctctgg gcgagagggc caccatcaac tgcaagtcca gccagagtgt tttgtggggc     120
cccaacaata gaactacttt agcttggtac cagcagaaac caggacagtc tcctaagttg     180
ctcatttact ggggatctac ccggaaatcc ggggtccctg accgattcag tggcagcggg     240
tctgggacag atttcactct caccatcagc agcctgcagg ctgaagatgt ggcagtttat     300
tactgtcagc attatcatac tccaccgtac acttttggcc aggggaccaa gctggagatc     360
aaacgaactg tggctgcacc atctg                                          385

<210> SEQ ID NO 884
<211> LENGTH: 363
<212> TYPE: DNA
<213> ORGANISM: Homo sapiens

<400> SEQUENCE: 884
tctgggtccc aggtgccaaa tgtgtcgtcc agatgaccca gtctccttcc accctgtctg      60
catctgtagg agacagagtc accatcactt gccgggccag tgagactgtt ggaacgtggt     120
tggcctggta tcgcagaaaa ccagggaaag cccctaacct cctgatctat gaggcctcta     180
ttttagaaag tggggtccca tcgaggttca gcggcagtgg atctgggaca gagttcactc     240
tcaccatcag cagcctgcag cctgatgatt ttgcaactta ttactgccaa cagtataata     300
cctggtggac attcggccaa gggaccaagg tggaaatcaa gcgaactgtg gctgcaccat     360
ctg                                                                  363

<210> SEQ ID NO 885
<211> LENGTH: 376
<212> TYPE: DNA
<213> ORGANISM: Homo sapiens

<400> SEQUENCE: 885
cttgctgccc agggtccaat tcccaggctg tggtgactca ggagccctca ctgactgtgt      60
ccccaggagg gacagtcact ctcacctgtg gctccagcac tggagctgtc accagtggtc     120
attatcccta ctggtttcag cagaaggctg gccaagcccc caggacactg atgtatgata     180
taagcatcaa actgtcctgg acccctgccc ggttctcagg cgccctcctt gggggcaaag     240

```
ctgccctgac cctttcgggt gcgcagcctg aggatgaggc tgaatattat tgtttactct    300
attataatgg tgtcagggtg ttcggcggag ggaccaaact gacagtccta ggtcagccca    360
aggctgcccc ctcggt                                                    376
```

<210> SEQ ID NO 886
<211> LENGTH: 378
<212> TYPE: DNA
<213> ORGANISM: Homo sapiens

<400> SEQUENCE: 886

```
cctcactctt tgcataggtt ctgtggtttc ttctgagctg actcaggacc ctgctgtgtc     60
tgtggccttg ggacagacag tcaggatcac atgccaagga cagcctcaa gaagctatta    120 tgcaagctgg taccagcaga agccaggaca ggcccctgta cttgtcatct atggtaaaaa    180
caaccggccc tcagggatcc cagaccgatt ctctggctcc agctcaggaa acacagcttc    240
cttgaccatc actggggctc aggcggaaga tgaggctgac tattactgta actcccggga    300
cagcagtggt aaccatgtgg tattcggcgg agggaccaag ctgaccgtcc taggtcagcc    360
caaggctgcc cctcggt                                                  378
```

<210> SEQ ID NO 887
<211> LENGTH: 379
<212> TYPE: DNA
<213> ORGANISM: Homo sapiens

<400> SEQUENCE: 887

```
ctcgggacac agggtcctgg gcccagtctg ccctgactca gcctgcctcc gtgtctgggt     60
ctcctggaca gtcgatcacc atctcctgca ctggaaccag cagtgatgtt gggagatata    120
accttgtctc ctggtaccaa caacacccag gcaaagcccc caaattcttg atttatgagg    180
tcagtaaggg gccctcaggg gtttctaatc gcttctctgg ctccaagtct ggcaacacgg    240
cctccctgac aatctctggg ctccaggctg aggacgaggc agattattac tgctgctcat    300
atgcaggtag tagcactttt gtcttcggaa ctgggaccac ggtcaccgtc ctaggtcagc    360
ccaaggccaa ccccacggt                                                379
```

<210> SEQ ID NO 888
<211> LENGTH: 373
<212> TYPE: DNA
<213> ORGANISM: Homo sapiens

<400> SEQUENCE: 888

```
ctcactgcac aggctctgag gcctcctatg agctgacaca gccaccctcg gtgtcagtgt     60
ccccaggaca gacggccagg atcacctgct ctggagatgc attgccaaag caatatgctt    120
attggtacca gcagaagcca ggccaggccc ctgtgctggt gatatataaa gacagtgaga    180
ggccctcagg gatccctgag cgattctctg gctccagctc agggacaaca gtcacgttga    240
ccatcagtgg agtccaggca gaagacgagg ctgactatta ctgtcaatca gcagacagca    300 gtggtacttta tgtggtattc ggcggaggga ccaagctgac cgtcctaggt cagcccaagg    360
ctgccccctc ggt                                                      373
```

<210> SEQ ID NO 889
<211> LENGTH: 381
<212> TYPE: DNA
<213> ORGANISM: Homo sapiens

<400> SEQUENCE: 889

```
cactcactct gcagtgtcag tggtccaggc aggactgact cagccaccct cggtgtccaa    60
ggacttgaga cagaccgcca cactcacctg cactgggaac agcaacaatg ttggcaacct   120
aggagcagct tggctgcagc agcaccaggg ccaccctccc acactcctat cctacaggga   180
taacaaccgg ccctcaggga tctcagagag attctctgca tccaggtcag gaaatacagc   240
ctccctgtcc attactggac tccagcctga cgacgaggct gactattact gctcagcatg   300
ggacagcagc tcagtgctt gggtgttcgg cggagggacc aagctgaccg tcctaggtca   360
gcccaaggct gcccctcgg t                                              381

<210> SEQ ID NO 890
<211> LENGTH: 367
<212> TYPE: DNA
<213> ORGANISM: Homo sapiens

<400> SEQUENCE: 890
cttactgcac aggatccgtg gcctcctatg agctgactca gccaccctca gtgtccgtgt    60
ccccaggaca gacagccagc atcacctgct ctggagataa attgggggat aaatatgctt   120
gctggtatca gcagaagcca ggccagtccc ctgtgctggt catctatcaa gatagcaagc   180
ggccctcagg gatccctgag cgattctctg gctccaactc tgggaacaca gccactctga   240
ccatcagcgg gacccaggct atggatgagg ctgactatta ctgtcaggcg tgggacagca   300
gcactgtggt attcggcgga gggaccaagc tgaccgtcct aggtcagccc aaggctgccc   360
cctcggt                                                             367

<210> SEQ ID NO 891
<211> LENGTH: 376
<212> TYPE: DNA
<213> ORGANISM: Homo sapiens

<400> SEQUENCE: 891
ctcagggcac agggtcctgg gctcagtctg ccctgactca gcctcgctca gtgtccgggt    60
ctcctggaca gtcagtcacc atctcctgca ctggaaccag cagtgatgtt ggtagttata   120
actatgtctc ctggtaccaa cagcacccag gcaaagcccc cacactcatg atttatgatg   180
tcactaagcg gccctcaggg gtccctgatc gcttctctgg ttccaagtct ggcaacacgg   240
cctccctgac catctctggg ctccaggctg aggatgaggc tgattattac tgctgctcat   300
atgcaggcaa ctcttatgtc ttcggaactg ggaccaaggt caccgtccta ggtcagccca   360
aggccaaccc cacggt                                                   376

<210> SEQ ID NO 892
<211> LENGTH: 373
<212> TYPE: DNA
<213> ORGANISM: Homo sapiens

<400> SEQUENCE: 892
ctcactgcac aggctctgag gcctcctatg agctgacaca gccaccctcg gtgtcagtgt    60
ccccaggaca gacggccagg atcacctgct ctggagatgc attgccaaag cactttgctt   120
attggtacca gcagaagcca ggccaggccc tgtactggt gatatataaa gacactgaga   180
ggccctcagg gatccctgag cgattctctg gctccagctc agggacaaca gtcacgttga   240
ccatcagtgg agtccaggca gaagacgagg ctgactatta ctgtcaatca ccagacagca   300
gtggtactaa tgaagtcttc ggaactggga ccaaggtcac cgtcctaagt cagcccaagg   360
```

| | |
|---|---|
| ccaaccccac ggt | 373 |

<210> SEQ ID NO 893
<211> LENGTH: 371
<212> TYPE: DNA
<213> ORGANISM: Homo sapiens

<400> SEQUENCE: 893

| | |
|---|---|
| actctggctc acagatacca ccggagaaat tgtgttgacg cagtctccag gcaccctgtc | 60 |
| tttgtctcca ggggaaagag ccaccctctc ctgcagggcc agtcagagtg ttagcagcag | 120 |
| ctacttagcc tggtaccagc agaaacctgg ccaggctccc aggctcctca tctatggtgc | 180 |
| atccagcagg gccactggca tcccagacag gttcagtggc agtgggtctg ggacagactt | 240 |
| cactctcacc atcagcagac tggagcctga agattttgca gtgtattact gtcagcagta | 300 |
| tggtagctca ccttggacgt tcggccaagg gaccaaggtg gaaatcaaac gaactgtggc | 360 |
| tgcaccatct g | 371 |

<210> SEQ ID NO 894
<211> LENGTH: 368
<212> TYPE: DNA
<213> ORGANISM: Homo sapiens

<400> SEQUENCE: 894

| | |
|---|---|
| actctggctc acagatacca ccggagaaat tgtgttgacg cagtctccag gcaccctgtc | 60 |
| tttgtctcca ggggaaagag ccttcctctc ctgcagggcc agtcagactg ttcccagcag | 120 |
| ctacttagcc tggtaccagc agagacctgg ccaagttccc aggctcctca tctatgatgc | 180 |
| atccagcagg gccactggca tctcagacag gtttagtggc agtgggtctg ggacagactt | 240 |
| cactctcacc atcaacacac tggagcctga agattctgct gtgtattact gtcagcaata | 300 |
| tggtagctca ccgacgttcg gccaagggac caaggtggaa atcaaacgaa ctgtggctgc | 360 |
| accatctg | 368 |

<210> SEQ ID NO 895
<211> LENGTH: 378
<212> TYPE: DNA
<213> ORGANISM: Homo sapiens

<400> SEQUENCE: 895

| | |
|---|---|
| cctcactctt tgcataggtt ctgtggtttc ttctgagctg actcaggacc ctgctgtgtc | 60 |
| tgtggccttg ggacagacag tcaggatcac atgccaagga gacagcctca gaagctatta | 120 |
| tgcaagctgg taccagcaga agccaggaca ggcccctgta cttgtcatct atggtaaaaa | 180 |
| caaccggccc tcagggatcc cagaccgatt ctctggctcc agctcaggaa acacagcttc | 240 |
| cttgaccatc actggggctc aggcggaaga tgaggctgac tattactgta actcccggga | 300 |
| cagcagtggt aaccatgtgg tattcggcgg agggaccaag ctgaccgtcc taggtcagcc | 360 |
| caaggctgcc ccctcggt | 378 |

<210> SEQ ID NO 896
<211> LENGTH: 368
<212> TYPE: DNA
<213> ORGANISM: Homo sapiens

<400> SEQUENCE: 896

| | |
|---|---|
| actctggctc acagatacca ccggagaaat tgtgttgaca cagtctccag ccaccctgtc | 60 |
| tttgtctcca ggggaaagag ccaccctctc ctgcagggcc agtcagagtg ttagcaccta | 120 |

```
cttagcctgg taccaacaga aacctggcca gcctcccaga ctcctcatct atgatgcatc    180
caacagggcc actggcatcc cagccaggtt cagtggcagt gggtctggga cagacttcac    240
tctcaccatc agcagcctag agcctgaaga ttctgcagtt tattactgtc agcagcgtag    300
cacctggcct gcgactttcg gccctgggac caaagtggat atcaaacgaa ctgtggctgc    360
accatctg                                                             368
```

<210> SEQ ID NO 897
<211> LENGTH: 373
<212> TYPE: DNA
<213> ORGANISM: Homo sapiens

<400> SEQUENCE: 897

```
ctcactgcac aggctctgtg acctcctatg tgctgactca gccaccctcg gtgtcagtgg     60
ccccaggaaa gacggccagg attacctgtg ggggaaacaa cattggaagt aaaagtgtgc    120
actggtacca gcagaagcca ggccaggccc ctgtgctggt cgtctatgat gatagcgacc    180
ggccctcagg gatccctgag cgattctctg ctccaactc tgggaacacg gccaccctga    240
ccatcagcag ggtcgaagcc ggggatgagg ccgactatta ctgtcaggtg tgggatagta    300
gtagtgatca tgtggtattc ggcggaggga ccaagctgac cgtcctaggt cagcccaagg    360
ctgccccctc ggt                                                       373
```

<210> SEQ ID NO 898
<211> LENGTH: 373
<212> TYPE: DNA
<213> ORGANISM: Homo sapiens

<400> SEQUENCE: 898

```
ctcactgcac aggctctgag gcctcctatg agctgacaca gccaccctcg gtgtcagtgt     60
ccccaggaca gacggccagg atcacctgct ctggagatgc attgccaaag caatatgctt    120
attggtacca gcagaagcca ggccaggccc ctgtgctggt gatatataaa gacagtgaga    180
ggccctcagg gatccctgag cgattctctg ctccagctc agggacaaca gtcacgttga    240
ccatcagtgg agtccaggca gaagacgagg ctgactatta ctgtcaatca gcagacagca    300
gtggtactta tgtggtattc ggcggaggga ccaagctgac cgtcctaggt cagcccaagg    360
ctgccccctc ggt                                                       373
```

<210> SEQ ID NO 899
<211> LENGTH: 379
<212> TYPE: DNA
<213> ORGANISM: Homo sapiens

<400> SEQUENCE: 899

```
ctcactgcac agggtcctgg gcccagtctg tattgacgca gccgccctca gtgtctgcag     60
ccccaggaca gaaggtcacc atctcctgct ctggaagcac ctccaacata gttcataatt    120
ttgtatcgtg gttccagcat ctcccaggaa cagcccccaa acttctcata tatgacaata    180
agaggcggcc ctcagggatt cctgaccgat tctctggctc caagtctggc gcgtcagcca    240
ccctggacat cactgactc cagactgggg acgaggccga ttattactgc ggagcgtggg    300
atagcagcct gagtgctgtg gtcttcggcg gagggaccaa gctgaccgtc ctgggtcagc    360
ccaaggctgc cccctcggt                                                 379
```

<210> SEQ ID NO 900

```
<211> LENGTH: 29
<212> TYPE: DNA
<213> ORGANISM: Artificial
<220> FEATURE:
<223> OTHER INFORMATION: PCR primer

<400> SEQUENCE: 900
ccactacgcc tccgctttcc tctctatgg                                29

<210> SEQ ID NO 901
<211> LENGTH: 19
<212> TYPE: DNA
<213> ORGANISM: Artificial
<220> FEATURE:
<223> OTHER INFORMATION: PCR primer

<400> SEQUENCE: 901
ctgccccggg ttcctcatt                                           19

<210> SEQ ID NO 902
<211> LENGTH: 18
<212> TYPE: DNA
<213> ORGANISM: Artificial
<220> FEATURE:
<223> OTHER INFORMATION: PCR primer

<400> SEQUENCE: 902
acagaagttc cagggcag                                            18

<210> SEQ ID NO 903
<211> LENGTH: 18
<212> TYPE: DNA
<213> ORGANISM: Artificial
<220> FEATURE:
<223> OTHER INFORMATION: PCR primer

<400> SEQUENCE: 903
agactccagg aagggcag                                            18

<210> SEQ ID NO 904
<211> LENGTH: 18
<212> TYPE: DNA
<213> ORGANISM: Artificial
<220> FEATURE:
<223> OTHER INFORMATION: PCR primer

<400> SEQUENCE: 904
agactccatg aagggcca                                            18

<210> SEQ ID NO 905
<211> LENGTH: 18
<212> TYPE: DNA
<213> ORGANISM: Artificial
<220> FEATURE:
<223> OTHER INFORMATION: PCR primer

<400> SEQUENCE: 905
agactctgtg aaaggccg                                            18

<210> SEQ ID NO 906
<211> LENGTH: 20
<212> TYPE: DNA
<213> ORGANISM: Artificial
<220> FEATURE:
<223> OTHER INFORMATION: PCR primer

<400> SEQUENCE: 906
```
agcacatctc tgaagaccag                                         20

<210> SEQ ID NO 907
<211> LENGTH: 20
<212> TYPE: DNA
<213> ORGANISM: Artificial
<220> FEATURE:
<223> OTHER INFORMATION: PCR primer

<400> SEQUENCE: 907
agcacatctc tgaagagcag                                         20

<210> SEQ ID NO 908
<211> LENGTH: 20
<212> TYPE: DNA
<213> ORGANISM: Artificial
<220> FEATURE:
<223> OTHER INFORMATION: PCR primer

<400> SEQUENCE: 908
agcacgtctc tgaagaacag                                         20

<210> SEQ ID NO 909
<211> LENGTH: 25
<212> TYPE: DNA
<213> ORGANISM: Artificial
<220> FEATURE:
<223> OTHER INFORMATION: PCR primer

<400> SEQUENCE: 909
attatgcagt atctgtgaaa agtcg                                   25

<210> SEQ ID NO 910
<211> LENGTH: 17
<212> TYPE: DNA
<213> ORGANISM: Artificial
<220> FEATURE:
<223> OTHER INFORMATION: PCR primer

<400> SEQUENCE: 910
cagaagctcc agggcag                                            17

<210> SEQ ID NO 911
<211> LENGTH: 19
<212> TYPE: DNA
<213> ORGANISM: Artificial
<220> FEATURE:
<223> OTHER INFORMATION: PCR primer

<400> SEQUENCE: 911
cagactctgt gaagggcag                                          19

<210> SEQ ID NO 912
<211> LENGTH: 19
<212> TYPE: DNA
<213> ORGANISM: Artificial
<220> FEATURE:
<223> OTHER INFORMATION: PCR primer

<400> SEQUENCE: 912
cagagaagtt ccagggcag                                          19

<210> SEQ ID NO 913
<211> LENGTH: 17
<212> TYPE: DNA

```
<213> ORGANISM: Artificial
<220> FEATURE:
<223> OTHER INFORMATION: PCR primer

<400> SEQUENCE: 913
cagggcttca caggacg                                                  17

<210> SEQ ID NO 914
<211> LENGTH: 18
<212> TYPE: DNA
<213> ORGANISM: Artificial
<220> FEATURE:
<223> OTHER INFORMATION: PCR primer

<400> SEQUENCE: 914
cccctccctc aagagtcg                                                 18

<210> SEQ ID NO 915
<211> LENGTH: 18
<212> TYPE: DNA
<213> ORGANISM: Artificial
<220> FEATURE:
<223> OTHER INFORMATION: PCR primer

<400> SEQUENCE: 915
cccgtccctc aagagtct                                                 18

<210> SEQ ID NO 916
<211> LENGTH: 17
<212> TYPE: DNA
<213> ORGANISM: Artificial
<220> FEATURE:
<223> OTHER INFORMATION: PCR primer

<400> SEQUENCE: 916
ccgtccctca agagtcg                                                  17

<210> SEQ ID NO 917
<211> LENGTH: 17
<212> TYPE: DNA
<213> ORGANISM: Artificial
<220> FEATURE:
<223> OTHER INFORMATION: PCR primer

<400> SEQUENCE: 917
ccgtccttcc aaggcca                                                  17

<210> SEQ ID NO 918
<211> LENGTH: 21
<212> TYPE: DNA
<213> ORGANISM: Artificial
<220> FEATURE:
<223> OTHER INFORMATION: PCR primer

<400> SEQUENCE: 918
cgcacagaaa ttccaggaca g                                             21

<210> SEQ ID NO 919
<211> LENGTH: 21
<212> TYPE: DNA
<213> ORGANISM: Artificial
<220> FEATURE:
<223> OTHER INFORMATION: PCR primer

<400> SEQUENCE: 919
cgcacagaag ttccaggaaa g                                             21
```

<210> SEQ ID NO 920
<211> LENGTH: 18
<212> TYPE: DNA
<213> ORGANISM: Artificial
<220> FEATURE:
<223> OTHER INFORMATION: PCR primer

<400> SEQUENCE: 920
cgcgtctgtg aaaggcag                                                        18

<210> SEQ ID NO 921
<211> LENGTH: 17
<212> TYPE: DNA
<213> ORGANISM: Artificial
<220> FEATURE:
<223> OTHER INFORMATION: PCR primer

<400> SEQUENCE: 921
gactccgtga agggccg                                                         17

<210> SEQ ID NO 922
<211> LENGTH: 17
<212> TYPE: DNA
<213> ORGANISM: Artificial
<220> FEATURE:
<223> OTHER INFORMATION: PCR primer

<400> SEQUENCE: 922
gactcagtga agggccg                                                         17

<210> SEQ ID NO 923
<211> LENGTH: 17
<212> TYPE: DNA
<213> ORGANISM: Artificial
<220> FEATURE:
<223> OTHER INFORMATION: PCR primer

<400> SEQUENCE: 923
gactccgtga agggcag                                                         17

<210> SEQ ID NO 924
<211> LENGTH: 17
<212> TYPE: DNA
<213> ORGANISM: Artificial
<220> FEATURE:
<223> OTHER INFORMATION: PCR primer

<400> SEQUENCE: 924
gactctgtga agggccg                                                         17

<210> SEQ ID NO 925
<211> LENGTH: 20
<212> TYPE: DNA
<213> ORGANISM: Artificial
<220> FEATURE:
<223> OTHER INFORMATION: PCR primer

<400> SEQUENCE: 925
gcaaactctg tgaagggcag                                                      20

<210> SEQ ID NO 926
<211> LENGTH: 20
<212> TYPE: DNA
<213> ORGANISM: Artificial
<220> FEATURE:

```
<223> OTHER INFORMATION: PCR primer

<400> SEQUENCE: 926
gcacagaagt tcagggcag                                                   20

<210> SEQ ID NO 927
<211> LENGTH: 17
<212> TYPE: DNA
<213> ORGANISM: Artificial
<220> FEATURE:
<223> OTHER INFORMATION: PCR primer

<400> SEQUENCE: 927
gcacccgtga aaggcag                                                     17

<210> SEQ ID NO 928
<211> LENGTH: 19
<212> TYPE: DNA
<213> ORGANISM: Artificial
<220> FEATURE:
<223> OTHER INFORMATION: PCR primer

<400> SEQUENCE: 928
gcccatctct gaagagcag                                                   19

<210> SEQ ID NO 929
<211> LENGTH: 17
<212> TYPE: DNA
<213> ORGANISM: Artificial
<220> FEATURE:
<223> OTHER INFORMATION: PCR primer

<400> SEQUENCE: 929
gcgtcggtga aaggcag                                                     17

<210> SEQ ID NO 930
<211> LENGTH: 15
<212> TYPE: DNA
<213> ORGANISM: Artificial
<220> FEATURE:
<223> OTHER INFORMATION: PCR primer

<400> SEQUENCE: 930
ctccgtgaag cgccg                                                       15

<210> SEQ ID NO 931
<211> LENGTH: 18
<212> TYPE: DNA
<213> ORGANISM: Artificial
<220> FEATURE:
<223> OTHER INFORMATION: PCR primer

<400> SEQUENCE: 931
tgcgtctgtg aaaggcag                                                    18

<210> SEQ ID NO 932
<211> LENGTH: 22
<212> TYPE: DNA
<213> ORGANISM: Artificial
<220> FEATURE:
<223> OTHER INFORMATION: PCR primer

<400> SEQUENCE: 932
cttacctgag gagacggtga cc                                               22
```

```
<210> SEQ ID NO 933
<211> LENGTH: 22
<212> TYPE: DNA
<213> ORGANISM: Artificial
<220> FEATURE:
<223> OTHER INFORMATION: PCR primer

<400> SEQUENCE: 933
ctcacctgag gagacagtga cc                                              22

<210> SEQ ID NO 934
<211> LENGTH: 22
<212> TYPE: DNA
<213> ORGANISM: Artificial
<220> FEATURE:
<223> OTHER INFORMATION: PCR primer

<400> SEQUENCE: 934
cttacctgaa gagacggtga cc                                              22

<210> SEQ ID NO 935
<211> LENGTH: 55
<212> TYPE: DNA
<213> ORGANISM: Artificial
<220> FEATURE:
<223> OTHER INFORMATION: PCR primer

<400> SEQUENCE: 935
ctcggcattc ctgctgaacc gctcttccga tctcttacct gaggagacgg tgacc          55

<210> SEQ ID NO 936
<211> LENGTH: 55
<212> TYPE: DNA
<213> ORGANISM: Artificial
<220> FEATURE:
<223> OTHER INFORMATION: PCR primer

<400> SEQUENCE: 936
ctcggcattc ctgctgaacc gctcttccga tctctcacct gaggagacag tgacc          55

<210> SEQ ID NO 937
<211> LENGTH: 55
<212> TYPE: DNA
<213> ORGANISM: Artificial
<220> FEATURE:
<223> OTHER INFORMATION: PCR primer

<400> SEQUENCE: 937
ctcggcattc ctgctgaacc gctcttccga tctcttacct gaagagacgg tgacc          55

<210> SEQ ID NO 938
<211> LENGTH: 51
<212> TYPE: DNA
<213> ORGANISM: Artificial
<220> FEATURE:
<223> OTHER INFORMATION: PCR primer

<400> SEQUENCE: 938
acactctttc cctacacgac gctcttccga tctacagaag ttccagggca g              51

<210> SEQ ID NO 939
<211> LENGTH: 51
<212> TYPE: DNA
<213> ORGANISM: Artificial
<220> FEATURE:
<223> OTHER INFORMATION: PCR primer
```

```
<400> SEQUENCE: 939
acactctttc cctacacgac gctcttccga tctagactcc aggaagggca g            51

<210> SEQ ID NO 940
<211> LENGTH: 51
<212> TYPE: DNA
<213> ORGANISM: Artificial
<220> FEATURE:
<223> OTHER INFORMATION: PCR primer

<400> SEQUENCE: 940
acactctttc cctacacgac gctcttccga tctagactcc atgaagggcc a            51

<210> SEQ ID NO 941
<211> LENGTH: 51
<212> TYPE: DNA
<213> ORGANISM: Artificial
<220> FEATURE:
<223> OTHER INFORMATION: PCR primer

<400> SEQUENCE: 941
acactctttc cctacacgac gctcttccga tctagactct gtgaaaggcc g            51

<210> SEQ ID NO 942
<211> LENGTH: 53
<212> TYPE: DNA
<213> ORGANISM: Artificial
<220> FEATURE:
<223> OTHER INFORMATION: PCR primer

<400> SEQUENCE: 942
acactctttc cctacacgac gctcttccga tctagcacat ctctgaagac cag          53

<210> SEQ ID NO 943
<211> LENGTH: 53
<212> TYPE: DNA
<213> ORGANISM: Artificial
<220> FEATURE:
<223> OTHER INFORMATION: PCR primer

<400> SEQUENCE: 943
acactctttc cctacacgac gctcttccga tctagcacat ctctgaagag cag          53

<210> SEQ ID NO 944
<211> LENGTH: 53
<212> TYPE: DNA
<213> ORGANISM: Artificial
<220> FEATURE:
<223> OTHER INFORMATION: PCR primer

<400> SEQUENCE: 944
acactctttc cctacacgac gctcttccga tctagcacgt ctctgaagaa cag          53

<210> SEQ ID NO 945
<211> LENGTH: 58
<212> TYPE: DNA
<213> ORGANISM: Artificial
<220> FEATURE:
<223> OTHER INFORMATION: PCR primer

<400> SEQUENCE: 945
acactctttc cctacacgac gctcttccga tctattatgc agtatctgtg aaaagtcg     58

<210> SEQ ID NO 946
<211> LENGTH: 50
```

-continued

<212> TYPE: DNA
<213> ORGANISM: Artificial
<220> FEATURE:
<223> OTHER INFORMATION: PCR primer

<400> SEQUENCE: 946
acactctttc cctacacgac gctcttccga tctcagaagc tccagggcag    50

<210> SEQ ID NO 947
<211> LENGTH: 52
<212> TYPE: DNA
<213> ORGANISM: Artificial
<220> FEATURE:
<223> OTHER INFORMATION: PCR primer

<400> SEQUENCE: 947
acactctttc cctacacgac gctcttccga tctcagactc tgtgaagggc ag    52

<210> SEQ ID NO 948
<211> LENGTH: 52
<212> TYPE: DNA
<213> ORGANISM: Artificial
<220> FEATURE:
<223> OTHER INFORMATION: PCR primer

<400> SEQUENCE: 948
acactctttc cctacacgac gctcttccga tctcagagaa gttccagggc ag    52

<210> SEQ ID NO 949
<211> LENGTH: 50
<212> TYPE: DNA
<213> ORGANISM: Artificial
<220> FEATURE:
<223> OTHER INFORMATION: PCR primer

<400> SEQUENCE: 949
acactctttc cctacacgac gctcttccga tctcagggct tcacaggacg    50

<210> SEQ ID NO 950
<211> LENGTH: 51
<212> TYPE: DNA
<213> ORGANISM: Artificial
<220> FEATURE:
<223> OTHER INFORMATION: PCR primer

<400> SEQUENCE: 950
acactctttc cctacacgac gctcttccga tctcccctcc ctcaagagtc g    51

<210> SEQ ID NO 951
<211> LENGTH: 51
<212> TYPE: DNA
<213> ORGANISM: Artificial
<220> FEATURE:
<223> OTHER INFORMATION: PCR primer

<400> SEQUENCE: 951
acactctttc cctacacgac gctcttccga tctcccgtcc ctcaagagtc t    51

<210> SEQ ID NO 952
<211> LENGTH: 50
<212> TYPE: DNA
<213> ORGANISM: Artificial
<220> FEATURE:
<223> OTHER INFORMATION: PCR primer

<400> SEQUENCE: 952

```
acactctttc cctacacgac gctcttccga tctccgtccc tcaagagtcg          50

<210> SEQ ID NO 953
<211> LENGTH: 50
<212> TYPE: DNA
<213> ORGANISM: Artificial
<220> FEATURE:
<223> OTHER INFORMATION: PCR primer

<400> SEQUENCE: 953
acactctttc cctacacgac gctcttccga tctccgtcct tccaaggcca          50

<210> SEQ ID NO 954
<211> LENGTH: 54
<212> TYPE: DNA
<213> ORGANISM: Artificial
<220> FEATURE:
<223> OTHER INFORMATION: PCR primer

<400> SEQUENCE: 954
acactctttc cctacacgac gctcttccga tctcgcacag aaattccagg acag     54

<210> SEQ ID NO 955
<211> LENGTH: 54
<212> TYPE: DNA
<213> ORGANISM: Artificial
<220> FEATURE:
<223> OTHER INFORMATION: PCR primer

<400> SEQUENCE: 955
acactctttc cctacacgac gctcttccga tctcgcacag aagttccagg aaag     54

<210> SEQ ID NO 956
<211> LENGTH: 51
<212> TYPE: DNA
<213> ORGANISM: Artificial
<220> FEATURE:
<223> OTHER INFORMATION: PCR primer

<400> SEQUENCE: 956
acactctttc cctacacgac gctcttccga tctcgcgtct gtgaaaggca g        51

<210> SEQ ID NO 957
<211> LENGTH: 50
<212> TYPE: DNA
<213> ORGANISM: Artificial
<220> FEATURE:
<223> OTHER INFORMATION: PCR primer

<400> SEQUENCE: 957
acactctttc cctacacgac gctcttccga tctgactccg tgaagggccg          50

<210> SEQ ID NO 958
<211> LENGTH: 50
<212> TYPE: DNA
<213> ORGANISM: Artificial
<220> FEATURE:
<223> OTHER INFORMATION: PCR primer

<400> SEQUENCE: 958
acactctttc cctacacgac gctcttccga tctgactcag tgaagggccg          50

<210> SEQ ID NO 959
<211> LENGTH: 50
<212> TYPE: DNA
<213> ORGANISM: Artificial
```

```
<220> FEATURE:
<223> OTHER INFORMATION: PCR primer

<400> SEQUENCE: 959
acactctttc cctacacgac gctcttccga tctgactccg tgaagggcag                50

<210> SEQ ID NO 960
<211> LENGTH: 50
<212> TYPE: DNA
<213> ORGANISM: Artificial
<220> FEATURE:
<223> OTHER INFORMATION: PCR primer

<400> SEQUENCE: 960
acactctttc cctacacgac gctcttccga tctgactctg tgaagggccg                50

<210> SEQ ID NO 961
<211> LENGTH: 53
<212> TYPE: DNA
<213> ORGANISM: Artificial
<220> FEATURE:
<223> OTHER INFORMATION: PCR primer

<400> SEQUENCE: 961
acactctttc cctacacgac gctcttccga tctgcaaact ctgtgaaggg cag            53

<210> SEQ ID NO 962
<211> LENGTH: 53
<212> TYPE: DNA
<213> ORGANISM: Artificial
<220> FEATURE:
<223> OTHER INFORMATION: PCR primer

<400> SEQUENCE: 962
acactctttc cctacacgac gctcttccga tctgcacaga agtttcaggg cag            53

<210> SEQ ID NO 963
<211> LENGTH: 50
<212> TYPE: DNA
<213> ORGANISM: Artificial
<220> FEATURE:
<223> OTHER INFORMATION: PCR primer

<400> SEQUENCE: 963
acactctttc cctacacgac gctcttccga tctgcacccg tgaaaggcag                50

<210> SEQ ID NO 964
<211> LENGTH: 52
<212> TYPE: DNA
<213> ORGANISM: Artificial
<220> FEATURE:
<223> OTHER INFORMATION: PCR primer

<400> SEQUENCE: 964
acactctttc cctacacgac gctcttccga tctgcccatc tctgaagagc ag             52

<210> SEQ ID NO 965
<211> LENGTH: 50
<212> TYPE: DNA
<213> ORGANISM: Artificial
<220> FEATURE:
<223> OTHER INFORMATION: PCR primer

<400> SEQUENCE: 965
acactctttc cctacacgac gctcttccga tctgcgtcgg tgaaaggcag                50
```

<210> SEQ ID NO 966
<211> LENGTH: 48
<212> TYPE: DNA
<213> ORGANISM: Artificial
<220> FEATURE:
<223> OTHER INFORMATION: PCR primer

<400> SEQUENCE: 966
acactctttc cctacacgac gctcttccga tctctccgtg aagcgccg            48

<210> SEQ ID NO 967
<211> LENGTH: 51
<212> TYPE: DNA
<213> ORGANISM: Artificial
<220> FEATURE:
<223> OTHER INFORMATION: PCR primer

<400> SEQUENCE: 967
acactctttc cctacacgac gctcttccga tcttgcgtct gtgaaaggca g         51

<210> SEQ ID NO 968
<211> LENGTH: 53
<212> TYPE: DNA
<213> ORGANISM: Artificial
<220> FEATURE:
<223> OTHER INFORMATION: PCR primer

<400> SEQUENCE: 968
acactctttc cctacacgac gctcttccga tctcctggag tggatgggga tca       53

<210> SEQ ID NO 969
<211> LENGTH: 53
<212> TYPE: DNA
<213> ORGANISM: Artificial
<220> FEATURE:
<223> OTHER INFORMATION: PCR primer

<400> SEQUENCE: 969
acactctttc cctacacgac gctcttccga tctggctgga gtgggtctca gtt       53

<210> SEQ ID NO 970
<211> LENGTH: 53
<212> TYPE: DNA
<213> ORGANISM: Artificial
<220> FEATURE:
<223> OTHER INFORMATION: PCR primer

<400> SEQUENCE: 970
acactctttc cctacacgac gctcttccga tctagggctt gagtggatgg gac       53

<210> SEQ ID NO 971
<211> LENGTH: 53
<212> TYPE: DNA
<213> ORGANISM: Artificial
<220> FEATURE:
<223> OTHER INFORMATION: PCR primer

<400> SEQUENCE: 971
acactctttc cctacacgac gctcttccga tctagagctt gggtggatgg gac       53

<210> SEQ ID NO 972
<211> LENGTH: 52
<212> TYPE: DNA
<213> ORGANISM: Artificial
<220> FEATURE:
<223> OTHER INFORMATION: PCR primer

<400> SEQUENCE: 972
acactctttc cctacacgac gctcttccga tctaaggggc tggagtgggt tt        52

<210> SEQ ID NO 973
<211> LENGTH: 56
<212> TYPE: DNA
<213> ORGANISM: Artificial
<220> FEATURE:
<223> OTHER INFORMATION: PCR primer

<400> SEQUENCE: 973
acactctttc cctacacgac gctcttccga tctcctggag tggattgggt acatct    56

<210> SEQ ID NO 974
<211> LENGTH: 53
<212> TYPE: DNA
<213> ORGANISM: Artificial
<220> FEATURE:
<223> OTHER INFORMATION: PCR primer

<400> SEQUENCE: 974
acactctttc cctacacgac gctcttccga tctggaaggg gctggagtgg att       53

<210> SEQ ID NO 975
<211> LENGTH: 53
<212> TYPE: DNA
<213> ORGANISM: Artificial
<220> FEATURE:
<223> OTHER INFORMATION: PCR primer

<400> SEQUENCE: 975
acactctttc cctacacgac gctcttccga tctagggtct ggagtgggtc tca       53

<210> SEQ ID NO 976
<211> LENGTH: 52
<212> TYPE: DNA
<213> ORGANISM: Artificial
<220> FEATURE:
<223> OTHER INFORMATION: PCR primer

<400> SEQUENCE: 976
acactctttc cctacacgac gctcttccga tctctggagt ggcttgcaca ca        52

<210> SEQ ID NO 977
<211> LENGTH: 54
<212> TYPE: DNA
<213> ORGANISM: Artificial
<220> FEATURE:
<223> OTHER INFORMATION: PCR primer

<400> SEQUENCE: 977
acactctttc cctacacgac gctcttccga tctctggagt ggatggggag gatt      54

<210> SEQ ID NO 978
<211> LENGTH: 52
<212> TYPE: DNA
<213> ORGANISM: Artificial
<220> FEATURE:
<223> OTHER INFORMATION: PCR primer

<400> SEQUENCE: 978
acactctttc cctacacgac gctcttccga tctaaaggcc ctggagtggc tt        52

<210> SEQ ID NO 979

```
<211> LENGTH: 53
<212> TYPE: DNA
<213> ORGANISM: Artificial
<220> FEATURE:
<223> OTHER INFORMATION: PCR primer

<400> SEQUENCE: 979
acactctttc cctacacgac gctcttccga tctcctggag tggcttgcac tca          53

<210> SEQ ID NO 980
<211> LENGTH: 53
<212> TYPE: DNA
<213> ORGANISM: Artificial
<220> FEATURE:
<223> OTHER INFORMATION: PCR primer

<400> SEQUENCE: 980
acactctttc cctacacgac gctcttccga tctagggctt gagtggatgg gag          53

<210> SEQ ID NO 981
<211> LENGTH: 58
<212> TYPE: DNA
<213> ORGANISM: Artificial
<220> FEATURE:
<223> OTHER INFORMATION: PCR primer

<400> SEQUENCE: 981
acactctttc cctacacgac gctcttccga tctcagggaa gggactggaa tatgtttc     58

<210> SEQ ID NO 982
<211> LENGTH: 53
<212> TYPE: DNA
<213> ORGANISM: Artificial
<220> FEATURE:
<223> OTHER INFORMATION: PCR primer

<400> SEQUENCE: 982
acactctttc cctacacgac gctcttccga tctggaaagg gctggagtgg gtt          53

<210> SEQ ID NO 983
<211> LENGTH: 59
<212> TYPE: DNA
<213> ORGANISM: Artificial
<220> FEATURE:
<223> OTHER INFORMATION: PCR primer

<400> SEQUENCE: 983
acactctttc cctacacgac gctcttccga tctgagtggg tctctcttat tagttggga    59

<210> SEQ ID NO 984
<211> LENGTH: 53
<212> TYPE: DNA
<213> ORGANISM: Artificial
<220> FEATURE:
<223> OTHER INFORMATION: PCR primer

<400> SEQUENCE: 984
acactctttc cctacacgac gctcttccga tctgctggag tgggtctcat cca          53

<210> SEQ ID NO 985
<211> LENGTH: 53
<212> TYPE: DNA
<213> ORGANISM: Artificial
<220> FEATURE:
<223> OTHER INFORMATION: PCR primer

<400> SEQUENCE: 985
```
acactctttc cctacacgac gctcttccga tctgggctgg agtgggtagg ttt       53

<210> SEQ ID NO 986
<211> LENGTH: 57
<212> TYPE: DNA
<213> ORGANISM: Artificial
<220> FEATURE:
<223> OTHER INFORMATION: PCR primer

<400> SEQUENCE: 986
acactctttc cctacacgac gctcttccga tctgttggcc gtactagaaa caaagct   57

<210> SEQ ID NO 987
<211> LENGTH: 53
<212> TYPE: DNA
<213> ORGANISM: Artificial
<220> FEATURE:
<223> OTHER INFORMATION: PCR primer

<400> SEQUENCE: 987
acactctttc cctacacgac gctcttccga tctctggagt gggtatcggg tgt       53

<210> SEQ ID NO 988
<211> LENGTH: 54
<212> TYPE: DNA
<213> ORGANISM: Artificial
<220> FEATURE:
<223> OTHER INFORMATION: PCR primer

<400> SEQUENCE: 988
acactctttc cctacacgac gctcttccga tctgagtgga tgggattggt gtgc      54

<210> SEQ ID NO 989
<211> LENGTH: 58
<212> TYPE: DNA
<213> ORGANISM: Artificial
<220> FEATURE:
<223> OTHER INFORMATION: PCR primer

<400> SEQUENCE: 989
acactctttc cctacacgac gctcttccga tctcttgagt ggatgggagg ttttgatc  58

<210> SEQ ID NO 990
<211> LENGTH: 54
<212> TYPE: DNA
<213> ORGANISM: Artificial
<220> FEATURE:
<223> OTHER INFORMATION: PCR primer

<400> SEQUENCE: 990
acactctttc cctacacgac gctcttccga tctaggcttg agtggatggg atgg      54

<210> SEQ ID NO 991
<211> LENGTH: 53
<212> TYPE: DNA
<213> ORGANISM: Artificial
<220> FEATURE:
<223> OTHER INFORMATION: PCR primer

<400> SEQUENCE: 991
acactctttc cctacacgac gctcttccga tctcctggag tggcttgctc aca       53

<210> SEQ ID NO 992
<211> LENGTH: 58
<212> TYPE: DNA

```
<213> ORGANISM: Artificial
<220> FEATURE:
<223> OTHER INFORMATION: PCR primer

<400> SEQUENCE: 992
acactctttc cctacacgac gctcttccga tctagtgggt ggcagttata tggtatga       58

<210> SEQ ID NO 993
<211> LENGTH: 56
<212> TYPE: DNA
<213> ORGANISM: Artificial
<220> FEATURE:
<223> OTHER INFORMATION: PCR primer

<400> SEQUENCE: 993
acactctttc cctacacgac gctcttccga tcttgagtgg ataggatgga tcgtcg         56

<210> SEQ ID NO 994
<211> LENGTH: 58
<212> TYPE: DNA
<213> ORGANISM: Artificial
<220> FEATURE:
<223> OTHER INFORMATION: PCR primer

<400> SEQUENCE: 994
acactctttc cctacacgac gctcttccga tctgggttgg ccgtattaaa agcaaaac      58

<210> SEQ ID NO 995
<211> LENGTH: 59
<212> TYPE: DNA
<213> ORGANISM: Artificial
<220> FEATURE:
<223> OTHER INFORMATION: PCR primer

<400> SEQUENCE: 995
acactctttc cctacacgac gctcttccga tctactggag tggattgggt acatctatt     59

<210> SEQ ID NO 996
<211> LENGTH: 53
<212> TYPE: DNA
<213> ORGANISM: Artificial
<220> FEATURE:
<223> OTHER INFORMATION: PCR primer

<400> SEQUENCE: 996
acactctttc cctacacgac gctcttccga tctagggctt gagtggatgg gaa           53

<210> SEQ ID NO 997
<211> LENGTH: 59
<212> TYPE: DNA
<213> ORGANISM: Artificial
<220> FEATURE:
<223> OTHER INFORMATION: PCR primer

<400> SEQUENCE: 997
acactctttc cctacacgac gctcttccga tctctggagt ggattgggta catctatca     59

<210> SEQ ID NO 998
<211> LENGTH: 53
<212> TYPE: DNA
<213> ORGANISM: Artificial
<220> FEATURE:
<223> OTHER INFORMATION: PCR primer

<400> SEQUENCE: 998
acactctttc cctacacgac gctcttccga tctcgcttga gtggatggga tgg           53
```

<210> SEQ ID NO 999
<211> LENGTH: 55
<212> TYPE: DNA
<213> ORGANISM: Artificial
<220> FEATURE:
<223> OTHER INFORMATION: PCR primer

<400> SEQUENCE: 999
acactctttc cctacacgac gctcttccga tctgggtggc aacataaag caaga    55

<210> SEQ ID NO 1000
<211> LENGTH: 53
<212> TYPE: DNA
<213> ORGANISM: Artificial
<220> FEATURE:
<223> OTHER INFORMATION: PCR primer

<400> SEQUENCE: 1000
acactctttc cctacacgac gctcttccga tctgggactg gagtggattg ggt    53

<210> SEQ ID NO 1001
<211> LENGTH: 58
<212> TYPE: DNA
<213> ORGANISM: Artificial
<220> FEATURE:
<223> OTHER INFORMATION: PCR primer

<400> SEQUENCE: 1001
acactctttc cctacacgac gctcttccga tctgctagag tgggtggcag ttatatca    58

<210> SEQ ID NO 1002
<211> LENGTH: 57
<212> TYPE: DNA
<213> ORGANISM: Artificial
<220> FEATURE:
<223> OTHER INFORMATION: PCR primer

<400> SEQUENCE: 1002
acactctttc cctacacgac gctcttccga tctcttgagt ggatgggatg gatgaac    57

<210> SEQ ID NO 1003
<211> LENGTH: 58
<212> TYPE: DNA
<213> ORGANISM: Artificial
<220> FEATURE:
<223> OTHER INFORMATION: PCR primer

<400> SEQUENCE: 1003
acactctttc cctacacgac gctcttccga tctagtgggt ctcagctatt agtggtag    58

<210> SEQ ID NO 1004
<211> LENGTH: 53
<212> TYPE: DNA
<213> ORGANISM: Artificial
<220> FEATURE:
<223> OTHER INFORMATION: PCR primer

<400> SEQUENCE: 1004
acactctttc cctacacgac gctcttccga tctgctggag tgggtctctg gta    53

<210> SEQ ID NO 1005
<211> LENGTH: 53
<212> TYPE: DNA
<213> ORGANISM: Artificial
<220> FEATURE:

<223> OTHER INFORMATION: PCR primer

<400> SEQUENCE: 1005
acactctttc cctacacgac gctcttccga tctgctggtg tgggtctcac gta        53

<210> SEQ ID NO 1006
<211> LENGTH: 58
<212> TYPE: DNA
<213> ORGANISM: Artificial
<220> FEATURE:
<223> OTHER INFORMATION: PCR primer

<400> SEQUENCE: 1006
acactctttc cctacacgac gctcttccga tctgagtggg tctcaggtat tagttgga   58

<210> SEQ ID NO 1007
<211> LENGTH: 55
<212> TYPE: DNA
<213> ORGANISM: Artificial
<220> FEATURE:
<223> OTHER INFORMATION: PCR primer

<400> SEQUENCE: 1007
acactctttc cctacacgac gctcttccga tctcaggaaa aggtctggag tgggt      55

<210> SEQ ID NO 1008
<211> LENGTH: 56
<212> TYPE: DNA
<213> ORGANISM: Artificial
<220> FEATURE:
<223> OTHER INFORMATION: PCR primer

<400> SEQUENCE: 1008
acactctttc cctacacgac gctcttccga tcttggagtg ggtggcagtt atatca     56

<210> SEQ ID NO 1009
<211> LENGTH: 56
<212> TYPE: DNA
<213> ORGANISM: Artificial
<220> FEATURE:
<223> OTHER INFORMATION: PCR primer

<400> SEQUENCE: 1009
acactctttc cctacacgac gctcttccga tctgggactg gagtgggttt cataca     56

<210> SEQ ID NO 1010
<211> LENGTH: 54
<212> TYPE: DNA
<213> ORGANISM: Artificial
<220> FEATURE:
<223> OTHER INFORMATION: PCR primer

<400> SEQUENCE: 1010
acactctttc cctacacgac gctcttccga tctagggctt gagtggatgg gatg       54

<210> SEQ ID NO 1011
<211> LENGTH: 56
<212> TYPE: DNA
<213> ORGANISM: Artificial
<220> FEATURE:
<223> OTHER INFORMATION: PCR primer

<400> SEQUENCE: 1011
acactctttc cctacacgac gctcttccga tctagggaaa gggctagagt tggtag     56

-continued

```
<210> SEQ ID NO 1012
<211> LENGTH: 53
<212> TYPE: DNA
<213> ORGANISM: Artificial
<220> FEATURE:
<223> OTHER INFORMATION: PCR primer

<400> SEQUENCE: 1012
acactctttc cctacacgac gctcttccga tcttccccat cgagaggcct tga        53

<210> SEQ ID NO 1013
<211> LENGTH: 55
<212> TYPE: DNA
<213> ORGANISM: Artificial
<220> FEATURE:
<223> OTHER INFORMATION: PCR primer

<400> SEQUENCE: 1013
ctcggcattc ctgctgaacc gctcttccga tctcttacct gaggagacgg tgacc      55

<210> SEQ ID NO 1014
<211> LENGTH: 55
<212> TYPE: DNA
<213> ORGANISM: Artificial
<220> FEATURE:
<223> OTHER INFORMATION: PCR primer

<400> SEQUENCE: 1014
ctcggcattc ctgctgaacc gctcttccga tctctcacct gaggagacag tgacc      55

<210> SEQ ID NO 1015
<211> LENGTH: 55
<212> TYPE: DNA
<213> ORGANISM: Artificial
<220> FEATURE:
<223> OTHER INFORMATION: PCR primer

<400> SEQUENCE: 1015
ctcggcattc ctgctgaacc gctcttccga tctcttacct gaagagacgg tgacc      55

<210> SEQ ID NO 1016
<211> LENGTH: 23
<212> TYPE: DNA
<213> ORGANISM: Artificial
<220> FEATURE:
<223> OTHER INFORMATION: PCR primer

<400> SEQUENCE: 1016
ccatctcatc cctgcgtgtc tcc                                         23

<210> SEQ ID NO 1017
<211> LENGTH: 24
<212> TYPE: DNA
<213> ORGANISM: Artificial
<220> FEATURE:
<223> OTHER INFORMATION: PCR primer

<400> SEQUENCE: 1017
cctatcccct gtgtgccttg agag                                        24
```